(12) United States Patent
Iwata-Reuyl et al.

(10) Patent No.: US 8,993,293 B2
(45) Date of Patent: Mar. 31, 2015

(54) CRYSTAL STRUCTURE OF QUEUOSINE BIOSYNTHESIS ENZYME QUEF BOUND TO SUBSTRATE PREQ0

(76) Inventors: Dirk Iwata-Reuyl, Corbett, OR (US); Manal A. Swairjo, Pomona, CA (US)

( * ) Notice: Subject to any disclaimer, the term of this patent is extended or adjusted under 35 U.S.C. 154(b) by 0 days.

(21) Appl. No.: 12/981,883

(22) Filed: Dec. 30, 2010

(65) Prior Publication Data
US 2011/0295582 A1 Dec. 1, 2011

Related U.S. Application Data

(60) Provisional application No. 61/291,563, filed on Dec. 31, 2009, provisional application No. 61/297,999, filed on Jan. 25, 2010.

(51) Int. Cl.
*C12N 9/00* (2006.01)
*G01N 31/00* (2006.01)
*C12N 9/06* (2006.01)
*G06F 19/16* (2011.01)

(52) U.S. Cl.
CPC .............. *C12N 9/0044* (2013.01); *G06F 19/16* (2013.01)
USPC .............................................. 435/183; 436/4

(58) Field of Classification Search
None
See application file for complete search history.

(56) References Cited

U.S. PATENT DOCUMENTS 7,364,882 B1 * 4/2008 Iwata-Reuyl et al. ........ 435/128

OTHER PUBLICATIONS

Swairjo et al., "Crystallization and preliminary X-ray characterization of the nitrile reductase QueF:a queuosine-biosynthesis enzyme", Acta Crystallographica Section F, Structural Biology and Crystallization Communications, Sep. 30, 2005, vol. F61, pp. 945-948.*
Moon et al., "A synergistic approach to protein crystallization: Combination of a fixed-arm carrier with surface entropy reduction", Protein Science, 2010, 19:901-913.*
McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*

* cited by examiner

*Primary Examiner* — Suzanne M Noakes
(74) *Attorney, Agent, or Firm* — J.A. Lindeman & Co., PLLC

(57) ABSTRACT

This invention provides for the design of novel nitrile oxidoreductases that can be used as biocatalysts for industrial chemical processes and; and thus, provide attractive alternatives to traditional chemical synthesis. Generally, this technology relates to crystal structures of nitrile oxidoreductases, and of crystal structures of nitrile oxidoreductases complexed with substrates and co-factors. For example, the invention provides for the crystalline structure of the nitrile oxidoreductase, QueF, as well as for a computer-readable medium having QueF crystal structure information stored thereon.

1 Claim, 7 Drawing Sheets

A

B

SEQUENCE LISTING

```
<160> NUMBER OF SEQ ID NOS: 1

<210> SEQ ID NO 1
<211> LENGTH: 165
<212> TYPE: PRT
<213> ORGANISM: Bacillus subtilis

<400> SEQUENCE: 1

Met Thr Thr Arg Lys Glu Ser Glu Leu Glu Gly Val Thr Leu Leu Gly
1               5                   10                  15

Asn Gln Gly Thr Asn Tyr Leu Phe Glu Tyr Ala Pro Asp Val Leu Glu
            20                  25                  30

Ser Phe Pro Asn Lys His Val Asn Arg Asp Tyr Phe Val Lys Phe Asn
        35                  40                  45

Cys Pro Glu Phe Thr Ser Leu Cys Pro Lys Thr Gly Gln Pro Asp Phe
    50                  55                  60

Ala Thr Ile Tyr Ile Ser Tyr Ile Pro Asp Glu Lys Met Val Glu Ser
65                  70                  75                  80

Lys Ser Leu Lys Leu Tyr Leu Phe Ser Phe Arg Asn His Gly Asp Phe
                85                  90                  95

His Glu Asp Cys Met Asn Ile Ile Met Asn Asp Leu Ile Glu Leu Met
            100                 105                 110

Asp Pro Arg Tyr Ile Glu Val Trp Gly Lys Phe Thr Pro Arg Gly Gly
            115                 120                 125

Ile Ser Ile Asp Pro Tyr Thr Asn Tyr Gly Lys Pro Gly Thr Lys Tyr
        130                 135                 140

Glu Lys Met Ala Glu Tyr Arg Met Met Asn His Asp Leu Tyr Pro Glu
145                 150                 155                 160

Thr Ile Asp Asn Arg
            165
```

US 8,993,293 B2

CRYSTAL STRUCTURE OF QUEUOSINE BIOSYNTHESIS ENZYME QUEF BOUND TO SUBSTRATE PREQ0

CROSS REFERENCE TO RELATED APPLICATION

This application claims benefit of priority of U.S. Provisional Patent Application Ser. No. 61/291,563 filed on Dec. 31, 2009, and U.S. Provisional Patent Application Ser. No. 61/297,999 filed on Jan. 25, 2010, the entire disclosures of which are incorporated herein by reference.
Dirk Iwata-Reuyl[1] and Manal A. Swairjo[2]
[1]Department of Chemistry, Portland State University, P.O. Box 751, Portland, Oreg. 97207, USA.
[2]Department of Basic Medical Sciences, College of Osteopathic Medicine of the Pacific, Western University of Health Sciences, 309 E. 2$^{nd}$ Street, Pomona, Calif. 91766-1854, USA.

FIELD OF THE INVENTION

This invention relates to crystal structures of nitrile oxidoreductases, and the use of nitrile oxidoreductases as biocatalysts for chemical processes.

BACKGROUND OF THE INVENTION

The recently characterized QueF class of enzymes reduce nitrites to primary amines. Enzymes that catalyze such reactions are referred to as nitrile oxidoreductases. QueF orthologs can be found in bacteria (such as *Escherichia coli* QueF and *Bacilus subtilis* QueF).(SEQ ID NO: 1)). As described in U.S. Pat. No. 7,364,882, which is incorporated herein by reference, QueF catalyzes the first known example of a biological conversion of a nitrile containing metabolite to its corresponding amine. More specifically, QueF catalyzes a late step reaction in the biosynthesis of the transfer RNA (tRNA)-modified nucleoside, queuosine (Q), a key modulator of ribosomal translational fidelity. (Van Lanen, J. S. et al. 2005; Reader, Metzgar et al. 2004.) Specifically, QueF catalyzes the nicotinamide adenine diphosphate (NADPH)-dependent, two-fold reduction of 7-cyano-7-deazaguanine (preQ$_0$) to 7-aminomethyl-7-deazaguanine (preQ$_1$), the advanced, and last common intermediate in the biosynthesis of Q. (Id.) Subsequent to the conversion of preQ$_0$ to PreQ$_1$, PreQ$_1$ is inserted into the tRNA by the enzyme tRNA transglycosylase (TGT), and the remainder of the pathway occurs at the level of the tRNA. (Iwata-Reuyl 2003.)

Based on their amino acid sequences, QueF enzymes fall in two structural subfamilies (Van Lanen, J. S. et al. 2005). The YkvM subfamily is comprised of ~160-amino add unimodular proteins with a characteristic QueF motif, i.e., E(S/L)K(S/A)hK(L/Y)(Y/F/W) (wherein h is a hydrophobic amino acid) bracketed on the N- and C-terminal sides by an invariant Cys and Glu, respectively. The YqcD subfamily of QueF enzymes is characterized by ~280-amino acid bimodular proteins where the QueF motif and the invariant Cys and Glu are located separately, in the weakly homologous N- and C-terminal halves (modules) of the polypeptide chain, respectively. Functional analysis of an enzyme from each subfamily, YkvM (*B. subtilis* QueF) and YqcD (*E. coli* QueF), showed that YqcD enzymes are homodimers while YkvM enzymes function as higher order multimers.

The crystal structure of YkvM unimodular QueF complexed with preQ$_0$ reveals an asymmetric tunnel-fold homodecamer of two head-to-head facing pentameric subunits cyclically arranged to form a 20-stranded β-barrel, layered on the outside by 10α-helices, an architecture characteristic of unimodular pterin and purine binding enzymes. The structure harbors 10 active sites each located at the interface between three monomers. Eight active sites are each occupied with a preQ$_0$ molecule that is anchored by the invariant Glu98. The preQ$_0$ molecule also forms a covalent adduct with the catalytic residue, Cys55. The empty sites are associated with two subunits that are slightly off the 5-fold symmetry axis, and exhibit disordered C-terminal regions. A glucose-6-sulfate (G6S) or glucosamine moiety, originating from dextran sulfate, occupies the previously predicted NADP site comprised of residues from two subunits and includes residues from the conserved QueF motif $E_{79}$(S/L)K(S/A)hK(L/Y)(Y/F/W)$_{86}$. Based on the foregoing structural characterization of QueF, native QueF enzymes can be mutated to engineer other nitrile oxido-reductases which have specificities for other nitile containing substrates. Engineered QueF enzymes can be used, for example, in methods that provide a nitrile oxido-reductase (such as a recombinant nitrile oxido-reductase) and contacting the nitrile containing compound with the nitrile oxido-reductase under conditions sufficient for substantially reducing the nitrile containing compound to the corresponding amine. Such methods can be performed either in vitro or in vivo.

The discovery of QueF activity expands the chemistry of known nitrile metabolizing enzymes (Banerjee, Sharma et al. 2002), which includes hydrolysis (nitrile hydratase and nitrilase), oxidation (oxygenase), and cleavage (hydroxynitrile lyase). Prior to the discovery of QueF activity, the reduction of a nitrile was unprecedented in biology. Until then, industrial processes that relied on nitrile reduction had to resort to non-biological methods of reducing nitriles. Traditionally, the reduction of nitrites to amines has been carried out synthetically by hydrogenation over various transition metal catalysts or by metal hydride reductions. However, those reactions are typically non-selective; and thus, require the use of protecting groups when other reducible functional groups are present, and result in the formation of unwanted byproducts. Conversely, methods that utilize QueF as a biocatalyst in the transformation of nitriles to their corresponding amities can provide an environmentally sensitive alternative to the synthetic conversion of nitrites to amines. To that end, the present invention is directed to the crystal structure of *B. subtilis* QueF (19.4 kDa, 165 amino acids (SEQ ID NO: 1)). The crystal structure and structural data on the active site architecture and substrate and cofactor binding pockets of QueF may be used for the design and development of QueF mutants that bind to a variety of nitrite containing, industrially important substrates and catalyze the reduction of nitriles to their corresponding amines.

SUMMARY OF THE INVENTION

This invention provides for the design of novel nitrile oxidoreductases that can be used as biocatalysts for industrial chemical processes and; and thus, provide attractive alternatives to traditional chemical synthesis. Generally, this technology relates to crystal structures of nitrile oxidoreductases, and of crystal structures of nitrile oxidoreductases complexed with substrates and co-factors. One embodiment of the invention provides for the crystalline structure of the nitrite oxidoreductase, QueF. A related embodiment provides for the crystalline structure of QueF complexed with a substrate and a co-factor. Yet another related embodiment provides for a computer-readable medium having QueF crystal structure information stored thereon.

BRIEF DESCRIPTION OF THE TABLES

Table 1 provides the amino acids and three-dimensional atomic coordinates of the first of four QueF binding sites for preQ$_0$.

Table 2 provides the amino acids and three-dimensional atomic coordinates of the second of four QueF binding sites for preQ$_0$.

Table 3 provides the amino acids and three-dimensional atomic coordinates of third of four QueF binding sites for preQ$_0$.

Table 4 provides the amino acids and three-dimensional atomic coordinates of the fourth of four QueF binding sites for preQ$_0$.

Table 5 provides the amino acids and three-dimensional atomic coordinates of the first of four QueF binding sites for NADPH.

Table 6 provides the amino acids and three-dimensional atomic coordinates of the second of four QueF binding sites for NADPH.

Table 7 provides the amino adds and three-dimensional atomic coordinates of the third of four QueF binding sites for NADPH.

Table 8 provides the amino acids and three-dimensional atomic coordinates of the fourth of four QueF binding sites for NADPH.

DETAILED DESCRIPTION OF THE INVENTION

Figure 1:
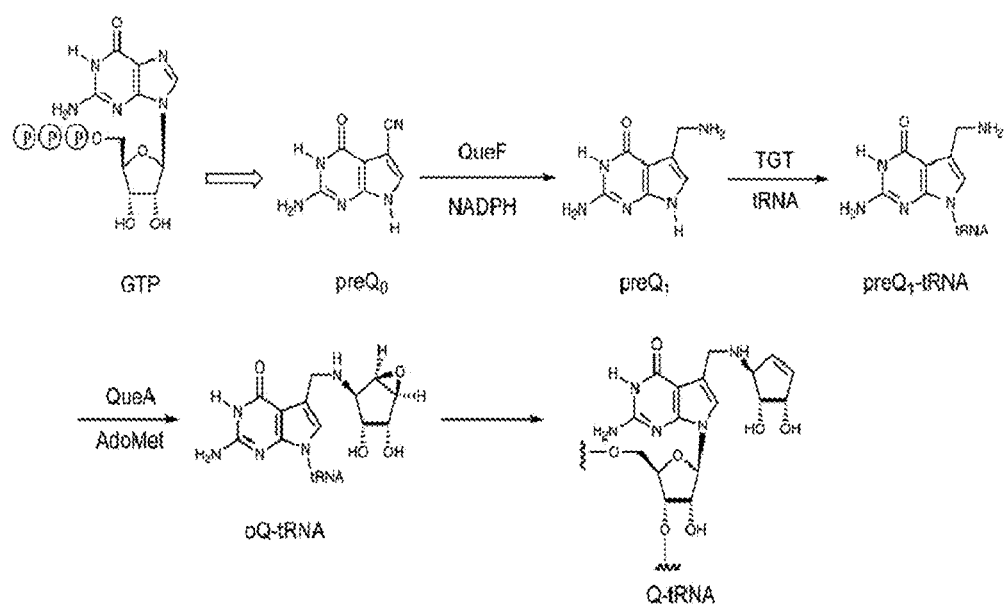
FIG. 1 is a graphic representation of the queuosine biosynthetic pathway in bacteria.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms "a," "an," and "the" include the plural reference and equivalents known to those skilled in the art unless the context clearly indicates otherwise. Other than in the operating examples, or where otherwise indicated, all numbers expressing quantities of ingredients or reaction conditions used herein should be understood as modified in all instances by the term "about."

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

Unless defined otherwise, all technical and scientific terms used herein have the same meaning as those commonly understood to one of ordinary skill in the art to which this invention pertains. Although methods and materials similar or equivalent to those described herein can be used in the practice or testing of the present disclosure, suitable methods and materials are described below. The materials, methods, and examples are illustrative only and not intended to be limiting. For example, the following terms have the following exemplary definitions.

NADPH: reduced form of nicotinamide adenine dinucleotide phosphate.

preQ$_o$: 7-cyano-7-deazaguanine preQ$_i$: 7-aminomethyl-7-deazaguanine

QueF: An exemplary group of nitrile oxido-reductases.

Amine: Organic compounds containing nitrogen as the key atom in the amine functional group. Amines have structures resembling ammonia where the nitrogen is bonded to a carbon atom, and where one or more hydrogen atoms are replaced by organic groups, such as: aliphatic or substituted aliphatic groups, including alkyl, alkenyl, or alkynyl groups (or combinations thereof); substituted aliphatic groups, including without limitation, aliphatic groups substituted with halogen, oxygen, sulfur, nitrogen, combinations of such elements and a functional or groups defined by such elements; aromatic groups; substituted aromatic groups; heterocycles; or other groups, and all possible combinations of such groups. The substitution of one hydrogen atom constitutes a primary amine (such as $NH_2CH_3$); that of two atoms, a secondary amine (such as $NH(CH_3)_2$); that of three atoms, a tertiary amine (such as $N(CH_3)_3$); and that of four atoms, a quaternary ammonium ion (such as $^+N(CH_3)_4$)' a positively charged ion isolated only in association with a negative ion.

In various embodiments, the crystal structural information disclosed herein is useful for the analysis of binding interactions with a ligand, e.g., for characterizing the interaction of QueF amino acid residues with nitrile group containing ligands (substrates). Such data is useful for a number of purposes, including the design of a modified QueF that can catalyze the conversion of a nitrile containing compound other than preQ$_0$ to the corresponding amine, such as primary amine. In some embodiments, a modified QueF will be useful, for example, in industrial applications aimed at converting nitrites and nitriles to amines.

The refined crystal structure of the *B. subtilis* QueF pentamer contains five QueF molecules, which are labeled A-E, four preQ$_0$, two glucose-6-sulfate or glucosamine molecules, two polyethylene glycol molecules, a glycerol molecule, two sulfate molecules, and four Mg$^{2+}$ ions. N-terminal 21 amino acid residues of all protein subunits are disordered. Subunit A is also disordered in the C-terminal region following Pro159.

Figure 2:
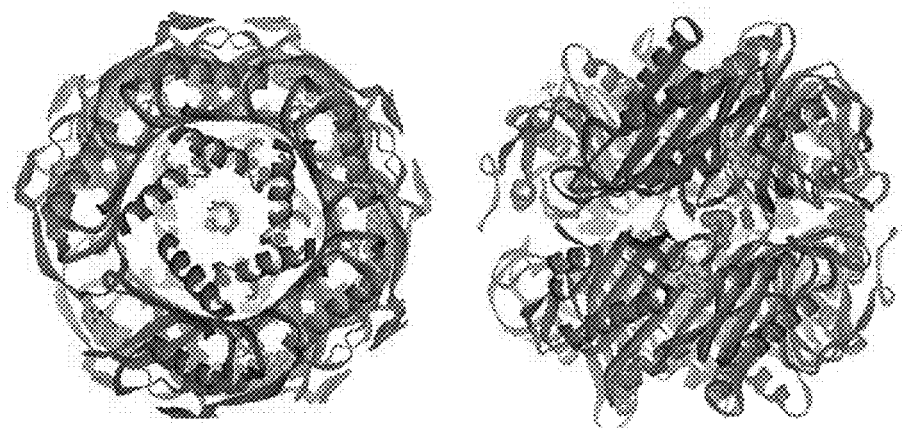
FIG. 2 shows a ribbon diagram of a C-alpha trace of *B. subtilis* QueF shown in a top view down the tunnel (left) and a side view (right). One subunit is highlighted in red. $Mg^{2+}$ ions are shown as magenta spheres. Bound PreQ$_0$ molecules are shown in cyan. Bound glucose-6-sulfate is shown in green in the putative NADPH binding pocket. PEG molecules in the tunnel center are shown as yellow sticks.

The crystal structure of QueF reveals a nonsymmetric homodecamer (FIG. 2) of two head-to-head facing pentamers, each comprised of a cyclic arrangement of monomeric $\beta_{2n}\alpha_n$ barrels characteristic of tunnel fold (T-fold) enzymes such as GTP cyclohydrolase I enzymes (Nar. Huber et al. 1995; Sankaran, Bonnett et al. 2009). The homodecamer is formed by applying the crystallographic two-fold symmetry operation on the asymmetric unit. The crystal structure also reveals that the decamer is characterized by a large molecular surface, a characteristic that is consistent with the decameric structure being the biological structure. In some embodiments, the QueF decamer comprises eight active sites which are occupied with preQ$_0$ and two which are empty (FIG. 2). The empty sites are associated with the two subunits that are slightly off the 5-fold symmetry axis and exhibit disordered C-termini. Amino acid residue numbers of the QueF crystal structure corresponds to sequence numbers beginning with the N-terminal methionine.

Substrate Binding Pocket

Figure 3:
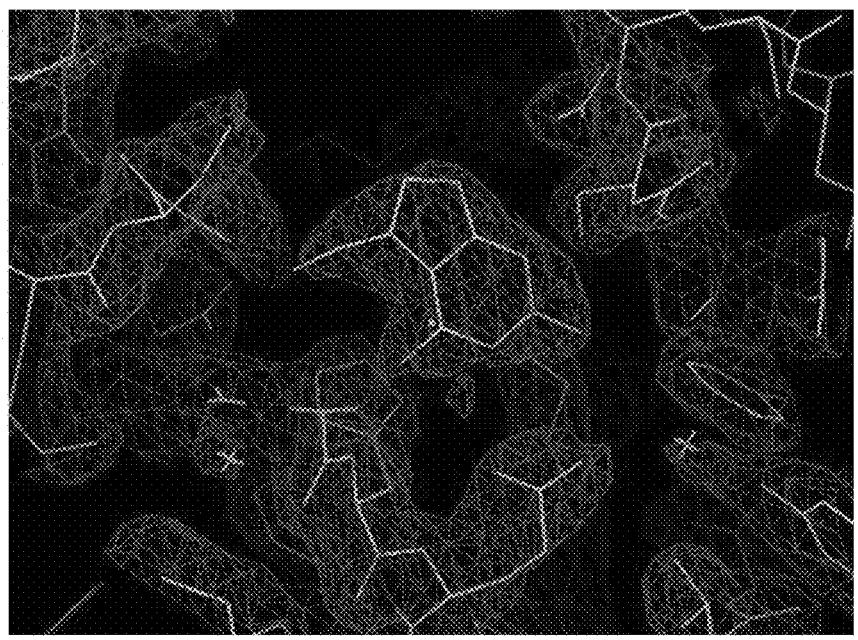
FIG. 3 shows a 2Fo-Fc electron density map superposed on the QueF model in the active site region, showing bound preQ$_0$ molecule.
Figure 5:
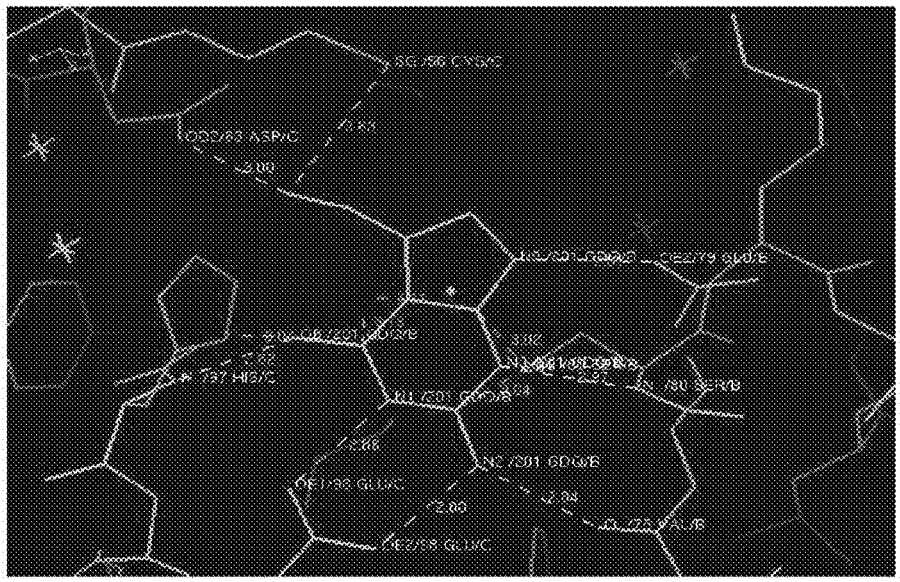
FIG. 5 schematically illustrates preQ0 binding pocket and substrate-enzyme interactions.
Figure 5:
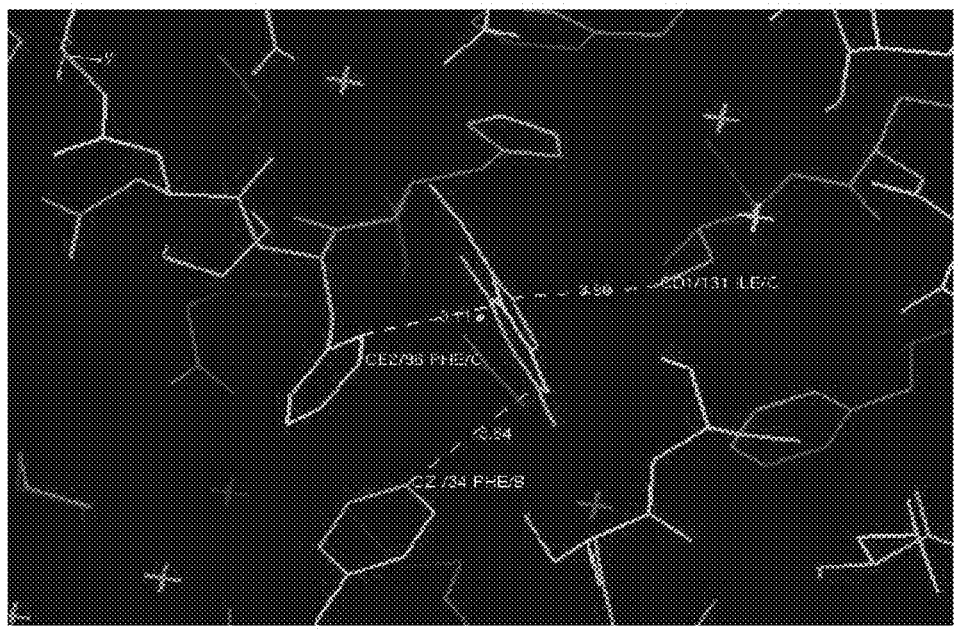

Each of the ten active sites of the QueF homodecamer are located at the interface between three subunits; two from one beta barrel, and one from the opposite beta barrel. The active site is comprised of the substrate and cofactor binding pockets. Electron density corresponding to preQ$_0$ is seen in the different Fourier maps in eight of the ten active sites in the homodecamer (FIG. 3). The preQ$_0$ binding pocket is defined by a cleft between the two subunits from the same beta barrel. FIG. 5 shows the interactions of bound preQ$_0$ with the enzyme. Tables 1-4 contain amino acid residues and three-dimensional (x,y,z) atomic coordinates of the QueF PreQ$_0$ binding site. PreQ$_0$ forms hydrogen bonds via its N1 and N2 atoms with the invariant Glu98 side chain, and via its N9 atom with the side chain of Glu79 (which is the first residue in the conserved QueF motif). PreQ$_0$ forms hydrogen bonds with the backbone amines of His97 and Ser80 via its O6 and N3 atoms. Another H-bond is formed between the exocyclic amine of preQ$_0$ and the carbonyl oxygen of Val78. The substrate binding pocket is also lined with hydrophobic residues that make Van der Waals interactions with preQ$_0$. These residues are Phe34, Phe96, and Ile131 (FIG. 5B).

In various embodiments of the invention, the crystalline structure of QueF is of QueF complex with preQ$_0$. In other embodiments of the invention, the binding of preQ$_0$ to the substrate binding pocket of QueF includes the amino acids and binding coordinates shown in any of Tables 1-4. In some embodiments, the binding coordinates of Tables 1-4 are obtained from a QueF-substrate complex that is not bound to a QueF co-factor. However, in other embodiments the binding coordinates of Tables 1-4 are obtained from a QueF-substrate complex that is bound to a QueF co-factor.

Cofactor Binding Pocket

Figure 4:
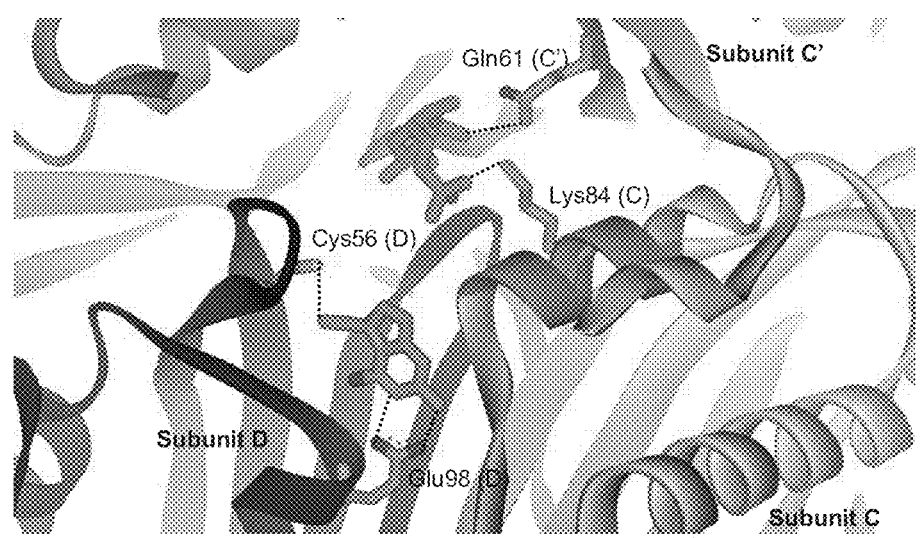
FIG. 4 shows a model of the active site between the three subunits D, C (from one pentamer) and C' (from the opposite pentamer) with hound preQ$_0$. Glucose-6-sulfate and QueF motif are shown in green. Subunit labels are shown next to residue names.
Figure 6:
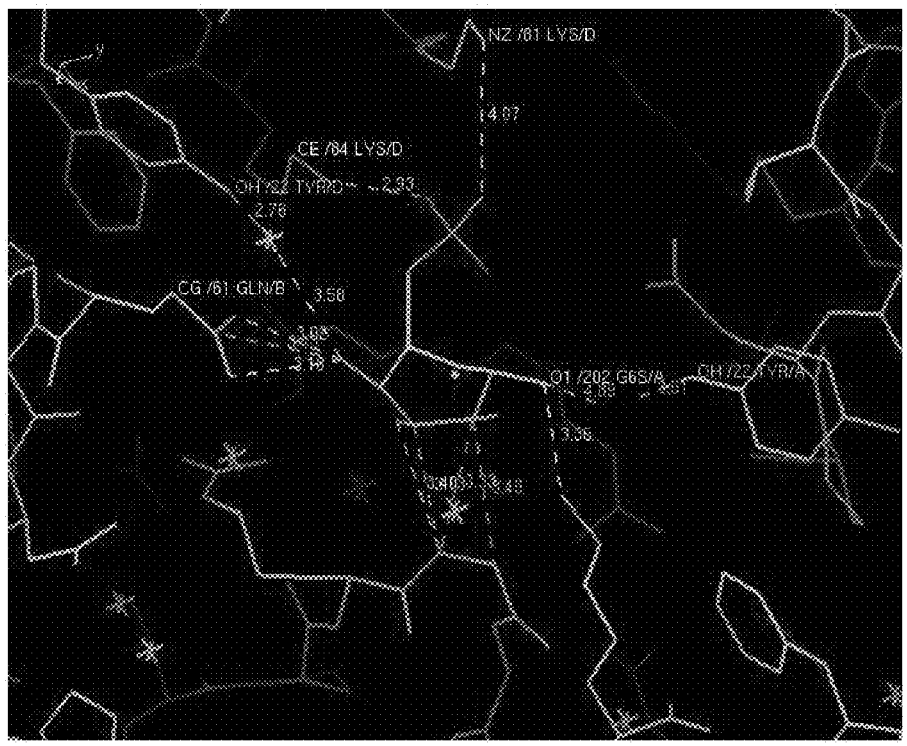
FIG. 6 depicts Glucose-6-sulfate interactions with QueF in the NADP binding pocket. Residues in green are from the adjacent subunit in the opposite beta barrel.

In addition to bound preQ$_0$, adjacent electron density is seen in two active sites for a glucose-6-sulfate (G6S) or glucosamine moiety, originating from dextran sulfate which was included as an additive in the crystallization buffer. G6S mimics the ribose and phosphate moieties of the enzyme cofactor NADPH and occupies the putative NADPH site predicted previously using modeling tools (Swairjo, Reddy et al. 2005). Tables 5-8 contain amino acid residues and three-dimensional (x,y,z) atomic coordinates of the QueF co-factor binding site. The cofactor pocket is at the interface between three subunits and involves residues from all three. The QueF motifs from two subunits contribute side chains to the recognition of G6S (FIGS. 4, 6). Specifically, these side chains are Lys81 and Lys84 which stabilize the electronegative sulfate moiety of G6S and Gln61 and Tyr22 that make direct and indirect H-bonds with the sugar hydroxyl groups.

In various embodiments of the invention, the crystalline structure of QueF is of QueF in complex with NADPH, while in other embodiments, QueF may be in complex with G6S. Further embodiments of the invention include the amino acids and binding coordinates that are involved with the binding of QueF co-factor to the QueF co-factor binding site, as shown in any of Tables 5-8.

Crystal Structure of QueF-Thioimide Intermediate

Figure 7:
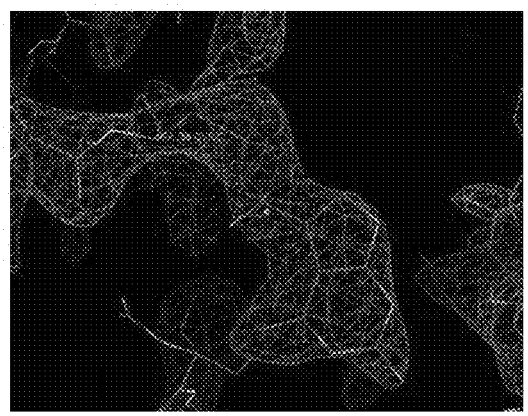
FIG. 7. A) Formation of the QueF thioimide intermediate demonstrated by annealed omit Fo-Fc electron density map (contour level 6 σ) showing covalent bond with Cys56. B) superposition of QueF thioimide complex (QueF·preQ$_0$, blue) with unreacted complex (yellow) showing thioimide-associated conformational changes.
Figure 7:
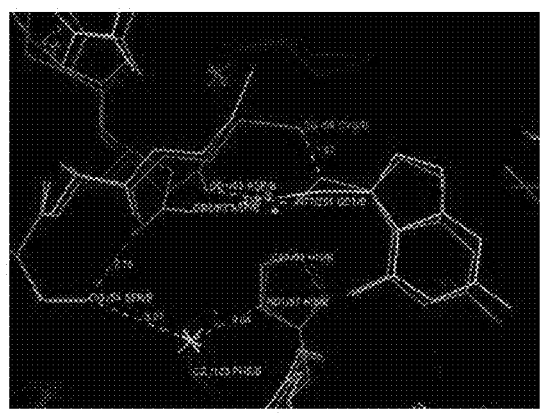

The crystal structure of the QueF·preQ$_0$ thioimide intermediate state complex in the absence of cofactor or cofactor surrogate shows that the Cys56 sulfur atom forms a 1.87 Å covalent bond with the preQ$_0$ nitrile carbon atom (FIG. 7). The conformational changes that are seen in the active site upon thioimide formation (FIG. 7B) are rotations in the side chains of Cys56 and Asp63, resulting in a rearranged network of hydrogen bonds with active site residues Ser54 and His97 and a tightly bound water molecule. The conformational changes suggest that these residues participate in proton transfer in the initial step of catalysis, leading to formation of the thioimide intermediate.

Computer Readable Medium Comprising QueF Structural Information

In various embodiments of the invention, QueF crystal structural information can be stored on a computer-readable medium. The invention, therefore, provides systems, particularly computer systems, that contain the atomic co-ordinate data of any one of the tables below, or selected coordinates thereof. The computer system may comprise: (i) a computer-readable data storage medium comprising data storage material encoded with the computer-readable data; (ii) a working memory for storing instructions for processing said computer-readable data; and (iii) a central-processing unit coupled to said working memory and to the computer-readable data storage medium for processing said computer-readable data and thereby generating structures.

The computer system may further comprise a display coupled to the central-processing unit for displaying the structures. The computer system may contain one or more remote devices. The remote device may comprise e.g. a computer system or computer readable media of one of the previous aspects of the invention. The device may be in a different country or jurisdiction from where the computer-readable data is received. The communication with a remote device may be via the internet, intranet, e-mail etc, or transmitted through wires or by wireless means such as by terrestrial radio or by satellite. Typically the communication will be electronic in nature, but some, or all, of the communication pathway may be optical, for example, over optical fibers. The data received may then be used in a computer-based method for the analysis of the interaction of a ligand as discussed above.

In some embodiments of the invention, the computer system discussed above may be used to analyze the fitting of a ligand to the amino acids of the QueF active site. Such embodiments may rely on a computer readable medium that comprises the amino acids and three-dimensional coordinates of any or all of Tables 1-4. In other embodiments of the invention, the computer system may be used to create a model of the interactions between QueF and its ligand, wherein any or all of the atomic coordinates of Tables 1-4 can be varied by a root mean square distance (rmsd) of less than 1.5 Å, or in other embodiments, less than 0.5 Å.

There are also embodiments of the invention that use the computer system described above to design QueF mutants that reduce nitrile-containing compounds other than preQ$_0$. For example, structural information about the amino acid residues and atomic coordinates that are involved in the fitting of a QueF substrate into the QueF active site, can be used to ascertain which amino acid residues can be substituted or deleted such that the QueF active site will bind to at least one ligand other than preQ$_0$ such that the ligand may reduced to its corresponding primary amine. Similarly, in certain embodiments, the computer system can be used to determine if certain amino acid residues should be added in order to alter QueF active site specificity. Regardless of whether an amino acid is substituted, deleted, or added as indicated in the foregoing embodiments, in some embodiments the amino acid substitution, deletion, or addition involves amino acids that interact with preQ$_0$. Whereas, in other embodiments the amino acid residue substitution, deletion, or addition involves amino acids that do not interact with preQ$_0$.

In other words, in various embodiments, it is possible to carry out virtual modeling of a modified QueF enzymes for analysis and optimization of their interactions with candidate nitrile containing compounds using the atomic coordinates shown in Tables 1-8, or coordinates derived thereof. Briefly, the atomic coordinates of the three-dimensional structure elucidated by the invention are input into a computer so that images of the structure and various parameters are shown on the display. Then, the structure and various parameters can be manipulated to create virtual models of the QueF active site, wherein the effect of at least one amino acid residue substitution, deletion, or addition on the virtual interaction between the active site and candidate nitrile containing compound can be analyzed.

Therefore, the potential reduction of a candidate nitrile containing compound by a modified QueF enzyme (i,e., a QueF enzyme in which at least one amino acid residue substitution, deletion, or addition has been made) may be analyzed prior to the actual synthesis and testing of the modified QueF enzyme by the use of computer modeling techniques. If the theoretical structure of the given modified QueF enzyme suggests insufficient interaction and association between it and a candidate nitrile containing compound, synthesis and testing of the compound may be obviated. However, if computer modeling indicates a desired interaction, the modified QueF may then be synthesized and tested for its ability to reduce the nitrile containing compound using various methods known in the art. In this manner, synthesis of inoperative modified QueF enzymes may be avoided In some embodiments, the interaction between a modified QueF enzyme and a candidate nitrile containing compound may be computationally evaluated and designed by means of a series of steps in which candidate compounds are screened and selected for their ability to interact with individual QueF active site binding sites or combinations thereof. Conversely, in other embodiments, the interactions between a series of differently modified QueF enzymes may be computationally evaluated by their ability to interact with a selected candidate nitrile containing compound. Modified QueF enzymes may also be selected for their ability to interact with the candidate compound at individual QueF active site binding sites or combinations thereof.

One skilled in the art may use any of several methods to assess the ability of candidate nitrile group-containing compounds to interact with a modified QueF enzyme, and more particularly with specific amino acid residues of the active site. This process may begin by visual inspection of, for example, the modified QueF active site on the computer screen based on coordinates in any of the Tables 1-4. Candidate nitrile containing compounds may then be positioned in a variety of orientations, or docked, within an individual binding site in the active site as defined supra. Positioning of the candidate compound may be accomplished using, for example, software such as QUANTA, SYBYL, followed by energy minimization and molecular dynamics with standard molecular mechanics forcefields, using, for example, software such as CHARMM and AMBER. Other software packages will be known to those skilled in the art.

Specialized computer programs may also assist in the process of selecting modified QueF active sites or candidate nitrile containing compounds. These include: (1) GRID (Goodford, P. J., "A Computational Procedure for Determining Energetically Favorable Binding Sites on Biologically Important Macromolecules" J. Med. Chem., 28, pp. 849-857 (1985)), available from Oxford University, Oxford, UK; (2) MCSS (Miranker, A. and M. Karplus, "Functionality Maps of Binding Sites: A Multiple Copy Simultaneous Search Method" Proteins: Structure, Function and Genetics, 11, pp. 29-34 (1991)), available from Molecular Simulations, Burlington, Mass.; (3) AUTODOCK (available from Scripps Research Institute, La Jolla, Calif.); and (4) DOCK (Kuntz, 1. D. at al., "A Geometric Approach to Macromolecule-Ligand Interactions" J. Mol. Biol., 161, pp. 269-288 (1982)), available from University of California, San Francisco, Calif.; (5) GLIDE available from Schrodinger Inc.; (6) FlexX available from Tripes Inc; (7) GOLD (Jones et al., J, Mol. Biol., 245, 43-53, 1995), available from the Cambridge Crystallographic Data Centre; (8) Molegro Virtual Docker (Molegro ApS, available from the University of Aarhus, Denmark); and GRAMM (available from the University of Kansas). Other software packages will be known to those skilled in the art.

Once a suitable modified QueF enzyme has been selected, it can be made in silico or made, for example, according to conventional methods for introducing mutations, and producing proteins using recombinant methods. Making the modified QueF in silico may proceed by visual inspection of the relationship of the candidate compound to the QueF active site on the three-dimensional image of the active site displayed on a computer screen in relation to the candidate compound.

In some embodiments, once a modified QueF enzyme has been designed or selected to reduce a particular nitrile containing compound by the above methods, the efficiency with which that compound may bind to the QueF active site may be tested and optimized by computational evaluation. For example, an effective interaction (e.g., binding) between a nitrile containing compound and a QueF active site must be such that the compound preferably demonstrate a relatively small difference in energy between its bound and free states (i.e., a small deformation energy of binding). Thus, in certain embodiments, the most efficient interaction between a QueF active site and a nitrile containing compound should preferably occur when the deformation energy of binding is not greater than about 10 kcal/mole, preferably, not greater than 7 kcal/mole. In various other embodiments, nitrile containing compounds may interact with the QueF active in more than one conformation that is similar in overall binding energy. In those cases, the deformation energy of binding is taken to be the difference between the energy of the free compound and the average energy of the conformations observed when the compound binds to the QueF active site.

In some embodiments, the designed or selected modified QueF enzyme may be further computationally optimized so that when the nitrile containing compound is in its bound state it would preferably lack repulsive electrostatic interaction with the modified QueF active site. Such non-complementary (e.g., electrostatic) interactions include repulsive charge-charge, dipole-dipole, and charge-dipole interactions. Specifically, the sum of all electrostatic interactions between the nitrile group-containg compound and the modified QueF when the compound is bound to the active site, preferably make a neutral or favorable contribution to the enthalpy of binding.

Specific computer softwares are available in the art to evaluate compound deformation energy and electrostatic interaction. Examples of programs designed for such uses include: Gaussian 09; AMBER, version 11. Other software packages will be known to those skilled in the art.

EXAMPLES

Example 1

Crystallization and Crystal Structure Determination of the Non-Covalent QueF/preQ$_0$ Complex QueF from *B. subtilis* (SEQ ID NO: 1) was overexpressed and purified as described previously (Swairjo, Reddy et al. 2005). The non-covalent enzyme/preQ$_0$ complex was crystallized at 293.15°K as described previously (Swairjo, Reddy et al, 2005) using the following crystallization conditions: A sample size of 4 mg/ml (0.2 mM) QueF; 1.2-5 mM preQ$_0$ (enzyme:substrate molar ratio of 1:6-1:25): and 1-2% dextran sulfate as an additive. The presence of dextran sulfate in the crystallization buffer was necessary to obtain improved and larger crystals. The reservoir contained the following compounds at the specified amounts: 16-24% (v/v) PEG 550 MME; 100 mM HEPES or imidazole pH 7.2-7.8; 30 mM CaCl$_2$: and 0.05% (w/v) NaN$_3$. The X-ray data were collected using synchrotron radiation at the Stanford Synchrotron Research Laboratory, beamline 1-5. The data were processed using HKL-2000 (HKL Research, Inc., Charlottesville, Va.). The structure was determined using the molecular replacement (MR) Bayesian protocol in the program Phaser (Storoni, McCoy et al. 2004). The search model used for MR was a previously generated partial homology model based on the structure of *E. coli* GTP cyclohydrolase I (Swairjo, Reddy et al. 2005). Both alternative space groups in the P321 Bravais lattice were tested and the solution with significantly higher likelihood gain was obtained in the P3$_2$21 space group, The partial model obtained in Phaser and describing the asymmetric unit was used for automatic tracing and refinement in the program ArplWarp (Perrakis, Morris et al. 1999), which produced a significantly more complete model with a crystallographic R-factor of 0.35. Structure refinement was done using Refmac (Murshudov, Vagin at al. 1997) and Coot (Ernsley and Cowtan 2004).

Example 2

Crystallization of the Covalent QueF·preQ$_0$ Thioimide Complex

Wild-type purified *B. subtilis* QueF was crystallized in sitting drops using the vapor diffusion method at 20° C. A 4 mg/mL QueF (~200 μM) sample was prepared in 100 mM Tris (pH 7.5), 100 mM KCl, and then mixed with PreQ$_0$ and dextran sulfate (average Mr 5000 Da) to final concentrations of 1.1 mM (protein:preQ$_0$ molar ratio ~1:5) and 0.5%, respectively. A 2 μl aliquot of that solution was mixed with 2 μm of crystallization buffer (16% PEG500 mme, 60 mM imidazole, 40 mM imidazole-Cl (final pH 7.4), and 30 mM CaCl$_2$), and equilibrated in a sitting drop against a 500 μl reservoir of the same crystallization buffer. The crystal was harvested after 18 days of setup, soaked in 50 mM BaCl$_2$ for 24 hours, and then cryoprotected and stored in liquid nitrogen. X-ray data were collected from the crystal of the QueF·preQ$_0$ covalent complex at the Stanford Synchrotron Research Laboratory beamline BL9-1, using X-rays with wavelength 1.00002 Å (12398.2 eV). The crystal diffracted with a mosaicity of 0.5 deg, yielding 2.5 Å diffraction data with R-merge 0.38. The data were processed using HKL-2000 (HKL Research, Inc., Charlottesville, Va.). The crystal structure of the QueF·preQ$_0$ covalent thioimide complex was determined by direct difference Fourier methods using phases calculated from the QueF/preQ$_0$ no-covalent structure, and refined using Refmac.

Example 3

Determination of the Overall Structure *B. Subtilis* Quef

The crystal structure of *B. subtilis* QueF was determined by molecular replacement. The refined structure of the asymmetric unit contained five QueF molecules (labeled A-E), 4 preQ$_0$, 2 glucose-6-sulfate or glucosamine, 2 polyethylene glycol molecules, a glycerol molecule, and two sulfate and 4 Mg$^{2+}$ ions. All protein subunits were disordered in their N-terminal stretch of 21 residues. Subunit A was also disordered in the C-terminal region following Pro159.

The crystal structure revealed a nonsymmetric homodecamer (FIG. 2) of two head-to-head facing pentamers, each comprised of a cyclic arrangement of monomeric $\beta_{2n}\alpha_n$ barrels characteristic of tunnel fold (T-fold) enzymes such as GTP cyclohydrolase I enzymes (Nar, Huber et al. 1995; Sankaran, Bonnett et al. 2009). The hornodecamer was formed by applying the crystallographic two-fold symmetry operation on the asymmetric unit. The crystal structure also revealed a large molecular surface area that was covered by the formation of the decamer, consistent with the decameric structure being the biological structure. In the QueF decamer, eight active sites are occupied with preQ$_0$ and two are empty (FIG. 2). The empty sites are associated with the two subunits that are slightly off the 5-fold symmetry axis and exhibit disordered C-termini. Residue numbers of the present QueF crystal structures correspond to sequence numbers beginning with the N-terminal methionine.

REFERENCES

Banerjee, A., R. Sharma, at al. (2002). "The nitriledegrading enzymes: current status and future prospects." *Appl. Microbiol. Biotechnol* 60: 33-44.

Emsley, P. and K. Cowtan (2004). "COOT: Model-building tools for molecular graphics." *Acta Crystallogr D Biol Crystallogr* D60: 2126-32.

Iwata-Reuyl, D. (2003). "Biosynthesis of the 7-deazaguanosine hypermodified nucleosides of transfer RNA." *Bioorg. Chem.* 31: 24-43.

Lee, B. W. K., S. G. Van Lanen, at al. (2007), "Mechanistic Studies of *Bacillus subtilis* QueF, the Nitrite Oxidoreductase Involved in Queuosine Biosynthesis." *Biochemistry* 46: 12844-12854.

Murshudov, G. N., A. A. Vagin, at al. (1997). "Refinement of Macromolecular Structures by the Maximum-Likelihood Method." *Acta Crystallogr D Biol Crystallogr* D53: 240-55.

Nar, H., R. Huber, at al. (1995). "Atomic structure of GTP cyclohydrolase." *Structure (Camb)* 3(5): 459-66.

Perrakis, A., R. Morris, at al. (1999). "Automated protein model building combined with iterative structure refinement." *Nature Structural and Molecular Biol* 6(5): 458-63.

Reader, J., D. Metzgar, at al. (2004). "Identification of four genes involved in the biosynthesis of Queuine by comparative genomics." *J Biol Chem* 279: 6280-5.

Sankaran, B., S. A. Bonnett, et al. (2009). "Zinc-independent folate biosynthesis: genetic, biochemical, and structural investigations reveal new metal dependence for GTP cyclohydrolase IB." *Journal of Bacteriology* 191(22): 6936-6949.

Storoni, L. C., A. J. McCoy, et al. (2004). "Likelihood-enhanced fast rotation functions." *Acta Crystallogr D Biol Crystallogr* 60: 432-438.

Swairjo, M. A., R. R. Reddy, at al. (2005). "Crystallization and preliminary X-ray characterization of the nitrile reductase QueF—a queuosine biosynthesis enzyme." *Acta Crystallogr D Biol Crystallogr* 61: 945-8.

Van Lanen, S. G., R. J. S., at al. (2005). "From cyclohydrolase to oxidoreductase: discovery of a nitrile reductase activity in a common fold." *Proceedings of the National Academy of Sciences of the United States of America* 102(12): 4264-4269.

TABLE 1

| REMARK | Accelrys ViewerPro PDB file | | | | | | | |
|---|---|---|---|---|---|---|---|---|
| REMARK | Created: Tue Dec 14 10:03:41 Pacific Standard Time 2010 | | | | | | | |
| ATOM | 1 | N | LEU | 31 | −1.590 | 41.456 | 38.913 | 1.00 37.74 |
| ATOM | 2 | CA | LEU | 31 | −0.689 | 40.305 | 38.699 | 1.00 36.82 |
| ATOM | 3 | CB | LEU | 31 | 0.712 | 40.657 | 39.105 | 1.00 35.87 |
| ATOM | 4 | CG | LEU | 31 | 1.458 | 41.613 | 38.208 | 1.00 33.54 |
| ATOM | 5 | CD1 | LEU | 31 | 2.712 | 42.126 | 38.902 | 1.00 28.95 |
| ATOM | 6 | CD2 | LEU | 31 | 1.788 | 40.988 | 36.814 | 1.00 28.94 |
| ATOM | 7 | C | LEU | 31 | −1.139 | 38.994 | 39.362 | 1.00 37.87 |
| ATOM | 8 | O | LEU | 31 | −1.606 | 38.988 | 40.505 | 1.00 38.40 |
| ATOM | 9 | N | GLU | 32 | −1.030 | 37.888 | 38.612 | 1.00 37.64 |
| ATOM | 10 | CA | GLU | 32 | −1.388 | 36.560 | 39.083 | 1.00 38.64 |
| ATOM | 11 | CB | GLU | 32 | −2.670 | 36.036 | 38.425 | 1.00 37.72 |
| ATOM | 12 | CG | GLU | 32 | −3.941 | 36.735 | 38.823 | 1.00 43.03 |
| ATOM | 13 | CD | GLU | 32 | −5.224 | 36.066 | 38.255 | 1.00 45.25 |
| ATOM | 14 | OE1 | GLU | 32 | −6.223 | 36.795 | 38.082 | 1.00 53.36 |
| ATOM | 15 | OE2 | GLU | 32 | −5.268 | 34.819 | 38.003 | 1.00 55.49 |
| ATOM | 16 | C | GLU | 32 | −0.279 | 35.542 | 38.763 | 1.00 36.66 |
| ATOM | 17 | O | GLU | 32 | 0.458 | 35.663 | 37.771 | 1.00 35.10 |
| ATOM | 18 | N | SER | 33 | −0.230 | 34.501 | 39.586 | 1.00 35.44 |
| ATOM | 19 | CA | SER | 33 | 0.736 | 33.420 | 39.412 | 1.00 33.42 |
| ATOM | 20 | CB | SER | 33 | 1.779 | 33.476 | 40.503 | 1.00 33.88 |
| ATOM | 21 | OG | SER | 33 | 1.171 | 33.210 | 41.748 | 1.00 34.87 |
| ATOM | 22 | C | SER | 33 | 0.031 | 32.100 | 39.422 | 1.00 31.85 |
| ATOM | 23 | O | SER | 33 | −1.099 | 31.970 | 39.880 | 1.00 30.19 |
| ATOM | 24 | N | PHE | 34 | 0.662 | 31.115 | 38.825 | 1.00 31.80 |
| ATOM | 25 | CA | PHE | 34 | 0.197 | 29.748 | 38.964 | 1.00 31.47 |
| ATOM | 26 | CB | PHE | 34 | −0.580 | 29.251 | 37.719 | 1.00 31.44 |
| ATOM | 27 | CG | PHE | 34 | 0.229 | 29.223 | 36.454 | 1.00 34.03 |
| ATOM | 28 | CD1 | PHE | 34 | 0.258 | 30.334 | 35.602 | 1.00 34.78 |
| ATOM | 29 | CE1 | PHE | 34 | 1.031 | 30.315 | 34.430 | 1.00 36.66 |
| ATOM | 30 | CZ | PHE | 34 | 1.784 | 29.181 | 34.119 | 1.00 35.97 |
| ATOM | 31 | CE2 | PHE | 34 | 1.746 | 28.073 | 34.972 | 1.00 33.64 |
| ATOM | 32 | CD2 | PHE | 34 | 0.973 | 28.098 | 36.111 | 1.00 33.16 |
| ATOM | 33 | C | PHE | 34 | 1.453 | 28.899 | 39.342 | 1.00 32.01 |
| ATOM | 34 | O | PHE | 34 | 2.595 | 29.361 | 39.097 | 1.00 30.56 |
| ATOM | 35 | N | PRO | 35 | 1.243 | 27.736 | 40.021 | 1.00 30.96 |
| ATOM | 36 | CA | PRO | 35 | 2.346 | 26.887 | 40.441 | 1.00 31.09 |
| ATOM | 37 | CB | PRO | 35 | 1.633 | 25.670 | 41.121 | 1.00 31.52 |
| ATOM | 38 | CG | PRO | 35 | 0.314 | 26.231 | 41.680 | 1.00 29.68 |
| ATOM | 39 | CD | PRO | 35 | −0.064 | 27.250 | 40.537 | 1.00 31.48 |
| ATOM | 40 | C | PRO | 35 | 3.212 | 26.419 | 39.289 | 1.00 31.28 |
| ATOM | 41 | O | PRO | 35 | 2.685 | 25.954 | 38.274 | 1.00 32.59 |
| ATOM | 42 | N | ASN | 36 | 4.519 | 26.529 | 39.443 | 1.00 30.38 |
| ATOM | 43 | CA | ASN | 36 | 5.433 | 25.780 | 38.599 | 1.00 31.68 |
| ATOM | 44 | CB | ASN | 36 | 6.840 | 26.318 | 38.801 | 1.00 29.80 |
| ATOM | 45 | CG | ASN | 36 | 7.899 | 25.573 | 37.974 | 1.00 27.45 |
| ATOM | 46 | OD1 | ASN | 36 | 9.070 | 25.739 | 38.211 | 1.00 27.68 |
| ATOM | 47 | ND2 | ASN | 36 | 7.490 | 24.737 | 37.081 | 1.00 23.47 |
| ATOM | 48 | C | ASN | 36 | 5.373 | 24.280 | 38.903 | 1.00 33.94 |
| ATOM | 49 | O | ASN | 36 | 5.591 | 23.870 | 40.049 | 1.00 34.49 |
| ATOM | 50 | N | LYS | 37 | 5.083 | 23.480 | 37.884 | 1.00 36.15 |
| ATOM | 51 | CA | LYS | 37 | 5.003 | 22.023 | 37.998 | 1.00 38.88 |
| ATOM | 52 | CB | LYS | 37 | 3.957 | 21.465 | 37.025 | 1.00 39.35 |
| ATOM | 53 | CG | LYS | 37 | 2.513 | 21.922 | 37.277 | 1.00 42.55 |
| ATOM | 54 | CD | LYS | 37 | 1.621 | 21.511 | 36.076 | 1.00 43.64 |
| ATOM | 55 | CE | LYS | 37 | 0.516 | 22.577 | 35.818 | 1.00 52.13 |
| ATOM | 56 | NZ | LYS | 37 | −0.879 | 22.011 | 35.575 | 1.00 54.32 |
| ATOM | 57 | C | LYS | 37 | 6.316 | 21.272 | 37.715 | 1.00 38.75 |
| ATOM | 58 | O | LYS | 37 | 6.326 | 20.058 | 37.819 | 1.00 39.78 |
| ATOM | 59 | N | HIS | 38 | 7.384 | 21.975 | 37.330 | 1.00 37.81 |

TABLE 1-continued

| | | | | | | | | | |
|---|---|---|---|---|---|---|---|---|---|
| ATOM | 60 | CA | HIS | 38 | 8.685 | 21.379 | 36.985 | 1.00 | 37.48 |
| ATOM | 61 | CB | HIS | 38 | 8.904 | 21.464 | 35.471 | 1.00 | 36.45 |
| ATOM | 62 | CG | HIS | 38 | 7.737 | 20.925 | 34.706 | 1.00 | 35.02 |
| ATOM | 63 | ND1 | HIS | 38 | 7.609 | 19.584 | 34.407 | 1.00 | 33.66 |
| ATOM | 64 | CE1 | HIS | 38 | 6.448 | 19.374 | 33.807 | 1.00 | 34.44 |
| ATOM | 65 | NE2 | HIS | 38 | 5.804 | 20.527 | 33.736 | 1.00 | 35.48 |
| ATOM | 66 | CD2 | HIS | 38 | 6.581 | 21.510 | 34.313 | 1.00 | 32.93 |
| ATOM | 67 | C | HIS | 38 | 9.756 | 22.111 | 37.776 | 1.00 | 38.04 |
| ATOM | 68 | O | HIS | 38 | 10.571 | 22.866 | 37.209 | 1.00 | 37.77 |
| ATOM | 69 | N | VAL | 39 | 9.711 | 21.923 | 39.105 | 1.00 | 38.98 |
| ATOM | 70 | CA | VAL | 39 | 10.573 | 22.676 | 40.013 | 1.00 | 38.82 |
| ATOM | 71 | CB | VAL | 39 | 9.989 | 22.909 | 41.435 | 1.00 | 39.30 |
| ATOM | 72 | CG1 | VAL | 39 | 8.595 | 23.415 | 41.371 | 1.00 | 36.13 |
| ATOM | 73 | CG2 | VAL | 39 | 10.093 | 21.608 | 42.302 | 1.00 | 39.64 |
| ATOM | 74 | C | VAL | 39 | 11.954 | 22.076 | 40.128 | 1.00 | 40.02 |
| ATOM | 75 | O | VAL | 39 | 12.834 | 22.756 | 40.639 | 1.00 | 40.36 |
| ATOM | 76 | N | TYR | 43 | 14.685 | 26.136 | 33.897 | 1.00 | 29.52 |
| ATOM | 77 | CA | TYR | 43 | 14.249 | 26.467 | 32.521 | 1.00 | 29.35 |
| ATOM | 78 | CB | TYR | 43 | 13.072 | 25.597 | 32.013 | 1.00 | 27.62 |
| ATOM | 79 | CG | TYR | 43 | 11.726 | 25.733 | 32.733 | 1.00 | 28.44 |
| ATOM | 80 | CD1 | TYR | 43 | 11.452 | 24.997 | 33.894 | 1.00 | 27.65 |
| ATOM | 81 | CE1 | TYR | 43 | 10.199 | 25.094 | 34.538 | 1.00 | 26.92 |
| ATOM | 82 | CZ | TYR | 43 | 9.181 | 25.893 | 33.994 | 1.00 | 28.88 |
| ATOM | 83 | OH | TYR | 43 | 7.940 | 25.967 | 34.628 | 1.00 | 31.13 |
| ATOM | 84 | CE2 | TYR | 43 | 9.424 | 26.624 | 32.852 | 1.00 | 27.33 |
| ATOM | 85 | CD2 | TYR | 43 | 10.695 | 26.520 | 32.208 | 1.00 | 26.76 |
| ATOM | 86 | C | TYR | 43 | 13.902 | 27.952 | 32.440 | 1.00 | 28.82 |
| ATOM | 87 | O | TYR | 43 | 13.568 | 28.590 | 33.476 | 1.00 | 29.32 |
| ATOM | 88 | N | PHE | 44 | 13.969 | 28.481 | 31.218 | 1.00 | 27.46 |
| ATOM | 89 | CA | PHE | 44 | 13.774 | 29.926 | 30.965 | 1.00 | 26.91 |
| ATOM | 90 | CB | PHE | 44 | 14.869 | 30.452 | 30.033 | 1.00 | 25.36 |
| ATOM | 91 | CG | PHE | 44 | 15.870 | 31.403 | 30.680 | 1.00 | 23.94 |
| ATOM | 92 | CD1 | PHE | 44 | 17.233 | 31.120 | 30.675 | 1.00 | 23.06 |
| ATOM | 93 | CE1 | PHE | 44 | 18.141 | 31.998 | 31.205 | 1.00 | 23.18 |
| ATOM | 94 | CZ | PHE | 44 | 17.713 | 33.239 | 31.740 | 1.00 | 25.93 |
| ATOM | 95 | CE2 | PHE | 44 | 16.374 | 33.521 | 31.763 | 1.00 | 24.24 |
| ATOM | 96 | CD2 | PHE | 44 | 15.463 | 32.613 | 31.197 | 1.00 | 20.63 |
| ATOM | 97 | C | PHE | 44 | 12.389 | 30.124 | 30.357 | 1.00 | 26.11 |
| ATOM | 98 | O | PHE | 44 | 11.916 | 29.333 | 29.582 | 1.00 | 24.99 |
| ATOM | 99 | N | VAL | 45 | 11.730 | 31.176 | 30.776 | 1.00 | 26.48 |
| ATOM | 100 | CA | VAL | 45 | 10.472 | 31.580 | 30.195 | 1.00 | 26.88 |
| ATOM | 101 | CB | VAL | 45 | 9.290 | 31.488 | 31.208 | 1.00 | 27.53 |
| ATOM | 102 | CG1 | VAL | 45 | 9.192 | 30.050 | 31.785 | 1.00 | 25.52 |
| ATOM | 103 | CG2 | VAL | 45 | 7.959 | 31.843 | 30.499 | 1.00 | 24.38 |
| ATOM | 104 | C | VAL | 45 | 10.667 | 33.037 | 29.735 | 1.00 | 27.93 |
| ATOM | 105 | O | VAL | 45 | 11.044 | 33.879 | 30.545 | 1.00 | 27.97 |
| ATOM | 106 | N | LYS | 46 | 10.453 | 33.285 | 28.438 | 1.00 | 27.94 |
| ATOM | 107 | CA | LYS | 46 | 10.531 | 34.598 | 27.837 | 1.00 | 28.72 |
| ATOM | 108 | CB | LYS | 46 | 11.491 | 34.625 | 26.662 | 1.00 | 28.72 |
| ATOM | 109 | CG | LYS | 46 | 12.224 | 35.959 | 26.689 | 1.00 | 31.74 |
| ATOM | 110 | CD | LYS | 46 | 12.314 | 36.760 | 25.416 | 1.00 | 29.01 |
| ATOM | 111 | CE | LYS | 46 | 13.376 | 36.246 | 24.485 | 1.00 | 34.07 |
| ATOM | 112 | NZ | LYS | 46 | 12.807 | 35.101 | 23.697 | 1.00 | 35.61 |
| ATOM | 113 | C | LYS | 46 | 9.171 | 35.191 | 27.417 | 1.00 | 29.00 |
| ATOM | 114 | O | LYS | 46 | 8.353 | 34.518 | 26.764 | 1.00 | 27.85 |
| ATOM | 115 | N | PHE | 47 | 8.933 | 36.433 | 27.858 | 1.00 | 28.08 |
| ATOM | 116 | CA | PHE | 47 | 7.786 | 37.200 | 27.463 | 1.00 | 28.15 |
| ATOM | 117 | CB | PHE | 47 | 7.108 | 37.820 | 28.682 | 1.00 | 28.54 |
| ATOM | 118 | CG | PHE | 47 | 6.344 | 36.827 | 29.507 | 1.00 | 30.57 |
| ATOM | 119 | CD1 | PHE | 47 | 6.833 | 36.400 | 30.730 | 1.00 | 29.34 |
| ATOM | 120 | CE1 | PHE | 47 | 6.152 | 35.470 | 31.449 | 1.00 | 30.06 |
| ATOM | 121 | CZ | PHE | 47 | 4.997 | 34.956 | 30.967 | 1.00 | 29.14 |
| ATOM | 122 | CE2 | PHE | 47 | 4.514 | 35.351 | 29.762 | 1.00 | 34.66 |
| ATOM | 123 | CD2 | PHE | 47 | 5.181 | 36.270 | 29.031 | 1.00 | 31.25 |
| ATOM | 124 | C | PHE | 47 | 8.248 | 38.338 | 26.541 | 1.00 | 27.47 |
| ATOM | 125 | O | PHE | 47 | 9.012 | 39.173 | 26.960 | 1.00 | 26.08 |
| ATOM | 126 | N | ASN | 48 | 7.822 | 38.309 | 25.283 | 1.00 | 26.85 |
| ATOM | 127 | CA | ASN | 48 | 7.988 | 39.465 | 24.364 | 1.00 | 26.60 |
| ATOM | 128 | CB | ASN | 48 | 8.156 | 38.961 | 22.934 | 1.00 | 25.19 |
| ATOM | 129 | CG | ASN | 48 | 9.282 | 37.912 | 22.807 | 1.00 | 26.61 |
| ATOM | 130 | OD1 | ASN | 48 | 10.459 | 38.211 | 23.018 | 1.00 | 25.77 |
| ATOM | 131 | ND2 | ASN | 48 | 8.910 | 36.693 | 22.456 | 1.00 | 23.18 |
| ATOM | 132 | C | ASN | 48 | 6.761 | 40.377 | 24.421 | 1.00 | 26.17 |
| ATOM | 133 | O | ASN | 48 | 5.644 | 39.930 | 24.193 | 1.00 | 24.72 |
| ATOM | 134 | N | CYS | 49 | 6.993 | 41.642 | 24.725 | 1.00 | 28.49 |
| ATOM | 135 | CA | CYS | 49 | 5.933 | 42.614 | 25.032 | 1.00 | 30.12 |
| ATOM | 136 | CB | CYS | 49 | 5.926 | 42.920 | 26.545 | 1.00 | 30.40 |
| ATOM | 137 | SG | CYS | 49 | 6.104 | 41.440 | 27.648 | 1.00 | 32.24 |
| ATOM | 138 | C | CYS | 49 | 6.185 | 43.923 | 24.237 | 1.00 | 31.25 |
| ATOM | 139 | O | CYS | 49 | 6.664 | 44.930 | 24.816 | 1.00 | 30.05 |

TABLE 1-continued

| | | | | | | | | | |
|---|---|---|---|---|---|---|---|---|---|
| ATOM | 140 | N | ILE | 69 | 10.937 | 40.191 | 28.913 | 1.00 | 31.19 |
| ATOM | 141 | CA | ILE | 69 | 11.117 | 39.636 | 30.262 | 1.00 | 31.82 |
| ATOM | 142 | CB | ILE | 69 | 9.858 | 39.799 | 31.042 | 1.00 | 32.03 |
| ATOM | 143 | CG1 | ILE | 69 | 9.503 | 41.302 | 31.104 | 1.00 | 33.21 |
| ATOM | 144 | CD1 | ILE | 69 | 8.117 | 41.583 | 31.677 | 1.00 | 35.10 |
| ATOM | 145 | CG2 | ILE | 69 | 9.993 | 39.168 | 32.464 | 1.00 | 31.60 |
| ATOM | 146 | C | ILE | 69 | 11.509 | 38.158 | 30.194 | 1.00 | 31.32 |
| ATOM | 147 | O | ILE | 69 | 10.769 | 37.358 | 29.666 | 1.00 | 30.99 |
| ATOM | 148 | N | SER | 70 | 12.714 | 37.836 | 30.669 | 1.00 | 31.90 |
| ATOM | 149 | CA | SER | 70 | 13.176 | 36.451 | 30.783 | 1.00 | 32.15 |
| ATOM | 150 | CB | SER | 70 | 14.450 | 36.235 | 30.014 | 1.00 | 32.21 |
| ATOM | 151 | OG | SER | 70 | 14.262 | 36.495 | 28.667 | 1.00 | 34.21 |
| ATOM | 152 | C | SER | 70 | 13.407 | 36.083 | 32.251 | 1.00 | 31.87 |
| ATOM | 153 | O | SER | 70 | 14.051 | 36.818 | 33.012 | 1.00 | 32.36 |
| ATOM | 154 | N | TYR | 71 | 12.852 | 34.956 | 32.653 | 1.00 | 30.91 |
| ATOM | 155 | CA | TYR | 71 | 13.082 | 34.472 | 33.996 | 1.00 | 29.16 |
| ATOM | 156 | CB | TYR | 71 | 12.015 | 35.036 | 34.948 | 1.00 | 29.12 |
| ATOM | 157 | CG | TYR | 71 | 10.713 | 34.297 | 34.963 | 1.00 | 28.53 |
| ATOM | 158 | CD1 | TYR | 71 | 9.760 | 34.505 | 33.960 | 1.00 | 27.08 |
| ATOM | 159 | CE1 | TYR | 71 | 8.534 | 33.842 | 33.954 | 1.00 | 23.64 |
| ATOM | 160 | CZ | TYR | 71 | 8.216 | 32.957 | 34.984 | 1.00 | 28.61 |
| ATOM | 161 | OH | TYR | 71 | 6.975 | 32.313 | 34.979 | 1.00 | 28.75 |
| ATOM | 162 | CE2 | TYR | 71 | 9.151 | 32.706 | 36.002 | 1.00 | 23.24 |
| ATOM | 163 | CD2 | TYR | 71 | 10.395 | 33.415 | 36.004 | 1.00 | 29.21 |
| ATOM | 164 | C | TYR | 71 | 13.186 | 32.936 | 34.108 | 1.00 | 27.67 |
| ATOM | 165 | O | TYR | 71 | 12.777 | 32.190 | 33.192 | 1.00 | 26.91 |
| ATOM | 166 | N | ILE | 72 | 13.796 | 32.484 | 35.210 | 1.00 | 25.56 |
| ATOM | 167 | CA | ILE | 72 | 13.910 | 31.045 | 35.538 | 1.00 | 23.78 |
| ATOM | 168 | CB | ILE | 72 | 15.392 | 30.629 | 35.872 | 1.00 | 24.49 |
| ATOM | 169 | CG1 | ILE | 72 | 16.279 | 30.747 | 34.635 | 1.00 | 22.18 |
| ATOM | 170 | CD1 | ILE | 72 | 17.850 | 30.458 | 34.891 | 1.00 | 20.61 |
| ATOM | 171 | CG2 | ILE | 72 | 15.473 | 29.204 | 36.377 | 1.00 | 23.63 |
| ATOM | 172 | C | ILE | 72 | 12.986 | 30.897 | 36.747 | 1.00 | 24.26 |
| ATOM | 173 | O | ILE | 72 | 13.266 | 31.475 | 37.751 | 1.00 | 23.51 |
| ATOM | 174 | N | PRO | 73 | 11.840 | 30.167 | 36.630 | 1.00 | 24.87 |
| ATOM | 175 | CA | PRO | 73 | 11.006 | 30.155 | 37.795 | 1.00 | 25.95 |
| ATOM | 176 | CB | PRO | 73 | 9.641 | 29.564 | 37.274 | 1.00 | 25.51 |
| ATOM | 177 | CG | PRO | 73 | 10.020 | 28.737 | 36.191 | 1.00 | 26.57 |
| ATOM | 178 | CD | PRO | 73 | 11.263 | 29.349 | 35.555 | 1.00 | 24.60 |
| ATOM | 179 | C | PRO | 73 | 11.597 | 29.287 | 38.930 | 1.00 | 26.15 |
| ATOM | 180 | O | PRO | 73 | 12.455 | 28.396 | 38.701 | 1.00 | 24.83 |
| ATOM | 181 | N | ASP | 74 | 11.166 | 29.607 | 40.149 | 1.00 | 26.86 |
| ATOM | 182 | CA | ASP | 74 | 11.410 | 28.706 | 41.275 | 1.00 | 27.78 |
| ATOM | 183 | CB | ASP | 74 | 11.758 | 29.488 | 42.509 | 1.00 | 28.25 |
| ATOM | 184 | CG | ASP | 74 | 12.170 | 28.584 | 43.698 | 1.00 | 34.79 |
| ATOM | 185 | OD1 | ASP | 74 | 12.212 | 29.156 | 44.825 | 1.00 | 37.76 |
| ATOM | 186 | OD2 | ASP | 74 | 12.487 | 27.352 | 43.496 | 1.00 | 33.40 |
| ATOM | 187 | C | ASP | 74 | 10.133 | 27.931 | 41.422 | 1.00 | 27.61 |
| ATOM | 188 | O | ASP | 74 | 9.947 | 26.952 | 40.713 | 1.00 | 29.70 |
| ATOM | 189 | N | GLU | 75 | 9.204 | 28.403 | 42.238 | 1.00 | 28.13 |
| ATOM | 190 | CA | GLU | 75 | 7.942 | 27.648 | 42.484 | 1.00 | 30.82 |
| ATOM | 191 | CB | GLU | 75 | 7.693 | 27.432 | 44.027 | 1.00 | 28.43 |
| ATOM | 192 | CG | GLU | 75 | 8.660 | 26.502 | 44.698 | 1.00 | 31.56 |
| ATOM | 193 | CD | GLU | 75 | 8.896 | 26.790 | 46.223 | 1.00 | 34.21 |
| ATOM | 194 | OE1 | GLU | 75 | 8.406 | 27.823 | 46.753 | 1.00 | 39.16 |
| ATOM | 195 | OE2 | GLU | 75 | 9.604 | 25.991 | 46.894 | 1.00 | 38.20 |
| ATOM | 196 | C | GLU | 75 | 6.659 | 28.278 | 41.884 | 1.00 | 30.56 |
| ATOM | 197 | O | GLU | 75 | 5.633 | 27.640 | 41.902 | 1.00 | 30.04 |
| ATOM | 198 | N | LYS | 76 | 6.732 | 29.524 | 41.391 | 1.00 | 31.29 |
| ATOM | 199 | CA | LYS | 76 | 5.553 | 30.268 | 40.899 | 1.00 | 32.20 |
| ATOM | 200 | CB | LYS | 76 | 5.136 | 31.341 | 41.899 | 1.00 | 30.64 |
| ATOM | 201 | CG | LYS | 76 | 4.872 | 30.780 | 43.277 | 1.00 | 35.37 |
| ATOM | 202 | CD | LYS | 76 | 4.285 | 31.801 | 44.293 | 1.00 | 34.43 |
| ATOM | 203 | CE | LYS | 76 | 5.374 | 32.742 | 44.717 | 1.00 | 41.16 |
| ATOM | 204 | NZ | LYS | 76 | 4.883 | 33.766 | 45.690 | 1.00 | 40.80 |
| ATOM | 205 | C | LYS | 76 | 5.820 | 30.888 | 39.506 | 1.00 | 30.94 |
| ATOM | 206 | O | LYS | 76 | 6.959 | 31.234 | 39.183 | 1.00 | 30.29 |
| ATOM | 207 | N | MET | 77 | 4.771 | 30.965 | 38.686 | 1.00 | 31.18 |
| ATOM | 208 | CA | MET | 77 | 4.877 | 31.393 | 37.279 | 1.00 | 31.12 |
| ATOM | 209 | CB | MET | 77 | 4.453 | 30.276 | 36.354 | 1.00 | 31.49 |
| ATOM | 210 | CG | MET | 77 | 4.778 | 28.863 | 36.716 | 1.00 | 33.87 |
| ATOM | 211 | SD | MET | 77 | 6.325 | 28.385 | 36.007 | 1.00 | 39.96 |
| ATOM | 212 | CE | MET | 77 | 6.131 | 28.685 | 34.257 | 1.00 | 33.38 |
| ATOM | 213 | C | MET | 77 | 3.892 | 32.511 | 37.072 | 1.00 | 30.39 |
| ATOM | 214 | O | MET | 77 | 2.770 | 32.366 | 37.491 | 1.00 | 30.57 |
| ATOM | 215 | N | VAL | 78 | 4.282 | 33.624 | 36.450 | 1.00 | 31.28 |
| ATOM | 216 | CA | VAL | 78 | 3.331 | 34.699 | 36.115 | 1.00 | 30.77 |
| ATOM | 217 | CB | VAL | 78 | 4.029 | 36.003 | 35.753 | 1.00 | 31.61 |
| ATOM | 218 | CG1 | VAL | 78 | 4.974 | 35.840 | 34.617 | 1.00 | 31.77 |
| ATOM | 219 | CG2 | VAL | 78 | 2.992 | 37.155 | 35.449 | 1.00 | 32.13 |

TABLE 1-continued

| | | | | | | | | |
|---|---|---|---|---|---|---|---|---|
| ATOM | 220 | C | VAL | 78 | 2.409 | 34.242 | 34.985 | 1.00 | 31.34 |
| ATOM | 221 | O | VAL | 78 | 2.855 | 33.629 | 34.019 | 1.00 | 31.93 |
| ATOM | 222 | N | GLU | 79 | 1.118 | 34.478 | 35.161 | 1.00 | 31.85 |
| ATOM | 223 | CA | GLU | 79 | 0.098 | 34.217 | 34.162 | 1.00 | 32.97 |
| ATOM | 224 | CB | GLU | 79 | −1.251 | 34.040 | 34.881 | 1.00 | 33.09 |
| ATOM | 225 | CG | GLU | 79 | −2.371 | 33.400 | 34.069 | 1.00 | 36.28 |
| ATOM | 226 | CD | GLU | 79 | −3.084 | 34.418 | 33.138 | 1.00 | 42.29 |
| ATOM | 227 | OE1 | GLU | 79 | −3.536 | 35.492 | 33.639 | 1.00 | 43.14 |
| ATOM | 228 | OE2 | GLU | 79 | −3.190 | 34.139 | 31.903 | 1.00 | 42.65 |
| ATOM | 229 | C | GLU | 79 | 0.082 | 35.426 | 33.168 | 1.00 | 33.16 |
| ATOM | 230 | O | GLU | 79 | 0.010 | 36.580 | 33.568 | 1.00 | 33.58 |
| ATOM | 231 | N | SER | 80 | 0.239 | 35.109 | 31.883 | 1.00 | 33.78 |
| ATOM | 232 | CA | SER | 80 | 0.282 | 36.004 | 30.721 | 1.00 | 34.02 |
| ATOM | 233 | CB | SER | 80 | 0.115 | 35.128 | 29.464 | 1.00 | 35.89 |
| ATOM | 234 | OG | SER | 80 | 0.695 | 35.707 | 28.309 | 1.00 | 38.47 |
| ATOM | 235 | C | SER | 80 | −0.753 | 37.118 | 30.680 | 1.00 | 34.03 |
| ATOM | 236 | O | SER | 80 | −0.396 | 38.294 | 30.496 | 1.00 | 34.32 |
| ATOM | 237 | N | LYS | 81 | −2.030 | 36.774 | 30.832 | 1.00 | 33.56 |
| ATOM | 238 | CA | LYS | 81 | −3.088 | 37.772 | 30.829 | 1.00 | 34.79 |
| ATOM | 239 | CB | LYS | 81 | −4.470 | 37.127 | 30.963 | 1.00 | 35.88 |
| ATOM | 240 | CG | LYS | 81 | −5.628 | 38.117 | 30.655 | 1.00 | 39.71 |
| ATOM | 241 | CD | LYS | 81 | −6.995 | 37.453 | 30.763 | 1.00 | 38.34 |
| ATOM | 242 | CE | LYS | 81 | −7.950 | 38.381 | 31.571 | 1.00 | 47.73 |
| ATOM | 243 | NZ | LYS | 81 | −9.272 | 37.719 | 32.040 | 1.00 | 47.03 |
| ATOM | 244 | C | LYS | 81 | −2.938 | 38.801 | 31.939 | 1.00 | 34.02 |
| ATOM | 245 | O | LYS | 81 | −3.196 | 39.999 | 31.688 | 1.00 | 33.61 |
| ATOM | 246 | N | SER | 82 | −2.562 | 38.356 | 33.165 | 1.00 | 31.13 |
| ATOM | 247 | CA | SER | 82 | −2.343 | 39.317 | 34.235 | 1.00 | 29.46 |
| ATOM | 248 | CB | SER | 82 | −2.158 | 38.596 | 35.611 | 1.00 | 30.51 |
| ATOM | 249 | OG | SER | 82 | −0.899 | 37.939 | 35.750 | 1.00 | 25.05 |
| ATOM | 250 | C | SER | 82 | −1.182 | 40.242 | 33.906 | 1.00 | 28.45 |
| ATOM | 251 | O | SER | 82 | −1.176 | 41.409 | 34.279 | 1.00 | 28.02 |
| ATOM | 252 | N | LEU | 83 | −0.185 | 39.720 | 33.203 | 1.00 | 28.58 |
| ATOM | 253 | CA | LEU | 83 | 0.981 | 40.513 | 32.860 | 1.00 | 28.75 |
| ATOM | 254 | CB | LEU | 83 | 2.080 | 39.587 | 32.304 | 1.00 | 28.91 |
| ATOM | 255 | CG | LEU | 83 | 3.297 | 40.342 | 31.753 | 1.00 | 28.13 |
| ATOM | 256 | CD1 | LEU | 83 | 3.924 | 41.269 | 32.851 | 1.00 | 22.93 |
| ATOM | 257 | CD2 | LEU | 83 | 4.298 | 39.411 | 31.209 | 1.00 | 25.01 |
| ATOM | 258 | C | LEU | 83 | 0.614 | 41.627 | 31.827 | 1.00 | 29.90 |
| ATOM | 259 | O | LEU | 83 | 1.102 | 42.787 | 31.915 | 1.00 | 29.32 |
| ATOM | 260 | N | LYS | 84 | −0.273 | 41.269 | 30.884 | 1.00 | 30.73 |
| ATOM | 261 | CA | LYS | 84 | −0.836 | 42.194 | 29.881 | 1.00 | 31.05 |
| ATOM | 262 | CB | LYS | 84 | −1.823 | 41.456 | 28.973 | 1.00 | 31.72 |
| ATOM | 263 | CG | LYS | 84 | −2.601 | 42.363 | 27.983 | 1.00 | 33.82 |
| ATOM | 264 | CD | LYS | 84 | −3.687 | 41.588 | 27.240 | 1.00 | 33.38 |
| ATOM | 265 | CE | LYS | 84 | −4.966 | 41.607 | 28.021 | 1.00 | 37.80 |
| ATOM | 266 | NZ | LYS | 84 | −5.931 | 40.584 | 27.461 | 1.00 | 41.84 |
| ATOM | 267 | C | LYS | 84 | −1.571 | 43.273 | 30.624 | 1.00 | 30.38 |
| ATOM | 268 | O | LYS | 84 | −1.266 | 44.427 | 30.473 | 1.00 | 29.79 |
| ATOM | 269 | N | LEU | 85 | −2.506 | 42.894 | 31.494 | 1.00 | 31.88 |
| ATOM | 270 | CA | LEU | 85 | −3.211 | 43.909 | 32.292 | 1.00 | 31.86 |
| ATOM | 271 | CB | LEU | 85 | −4.270 | 43.267 | 33.162 | 1.00 | 32.09 |
| ATOM | 272 | CG | LEU | 85 | −5.308 | 42.558 | 32.300 | 1.00 | 34.28 |
| ATOM | 273 | CD1 | LEU | 85 | −6.144 | 41.582 | 33.135 | 1.00 | 32.52 |
| ATOM | 274 | CD2 | LEU | 85 | −6.190 | 43.570 | 31.451 | 1.00 | 31.60 |
| ATOM | 275 | C | LEU | 85 | −2.273 | 44.772 | 33.129 | 1.00 | 32.05 |
| ATOM | 276 | O | LEU | 85 | −2.472 | 45.980 | 33.231 | 1.00 | 33.60 |
| ATOM | 277 | N | MET | 112 | 6.623 | 36.321 | 42.204 | 1.00 | 33.69 |
| ATOM | 278 | CA | MET | 112 | 7.070 | 35.004 | 41.818 | 1.00 | 35.66 |
| ATOM | 279 | CB | MET | 112 | 7.543 | 35.019 | 40.364 | 1.00 | 34.45 |
| ATOM | 280 | CG | MET | 112 | 6.443 | 35.029 | 39.377 | 1.00 | 38.18 |
| ATOM | 281 | SD | MET | 112 | 7.321 | 35.437 | 37.877 | 1.00 | 41.03 |
| ATOM | 282 | CE | MET | 112 | 7.572 | 33.786 | 37.335 | 1.00 | 44.67 |
| ATOM | 283 | C | MET | 112 | 8.243 | 34.444 | 42.612 | 1.00 | 34.33 |
| ATOM | 284 | O | MET | 112 | 8.597 | 33.263 | 42.454 | 1.00 | 34.83 |
| ATOM | 285 | N | ASP | 113 | 8.926 | 35.297 | 43.343 | 1.00 | 34.05 |
| ATOM | 286 | CA | ASP | 113 | 10.176 | 34.892 | 43.996 | 1.00 | 34.38 |
| ATOM | 287 | CB | ASP | 113 | 9.824 | 34.182 | 45.300 | 1.00 | 35.18 |
| ATOM | 288 | CG | ASP | 113 | 11.009 | 34.028 | 46.226 | 1.00 | 39.45 |
| ATOM | 289 | OD1 | ASP | 113 | 12.141 | 34.518 | 45.930 | 1.00 | 40.40 |
| ATOM | 290 | OD2 | ASP | 113 | 10.777 | 33.385 | 47.258 | 1.00 | 44.42 |
| ATOM | 291 | C | ASP | 113 | 10.991 | 33.959 | 43.083 | 1.00 | 33.52 |
| ATOM | 292 | O | ASP | 113 | 11.169 | 32.791 | 43.408 | 1.00 | 32.76 |
| ATOM | 293 | N | PRO | 114 | 11.470 | 34.466 | 41.920 | 1.00 | 32.30 |
| ATOM | 294 | CA | PRO | 114 | 12.074 | 33.582 | 40.907 | 1.00 | 31.33 |
| ATOM | 295 | CB | PRO | 114 | 12.038 | 34.450 | 39.640 | 1.00 | 30.10 |
| ATOM | 296 | CG | PRO | 114 | 12.213 | 35.847 | 40.188 | 1.00 | 31.53 |
| ATOM | 297 | CD | PRO | 114 | 11.486 | 35.879 | 41.501 | 1.00 | 31.75 |
| ATOM | 298 | C | PRO | 114 | 13.527 | 33.269 | 41.255 | 1.00 | 30.89 |
| ATOM | 299 | O | PRO | 114 | 14.128 | 33.985 | 42.083 | 1.00 | 32.21 |

TABLE 1-continued

| | | | | | | | | | |
|---|---|---|---|---|---|---|---|---|---|
| ATOM | 300 | N | ARG | 115 | 14.108 | 32.250 | 40.629 | 1.00 | 29.64 |
| ATOM | 301 | CA | ARG | 115 | 15.555 | 32.042 | 40.728 | 1.00 | 28.62 |
| ATOM | 302 | CB | ARG | 115 | 15.965 | 30.708 | 40.062 | 1.00 | 27.29 |
| ATOM | 303 | CG | ARG | 115 | 15.531 | 29.487 | 40.922 | 1.00 | 27.32 |
| ATOM | 304 | CD | ARG | 115 | 15.732 | 28.068 | 40.327 | 1.00 | 28.55 |
| ATOM | 305 | NE | ARG | 115 | 14.748 | 27.208 | 41.014 | 1.00 | 29.15 |
| ATOM | 306 | CZ | ARG | 115 | 14.217 | 26.065 | 40.573 | 1.00 | 30.02 |
| ATOM | 307 | NH1 | ARG | 115 | 14.537 | 25.533 | 39.412 | 1.00 | 29.70 |
| ATOM | 308 | NH2 | ARG | 115 | 13.337 | 25.449 | 41.328 | 1.00 | 31.72 |
| ATOM | 309 | C | ARG | 115 | 16.350 | 33.186 | 40.115 | 1.00 | 30.01 |
| ATOM | 310 | O | ARG | 115 | 17.391 | 33.579 | 40.636 | 1.00 | 29.45 |
| ATOM | 311 | O6 | MOL | 1 | 0.515 | 29.222 | 28.162 | 1.00 | 43.84 |
| ATOM | 312 | C6 | MOL | 1 | 0.419 | 30.194 | 29.119 | 1.00 | 45.00 |
| ATOM | 313 | N1 | MOL | 1 | 1.449 | 30.560 | 29.944 | 1.00 | 44.21 |
| ATOM | 314 | C5 | MOL | 1 | −0.807 | 30.859 | 29.254 | 1.00 | 45.89 |
| ATOM | 315 | C7 | MOL | 1 | −2.054 | 30.809 | 28.651 | 1.00 | 46.72 |
| ATOM | 316 | C77 | MOL | 1 | −2.336 | 29.940 | 27.667 | 1.00 | 46.41 |
| ATOM | 317 | N77 | MOL | 1 | −2.584 | 29.093 | 26.837 | 1.00 | 49.81 |
| ATOM | 318 | C8 | MOL | 1 | −2.963 | 31.704 | 29.207 | 1.00 | 45.82 |
| ATOM | 319 | N9 | MOL | 1 | −2.231 | 32.333 | 30.182 | 1.00 | 46.97 |
| ATOM | 320 | C4 | MOL | 1 | −0.955 | 31.832 | 30.219 | 1.00 | 45.63 |
| ATOM | 321 | N3 | MOL | 1 | 0.091 | 32.208 | 31.007 | 1.00 | 43.30 |
| ATOM | 322 | C2 | MOL | 1 | 1.268 | 31.561 | 30.861 | 1.00 | 44.23 |
| ATOM | 323 | N2 | MOL | 1 | 2.283 | 31.921 | 31.666 | 1.00 | 46.22 |
| ATOM | 324 | N | LYS | 46 | 18.626 | 18.344 | 15.095 | 1.00 | 28.21 |
| ATOM | 325 | CA | LYS | 46 | 17.560 | 19.364 | 15.343 | 1.00 | 27.33 |
| ATOM | 326 | CB | LYS | 46 | 18.039 | 20.788 | 15.009 | 1.00 | 26.71 |
| ATOM | 327 | CG | LYS | 46 | 16.993 | 21.890 | 15.301 | 1.00 | 28.68 |
| ATOM | 328 | CD | LYS | 46 | 17.108 | 23.041 | 14.364 | 1.00 | 29.59 |
| ATOM | 329 | CE | LYS | 46 | 18.101 | 24.025 | 14.801 | 1.00 | 35.72 |
| ATOM | 330 | NZ | LYS | 46 | 18.767 | 24.737 | 13.550 | 1.00 | 33.53 |
| ATOM | 331 | C | LYS | 46 | 16.302 | 19.057 | 14.565 | 1.00 | 26.64 |
| ATOM | 332 | O | LYS | 46 | 16.376 | 18.817 | 13.399 | 1.00 | 26.42 |
| ATOM | 333 | N | PHE | 47 | 15.146 | 19.105 | 15.209 | 1.00 | 27.04 |
| ATOM | 334 | CA | PHE | 47 | 13.869 | 19.117 | 14.514 | 1.00 | 26.96 |
| ATOM | 335 | CB | PHE | 47 | 12.895 | 18.179 | 15.158 | 1.00 | 27.29 |
| ATOM | 336 | CG | PHE | 47 | 13.386 | 16.819 | 15.167 | 1.00 | 32.14 |
| ATOM | 337 | CD1 | PHE | 47 | 14.281 | 16.400 | 16.147 | 1.00 | 32.34 |
| ATOM | 338 | CE1 | PHE | 47 | 14.802 | 15.100 | 16.093 | 1.00 | 34.46 |
| ATOM | 339 | CZ | PHE | 47 | 14.418 | 14.230 | 15.091 | 1.00 | 33.35 |
| ATOM | 340 | CE2 | PHE | 47 | 13.527 | 14.630 | 14.125 | 1.00 | 35.35 |
| ATOM | 341 | CD2 | PHE | 47 | 13.022 | 15.934 | 14.155 | 1.00 | 35.90 |
| ATOM | 342 | C | PHE | 47 | 13.298 | 20.518 | 14.521 | 1.00 | 26.50 |
| ATOM | 343 | O | PHE | 47 | 13.175 | 21.143 | 15.586 | 1.00 | 25.24 |
| ATOM | 344 | N | ASN | 48 | 12.925 | 20.988 | 13.326 | 1.00 | 26.57 |
| ATOM | 345 | CA | ASN | 48 | 12.216 | 22.271 | 13.191 | 1.00 | 26.60 |
| ATOM | 346 | CB | ASN | 48 | 12.729 | 23.062 | 11.972 | 1.00 | 26.14 |
| ATOM | 347 | CG | ASN | 48 | 14.185 | 23.276 | 12.012 | 1.00 | 23.57 |
| ATOM | 348 | OD1 | ASN | 48 | 14.689 | 23.874 | 12.944 | 1.00 | 28.74 |
| ATOM | 349 | ND2 | ASN | 48 | 14.898 | 22.780 | 11.025 | 1.00 | 24.59 |
| ATOM | 350 | C | ASN | 48 | 10.759 | 21.965 | 13.071 | 1.00 | 26.71 |
| ATOM | 351 | O | ASN | 48 | 10.367 | 21.265 | 12.153 | 1.00 | 26.51 |
| ATOM | 352 | N | CYS | 49 | 9.937 | 22.501 | 13.980 | 1.00 | 27.64 |
| ATOM | 353 | CA | CYS | 49 | 8.530 | 22.095 | 14.036 | 1.00 | 28.17 |
| ATOM | 354 | CB | CYS | 49 | 8.263 | 21.281 | 15.311 | 1.00 | 28.79 |
| ATOM | 355 | SG | CYS | 49 | 9.439 | 19.944 | 15.608 | 1.00 | 32.41 |
| ATOM | 356 | C | CYS | 49 | 7.620 | 23.317 | 14.012 | 1.00 | 28.06 |
| ATOM | 357 | O | CYS | 49 | 7.183 | 23.740 | 15.046 | 1.00 | 26.43 |
| ATOM | 358 | N | PRO | 50 | 7.371 | 23.909 | 12.810 | 1.00 | 28.99 |
| ATOM | 359 | CA | PRO | 50 | 6.627 | 25.176 | 12.676 | 1.00 | 29.58 |
| ATOM | 360 | CB | PRO | 50 | 7.035 | 25.698 | 11.271 | 1.00 | 29.17 |
| ATOM | 361 | CG | PRO | 50 | 7.856 | 24.653 | 10.687 | 1.00 | 29.81 |
| ATOM | 362 | CD | PRO | 50 | 7.877 | 23.434 | 11.507 | 1.00 | 28.43 |
| ATOM | 363 | C | PRO | 50 | 5.129 | 25.037 | 12.734 | 1.00 | 29.99 |
| ATOM | 364 | O | PRO | 50 | 4.437 | 26.042 | 12.772 | 1.00 | 31.25 |
| ATOM | 365 | N | GLU | 51 | 4.638 | 23.818 | 12.762 | 1.00 | 30.28 |
| ATOM | 366 | CA | GLU | 51 | 3.222 | 23.566 | 12.687 | 1.00 | 31.01 |
| ATOM | 367 | CB | GLU | 51 | 2.970 | 22.532 | 11.618 | 1.00 | 31.20 |
| ATOM | 368 | CG | GLU | 51 | 3.336 | 23.048 | 10.233 | 1.00 | 31.72 |
| ATOM | 369 | CD | GLU | 51 | 3.202 | 21.987 | 9.152 | 1.00 | 39.70 |
| ATOM | 370 | OE1 | GLU | 51 | 2.737 | 20.845 | 9.483 | 1.00 | 41.03 |
| ATOM | 371 | OE2 | GLU | 51 | 3.580 | 22.291 | 7.977 | 1.00 | 39.79 |
| ATOM | 372 | C | GLU | 51 | 2.573 | 23.169 | 13.992 | 1.00 | 30.89 |
| ATOM | 373 | O | GLU | 51 | 1.545 | 22.525 | 14.014 | 1.00 | 32.20 |
| ATOM | 374 | N | PHE | 52 | 3.147 | 23.583 | 15.105 | 1.00 | 30.63 |
| ATOM | 375 | CA | PHE | 52 | 2.616 | 23.108 | 16.364 | 1.00 | 29.27 |
| ATOM | 376 | CB | PHE | 52 | 3.717 | 23.089 | 17.437 | 1.00 | 29.89 |
| ATOM | 377 | CG | PHE | 52 | 3.203 | 22.709 | 18.814 | 1.00 | 28.40 |
| ATOM | 378 | CD1 | PHE | 52 | 3.178 | 21.381 | 19.225 | 1.00 | 28.58 |
| ATOM | 379 | CE1 | PHE | 52 | 2.699 | 21.019 | 20.491 | 1.00 | 24.69 |

TABLE 1-continued

| | | | | | | | | | |
|---|---|---|---|---|---|---|---|---|---|
| ATOM | 380 | CZ | PHE | 52 | 2.256 | 21.980 | 21.332 | 1.00 | 27.97 |
| ATOM | 381 | CE2 | PHE | 52 | 2.247 | 23.333 | 20.921 | 1.00 | 29.23 |
| ATOM | 382 | CD2 | PHE | 52 | 2.732 | 23.678 | 19.678 | 1.00 | 26.27 |
| ATOM | 383 | C | PHE | 52 | 1.456 | 23.981 | 16.807 | 1.00 | 29.10 |
| ATOM | 384 | O | PHE | 52 | 1.533 | 25.206 | 16.718 | 1.00 | 28.69 |
| ATOM | 385 | N | THR | 53 | 0.382 | 23.317 | 17.264 | 1.00 | 29.45 |
| ATOM | 386 | CA | THR | 53 | −0.793 | 23.959 | 17.845 | 1.00 | 29.09 |
| ATOM | 387 | CB | THR | 53 | −1.860 | 24.254 | 16.767 | 1.00 | 28.45 |
| ATOM | 388 | OG1 | THR | 53 | −2.985 | 24.906 | 17.385 | 1.00 | 27.24 |
| ATOM | 389 | CG2 | THR | 53 | −2.277 | 22.976 | 16.080 | 1.00 | 25.51 |
| ATOM | 390 | C | THR | 53 | −1.395 | 23.108 | 18.990 | 1.00 | 30.39 |
| ATOM | 391 | O | THR | 53 | −1.329 | 21.888 | 18.964 | 1.00 | 29.67 |
| ATOM | 392 | N | SER | 54 | −2.012 | 23.788 | 19.960 | 1.00 | 31.83 |
| ATOM | 393 | CA | SER | 54 | −2.610 | 23.179 | 21.146 | 1.00 | 33.32 |
| ATOM | 394 | CB | SER | 54 | −1.544 | 22.902 | 22.229 | 1.00 | 33.47 |
| ATOM | 395 | OG | SER | 54 | −0.994 | 24.120 | 22.715 | 1.00 | 33.23 |
| ATOM | 396 | C | SER | 54 | −3.661 | 24.144 | 21.696 | 1.00 | 34.99 |
| ATOM | 397 | O | SER | 54 | −3.961 | 25.141 | 21.075 | 1.00 | 34.15 |
| ATOM | 398 | N | LEU | 55 | −4.208 | 23.855 | 22.875 | 1.00 | 38.17 |
| ATOM | 399 | CA | LEU | 55 | −5.315 | 24.640 | 23.414 | 1.00 | 40.67 |
| ATOM | 400 | CB | LEU | 55 | −6.559 | 23.778 | 23.595 | 1.00 | 40.34 |
| ATOM | 401 | CG | LEU | 55 | −7.119 | 23.063 | 22.367 | 1.00 | 37.91 |
| ATOM | 402 | CD1 | LEU | 55 | −8.373 | 22.345 | 22.800 | 1.00 | 37.30 |
| ATOM | 403 | CD2 | LEU | 55 | −7.432 | 24.012 | 21.230 | 1.00 | 39.20 |
| ATOM | 404 | C | LEU | 55 | −4.935 | 25.321 | 24.692 | 1.00 | 43.65 |
| ATOM | 405 | O | LEU | 55 | −4.064 | 24.834 | 25.425 | 1.00 | 44.27 |
| ATOM | 406 | N | CYS | 56 | −5.529 | 26.494 | 24.896 | 1.00 | 46.46 |
| ATOM | 407 | CA | CYS | 56 | −5.442 | 27.214 | 26.148 | 1.00 | 48.90 |
| ATOM | 408 | CB | CYS | 56 | −5.937 | 28.650 | 25.952 | 1.00 | 49.06 |
| ATOM | 409 | SG | CYS | 56 | −5.837 | 29.698 | 27.414 | 1.00 | 50.31 |
| ATOM | 410 | C | CYS | 56 | −6.286 | 26.463 | 27.205 | 1.00 | 50.34 |
| ATOM | 411 | O | CYS | 56 | −7.471 | 26.153 | 26.961 | 1.00 | 50.82 |
| ATOM | 412 | N | PRO | 57 | −5.677 | 26.132 | 28.362 | 1.00 | 51.54 |
| ATOM | 413 | CA | PRO | 57 | −6.344 | 25.179 | 29.267 | 1.00 | 52.63 |
| ATOM | 414 | CB | PRO | 57 | −5.274 | 24.902 | 30.330 | 1.00 | 52.63 |
| ATOM | 415 | CG | PRO | 57 | −4.377 | 26.143 | 30.303 | 1.00 | 51.98 |
| ATOM | 416 | CD | PRO | 57 | −4.366 | 26.585 | 28.879 | 1.00 | 50.82 |
| ATOM | 417 | C | PRO | 57 | −7.618 | 25.738 | 29.917 | 1.00 | 53.90 |
| ATOM | 418 | O | PRO | 57 | −8.503 | 24.962 | 30.324 | 1.00 | 54.88 |
| ATOM | 419 | N | LYS | 58 | −7.707 | 27.065 | 29.975 | 1.00 | 54.79 |
| ATOM | 420 | CA | LYS | 58 | −8.760 | 27.785 | 30.656 | 1.00 | 55.67 |
| ATOM | 421 | CB | LYS | 58 | −8.185 | 28.994 | 31.424 | 1.00 | 56.91 |
| ATOM | 422 | CG | LYS | 58 | −7.868 | 28.699 | 32.904 | 1.00 | 59.21 |
| ATOM | 423 | CD | LYS | 58 | −6.400 | 28.263 | 33.166 | 1.00 | 62.63 |
| ATOM | 424 | CE | LYS | 58 | −6.232 | 27.349 | 34.438 | 1.00 | 62.29 |
| ATOM | 425 | NZ | LYS | 58 | −6.393 | 25.849 | 34.167 | 1.00 | 63.69 |
| ATOM | 426 | C | LYS | 58 | −9.873 | 28.225 | 29.715 | 1.00 | 55.58 |
| ATOM | 427 | O | LYS | 58 | −11.048 | 28.018 | 30.032 | 1.00 | 56.09 |
| ATOM | 428 | N | VAL | 59 | −9.516 | 28.835 | 28.576 | 1.00 | 54.74 |
| ATOM | 429 | CA | VAL | 59 | −10.495 | 29.254 | 27.545 | 1.00 | 52.88 |
| ATOM | 430 | CB | VAL | 59 | −10.062 | 30.547 | 26.843 | 1.00 | 52.91 |
| ATOM | 431 | CG1 | VAL | 59 | −10.096 | 31.737 | 27.800 | 1.00 | 53.31 |
| ATOM | 432 | CG2 | VAL | 59 | −8.689 | 30.412 | 26.261 | 1.00 | 52.44 |
| ATOM | 433 | C | VAL | 59 | −10.794 | 28.197 | 26.455 | 1.00 | 52.24 |
| ATOM | 434 | O | VAL | 59 | −11.843 | 28.249 | 25.814 | 1.00 | 52.31 |
| ATOM | 435 | N | GLY | 60 | −9.883 | 27.253 | 26.220 | 1.00 | 50.54 |
| ATOM | 436 | CA | GLY | 60 | −10.030 | 26.353 | 25.061 | 1.00 | 48.58 |
| ATOM | 437 | C | GLY | 60 | −9.691 | 27.000 | 23.704 | 1.00 | 47.45 |
| ATOM | 438 | O | GLY | 60 | −9.919 | 26.371 | 22.641 | 1.00 | 46.89 |
| ATOM | 439 | N | GLN | 61 | −9.165 | 28.241 | 23.728 | 1.00 | 45.26 |
| ATOM | 440 | CA | GLN | 61 | −8.682 | 28.935 | 22.505 | 1.00 | 44.42 |
| ATOM | 441 | CB | GLN | 61 | −8.461 | 30.445 | 22.743 | 1.00 | 43.87 |
| ATOM | 442 | CG | GLN | 61 | −8.509 | 31.305 | 21.438 | 1.00 | 49.56 |
| ATOM | 443 | CD | GLN | 61 | −7.584 | 32.609 | 21.424 | 1.00 | 49.55 |
| ATOM | 444 | OE1 | GLN | 61 | −6.818 | 32.872 | 22.372 | 1.00 | 58.03 |
| ATOM | 445 | NE2 | GLN | 61 | −7.703 | 33.421 | 20.351 | 1.00 | 50.79 |
| ATOM | 446 | C | GLN | 61 | −7.391 | 28.259 | 21.985 | 1.00 | 40.55 |
| ATOM | 447 | O | GLN | 61 | −6.489 | 27.907 | 22.768 | 1.00 | 39.97 |
| ATOM | 448 | N | PRO | 62 | −7.330 | 28.002 | 20.667 | 1.00 | 37.57 |
| ATOM | 449 | CA | PRO | 62 | −6.092 | 27.504 | 20.049 | 1.00 | 34.50 |
| ATOM | 450 | CB | PRO | 62 | −6.479 | 27.258 | 18.597 | 1.00 | 34.78 |
| ATOM | 451 | CG | PRO | 62 | −7.804 | 27.949 | 18.411 | 1.00 | 35.70 |
| ATOM | 452 | CD | PRO | 62 | −8.458 | 28.063 | 19.728 | 1.00 | 36.57 |
| ATOM | 453 | C | PRO | 62 | −4.880 | 28.447 | 20.155 | 1.00 | 32.05 |
| ATOM | 454 | O | PRO | 62 | −5.026 | 29.633 | 20.185 | 1.00 | 29.71 |
| ATOM | 455 | N | ASP | 63 | −3.694 | 27.846 | 20.236 | 1.00 | 31.14 |
| ATOM | 456 | CA | ASP | 63 | −2.413 | 28.498 | 20.359 | 1.00 | 30.90 |
| ATOM | 457 | CB | ASP | 63 | −1.861 | 28.261 | 21.785 | 1.00 | 32.30 |
| ATOM | 458 | CG | ASP | 63 | −2.528 | 29.168 | 22.831 | 1.00 | 41.48 |
| ATOM | 459 | OD1 | ASP | 63 | −3.089 | 30.261 | 22.489 | 1.00 | 48.28 |

TABLE 1-continued

| | | | | | | | | |
|---|---|---|---|---|---|---|---|---|
| ATOM | 460 | OD2 | ASP | 63 | −2.502 | 28.800 | 24.033 | 1.00 | 51.27 |
| ATOM | 461 | C | ASP | 63 | −1.523 | 27.848 | 19.287 | 1.00 | 28.42 |
| ATOM | 462 | O | ASP | 63 | −1.793 | 26.708 | 18.885 | 1.00 | 27.04 |
| ATOM | 463 | N | PHE | 64 | −0.455 | 28.544 | 18.857 | 1.00 | 26.58 |
| ATOM | 464 | CA | PHE | 64 | 0.423 | 28.044 | 17.757 | 1.00 | 25.17 |
| ATOM | 465 | CB | PHE | 64 | 0.027 | 28.751 | 16.425 | 1.00 | 24.80 |
| ATOM | 466 | CG | PHE | 64 | −1.394 | 28.535 | 16.076 | 1.00 | 23.25 |
| ATOM | 467 | CD1 | PHE | 64 | −2.374 | 29.210 | 16.765 | 1.00 | 18.99 |
| ATOM | 468 | CE1 | PHE | 64 | −3.701 | 28.940 | 16.511 | 1.00 | 25.96 |
| ATOM | 469 | CZ | PHE | 64 | −4.049 | 28.022 | 15.551 | 1.00 | 22.65 |
| ATOM | 470 | CE2 | PHE | 64 | −3.061 | 27.321 | 14.900 | 1.00 | 25.11 |
| ATOM | 471 | CD2 | PHE | 64 | −1.748 | 27.577 | 15.155 | 1.00 | 17.63 |
| ATOM | 472 | C | PHE | 64 | 1.885 | 28.383 | 18.085 | 1.00 | 24.81 |
| ATOM | 473 | O | PHE | 64 | 2.139 | 29.397 | 18.671 | 1.00 | 24.53 |
| ATOM | 474 | N | ALA | 65 | 2.831 | 27.571 | 17.656 | 1.00 | 25.05 |
| ATOM | 475 | CA | ALA | 65 | 4.215 | 27.831 | 17.987 | 1.00 | 25.65 |
| ATOM | 476 | CB | ALA | 65 | 4.577 | 27.021 | 19.319 | 1.00 | 25.77 |
| ATOM | 477 | C | ALA | 65 | 5.089 | 27.297 | 16.912 | 1.00 | 24.74 |
| ATOM | 478 | O | ALA | 65 | 4.742 | 26.361 | 16.241 | 1.00 | 23.37 |
| ATOM | 479 | N | THR | 66 | 6.290 | 27.800 | 16.827 | 1.00 | 25.21 |
| ATOM | 480 | CA | THR | 66 | 7.311 | 26.965 | 16.212 | 1.00 | 26.25 |
| ATOM | 481 | CB | THR | 66 | 8.168 | 27.805 | 15.251 | 1.00 | 25.43 |
| ATOM | 482 | OG1 | THR | 66 | 7.324 | 28.233 | 14.174 | 1.00 | 27.57 |
| ATOM | 483 | CG2 | THR | 66 | 9.227 | 26.978 | 14.693 | 1.00 | 27.62 |
| ATOM | 484 | C | THR | 66 | 8.143 | 26.350 | 17.355 | 1.00 | 26.46 |
| ATOM | 485 | O | THR | 66 | 8.485 | 27.061 | 18.295 | 1.00 | 27.05 |
| ATOM | 486 | N | ILE | 67 | 8.450 | 25.060 | 17.283 | 1.00 | 26.09 |
| ATOM | 487 | CA | ILE | 67 | 9.262 | 24.400 | 18.320 | 1.00 | 25.88 |
| ATOM | 488 | CB | ILE | 67 | 8.491 | 23.211 | 18.964 | 1.00 | 27.19 |
| ATOM | 489 | CG1 | ILE | 67 | 7.221 | 23.695 | 19.674 | 1.00 | 26.17 |
| ATOM | 490 | CD1 | ILE | 67 | 6.369 | 22.525 | 19.940 | 1.00 | 28.34 |
| ATOM | 491 | CG2 | ILE | 67 | 9.313 | 22.553 | 20.046 | 1.00 | 27.68 |
| ATOM | 492 | C | ILE | 67 | 10.535 | 23.870 | 17.713 | 1.00 | 25.12 |
| ATOM | 493 | O | ILE | 67 | 10.509 | 23.231 | 16.655 | 1.00 | 23.17 |
| ATOM | 494 | N | TYR | 68 | 11.657 | 24.191 | 18.347 | 1.00 | 25.62 |
| ATOM | 495 | CA | TYR | 68 | 12.994 | 23.673 | 17.937 | 1.00 | 25.42 |
| ATOM | 496 | CB | TYR | 68 | 14.002 | 24.810 | 17.833 | 1.00 | 24.80 |
| ATOM | 497 | CG | TYR | 68 | 13.560 | 25.871 | 16.820 | 1.00 | 28.39 |
| ATOM | 498 | CD1 | TYR | 68 | 12.891 | 27.021 | 17.249 | 1.00 | 23.93 |
| ATOM | 499 | CE1 | TYR | 68 | 12.443 | 27.960 | 16.360 | 1.00 | 29.14 |
| ATOM | 500 | CZ | TYR | 68 | 12.674 | 27.784 | 14.974 | 1.00 | 31.13 |
| ATOM | 501 | OH | TYR | 68 | 12.240 | 28.772 | 14.091 | 1.00 | 29.59 |
| ATOM | 502 | CE2 | TYR | 68 | 13.322 | 26.650 | 14.515 | 1.00 | 30.72 |
| ATOM | 503 | CD2 | TYR | 68 | 13.781 | 25.700 | 15.440 | 1.00 | 25.51 |
| ATOM | 504 | C | TYR | 68 | 13.488 | 22.631 | 18.946 | 1.00 | 25.82 |
| ATOM | 505 | O | TYR | 68 | 13.677 | 22.958 | 20.107 | 1.00 | 26.19 |
| ATOM | 506 | N | ILE | 69 | 13.727 | 21.399 | 18.507 | 1.00 | 25.80 |
| ATOM | 507 | CA | ILE | 69 | 14.164 | 20.366 | 19.438 | 1.00 | 26.12 |
| ATOM | 508 | CB | ILE | 69 | 13.192 | 19.155 | 19.435 | 1.00 | 25.81 |
| ATOM | 509 | CG1 | ILE | 69 | 11.800 | 19.560 | 19.904 | 1.00 | 25.28 |
| ATOM | 510 | CD1 | ILE | 69 | 10.647 | 18.610 | 19.326 | 1.00 | 25.09 |
| ATOM | 511 | CG2 | ILE | 69 | 13.669 | 18.025 | 20.326 | 1.00 | 24.45 |
| ATOM | 512 | C | ILE | 69 | 15.537 | 19.970 | 18.980 | 1.00 | 27.18 |
| ATOM | 513 | O | ILE | 69 | 15.711 | 19.595 | 17.839 | 1.00 | 29.73 |
| ATOM | 514 | N | HIS | 93 | −5.482 | 19.281 | 22.985 | 1.00 | 43.46 |
| ATOM | 515 | CA | HIS | 93 | −5.053 | 19.119 | 24.378 | 1.00 | 43.34 |
| ATOM | 516 | CB | HIS | 93 | −3.732 | 18.335 | 24.385 | 1.00 | 43.87 |
| ATOM | 517 | CG | HIS | 93 | −3.136 | 18.126 | 25.750 | 1.00 | 46.71 |
| ATOM | 518 | ND1 | HIS | 93 | −1.938 | 18.696 | 26.131 | 1.00 | 49.45 |
| ATOM | 519 | CE1 | HIS | 93 | −1.649 | 18.329 | 27.367 | 1.00 | 49.71 |
| ATOM | 520 | NE2 | HIS | 93 | −2.623 | 17.551 | 27.808 | 1.00 | 49.32 |
| ATOM | 521 | CD2 | HIS | 93 | −3.568 | 17.409 | 26.818 | 1.00 | 46.55 |
| ATOM | 522 | C | HIS | 93 | −4.805 | 20.478 | 25.011 | 1.00 | 42.85 |
| ATOM | 523 | O | HIS | 93 | −4.069 | 21.295 | 24.439 | 1.00 | 42.79 |
| ATOM | 524 | N | GLY | 94 | −5.374 | 20.711 | 26.191 | 1.00 | 42.52 |
| ATOM | 525 | CA | GLY | 94 | −5.185 | 21.974 | 26.911 | 1.00 | 43.43 |
| ATOM | 526 | C | GLY | 94 | −4.019 | 21.964 | 27.881 | 1.00 | 44.21 |
| ATOM | 527 | O | GLY | 94 | −3.951 | 21.072 | 28.692 | 1.00 | 45.14 |
| ATOM | 528 | N | ASP | 95 | −3.101 | 22.933 | 27.762 | 1.00 | 44.94 |
| ATOM | 529 | CA | ASP | 95 | −1.947 | 23.154 | 28.658 | 1.00 | 46.47 |
| ATOM | 530 | CB | ASP | 95 | −0.856 | 22.122 | 28.397 | 1.00 | 47.33 |
| ATOM | 531 | CG | ASP | 95 | −0.651 | 21.156 | 29.584 | 1.00 | 53.62 |
| ATOM | 532 | OD1 | ASP | 95 | −0.417 | 21.621 | 30.746 | 1.00 | 56.28 |
| ATOM | 533 | OD2 | ASP | 95 | −0.695 | 19.919 | 29.336 | 1.00 | 58.53 |
| ATOM | 534 | C | ASP | 95 | −1.298 | 24.527 | 28.466 | 1.00 | 45.22 |
| ATOM | 535 | O | ASP | 95 | −1.295 | 25.036 | 27.342 | 1.00 | 46.69 |
| ATOM | 536 | N | PHE | 96 | −0.747 | 25.105 | 29.525 | 1.00 | 43.39 |
| ATOM | 537 | CA | PHE | 96 | 0.079 | 26.303 | 29.365 | 1.00 | 42.48 |
| ATOM | 538 | CB | PHE | 96 | 0.455 | 26.930 | 30.706 | 1.00 | 43.24 |
| ATOM | 539 | CG | PHE | 96 | −0.694 | 27.333 | 31.532 | 1.00 | 46.02 |

TABLE 1-continued

| | | | | | | | | | |
|---|---|---|---|---|---|---|---|---|---|
| ATOM | 540 | CD1 | PHE | 96 | −0.938 | 26.715 | 32.751 | 1.00 | 48.97 |
| ATOM | 541 | CE1 | PHE | 96 | −2.005 | 27.116 | 33.541 | 1.00 | 50.20 |
| ATOM | 542 | CZ | PHE | 96 | −2.836 | 28.138 | 33.119 | 1.00 | 47.57 |
| ATOM | 543 | CE2 | PHE | 96 | −2.616 | 28.743 | 31.924 | 1.00 | 48.84 |
| ATOM | 544 | CD2 | PHE | 96 | −1.541 | 28.342 | 31.129 | 1.00 | 49.04 |
| ATOM | 545 | C | PHE | 96 | 1.359 | 25.976 | 28.604 | 1.00 | 40.80 |
| ATOM | 546 | O | PHE | 96 | 1.812 | 24.823 | 28.604 | 1.00 | 41.02 |
| ATOM | 547 | N | HIS | 97 | 1.963 | 26.990 | 27.981 | 1.00 | 39.09 |
| ATOM | 548 | CA | HIS | 97 | 3.140 | 26.774 | 27.092 | 1.00 | 37.64 |
| ATOM | 549 | CB | HIS | 97 | 3.529 | 28.060 | 26.335 | 1.00 | 37.32 |
| ATOM | 550 | CG | HIS | 97 | 2.377 | 28.743 | 25.671 | 1.00 | 37.82 |
| ATOM | 551 | ND1 | HIS | 97 | 1.270 | 28.058 | 25.218 | 1.00 | 35.22 |
| ATOM | 552 | CE1 | HIS | 97 | 0.406 | 28.914 | 24.714 | 1.00 | 36.09 |
| ATOM | 553 | NE2 | HIS | 97 | 0.910 | 30.128 | 24.821 | 1.00 | 40.33 |
| ATOM | 554 | CD2 | HIS | 97 | 2.154 | 30.049 | 25.398 | 1.00 | 38.12 |
| ATOM | 555 | C | HIS | 97 | 4.383 | 26.254 | 27.799 | 1.00 | 35.95 |
| ATOM | 556 | O | HIS | 97 | 5.130 | 25.458 | 27.242 | 1.00 | 35.74 |
| ATOM | 557 | N | GLU | 98 | 4.612 | 26.741 | 29.010 | 1.00 | 35.36 |
| ATOM | 558 | CA | GLU | 98 | 5.784 | 26.349 | 29.763 | 1.00 | 35.63 |
| ATOM | 559 | CB | GLU | 98 | 5.962 | 27.205 | 31.007 | 1.00 | 35.92 |
| ATOM | 560 | CG | GLU | 98 | 6.029 | 28.723 | 30.781 | 1.00 | 35.01 |
| ATOM | 561 | CD | GLU | 98 | 4.686 | 29.396 | 30.817 | 1.00 | 34.70 |
| ATOM | 562 | OE1 | GLU | 98 | 3.736 | 28.848 | 30.214 | 1.00 | 38.79 |
| ATOM | 563 | OE2 | GLU | 98 | 4.568 | 30.486 | 31.416 | 1.00 | 33.39 |
| ATOM | 564 | C | GLU | 98 | 5.680 | 24.883 | 30.118 | 1.00 | 35.51 |
| ATOM | 565 | O | GLU | 98 | 6.643 | 24.138 | 29.916 | 1.00 | 36.38 |
| ATOM | 566 | N | ASP | 99 | 4.507 | 24.464 | 30.603 | 1.00 | 36.06 |
| ATOM | 567 | CA | ASP | 99 | 4.242 | 23.050 | 30.905 | 1.00 | 37.07 |
| ATOM | 568 | CB | ASP | 99 | 2.799 | 22.872 | 31.430 | 1.00 | 37.29 |
| ATOM | 569 | CG | ASP | 99 | 2.576 | 23.545 | 32.769 | 1.00 | 44.55 |
| ATOM | 570 | OD1 | ASP | 99 | 3.589 | 23.894 | 33.448 | 1.00 | 52.53 |
| ATOM | 571 | OD2 | ASP | 99 | 1.380 | 23.744 | 33.179 | 1.00 | 52.70 |
| ATOM | 572 | C | ASP | 99 | 4.475 | 22.171 | 29.671 | 1.00 | 36.53 |
| ATOM | 573 | O | ASP | 99 | 5.211 | 21.149 | 29.697 | 1.00 | 34.85 |
| ATOM | 574 | N | CYS | 100 | 3.857 | 22.626 | 28.582 | 1.00 | 36.53 |
| ATOM | 575 | CA | CYS | 100 | 3.931 | 21.993 | 27.312 | 1.00 | 34.40 |
| ATOM | 576 | CB | CYS | 100 | 3.131 | 22.839 | 26.342 | 1.00 | 36.53 |
| ATOM | 577 | SG | CYS | 100 | 2.637 | 21.917 | 24.911 | 1.00 | 43.47 |
| ATOM | 578 | C | CYS | 100 | 5.350 | 21.725 | 26.797 | 1.00 | 32.45 |
| ATOM | 579 | O | CYS | 100 | 5.672 | 20.621 | 26.373 | 1.00 | 31.15 |
| ATOM | 580 | N | MET | 101 | 6.226 | 22.711 | 26.847 | 1.00 | 30.30 |
| ATOM | 581 | CA | MET | 101 | 7.568 | 22.440 | 26.437 | 1.00 | 28.53 |
| ATOM | 582 | CB | MET | 101 | 8.359 | 23.755 | 26.387 | 1.00 | 29.23 |
| ATOM | 583 | CG | MET | 101 | 7.747 | 24.869 | 25.431 | 1.00 | 31.66 |
| ATOM | 584 | SD | MET | 101 | 7.062 | 24.205 | 23.886 | 1.00 | 34.37 |
| ATOM | 585 | CE | MET | 101 | 8.620 | 24.136 | 23.212 | 1.00 | 27.81 |
| ATOM | 586 | C | MET | 101 | 8.299 | 21.390 | 27.353 | 1.00 | 28.84 |
| ATOM | 587 | O | MET | 101 | 9.131 | 20.639 | 26.857 | 1.00 | 27.62 |
| ATOM | 588 | N | ASN | 102 | 8.003 | 21.380 | 28.674 | 1.00 | 27.97 |
| ATOM | 589 | CA | ASN | 102 | 8.595 | 20.412 | 29.664 | 1.00 | 27.65 |
| ATOM | 590 | CB | ASN | 102 | 8.279 | 20.892 | 31.082 | 1.00 | 26.72 |
| ATOM | 591 | CG | ASN | 102 | 9.272 | 21.933 | 31.580 | 1.00 | 26.15 |
| ATOM | 592 | OD1 | ASN | 102 | 10.437 | 21.654 | 31.732 | 1.00 | 28.57 |
| ATOM | 593 | ND2 | ASN | 102 | 8.802 | 23.121 | 31.833 | 1.00 | 29.55 |
| ATOM | 594 | C | ASN | 102 | 8.065 | 19.008 | 29.441 | 1.00 | 26.89 |
| ATOM | 595 | O | ASN | 102 | 8.814 | 18.050 | 29.461 | 1.00 | 27.39 |
| ATOM | 596 | N | ILE | 103 | 6.773 | 18.913 | 29.151 | 1.00 | 27.72 |
| ATOM | 597 | CA | ILE | 103 | 6.113 | 17.667 | 28.745 | 1.00 | 29.32 |
| ATOM | 598 | CB | ILE | 103 | 4.594 | 17.915 | 28.544 | 1.00 | 29.95 |
| ATOM | 599 | CG1 | ILE | 103 | 3.913 | 18.326 | 29.858 | 1.00 | 29.60 |
| ATOM | 600 | CD1 | ILE | 103 | 2.391 | 18.559 | 29.676 | 1.00 | 31.92 |
| ATOM | 601 | CG2 | ILE | 103 | 3.874 | 16.686 | 28.102 | 1.00 | 29.82 |
| ATOM | 602 | C | ILE | 103 | 6.757 | 17.014 | 27.492 | 1.00 | 30.80 |
| ATOM | 603 | O | ILE | 103 | 7.015 | 15.791 | 27.458 | 1.00 | 32.50 |
| ATOM | 604 | N | ILE | 104 | 7.047 | 17.807 | 26.458 | 1.00 | 30.71 |
| ATOM | 605 | CA | ILE | 104 | 7.614 | 17.264 | 25.241 | 1.00 | 28.75 |
| ATOM | 606 | CB | ILE | 104 | 7.599 | 18.337 | 24.108 | 1.00 | 28.67 |
| ATOM | 607 | CG1 | ILE | 104 | 6.145 | 18.655 | 23.727 | 1.00 | 28.45 |
| ATOM | 608 | CD1 | ILE | 104 | 5.925 | 19.806 | 22.805 | 1.00 | 29.03 |
| ATOM | 609 | CG2 | ILE | 104 | 8.550 | 17.942 | 22.989 | 1.00 | 23.02 |
| ATOM | 610 | C | ILE | 104 | 9.044 | 16.860 | 25.522 | 1.00 | 29.62 |
| ATOM | 611 | O | ILE | 104 | 9.501 | 15.823 | 25.064 | 1.00 | 30.90 |
| ATOM | 612 | N | MET | 105 | 9.784 | 17.680 | 26.262 | 1.00 | 29.08 |
| ATOM | 613 | CA | MET | 105 | 11.146 | 17.301 | 26.578 | 1.00 | 29.00 |
| ATOM | 614 | CB | MET | 105 | 11.877 | 18.405 | 27.344 | 1.00 | 28.17 |
| ATOM | 615 | CG | MET | 105 | 13.341 | 18.103 | 27.381 | 1.00 | 25.15 |
| ATOM | 616 | SD | MET | 105 | 14.271 | 19.374 | 28.221 | 1.00 | 32.36 |
| ATOM | 617 | CE | MET | 105 | 13.528 | 19.335 | 29.864 | 1.00 | 26.78 |
| ATOM | 618 | C | MET | 105 | 11.209 | 16.017 | 27.400 | 1.00 | 28.87 |
| ATOM | 619 | O | MET | 105 | 12.038 | 15.171 | 27.144 | 1.00 | 29.51 |

TABLE 1-continued

| | | | | | | | | | |
|---|---|---|---|---|---|---|---|---|---|
| ATOM | 620 | N | ASN | 106 | 10.339 | 15.900 | 28.400 | 1.00 | 29.35 |
| ATOM | 621 | CA | ASN | 106 | 10.332 | 14.742 | 29.319 | 1.00 | 29.59 |
| ATOM | 622 | CB | ASN | 106 | 9.366 | 14.937 | 30.509 | 1.00 | 27.43 |
| ATOM | 623 | CG | ASN | 106 | 9.854 | 15.978 | 31.527 | 1.00 | 27.79 |
| ATOM | 624 | OD1 | ASN | 106 | 10.967 | 16.529 | 31.455 | 1.00 | 27.05 |
| ATOM | 625 | ND2 | ASN | 106 | 8.991 | 16.284 | 32.466 | 1.00 | 27.32 |
| ATOM | 626 | C | ASN | 106 | 9.933 | 13.525 | 28.536 | 1.00 | 30.17 |
| ATOM | 627 | O | ASN | 106 | 10.576 | 12.474 | 28.664 | 1.00 | 30.56 |
| ATOM | 628 | N | ASP | 107 | 8.889 | 13.656 | 27.705 | 1.00 | 30.25 |
| ATOM | 629 | CA | ASP | 107 | 8.458 | 12.514 | 26.917 | 1.00 | 30.02 |
| ATOM | 630 | CB | ASP | 107 | 7.227 | 12.796 | 26.104 | 1.00 | 30.96 |
| ATOM | 631 | CG | ASP | 107 | 6.000 | 12.670 | 26.900 | 1.00 | 35.87 |
| ATOM | 632 | OD1 | ASP | 107 | 6.058 | 12.098 | 28.020 | 1.00 | 39.79 |
| ATOM | 633 | OD2 | ASP | 107 | 4.965 | 13.143 | 26.424 | 1.00 | 41.99 |
| ATOM | 634 | C | ASP | 107 | 9.538 | 12.053 | 26.017 | 1.00 | 29.77 |
| ATOM | 635 | O | ASP | 107 | 9.607 | 10.873 | 25.757 | 1.00 | 32.55 |
| ATOM | 636 | N | LEU | 108 | 10.416 | 12.939 | 25.558 | 1.00 | 29.21 |
| ATOM | 637 | CA | LEU | 108 | 11.547 | 12.485 | 24.710 | 1.00 | 29.45 |
| ATOM | 638 | CB | LEU | 108 | 12.008 | 13.582 | 23.719 | 1.00 | 27.71 |
| ATOM | 639 | CG | LEU | 108 | 11.033 | 14.016 | 22.592 | 1.00 | 28.91 |
| ATOM | 640 | CD1 | LEU | 108 | 11.304 | 15.414 | 22.065 | 1.00 | 25.44 |
| ATOM | 641 | CD2 | LEU | 108 | 11.048 | 12.984 | 21.486 | 1.00 | 27.35 |
| ATOM | 642 | C | LEU | 108 | 12.761 | 11.949 | 25.488 | 1.00 | 29.54 |
| ATOM | 643 | O | LEU | 108 | 13.485 | 11.090 | 25.003 | 1.00 | 29.35 |
| ATOM | 644 | N | VAL | 119 | 14.460 | 22.055 | 24.286 | 1.00 | 26.85 |
| ATOM | 645 | CA | VAL | 119 | 13.244 | 22.308 | 23.566 | 1.00 | 26.53 |
| ATOM | 646 | CB | VAL | 119 | 12.055 | 21.539 | 24.169 | 1.00 | 26.83 |
| ATOM | 647 | CG1 | VAL | 119 | 10.767 | 21.999 | 23.540 | 1.00 | 22.98 |
| ATOM | 648 | CG2 | VAL | 119 | 12.265 | 19.977 | 23.977 | 1.00 | 26.48 |
| ATOM | 649 | C | VAL | 119 | 13.087 | 23.788 | 23.707 | 1.00 | 28.09 |
| ATOM | 650 | O | VAL | 119 | 13.156 | 24.296 | 24.836 | 1.00 | 28.03 |
| ATOM | 651 | N | TRP | 120 | 13.015 | 24.486 | 22.549 | 1.00 | 26.68 |
| ATOM | 652 | CA | TRP | 120 | 12.795 | 25.903 | 22.532 | 1.00 | 25.73 |
| ATOM | 653 | CB | TRP | 120 | 13.960 | 26.597 | 21.891 | 1.00 | 24.90 |
| ATOM | 654 | CG | TRP | 120 | 13.953 | 28.039 | 22.126 | 1.00 | 24.58 |
| ATOM | 655 | CD1 | TRP | 120 | 12.909 | 28.825 | 22.594 | 1.00 | 25.77 |
| ATOM | 656 | NE1 | TRP | 120 | 13.332 | 30.139 | 22.684 | 1.00 | 24.65 |
| ATOM | 657 | CE2 | TRP | 120 | 14.636 | 30.212 | 22.278 | 1.00 | 21.13 |
| ATOM | 658 | CD2 | TRP | 120 | 15.046 | 28.924 | 21.901 | 1.00 | 22.88 |
| ATOM | 659 | CE3 | TRP | 120 | 16.364 | 28.736 | 21.447 | 1.00 | 25.22 |
| ATOM | 660 | CZ3 | TRP | 120 | 17.199 | 29.833 | 21.371 | 1.00 | 23.43 |
| ATOM | 661 | CH2 | TRP | 120 | 16.747 | 31.121 | 21.696 | 1.00 | 23.39 |
| ATOM | 662 | CZ2 | TRP | 120 | 15.487 | 31.332 | 22.178 | 1.00 | 22.89 |
| ATOM | 663 | C | TRP | 120 | 11.472 | 26.218 | 21.776 | 1.00 | 25.94 |
| ATOM | 664 | O | TRP | 120 | 11.390 | 26.012 | 20.585 | 1.00 | 25.78 |
| ATOM | 665 | N | GLY | 121 | 10.457 | 26.719 | 22.476 | 1.00 | 26.21 |
| ATOM | 666 | CA | GLY | 121 | 9.111 | 26.915 | 21.904 | 1.00 | 25.55 |
| ATOM | 667 | C | GLY | 121 | 8.952 | 28.405 | 21.632 | 1.00 | 25.37 |
| ATOM | 668 | O | GLY | 121 | 9.430 | 29.229 | 22.405 | 1.00 | 25.74 |
| ATOM | 669 | N | LYS | 122 | 8.301 | 28.770 | 20.527 | 1.00 | 24.36 |
| ATOM | 670 | CA | LYS | 122 | 8.171 | 30.194 | 20.172 | 1.00 | 23.32 |
| ATOM | 671 | CB | LYS | 122 | 9.177 | 30.579 | 19.066 | 1.00 | 23.06 |
| ATOM | 672 | CG | LYS | 122 | 10.643 | 30.678 | 19.617 | 1.00 | 24.84 |
| ATOM | 673 | CD | LYS | 122 | 11.621 | 31.000 | 18.505 | 1.00 | 25.66 |
| ATOM | 674 | CE | LYS | 122 | 12.979 | 31.407 | 19.033 | 1.00 | 30.58 |
| ATOM | 675 | NZ | LYS | 122 | 13.698 | 32.166 | 17.957 | 1.00 | 28.48 |
| ATOM | 676 | C | LYS | 122 | 6.774 | 30.444 | 19.737 | 1.00 | 23.02 |
| ATOM | 677 | O | LYS | 122 | 6.439 | 30.296 | 18.583 | 1.00 | 21.33 |
| ATOM | 678 | N | PHE | 123 | 5.949 | 30.881 | 20.674 | 1.00 | 24.66 |
| ATOM | 679 | CA | PHE | 123 | 4.519 | 30.898 | 20.469 | 1.00 | 25.71 |
| ATOM | 680 | CB | PHE | 123 | 3.793 | 30.683 | 21.792 | 1.00 | 25.39 |
| ATOM | 681 | CG | PHE | 123 | 3.680 | 29.227 | 22.165 | 1.00 | 25.58 |
| ATOM | 682 | CD1 | PHE | 123 | 4.756 | 28.564 | 22.787 | 1.00 | 23.88 |
| ATOM | 683 | CE1 | PHE | 123 | 4.686 | 27.216 | 23.095 | 1.00 | 27.12 |
| ATOM | 684 | CZ | PHE | 123 | 3.508 | 26.513 | 22.797 | 1.00 | 25.61 |
| ATOM | 685 | CE2 | PHE | 123 | 2.419 | 27.189 | 22.208 | 1.00 | 25.86 |
| ATOM | 686 | CD2 | PHE | 123 | 2.526 | 28.534 | 21.887 | 1.00 | 21.27 |
| ATOM | 687 | C | PHE | 123 | 4.099 | 32.203 | 19.858 | 1.00 | 27.78 |
| ATOM | 688 | O | PHE | 123 | 4.863 | 33.172 | 19.935 | 1.00 | 26.73 |
| ATOM | 689 | N | THR | 124 | 2.902 | 32.225 | 19.251 | 1.00 | 28.45 |
| ATOM | 690 | CA | THR | 124 | 2.394 | 33.468 | 18.678 | 1.00 | 29.21 |
| ATOM | 691 | CB | THR | 124 | 1.377 | 33.216 | 17.560 | 1.00 | 29.38 |
| ATOM | 692 | OG1 | THR | 124 | 0.295 | 32.413 | 18.054 | 1.00 | 29.10 |
| ATOM | 693 | CG2 | THR | 124 | 2.024 | 32.537 | 16.347 | 1.00 | 28.56 |
| ATOM | 694 | C | THR | 124 | 1.705 | 34.268 | 19.758 | 1.00 | 30.74 |
| ATOM | 695 | O | THR | 124 | 1.272 | 33.677 | 20.770 | 1.00 | 30.61 |
| ATOM | 696 | N | PRO | 125 | 1.584 | 35.609 | 19.566 | 1.00 | 31.11 |
| ATOM | 697 | CA | PRO | 125 | 1.093 | 36.383 | 20.694 | 1.00 | 31.41 |
| ATOM | 698 | CB | PRO | 125 | 1.441 | 37.821 | 20.312 | 1.00 | 31.81 |
| ATOM | 699 | CG | PRO | 125 | 1.426 | 37.818 | 18.814 | 1.00 | 31.39 |

TABLE 1-continued

| | | | | | | | | | |
|---|---|---|---|---|---|---|---|---|---|
| ATOM | 700 | CD | PRO | 125 | 1.955 | 36.471 | 18.426 | 1.00 | 30.80 |
| ATOM | 701 | C | PRO | 125 | −0.375 | 36.254 | 21.001 | 1.00 | 31.85 |
| ATOM | 702 | O | PRO | 125 | −1.142 | 35.815 | 20.168 | 1.00 | 31.82 |
| ATOM | 703 | N | ARG | 126 | −0.739 | 36.651 | 22.218 | 1.00 | 33.65 |
| ATOM | 704 | CA | ARG | 126 | −2.123 | 36.671 | 22.722 | 1.00 | 35.35 |
| ATOM | 705 | CB | ARG | 126 | −2.375 | 35.471 | 23.626 | 1.00 | 35.69 |
| ATOM | 706 | CG | ARG | 126 | −2.148 | 34.137 | 22.932 | 1.00 | 43.61 |
| ATOM | 707 | CD | ARG | 126 | −3.499 | 33.548 | 22.502 | 1.00 | 50.39 |
| ATOM | 708 | NE | ARG | 126 | −3.451 | 32.934 | 21.173 | 1.00 | 55.49 |
| ATOM | 709 | CZ | ARG | 126 | −3.722 | 33.575 | 20.038 | 1.00 | 55.94 |
| ATOM | 710 | NH1 | ARG | 126 | −4.058 | 34.856 | 20.065 | 1.00 | 56.17 |
| ATOM | 711 | NH2 | ARG | 126 | −3.659 | 32.930 | 18.885 | 1.00 | 53.93 |
| ATOM | 712 | C | ARG | 126 | −2.174 | 37.849 | 23.636 | 1.00 | 33.98 |
| ATOM | 713 | O | ARG | 126 | −1.427 | 37.875 | 24.590 | 1.00 | 34.55 |
| ATOM | 714 | N | GLY | 127 | −3.067 | 38.796 | 23.398 | 1.00 | 33.08 |
| ATOM | 715 | CA | GLY | 127 | −3.086 | 40.063 | 24.155 | 1.00 | 31.37 |
| ATOM | 716 | C | GLY | 127 | −1.787 | 40.837 | 23.987 | 1.00 | 31.90 |
| ATOM | 717 | O | GLY | 127 | −1.358 | 41.585 | 24.913 | 1.00 | 32.33 |
| ATOM | 718 | N | GLY | 128 | −1.162 | 40.662 | 22.815 | 1.00 | 29.85 |
| ATOM | 719 | CA | GLY | 128 | 0.070 | 41.349 | 22.481 | 1.00 | 29.52 |
| ATOM | 720 | C | GLY | 128 | 1.369 | 40.758 | 23.014 | 1.00 | 29.89 |
| ATOM | 721 | O | GLY | 128 | 2.428 | 41.286 | 22.720 | 1.00 | 31.57 |
| ATOM | 722 | N | ILE | 129 | 1.291 | 39.699 | 23.817 | 1.00 | 28.05 |
| ATOM | 723 | CA | ILE | 129 | 2.478 | 39.104 | 24.493 | 1.00 | 28.03 |
| ATOM | 724 | CB | ILE | 129 | 2.202 | 38.969 | 26.050 | 1.00 | 27.24 |
| ATOM | 725 | CG1 | ILE | 129 | 1.958 | 40.361 | 26.644 | 1.00 | 25.80 |
| ATOM | 726 | CD1 | ILE | 129 | 2.089 | 40.395 | 28.153 | 1.00 | 30.11 |
| ATOM | 727 | CG2 | ILE | 129 | 3.333 | 38.145 | 26.789 | 1.00 | 26.81 |
| ATOM | 728 | C | ILE | 129 | 2.732 | 37.707 | 23.943 | 1.00 | 26.21 |
| ATOM | 729 | O | ILE | 129 | 1.808 | 36.919 | 23.894 | 1.00 | 27.19 |
| ATOM | 730 | N | SER | 130 | 3.947 | 37.391 | 23.546 | 1.00 | 24.89 |
| ATOM | 731 | CA | SER | 130 | 4.217 | 36.024 | 23.166 | 1.00 | 27.04 |
| ATOM | 732 | CB | SER | 130 | 4.803 | 35.976 | 21.770 | 1.00 | 26.36 |
| ATOM | 733 | OG | SER | 130 | 5.830 | 36.922 | 21.748 | 1.00 | 29.36 |
| ATOM | 734 | C | SER | 130 | 5.169 | 35.406 | 24.211 | 1.00 | 27.61 |
| ATOM | 735 | O | SER | 130 | 5.897 | 36.120 | 24.915 | 1.00 | 28.20 |
| ATOM | 736 | N | ILE | 131 | 5.105 | 34.094 | 24.346 | 1.00 | 29.41 |
| ATOM | 737 | CA | ILE | 131 | 5.857 | 33.352 | 25.394 | 1.00 | 28.69 |
| ATOM | 738 | CB | ILE | 131 | 4.872 | 32.597 | 26.303 | 1.00 | 29.39 |
| ATOM | 739 | CG1 | ILE | 131 | 3.814 | 33.571 | 26.816 | 1.00 | 26.63 |
| ATOM | 740 | CD1 | ILE | 131 | 2.668 | 32.883 | 27.568 | 1.00 | 32.14 |
| ATOM | 741 | CG2 | ILE | 131 | 5.600 | 31.911 | 27.480 | 1.00 | 29.11 |
| ATOM | 742 | C | ILE | 131 | 6.739 | 32.349 | 24.693 | 1.00 | 29.13 |
| ATOM | 743 | O | ILE | 131 | 6.219 | 31.520 | 23.940 | 1.00 | 30.99 |
| ATOM | 744 | N | ASP | 132 | 8.047 | 32.442 | 24.921 | 1.00 | 28.25 |
| ATOM | 745 | CA | ASP | 132 | 9.033 | 31.541 | 24.383 | 1.00 | 28.57 |
| ATOM | 746 | CB | ASP | 132 | 10.072 | 32.355 | 23.599 | 1.00 | 29.24 |
| ATOM | 747 | CG | ASP | 132 | 9.423 | 33.268 | 22.466 | 1.00 | 31.19 |
| ATOM | 748 | OD1 | ASP | 132 | 8.235 | 33.051 | 22.043 | 1.00 | 29.77 |
| ATOM | 749 | OD2 | ASP | 132 | 10.137 | 34.175 | 22.000 | 1.00 | 31.92 |
| ATOM | 750 | C | ASP | 132 | 9.726 | 30.729 | 25.532 | 1.00 | 29.15 |
| ATOM | 751 | O | ASP | 132 | 10.765 | 31.138 | 26.058 | 1.00 | 30.13 |
| ATOM | 752 | N | PRO | 133 | 9.168 | 29.570 | 25.919 | 1.00 | 28.35 |
| ATOM | 753 | CA | PRO | 133 | 9.868 | 28.720 | 26.952 | 1.00 | 27.52 |
| ATOM | 754 | CB | PRO | 133 | 8.790 | 27.755 | 27.429 | 1.00 | 26.66 |
| ATOM | 755 | CG | PRO | 133 | 7.456 | 28.244 | 26.752 | 1.00 | 28.85 |
| ATOM | 756 | CD | PRO | 133 | 7.862 | 29.013 | 25.526 | 1.00 | 28.03 |
| ATOM | 757 | C | PRO | 133 | 11.010 | 27.900 | 26.361 | 1.00 | 27.31 |
| ATOM | 758 | O | PRO | 133 | 10.890 | 27.305 | 25.265 | 1.00 | 26.04 |
| ATOM | 759 | N | TYR | 134 | 12.122 | 27.882 | 27.104 | 1.00 | 26.45 |
| ATOM | 760 | CA | TYR | 134 | 13.262 | 27.096 | 26.742 | 1.00 | 26.35 |
| ATOM | 761 | CB | TYR | 134 | 14.408 | 28.049 | 26.500 | 1.00 | 26.01 |
| ATOM | 762 | CG | TYR | 134 | 15.728 | 27.349 | 26.336 | 1.00 | 25.57 |
| ATOM | 763 | CD1 | TYR | 134 | 16.651 | 27.352 | 27.354 | 1.00 | 23.87 |
| ATOM | 764 | CE1 | TYR | 134 | 17.923 | 26.711 | 27.189 | 1.00 | 21.07 |
| ATOM | 765 | CZ | TYR | 134 | 18.241 | 26.108 | 26.021 | 1.00 | 24.07 |
| ATOM | 766 | OH | TYR | 134 | 19.489 | 25.492 | 25.878 | 1.00 | 26.19 |
| ATOM | 767 | CE2 | TYR | 134 | 17.321 | 26.123 | 24.947 | 1.00 | 25.33 |
| ATOM | 768 | CD2 | TYR | 134 | 16.081 | 26.756 | 25.120 | 1.00 | 23.53 |
| ATOM | 769 | C | TYR | 134 | 13.600 | 26.147 | 27.904 | 1.00 | 26.71 |
| ATOM | 770 | O | TYR | 134 | 13.870 | 26.613 | 29.015 | 1.00 | 24.61 |
| ATOM | 771 | N | THR | 135 | 13.562 | 24.842 | 27.623 | 1.00 | 26.48 |
| ATOM | 772 | CA | THR | 135 | 13.863 | 23.814 | 28.597 | 1.00 | 27.81 |
| ATOM | 773 | CB | THR | 135 | 12.602 | 22.932 | 28.947 | 1.00 | 28.09 |
| ATOM | 774 | OG1 | THR | 135 | 12.286 | 22.062 | 27.870 | 1.00 | 28.86 |
| ATOM | 775 | CG2 | THR | 135 | 11.401 | 23.754 | 29.095 | 1.00 | 28.26 |
| ATOM | 776 | C | THR | 135 | 15.026 | 22.995 | 28.031 | 1.00 | 28.05 |
| ATOM | 777 | O | THR | 135 | 15.103 | 22.824 | 26.802 | 1.00 | 27.50 |
| ATOM | 778 | N | ASN | 164 | 5.372 | 41.527 | 16.756 | 1.00 | 38.98 |
| ATOM | 779 | CA | ASN | 164 | 4.101 | 40.866 | 16.413 | 1.00 | 38.82 |

TABLE 1-continued

| | | | | | | | | |
|---|---|---|---|---|---|---|---|---|
| ATOM | 780 | CB | ASN | 164 | 2.995 | 41.248 | 17.394 | 1.00 | 37.51 |
| ATOM | 781 | CG | ASN | 164 | 3.375 | 40.979 | 18.868 | 1.00 | 38.10 |
| ATOM | 782 | OD1 | ASN | 164 | 4.311 | 40.218 | 19.167 | 1.00 | 33.68 |
| ATOM | 783 | ND2 | ASN | 164 | 2.665 | 41.636 | 19.780 | 1.00 | 34.99 |
| ATOM | 784 | C | ASN | 164 | 3.639 | 40.958 | 14.938 | 1.00 | 38.77 |
| ATOM | 785 | O | ASN | 164 | 2.420 | 40.817 | 14.640 | 1.00 | 39.55 |
| ATOM | 786 | O3S | G6S | 202 | 0.434 | 13.616 | 0.144 | 1.00 | 0.87 |
| ATOM | 787 | S | G6S | 202 | 1.692 | 12.947 | 0.560 | 1.00 | 0.84 |
| ATOM | 788 | O1S | G6S | 202 | 2.743 | 13.992 | 0.551 | 1.00 | 0.00 |
| ATOM | 789 | O2S | G6S | 202 | 2.056 | 11.920 | −0.446 | 1.00 | 0.46 |
| ATOM | 790 | O6 | G6S | 202 | 1.568 | 12.213 | 2.048 | 1.00 | 0.15 |
| ATOM | 791 | C6 | G6S | 202 | 2.509 | 11.226 | 2.527 | 1.00 | 0.76 |
| ATOM | 792 | C5 | G6S | 202 | 3.154 | 11.525 | 3.905 | 1.00 | 0.20 |
| ATOM | 793 | O5 | G6S | 202 | 2.710 | 12.762 | 4.508 | 1.00 | 0.47 |
| ATOM | 794 | C4 | G6S | 202 | 4.704 | 11.422 | 3.901 | 1.00 | 0.65 |
| ATOM | 795 | O4 | G6S | 202 | 5.144 | 10.447 | 2.925 | 1.00 | 0.12 |
| ATOM | 796 | C3 | G6S | 202 | 5.498 | 12.749 | 3.721 | 1.00 | 0.92 |
| ATOM | 797 | O3 | G6S | 202 | 5.997 | 12.885 | 2.375 | 1.00 | 0.71 |
| ATOM | 798 | C2 | G6S | 202 | 4.758 | 14.031 | 4.163 | 1.00 | 0.85 |
| ATOM | 799 | O2 | G6S | 202 | 5.303 | 15.204 | 3.529 | 1.00 | 0.58 |
| ATOM | 800 | C1 | G6S | 202 | 3.250 | 13.956 | 3.923 | 1.00 | 0.56 |
| ATOM | 801 | O1 | G6S | 202 | 2.611 | 15.091 | 4.502 | 1.00 | 0.12 |
| ATOM | 802 | N | ASN | 164 | 8.802 | 26.590 | 6.917 | 1.00 | 33.87 |
| ATOM | 803 | CA | ASN | 164 | 8.479 | 25.672 | 5.830 | 1.00 | 34.28 |
| ATOM | 804 | CB | ASN | 164 | 7.383 | 24.655 | 6.231 | 1.00 | 32.50 |
| ATOM | 805 | CG | ASN | 164 | 7.827 | 23.673 | 7.325 | 1.00 | 32.82 |
| ATOM | 806 | OD1 | ASN | 164 | 9.016 | 23.590 | 7.685 | 1.00 | 30.94 |
| ATOM | 807 | ND2 | ASN | 164 | 6.852 | 22.923 | 7.862 | 1.00 | 29.12 |
| ATOM | 808 | C | ASN | 164 | 8.121 | 26.320 | 4.469 | 1.00 | 34.97 |
| ATOM | 809 | O | ASN | 164 | 7.603 | 25.637 | 3.594 | 1.00 | 35.11 |
| ATOM | 810 | O6 | GDQ | 201 | 39.880 | 25.293 | −6.152 | 1.00 | 46.27 |
| ATOM | 811 | C6 | GDQ | 201 | 39.593 | 23.968 | −5.959 | 1.00 | 47.77 |
| ATOM | 812 | N1 | GDQ | 201 | 39.601 | 23.364 | −4.728 | 1.00 | 47.90 |
| ATOM | 813 | C5 | GDQ | 201 | 39.301 | 23.178 | −7.050 | 1.00 | 48.17 |
| ATOM | 814 | C7 | GDQ | 201 | 39.166 | 23.330 | −8.414 | 1.00 | 49.49 |
| ATOM | 815 | C77 | GDQ | 201 | 39.375 | 24.484 | −9.040 | 1.00 | 48.63 |
| ATOM | 816 | N77 | GDQ | 201 | 39.668 | 25.525 | −9.571 | 1.00 | 53.62 |
| ATOM | 817 | C8 | GDQ | 201 | 38.829 | 22.148 | −9.069 | 1.00 | 47.67 |
| ATOM | 818 | N9 | GDQ | 201 | 38.739 | 21.226 | −8.070 | 1.00 | 46.70 |
| ATOM | 819 | C4 | GDQ | 201 | 39.015 | 21.838 | −6.880 | 1.00 | 47.89 |
| ATOM | 820 | N3 | GDQ | 201 | 39.029 | 21.264 | −5.651 | 1.00 | 47.83 |
| ATOM | 821 | C2 | GDQ | 201 | 39.318 | 22.021 | −4.572 | 1.00 | 48.19 |
| ATOM | 822 | N2 | GDQ | 201 | 39.322 | 21.396 | −3.361 | 1.00 | 46.97 |
| ATOM | 823 | N | ASN | 164 | 22.549 | 28.669 | −4.503 | 1.00 | 35.87 |
| ATOM | 824 | CA | ASN | 164 | 23.118 | 28.694 | −5.850 | 1.00 | 37.23 |
| ATOM | 825 | CB | ASN | 164 | 23.262 | 27.279 | −6.439 | 1.00 | 36.18 |
| ATOM | 826 | CG | ASN | 164 | 24.431 | 26.534 | −5.820 | 1.00 | 38.54 |
| ATOM | 827 | OD1 | ASN | 164 | 25.175 | 27.109 | −4.993 | 1.00 | 35.02 |
| ATOM | 828 | ND2 | ASN | 164 | 24.601 | 25.253 | −6.191 | 1.00 | 36.60 |
| ATOM | 829 | C | ASN | 164 | 22.419 | 29.671 | −6.794 | 1.00 | 37.19 |
| ATOM | 830 | O | ASN | 164 | 22.632 | 29.654 | −7.995 | 1.00 | 37.79 |
| ATOM | 831 | O6 | GDQ | 201 | 41.711 | 55.587 | 1.265 | 1.00 | 47.86 |
| ATOM | 832 | C6 | GDQ | 201 | 42.655 | 54.798 | 0.686 | 1.00 | 49.13 |
| ATOM | 833 | N1 | GDQ | 201 | 43.162 | 53.755 | 1.386 | 1.00 | 48.48 |
| ATOM | 834 | C5 | GDQ | 201 | 43.114 | 55.030 | −0.629 | 1.00 | 50.29 |
| ATOM | 835 | C7 | GDQ | 201 | 42.895 | 55.934 | −1.676 | 1.00 | 49.19 |
| ATOM | 836 | C77 | GDQ | 201 | 42.018 | 56.941 | −1.586 | 1.00 | 49.79 |
| ATOM | 837 | N77 | GDQ | 201 | 41.272 | 57.892 | −1.409 | 1.00 | 52.99 |
| ATOM | 838 | C8 | GDQ | 201 | 43.665 | 55.676 | −2.796 | 1.00 | 48.54 |
| ATOM | 839 | N9 | GDQ | 201 | 44.390 | 54.565 | −2.444 | 1.00 | 49.38 |
| ATOM | 840 | C4 | GDQ | 201 | 44.083 | 54.188 | −1.156 | 1.00 | 49.87 |
| ATOM | 841 | N3 | GDQ | 201 | 44.571 | 53.140 | −0.425 | 1.00 | 49.70 |
| ATOM | 842 | C2 | GDQ | 201 | 44.090 | 52.944 | 0.845 | 1.00 | 48.62 |
| ATOM | 843 | N2 | GDQ | 201 | 44.543 | 51.925 | 1.604 | 1.00 | 49.10 |
| ATOM | 844 | O | HOH | 7 | 9.135 | 31.427 | 40.622 | 1.00 | 26.97 |
| ATOM | 845 | O | HOH | 16 | 2.116 | 33.380 | 23.561 | 1.00 | 28.45 |
| ATOM | 846 | O | HOH | 22 | 5.725 | 20.960 | 12.801 | 1.00 | 32.23 |
| ATOM | 847 | O | HOH | 43 | −0.444 | 31.320 | 20.335 | 1.00 | 25.27 |
| ATOM | 848 | O | HOH | 45 | 8.832 | 30.704 | 43.657 | 1.00 | 34.80 |
| ATOM | 849 | O | HOH | 58 | 5.315 | 32.277 | 33.211 | 1.00 | 32.17 |
| ATOM | 850 | O | HOH | 59 | 6.261 | 31.224 | 16.269 | 1.00 | 31.40 |
| ATOM | 851 | O | HOH | 60 | 13.459 | 31.592 | 25.962 | 1.00 | 30.16 |
| ATOM | 852 | O | HOH | 67 | 0.659 | 25.252 | 24.982 | 1.00 | 47.03 |
| ATOM | 853 | O | HOH | 77 | 3.601 | 20.333 | 32.769 | 1.00 | 51.59 |
| ATOM | 854 | O | HOH | 80 | 12.551 | 37.938 | 21.807 | 1.00 | 27.25 |
| ATOM | 855 | O | HOH | 87 | 10.805 | 31.014 | 15.075 | 1.00 | 32.69 |
| ATOM | 856 | O | HOH | 99 | 0.444 | 24.737 | 37.523 | 1.00 | 49.59 |
| ATOM | 857 | O | HOH | 112 | −5.998 | 32.041 | 25.975 | 1.00 | 53.31 |
| ATOM | 858 | O | HOH | 130 | 12.471 | 33.518 | 21.473 | 1.00 | 37.86 |
| ATOM | 859 | O | HOH | 146 | 2.212 | 26.772 | 14.171 | 1.00 | 34.34 |

TABLE 1-continued

| | | | | | | | | | |
|---|---|---|---|---|---|---|---|---|---|
| ATOM | 860 | O | HOH | 164 | 16.560 | 23.554 | 19.744 | 1.00 | 30.02 |
| ATOM | 861 | O | HOH | 165 | 6.514 | 15.445 | 32.058 | 1.00 | 40.48 |
| ATOM | 862 | O | HOH | 169 | 6.036 | 24.653 | 33.818 | 1.00 | 57.02 |
| ATOM | 863 | O | HOH | 187 | −0.110 | 31.485 | 22.841 | 1.00 | 46.21 |
| ATOM | 864 | O | HOH | 197 | −5.204 | 37.964 | 26.824 | 1.00 | 40.46 |
| ATOM | 865 | O | HOH | 203 | −0.892 | 23.472 | 32.034 | 1.00 | 35.99 |
| ATOM | 866 | O | HOH | 223 | −7.059 | 18.630 | 27.537 | 1.00 | 44.78 |
| ATOM | 867 | O | HOH | 239 | −8.523 | 26.976 | 36.532 | 1.00 | 63.57 |
| ATOM | 868 | O | HOH | 250 | 8.142 | 29.477 | 12.219 | 1.00 | 43.13 |
| ATOM | 869 | N | TYR | 158 | 14.553 | 51.970 | −15.813 | 1.00 | 64.09 |
| ATOM | 870 | CA | TYR | 158 | 15.385 | 51.348 | −14.747 | 1.00 | 65.51 |
| ATOM | 871 | CB | TYR | 158 | 15.471 | 49.830 | −14.932 | 1.00 | 66.55 |
| ATOM | 872 | CG | TYR | 158 | 14.250 | 49.084 | −14.493 | 1.00 | 69.02 |
| ATOM | 873 | CD1 | TYR | 158 | 14.255 | 48.354 | −13.301 | 1.00 | 72.73 |
| ATOM | 874 | CE1 | TYR | 158 | 13.107 | 47.659 | −12.875 | 1.00 | 72.44 |
| ATOM | 875 | CZ | TYR | 158 | 11.945 | 47.700 | −13.660 | 1.00 | 70.37 |
| ATOM | 876 | OH | TYR | 158 | 10.814 | 47.029 | −13.241 | 1.00 | 69.24 |
| ATOM | 877 | CE2 | TYR | 158 | 11.931 | 48.421 | −14.843 | 1.00 | 70.14 |
| ATOM | 878 | CD2 | TYR | 158 | 13.080 | 49.103 | −15.254 | 1.00 | 69.89 |
| ATOM | 879 | C | TYR | 158 | 16.821 | 51.897 | −14.690 | 1.00 | 65.48 |
| ATOM | 880 | O | TYR | 158 | 17.741 | 51.280 | −15.255 | 1.00 | 65.62 |
| ATOM | 881 | O3S | G6S | 202 | 53.558 | 50.380 | −15.824 | 1.00 | 0.80 |
| ATOM | 882 | S | G6S | 202 | 52.441 | 49.420 | −15.564 | 1.00 | 0.32 |
| ATOM | 883 | O1S | G6S | 202 | 51.398 | 50.093 | −14.748 | 1.00 | 0.47 |
| ATOM | 884 | O2S | G6S | 202 | 52.923 | 48.246 | −14.787 | 1.00 | 0.44 |
| ATOM | 885 | O6 | G6S | 202 | 51.799 | 48.904 | −17.004 | 1.00 | 0.52 |
| ATOM | 886 | C6 | G6S | 202 | 51.924 | 49.575 | −18.273 | 1.00 | 0.05 |
| ATOM | 887 | C5 | G6S | 202 | 50.558 | 49.948 | −18.902 | 1.00 | 0.81 |
| ATOM | 888 | O5 | G6S | 202 | 50.235 | 51.331 | −18.643 | 1.00 | 0.85 |
| ATOM | 889 | C4 | G6S | 202 | 49.339 | 49.014 | −18.623 | 1.00 | 0.89 |
| ATOM | 890 | O4 | G6S | 202 | 49.690 | 47.679 | −18.220 | 1.00 | 99.16 |
| ATOM | 891 | C3 | G6S | 202 | 48.264 | 49.536 | −17.650 | 1.00 | 99.15 |
| ATOM | 892 | O3 | G6S | 202 | 47.953 | 48.529 | −16.675 | 1.00 | 96.07 |
| ATOM | 893 | C2 | G6S | 202 | 48.477 | 50.927 | −17.001 | 1.00 | 99.78 |
| ATOM | 894 | O2 | G6S | 202 | 48.212 | 50.895 | −15.588 | 1.00 | 97.61 |
| ATOM | 895 | C1 | G6S | 202 | 49.828 | 51.591 | −17.293 | 1.00 | 0.22 |
| ATOM | 896 | O1 | G6S | 202 | 49.719 | 53.004 | −17.090 | 1.00 | 0.17 |
| ATOM | 897 | O | HOH | 82 | 1.115 | 35.104 | 10.368 | 1.00 | 38.48 |
| ATOM | 898 | O | HOH | 233 | 3.922 | 25.061 | 8.070 | 1.00 | 44.46 |
| ATOM | 899 | O | HOH | 243 | 4.102 | 29.321 | 8.205 | 1.00 | 32.22 |
| ATOM | 900 | O | HOH | 247 | 2.185 | 28.151 | 7.604 | 1.00 | 38.90 |
| TER | | | | | | | | | |

TABLE 2

| | | | | | | | | | |
|---|---|---|---|---|---|---|---|---|---|
| REMARK | Accelrys ViewerPro PDB file | | | | | | | | |
| REMARK | Created: | Tue Dec 14 10:09:27 Pacific Standard Time 2010 | | | | | | | |
| ATOM | 1 | N | VAL | 30 | 2.730 | 7.158 | 20.809 | 1.00 | 39.88 |
| ATOM | 2 | CA | VAL | 30 | 3.057 | 7.082 | 19.373 | 1.00 | 38.85 |
| ATOM | 3 | CB | VAL | 30 | 2.234 | 8.031 | 18.461 | 1.00 | 38.91 |
| ATOM | 4 | CG1 | VAL | 30 | 2.470 | 9.486 | 18.798 | 1.00 | 37.59 |
| ATOM | 5 | CG2 | VAL | 30 | 0.767 | 7.685 | 18.552 | 1.00 | 39.29 |
| ATOM | 6 | C | VAL | 30 | 4.524 | 7.208 | 19.055 | 1.00 | 38.01 |
| ATOM | 7 | O | VAL | 30 | 4.937 | 6.813 | 17.968 | 1.00 | 39.15 |
| ATOM | 8 | N | LEU | 31 | 5.315 | 7.719 | 19.997 | 1.00 | 36.59 |
| ATOM | 9 | CA | LEU | 31 | 6.746 | 7.915 | 19.767 | 1.00 | 36.17 |
| ATOM | 10 | CB | LEU | 31 | 7.397 | 8.697 | 20.893 | 1.00 | 36.01 |
| ATOM | 11 | CG | LEU | 31 | 7.004 | 10.142 | 21.071 | 1.00 | 33.94 |
| ATOM | 12 | CD1 | LEU | 31 | 7.514 | 10.616 | 22.392 | 1.00 | 31.75 |
| ATOM | 13 | CD2 | LEU | 31 | 7.636 | 10.950 | 19.947 | 1.00 | 31.12 |
| ATOM | 14 | C | LEU | 31 | 7.514 | 6.628 | 19.583 | 1.00 | 36.98 |
| ATOM | 15 | O | LEU | 31 | 7.290 | 5.639 | 20.305 | 1.00 | 36.75 |
| ATOM | 16 | N | GLU | 32 | 8.444 | 6.648 | 18.644 | 1.00 | 36.41 |
| ATOM | 17 | CA | GLU | 32 | 9.228 | 5.472 | 18.372 | 1.00 | 38.40 |
| ATOM | 18 | CB | GLU | 32 | 8.708 | 4.786 | 17.114 | 1.00 | 39.11 |
| ATOM | 19 | CG | GLU | 32 | 7.200 | 4.749 | 17.161 | 1.00 | 45.28 |
| ATOM | 20 | CD | GLU | 32 | 6.609 | 3.553 | 16.498 | 1.00 | 53.25 |
| ATOM | 21 | OE1 | GLU | 32 | 5.790 | 2.845 | 17.156 | 1.00 | 55.01 |
| ATOM | 22 | OE2 | GLU | 32 | 6.970 | 3.340 | 15.307 | 1.00 | 57.83 |
| ATOM | 23 | C | GLU | 32 | 10.667 | 5.854 | 18.228 | 1.00 | 38.80 |
| ATOM | 24 | O | GLU | 32 | 10.999 | 7.040 | 17.961 | 1.00 | 38.77 |
| ATOM | 25 | N | SER | 33 | 11.544 | 4.882 | 18.418 | 1.00 | 38.22 |
| ATOM | 26 | CA | SER | 33 | 12.947 | 5.190 | 18.229 | 1.00 | 38.82 |
| ATOM | 27 | CB | SER | 33 | 13.687 | 5.359 | 19.560 | 1.00 | 39.38 |
| ATOM | 28 | OG | SER | 33 | 13.593 | 4.189 | 20.326 | 1.00 | 41.14 |
| ATOM | 29 | C | SER | 33 | 13.636 | 4.162 | 17.394 | 1.00 | 38.71 |
| ATOM | 30 | O | SER | 33 | 13.044 | 3.196 | 17.003 | 1.00 | 38.26 |

TABLE 2-continued

| | | | | | | | | | |
|---|---|---|---|---|---|---|---|---|---|
| ATOM | 31 | N | PHE | 34 | 14.902 | 4.406 | 17.097 | 1.00 | 39.12 |
| ATOM | 32 | CA | PHE | 34 | 15.677 | 3.442 | 16.394 | 1.00 | 40.33 |
| ATOM | 33 | CB | PHE | 34 | 15.529 | 3.547 | 14.853 | 1.00 | 40.48 |
| ATOM | 34 | CG | PHE | 34 | 15.877 | 4.898 | 14.270 | 1.00 | 40.30 |
| ATOM | 35 | CD1 | PHE | 34 | 14.886 | 5.852 | 14.066 | 1.00 | 41.74 |
| ATOM | 36 | CE1 | PHE | 34 | 15.206 | 7.116 | 13.494 | 1.00 | 43.82 |
| ATOM | 37 | CZ | PHE | 34 | 16.541 | 7.417 | 13.127 | 1.00 | 41.69 |
| ATOM | 38 | CE2 | PHE | 34 | 17.536 | 6.460 | 13.325 | 1.00 | 42.27 |
| ATOM | 39 | CD2 | PHE | 34 | 17.190 | 5.192 | 13.873 | 1.00 | 40.34 |
| ATOM | 40 | C | PHE | 34 | 17.079 | 3.626 | 16.898 | 1.00 | 41.15 |
| ATOM | 41 | O | PHE | 34 | 17.399 | 4.682 | 17.484 | 1.00 | 42.09 |
| ATOM | 42 | N | PRO | 35 | 17.899 | 2.571 | 16.771 | 1.00 | 41.12 |
| ATOM | 43 | CA | PRO | 35 | 19.294 | 2.614 | 17.218 | 1.00 | 40.34 |
| ATOM | 44 | CB | PRO | 35 | 19.829 | 1.235 | 16.780 | 1.00 | 40.97 |
| ATOM | 45 | CG | PRO | 35 | 18.588 | 0.349 | 16.878 | 1.00 | 40.63 |
| ATOM | 46 | CD | PRO | 35 | 17.520 | 1.222 | 16.287 | 1.00 | 40.98 |
| ATOM | 47 | C | PRO | 35 | 20.132 | 3.751 | 16.636 | 1.00 | 39.57 |
| ATOM | 48 | O | PRO | 35 | 20.001 | 4.100 | 15.474 | 1.00 | 39.66 |
| ATOM | 49 | N | ASN | 36 | 20.981 | 4.325 | 17.476 | 1.00 | 38.69 |
| ATOM | 50 | CA | ASN | 36 | 22.053 | 5.178 | 17.036 | 1.00 | 37.82 |
| ATOM | 51 | CB | ASN | 36 | 22.457 | 6.053 | 18.200 | 1.00 | 36.54 |
| ATOM | 52 | CG | ASN | 36 | 23.478 | 7.104 | 17.852 | 1.00 | 34.98 |
| ATOM | 53 | OD1 | ASN | 36 | 23.995 | 7.781 | 18.752 | 1.00 | 36.05 |
| ATOM | 54 | ND2 | ASN | 36 | 23.798 | 7.255 | 16.591 | 1.00 | 30.63 |
| ATOM | 55 | C | ASN | 36 | 23.204 | 4.264 | 16.545 | 1.00 | 39.04 |
| ATOM | 56 | O | ASN | 36 | 23.688 | 3.361 | 17.239 | 1.00 | 38.06 |
| ATOM | 57 | N | LYS | 37 | 23.679 | 4.562 | 15.345 | 1.00 | 39.82 |
| ATOM | 58 | CA | LYS | 37 | 24.559 | 3.712 | 14.611 | 1.00 | 40.00 |
| ATOM | 59 | CB | LYS | 37 | 24.051 | 3.740 | 13.180 | 1.00 | 41.30 |
| ATOM | 60 | CG | LYS | 37 | 24.578 | 2.689 | 12.235 | 1.00 | 48.42 |
| ATOM | 61 | CD | LYS | 37 | 23.628 | 2.551 | 11.016 | 1.00 | 55.23 |
| ATOM | 62 | CE | LYS | 37 | 22.384 | 1.698 | 11.343 | 1.00 | 57.91 |
| ATOM | 63 | NZ | LYS | 37 | 21.337 | 2.463 | 12.101 | 1.00 | 61.73 |
| ATOM | 64 | C | LYS | 37 | 25.919 | 4.338 | 14.738 | 1.00 | 39.47 |
| ATOM | 65 | O | LYS | 37 | 26.914 | 3.783 | 14.283 | 1.00 | 39.65 |
| ATOM | 66 | N | HIS | 38 | 25.949 | 5.508 | 15.378 | 1.00 | 38.34 |
| ATOM | 67 | CA | HIS | 38 | 27.143 | 6.288 | 15.573 | 1.00 | 37.56 |
| ATOM | 68 | CB | HIS | 38 | 27.129 | 7.481 | 14.587 | 1.00 | 37.47 |
| ATOM | 69 | CG | HIS | 38 | 27.098 | 7.045 | 13.152 | 1.00 | 37.11 |
| ATOM | 70 | ND1 | HIS | 38 | 28.220 | 6.564 | 12.500 | 1.00 | 36.48 |
| ATOM | 71 | CE1 | HIS | 38 | 27.889 | 6.195 | 11.277 | 1.00 | 36.22 |
| ATOM | 72 | NE2 | HIS | 38 | 26.587 | 6.393 | 11.120 | 1.00 | 38.61 |
| ATOM | 73 | CD2 | HIS | 38 | 26.067 | 6.902 | 12.286 | 1.00 | 34.88 |
| ATOM | 74 | C | HIS | 38 | 27.333 | 6.718 | 17.029 | 1.00 | 38.03 |
| ATOM | 75 | O | HIS | 38 | 27.654 | 7.863 | 17.295 | 1.00 | 37.92 |
| ATOM | 76 | N | VAL | 39 | 27.183 | 5.767 | 17.962 | 1.00 | 40.02 |
| ATOM | 77 | CA | VAL | 39 | 27.302 | 5.991 | 19.417 | 1.00 | 40.94 |
| ATOM | 78 | CB | VAL | 39 | 26.980 | 4.723 | 20.244 | 1.00 | 42.63 |
| ATOM | 79 | CG1 | VAL | 39 | 25.562 | 4.228 | 19.958 | 1.00 | 42.51 |
| ATOM | 80 | CG2 | VAL | 39 | 28.029 | 3.580 | 19.967 | 1.00 | 42.25 |
| ATOM | 81 | C | VAL | 39 | 28.634 | 6.554 | 19.879 | 1.00 | 41.41 |
| ATOM | 82 | O | VAL | 39 | 28.693 | 7.225 | 20.872 | 1.00 | 41.00 |
| ATOM | 83 | N | ARG | 41 | 30.495 | 9.017 | 18.601 | 1.00 | 45.41 |
| ATOM | 84 | CA | ARG | 41 | 30.667 | 10.477 | 18.643 | 1.00 | 43.05 |
| ATOM | 85 | CB | ARG | 41 | 31.097 | 11.088 | 17.289 | 1.00 | 45.18 |
| ATOM | 86 | CG | ARG | 41 | 29.996 | 11.161 | 16.204 | 1.00 | 46.63 |
| ATOM | 87 | CD | ARG | 41 | 29.907 | 9.832 | 15.545 | 1.00 | 53.21 |
| ATOM | 88 | NE | ARG | 41 | 30.339 | 9.818 | 14.138 | 1.00 | 60.30 |
| ATOM | 89 | CZ | ARG | 41 | 31.534 | 10.165 | 13.650 | 1.00 | 60.36 |
| ATOM | 90 | NH1 | ARG | 41 | 32.515 | 10.646 | 14.423 | 1.00 | 58.35 |
| ATOM | 91 | NH2 | ARG | 41 | 31.708 | 10.068 | 12.338 | 1.00 | 60.11 |
| ATOM | 92 | C | ARG | 41 | 29.428 | 11.151 | 19.135 | 1.00 | 41.03 |
| ATOM | 93 | O | ARG | 41 | 28.302 | 10.616 | 19.031 | 1.00 | 39.70 |
| ATOM | 94 | N | ASP | 42 | 29.672 | 12.322 | 19.719 | 1.00 | 38.00 |
| ATOM | 95 | CA | ASP | 42 | 28.643 | 13.282 | 20.060 | 1.00 | 35.16 |
| ATOM | 96 | CB | ASP | 42 | 29.220 | 14.249 | 21.075 | 1.00 | 34.84 |
| ATOM | 97 | CG | ASP | 42 | 29.166 | 13.696 | 22.483 | 1.00 | 36.63 |
| ATOM | 98 | OD1 | ASP | 42 | 28.668 | 12.558 | 22.613 | 1.00 | 31.87 |
| ATOM | 99 | OD2 | ASP | 42 | 29.594 | 14.414 | 23.438 | 1.00 | 37.57 |
| ATOM | 100 | C | ASP | 42 | 28.279 | 14.058 | 18.803 | 1.00 | 33.84 |
| ATOM | 101 | O | ASP | 42 | 29.154 | 14.636 | 18.175 | 1.00 | 33.55 |
| ATOM | 102 | N | TYR | 43 | 27.012 | 14.056 | 18.416 | 1.00 | 31.87 |
| ATOM | 103 | CA | TYR | 43 | 26.544 | 14.944 | 17.358 | 1.00 | 30.89 |
| ATOM | 104 | CB | TYR | 43 | 26.630 | 14.285 | 15.970 | 1.00 | 29.12 |
| ATOM | 105 | CG | TYR | 43 | 25.766 | 13.057 | 15.831 | 1.00 | 29.86 |
| ATOM | 106 | CD1 | TYR | 43 | 26.207 | 11.792 | 16.290 | 1.00 | 29.44 |
| ATOM | 107 | CE1 | TYR | 43 | 25.413 | 10.668 | 16.166 | 1.00 | 27.88 |
| ATOM | 108 | CZ | TYR | 43 | 24.158 | 10.775 | 15.603 | 1.00 | 27.82 |
| ATOM | 109 | OH | TYR | 43 | 23.338 | 9.655 | 15.447 | 1.00 | 28.72 |
| ATOM | 110 | CE2 | TYR | 43 | 23.699 | 11.999 | 15.175 | 1.00 | 25.62 |

TABLE 2-continued

| | | | | | | | | | |
|---|---|---|---|---|---|---|---|---|---|
| ATOM | 111 | CD2 | TYR | 43 | 24.516 | 13.139 | 15.281 | 1.00 | 25.63 |
| ATOM | 112 | C | TYR | 43 | 25.108 | 15.325 | 17.717 | 1.00 | 30.53 |
| ATOM | 113 | O | TYR | 43 | 24.488 | 14.636 | 18.525 | 1.00 | 29.48 |
| ATOM | 114 | N | PHE | 44 | 24.635 | 16.416 | 17.093 | 1.00 | 29.37 |
| ATOM | 115 | CA | PHE | 44 | 23.390 | 17.140 | 17.385 | 1.00 | 28.32 |
| ATOM | 116 | CB | PHE | 44 | 23.675 | 18.667 | 17.406 | 1.00 | 28.58 |
| ATOM | 117 | CG | PHE | 44 | 23.566 | 19.326 | 18.786 | 1.00 | 24.77 |
| ATOM | 118 | CD1 | PHE | 44 | 24.650 | 20.032 | 19.326 | 1.00 | 26.77 |
| ATOM | 119 | CE1 | PHE | 44 | 24.533 | 20.714 | 20.593 | 1.00 | 20.65 |
| ATOM | 120 | CZ | PHE | 44 | 23.334 | 20.665 | 21.282 | 1.00 | 24.87 |
| ATOM | 121 | CE2 | PHE | 44 | 22.251 | 19.920 | 20.774 | 1.00 | 21.14 |
| ATOM | 122 | CD2 | PHE | 44 | 22.380 | 19.293 | 19.489 | 1.00 | 21.59 |
| ATOM | 123 | C | PHE | 44 | 22.419 | 16.876 | 16.281 | 1.00 | 28.43 |
| ATOM | 124 | O | PHE | 44 | 22.799 | 16.807 | 15.106 | 1.00 | 28.39 |
| ATOM | 125 | N | VAL | 45 | 21.164 | 16.684 | 16.663 | 1.00 | 28.52 |
| ATOM | 126 | CA | VAL | 45 | 20.098 | 16.490 | 15.736 | 1.00 | 29.08 |
| ATOM | 127 | CB | VAL | 45 | 19.430 | 15.109 | 15.823 | 1.00 | 29.44 |
| ATOM | 128 | CG1 | VAL | 45 | 20.433 | 13.942 | 15.682 | 1.00 | 28.43 |
| ATOM | 129 | CG2 | VAL | 45 | 18.400 | 15.010 | 14.704 | 1.00 | 29.46 |
| ATOM | 130 | C | VAL | 45 | 19.067 | 17.544 | 16.084 | 1.00 | 29.28 |
| ATOM | 131 | O | VAL | 45 | 18.660 | 17.622 | 17.247 | 1.00 | 28.86 |
| ATOM | 132 | N | LYS | 46 | 18.626 | 18.344 | 15.095 | 1.00 | 28.21 |
| ATOM | 133 | CA | LYS | 46 | 17.560 | 19.364 | 15.343 | 1.00 | 27.33 |
| ATOM | 134 | CB | LYS | 46 | 18.039 | 20.788 | 15.009 | 1.00 | 26.71 |
| ATOM | 135 | CG | LYS | 46 | 16.993 | 21.890 | 15.301 | 1.00 | 28.68 |
| ATOM | 136 | CD | LYS | 46 | 17.108 | 23.041 | 14.364 | 1.00 | 29.59 |
| ATOM | 137 | CE | LYS | 46 | 18.101 | 24.025 | 14.801 | 1.00 | 35.72 |
| ATOM | 138 | NZ | LYS | 46 | 18.767 | 24.737 | 13.550 | 1.00 | 33.53 |
| ATOM | 139 | C | LYS | 46 | 16.302 | 19.057 | 14.565 | 1.00 | 26.64 |
| ATOM | 140 | O | LYS | 46 | 16.376 | 18.817 | 13.399 | 1.00 | 26.42 |
| ATOM | 141 | N | PHE | 47 | 15.146 | 19.105 | 15.209 | 1.00 | 27.04 |
| ATOM | 142 | CA | PHE | 47 | 13.869 | 19.117 | 14.514 | 1.00 | 26.96 |
| ATOM | 143 | CB | PHE | 47 | 12.895 | 18.179 | 15.158 | 1.00 | 27.29 |
| ATOM | 144 | CG | PHE | 47 | 13.386 | 16.819 | 15.167 | 1.00 | 32.14 |
| ATOM | 145 | CD1 | PHE | 47 | 14.281 | 16.400 | 16.147 | 1.00 | 32.34 |
| ATOM | 146 | CE1 | PHE | 47 | 14.802 | 15.100 | 16.093 | 1.00 | 34.46 |
| ATOM | 147 | CZ | PHE | 47 | 14.418 | 14.230 | 15.091 | 1.00 | 33.35 |
| ATOM | 148 | CE2 | PHE | 47 | 13.527 | 14.630 | 14.125 | 1.00 | 35.35 |
| ATOM | 149 | CD2 | PHE | 47 | 13.022 | 15.934 | 14.155 | 1.00 | 35.90 |
| ATOM | 150 | C | PHE | 47 | 13.298 | 20.518 | 14.521 | 1.00 | 26.50 |
| ATOM | 151 | O | PHE | 47 | 13.175 | 21.143 | 15.586 | 1.00 | 25.24 |
| ATOM | 152 | N | ASN | 48 | 12.925 | 20.988 | 13.326 | 1.00 | 26.57 |
| ATOM | 153 | CA | ASN | 48 | 12.216 | 22.271 | 13.191 | 1.00 | 26.60 |
| ATOM | 154 | CB | ASN | 48 | 12.729 | 23.062 | 11.972 | 1.00 | 26.14 |
| ATOM | 155 | CG | ASN | 48 | 14.185 | 23.276 | 12.012 | 1.00 | 23.57 |
| ATOM | 156 | OD1 | ASN | 48 | 14.689 | 23.874 | 12.944 | 1.00 | 28.74 |
| ATOM | 157 | ND2 | ASN | 48 | 14.898 | 22.780 | 11.025 | 1.00 | 24.59 |
| ATOM | 158 | C | ASN | 48 | 10.759 | 21.965 | 13.071 | 1.00 | 26.71 |
| ATOM | 159 | O | ASN | 48 | 10.367 | 21.265 | 12.153 | 1.00 | 26.51 |
| ATOM | 160 | N | CYS | 49 | 9.937 | 22.501 | 13.980 | 1.00 | 27.64 |
| ATOM | 161 | CA | CYS | 49 | 8.530 | 22.095 | 14.036 | 1.00 | 28.17 |
| ATOM | 162 | CB | CYS | 49 | 8.263 | 21.281 | 15.311 | 1.00 | 28.79 |
| ATOM | 163 | SG | CYS | 49 | 9.439 | 19.944 | 15.608 | 1.00 | 32.41 |
| ATOM | 164 | C | CYS | 49 | 7.620 | 23.317 | 14.012 | 1.00 | 28.06 |
| ATOM | 165 | O | CYS | 49 | 7.183 | 23.740 | 15.046 | 1.00 | 26.43 |
| ATOM | 166 | N | PRO | 50 | 7.371 | 23.909 | 12.810 | 1.00 | 28.99 |
| ATOM | 167 | CA | PRO | 50 | 6.627 | 25.176 | 12.676 | 1.00 | 29.58 |
| ATOM | 168 | CB | PRO | 50 | 7.035 | 25.698 | 11.271 | 1.00 | 29.17 |
| ATOM | 169 | CG | PRO | 50 | 7.856 | 24.653 | 10.687 | 1.00 | 29.81 |
| ATOM | 170 | CD | PRO | 50 | 7.877 | 23.434 | 11.507 | 1.00 | 28.43 |
| ATOM | 171 | C | PRO | 50 | 5.129 | 25.037 | 12.734 | 1.00 | 29.99 |
| ATOM | 172 | O | PRO | 50 | 4.437 | 26.042 | 12.772 | 1.00 | 31.25 |
| ATOM | 173 | N | GLU | 51 | 4.638 | 23.818 | 12.762 | 1.00 | 30.28 |
| ATOM | 174 | CA | GLU | 51 | 3.222 | 23.566 | 12.687 | 1.00 | 31.01 |
| ATOM | 175 | CB | GLU | 51 | 2.970 | 22.532 | 11.618 | 1.00 | 31.20 |
| ATOM | 176 | CG | GLU | 51 | 3.336 | 23.048 | 10.233 | 1.00 | 31.72 |
| ATOM | 177 | CD | GLU | 51 | 3.202 | 21.987 | 9.152 | 1.00 | 39.70 |
| ATOM | 178 | OE1 | GLU | 51 | 2.737 | 20.845 | 9.483 | 1.00 | 41.03 |
| ATOM | 179 | OE2 | GLU | 51 | 3.580 | 22.291 | 7.977 | 1.00 | 39.79 |
| ATOM | 180 | C | GLU | 51 | 2.573 | 23.169 | 13.992 | 1.00 | 30.89 |
| ATOM | 181 | O | GLU | 51 | 1.545 | 22.525 | 14.014 | 1.00 | 32.20 |
| ATOM | 182 | N | ILE | 67 | 8.450 | 25.060 | 17.283 | 1.00 | 26.09 |
| ATOM | 183 | CA | ILE | 67 | 9.262 | 24.400 | 18.320 | 1.00 | 25.88 |
| ATOM | 184 | CB | ILE | 67 | 8.491 | 23.211 | 18.964 | 1.00 | 27.19 |
| ATOM | 185 | CG1 | ILE | 67 | 7.221 | 23.695 | 19.674 | 1.00 | 26.17 |
| ATOM | 186 | CD1 | ILE | 67 | 6.369 | 22.525 | 19.940 | 1.00 | 28.34 |
| ATOM | 187 | CG2 | ILE | 67 | 9.313 | 22.553 | 20.046 | 1.00 | 27.68 |
| ATOM | 188 | C | ILE | 67 | 10.535 | 23.870 | 17.713 | 1.00 | 25.12 |
| ATOM | 189 | O | ILE | 67 | 10.509 | 23.231 | 16.655 | 1.00 | 23.17 |
| ATOM | 190 | N | TYR | 68 | 11.657 | 24.191 | 18.347 | 1.00 | 25.62 |

TABLE 2-continued

| | | | | | | | | | |
|---|---|---|---|---|---|---|---|---|---|
| ATOM | 191 | CA | TYR | 68 | 12.994 | 23.673 | 17.937 | 1.00 | 25.42 |
| ATOM | 192 | CB | TYR | 68 | 14.002 | 24.810 | 17.833 | 1.00 | 24.80 |
| ATOM | 193 | CG | TYR | 68 | 13.560 | 25.871 | 16.820 | 1.00 | 28.39 |
| ATOM | 194 | CD1 | TYR | 68 | 12.891 | 27.021 | 17.249 | 1.00 | 23.93 |
| ATOM | 195 | CE1 | TYR | 68 | 12.443 | 27.960 | 16.360 | 1.00 | 29.14 |
| ATOM | 196 | CZ | TYR | 68 | 12.674 | 27.784 | 14.974 | 1.00 | 31.13 |
| ATOM | 197 | OH | TYR | 68 | 12.240 | 28.772 | 14.091 | 1.00 | 29.59 |
| ATOM | 198 | CE2 | TYR | 68 | 13.322 | 26.650 | 14.515 | 1.00 | 30.72 |
| ATOM | 199 | CD2 | TYR | 68 | 13.781 | 25.700 | 15.440 | 1.00 | 25.51 |
| ATOM | 200 | C | TYR | 68 | 13.488 | 22.631 | 18.946 | 1.00 | 25.82 |
| ATOM | 201 | O | TYR | 68 | 13.677 | 22.958 | 20.107 | 1.00 | 26.19 |
| ATOM | 202 | N | ILE | 69 | 13.727 | 21.399 | 18.507 | 1.00 | 25.80 |
| ATOM | 203 | CA | ILE | 69 | 14.164 | 20.366 | 19.438 | 1.00 | 26.12 |
| ATOM | 204 | CB | ILE | 69 | 13.192 | 19.155 | 19.435 | 1.00 | 25.81 |
| ATOM | 205 | CG1 | ILE | 69 | 11.800 | 19.560 | 19.904 | 1.00 | 25.28 |
| ATOM | 206 | CD1 | ILE | 69 | 10.647 | 18.610 | 19.326 | 1.00 | 25.09 |
| ATOM | 207 | CG2 | ILE | 69 | 13.669 | 18.025 | 20.326 | 1.00 | 24.45 |
| ATOM | 208 | C | ILE | 69 | 15.537 | 19.970 | 18.980 | 1.00 | 27.18 |
| ATOM | 209 | O | ILE | 69 | 15.711 | 19.595 | 17.839 | 1.00 | 29.73 |
| ATOM | 210 | N | SER | 70 | 16.530 | 20.095 | 19.844 | 1.00 | 27.73 |
| ATOM | 211 | CA | SER | 70 | 17.873 | 19.772 | 19.497 | 1.00 | 28.67 |
| ATOM | 212 | CB | SER | 70 | 18.704 | 21.025 | 19.410 | 1.00 | 29.42 |
| ATOM | 213 | OG | SER | 70 | 18.208 | 21.886 | 18.296 | 1.00 | 34.23 |
| ATOM | 214 | C | SER | 70 | 18.380 | 18.851 | 20.597 | 1.00 | 29.55 |
| ATOM | 215 | O | SER | 70 | 18.217 | 19.157 | 21.798 | 1.00 | 29.82 |
| ATOM | 216 | N | TYR | 71 | 18.932 | 17.697 | 20.198 | 1.00 | 29.35 |
| ATOM | 217 | CA | TYR | 71 | 19.378 | 16.734 | 21.168 | 1.00 | 27.96 |
| ATOM | 218 | CB | TYR | 71 | 18.269 | 15.743 | 21.482 | 1.00 | 27.91 |
| ATOM | 219 | CG | TYR | 71 | 18.063 | 14.619 | 20.507 | 1.00 | 28.69 |
| ATOM | 220 | CD1 | TYR | 71 | 17.414 | 14.814 | 19.280 | 1.00 | 29.56 |
| ATOM | 221 | CE1 | TYR | 71 | 17.218 | 13.737 | 18.375 | 1.00 | 27.79 |
| ATOM | 222 | CZ | TYR | 71 | 17.658 | 12.490 | 18.722 | 1.00 | 29.89 |
| ATOM | 223 | OH | TYR | 71 | 17.486 | 11.417 | 17.869 | 1.00 | 28.88 |
| ATOM | 224 | CE2 | TYR | 71 | 18.301 | 12.290 | 19.944 | 1.00 | 27.21 |
| ATOM | 225 | CD2 | TYR | 71 | 18.498 | 13.353 | 20.809 | 1.00 | 28.69 |
| ATOM | 226 | C | TYR | 71 | 20.606 | 16.047 | 20.662 | 1.00 | 28.99 |
| ATOM | 227 | O | TYR | 71 | 20.816 | 15.999 | 19.436 | 1.00 | 28.16 |
| ATOM | 228 | N | ILE | 72 | 21.403 | 15.512 | 21.608 | 1.00 | 28.15 |
| ATOM | 229 | CA | ILE | 72 | 22.527 | 14.632 | 21.330 | 1.00 | 27.77 |
| ATOM | 230 | CB | ILE | 72 | 23.778 | 15.117 | 22.058 | 1.00 | 28.36 |
| ATOM | 231 | CG1 | ILE | 72 | 24.037 | 16.580 | 21.681 | 1.00 | 25.91 |
| ATOM | 232 | CD1 | ILE | 72 | 25.211 | 17.194 | 22.264 | 1.00 | 25.97 |
| ATOM | 233 | CG2 | ILE | 72 | 24.916 | 14.148 | 21.853 | 1.00 | 27.34 |
| ATOM | 234 | C | ILE | 72 | 22.189 | 13.242 | 21.817 | 1.00 | 29.26 |
| ATOM | 235 | O | ILE | 72 | 21.985 | 13.031 | 23.023 | 1.00 | 28.17 |
| ATOM | 236 | N | PRO | 73 | 22.096 | 12.298 | 20.879 | 1.00 | 30.21 |
| ATOM | 237 | CA | PRO | 73 | 21.661 | 10.945 | 21.158 | 1.00 | 31.77 |
| ATOM | 238 | CB | PRO | 73 | 21.523 | 10.285 | 19.763 | 1.00 | 31.45 |
| ATOM | 239 | CG | PRO | 73 | 21.822 | 11.320 | 18.777 | 1.00 | 31.27 |
| ATOM | 240 | CD | PRO | 73 | 22.440 | 12.493 | 19.457 | 1.00 | 30.65 |
| ATOM | 241 | C | PRO | 73 | 22.696 | 10.182 | 21.950 | 1.00 | 32.63 |
| ATOM | 242 | O | PRO | 73 | 23.932 | 10.405 | 21.813 | 1.00 | 31.96 |
| ATOM | 243 | N | ASP | 74 | 22.189 | 9.281 | 22.780 | 1.00 | 34.84 |
| ATOM | 244 | CA | ASP | 74 | 23.064 | 8.276 | 23.347 | 1.00 | 37.48 |
| ATOM | 245 | CB | ASP | 74 | 22.806 | 7.968 | 24.831 | 1.00 | 37.93 |
| ATOM | 246 | CG | ASP | 74 | 23.936 | 7.070 | 25.457 | 1.00 | 42.79 |
| ATOM | 247 | OD1 | ASP | 74 | 24.844 | 6.568 | 24.731 | 1.00 | 42.65 |
| ATOM | 248 | OD2 | ASP | 74 | 23.910 | 6.873 | 26.697 | 1.00 | 49.88 |
| ATOM | 249 | C | ASP | 74 | 22.919 | 7.059 | 22.460 | 1.00 | 37.65 |
| ATOM | 250 | O | ASP | 74 | 23.629 | 6.951 | 21.488 | 1.00 | 38.69 |
| ATOM | 251 | N | GLU | 75 | 21.995 | 6.165 | 22.745 | 1.00 | 38.85 |
| ATOM | 252 | CA | GLU | 75 | 21.892 | 4.942 | 21.950 | 1.00 | 40.70 |
| ATOM | 253 | CB | GLU | 75 | 21.909 | 3.714 | 22.867 | 1.00 | 40.16 |
| ATOM | 254 | CG | GLU | 75 | 23.314 | 3.449 | 23.408 | 1.00 | 44.92 |
| ATOM | 255 | CD | GLU | 75 | 23.357 | 2.511 | 24.640 | 1.00 | 46.78 |
| ATOM | 256 | OE1 | GLU | 75 | 22.296 | 2.321 | 25.319 | 1.00 | 54.36 |
| ATOM | 257 | OE2 | GLU | 75 | 24.472 | 1.979 | 24.927 | 1.00 | 54.45 |
| ATOM | 258 | C | GLU | 75 | 20.649 | 4.897 | 21.111 | 1.00 | 39.36 |
| ATOM | 259 | O | GLU | 75 | 20.529 | 4.080 | 20.235 | 1.00 | 38.59 |
| ATOM | 260 | N | LYS | 76 | 19.697 | 5.764 | 21.400 | 1.00 | 40.19 |
| ATOM | 261 | CA | LYS | 76 | 18.416 | 5.703 | 20.702 | 1.00 | 40.59 |
| ATOM | 262 | CB | LYS | 76 | 17.306 | 5.329 | 21.669 | 1.00 | 40.27 |
| ATOM | 263 | CG | LYS | 76 | 17.579 | 4.062 | 22.379 | 1.00 | 41.53 |
| ATOM | 264 | CD | LYS | 76 | 16.310 | 3.496 | 22.950 | 1.00 | 48.56 |
| ATOM | 265 | CE | LYS | 76 | 16.606 | 2.336 | 23.891 | 1.00 | 50.36 |
| ATOM | 266 | NZ | LYS | 76 | 15.543 | 2.252 | 24.940 | 1.00 | 53.45 |
| ATOM | 267 | C | LYS | 76 | 18.130 | 7.041 | 20.037 | 1.00 | 39.88 |
| ATOM | 268 | O | LYS | 76 | 18.556 | 8.076 | 20.541 | 1.00 | 39.23 |
| ATOM | 269 | N | MET | 77 | 17.423 | 6.985 | 18.903 | 1.00 | 39.37 |
| ATOM | 270 | CA | MET | 77 | 17.086 | 8.162 | 18.110 | 1.00 | 39.16 |

TABLE 2-continued

| | | | | | | | | | |
|---|---|---|---|---|---|---|---|---|---|
| ATOM | 271 | CB | MET | 77 | 17.740 | 8.031 | 16.792 | 1.00 | 39.27 |
| ATOM | 272 | CG | MET | 77 | 18.609 | 9.189 | 16.485 | 1.00 | 44.87 |
| ATOM | 273 | SD | MET | 77 | 20.263 | 8.615 | 16.645 | 1.00 | 47.51 |
| ATOM | 274 | CE | MET | 77 | 20.467 | 8.068 | 14.957 | 1.00 | 48.97 |
| ATOM | 275 | C | MET | 77 | 15.599 | 8.184 | 17.897 | 1.00 | 37.73 |
| ATOM | 276 | O | MET | 77 | 15.023 | 7.150 | 17.709 | 1.00 | 38.50 |
| ATOM | 277 | N | VAL | 78 | 14.951 | 9.338 | 17.949 | 1.00 | 36.61 |
| ATOM | 278 | CA | VAL | 78 | 13.497 | 9.377 | 17.676 | 1.00 | 35.17 |
| ATOM | 279 | CB | VAL | 78 | 12.739 | 10.540 | 18.393 | 1.00 | 36.02 |
| ATOM | 280 | CG1 | VAL | 78 | 13.302 | 11.919 | 18.008 | 1.00 | 36.14 |
| ATOM | 281 | CG2 | VAL | 78 | 11.229 | 10.482 | 18.121 | 1.00 | 33.46 |
| ATOM | 282 | C | VAL | 78 | 13.222 | 9.379 | 16.168 | 1.00 | 35.32 |
| ATOM | 283 | O | VAL | 78 | 13.955 | 9.990 | 15.372 | 1.00 | 33.32 |
| ATOM | 284 | N | GLU | 79 | 12.148 | 8.688 | 15.805 | 1.00 | 35.31 |
| ATOM | 285 | CA | GLU | 79 | 11.756 | 8.567 | 14.440 | 1.00 | 35.07 |
| ATOM | 286 | CB | GLU | 79 | 11.061 | 7.215 | 14.250 | 1.00 | 35.69 |
| ATOM | 287 | CG | GLU | 79 | 10.883 | 6.837 | 12.764 | 1.00 | 40.72 |
| ATOM | 288 | CD | GLU | 79 | 9.675 | 7.492 | 12.125 | 1.00 | 45.36 |
| ATOM | 289 | OE1 | GLU | 79 | 8.556 | 7.333 | 12.684 | 1.00 | 47.59 |
| ATOM | 290 | OE2 | GLU | 79 | 9.844 | 8.153 | 11.060 | 1.00 | 47.64 |
| ATOM | 291 | C | GLU | 79 | 10.847 | 9.756 | 14.132 | 1.00 | 33.69 |
| ATOM | 292 | O | GLU | 79 | 9.898 | 10.008 | 14.853 | 1.00 | 31.63 |
| ATOM | 293 | N | SER | 80 | 11.172 | 10.492 | 13.064 | 1.00 | 33.31 |
| ATOM | 294 | CA | SER | 80 | 10.411 | 11.664 | 12.599 | 1.00 | 33.28 |
| ATOM | 295 | CB | SER | 80 | 10.840 | 12.005 | 11.210 | 1.00 | 33.95 |
| ATOM | 296 | OG | SER | 80 | 12.232 | 12.182 | 11.237 | 1.00 | 40.59 |
| ATOM | 297 | C | SER | 80 | 8.918 | 11.592 | 12.513 | 1.00 | 33.46 |
| ATOM | 298 | O | SER | 80 | 8.229 | 12.506 | 13.010 | 1.00 | 33.68 |
| ATOM | 299 | N | LYS | 81 | 8.407 | 10.565 | 11.814 | 1.00 | 33.65 |
| ATOM | 300 | CA | LYS | 81 | 6.991 | 10.458 | 11.624 | 1.00 | 34.76 |
| ATOM | 301 | CB | LYS | 81 | 6.625 | 9.300 | 10.717 | 1.00 | 35.65 |
| ATOM | 302 | CG | LYS | 81 | 5.064 | 9.048 | 10.586 | 1.00 | 39.18 |
| ATOM | 303 | CD | LYS | 81 | 4.755 | 7.840 | 9.678 | 1.00 | 39.66 |
| ATOM | 304 | CE | LYS | 81 | 5.604 | 7.895 | 8.332 | 1.00 | 48.39 |
| ATOM | 305 | NZ | LYS | 81 | 5.467 | 6.699 | 7.349 | 1.00 | 47.55 |
| ATOM | 306 | C | LYS | 81 | 6.338 | 10.291 | 12.972 | 1.00 | 33.64 |
| ATOM | 307 | O | LYS | 81 | 5.253 | 10.843 | 13.196 | 1.00 | 33.95 |
| ATOM | 308 | N | SER | 82 | 7.000 | 9.553 | 13.881 | 1.00 | 32.20 |
| ATOM | 309 | CA | SER | 82 | 6.409 | 9.355 | 15.201 | 1.00 | 30.55 |
| ATOM | 310 | CB | SER | 82 | 7.069 | 8.204 | 15.986 | 1.00 | 30.70 |
| ATOM | 311 | OG | SER | 82 | 8.379 | 8.507 | 16.454 | 1.00 | 29.50 |
| ATOM | 312 | C | SER | 82 | 6.400 | 10.668 | 15.992 | 1.00 | 29.19 |
| ATOM | 313 | O | SER | 82 | 5.438 | 10.987 | 16.681 | 1.00 | 27.98 |
| ATOM | 314 | N | LEU | 83 | 7.470 | 11.425 | 15.877 | 1.00 | 28.73 |
| ATOM | 315 | CA | LEU | 83 | 7.485 | 12.755 | 16.451 | 1.00 | 29.29 |
| ATOM | 316 | CB | LEU | 83 | 8.880 | 13.372 | 16.227 | 1.00 | 30.66 |
| ATOM | 317 | CG | LEU | 83 | 8.823 | 14.764 | 16.853 | 1.00 | 28.90 |
| ATOM | 318 | CD1 | LEU | 83 | 8.651 | 14.650 | 18.377 | 1.00 | 26.97 |
| ATOM | 319 | CD2 | LEU | 83 | 10.032 | 15.521 | 16.451 | 1.00 | 25.69 |
| ATOM | 320 | C | LEU | 83 | 6.331 | 13.656 | 15.893 | 1.00 | 29.47 |
| ATOM | 321 | O | LEU | 83 | 5.555 | 14.263 | 16.669 | 1.00 | 28.25 |
| ATOM | 322 | N | LYS | 84 | 6.144 | 13.657 | 14.563 | 1.00 | 29.53 |
| ATOM | 323 | CA | LYS | 84 | 5.027 | 14.392 | 13.981 | 1.00 | 29.62 |
| ATOM | 324 | CB | LYS | 84 | 5.065 | 14.320 | 12.452 | 1.00 | 30.52 |
| ATOM | 325 | CG | LYS | 84 | 3.756 | 14.693 | 11.746 | 1.00 | 33.47 |
| ATOM | 326 | CD | LYS | 84 | 3.702 | 14.115 | 10.337 | 1.00 | 38.12 |
| ATOM | 327 | CE | LYS | 84 | 2.966 | 12.798 | 10.340 | 1.00 | 42.09 |
| ATOM | 328 | NZ | LYS | 84 | 2.748 | 12.320 | 8.952 | 1.00 | 45.75 |
| ATOM | 329 | C | LYS | 84 | 3.657 | 13.995 | 14.540 | 1.00 | 29.83 |
| ATOM | 330 | O | LYS | 84 | 2.830 | 14.844 | 14.899 | 1.00 | 28.57 |
| ATOM | 331 | N | LEU | 85 | 3.392 | 12.701 | 14.621 | 1.00 | 30.73 |
| ATOM | 332 | CA | LEU | 85 | 2.080 | 12.277 | 15.187 | 1.00 | 31.39 |
| ATOM | 333 | CB | LEU | 85 | 1.865 | 10.780 | 15.005 | 1.00 | 32.27 |
| ATOM | 334 | CG | LEU | 85 | 2.045 | 10.305 | 13.579 | 1.00 | 34.28 |
| ATOM | 335 | CD1 | LEU | 85 | 2.180 | 8.766 | 13.544 | 1.00 | 36.91 |
| ATOM | 336 | CD2 | LEU | 85 | 0.800 | 10.842 | 12.846 | 1.00 | 35.13 |
| ATOM | 337 | C | LEU | 85 | 1.974 | 12.629 | 16.665 | 1.00 | 30.61 |
| ATOM | 338 | O | LEU | 85 | 0.910 | 13.001 | 17.183 | 1.00 | 31.60 |
| ATOM | 339 | N | LEU | 108 | 10.416 | 12.939 | 25.558 | 1.00 | 29.21 |
| ATOM | 340 | CA | LEU | 108 | 11.547 | 12.485 | 24.710 | 1.00 | 29.45 |
| ATOM | 341 | CB | LEU | 108 | 12.008 | 13.582 | 23.719 | 1.00 | 27.71 |
| ATOM | 342 | CG | LEU | 108 | 11.033 | 14.016 | 22.592 | 1.00 | 28.91 |
| ATOM | 343 | CD1 | LEU | 108 | 11.304 | 15.414 | 22.065 | 1.00 | 25.44 |
| ATOM | 344 | CD2 | LEU | 108 | 11.048 | 12.984 | 21.486 | 1.00 | 27.35 |
| ATOM | 345 | C | LEU | 108 | 12.761 | 11.949 | 25.488 | 1.00 | 29.54 |
| ATOM | 346 | O | LEU | 108 | 13.485 | 11.090 | 25.003 | 1.00 | 29.35 |
| ATOM | 347 | N | ILE | 109 | 13.026 | 12.506 | 26.656 | 1.00 | 31.05 |
| ATOM | 348 | CA | ILE | 109 | 14.003 | 11.891 | 27.612 | 1.00 | 31.94 |
| ATOM | 349 | CB | ILE | 109 | 14.168 | 12.751 | 28.917 | 1.00 | 31.14 |
| ATOM | 350 | CG1 | ILE | 109 | 14.791 | 14.088 | 28.562 | 1.00 | 27.52 |

TABLE 2-continued

| | | | | | | | | | |
|---|---|---|---|---|---|---|---|---|---|
| ATOM | 351 | CD1 | ILE | 109 | 14.643 | 15.182 | 29.578 | 1.00 | 20.42 |
| ATOM | 352 | CG2 | ILE | 109 | 15.051 | 11.966 | 30.036 | 1.00 | 31.36 |
| ATOM | 353 | C | ILE | 109 | 13.585 | 10.434 | 27.908 | 1.00 | 32.87 |
| ATOM | 354 | O | ILE | 109 | 14.330 | 9.472 | 27.708 | 1.00 | 33.43 |
| ATOM | 355 | N | LEU | 111 | 11.841 | 8.551 | 26.120 | 1.00 | 37.15 |
| ATOM | 356 | CA | LEU | 111 | 11.960 | 7.704 | 24.939 | 1.00 | 35.89 |
| ATOM | 357 | CB | LEU | 111 | 11.356 | 8.414 | 23.693 | 1.00 | 36.43 |
| ATOM | 358 | CG | LEU | 111 | 11.349 | 7.580 | 22.412 | 1.00 | 36.11 |
| ATOM | 359 | CD1 | LEU | 111 | 10.145 | 6.607 | 22.432 | 1.00 | 37.90 |
| ATOM | 360 | CD2 | LEU | 111 | 11.315 | 8.495 | 21.211 | 1.00 | 37.24 |
| ATOM | 361 | C | LEU | 111 | 13.381 | 7.306 | 24.644 | 1.00 | 35.65 |
| ATOM | 362 | O | LEU | 111 | 13.653 | 6.201 | 24.221 | 1.00 | 34.88 |
| ATOM | 363 | N | MET | 112 | 14.315 | 8.212 | 24.848 | 1.00 | 35.91 |
| ATOM | 364 | CA | MET | 112 | 15.604 | 8.018 | 24.256 | 1.00 | 36.32 |
| ATOM | 365 | CB | MET | 112 | 15.889 | 9.211 | 23.353 | 1.00 | 35.34 |
| ATOM | 366 | CG | MET | 112 | 14.937 | 9.328 | 22.184 | 1.00 | 38.19 |
| ATOM | 367 | SD | MET | 112 | 15.438 | 10.856 | 21.291 | 1.00 | 41.36 |
| ATOM | 368 | CE | MET | 112 | 17.044 | 10.327 | 20.756 | 1.00 | 45.22 |
| ATOM | 369 | C | MET | 112 | 16.770 | 7.911 | 25.217 | 1.00 | 36.50 |
| ATOM | 370 | O | MET | 112 | 17.882 | 7.476 | 24.800 | 1.00 | 36.67 |
| ATOM | 371 | N | ASP | 113 | 16.586 | 8.399 | 26.449 | 1.00 | 35.83 |
| ATOM | 372 | CA | ASP | 113 | 17.720 | 8.582 | 27.361 | 1.00 | 35.39 |
| ATOM | 373 | CB | ASP | 113 | 18.141 | 7.215 | 27.921 | 1.00 | 36.49 |
| ATOM | 374 | CG | ASP | 113 | 18.777 | 7.297 | 29.298 | 1.00 | 39.41 |
| ATOM | 375 | OD1 | ASP | 113 | 18.637 | 8.317 | 29.990 | 1.00 | 43.60 |
| ATOM | 376 | OD2 | ASP | 113 | 19.389 | 6.298 | 29.714 | 1.00 | 45.15 |
| ATOM | 377 | C | ASP | 113 | 18.903 | 9.276 | 26.668 | 1.00 | 33.49 |
| ATOM | 378 | O | ASP | 113 | 19.947 | 8.681 | 26.508 | 1.00 | 32.99 |
| ATOM | 379 | N | PRO | 114 | 18.738 | 10.566 | 26.249 | 1.00 | 32.68 |
| ATOM | 380 | CA | PRO | 114 | 19.798 | 11.226 | 25.457 | 1.00 | 30.79 |
| ATOM | 381 | CB | PRO | 114 | 19.069 | 12.431 | 24.860 | 1.00 | 30.42 |
| ATOM | 382 | CG | PRO | 114 | 17.961 | 12.720 | 25.771 | 1.00 | 29.14 |
| ATOM | 383 | CD | PRO | 114 | 17.559 | 11.435 | 26.420 | 1.00 | 31.41 |
| ATOM | 384 | C | PRO | 114 | 20.916 | 11.717 | 26.308 | 1.00 | 30.07 |
| ATOM | 385 | O | PRO | 114 | 20.710 | 11.869 | 27.466 | 1.00 | 30.91 |
| ATOM | 386 | N | ARG | 115 | 22.076 | 12.025 | 25.741 | 1.00 | 28.48 |
| ATOM | 387 | CA | ARG | 115 | 23.066 | 12.751 | 26.472 | 1.00 | 28.18 |
| ATOM | 388 | CB | ARG | 115 | 24.346 | 12.786 | 25.662 | 1.00 | 28.21 |
| ATOM | 389 | CG | ARG | 115 | 24.632 | 11.459 | 25.053 | 1.00 | 25.85 |
| ATOM | 390 | CD | ARG | 115 | 26.071 | 11.295 | 24.625 | 1.00 | 28.97 |
| ATOM | 391 | NE | ARG | 115 | 26.197 | 9.894 | 24.235 | 1.00 | 34.99 |
| ATOM | 392 | CZ | ARG | 115 | 26.858 | 9.430 | 23.186 | 1.00 | 38.60 |
| ATOM | 393 | NH1 | ARG | 115 | 27.516 | 10.259 | 22.373 | 1.00 | 38.73 |
| ATOM | 394 | NH2 | ARG | 115 | 26.816 | 8.126 | 22.935 | 1.00 | 38.83 |
| ATOM | 395 | C | ARG | 115 | 22.635 | 14.179 | 26.823 | 1.00 | 28.80 |
| ATOM | 396 | O | ARG | 115 | 22.912 | 14.687 | 27.936 | 1.00 | 28.39 |
| ATOM | 397 | N | TYR | 116 | 21.927 | 14.812 | 25.883 | 1.00 | 28.65 |
| ATOM | 398 | CA | TYR | 116 | 21.518 | 16.195 | 25.960 | 1.00 | 29.17 |
| ATOM | 399 | CB | TYR | 116 | 22.645 | 17.088 | 25.448 | 1.00 | 29.36 |
| ATOM | 400 | CG | TYR | 116 | 22.216 | 18.526 | 25.538 | 1.00 | 32.26 |
| ATOM | 401 | CD1 | TYR | 116 | 22.308 | 19.208 | 26.760 | 1.00 | 28.21 |
| ATOM | 402 | CE1 | TYR | 116 | 21.913 | 20.499 | 26.881 | 1.00 | 30.01 |
| ATOM | 403 | CZ | TYR | 116 | 21.393 | 21.168 | 25.779 | 1.00 | 31.19 |
| ATOM | 404 | OH | TYR | 116 | 20.975 | 22.467 | 25.966 | 1.00 | 33.77 |
| ATOM | 405 | CE2 | TYR | 116 | 21.291 | 20.553 | 24.551 | 1.00 | 29.32 |
| ATOM | 406 | CD2 | TYR | 116 | 21.688 | 19.213 | 24.411 | 1.00 | 29.15 |
| ATOM | 407 | C | TYR | 116 | 20.284 | 16.416 | 25.088 | 1.00 | 29.33 |
| ATOM | 408 | O | TYR | 116 | 20.154 | 15.776 | 24.056 | 1.00 | 29.53 |
| ATOM | 409 | N | ILE | 117 | 19.388 | 17.285 | 25.525 | 1.00 | 27.82 |
| ATOM | 410 | CA | ILE | 117 | 18.223 | 17.672 | 24.780 | 1.00 | 27.63 |
| ATOM | 411 | CB | ILE | 117 | 17.040 | 16.686 | 24.926 | 1.00 | 29.09 |
| ATOM | 412 | CG1 | ILE | 117 | 15.858 | 17.154 | 24.080 | 1.00 | 25.55 |
| ATOM | 413 | CD1 | ILE | 117 | 14.911 | 16.060 | 23.690 | 1.00 | 23.85 |
| ATOM | 414 | CG2 | ILE | 117 | 16.578 | 16.564 | 26.426 | 1.00 | 26.67 |
| ATOM | 415 | C | ILE | 117 | 17.798 | 19.045 | 25.314 | 1.00 | 28.11 |
| ATOM | 416 | O | ILE | 117 | 18.017 | 19.367 | 26.521 | 1.00 | 27.07 |
| ATOM | 417 | N | GLU | 118 | 17.285 | 19.866 | 24.383 | 1.00 | 27.21 |
| ATOM | 418 | CA | GLU | 118 | 16.648 | 21.131 | 24.681 | 1.00 | 27.80 |
| ATOM | 419 | CB | GLU | 118 | 17.615 | 22.270 | 24.505 | 1.00 | 26.73 |
| ATOM | 420 | CG | GLU | 118 | 18.168 | 22.420 | 23.089 | 1.00 | 29.93 |
| ATOM | 421 | CD | GLU | 118 | 19.109 | 23.586 | 22.987 | 1.00 | 34.46 |
| ATOM | 422 | OE1 | GLU | 118 | 19.928 | 23.827 | 23.924 | 1.00 | 29.71 |
| ATOM | 423 | OE2 | GLU | 118 | 19.000 | 24.295 | 21.957 | 1.00 | 38.97 |
| ATOM | 424 | C | GLU | 118 | 15.428 | 21.323 | 23.778 | 1.00 | 28.08 |
| ATOM | 425 | O | GLU | 118 | 15.382 | 20.830 | 22.638 | 1.00 | 28.69 |
| ATOM | 426 | N | VAL | 119 | 14.460 | 22.055 | 24.286 | 1.00 | 26.85 |
| ATOM | 427 | CA | VAL | 119 | 13.244 | 22.308 | 23.566 | 1.00 | 26.53 |
| ATOM | 428 | CB | VAL | 119 | 12.055 | 21.539 | 24.169 | 1.00 | 26.83 |
| ATOM | 429 | CG1 | VAL | 119 | 10.767 | 21.999 | 23.540 | 1.00 | 22.98 |
| ATOM | 430 | CG2 | VAL | 119 | 12.265 | 19.977 | 23.977 | 1.00 | 26.48 |

TABLE 2-continued

| | | | | | | | | | |
|---|---|---|---|---|---|---|---|---|---|
| ATOM | 431 | C | VAL | 119 | 13.087 | 23.788 | 23.707 | 1.00 | 28.09 |
| ATOM | 432 | O | VAL | 119 | 13.156 | 24.296 | 24.836 | 1.00 | 28.03 |
| ATOM | 433 | N | TYR | 137 | 18.338 | 19.727 | 29.299 | 1.00 | 27.60 |
| ATOM | 434 | CA | TYR | 137 | 18.612 | 18.584 | 30.111 | 1.00 | 29.91 |
| ATOM | 435 | CB | TYR | 137 | 17.438 | 17.617 | 30.008 | 1.00 | 29.40 |
| ATOM | 436 | CG | TYR | 137 | 17.752 | 16.214 | 30.425 | 1.00 | 32.68 |
| ATOM | 437 | CD1 | TYR | 137 | 18.344 | 15.316 | 29.524 | 1.00 | 33.25 |
| ATOM | 438 | CE1 | TYR | 137 | 18.669 | 14.017 | 29.879 | 1.00 | 32.68 |
| ATOM | 439 | CZ | TYR | 137 | 18.356 | 13.567 | 31.175 | 1.00 | 36.06 |
| ATOM | 440 | OH | TYR | 137 | 18.674 | 12.245 | 31.569 | 1.00 | 35.08 |
| ATOM | 441 | CE2 | TYR | 137 | 17.741 | 14.440 | 32.091 | 1.00 | 35.15 |
| ATOM | 442 | CD2 | TYR | 137 | 17.443 | 15.757 | 31.719 | 1.00 | 34.21 |
| ATOM | 443 | C | TYR | 137 | 19.897 | 17.949 | 29.597 | 1.00 | 30.63 |
| ATOM | 444 | O | TYR | 137 | 20.101 | 17.909 | 28.392 | 1.00 | 29.44 |
| ATOM | 445 | N | TYR | 150 | 25.459 | 25.324 | 31.174 | 1.00 | 32.57 |
| ATOM | 446 | CA | TYR | 150 | 26.162 | 26.349 | 30.435 | 1.00 | 32.62 |
| ATOM | 447 | CB | TYR | 150 | 27.343 | 25.742 | 29.738 | 1.00 | 32.80 |
| ATOM | 448 | CG | TYR | 150 | 28.000 | 26.634 | 28.720 | 1.00 | 32.42 |
| ATOM | 449 | CD1 | TYR | 150 | 28.983 | 27.571 | 29.089 | 1.00 | 32.30 |
| ATOM | 450 | CE1 | TYR | 150 | 29.593 | 28.388 | 28.111 | 1.00 | 34.19 |
| ATOM | 451 | CZ | TYR | 150 | 29.217 | 28.202 | 26.742 | 1.00 | 35.25 |
| ATOM | 452 | OH | TYR | 150 | 29.770 | 28.959 | 25.709 | 1.00 | 36.34 |
| ATOM | 453 | CE2 | TYR | 150 | 28.276 | 27.277 | 26.390 | 1.00 | 29.47 |
| ATOM | 454 | CD2 | TYR | 150 | 27.687 | 26.495 | 27.369 | 1.00 | 32.67 |
| ATOM | 455 | C | TYR | 150 | 25.178 | 26.953 | 29.403 | 1.00 | 32.73 |
| ATOM | 456 | O | TYR | 150 | 25.046 | 28.169 | 29.322 | 1.00 | 32.79 |
| ATOM | 457 | N | ARG | 151 | 24.471 | 26.091 | 28.676 | 1.00 | 31.98 |
| ATOM | 458 | CA | ARG | 151 | 23.510 | 26.560 | 27.684 | 1.00 | 32.65 |
| ATOM | 459 | CB | ARG | 151 | 23.102 | 25.432 | 26.725 | 1.00 | 31.68 |
| ATOM | 460 | CG | ARG | 151 | 24.243 | 25.070 | 25.737 | 1.00 | 29.13 |
| ATOM | 461 | CD | ARG | 151 | 23.870 | 23.831 | 24.912 | 1.00 | 32.01 |
| ATOM | 462 | NE | ARG | 151 | 22.950 | 24.165 | 23.819 | 1.00 | 34.34 |
| ATOM | 463 | CZ | ARG | 151 | 23.303 | 24.320 | 22.545 | 1.00 | 34.17 |
| ATOM | 464 | NH1 | ARG | 151 | 24.552 | 24.117 | 22.147 | 1.00 | 32.39 |
| ATOM | 465 | NH2 | ARG | 151 | 22.388 | 24.650 | 21.652 | 1.00 | 37.11 |
| ATOM | 466 | C | ARG | 151 | 22.331 | 27.321 | 28.272 | 1.00 | 33.84 |
| ATOM | 467 | O | ARG | 151 | 21.877 | 28.275 | 27.672 | 1.00 | 34.65 |
| ATOM | 468 | O6 | GDQ | 201 | 16.252 | 10.579 | 8.263 | 1.00 | 46.59 |
| ATOM | 469 | C6 | GDQ | 201 | 15.270 | 10.328 | 9.202 | 1.00 | 48.37 |
| ATOM | 470 | N1 | GDQ | 201 | 15.542 | 10.525 | 10.528 | 1.00 | 46.85 |
| ATOM | 471 | C5 | GDQ | 201 | 13.991 | 9.855 | 8.867 | 1.00 | 46.54 |
| ATOM | 472 | C7 | GDQ | 201 | 13.276 | 9.517 | 7.718 | 1.00 | 48.07 |
| ATOM | 473 | C77 | GDQ | 201 | 13.836 | 9.542 | 6.477 | 1.00 | 48.31 |
| ATOM | 474 | N77 | GDQ | 201 | 14.649 | 9.596 | 5.520 | 1.00 | 47.22 |
| ATOM | 475 | C8 | GDQ | 201 | 11.979 | 9.046 | 8.000 | 1.00 | 46.57 |
| ATOM | 476 | N9 | GDQ | 201 | 11.862 | 9.143 | 9.373 | 1.00 | 46.58 |
| ATOM | 477 | C4 | GDQ | 201 | 13.063 | 9.610 | 9.883 | 1.00 | 46.73 |
| ATOM | 478 | N3 | GDQ | 201 | 13.377 | 9.834 | 11.192 | 1.00 | 45.07 |
| ATOM | 479 | C2 | GDQ | 201 | 14.604 | 10.305 | 11.490 | 1.00 | 45.80 |
| ATOM | 480 | N2 | GDQ | 201 | 14.938 | 10.550 | 12.771 | 1.00 | 47.19 |
| ATOM | 481 | N | PHE | 47 | 32.632 | 23.771 | 1.969 | 1.00 | 25.69 |
| ATOM | 482 | CA | PHE | 47 | 31.781 | 23.461 | 0.804 | 1.00 | 25.78 |
| ATOM | 483 | CB | PHE | 47 | 32.013 | 22.023 | 0.346 | 1.00 | 26.07 |
| ATOM | 484 | CG | PHE | 47 | 33.463 | 21.733 | 0.066 | 1.00 | 25.38 |
| ATOM | 485 | CD1 | PHE | 47 | 34.320 | 21.390 | 1.105 | 1.00 | 29.07 |
| ATOM | 486 | CE1 | PHE | 47 | 35.721 | 21.147 | 0.851 | 1.00 | 29.50 |
| ATOM | 487 | CZ | PHE | 47 | 36.214 | 21.277 | −0.450 | 1.00 | 26.40 |
| ATOM | 488 | CE2 | PHE | 47 | 35.369 | 21.631 | −1.463 | 1.00 | 24.93 |
| ATOM | 489 | CD2 | PHE | 47 | 33.991 | 21.858 | −1.213 | 1.00 | 27.19 |
| ATOM | 490 | C | PHE | 47 | 30.316 | 23.676 | 1.087 | 1.00 | 26.50 |
| ATOM | 491 | O | PHE | 47 | 29.767 | 23.098 | 2.041 | 1.00 | 26.93 |
| ATOM | 492 | N | ASN | 48 | 29.687 | 24.497 | 0.252 | 1.00 | 26.28 |
| ATOM | 493 | CA | ASN | 48 | 28.235 | 24.684 | 0.232 | 1.00 | 26.70 |
| ATOM | 494 | CB | ASN | 48 | 27.922 | 26.101 | −0.167 | 1.00 | 26.63 |
| ATOM | 495 | CG | ASN | 48 | 28.611 | 27.143 | 0.712 | 1.00 | 27.75 |
| ATOM | 496 | OD1 | ASN | 48 | 28.397 | 27.164 | 1.918 | 1.00 | 26.90 |
| ATOM | 497 | ND2 | ASN | 48 | 29.402 | 28.026 | 0.107 | 1.00 | 21.97 |
| ATOM | 498 | C | ASN | 48 | 27.658 | 23.762 | −0.816 | 1.00 | 27.42 |
| ATOM | 499 | O | ASN | 48 | 28.023 | 23.869 | −2.013 | 1.00 | 27.74 |
| ATOM | 500 | N | CYS | 49 | 26.787 | 22.842 | −0.398 | 1.00 | 27.81 |
| ATOM | 501 | CA | CYS | 49 | 26.273 | 21.767 | −1.259 | 1.00 | 27.79 |
| ATOM | 502 | CB | CYS | 49 | 26.793 | 20.400 | −0.837 | 1.00 | 27.88 |
| ATOM | 503 | SG | CYS | 49 | 28.577 | 20.421 | −0.479 | 1.00 | 33.42 |
| ATOM | 504 | C | CYS | 49 | 24.770 | 21.767 | −1.237 | 1.00 | 27.42 |
| ATOM | 505 | O | CYS | 49 | 24.198 | 20.917 | −0.654 | 1.00 | 27.36 |
| ATOM | 506 | N | PRO | 50 | 24.124 | 22.730 | −1.924 | 1.00 | 28.25 |
| ATOM | 507 | CA | PRO | 50 | 22.686 | 22.818 | −1.939 | 1.00 | 28.95 |
| ATOM | 508 | CB | PRO | 50 | 22.443 | 24.247 | −2.402 | 1.00 | 28.68 |
| ATOM | 509 | CG | PRO | 50 | 23.565 | 24.504 | −3.259 | 1.00 | 29.66 |
| ATOM | 510 | CD | PRO | 50 | 24.733 | 23.791 | −2.741 | 1.00 | 27.22 |

TABLE 2-continued

| | | | | | | | | | |
|---|---|---|---|---|---|---|---|---|---|
| ATOM | 511 | C | PRO | 50 | 22.014 | 21.801 | −2.884 | 1.00 | 30.16 |
| ATOM | 512 | O | PRO | 50 | 20.791 | 21.723 | −2.931 | 1.00 | 30.23 |
| ATOM | 513 | N | GLU | 51 | 22.771 | 20.946 | −3.565 | 1.00 | 30.75 |
| ATOM | 514 | CA | GLU | 51 | 22.071 | 19.985 | −4.423 | 1.00 | 30.88 |
| ATOM | 515 | CB | GLU | 51 | 22.673 | 20.023 | −5.841 | 1.00 | 30.96 |
| ATOM | 516 | CG | GLU | 51 | 22.258 | 21.350 | −6.510 | 1.00 | 30.27 |
| ATOM | 517 | CD | GLU | 51 | 23.061 | 21.699 | −7.748 | 1.00 | 34.08 |
| ATOM | 518 | OE1 | GLU | 51 | 23.852 | 20.862 | −8.240 | 1.00 | 37.55 |
| ATOM | 519 | OE2 | GLU | 51 | 22.926 | 22.838 | −8.208 | 1.00 | 33.25 |
| ATOM | 520 | C | GLU | 51 | 21.912 | 18.575 | −3.887 | 1.00 | 31.31 |
| ATOM | 521 | O | GLU | 51 | 21.585 | 17.655 | −4.633 | 1.00 | 32.45 |
| ATOM | 522 | N | PHE | 52 | 22.124 | 18.375 | −2.589 | 1.00 | 30.57 |
| ATOM | 523 | CA | PHE | 52 | 22.131 | 17.018 | −2.077 | 1.00 | 29.32 |
| ATOM | 524 | CB | PHE | 52 | 22.611 | 16.980 | −0.630 | 1.00 | 29.38 |
| ATOM | 525 | CG | PHE | 52 | 22.723 | 15.591 | −0.098 | 1.00 | 28.90 |
| ATOM | 526 | CD1 | PHE | 52 | 23.853 | 14.826 | −0.386 | 1.00 | 25.64 |
| ATOM | 527 | CE1 | PHE | 52 | 23.970 | 13.539 | 0.110 | 1.00 | 26.75 |
| ATOM | 528 | CZ | PHE | 52 | 22.931 | 12.979 | 0.832 | 1.00 | 25.36 |
| ATOM | 529 | CE2 | PHE | 52 | 21.775 | 13.732 | 1.108 | 1.00 | 28.36 |
| ATOM | 530 | CD2 | PHE | 52 | 21.671 | 15.023 | 0.633 | 1.00 | 26.05 |
| ATOM | 531 | C | PHE | 52 | 20.763 | 16.399 | −2.163 | 1.00 | 29.42 |
| ATOM | 532 | O | PHE | 52 | 19.775 | 17.081 | −1.906 | 1.00 | 29.42 |
| ATOM | 533 | N | THR | 53 | 20.707 | 15.108 | −2.500 | 1.00 | 28.87 |
| ATOM | 534 | CA | THR | 53 | 19.463 | 14.351 | −2.526 | 1.00 | 29.86 |
| ATOM | 535 | CB | THR | 53 | 18.606 | 14.633 | −3.824 | 1.00 | 29.43 |
| ATOM | 536 | OG1 | THR | 53 | 17.338 | 14.042 | −3.678 | 1.00 | 29.24 |
| ATOM | 537 | CG2 | THR | 53 | 19.190 | 14.011 | −5.095 | 1.00 | 29.41 |
| ATOM | 538 | C | THR | 53 | 19.716 | 12.833 | −2.291 | 1.00 | 30.60 |
| ATOM | 539 | O | THR | 53 | 20.768 | 12.324 | −2.666 | 1.00 | 31.11 |
| ATOM | 540 | N | SER | 54 | 18.781 | 12.147 | −1.631 | 1.00 | 31.90 |
| ATOM | 541 | CA | SER | 54 | 18.856 | 10.702 | −1.377 | 1.00 | 34.24 |
| ATOM | 542 | CB | SER | 54 | 19.842 | 10.349 | −0.231 | 1.00 | 33.85 |
| ATOM | 543 | OG | SER | 54 | 19.567 | 11.019 | 0.994 | 1.00 | 34.45 |
| ATOM | 544 | C | SER | 54 | 17.481 | 10.156 | −1.061 | 1.00 | 36.26 |
| ATOM | 545 | O | SER | 54 | 16.481 | 10.824 | −1.267 | 1.00 | 36.99 |
| ATOM | 546 | N | LEU | 55 | 17.436 | 8.942 | −0.525 | 1.00 | 38.76 |
| ATOM | 547 | CA | LEU | 55 | 16.202 | 8.215 | −0.362 | 1.00 | 40.65 |
| ATOM | 548 | CB | LEU | 55 | 16.269 | 6.944 | −1.230 | 1.00 | 40.22 |
| ATOM | 549 | CG | LEU | 55 | 16.388 | 7.100 | −2.768 | 1.00 | 39.91 |
| ATOM | 550 | CD1 | LEU | 55 | 16.411 | 5.781 | −3.485 | 1.00 | 36.87 |
| ATOM | 551 | CD2 | LEU | 55 | 15.247 | 7.942 | −3.330 | 1.00 | 37.75 |
| ATOM | 552 | C | LEU | 55 | 15.924 | 7.856 | 1.091 | 1.00 | 42.66 |
| ATOM | 553 | O | LEU | 55 | 16.855 | 7.595 | 1.853 | 1.00 | 42.18 |
| ATOM | 554 | N | CYS | 56 | 14.639 | 7.851 | 1.459 | 1.00 | 45.64 |
| ATOM | 555 | CA | CYS | 56 | 14.151 | 7.328 | 2.741 | 1.00 | 47.46 |
| ATOM | 556 | CB | CYS | 56 | 12.653 | 7.597 | 2.847 | 1.00 | 47.73 |
| ATOM | 557 | SG | CYS | 56 | 11.877 | 7.181 | 4.439 | 1.00 | 49.73 |
| ATOM | 558 | C | CYS | 56 | 14.391 | 5.806 | 2.715 | 1.00 | 49.16 |
| ATOM | 559 | O | CYS | 56 | 13.992 | 5.153 | 1.744 | 1.00 | 48.69 |
| ATOM | 560 | N | PRO | 57 | 15.051 | 5.237 | 3.759 | 1.00 | 50.23 |
| ATOM | 561 | CA | PRO | 57 | 15.432 | 3.824 | 3.665 | 1.00 | 51.27 |
| ATOM | 562 | CB | PRO | 57 | 16.373 | 3.626 | 4.856 | 1.00 | 50.81 |
| ATOM | 563 | CG | PRO | 57 | 15.940 | 4.618 | 5.831 | 1.00 | 49.99 |
| ATOM | 564 | CD | PRO | 57 | 15.455 | 5.815 | 5.052 | 1.00 | 50.40 |
| ATOM | 565 | C | PRO | 57 | 14.233 | 2.848 | 3.719 | 1.00 | 52.30 |
| ATOM | 566 | O | PRO | 57 | 14.320 | 1.757 | 3.183 | 1.00 | 52.64 |
| ATOM | 567 | N | LYS | 58 | 13.125 | 3.254 | 4.326 | 1.00 | 54.16 |
| ATOM | 568 | CA | LYS | 58 | 11.951 | 2.384 | 4.406 | 1.00 | 56.16 |
| ATOM | 569 | CB | LYS | 58 | 11.181 | 2.556 | 5.731 | 1.00 | 57.06 |
| ATOM | 570 | CG | LYS | 58 | 10.979 | 1.203 | 6.467 | 1.00 | 60.28 |
| ATOM | 571 | CD | LYS | 58 | 9.562 | 1.010 | 7.050 | 1.00 | 64.21 |
| ATOM | 572 | CE | LYS | 58 | 9.486 | −0.294 | 7.871 | 1.00 | 64.13 |
| ATOM | 573 | NZ | LYS | 58 | 8.711 | −0.082 | 9.156 | 1.00 | 65.58 |
| ATOM | 574 | C | LYS | 58 | 11.037 | 2.556 | 3.178 | 1.00 | 56.38 |
| ATOM | 575 | O | LYS | 58 | 10.947 | 1.645 | 2.359 | 1.00 | 57.38 |
| ATOM | 576 | N | VAL | 59 | 10.375 | 3.710 | 3.033 | 1.00 | 56.15 |
| ATOM | 577 | CA | VAL | 59 | 9.676 | 4.053 | 1.774 | 1.00 | 55.14 |
| ATOM | 578 | CB | VAL | 59 | 8.771 | 5.277 | 1.954 | 1.00 | 55.05 |
| ATOM | 579 | CG1 | VAL | 59 | 7.916 | 5.111 | 3.200 | 1.00 | 55.49 |
| ATOM | 580 | CG2 | VAL | 59 | 9.590 | 6.529 | 2.059 | 1.00 | 54.75 |
| ATOM | 581 | C | VAL | 59 | 10.731 | 4.349 | 0.714 | 1.00 | 54.81 |
| ATOM | 582 | O | VAL | 59 | 11.901 | 4.566 | 1.033 | 1.00 | 55.98 |
| ATOM | 583 | N | GLY | 60 | 10.391 | 4.364 | −0.555 | 1.00 | 53.64 |
| ATOM | 584 | CA | GLY | 60 | 11.477 | 4.725 | −1.480 | 1.00 | 52.33 |
| ATOM | 585 | C | GLY | 60 | 11.698 | 6.226 | −1.691 | 1.00 | 50.31 |
| ATOM | 586 | O | GLY | 60 | 12.462 | 6.601 | −2.557 | 1.00 | 50.01 |
| ATOM | 587 | N | GLN | 61 | 11.025 | 7.072 | −0.916 | 1.00 | 48.88 |
| ATOM | 588 | CA | GLN | 61 | 10.866 | 8.502 | −1.255 | 1.00 | 49.29 |
| ATOM | 589 | CB | GLN | 61 | 9.763 | 9.143 | −0.416 | 1.00 | 49.10 |
| ATOM | 590 | CG | GLN | 61 | 8.392 | 8.540 | −0.650 | 1.00 | 53.70 |

TABLE 2-continued

| | | | | | | | | |
|---|---|---|---|---|---|---|---|---|
| ATOM | 591 | CD | GLN | 61 | 7.223 | 9.398 | −0.099 | 1.00 | 55.70 |
| ATOM | 592 | OE1 | GLN | 61 | 6.307 | 8.865 | 0.587 | 1.00 | 62.01 |
| ATOM | 593 | NE2 | GLN | 61 | 7.251 | 10.733 | −0.389 | 1.00 | 60.03 |
| ATOM | 594 | C | GLN | 61 | 12.159 | 9.328 | −1.145 | 1.00 | 45.89 |
| ATOM | 595 | O | GLN | 61 | 12.932 | 9.120 | −0.212 | 1.00 | 45.98 |
| ATOM | 596 | N | PRO | 62 | 12.393 | 10.266 | −2.102 | 1.00 | 43.29 |
| ATOM | 597 | CA | PRO | 62 | 13.559 | 11.153 | −2.095 | 1.00 | 40.15 |
| ATOM | 598 | CB | PRO | 62 | 13.510 | 11.818 | −3.476 | 1.00 | 40.40 |
| ATOM | 599 | CG | PRO | 62 | 12.546 | 11.045 | −4.272 | 1.00 | 40.75 |
| ATOM | 600 | CD | PRO | 62 | 11.560 | 10.506 | −3.298 | 1.00 | 43.04 |
| ATOM | 601 | C | PRO | 62 | 13.498 | 12.229 | −1.026 | 1.00 | 37.93 |
| ATOM | 602 | O | PRO | 62 | 12.404 | 12.729 | −0.685 | 1.00 | 37.34 |
| ATOM | 603 | N | ASP | 63 | 14.672 | 12.566 | −0.503 | 1.00 | 34.80 |
| ATOM | 604 | CA | ASP | 63 | 14.838 | 13.679 | 0.427 | 1.00 | 34.59 |
| ATOM | 605 | CB | ASP | 63 | 15.386 | 13.249 | 1.794 | 1.00 | 35.69 |
| ATOM | 606 | CG | ASP | 63 | 14.546 | 12.187 | 2.493 | 1.00 | 43.45 |
| ATOM | 607 | OD1 | ASP | 63 | 13.279 | 12.244 | 2.460 | 1.00 | 49.93 |
| ATOM | 608 | OD2 | ASP | 63 | 15.190 | 11.265 | 3.089 | 1.00 | 50.25 |
| ATOM | 609 | C | ASP | 63 | 15.877 | 14.615 | −0.176 | 1.00 | 31.59 |
| ATOM | 610 | O | ASP | 63 | 16.629 | 14.243 | −1.066 | 1.00 | 29.24 |
| ATOM | 611 | N | PHE | 64 | 15.914 | 15.835 | 0.328 | 1.00 | 30.47 |
| ATOM | 612 | CA | PHE | 64 | 16.764 | 16.880 | −0.256 | 1.00 | 28.47 |
| ATOM | 613 | CB | PHE | 64 | 15.908 | 17.789 | −1.159 | 1.00 | 28.12 |
| ATOM | 614 | CG | PHE | 64 | 15.310 | 17.066 | −2.356 | 1.00 | 28.68 |
| ATOM | 615 | CD1 | PHE | 64 | 14.170 | 16.281 | −2.218 | 1.00 | 30.31 |
| ATOM | 616 | CE1 | PHE | 64 | 13.626 | 15.616 | −3.304 | 1.00 | 31.76 |
| ATOM | 617 | CZ | PHE | 64 | 14.252 | 15.717 | −4.582 | 1.00 | 27.12 |
| ATOM | 618 | CE2 | PHE | 64 | 15.394 | 16.481 | −4.728 | 1.00 | 30.78 |
| ATOM | 619 | CD2 | PHE | 64 | 15.913 | 17.165 | −3.620 | 1.00 | 30.18 |
| ATOM | 620 | C | PHE | 64 | 17.363 | 17.683 | 0.868 | 1.00 | 27.63 |
| ATOM | 621 | O | PHE | 64 | 16.713 | 17.873 | 1.873 | 1.00 | 28.69 |
| ATOM | 622 | N | ALA | 65 | 18.563 | 18.232 | 0.663 | 1.00 | 26.33 |
| ATOM | 623 | CA | ALA | 65 | 19.204 | 18.997 | 1.652 | 1.00 | 25.69 |
| ATOM | 624 | CB | ALA | 65 | 19.914 | 18.004 | 2.719 | 1.00 | 24.22 |
| ATOM | 625 | C | ALA | 65 | 20.231 | 19.941 | 1.047 | 1.00 | 25.67 |
| ATOM | 626 | O | ALA | 65 | 20.689 | 19.757 | −0.068 | 1.00 | 26.66 |
| ATOM | 627 | N | THR | 66 | 20.596 | 20.942 | 1.819 | 1.00 | 25.39 |
| ATOM | 628 | CA | THR | 66 | 21.827 | 21.677 | 1.651 | 1.00 | 27.61 |
| ATOM | 629 | CB | THR | 66 | 21.592 | 23.154 | 1.861 | 1.00 | 27.25 |
| ATOM | 630 | OG1 | THR | 66 | 20.752 | 23.615 | 0.820 | 1.00 | 30.69 |
| ATOM | 631 | CG2 | THR | 66 | 22.868 | 23.915 | 1.735 | 1.00 | 31.40 |
| ATOM | 632 | C | THR | 66 | 22.780 | 21.182 | 2.743 | 1.00 | 28.30 |
| ATOM | 633 | O | THR | 66 | 22.431 | 21.123 | 3.933 | 1.00 | 28.10 |
| ATOM | 634 | N | ILE | 67 | 23.989 | 20.838 | 2.343 | 1.00 | 28.94 |
| ATOM | 635 | CA | ILE | 67 | 24.990 | 20.392 | 3.301 | 1.00 | 28.94 |
| ATOM | 636 | CB | ILE | 67 | 25.489 | 18.986 | 2.870 | 1.00 | 29.43 |
| ATOM | 637 | CG1 | ILE | 67 | 24.280 | 18.048 | 2.848 | 1.00 | 28.57 |
| ATOM | 638 | CD1 | ILE | 67 | 24.620 | 16.709 | 2.398 | 1.00 | 29.91 |
| ATOM | 639 | CG2 | ILE | 67 | 26.608 | 18.471 | 3.775 | 1.00 | 29.92 |
| ATOM | 640 | C | ILE | 67 | 26.077 | 21.424 | 3.311 | 1.00 | 28.85 |
| ATOM | 641 | O | ILE | 67 | 26.424 | 21.922 | 2.236 | 1.00 | 29.21 |
| ATOM | 642 | N | TYR | 68 | 26.586 | 21.770 | 4.505 | 1.00 | 28.85 |
| ATOM | 643 | CA | TYR | 68 | 27.710 | 22.685 | 4.692 | 1.00 | 27.65 |
| ATOM | 644 | CB | TYR | 68 | 27.343 | 23.892 | 5.554 | 1.00 | 28.00 |
| ATOM | 645 | CG | TYR | 68 | 26.169 | 24.669 | 4.985 | 1.00 | 27.25 |
| ATOM | 646 | CD1 | TYR | 68 | 24.864 | 24.443 | 5.411 | 1.00 | 23.97 |
| ATOM | 647 | CE1 | TYR | 68 | 23.774 | 25.180 | 4.854 | 1.00 | 28.38 |
| ATOM | 648 | CZ | TYR | 68 | 24.039 | 26.098 | 3.817 | 1.00 | 28.49 |
| ATOM | 649 | OH | TYR | 68 | 23.061 | 26.851 | 3.171 | 1.00 | 26.21 |
| ATOM | 650 | CE2 | TYR | 68 | 25.356 | 26.292 | 3.374 | 1.00 | 29.17 |
| ATOM | 651 | CD2 | TYR | 68 | 26.388 | 25.605 | 3.943 | 1.00 | 27.85 |
| ATOM | 652 | C | TYR | 68 | 28.791 | 21.837 | 5.337 | 1.00 | 29.20 |
| ATOM | 653 | O | TYR | 68 | 28.563 | 21.226 | 6.411 | 1.00 | 29.47 |
| ATOM | 654 | N | ILE | 69 | 29.938 | 21.743 | 4.665 | 1.00 | 28.12 |
| ATOM | 655 | CA | ILE | 69 | 30.978 | 20.873 | 5.122 | 1.00 | 28.68 |
| ATOM | 656 | CB | ILE | 69 | 31.367 | 19.781 | 4.122 | 1.00 | 29.11 |
| ATOM | 657 | CG1 | ILE | 69 | 30.180 | 18.885 | 3.756 | 1.00 | 30.41 |
| ATOM | 658 | CD1 | ILE | 69 | 30.590 | 17.811 | 2.756 | 1.00 | 32.90 |
| ATOM | 659 | CG2 | ILE | 69 | 32.443 | 18.900 | 4.743 | 1.00 | 27.69 |
| ATOM | 660 | C | ILE | 69 | 32.182 | 21.770 | 5.276 | 1.00 | 28.58 |
| ATOM | 661 | O | ILE | 69 | 32.658 | 22.336 | 4.283 | 1.00 | 29.06 |
| ATOM | 662 | N | SER | 70 | 32.661 | 21.910 | 6.508 | 1.00 | 27.09 |
| ATOM | 663 | CA | SER | 70 | 33.785 | 22.801 | 6.780 | 1.00 | 28.38 |
| ATOM | 664 | CB | SER | 70 | 33.358 | 23.914 | 7.713 | 1.00 | 27.46 |
| ATOM | 665 | OG | SER | 70 | 32.356 | 24.705 | 7.126 | 1.00 | 31.79 |
| ATOM | 666 | C | SER | 70 | 34.885 | 22.010 | 7.455 | 1.00 | 29.12 |
| ATOM | 667 | O | SER | 70 | 34.616 | 21.271 | 8.405 | 1.00 | 29.98 |
| ATOM | 668 | N | TYR | 71 | 36.117 | 22.155 | 7.009 | 1.00 | 29.92 |
| ATOM | 669 | CA | TYR | 71 | 37.160 | 21.367 | 7.623 | 1.00 | 30.12 |
| ATOM | 670 | CB | TYR | 71 | 37.288 | 20.027 | 6.896 | 1.00 | 31.24 |

TABLE 2-continued

| | | | | | | | | | |
|---|---|---|---|---|---|---|---|---|---|
| ATOM | 671 | CG | TYR | 71 | 38.057 | 20.049 | 5.624 | 1.00 | 34.13 |
| ATOM | 672 | CD1 | TYR | 71 | 37.440 | 20.384 | 4.411 | 1.00 | 36.91 |
| ATOM | 673 | CE1 | TYR | 71 | 38.177 | 20.415 | 3.205 | 1.00 | 37.18 |
| ATOM | 674 | CZ | TYR | 71 | 39.501 | 20.082 | 3.228 | 1.00 | 35.60 |
| ATOM | 675 | OH | TYR | 71 | 40.238 | 20.092 | 2.087 | 1.00 | 35.76 |
| ATOM | 676 | CE2 | TYR | 71 | 40.119 | 19.712 | 4.422 | 1.00 | 35.87 |
| ATOM | 677 | CD2 | TYR | 71 | 39.384 | 19.678 | 5.604 | 1.00 | 33.90 |
| ATOM | 678 | C | TYR | 71 | 38.443 | 22.145 | 7.689 | 1.00 | 30.03 |
| ATOM | 679 | O | TYR | 71 | 38.617 | 23.077 | 6.913 | 1.00 | 30.38 |
| ATOM | 680 | N | HIS | 93 | 20.358 | 5.944 | −2.990 | 1.00 | 47.52 |
| ATOM | 681 | CA | HIS | 93 | 20.765 | 5.322 | −1.732 | 1.00 | 48.56 |
| ATOM | 682 | CB | HIS | 93 | 22.195 | 5.740 | −1.421 | 1.00 | 48.57 |
| ATOM | 683 | CG | HIS | 93 | 22.758 | 5.106 | −0.192 | 1.00 | 52.23 |
| ATOM | 684 | ND1 | HIS | 93 | 22.860 | 5.775 | 1.013 | 1.00 | 54.40 |
| ATOM | 685 | CE1 | HIS | 93 | 23.396 | 4.973 | 1.916 | 1.00 | 55.42 |
| ATOM | 686 | NE2 | HIS | 93 | 23.646 | 3.809 | 1.340 | 1.00 | 57.29 |
| ATOM | 687 | CD2 | HIS | 93 | 23.250 | 3.862 | 0.023 | 1.00 | 54.08 |
| ATOM | 688 | C | HIS | 93 | 19.867 | 5.720 | −0.556 | 1.00 | 48.30 |
| ATOM | 689 | O | HIS | 93 | 19.671 | 6.927 | −0.269 | 1.00 | 48.07 |
| ATOM | 690 | N | GLY | 94 | 19.355 | 4.697 | 0.129 | 1.00 | 47.98 |
| ATOM | 691 | CA | GLY | 94 | 18.500 | 4.857 | 1.314 | 1.00 | 48.09 |
| ATOM | 692 | C | GLY | 94 | 19.275 | 4.869 | 2.645 | 1.00 | 48.30 |
| ATOM | 693 | O | GLY | 94 | 20.181 | 4.042 | 2.874 | 1.00 | 48.30 |
| ATOM | 694 | N | ASP | 95 | 18.918 | 5.828 | 3.505 | 1.00 | 47.87 |
| ATOM | 695 | CA | ASP | 95 | 19.513 | 6.064 | 4.839 | 1.00 | 47.26 |
| ATOM | 696 | CB | ASP | 95 | 21.035 | 6.282 | 4.813 | 1.00 | 47.30 |
| ATOM | 697 | CG | ASP | 95 | 21.838 | 5.046 | 5.328 | 1.00 | 53.37 |
| ATOM | 698 | OD1 | ASP | 95 | 21.253 | 4.127 | 5.991 | 1.00 | 57.20 |
| ATOM | 699 | OD2 | ASP | 95 | 23.075 | 4.986 | 5.062 | 1.00 | 56.37 |
| ATOM | 700 | C | ASP | 95 | 18.829 | 7.269 | 5.439 | 1.00 | 45.93 |
| ATOM | 701 | O | ASP | 95 | 18.424 | 8.188 | 4.715 | 1.00 | 44.85 |
| ATOM | 702 | N | PHE | 96 | 18.673 | 7.230 | 6.759 | 1.00 | 45.16 |
| ATOM | 703 | CA | PHE | 96 | 18.244 | 8.384 | 7.568 | 1.00 | 44.14 |
| ATOM | 704 | CB | PHE | 96 | 17.975 | 7.956 | 9.021 | 1.00 | 45.17 |
| ATOM | 705 | CG | PHE | 96 | 16.845 | 6.950 | 9.187 | 1.00 | 46.90 |
| ATOM | 706 | CD1 | PHE | 96 | 17.049 | 5.777 | 9.899 | 1.00 | 50.69 |
| ATOM | 707 | CE1 | PHE | 96 | 16.004 | 4.853 | 10.087 | 1.00 | 51.94 |
| ATOM | 708 | CZ | PHE | 96 | 14.748 | 5.115 | 9.538 | 1.00 | 50.11 |
| ATOM | 709 | CE2 | PHE | 96 | 14.551 | 6.297 | 8.835 | 1.00 | 50.44 |
| ATOM | 710 | CD2 | PHE | 96 | 15.582 | 7.194 | 8.674 | 1.00 | 48.33 |
| ATOM | 711 | C | PHE | 96 | 19.278 | 9.536 | 7.523 | 1.00 | 42.30 |
| ATOM | 712 | O | PHE | 96 | 20.478 | 9.313 | 7.278 | 1.00 | 41.46 |
| ATOM | 713 | N | HIS | 97 | 18.813 | 10.766 | 7.750 | 1.00 | 40.24 |
| ATOM | 714 | CA | HIS | 97 | 19.644 | 11.929 | 7.485 | 1.00 | 38.57 |
| ATOM | 715 | CB | HIS | 97 | 18.862 | 13.246 | 7.612 | 1.00 | 38.59 |
| ATOM | 716 | CG | HIS | 97 | 17.566 | 13.243 | 6.886 | 1.00 | 39.30 |
| ATOM | 717 | ND1 | HIS | 97 | 17.353 | 12.495 | 5.749 | 1.00 | 39.03 |
| ATOM | 718 | CE1 | HIS | 97 | 16.105 | 12.657 | 5.355 | 1.00 | 39.99 |
| ATOM | 719 | NE2 | HIS | 97 | 15.500 | 13.477 | 6.194 | 1.00 | 39.16 |
| ATOM | 720 | CD2 | HIS | 97 | 16.394 | 13.865 | 7.154 | 1.00 | 41.09 |
| ATOM | 721 | C | HIS | 97 | 20.807 | 11.958 | 8.428 | 1.00 | 37.66 |
| ATOM | 722 | O | HIS | 97 | 21.936 | 12.324 | 8.027 | 1.00 | 35.95 |
| ATOM | 723 | N | GLU | 98 | 20.516 | 11.602 | 9.690 | 1.00 | 36.80 |
| ATOM | 724 | CA | GLU | 98 | 21.535 | 11.574 | 10.764 | 1.00 | 36.97 |
| ATOM | 725 | CB | GLU | 98 | 20.936 | 11.072 | 12.092 | 1.00 | 37.03 |
| ATOM | 726 | CG | GLU | 98 | 19.820 | 11.966 | 12.647 | 1.00 | 37.99 |
| ATOM | 727 | CD | GLU | 98 | 18.454 | 11.486 | 12.242 | 1.00 | 40.12 |
| ATOM | 728 | OE1 | GLU | 98 | 18.295 | 11.083 | 11.042 | 1.00 | 41.19 |
| ATOM | 729 | OE2 | GLU | 98 | 17.551 | 11.485 | 13.132 | 1.00 | 36.97 |
| ATOM | 730 | C | GLU | 98 | 22.702 | 10.713 | 10.355 | 1.00 | 36.15 |
| ATOM | 731 | O | GLU | 98 | 23.852 | 11.147 | 10.417 | 1.00 | 35.60 |
| ATOM | 732 | N | ASP | 99 | 22.367 | 9.511 | 9.881 | 1.00 | 37.24 |
| ATOM | 733 | CA | ASP | 99 | 23.332 | 8.504 | 9.449 | 1.00 | 39.23 |
| ATOM | 734 | CB | ASP | 99 | 22.617 | 7.192 | 9.066 | 1.00 | 40.69 |
| ATOM | 735 | CG | ASP | 99 | 21.899 | 6.552 | 10.265 | 1.00 | 46.52 |
| ATOM | 736 | OD1 | ASP | 99 | 21.905 | 7.165 | 11.369 | 1.00 | 52.45 |
| ATOM | 737 | OD2 | ASP | 99 | 21.304 | 5.441 | 10.120 | 1.00 | 55.36 |
| ATOM | 738 | C | ASP | 99 | 24.146 | 9.032 | 8.297 | 1.00 | 38.47 |
| ATOM | 739 | O | ASP | 99 | 25.384 | 9.033 | 8.361 | 1.00 | 38.11 |
| ATOM | 740 | N | CYS | 100 | 23.439 | 9.530 | 7.272 | 1.00 | 37.61 |
| ATOM | 741 | CA | CYS | 100 | 24.069 | 10.193 | 6.140 | 1.00 | 36.59 |
| ATOM | 742 | CB | CYS | 100 | 23.016 | 10.943 | 5.370 | 1.00 | 38.17 |
| ATOM | 743 | SG | CYS | 100 | 22.985 | 10.394 | 3.736 | 1.00 | 50.51 |
| ATOM | 744 | C | CYS | 100 | 25.124 | 11.196 | 6.476 | 1.00 | 34.11 |
| ATOM | 745 | O | CYS | 100 | 26.183 | 11.179 | 5.860 | 1.00 | 34.37 |
| ATOM | 746 | N | MET | 101 | 24.837 | 12.120 | 7.406 | 1.00 | 32.07 |
| ATOM | 747 | CA | MET | 101 | 25.789 | 13.170 | 7.727 | 1.00 | 30.50 |
| ATOM | 748 | CB | MET | 101 | 25.177 | 14.258 | 8.633 | 1.00 | 29.72 |
| ATOM | 749 | CG | MET | 101 | 23.944 | 15.068 | 8.074 | 1.00 | 30.97 |
| ATOM | 750 | SD | MET | 101 | 24.038 | 15.616 | 6.312 | 1.00 | 34.79 |

TABLE 2-continued

| | | | | | | | | | |
|---|---|---|---|---|---|---|---|---|---|
| ATOM | 751 | CE | MET | 101 | 25.767 | 15.923 | 6.142 | 1.00 | 34.90 |
| ATOM | 752 | C | MET | 101 | 27.060 | 12.566 | 8.328 | 1.00 | 30.76 |
| ATOM | 753 | O | MET | 101 | 28.181 | 13.042 | 8.041 | 1.00 | 30.83 |
| ATOM | 754 | N | ASN | 102 | 26.882 | 11.532 | 9.172 | 1.00 | 30.68 |
| ATOM | 755 | CA | ASN | 102 | 28.025 | 10.756 | 9.803 | 1.00 | 30.56 |
| ATOM | 756 | CB | ASN | 102 | 27.525 | 9.863 | 10.943 | 1.00 | 30.26 |
| ATOM | 757 | CG | ASN | 102 | 27.218 | 10.648 | 12.193 | 1.00 | 29.61 |
| ATOM | 758 | OD1 | ASN | 102 | 28.087 | 11.279 | 12.731 | 1.00 | 33.98 |
| ATOM | 759 | ND2 | ASN | 102 | 25.985 | 10.586 | 12.672 | 1.00 | 30.94 |
| ATOM | 760 | C | ASN | 102 | 28.805 | 9.931 | 8.784 | 1.00 | 30.63 |
| ATOM | 761 | O | ASN | 102 | 30.071 | 10.013 | 8.741 | 1.00 | 31.00 |
| ATOM | 762 | N | ILE | 103 | 28.074 | 9.202 | 7.932 | 1.00 | 30.13 |
| ATOM | 763 | CA | ILE | 103 | 28.707 | 8.540 | 6.782 | 1.00 | 31.39 |
| ATOM | 764 | CB | ILE | 103 | 27.726 | 7.765 | 5.871 | 1.00 | 32.20 |
| ATOM | 765 | CG1 | ILE | 103 | 27.180 | 6.532 | 6.582 | 1.00 | 31.35 |
| ATOM | 766 | CD1 | ILE | 103 | 25.741 | 6.245 | 6.218 | 1.00 | 34.06 |
| ATOM | 767 | CG2 | ILE | 103 | 28.440 | 7.328 | 4.590 | 1.00 | 32.53 |
| ATOM | 768 | C | ILE | 103 | 29.527 | 9.515 | 5.966 | 1.00 | 31.52 |
| ATOM | 769 | O | ILE | 103 | 30.718 | 9.291 | 5.709 | 1.00 | 33.07 |
| ATOM | 770 | N | ILE | 104 | 28.943 | 10.646 | 5.605 | 1.00 | 31.97 |
| ATOM | 771 | CA | ILE | 104 | 29.743 | 11.642 | 4.850 | 1.00 | 31.51 |
| ATOM | 772 | CB | ILE | 104 | 28.874 | 12.853 | 4.381 | 1.00 | 30.18 |
| ATOM | 773 | CG1 | ILE | 104 | 27.902 | 12.388 | 3.312 | 1.00 | 28.58 |
| ATOM | 774 | CD1 | ILE | 104 | 26.775 | 13.385 | 3.032 | 1.00 | 28.59 |
| ATOM | 775 | CG2 | ILE | 104 | 29.762 | 13.991 | 3.863 | 1.00 | 29.37 |
| ATOM | 776 | C | ILE | 104 | 31.013 | 12.092 | 5.624 | 1.00 | 32.50 |
| ATOM | 777 | O | ILE | 104 | 32.122 | 12.083 | 5.079 | 1.00 | 32.76 |
| ATOM | 778 | N | MET | 105 | 30.841 | 12.496 | 6.891 | 1.00 | 32.90 |
| ATOM | 779 | CA | MET | 105 | 31.993 | 12.914 | 7.665 | 1.00 | 33.18 |
| ATOM | 780 | CB | MET | 105 | 31.587 | 13.402 | 9.043 | 1.00 | 33.13 |
| ATOM | 781 | CG | MET | 105 | 32.741 | 14.085 | 9.726 | 1.00 | 32.87 |
| ATOM | 782 | SD | MET | 105 | 32.368 | 14.745 | 11.346 | 1.00 | 34.05 |
| ATOM | 783 | CE | MET | 105 | 31.675 | 13.253 | 12.068 | 1.00 | 24.36 |
| ATOM | 784 | C | MET | 105 | 33.038 | 11.797 | 7.814 | 1.00 | 33.29 |
| ATOM | 785 | O | MET | 105 | 34.231 | 12.077 | 7.782 | 1.00 | 32.49 |
| ATOM | 786 | N | TYR | 116 | 40.382 | 19.325 | 11.802 | 1.00 | 32.16 |
| ATOM | 787 | CA | TYR | 116 | 38.970 | 19.428 | 12.212 | 1.00 | 30.52 |
| ATOM | 788 | CB | TYR | 116 | 38.754 | 20.794 | 12.826 | 1.00 | 29.77 |
| ATOM | 789 | CG | TYR | 116 | 37.326 | 21.039 | 13.215 | 1.00 | 31.85 |
| ATOM | 790 | CD1 | TYR | 116 | 36.812 | 20.513 | 14.408 | 1.00 | 30.34 |
| ATOM | 791 | CE1 | TYR | 116 | 35.481 | 20.738 | 14.761 | 1.00 | 31.25 |
| ATOM | 792 | CZ | TYR | 116 | 34.645 | 21.495 | 13.916 | 1.00 | 30.45 |
| ATOM | 793 | OH | TYR | 116 | 33.333 | 21.695 | 14.289 | 1.00 | 33.06 |
| ATOM | 794 | CE2 | TYR | 116 | 35.134 | 22.033 | 12.740 | 1.00 | 31.10 |
| ATOM | 795 | CD2 | TYR | 116 | 36.460 | 21.807 | 12.383 | 1.00 | 28.87 |
| ATOM | 796 | C | TYR | 116 | 38.024 | 19.208 | 11.014 | 1.00 | 30.65 |
| ATOM | 797 | O | TYR | 116 | 38.345 | 19.614 | 9.892 | 1.00 | 30.59 |
| ATOM | 798 | N | ILE | 117 | 36.858 | 18.598 | 11.241 | 1.00 | 28.73 |
| ATOM | 799 | CA | ILE | 117 | 35.854 | 18.601 | 10.231 | 1.00 | 28.16 |
| ATOM | 800 | CB | ILE | 117 | 35.966 | 17.372 | 9.240 | 1.00 | 29.12 |
| ATOM | 801 | CG1 | ILE | 117 | 34.970 | 17.520 | 8.055 | 1.00 | 26.39 |
| ATOM | 802 | CD1 | ILE | 117 | 35.060 | 16.421 | 6.957 | 1.00 | 27.24 |
| ATOM | 803 | CG2 | ILE | 117 | 35.787 | 16.049 | 9.984 | 1.00 | 26.00 |
| ATOM | 804 | C | ILE | 117 | 34.465 | 18.682 | 10.879 | 1.00 | 28.42 |
| ATOM | 805 | O | ILE | 117 | 34.260 | 18.187 | 11.981 | 1.00 | 28.48 |
| ATOM | 806 | N | GLU | 118 | 33.529 | 19.334 | 10.195 | 1.00 | 27.95 |
| ATOM | 807 | CA | GLU | 118 | 32.112 | 19.252 | 10.530 | 1.00 | 28.61 |
| ATOM | 808 | CB | GLU | 118 | 31.668 | 20.450 | 11.359 | 1.00 | 28.35 |
| ATOM | 809 | CG | GLU | 118 | 32.180 | 21.743 | 10.808 | 1.00 | 33.29 |
| ATOM | 810 | CD | GLU | 118 | 31.593 | 22.927 | 11.498 | 1.00 | 36.95 |
| ATOM | 811 | OE1 | GLU | 118 | 31.715 | 23.099 | 12.730 | 1.00 | 37.45 |
| ATOM | 812 | OE2 | GLU | 118 | 30.996 | 23.727 | 10.782 | 1.00 | 42.14 |
| ATOM | 813 | C | GLU | 118 | 31.266 | 19.141 | 9.266 | 1.00 | 28.90 |
| ATOM | 814 | O | GLU | 118 | 31.639 | 19.581 | 8.163 | 1.00 | 29.81 |
| ATOM | 815 | N | VAL | 119 | 30.133 | 18.505 | 9.428 | 1.00 | 27.93 |
| ATOM | 816 | CA | VAL | 119 | 29.186 | 18.389 | 8.394 | 1.00 | 26.65 |
| ATOM | 817 | CB | VAL | 119 | 29.072 | 16.936 | 7.927 | 1.00 | 27.76 |
| ATOM | 818 | CG1 | VAL | 119 | 27.955 | 16.810 | 6.857 | 1.00 | 25.00 |
| ATOM | 819 | CG2 | VAL | 119 | 30.419 | 16.408 | 7.377 | 1.00 | 24.38 |
| ATOM | 820 | C | VAL | 119 | 27.852 | 18.812 | 9.041 | 1.00 | 27.53 |
| ATOM | 821 | O | VAL | 119 | 27.443 | 18.201 | 10.034 | 1.00 | 26.65 |
| ATOM | 822 | N | TRP | 120 | 27.207 | 19.855 | 8.480 | 1.00 | 26.32 |
| ATOM | 823 | CA | TRP | 120 | 25.868 | 20.268 | 8.865 | 1.00 | 25.22 |
| ATOM | 824 | CB | TRP | 120 | 25.916 | 21.710 | 9.300 | 1.00 | 24.66 |
| ATOM | 825 | CG | TRP | 120 | 24.772 | 22.213 | 10.090 | 1.00 | 23.83 |
| ATOM | 826 | CD1 | TRP | 120 | 23.579 | 21.635 | 10.258 | 1.00 | 24.59 |
| ATOM | 827 | NE1 | TRP | 120 | 22.795 | 22.427 | 11.084 | 1.00 | 29.40 |
| ATOM | 828 | CE2 | TRP | 120 | 23.501 | 23.551 | 11.434 | 1.00 | 24.59 |
| ATOM | 829 | CD2 | TRP | 120 | 24.753 | 23.450 | 10.825 | 1.00 | 22.94 |
| ATOM | 830 | CE3 | TRP | 120 | 25.730 | 24.447 | 11.087 | 1.00 | 25.61 |

TABLE 2-continued

| | | | | | | | | | |
|---|---|---|---|---|---|---|---|---|---|
| ATOM | 831 | CZ3 | TRP | 120 | 25.375 | 25.543 | 11.896 | 1.00 | 25.81 |
| ATOM | 832 | CH2 | TRP | 120 | 24.079 | 25.624 | 12.463 | 1.00 | 21.59 |
| ATOM | 833 | CZ2 | TRP | 120 | 23.149 | 24.625 | 12.276 | 1.00 | 22.78 |
| ATOM | 834 | C | TRP | 120 | 24.914 | 20.147 | 7.694 | 1.00 | 25.58 |
| ATOM | 835 | O | TRP | 120 | 25.110 | 20.784 | 6.644 | 1.00 | 24.48 |
| ATOM | 836 | N | GLY | 121 | 23.899 | 19.321 | 7.876 | 1.00 | 24.73 |
| ATOM | 837 | CA | GLY | 121 | 22.924 | 19.091 | 6.873 | 1.00 | 25.93 |
| ATOM | 838 | C | GLY | 121 | 21.616 | 19.716 | 7.277 | 1.00 | 27.00 |
| ATOM | 839 | O | GLY | 121 | 21.233 | 19.681 | 8.450 | 1.00 | 27.37 |
| ATOM | 840 | N | LYS | 122 | 20.921 | 20.280 | 6.298 | 1.00 | 26.41 |
| ATOM | 841 | CA | LYS | 122 | 19.667 | 20.964 | 6.533 | 1.00 | 26.76 |
| ATOM | 842 | CB | LYS | 122 | 19.904 | 22.492 | 6.423 | 1.00 | 27.37 |
| ATOM | 843 | CG | LYS | 122 | 20.900 | 23.024 | 7.484 | 1.00 | 25.44 |
| ATOM | 844 | CD | LYS | 122 | 21.018 | 24.514 | 7.423 | 1.00 | 27.60 |
| ATOM | 845 | CE | LYS | 122 | 22.046 | 24.964 | 8.409 | 1.00 | 31.63 |
| ATOM | 846 | NZ | LYS | 122 | 21.799 | 26.326 | 8.922 | 1.00 | 40.28 |
| ATOM | 847 | C | LYS | 122 | 18.657 | 20.496 | 5.519 | 1.00 | 26.44 |
| ATOM | 848 | O | LYS | 122 | 18.704 | 20.909 | 4.353 | 1.00 | 27.76 |
| ATOM | 849 | N | PHE | 123 | 17.765 | 19.622 | 5.946 | 1.00 | 26.32 |
| ATOM | 850 | CA | PHE | 123 | 16.865 | 18.894 | 5.067 | 1.00 | 26.09 |
| ATOM | 851 | CB | PHE | 123 | 16.605 | 17.465 | 5.583 | 1.00 | 25.12 |
| ATOM | 852 | CG | PHE | 123 | 17.703 | 16.522 | 5.238 | 1.00 | 24.90 |
| ATOM | 853 | CD1 | PHE | 123 | 18.921 | 16.580 | 5.928 | 1.00 | 22.78 |
| ATOM | 854 | CE1 | PHE | 123 | 20.024 | 15.745 | 5.540 | 1.00 | 26.27 |
| ATOM | 855 | CZ | PHE | 123 | 19.847 | 14.839 | 4.489 | 1.00 | 27.25 |
| ATOM | 856 | CE2 | PHE | 123 | 18.597 | 14.764 | 3.809 | 1.00 | 25.30 |
| ATOM | 857 | CD2 | PHE | 123 | 17.551 | 15.609 | 4.177 | 1.00 | 24.32 |
| ATOM | 858 | C | PHE | 123 | 15.576 | 19.635 | 4.922 | 1.00 | 27.81 |
| ATOM | 859 | O | PHE | 123 | 15.261 | 20.468 | 5.750 | 1.00 | 28.26 |
| ATOM | 860 | N | THR | 124 | 14.833 | 19.321 | 3.852 | 1.00 | 28.52 |
| ATOM | 861 | CA | THR | 124 | 13.525 | 19.924 | 3.604 | 1.00 | 28.16 |
| ATOM | 862 | CB | THR | 124 | 13.196 | 19.913 | 2.061 | 1.00 | 28.66 |
| ATOM | 863 | OG1 | THR | 124 | 13.159 | 18.555 | 1.567 | 1.00 | 24.86 |
| ATOM | 864 | CG2 | THR | 124 | 14.299 | 20.723 | 1.255 | 1.00 | 25.85 |
| ATOM | 865 | C | THR | 124 | 12.471 | 19.134 | 4.432 | 1.00 | 29.59 |
| ATOM | 866 | O | THR | 124 | 12.682 | 17.947 | 4.731 | 1.00 | 29.24 |
| ATOM | 867 | N | PRO | 125 | 11.362 | 19.793 | 4.824 | 1.00 | 29.30 |
| ATOM | 868 | CA | PRO | 125 | 10.530 | 19.080 | 5.725 | 1.00 | 30.23 |
| ATOM | 869 | CB | PRO | 125 | 9.591 | 20.172 | 6.295 | 1.00 | 29.73 |
| ATOM | 870 | CG | PRO | 125 | 9.486 | 21.185 | 5.206 | 1.00 | 29.08 |
| ATOM | 871 | CD | PRO | 125 | 10.870 | 21.176 | 4.578 | 1.00 | 28.72 |
| ATOM | 872 | C | PRO | 125 | 9.754 | 17.938 | 5.114 | 1.00 | 31.25 |
| ATOM | 873 | O | PRO | 125 | 9.627 | 17.859 | 3.901 | 1.00 | 31.50 |
| ATOM | 874 | N | ARG | 126 | 9.287 | 17.040 | 5.987 | 1.00 | 32.08 |
| ATOM | 875 | CA | ARG | 126 | 8.391 | 15.886 | 5.652 | 1.00 | 33.66 |
| ATOM | 876 | CB | ARG | 126 | 9.161 | 14.548 | 5.698 | 1.00 | 33.84 |
| ATOM | 877 | CG | ARG | 126 | 9.629 | 13.958 | 4.391 | 1.00 | 40.80 |
| ATOM | 878 | CD | ARG | 126 | 10.157 | 15.048 | 3.470 | 1.00 | 49.19 |
| ATOM | 879 | NE | ARG | 126 | 10.468 | 14.620 | 2.095 | 1.00 | 53.43 |
| ATOM | 880 | CZ | ARG | 126 | 10.260 | 15.383 | 1.019 | 1.00 | 54.41 |
| ATOM | 881 | NH1 | ARG | 126 | 9.697 | 16.583 | 1.154 | 1.00 | 52.21 |
| ATOM | 882 | NH2 | ARG | 126 | 10.591 | 14.933 | −0.190 | 1.00 | 55.80 |
| ATOM | 883 | C | ARG | 126 | 7.398 | 15.872 | 6.787 | 1.00 | 32.80 |
| ATOM | 884 | O | ARG | 126 | 7.782 | 15.809 | 7.949 | 1.00 | 32.63 |
| ATOM | 885 | N | GLY | 127 | 6.130 | 15.965 | 6.490 | 1.00 | 32.28 |
| ATOM | 886 | CA | GLY | 127 | 5.175 | 15.898 | 7.529 | 1.00 | 33.33 |
| ATOM | 887 | C | GLY | 127 | 5.223 | 17.151 | 8.367 | 1.00 | 33.71 |
| ATOM | 888 | O | GLY | 127 | 4.661 | 17.163 | 9.448 | 1.00 | 36.24 |
| ATOM | 889 | N | GLY | 128 | 5.898 | 18.200 | 7.890 | 1.00 | 33.07 |
| ATOM | 890 | CA | GLY | 128 | 5.878 | 19.513 | 8.545 | 1.00 | 31.01 |
| ATOM | 891 | C | GLY | 128 | 7.096 | 19.756 | 9.403 | 1.00 | 30.37 |
| ATOM | 892 | O | GLY | 128 | 7.247 | 20.806 | 9.995 | 1.00 | 29.97 |
| ATOM | 893 | N | ILE | 129 | 7.995 | 18.792 | 9.417 | 1.00 | 30.13 |
| ATOM | 894 | CA | ILE | 129 | 9.097 | 18.777 | 10.352 | 1.00 | 30.80 |
| ATOM | 895 | CB | ILE | 129 | 8.881 | 17.556 | 11.360 | 1.00 | 31.06 |
| ATOM | 896 | CG1 | ILE | 129 | 7.837 | 17.934 | 12.405 | 1.00 | 31.42 |
| ATOM | 897 | CD1 | ILE | 129 | 7.494 | 16.802 | 13.347 | 1.00 | 31.28 |
| ATOM | 898 | CG2 | ILE | 129 | 10.173 | 17.094 | 12.021 | 1.00 | 30.12 |
| ATOM | 899 | C | ILE | 129 | 10.371 | 18.585 | 9.523 | 1.00 | 30.22 |
| ATOM | 900 | O | ILE | 129 | 10.432 | 17.662 | 8.765 | 1.00 | 29.71 |
| ATOM | 901 | N | SER | 130 | 11.378 | 19.443 | 9.697 | 1.00 | 29.49 |
| ATOM | 902 | CA | SER | 130 | 12.628 | 19.267 | 9.021 | 1.00 | 29.39 |
| ATOM | 903 | CB | SER | 130 | 13.054 | 20.535 | 8.265 | 1.00 | 29.82 |
| ATOM | 904 | OG | SER | 130 | 12.895 | 21.700 | 9.066 | 1.00 | 33.34 |
| ATOM | 905 | C | SER | 130 | 13.699 | 18.932 | 10.019 | 1.00 | 28.67 |
| ATOM | 906 | O | SER | 130 | 13.638 | 19.323 | 11.181 | 1.00 | 28.81 |
| ATOM | 907 | N | ILE | 131 | 14.717 | 18.255 | 9.535 | 1.00 | 28.29 |
| ATOM | 908 | CA | ILE | 131 | 15.707 | 17.664 | 10.398 | 1.00 | 28.60 |
| ATOM | 909 | CB | ILE | 131 | 15.790 | 16.156 | 10.178 | 1.00 | 28.00 |
| ATOM | 910 | CG1 | ILE | 131 | 14.469 | 15.478 | 10.509 | 1.00 | 29.12 |

TABLE 2-continued

| | | | | | | | | | |
|---|---|---|---|---|---|---|---|---|---|
| ATOM | 911 | CD1 | ILE | 131 | 14.627 | 13.943 | 10.523 | 1.00 | 31.67 |
| ATOM | 912 | CG2 | ILE | 131 | 16.846 | 15.553 | 11.098 | 1.00 | 30.30 |
| ATOM | 913 | C | ILE | 131 | 17.040 | 18.173 | 10.015 | 1.00 | 28.51 |
| ATOM | 914 | O | ILE | 131 | 17.419 | 17.993 | 8.875 | 1.00 | 30.21 |
| ATOM | 915 | N | ASP | 132 | 17.794 | 18.754 | 10.939 | 1.00 | 28.50 |
| ATOM | 916 | CA | ASP | 132 | 19.112 | 19.247 | 10.589 | 1.00 | 28.58 |
| ATOM | 917 | CB | ASP | 132 | 19.167 | 20.775 | 10.742 | 1.00 | 28.59 |
| ATOM | 918 | CG | ASP | 132 | 18.050 | 21.518 | 9.972 | 1.00 | 32.67 |
| ATOM | 919 | OD1 | ASP | 132 | 17.413 | 20.908 | 9.047 | 1.00 | 33.13 |
| ATOM | 920 | OD2 | ASP | 132 | 17.832 | 22.734 | 10.281 | 1.00 | 30.84 |
| ATOM | 921 | C | ASP | 132 | 20.210 | 18.639 | 11.454 | 1.00 | 28.06 |
| ATOM | 922 | O | ASP | 132 | 20.569 | 19.228 | 12.481 | 1.00 | 29.94 |
| ATOM | 923 | N | PRO | 133 | 20.839 | 17.547 | 10.997 | 1.00 | 27.68 |
| ATOM | 924 | CA | PRO | 133 | 21.936 | 17.031 | 11.821 | 1.00 | 26.24 |
| ATOM | 925 | CB | PRO | 133 | 22.078 | 15.559 | 11.365 | 1.00 | 26.83 |
| ATOM | 926 | CG | PRO | 133 | 20.930 | 15.323 | 10.234 | 1.00 | 26.13 |
| ATOM | 927 | CD | PRO | 133 | 20.617 | 16.733 | 9.765 | 1.00 | 26.41 |
| ATOM | 928 | C | PRO | 133 | 23.258 | 17.746 | 11.623 | 1.00 | 27.02 |
| ATOM | 929 | O | PRO | 133 | 23.634 | 18.075 | 10.463 | 1.00 | 26.96 |
| ATOM | 930 | N | TYR | 134 | 24.006 | 17.887 | 12.730 | 1.00 | 25.47 |
| ATOM | 931 | CA | TYR | 134 | 25.353 | 18.441 | 12.739 | 1.00 | 25.89 |
| ATOM | 932 | CB | TYR | 134 | 25.311 | 19.763 | 13.512 | 1.00 | 25.31 |
| ATOM | 933 | CG | TYR | 134 | 26.660 | 20.370 | 13.838 | 1.00 | 24.35 |
| ATOM | 934 | CD1 | TYR | 134 | 27.193 | 20.315 | 15.160 | 1.00 | 23.18 |
| ATOM | 935 | CE1 | TYR | 134 | 28.464 | 20.875 | 15.453 | 1.00 | 24.08 |
| ATOM | 936 | CZ | TYR | 134 | 29.136 | 21.535 | 14.468 | 1.00 | 21.88 |
| ATOM | 937 | OH | TYR | 134 | 30.320 | 22.155 | 14.703 | 1.00 | 23.60 |
| ATOM | 938 | CE2 | TYR | 134 | 28.575 | 21.692 | 13.175 | 1.00 | 25.78 |
| ATOM | 939 | CD2 | TYR | 134 | 27.337 | 21.105 | 12.887 | 1.00 | 23.05 |
| ATOM | 940 | C | TYR | 134 | 26.331 | 17.477 | 13.464 | 1.00 | 27.74 |
| ATOM | 941 | O | TYR | 134 | 26.066 | 17.083 | 14.598 | 1.00 | 27.04 |
| ATOM | 942 | N | THR | 135 | 27.471 | 17.150 | 12.848 | 1.00 | 27.77 |
| ATOM | 943 | CA | THR | 135 | 28.403 | 16.194 | 13.401 | 1.00 | 27.90 |
| ATOM | 944 | CB | THR | 135 | 28.394 | 14.886 | 12.563 | 1.00 | 29.73 |
| ATOM | 945 | OG1 | THR | 135 | 28.743 | 15.179 | 11.191 | 1.00 | 26.82 |
| ATOM | 946 | CG2 | THR | 135 | 27.005 | 14.317 | 12.501 | 1.00 | 31.70 |
| ATOM | 947 | C | THR | 135 | 29.699 | 16.946 | 13.214 | 1.00 | 28.27 |
| ATOM | 948 | O | THR | 135 | 29.785 | 17.707 | 12.252 | 1.00 | 26.29 |
| ATOM | 949 | N | ASN | 136 | 30.653 | 16.831 | 14.148 | 1.00 | 27.30 |
| ATOM | 950 | CA | ASN | 136 | 32.002 | 17.319 | 13.914 | 1.00 | 29.52 |
| ATOM | 951 | CB | ASN | 136 | 32.146 | 18.721 | 14.480 | 1.00 | 30.32 |
| ATOM | 952 | CG | ASN | 136 | 32.092 | 18.720 | 15.989 | 1.00 | 33.09 |
| ATOM | 953 | OD1 | ASN | 136 | 31.961 | 17.636 | 16.598 | 1.00 | 33.19 |
| ATOM | 954 | ND2 | ASN | 136 | 32.190 | 19.908 | 16.606 | 1.00 | 29.70 |
| ATOM | 955 | C | ASN | 136 | 33.094 | 16.332 | 14.492 | 1.00 | 30.64 |
| ATOM | 956 | O | ASN | 136 | 32.777 | 15.211 | 14.918 | 1.00 | 30.23 |
| ATOM | 957 | N | TYR | 137 | 34.354 | 16.737 | 14.516 | 1.00 | 31.44 |
| ATOM | 958 | CA | TYR | 137 | 35.400 | 15.800 | 14.836 | 1.00 | 33.26 |
| ATOM | 959 | CB | TYR | 137 | 35.489 | 14.757 | 13.753 | 1.00 | 33.53 |
| ATOM | 960 | CG | TYR | 137 | 36.833 | 14.100 | 13.657 | 1.00 | 37.68 |
| ATOM | 961 | CD1 | TYR | 137 | 37.882 | 14.695 | 12.916 | 1.00 | 39.03 |
| ATOM | 962 | CE1 | TYR | 137 | 39.122 | 14.089 | 12.833 | 1.00 | 38.62 |
| ATOM | 963 | CZ | TYR | 137 | 39.312 | 12.858 | 13.475 | 1.00 | 37.04 |
| ATOM | 964 | OH | TYR | 137 | 40.525 | 12.236 | 13.388 | 1.00 | 37.95 |
| ATOM | 965 | CE2 | TYR | 137 | 38.311 | 12.257 | 14.205 | 1.00 | 39.58 |
| ATOM | 966 | CD2 | TYR | 137 | 37.077 | 12.876 | 14.306 | 1.00 | 39.01 |
| ATOM | 967 | C | TYR | 137 | 36.684 | 16.558 | 14.878 | 1.00 | 34.30 |
| ATOM | 968 | O | TYR | 137 | 36.897 | 17.336 | 13.999 | 1.00 | 34.65 |
| ATOM | 969 | N | GLY | 138 | 37.514 | 16.329 | 15.904 | 1.00 | 34.97 |
| ATOM | 970 | CA | GLY | 138 | 38.871 | 16.847 | 16.012 | 1.00 | 36.70 |
| ATOM | 971 | C | GLY | 138 | 39.852 | 15.671 | 16.087 | 1.00 | 38.86 |
| ATOM | 972 | O | GLY | 138 | 39.526 | 14.615 | 16.616 | 1.00 | 39.30 |
| ATOM | 973 | N | MET | 147 | 38.468 | 21.956 | 20.283 | 1.00 | 37.42 |
| ATOM | 974 | CA | MET | 147 | 37.682 | 22.767 | 19.336 | 1.00 | 36.40 |
| ATOM | 975 | CB | MET | 147 | 38.459 | 23.029 | 18.060 | 1.00 | 36.69 |
| ATOM | 976 | CG | MET | 147 | 37.593 | 23.631 | 16.948 | 1.00 | 36.55 |
| ATOM | 977 | SD | MET | 147 | 38.714 | 24.162 | 15.672 | 1.00 | 38.00 |
| ATOM | 978 | CE | MET | 147 | 37.547 | 24.843 | 14.490 | 1.00 | 37.25 |
| ATOM | 979 | C | MET | 147 | 36.366 | 22.103 | 18.976 | 1.00 | 33.80 |
| ATOM | 980 | O | MET | 147 | 35.305 | 22.744 | 19.030 | 1.00 | 34.54 |
| ATOM | 981 | N | ALA | 148 | 36.429 | 20.827 | 18.635 | 1.00 | 30.79 |
| ATOM | 982 | CA | ALA | 148 | 35.230 | 20.089 | 18.325 | 1.00 | 30.36 |
| ATOM | 983 | CB | ALA | 148 | 35.582 | 18.690 | 17.935 | 1.00 | 29.44 |
| ATOM | 984 | C | ALA | 148 | 34.236 | 20.072 | 19.479 | 1.00 | 30.74 |
| ATOM | 985 | O | ALA | 148 | 33.012 | 20.234 | 19.270 | 1.00 | 30.28 |
| ATOM | 986 | N | GLU | 149 | 34.743 | 19.849 | 20.696 | 1.00 | 31.65 |
| ATOM | 987 | CA | GLU | 149 | 33.881 | 19.835 | 21.899 | 1.00 | 34.35 |
| ATOM | 988 | CB | GLU | 149 | 34.687 | 19.538 | 23.186 | 1.00 | 33.19 |
| ATOM | 989 | CG | GLU | 149 | 34.830 | 18.057 | 23.481 | 1.00 | 38.88 |
| ATOM | 990 | CD | GLU | 149 | 36.210 | 17.658 | 24.163 | 1.00 | 42.14 |

TABLE 2-continued

| | | | | | | | | | |
|---|---|---|---|---|---|---|---|---|---|
| ATOM | 991 | OE1 | GLU | 149 | 36.848 | 18.531 | 24.832 | 1.00 | 47.60 |
| ATOM | 992 | OE2 | GLU | 149 | 36.641 | 16.452 | 24.008 | 1.00 | 50.65 |
| ATOM | 993 | C | GLU | 149 | 33.213 | 21.164 | 22.061 | 1.00 | 31.67 |
| ATOM | 994 | O | GLU | 149 | 32.036 | 21.261 | 22.343 | 1.00 | 31.83 |
| ATOM | 995 | N | TYR | 150 | 34.013 | 22.189 | 21.902 | 1.00 | 31.60 |
| ATOM | 996 | CA | TYR | 150 | 33.571 | 23.548 | 22.014 | 1.00 | 32.38 |
| ATOM | 997 | CB | TYR | 150 | 34.783 | 24.435 | 21.874 | 1.00 | 32.16 |
| ATOM | 998 | CG | TYR | 150 | 34.409 | 25.874 | 21.801 | 1.00 | 36.56 |
| ATOM | 999 | CD1 | TYR | 150 | 34.387 | 26.670 | 22.953 | 1.00 | 35.94 |
| ATOM | 1000 | CE1 | TYR | 150 | 34.037 | 28.033 | 22.867 | 1.00 | 38.57 |
| ATOM | 1001 | CZ | TYR | 150 | 33.684 | 28.584 | 21.599 | 1.00 | 36.14 |
| ATOM | 1002 | OH | TYR | 150 | 33.322 | 29.902 | 21.495 | 1.00 | 36.38 |
| ATOM | 1003 | CE2 | TYR | 150 | 33.692 | 27.813 | 20.458 | 1.00 | 36.52 |
| ATOM | 1004 | CD2 | TYR | 150 | 34.061 | 26.463 | 20.557 | 1.00 | 39.37 |
| ATOM | 1005 | C | TYR | 150 | 32.491 | 23.943 | 20.961 | 1.00 | 31.78 |
| ATOM | 1006 | O | TYR | 150 | 31.538 | 24.634 | 21.301 | 1.00 | 31.53 |
| ATOM | 1007 | N | ARG | 151 | 32.649 | 23.502 | 19.711 | 1.00 | 30.58 |
| ATOM | 1008 | CA | ARG | 151 | 31.679 | 23.869 | 18.629 | 1.00 | 31.25 |
| ATOM | 1009 | CB | ARG | 151 | 32.270 | 23.750 | 17.213 | 1.00 | 29.31 |
| ATOM | 1010 | CG | ARG | 151 | 33.403 | 24.722 | 17.014 | 1.00 | 29.65 |
| ATOM | 1011 | CD | ARG | 151 | 34.070 | 24.685 | 15.627 | 1.00 | 33.04 |
| ATOM | 1012 | NE | ARG | 151 | 33.214 | 25.051 | 14.483 | 1.00 | 34.09 |
| ATOM | 1013 | CZ | ARG | 151 | 33.217 | 26.222 | 13.823 | 1.00 | 29.45 |
| ATOM | 1014 | NH1 | ARG | 151 | 34.015 | 27.264 | 14.154 | 1.00 | 18.79 |
| ATOM | 1015 | NH2 | ARG | 151 | 32.400 | 26.339 | 12.797 | 1.00 | 26.66 |
| ATOM | 1016 | C | ARG | 151 | 30.417 | 23.061 | 18.793 | 1.00 | 31.29 |
| ATOM | 1017 | O | ARG | 151 | 29.337 | 23.531 | 18.460 | 1.00 | 31.42 |
| ATOM | 1018 | N | MET | 152 | 30.542 | 21.877 | 19.390 | 1.00 | 31.99 |
| ATOM | 1019 | CA | MET | 152 | 29.385 | 21.051 | 19.710 | 1.00 | 33.41 |
| ATOM | 1020 | CB | MET | 152 | 29.852 | 19.593 | 19.905 | 1.00 | 33.49 |
| ATOM | 1021 | CG | MET | 152 | 28.787 | 18.496 | 19.908 | 1.00 | 32.71 |
| ATOM | 1022 | SD | MET | 152 | 27.733 | 18.391 | 18.436 | 1.00 | 30.92 |
| ATOM | 1023 | CE | MET | 152 | 28.887 | 17.745 | 17.203 | 1.00 | 33.44 |
| ATOM | 1024 | C | MET | 152 | 28.647 | 21.653 | 20.935 | 1.00 | 34.99 |
| ATOM | 1025 | O | MET | 152 | 27.423 | 21.797 | 20.947 | 1.00 | 34.46 |
| ATOM | 1026 | N | MET | 153 | 29.405 | 22.060 | 21.943 | 1.00 | 37.09 |
| ATOM | 1027 | CA | MET | 153 | 28.831 | 22.638 | 23.160 | 1.00 | 40.13 |
| ATOM | 1028 | CB | MET | 153 | 29.895 | 22.908 | 24.226 | 1.00 | 38.85 |
| ATOM | 1029 | CG | MET | 153 | 29.292 | 23.367 | 25.559 | 1.00 | 45.87 |
| ATOM | 1030 | SD | MET | 153 | 30.249 | 22.912 | 27.096 | 1.00 | 49.98 |
| ATOM | 1031 | CE | MET | 153 | 30.843 | 21.220 | 26.665 | 1.00 | 48.92 |
| ATOM | 1032 | C | MET | 153 | 28.089 | 23.914 | 22.840 | 1.00 | 36.91 |
| ATOM | 1033 | O | MET | 153 | 27.057 | 24.183 | 23.431 | 1.00 | 36.31 |
| ATOM | 1034 | N | ASN | 154 | 28.613 | 24.680 | 21.888 | 1.00 | 35.83 |
| ATOM | 1035 | CA | ASN | 154 | 28.030 | 25.983 | 21.510 | 1.00 | 34.38 |
| ATOM | 1036 | CB | ASN | 154 | 29.136 | 27.010 | 21.408 | 1.00 | 34.16 |
| ATOM | 1037 | CG | ASN | 154 | 29.770 | 27.318 | 22.730 | 1.00 | 34.51 |
| ATOM | 1038 | OD1 | ASN | 154 | 29.320 | 28.204 | 23.433 | 1.00 | 36.25 |
| ATOM | 1039 | ND2 | ASN | 154 | 30.845 | 26.608 | 23.065 | 1.00 | 33.62 |
| ATOM | 1040 | C | ASN | 154 | 27.286 | 25.948 | 20.143 | 1.00 | 34.41 |
| ATOM | 1041 | O | ASN | 154 | 27.190 | 26.983 | 19.430 | 1.00 | 34.63 |
| ATOM | 1042 | N | HIS | 155 | 26.844 | 24.765 | 19.730 | 1.00 | 33.08 |
| ATOM | 1043 | CA | HIS | 155 | 26.248 | 24.634 | 18.432 | 1.00 | 31.09 |
| ATOM | 1044 | CB | HIS | 155 | 26.104 | 23.207 | 18.044 | 1.00 | 31.32 |
| ATOM | 1045 | CG | HIS | 155 | 25.396 | 23.012 | 16.730 | 1.00 | 30.25 |
| ATOM | 1046 | ND1 | HIS | 155 | 25.856 | 23.551 | 15.543 | 1.00 | 27.73 |
| ATOM | 1047 | CE1 | HIS | 155 | 25.026 | 23.219 | 14.573 | 1.00 | 29.09 |
| ATOM | 1048 | NE2 | HIS | 155 | 24.077 | 22.447 | 15.074 | 1.00 | 28.79 |
| ATOM | 1049 | CD2 | HIS | 155 | 24.284 | 22.309 | 16.419 | 1.00 | 28.65 |
| ATOM | 1050 | C | HIS | 155 | 24.873 | 25.175 | 18.488 | 1.00 | 31.08 |
| ATOM | 1051 | O | HIS | 155 | 24.076 | 24.835 | 19.403 | 1.00 | 28.75 |
| ATOM | 1052 | N | ASP | 156 | 24.585 | 26.002 | 17.479 | 1.00 | 30.62 |
| ATOM | 1053 | CA | ASP | 156 | 23.260 | 26.453 | 17.233 | 1.00 | 31.29 |
| ATOM | 1054 | CB | ASP | 156 | 22.517 | 25.325 | 16.598 | 1.00 | 32.05 |
| ATOM | 1055 | CG | ASP | 156 | 21.363 | 25.797 | 15.752 | 1.00 | 33.74 |
| ATOM | 1056 | OD1 | ASP | 156 | 21.378 | 26.950 | 15.278 | 1.00 | 33.95 |
| ATOM | 1057 | OD2 | ASP | 156 | 20.436 | 24.979 | 15.589 | 1.00 | 33.43 |
| ATOM | 1058 | C | ASP | 156 | 22.559 | 26.967 | 18.494 | 1.00 | 31.76 |
| ATOM | 1059 | O | ASP | 156 | 21.532 | 26.487 | 18.884 | 1.00 | 32.57 |
| ATOM | 1060 | N | LEU | 157 | 23.156 | 27.957 | 19.133 | 1.00 | 32.78 |
| ATOM | 1061 | CA | LEU | 157 | 22.570 | 28.577 | 20.301 | 1.00 | 34.05 |
| ATOM | 1062 | CB | LEU | 157 | 23.635 | 29.418 | 20.980 | 1.00 | 34.15 |
| ATOM | 1063 | CG | LEU | 157 | 24.744 | 28.663 | 21.731 | 1.00 | 35.92 |
| ATOM | 1064 | CD1 | LEU | 157 | 25.906 | 29.625 | 21.958 | 1.00 | 36.14 |
| ATOM | 1065 | CD2 | LEU | 157 | 24.241 | 28.121 | 23.056 | 1.00 | 34.26 |
| ATOM | 1066 | C | LEU | 157 | 21.371 | 29.477 | 19.948 | 1.00 | 34.83 |
| ATOM | 1067 | O | LEU | 157 | 20.516 | 29.751 | 20.806 | 1.00 | 34.79 |
| ATOM | 1068 | N | TYR | 158 | 21.312 | 23.931 | 18.683 | 1.00 | 34.65 |
| ATOM | 1069 | CA | TYR | 158 | 20.195 | 30.746 | 18.183 | 1.00 | 34.37 |
| ATOM | 1070 | CB | TYR | 158 | 20.616 | 32.208 | 17.918 | 1.00 | 35.77 |

TABLE 2-continued

| | | | | | | | | |
|---|---|---|---|---|---|---|---|---|
| ATOM | 1071 | CG | TYR | 158 | 21.019 | 32.940 | 19.181 | 1.00 | 38.74 |
| ATOM | 1072 | CD1 | TYR | 158 | 20.057 | 33.598 | 19.965 | 1.00 | 38.20 |
| ATOM | 1073 | CE1 | TYR | 158 | 20.410 | 34.257 | 21.150 | 1.00 | 37.71 |
| ATOM | 1074 | CZ | TYR | 158 | 21.733 | 34.252 | 21.567 | 1.00 | 38.93 |
| ATOM | 1075 | OH | TYR | 158 | 22.061 | 34.900 | 22.743 | 1.00 | 41.49 |
| ATOM | 1076 | CE2 | TYR | 158 | 22.732 | 33.596 | 20.821 | 1.00 | 40.00 |
| ATOM | 1077 | CD2 | TYR | 158 | 22.369 | 32.953 | 19.609 | 1.00 | 39.09 |
| ATOM | 1078 | C | TYR | 158 | 19.782 | 30.119 | 16.899 | 1.00 | 32.77 |
| ATOM | 1079 | O | TYR | 158 | 20.260 | 30.514 | 15.869 | 1.00 | 33.47 |
| ATOM | 1080 | N | PRO | 159 | 18.872 | 29.176 | 16.952 | 1.00 | 31.26 |
| ATOM | 1081 | CA | PRO | 159 | 18.385 | 28.472 | 15.784 | 1.00 | 30.51 |
| ATOM | 1082 | CB | PRO | 159 | 17.350 | 27.474 | 16.366 | 1.00 | 30.21 |
| ATOM | 1083 | CG | PRO | 159 | 17.594 | 27.464 | 17.887 | 1.00 | 31.97 |
| ATOM | 1084 | CD | PRO | 159 | 18.142 | 28.826 | 18.185 | 1.00 | 31.36 |
| ATOM | 1085 | C | PRO | 159 | 17.657 | 29.371 | 14.774 | 1.00 | 30.10 |
| ATOM | 1086 | O | PRO | 159 | 16.800 | 30.146 | 15.154 | 1.00 | 29.37 |
| ATOM | 1087 | N | GLU | 160 | 17.972 | 29.229 | 13.492 | 1.00 | 30.16 |
| ATOM | 1088 | CA | GLU | 160 | 17.340 | 30.039 | 12.439 | 1.00 | 32.04 |
| ATOM | 1089 | CB | GLU | 160 | 17.940 | 29.655 | 11.078 | 1.00 | 30.18 |
| ATOM | 1090 | CG | GLU | 160 | 17.451 | 28.269 | 10.560 | 1.00 | 34.46 |
| ATOM | 1091 | CD | GLU | 160 | 18.176 | 27.789 | 9.280 | 1.00 | 35.57 |
| ATOM | 1092 | OE1 | GLU | 160 | 18.892 | 28.583 | 8.668 | 1.00 | 41.25 |
| ATOM | 1093 | OE2 | GLU | 160 | 18.043 | 26.610 | 8.882 | 1.00 | 41.34 |
| ATOM | 1094 | C | GLU | 160 | 15.796 | 29.901 | 12.440 | 1.00 | 30.49 |
| ATOM | 1095 | O | GLU | 160 | 15.265 | 28.826 | 12.745 | 1.00 | 31.95 |
| ATOM | 1096 | N | THR | 161 | 15.079 | 30.977 | 12.145 | 1.00 | 29.64 |
| ATOM | 1097 | CA | THR | 161 | 13.628 | 30.878 | 11.976 | 1.00 | 29.93 |
| ATOM | 1098 | CB | THR | 161 | 12.989 | 32.244 | 11.817 | 1.00 | 29.91 |
| ATOM | 1099 | OG1 | THR | 161 | 13.379 | 33.017 | 12.930 | 1.00 | 31.93 |
| ATOM | 1100 | CG2 | THR | 161 | 11.475 | 32.196 | 11.839 | 1.00 | 30.92 |
| ATOM | 1101 | C | THR | 161 | 13.283 | 30.018 | 10.776 | 1.00 | 29.45 |
| ATOM | 1102 | O | THR | 161 | 13.856 | 30.195 | 9.712 | 1.00 | 26.77 |
| ATOM | 1103 | N | ILE | 162 | 12.415 | 29.040 | 11.003 | 1.00 | 29.30 |
| ATOM | 1104 | CA | ILE | 162 | 11.966 | 28.158 | 9.973 | 1.00 | 30.78 |
| ATOM | 1105 | CB | ILE | 162 | 12.415 | 26.699 | 10.241 | 1.00 | 30.32 |
| ATOM | 1106 | CG1 | ILE | 162 | 13.955 | 26.574 | 10.160 | 1.00 | 32.82 |
| ATOM | 1107 | CD1 | ILE | 162 | 14.639 | 26.722 | 8.752 | 1.00 | 30.34 |
| ATOM | 1108 | CG2 | ILE | 162 | 11.698 | 25.722 | 9.318 | 1.00 | 29.66 |
| ATOM | 1109 | C | ILE | 162 | 10.438 | 28.188 | 9.964 | 1.00 | 31.75 |
| ATOM | 1110 | O | ILE | 162 | 9.826 | 28.114 | 11.040 | 1.00 | 31.45 |
| ATOM | 1111 | N | ASP | 163 | 9.843 | 28.306 | 8.766 | 1.00 | 32.01 |
| ATOM | 1112 | CA | ASP | 163 | 8.378 | 28.328 | 8.588 | 1.00 | 33.79 |
| ATOM | 1113 | CB | ASP | 163 | 7.854 | 29.768 | 8.337 | 1.00 | 34.23 |
| ATOM | 1114 | CG | ASP | 163 | 8.388 | 30.389 | 7.033 | 1.00 | 36.10 |
| ATOM | 1115 | OD1 | ASP | 163 | 9.275 | 29.759 | 6.362 | 1.00 | 36.53 |
| ATOM | 1116 | OD2 | ASP | 163 | 7.942 | 31.523 | 6.676 | 1.00 | 34.45 |
| ATOM | 1117 | C | ASP | 163 | 7.892 | 27.387 | 7.475 | 1.00 | 34.13 |
| ATOM | 1118 | O | ASP | 163 | 6.723 | 27.397 | 7.129 | 1.00 | 34.59 |
| ATOM | 1119 | N | ASN | 164 | 8.802 | 26.590 | 6.917 | 1.00 | 33.87 |
| ATOM | 1120 | CA | ASN | 164 | 8.479 | 25.672 | 5.830 | 1.00 | 34.28 |
| ATOM | 1121 | CB | ASN | 164 | 7.383 | 24.655 | 6.231 | 1.00 | 32.50 |
| ATOM | 1122 | CG | ASN | 164 | 7.827 | 23.673 | 7.325 | 1.00 | 32.82 |
| ATOM | 1123 | OD1 | ASN | 164 | 9.016 | 23.590 | 7.685 | 1.00 | 30.94 |
| ATOM | 1124 | ND2 | ASN | 164 | 6.852 | 22.923 | 7.862 | 1.00 | 29.12 |
| ATOM | 1125 | C | ASN | 164 | 8.121 | 26.320 | 4.469 | 1.00 | 34.97 |
| ATOM | 1126 | O | ASN | 164 | 7.603 | 25.637 | 3.594 | 1.00 | 35.11 |
| ATOM | 1127 | O6 | GDQ | 201 | 39.880 | 25.293 | −6.152 | 1.00 | 46.27 |
| ATOM | 1128 | C6 | GDQ | 201 | 39.593 | 23.968 | −5.959 | 1.00 | 47.77 |
| ATOM | 1129 | N1 | GDQ | 201 | 39.601 | 23.364 | −4.728 | 1.00 | 47.90 |
| ATOM | 1130 | C5 | GDQ | 201 | 39.301 | 23.178 | −7.050 | 1.00 | 48.17 |
| ATOM | 1131 | C7 | GDQ | 201 | 39.166 | 23.330 | −8.414 | 1.00 | 49.49 |
| ATOM | 1132 | C77 | GDQ | 201 | 39.375 | 24.484 | −9.040 | 1.00 | 48.63 |
| ATOM | 1133 | N77 | GDQ | 201 | 39.668 | 25.525 | −9.571 | 1.00 | 53.62 |
| ATOM | 1134 | C8 | GDQ | 201 | 38.829 | 22.148 | −9.069 | 1.00 | 47.67 |
| ATOM | 1135 | N9 | GDQ | 201 | 38.739 | 21.226 | −8.070 | 1.00 | 46.70 |
| ATOM | 1136 | C4 | GDQ | 201 | 39.015 | 21.838 | −6.880 | 1.00 | 47.89 |
| ATOM | 1137 | N3 | GDQ | 201 | 39.029 | 21.264 | −5.651 | 1.00 | 47.83 |
| ATOM | 1138 | C2 | GDQ | 201 | 39.318 | 22.021 | −4.572 | 1.00 | 48.19 |
| ATOM | 1139 | N2 | GDQ | 201 | 39.322 | 21.396 | −3.361 | 1.00 | 46.97 |
| ATOM | 1140 | O | HOH | 8 | 19.757 | 8.705 | 23.115 | 1.00 | 21.93 |
| ATOM | 1141 | O | HOH | 9 | 16.730 | 33.364 | 11.382 | 1.00 | 40.66 |
| ATOM | 1142 | O | HOH | 11 | 27.237 | 28.759 | 3.717 | 1.00 | 29.18 |
| ATOM | 1143 | O | HOH | 15 | 16.223 | 26.099 | 12.905 | 1.00 | 22.43 |
| ATOM | 1144 | O | HOH | 22 | 5.725 | 20.960 | 12.801 | 1.00 | 32.23 |
| ATOM | 1145 | O | HOH | 23 | 26.483 | 26.881 | 15.694 | 1.00 | 26.29 |
| ATOM | 1146 | O | HOH | 26 | 20.142 | 27.693 | 13.096 | 1.00 | 27.14 |
| ATOM | 1147 | O | HOH | 27 | 21.868 | 6.130 | 13.585 | 1.00 | 36.47 |
| ATOM | 1148 | O | HOH | 30 | 28.511 | 2.826 | 16.753 | 1.00 | 64.34 |
| ATOM | 1149 | O | HOH | 42 | 21.767 | 21.118 | 14.240 | 1.00 | 27.24 |
| ATOM | 1150 | O | HOH | 54 | 13.783 | 16.099 | 2.576 | 1.00 | 43.09 |

TABLE 2-continued

| ATOM | 1151 | O | HOH | 55 | 28.165 | 24.628 | 15.612 | 1.00 | 39.26 |
|------|------|---|-----|-----|--------|--------|--------|------|-------|
| ATOM | 1152 | O | HOH | 56 | 19.625 | 24.149 | 10.924 | 1.00 | 40.09 |
| ATOM | 1153 | O | HOH | 64 | 13.811 | 16.584 | 6.994 | 1.00 | 28.09 |
| ATOM | 1154 | O | HOH | 65 | 20.835 | 31.317 | 12.975 | 1.00 | 40.30 |
| ATOM | 1155 | O | HOH | 78 | 16.145 | 11.484 | 15.642 | 1.00 | 27.30 |
| ATOM | 1156 | O | HOH | 83 | 7.785 | 13.582 | 9.680 | 1.00 | 34.38 |
| ATOM | 1157 | O | HOH | 87 | 10.805 | 31.014 | 15.075 | 1.00 | 32.69 |
| ATOM | 1158 | O | HOH | 103 | 25.573 | 11.359 | 19.680 | 1.00 | 45.74 |
| ATOM | 1159 | O | HOH | 108 | 18.579 | 19.668 | −2.773 | 1.00 | 36.21 |
| ATOM | 1160 | O | HOH | 115 | 15.369 | 1.539 | 19.644 | 1.00 | 54.53 |
| ATOM | 1161 | O | HOH | 126 | 10.486 | 32.719 | 8.446 | 1.00 | 49.09 |
| ATOM | 1162 | O | HOH | 131 | 9.705 | 2.773 | 20.602 | 1.00 | 44.26 |
| ATOM | 1163 | O | HOH | 163 | 6.170 | 18.948 | 5.019 | 1.00 | 33.75 |
| ATOM | 1164 | O | HOH | 164 | 16.560 | 23.554 | 19.744 | 1.00 | 30.02 |
| ATOM | 1165 | O | HOH | 166 | 20.824 | 31.198 | 23.480 | 1.00 | 34.22 |
| ATOM | 1166 | O | HOH | 168 | 22.284 | 28.913 | 10.899 | 1.00 | 55.89 |
| ATOM | 1167 | O | HOH | 170 | 20.747 | 22.169 | 16.695 | 1.00 | 28.84 |
| ATOM | 1168 | O | HOH | 172 | 11.496 | 15.234 | 8.686 | 1.00 | 32.80 |
| ATOM | 1169 | O | HOH | 195 | 5.378 | 11.950 | 7.154 | 1.00 | 49.16 |
| ATOM | 1170 | O | HOH | 196 | 17.471 | 11.917 | 1.596 | 1.00 | 40.63 |
| ATOM | 1171 | O | HOH | 199 | 17.835 | 23.153 | 3.180 | 1.00 | 34.48 |
| ATOM | 1172 | O | HOH | 204 | 5.483 | 3.538 | 20.359 | 1.00 | 49.50 |
| ATOM | 1173 | O | HOH | 212 | 20.741 | 26.123 | 4.224 | 1.00 | 49.25 |
| ATOM | 1174 | O | HOH | 222 | 4.055 | 18.607 | 11.579 | 1.00 | 44.82 |
| ATOM | 1175 | O | HOH | 225 | 21.043 | −0.503 | 13.604 | 1.00 | 53.59 |
| ATOM | 1176 | O | HOH | 231 | 18.836 | 10.804 | 3.944 | 1.00 | 47.28 |
| ATOM | 1177 | O | HOH | 234 | 18.541 | 25.663 | 3.735 | 1.00 | 40.94 |
| ATOM | 1178 | O | HOH | 236 | 19.233 | 2.370 | 13.665 | 1.00 | 50.27 |
| ATOM | 1179 | O | HOH | 250 | 8.142 | 29.477 | 12.219 | 1.00 | 43.13 |
| TER | | | | | | | | | |

TABLE 3

| REMARK | | Accelrys ViewerPro PDB file | | | | | | | |
|--------|-----|-----|-----|-----|-----|-----|-----|-----|-----|
| REMARK | | Created: Tue Dec 14 10:14:33 Pacific Standard Time 2010 | | | | | | | |
| ATOM | 1 | N | VAL | 30 | 35.188 | 7.208 | −5.182 | 1.00 | 49.20 |
| ATOM | 2 | CA | VAL | 30 | 35.454 | 8.332 | −6.081 | 1.00 | 47.94 |
| ATOM | 3 | CB | VAL | 30 | 34.221 | 8.864 | −6.770 | 1.00 | 48.69 |
| ATOM | 4 | CG1 | VAL | 30 | 33.080 | 9.166 | −5.764 | 1.00 | 48.60 |
| ATOM | 5 | CG2 | VAL | 30 | 33.777 | 7.884 | −7.796 | 1.00 | 49.82 |
| ATOM | 6 | C | VAL | 30 | 36.110 | 9.501 | −5.411 | 1.00 | 47.63 |
| ATOM | 7 | O | VAL | 30 | 36.705 | 10.336 | −6.102 | 1.00 | 47.83 |
| ATOM | 8 | N | LEU | 31 | 35.997 | 9.589 | −4.083 | 1.00 | 46.39 |
| ATOM | 9 | CA | LEU | 31 | 36.623 | 10.701 | −3.349 | 1.00 | 46.10 |
| ATOM | 10 | CB | LEU | 31 | 36.418 | 10.555 | −1.831 | 1.00 | 45.42 |
| ATOM | 11 | CG | LEU | 31 | 35.467 | 11.410 | −0.990 | 1.00 | 44.53 |
| ATOM | 12 | CD1 | LEU | 31 | 34.649 | 12.453 | −1.769 | 1.00 | 40.66 |
| ATOM | 13 | CD2 | LEU | 31 | 34.593 | 10.516 | −0.105 | 1.00 | 38.57 |
| ATOM | 14 | C | LEU | 31 | 38.104 | 10.771 | −3.656 | 1.00 | 45.76 |
| ATOM | 15 | O | LEU | 31 | 38.776 | 9.764 | −3.587 | 1.00 | 46.94 |
| ATOM | 16 | N | GLU | 32 | 38.621 | 11.953 | −3.948 | 1.00 | 45.42 |
| ATOM | 17 | CA | GLU | 32 | 40.029 | 12.108 | −4.271 | 1.00 | 46.01 |
| ATOM | 18 | CB | GLU | 32 | 40.226 | 12.276 | −5.787 | 1.00 | 46.13 |
| ATOM | 19 | CG | GLU | 32 | 40.517 | 10.940 | −6.509 | 1.00 | 53.01 |
| ATOM | 20 | CD | GLU | 32 | 39.789 | 10.828 | −7.863 | 1.00 | 60.62 |
| ATOM | 21 | OE1 | GLU | 32 | 39.404 | 9.697 | −8.281 | 1.00 | 61.89 |
| ATOM | 22 | OE2 | GLU | 32 | 39.591 | 11.890 | −8.505 | 1.00 | 64.13 |
| ATOM | 23 | C | GLU | 32 | 40.614 | 13.287 | −3.514 | 1.00 | 45.29 |
| ATOM | 24 | O | GLU | 32 | 39.881 | 14.147 | −3.049 | 1.00 | 45.17 |
| ATOM | 25 | N | SER | 33 | 41.932 | 13.324 | −3.382 | 1.00 | 44.52 |
| ATOM | 26 | CA | SER | 33 | 42.562 | 14.412 | −2.671 | 1.00 | 44.63 |
| ATOM | 27 | CB | SER | 33 | 42.827 | 14.003 | −1.208 | 1.00 | 44.45 |
| ATOM | 28 | OG | SER | 33 | 43.687 | 12.891 | −1.127 | 1.00 | 43.96 |
| ATOM | 29 | C | SER | 33 | 43.844 | 14.931 | −3.326 | 1.00 | 44.72 |
| ATOM | 30 | O | SER | 33 | 44.326 | 14.393 | −4.300 | 1.00 | 44.65 |
| ATOM | 31 | N | PHE | 34 | 44.398 | 16.004 | −2.776 | 1.00 | 45.71 |
| ATOM | 32 | CA | PHE | 34 | 45.679 | 16.519 | −3.237 | 1.00 | 45.35 |
| ATOM | 33 | CB | PHE | 34 | 45.468 | 17.496 | −4.391 | 1.00 | 44.62 |
| ATOM | 34 | CG | PHE | 34 | 44.641 | 18.688 | −4.034 | 1.00 | 44.25 |
| ATOM | 35 | CD1 | PHE | 34 | 43.278 | 18.696 | −4.273 | 1.00 | 43.81 |
| ATOM | 36 | CE1 | PHE | 34 | 42.491 | 19.782 | −3.950 | 1.00 | 44.48 |
| ATOM | 37 | CZ | PHE | 34 | 43.058 | 20.909 | −3.382 | 1.00 | 44.76 |
| ATOM | 38 | CE2 | PHE | 34 | 44.435 | 20.926 | −3.135 | 1.00 | 46.87 |
| ATOM | 39 | CD2 | PHE | 34 | 45.222 | 19.804 | −3.468 | 1.00 | 44.56 |
| ATOM | 40 | C | PHE | 34 | 46.377 | 17.142 | −2.018 | 1.00 | 46.33 |
| ATOM | 41 | O | PHE | 34 | 45.723 | 17.367 | −1.001 | 1.00 | 46.77 |
| ATOM | 42 | N | PRO | 35 | 47.696 | 17.424 | −2.100 | 1.00 | 46.81 |

TABLE 3-continued

| | | | | | | | | | |
|---|---|---|---|---|---|---|---|---|---|
| ATOM | 43 | CA | PRO | 35 | 48.403 | 17.872 | −0.882 | 1.00 | 46.68 |
| ATOM | 44 | CB | PRO | 35 | 49.889 | 17.779 | −1.289 | 1.00 | 46.82 |
| ATOM | 45 | CG | PRO | 35 | 49.887 | 16.917 | −2.611 | 1.00 | 46.99 |
| ATOM | 46 | CD | PRO | 35 | 48.611 | 17.343 | −3.255 | 1.00 | 46.24 |
| ATOM | 47 | C | PRO | 35 | 48.082 | 19.315 | −0.443 | 1.00 | 46.56 |
| ATOM | 48 | O | PRO | 35 | 47.841 | 20.193 | −1.287 | 1.00 | 46.34 |
| ATOM | 49 | N | ASN | 36 | 48.114 | 19.559 | 0.866 | 1.00 | 45.58 |
| ATOM | 50 | CA | ASN | 36 | 47.993 | 20.913 | 1.369 | 1.00 | 45.10 |
| ATOM | 51 | CB | ASN | 36 | 47.523 | 20.905 | 2.849 | 1.00 | 44.56 |
| ATOM | 52 | CG | ASN | 36 | 47.318 | 22.324 | 3.444 | 1.00 | 44.20 |
| ATOM | 53 | OD1 | ASN | 36 | 47.183 | 22.473 | 4.664 | 1.00 | 43.49 |
| ATOM | 54 | ND2 | ASN | 36 | 47.288 | 23.351 | 2.593 | 1.00 | 39.78 |
| ATOM | 55 | C | ASN | 36 | 49.338 | 21.606 | 1.159 | 1.00 | 45.45 |
| ATOM | 56 | O | ASN | 36 | 50.364 | 21.110 | 1.609 | 1.00 | 45.50 |
| ATOM | 57 | N | LYS | 37 | 49.334 | 22.728 | 0.439 | 1.00 | 45.81 |
| ATOM | 58 | CA | LYS | 37 | 50.546 | 23.501 | 0.156 | 1.00 | 45.78 |
| ATOM | 59 | CB | LYS | 37 | 50.361 | 24.378 | −1.108 | 1.00 | 47.74 |
| ATOM | 60 | CG | LYS | 37 | 50.617 | 23.748 | −2.491 | 1.00 | 48.95 |
| ATOM | 61 | CD | LYS | 37 | 49.376 | 23.014 | −2.987 | 1.00 | 53.72 |
| ATOM | 62 | CE | LYS | 37 | 49.649 | 22.056 | −4.191 | 1.00 | 54.90 |
| ATOM | 63 | NZ | LYS | 37 | 48.841 | 20.741 | −4.126 | 1.00 | 55.89 |
| ATOM | 64 | C | LYS | 37 | 50.808 | 24.440 | 1.326 | 1.00 | 45.97 |
| ATOM | 65 | O | LYS | 37 | 51.790 | 25.187 | 1.308 | 1.00 | 45.48 |
| ATOM | 66 | N | HIS | 38 | 49.897 | 24.453 | 2.313 | 1.00 | 45.10 |
| ATOM | 67 | CA | HIS | 38 | 49.975 | 25.401 | 3.416 | 1.00 | 44.15 |
| ATOM | 68 | CB | HIS | 38 | 48.973 | 26.530 | 3.159 | 1.00 | 44.09 |
| ATOM | 69 | CG | HIS | 38 | 49.226 | 27.281 | 1.883 | 1.00 | 41.33 |
| ATOM | 70 | ND1 | HIS | 38 | 50.176 | 28.273 | 1.786 | 1.00 | 38.05 |
| ATOM | 71 | CE1 | HIS | 38 | 50.183 | 28.755 | 0.553 | 1.00 | 39.46 |
| ATOM | 72 | NE2 | HIS | 38 | 49.266 | 28.112 | −0.152 | 1.00 | 38.19 |
| ATOM | 73 | CD2 | HIS | 38 | 48.652 | 27.186 | 0.659 | 1.00 | 39.28 |
| ATOM | 74 | C | HIS | 38 | 49.743 | 24.727 | 4.778 | 1.00 | 44.46 |
| ATOM | 75 | O | HIS | 38 | 48.912 | 25.167 | 5.569 | 1.00 | 44.12 |
| ATOM | 76 | N | VAL | 39 | 50.485 | 23.647 | 5.021 | 1.00 | 45.16 |
| ATOM | 77 | CA | VAL | 39 | 50.414 | 22.831 | 6.240 | 1.00 | 46.22 |
| ATOM | 78 | CB | VAL | 39 | 51.230 | 21.509 | 6.093 | 1.00 | 46.86 |
| ATOM | 79 | CG1 | VAL | 39 | 50.583 | 20.609 | 5.071 | 1.00 | 46.70 |
| ATOM | 80 | CG2 | VAL | 39 | 52.713 | 21.774 | 5.666 | 1.00 | 46.70 |
| ATOM | 81 | C | VAL | 39 | 50.853 | 23.614 | 7.480 | 1.00 | 46.80 |
| ATOM | 82 | O | VAL | 39 | 50.400 | 23.332 | 8.581 | 1.00 | 46.55 |
| ATOM | 83 | N | ASP | 40 | 51.679 | 24.637 | 7.264 | 1.00 | 47.39 |
| ATOM | 84 | CA | ASP | 40 | 52.160 | 25.505 | 8.313 | 1.00 | 48.74 |
| ATOM | 85 | CB | ASP | 40 | 53.379 | 26.327 | 7.829 | 1.00 | 49.43 |
| ATOM | 86 | CG | ASP | 40 | 53.040 | 27.305 | 6.656 | 1.00 | 54.95 |
| ATOM | 87 | OD1 | ASP | 40 | 53.547 | 28.461 | 6.703 | 1.00 | 59.95 |
| ATOM | 88 | OD2 | ASP | 40 | 52.293 | 26.945 | 5.698 | 1.00 | 56.38 |
| ATOM | 89 | C | ASP | 40 | 51.100 | 26.423 | 8.938 | 1.00 | 48.10 |
| ATOM | 90 | O | ASP | 40 | 51.456 | 27.326 | 9.682 | 1.00 | 48.66 |
| ATOM | 91 | N | ARG | 41 | 49.813 | 26.236 | 8.634 | 1.00 | 46.73 |
| ATOM | 92 | CA | ARG | 41 | 48.770 | 27.046 | 9.268 | 1.00 | 44.46 |
| ATOM | 93 | CB | ARG | 41 | 48.696 | 28.427 | 8.683 | 1.00 | 45.28 |
| ATOM | 94 | CG | ARG | 41 | 48.120 | 28.481 | 7.262 | 1.00 | 47.01 |
| ATOM | 95 | CD | ARG | 41 | 47.634 | 29.863 | 7.047 | 1.00 | 51.86 |
| ATOM | 96 | NE | ARG | 41 | 48.705 | 30.821 | 7.369 | 1.00 | 55.98 |
| ATOM | 97 | CZ | ARG | 41 | 49.581 | 31.297 | 6.478 | 1.00 | 59.14 |
| ATOM | 98 | NH1 | ARG | 41 | 49.515 | 30.928 | 5.177 | 1.00 | 59.08 |
| ATOM | 99 | NH2 | ARG | 41 | 50.516 | 32.160 | 6.893 | 1.00 | 57.34 |
| ATOM | 100 | C | ARG | 41 | 47.403 | 26.424 | 9.233 | 1.00 | 42.72 |
| ATOM | 101 | O | ARG | 41 | 47.114 | 25.556 | 8.411 | 1.00 | 42.40 |
| ATOM | 102 | N | ASP | 42 | 46.572 | 26.864 | 10.168 | 1.00 | 40.89 |
| ATOM | 103 | CA | ASP | 42 | 45.205 | 26.377 | 10.275 | 1.00 | 38.92 |
| ATOM | 104 | CB | ASP | 42 | 44.720 | 26.367 | 11.705 | 1.00 | 38.95 |
| ATOM | 105 | CG | ASP | 42 | 45.337 | 25.268 | 12.540 | 1.00 | 40.24 |
| ATOM | 106 | OD1 | ASP | 42 | 46.079 | 24.436 | 12.007 | 1.00 | 42.34 |
| ATOM | 107 | OD2 | ASP | 42 | 45.064 | 25.236 | 13.756 | 1.00 | 42.98 |
| ATOM | 108 | C | ASP | 42 | 44.367 | 27.358 | 9.507 | 1.00 | 37.39 |
| ATOM | 109 | O | ASP | 42 | 44.520 | 28.571 | 9.709 | 1.00 | 36.84 |
| ATOM | 110 | N | TYR | 43 | 43.541 | 26.817 | 8.596 | 1.00 | 34.79 |
| ATOM | 111 | CA | TYR | 43 | 42.576 | 27.570 | 7.847 | 1.00 | 33.24 |
| ATOM | 112 | CB | TYR | 43 | 43.181 | 28.142 | 6.561 | 1.00 | 33.47 |
| ATOM | 113 | CG | TYR | 43 | 43.705 | 27.161 | 5.524 | 1.00 | 34.17 |
| ATOM | 114 | CD1 | TYR | 43 | 44.999 | 26.630 | 5.606 | 1.00 | 36.25 |
| ATOM | 115 | CE1 | TYR | 43 | 45.487 | 25.757 | 4.635 | 1.00 | 35.81 |
| ATOM | 116 | CZ | TYR | 43 | 44.688 | 25.425 | 3.545 | 1.00 | 37.09 |
| ATOM | 117 | OH | TYR | 43 | 45.151 | 24.559 | 2.569 | 1.00 | 37.14 |
| ATOM | 118 | CE2 | TYR | 43 | 43.414 | 25.942 | 3.446 | 1.00 | 36.49 |
| ATOM | 119 | CD2 | TYR | 43 | 42.934 | 26.815 | 4.426 | 1.00 | 35.18 |
| ATOM | 120 | C | TYR | 43 | 41.379 | 26.684 | 7.607 | 1.00 | 32.10 |
| ATOM | 121 | O | TYR | 43 | 41.468 | 25.484 | 7.762 | 1.00 | 31.66 |
| ATOM | 122 | N | PHE | 44 | 40.236 | 27.300 | 7.321 | 1.00 | 31.26 |

TABLE 3-continued

| | | | | | | | | | |
|---|---|---|---|---|---|---|---|---|---|
| ATOM | 123 | CA | PHE | 44 | 38.988 | 26.597 | 7.094 | 1.00 | 29.74 |
| ATOM | 124 | CB | PHE | 44 | 37.869 | 27.322 | 7.830 | 1.00 | 30.26 |
| ATOM | 125 | CG | PHE | 44 | 37.339 | 26.589 | 9.038 | 1.00 | 29.04 |
| ATOM | 126 | CD1 | PHE | 44 | 37.456 | 27.157 | 10.318 | 1.00 | 30.15 |
| ATOM | 127 | CE1 | PHE | 44 | 36.968 | 26.497 | 11.439 | 1.00 | 26.25 |
| ATOM | 128 | CZ | PHE | 44 | 36.325 | 25.269 | 11.274 | 1.00 | 28.00 |
| ATOM | 129 | CE2 | PHE | 44 | 36.215 | 24.701 | 10.006 | 1.00 | 27.40 |
| ATOM | 130 | CD2 | PHE | 44 | 36.716 | 25.372 | 8.905 | 1.00 | 27.57 |
| ATOM | 131 | C | PHE | 44 | 38.668 | 26.584 | 5.603 | 1.00 | 29.31 |
| ATOM | 132 | O | PHE | 44 | 38.965 | 27.529 | 4.848 | 1.00 | 26.50 |
| ATOM | 133 | N | VAL | 45 | 38.114 | 25.465 | 5.185 | 1.00 | 29.60 |
| ATOM | 134 | CA | VAL | 45 | 37.584 | 25.321 | 3.852 | 1.00 | 28.86 |
| ATOM | 135 | CB | VAL | 45 | 38.335 | 24.282 | 3.063 | 1.00 | 31.08 |
| ATOM | 136 | CG1 | VAL | 45 | 39.885 | 24.558 | 3.120 | 1.00 | 28.95 |
| ATOM | 137 | CG2 | VAL | 45 | 37.856 | 24.313 | 1.577 | 1.00 | 31.47 |
| ATOM | 138 | C | VAL | 45 | 36.179 | 24.854 | 4.031 | 1.00 | 28.57 |
| ATOM | 139 | O | VAL | 45 | 35.960 | 23.799 | 4.648 | 1.00 | 28.70 |
| ATOM | 140 | N | LYS | 46 | 35.231 | 25.669 | 3.548 | 1.00 | 26.60 |
| ATOM | 141 | CA | LYS | 46 | 33.826 | 25.318 | 3.495 | 1.00 | 26.09 |
| ATOM | 142 | CB | LYS | 46 | 32.941 | 26.480 | 3.964 | 1.00 | 24.81 |
| ATOM | 143 | CG | LYS | 46 | 31.427 | 26.115 | 3.984 | 1.00 | 26.07 |
| ATOM | 144 | CD | LYS | 46 | 30.531 | 27.097 | 4.709 | 1.00 | 26.57 |
| ATOM | 145 | CE | LYS | 46 | 30.861 | 28.589 | 4.348 | 1.00 | 33.60 |
| ATOM | 146 | NZ | LYS | 46 | 29.734 | 29.507 | 4.817 | 1.00 | 35.91 |
| ATOM | 147 | C | LYS | 46 | 33.364 | 24.893 | 2.060 | 1.00 | 25.98 |
| ATOM | 148 | O | LYS | 46 | 33.648 | 25.585 | 1.079 | 1.00 | 25.25 |
| ATOM | 149 | N | PHE | 47 | 32.632 | 23.771 | 1.969 | 1.00 | 25.69 |
| ATOM | 150 | CA | PHE | 47 | 31.781 | 23.461 | 0.804 | 1.00 | 25.78 |
| ATOM | 151 | CB | PHE | 47 | 32.013 | 22.023 | 0.346 | 1.00 | 26.07 |
| ATOM | 152 | CG | PHE | 47 | 33.463 | 21.733 | 0.066 | 1.00 | 25.38 |
| ATOM | 153 | CD1 | PHE | 47 | 34.320 | 21.390 | 1.105 | 1.00 | 29.07 |
| ATOM | 154 | CE1 | PHE | 47 | 35.721 | 21.147 | 0.851 | 1.00 | 29.50 |
| ATOM | 155 | CZ | PHE | 47 | 36.214 | 21.277 | −0.450 | 1.00 | 26.40 |
| ATOM | 156 | CE2 | PHE | 47 | 35.369 | 21.631 | −1.463 | 1.00 | 24.93 |
| ATOM | 157 | CD2 | PHE | 47 | 33.991 | 21.858 | −1.213 | 1.00 | 27.19 |
| ATOM | 158 | C | PHE | 47 | 30.316 | 23.676 | 1.087 | 1.00 | 26.50 |
| ATOM | 159 | O | PHE | 47 | 29.767 | 23.098 | 2.041 | 1.00 | 26.93 |
| ATOM | 160 | N | ASN | 48 | 29.687 | 24.497 | 0.252 | 1.00 | 26.28 |
| ATOM | 161 | CA | ASN | 48 | 28.235 | 24.684 | 0.232 | 1.00 | 26.70 |
| ATOM | 162 | CB | ASN | 48 | 27.922 | 26.101 | −0.167 | 1.00 | 26.63 |
| ATOM | 163 | CG | ASN | 48 | 28.611 | 27.143 | 0.712 | 1.00 | 27.75 |
| ATOM | 164 | OD1 | ASN | 48 | 28.397 | 27.164 | 1.918 | 1.00 | 26.90 |
| ATOM | 165 | ND2 | ASN | 48 | 29.402 | 28.026 | 0.107 | 1.00 | 21.97 |
| ATOM | 166 | C | ASN | 48 | 27.658 | 23.762 | −0.816 | 1.00 | 27.42 |
| ATOM | 167 | O | ASN | 48 | 28.023 | 23.869 | −2.013 | 1.00 | 27.74 |
| ATOM | 168 | N | CYS | 49 | 26.787 | 22.842 | −0.398 | 1.00 | 27.81 |
| ATOM | 169 | CA | CYS | 49 | 26.273 | 21.767 | −1.259 | 1.00 | 27.79 |
| ATOM | 170 | CB | CYS | 49 | 26.793 | 20.400 | −0.837 | 1.00 | 27.88 |
| ATOM | 171 | SG | CYS | 49 | 28.577 | 20.421 | −0.479 | 1.00 | 33.42 |
| ATOM | 172 | C | CYS | 49 | 24.770 | 21.767 | −1.237 | 1.00 | 27.42 |
| ATOM | 173 | O | CYS | 49 | 24.198 | 20.917 | −0.654 | 1.00 | 27.36 |
| ATOM | 174 | N | PRO | 50 | 24.124 | 22.730 | −1.924 | 1.00 | 28.25 |
| ATOM | 175 | CA | PRO | 50 | 22.686 | 22.818 | −1.939 | 1.00 | 28.95 |
| ATOM | 176 | CB | PRO | 50 | 22.443 | 24.247 | −2.402 | 1.00 | 28.68 |
| ATOM | 177 | CG | PRO | 50 | 23.565 | 24.504 | −3.259 | 1.00 | 29.66 |
| ATOM | 178 | CD | PRO | 50 | 24.733 | 23.791 | −2.741 | 1.00 | 27.22 |
| ATOM | 179 | C | PRO | 50 | 22.014 | 21.801 | −2.884 | 1.00 | 30.16 |
| ATOM | 180 | O | PRO | 50 | 20.791 | 21.723 | −2.931 | 1.00 | 30.23 |
| ATOM | 181 | N | GLU | 51 | 22.771 | 20.946 | −3.565 | 1.00 | 30.75 |
| ATOM | 182 | CA | GLU | 51 | 22.071 | 19.985 | −4.423 | 1.00 | 30.88 |
| ATOM | 183 | CB | GLU | 51 | 22.673 | 20.023 | −5.841 | 1.00 | 30.96 |
| ATOM | 184 | CG | GLU | 51 | 22.258 | 21.350 | −6.510 | 1.00 | 30.27 |
| ATOM | 185 | CD | GLU | 51 | 23.061 | 21.699 | −7.748 | 1.00 | 34.08 |
| ATOM | 186 | OE1 | GLU | 51 | 23.852 | 20.862 | −8.240 | 1.00 | 37.55 |
| ATOM | 187 | OE2 | GLU | 51 | 22.926 | 22.838 | −8.208 | 1.00 | 33.25 |
| ATOM | 188 | C | GLU | 51 | 21.912 | 18.575 | −3.887 | 1.00 | 31.31 |
| ATOM | 189 | O | GLU | 51 | 21.585 | 17.655 | −4.633 | 1.00 | 32.45 |
| ATOM | 190 | N | PHE | 52 | 22.124 | 18.375 | −2.589 | 1.00 | 30.57 |
| ATOM | 191 | CA | PHE | 52 | 22.131 | 17.018 | −2.077 | 1.00 | 29.32 |
| ATOM | 192 | CB | PHE | 52 | 22.611 | 16.980 | −0.630 | 1.00 | 29.38 |
| ATOM | 193 | CG | PHE | 52 | 22.723 | 15.591 | −0.098 | 1.00 | 28.90 |
| ATOM | 194 | CD1 | PHE | 52 | 23.853 | 14.826 | −0.386 | 1.00 | 25.64 |
| ATOM | 195 | CE1 | PHE | 52 | 23.970 | 13.539 | 0.110 | 1.00 | 26.75 |
| ATOM | 196 | CZ | PHE | 52 | 22.931 | 12.979 | 0.832 | 1.00 | 25.36 |
| ATOM | 197 | CE2 | PHE | 52 | 21.775 | 13.732 | 1.108 | 1.00 | 28.36 |
| ATOM | 198 | CD2 | PHE | 52 | 21.671 | 15.023 | 0.633 | 1.00 | 26.05 |
| ATOM | 199 | C | PHE | 52 | 20.763 | 16.399 | −2.163 | 1.00 | 29.42 |
| ATOM | 200 | O | PHE | 52 | 19.775 | 17.081 | −1.906 | 1.00 | 29.42 |
| ATOM | 201 | N | THR | 66 | 20.596 | 20.942 | 1.819 | 1.00 | 25.39 |
| ATOM | 202 | CA | THR | 66 | 21.827 | 21.677 | 1.651 | 1.00 | 27.61 |

TABLE 3-continued

| | | | | | | | | | |
|---|---|---|---|---|---|---|---|---|---|
| ATOM | 203 | CB | THR | 66 | 21.592 | 23.154 | 1.861 | 1.00 | 27.25 |
| ATOM | 204 | OG1 | THR | 66 | 20.752 | 23.615 | 0.820 | 1.00 | 30.69 |
| ATOM | 205 | CG2 | THR | 66 | 22.868 | 23.915 | 1.735 | 1.00 | 31.40 |
| ATOM | 206 | C | THR | 66 | 22.780 | 21.182 | 2.743 | 1.00 | 28.30 |
| ATOM | 207 | O | THR | 66 | 22.431 | 21.123 | 3.933 | 1.00 | 28.10 |
| ATOM | 208 | N | ILE | 67 | 23.989 | 20.838 | 2.343 | 1.00 | 28.94 |
| ATOM | 209 | CA | ILE | 67 | 24.990 | 20.392 | 3.301 | 1.00 | 28.94 |
| ATOM | 210 | CB | ILE | 67 | 25.489 | 18.986 | 2.870 | 1.00 | 29.43 |
| ATOM | 211 | CG1 | ILE | 67 | 24.280 | 18.048 | 2.848 | 1.00 | 28.57 |
| ATOM | 212 | CD1 | ILE | 67 | 24.620 | 16.709 | 2.398 | 1.00 | 29.91 |
| ATOM | 213 | CG2 | ILE | 67 | 26.608 | 18.471 | 3.775 | 1.00 | 29.92 |
| ATOM | 214 | C | ILE | 67 | 26.077 | 21.424 | 3.311 | 1.00 | 28.85 |
| ATOM | 215 | O | ILE | 67 | 26.424 | 21.922 | 2.236 | 1.00 | 29.21 |
| ATOM | 216 | N | TYR | 68 | 26.586 | 21.770 | 4.505 | 1.00 | 28.85 |
| ATOM | 217 | CA | TYR | 68 | 27.710 | 22.685 | 4.692 | 1.00 | 27.65 |
| ATOM | 218 | CB | TYR | 68 | 27.343 | 23.892 | 5.554 | 1.00 | 28.00 |
| ATOM | 219 | CG | TYR | 68 | 26.169 | 24.669 | 4.985 | 1.00 | 27.25 |
| ATOM | 220 | CD1 | TYR | 68 | 24.864 | 24.443 | 5.411 | 1.00 | 23.97 |
| ATOM | 221 | CE1 | TYR | 68 | 23.774 | 25.180 | 4.854 | 1.00 | 28.38 |
| ATOM | 222 | CZ | TYR | 68 | 24.039 | 26.098 | 3.817 | 1.00 | 28.49 |
| ATOM | 223 | OH | TYR | 68 | 23.061 | 26.851 | 3.171 | 1.00 | 26.21 |
| ATOM | 224 | CE2 | TYR | 68 | 25.356 | 26.292 | 3.374 | 1.00 | 29.17 |
| ATOM | 225 | CD2 | TYR | 68 | 26.388 | 25.605 | 3.943 | 1.00 | 27.85 |
| ATOM | 226 | C | TYR | 68 | 28.791 | 21.837 | 5.337 | 1.00 | 29.20 |
| ATOM | 227 | O | TYR | 68 | 28.563 | 21.226 | 6.411 | 1.00 | 29.47 |
| ATOM | 228 | N | ILE | 69 | 29.938 | 21.743 | 4.665 | 1.00 | 28.12 |
| ATOM | 229 | CA | ILE | 69 | 30.978 | 20.873 | 5.122 | 1.00 | 28.68 |
| ATOM | 230 | CB | ILE | 69 | 31.367 | 19.781 | 4.122 | 1.00 | 29.11 |
| ATOM | 231 | CG1 | ILE | 69 | 30.180 | 18.885 | 3.756 | 1.00 | 30.41 |
| ATOM | 232 | CD1 | ILE | 69 | 30.590 | 17.811 | 2.756 | 1.00 | 32.90 |
| ATOM | 233 | CG2 | ILE | 69 | 32.443 | 18.900 | 4.743 | 1.00 | 27.69 |
| ATOM | 234 | C | ILE | 69 | 32.182 | 21.770 | 5.276 | 1.00 | 28.58 |
| ATOM | 235 | O | ILE | 69 | 32.658 | 22.336 | 4.283 | 1.00 | 29.06 |
| ATOM | 236 | N | SER | 70 | 32.661 | 21.910 | 6.508 | 1.00 | 27.09 |
| ATOM | 237 | CA | SER | 70 | 33.785 | 22.801 | 6.780 | 1.00 | 28.38 |
| ATOM | 238 | CB | SER | 70 | 33.358 | 23.914 | 7.713 | 1.00 | 27.46 |
| ATOM | 239 | OG | SER | 70 | 32.356 | 24.705 | 7.126 | 1.00 | 31.79 |
| ATOM | 240 | C | SER | 70 | 34.885 | 22.010 | 7.455 | 1.00 | 29.12 |
| ATOM | 241 | O | SER | 70 | 34.616 | 21.271 | 8.405 | 1.00 | 29.98 |
| ATOM | 242 | N | TYR | 71 | 36.117 | 22.155 | 7.009 | 1.00 | 29.92 |
| ATOM | 243 | CA | TYR | 71 | 37.160 | 21.367 | 7.623 | 1.00 | 30.12 |
| ATOM | 244 | CB | TYR | 71 | 37.288 | 20.027 | 6.896 | 1.00 | 31.24 |
| ATOM | 245 | CG | TYR | 71 | 38.057 | 20.049 | 5.624 | 1.00 | 34.13 |
| ATOM | 246 | CD1 | TYR | 71 | 37.440 | 20.384 | 4.411 | 1.00 | 36.91 |
| ATOM | 247 | CE1 | TYR | 71 | 38.177 | 20.415 | 3.205 | 1.00 | 37.18 |
| ATOM | 248 | CZ | TYR | 71 | 39.501 | 20.082 | 3.228 | 1.00 | 35.60 |
| ATOM | 249 | OH | TYR | 71 | 40.238 | 20.092 | 2.087 | 1.00 | 35.76 |
| ATOM | 250 | CE2 | TYR | 71 | 40.119 | 19.712 | 4.422 | 1.00 | 35.87 |
| ATOM | 251 | CD2 | TYR | 71 | 39.384 | 19.678 | 5.604 | 1.00 | 33.90 |
| ATOM | 252 | C | TYR | 71 | 38.443 | 22.145 | 7.689 | 1.00 | 30.03 |
| ATOM | 253 | O | TYR | 71 | 38.617 | 23.077 | 6.913 | 1.00 | 30.38 |
| ATOM | 254 | N | ILE | 72 | 39.327 | 21.796 | 8.633 | 1.00 | 30.54 |
| ATOM | 255 | CA | ILE | 72 | 40.676 | 22.345 | 8.691 | 1.00 | 30.16 |
| ATOM | 256 | CB | ILE | 72 | 41.056 | 22.831 | 10.099 | 1.00 | 31.07 |
| ATOM | 257 | CG1 | ILE | 72 | 40.217 | 24.025 | 10.531 | 1.00 | 27.76 |
| ATOM | 258 | CD1 | ILE | 72 | 40.453 | 24.492 | 11.993 | 1.00 | 28.57 |
| ATOM | 259 | CG2 | ILE | 72 | 42.558 | 23.251 | 10.101 | 1.00 | 30.30 |
| ATOM | 260 | C | ILE | 72 | 41.659 | 21.225 | 8.246 | 1.00 | 32.37 |
| ATOM | 261 | O | ILE | 72 | 41.742 | 20.164 | 8.852 | 1.00 | 32.41 |
| ATOM | 262 | N | PRO | 73 | 42.327 | 21.412 | 7.116 | 1.00 | 33.84 |
| ATOM | 263 | CA | PRO | 73 | 43.051 | 20.259 | 6.658 | 1.00 | 34.85 |
| ATOM | 264 | CB | PRO | 73 | 43.381 | 20.618 | 5.205 | 1.00 | 34.72 |
| ATOM | 265 | CG | PRO | 73 | 43.443 | 22.092 | 5.192 | 1.00 | 32.26 |
| ATOM | 266 | CD | PRO | 73 | 42.463 | 22.566 | 6.201 | 1.00 | 33.49 |
| ATOM | 267 | C | PRO | 73 | 44.350 | 20.105 | 7.385 | 1.00 | 36.57 |
| ATOM | 268 | O | PRO | 73 | 44.896 | 21.079 | 7.914 | 1.00 | 37.10 |
| ATOM | 269 | N | ASP | 74 | 44.887 | 18.898 | 7.337 | 1.00 | 39.32 |
| ATOM | 270 | CA | ASP | 74 | 46.278 | 18.710 | 7.682 | 1.00 | 41.53 |
| ATOM | 271 | CB | ASP | 74 | 46.489 | 17.511 | 8.609 | 1.00 | 41.65 |
| ATOM | 272 | CG | ASP | 74 | 47.908 | 17.456 | 9.153 | 1.00 | 45.08 |
| ATOM | 273 | OD1 | ASP | 74 | 48.318 | 16.365 | 9.542 | 1.00 | 47.84 |
| ATOM | 274 | OD2 | ASP | 74 | 48.633 | 18.499 | 9.183 | 1.00 | 49.17 |
| ATOM | 275 | C | ASP | 74 | 47.079 | 18.557 | 6.397 | 1.00 | 42.93 |
| ATOM | 276 | O | ASP | 74 | 47.587 | 19.541 | 5.858 | 1.00 | 43.72 |
| ATOM | 277 | N | GLU | 75 | 47.198 | 17.344 | 5.883 | 1.00 | 44.15 |
| ATOM | 278 | CA | GLU | 75 | 48.095 | 17.178 | 4.750 | 1.00 | 45.93 |
| ATOM | 279 | CB | GLU | 75 | 49.132 | 16.106 | 5.039 | 1.00 | 45.93 |
| ATOM | 280 | CG | GLU | 75 | 50.354 | 16.748 | 5.666 | 1.00 | 51.03 |
| ATOM | 281 | CD | GLU | 75 | 50.993 | 15.907 | 6.756 | 1.00 | 58.31 |
| ATOM | 282 | OE1 | GLU | 75 | 50.383 | 14.879 | 7.164 | 1.00 | 58.75 |

TABLE 3-continued

| | | | | | | | | | |
|---|---|---|---|---|---|---|---|---|---|
| ATOM | 283 | OE2 | GLU | 75 | 52.109 | 16.291 | 7.207 | 1.00 | 59.99 |
| ATOM | 284 | C | GLU | 75 | 47.394 | 16.986 | 3.421 | 1.00 | 45.59 |
| ATOM | 285 | O | GLU | 75 | 47.938 | 17.364 | 2.378 | 1.00 | 46.34 |
| ATOM | 286 | N | LYS | 76 | 46.193 | 16.419 | 3.474 | 1.00 | 44.77 |
| ATOM | 287 | CA | LYS | 76 | 45.454 | 16.123 | 2.283 | 1.00 | 43.61 |
| ATOM | 288 | CB | LYS | 76 | 45.051 | 14.647 | 2.282 | 1.00 | 44.91 |
| ATOM | 289 | CG | LYS | 76 | 46.234 | 13.643 | 2.381 | 1.00 | 45.34 |
| ATOM | 290 | CD | LYS | 76 | 45.780 | 12.299 | 1.792 | 1.00 | 51.11 |
| ATOM | 291 | CE | LYS | 76 | 46.829 | 11.166 | 1.858 | 1.00 | 50.49 |
| ATOM | 292 | NZ | LYS | 76 | 46.536 | 10.316 | 3.046 | 1.00 | 52.97 |
| ATOM | 293 | C | LYS | 76 | 44.248 | 17.077 | 2.154 | 1.00 | 42.76 |
| ATOM | 294 | O | LYS | 76 | 43.717 | 17.584 | 3.148 | 1.00 | 41.56 |
| ATOM | 295 | N | MET | 77 | 43.841 | 17.344 | 0.922 | 1.00 | 41.45 |
| ATOM | 296 | CA | MET | 77 | 42.650 | 18.164 | 0.656 | 1.00 | 41.10 |
| ATOM | 297 | CB | MET | 77 | 43.093 | 19.509 | 0.165 | 1.00 | 39.55 |
| ATOM | 298 | CG | MET | 77 | 43.828 | 20.154 | 1.273 | 1.00 | 39.95 |
| ATOM | 299 | SD | MET | 77 | 44.204 | 21.847 | 1.049 | 1.00 | 46.16 |
| ATOM | 300 | CE | MET | 77 | 42.562 | 22.591 | 1.091 | 1.00 | 41.83 |
| ATOM | 301 | C | MET | 77 | 41.703 | 17.479 | −0.303 | 1.00 | 39.69 |
| ATOM | 302 | O | MET | 77 | 42.131 | 16.872 | −1.244 | 1.00 | 41.26 |
| ATOM | 303 | N | VAL | 78 | 40.415 | 17.523 | −0.047 | 1.00 | 39.01 |
| ATOM | 304 | CA | VAL | 78 | 39.491 | 16.834 | −0.898 | 1.00 | 37.71 |
| ATOM | 305 | CB | VAL | 78 | 38.110 | 16.612 | −0.201 | 1.00 | 37.41 |
| ATOM | 306 | CG1 | VAL | 78 | 37.490 | 17.927 | 0.314 | 1.00 | 38.48 |
| ATOM | 307 | CG2 | VAL | 78 | 37.137 | 15.886 | −1.096 | 1.00 | 36.33 |
| ATOM | 308 | C | VAL | 78 | 39.348 | 17.639 | −2.195 | 1.00 | 38.30 |
| ATOM | 309 | O | VAL | 78 | 39.364 | 18.877 | −2.174 | 1.00 | 36.79 |
| ATOM | 310 | N | GLU | 79 | 39.210 | 16.919 | −3.311 | 1.00 | 38.71 |
| ATOM | 311 | CA | GLU | 79 | 39.003 | 17.526 | −4.617 | 1.00 | 39.26 |
| ATOM | 312 | CB | GLU | 79 | 39.659 | 16.680 | −5.718 | 1.00 | 39.82 |
| ATOM | 313 | CG | GLU | 79 | 39.982 | 17.449 | −7.024 | 1.00 | 41.73 |
| ATOM | 314 | CD | GLU | 79 | 38.723 | 17.767 | −7.835 | 1.00 | 44.42 |
| ATOM | 315 | OE1 | GLU | 79 | 37.939 | 16.813 | −8.052 | 1.00 | 45.96 |
| ATOM | 316 | OE2 | GLU | 79 | 38.489 | 18.959 | −8.212 | 1.00 | 43.13 |
| ATOM | 317 | C | GLU | 79 | 37.514 | 17.795 | −4.842 | 1.00 | 39.15 |
| ATOM | 318 | O | GLU | 79 | 36.664 | 16.920 | −4.639 | 1.00 | 39.58 |
| ATOM | 319 | N | SER | 80 | 37.194 | 19.026 | −5.229 | 1.00 | 39.14 |
| ATOM | 320 | CA | SER | 80 | 35.806 | 19.457 | −5.389 | 1.00 | 40.45 |
| ATOM | 321 | CB | SER | 80 | 35.755 | 20.902 | −5.900 | 1.00 | 40.98 |
| ATOM | 322 | OG | SER | 80 | 34.415 | 21.367 | −5.840 | 1.00 | 43.76 |
| ATOM | 323 | C | SER | 80 | 34.941 | 18.577 | −6.283 | 1.00 | 39.97 |
| ATOM | 324 | O | SER | 80 | 33.780 | 18.316 | −5.966 | 1.00 | 40.91 |
| ATOM | 325 | N | LYS | 81 | 35.486 | 18.156 | −7.423 | 1.00 | 40.44 |
| ATOM | 326 | CA | LYS | 81 | 34.732 | 17.371 | −8.394 | 1.00 | 39.60 |
| ATOM | 327 | CB | LYS | 81 | 35.408 | 17.429 | −9.777 | 1.00 | 40.23 |
| ATOM | 328 | CG | LYS | 81 | 34.769 | 16.474 | −10.876 | 1.00 | 41.71 |
| ATOM | 329 | CD | LYS | 81 | 35.511 | 16.544 | −12.254 | 1.00 | 43.35 |
| ATOM | 330 | CE | LYS | 81 | 36.604 | 15.466 | −12.451 | 1.00 | 51.29 |
| ATOM | 331 | NZ | LYS | 81 | 36.033 | 14.133 | −12.943 | 1.00 | 51.65 |
| ATOM | 332 | C | LYS | 81 | 34.523 | 15.948 | −7.890 | 1.00 | 37.68 |
| ATOM | 333 | O | LYS | 81 | 33.413 | 15.407 | −8.043 | 1.00 | 36.22 |
| ATOM | 334 | N | SER | 82 | 35.535 | 15.361 | −7.230 | 1.00 | 36.37 |
| ATOM | 335 | CA | SER | 82 | 35.314 | 14.058 | −6.558 | 1.00 | 36.60 |
| ATOM | 336 | CB | SER | 82 | 36.600 | 13.464 | −5.957 | 1.00 | 37.83 |
| ATOM | 337 | OG | SER | 82 | 37.157 | 14.220 | −4.878 | 1.00 | 38.89 |
| ATOM | 338 | C | SER | 82 | 34.187 | 14.121 | −5.520 | 1.00 | 36.09 |
| ATOM | 339 | O | SER | 82 | 33.285 | 13.235 | −5.505 | 1.00 | 35.12 |
| ATOM | 340 | N | LEU | 83 | 34.206 | 15.197 | −4.717 | 1.00 | 34.52 |
| ATOM | 341 | CA | LEU | 83 | 33.134 | 15.471 | −3.740 | 1.00 | 34.68 |
| ATOM | 342 | CB | LEU | 83 | 33.417 | 16.745 | −2.912 | 1.00 | 34.38 |
| ATOM | 343 | CG | LEU | 83 | 32.458 | 17.011 | −1.726 | 1.00 | 35.18 |
| ATOM | 344 | CD1 | LEU | 83 | 32.349 | 15.798 | −0.718 | 1.00 | 28.46 |
| ATOM | 345 | CD2 | LEU | 83 | 32.833 | 18.311 | −1.025 | 1.00 | 33.77 |
| ATOM | 346 | C | LEU | 83 | 31.747 | 15.531 | −4.365 | 1.00 | 34.51 |
| ATOM | 347 | O | LEU | 83 | 30.777 | 14.995 | −3.830 | 1.00 | 33.59 |
| ATOM | 348 | N | LYS | 84 | 31.665 | 16.190 | −5.511 | 1.00 | 35.31 |
| ATOM | 349 | CA | LYS | 84 | 30.443 | 16.288 | −6.256 | 1.00 | 35.99 |
| ATOM | 350 | CB | LYS | 84 | 30.696 | 17.180 | −7.486 | 1.00 | 35.66 |
| ATOM | 351 | CG | LYS | 84 | 29.608 | 17.168 | −8.519 | 1.00 | 37.97 |
| ATOM | 352 | CD | LYS | 84 | 30.105 | 17.866 | −9.820 | 1.00 | 37.55 |
| ATOM | 353 | CE | LYS | 84 | 30.536 | 16.853 | −10.863 | 1.00 | 39.56 |
| ATOM | 354 | NZ | LYS | 84 | 30.531 | 17.379 | −12.263 | 1.00 | 41.94 |
| ATOM | 355 | C | LYS | 84 | 29.988 | 14.891 | −6.643 | 1.00 | 36.20 |
| ATOM | 356 | O | LYS | 84 | 28.830 | 14.516 | −6.421 | 1.00 | 36.55 |
| ATOM | 357 | N | LEU | 85 | 30.906 | 14.110 | −7.204 | 1.00 | 36.49 |
| ATOM | 358 | CA | LEU | 85 | 30.630 | 12.726 | −7.536 | 1.00 | 36.64 |
| ATOM | 359 | CB | LEU | 85 | 31.857 | 12.117 | −8.230 | 1.00 | 36.98 |
| ATOM | 360 | CG | LEU | 85 | 32.158 | 12.259 | −9.744 | 1.00 | 39.95 |
| ATOM | 361 | CD1 | LEU | 85 | 31.419 | 13.417 | −10.429 | 1.00 | 41.97 |
| ATOM | 362 | CD2 | LEU | 85 | 33.678 | 12.359 | −10.048 | 1.00 | 37.78 |

TABLE 3-continued

| | | | | | | | | | |
|---|---|---|---|---|---|---|---|---|---|
| ATOM | 363 | C | LEU | 85 | 30.259 | 11.917 | −6.304 | 1.00 | 36.28 |
| ATOM | 364 | O | LEU | 85 | 29.290 | 11.175 | −6.303 | 1.00 | 35.95 |
| ATOM | 365 | N | TYR | 85 | 31.011 | 12.057 | −5.222 | 1.00 | 36.01 |
| ATOM | 366 | CA | TYR | 86 | 30.610 | 11.368 | −3.993 | 1.00 | 35.20 |
| ATOM | 367 | CB | TYR | 86 | 31.600 | 11.712 | −2.904 | 1.00 | 36.62 |
| ATOM | 368 | CG | TYR | 86 | 31.282 | 11.124 | −1.574 | 1.00 | 38.86 |
| ATOM | 369 | CD1 | TYR | 86 | 31.237 | 9.726 | −1.378 | 1.00 | 37.52 |
| ATOM | 370 | CE1 | TYR | 86 | 30.940 | 9.206 | −0.104 | 1.00 | 39.96 |
| ATOM | 371 | CZ | TYR | 86 | 30.720 | 10.110 | 0.976 | 1.00 | 39.92 |
| ATOM | 372 | OH | TYR | 86 | 30.397 | 9.693 | 2.239 | 1.00 | 40.85 |
| ATOM | 373 | CE2 | TYR | 86 | 30.771 | 11.465 | 0.780 | 1.00 | 38.61 |
| ATOM | 374 | CD2 | TYR | 86 | 31.047 | 11.966 | −0.484 | 1.00 | 39.08 |
| ATOM | 375 | C | TYR | 86 | 29.181 | 11.706 | −3.573 | 1.00 | 34.75 |
| ATOM | 376 | O | TYR | 86 | 28.344 | 10.833 | −3.312 | 1.00 | 34.10 |
| ATOM | 377 | N | LEU | 87 | 28.844 | 12.985 | −3.544 | 1.00 | 35.13 |
| ATOM | 378 | CA | LEU | 87 | 27.466 | 13.332 | −3.154 | 1.00 | 35.00 |
| ATOM | 379 | CB | LEU | 37 | 27.341 | 14.791 | −2.760 | 1.00 | 35.12 |
| ATOM | 380 | CG | LEU | 87 | 28.271 | 15.301 | −1.653 | 1.00 | 36.20 |
| ATOM | 381 | CD1 | LEU | 87 | 28.215 | 16.813 | −1.558 | 1.00 | 32.77 |
| ATOM | 382 | CD2 | LEU | 87 | 27.935 | 14.650 | −0.291 | 1.00 | 34.84 |
| ATOM | 383 | C | LEU | 87 | 26.412 | 12.909 | −4.174 | 1.00 | 35.54 |
| ATOM | 384 | O | LEU | 87 | 25.281 | 12.527 | −3.792 | 1.00 | 33.45 |
| ATOM | 385 | N | PHE | 88 | 26.763 | 12.931 | −5.472 | 1.00 | 37.14 |
| ATOM | 386 | CA | PHE | 88 | 25.878 | 12.277 | −6.476 | 1.00 | 38.55 |
| ATOM | 387 | CB | PHE | 88 | 26.482 | 12.268 | −7.899 | 1.00 | 40.19 |
| ATOM | 388 | CG | PHE | 88 | 26.455 | 13.606 | −8.601 | 1.00 | 44.41 |
| ATOM | 389 | CD1 | PHE | 88 | 27.249 | 13.818 | −9.737 | 1.00 | 45.28 |
| ATOM | 390 | CE1 | PHE | 88 | 27.244 | 15.049 | −10.379 | 1.00 | 46.31 |
| ATOM | 391 | CZ | PHE | 88 | 26.440 | 16.094 | −9.893 | 1.00 | 45.62 |
| ATOM | 392 | CE2 | PHE | 88 | 25.650 | 15.896 | −8.766 | 1.00 | 46.65 |
| ATOM | 393 | CD2 | PHE | 88 | 25.655 | 14.659 | −8.129 | 1.00 | 46.40 |
| ATOM | 394 | C | PHE | 88 | 25.611 | 10.821 | −6.080 | 1.00 | 37.62 |
| ATOM | 395 | O | PHE | 88 | 24.514 | 10.328 | −6.258 | 1.00 | 37.12 |
| ATOM | 396 | N | LEU | 108 | 35.056 | 11.321 | 4.727 | 1.00 | 34.95 |
| ATOM | 397 | CA | LEU | 108 | 36.039 | 12.400 | 4.525 | 1.00 | 35.52 |
| ATOM | 398 | CB | LEU | 108 | 35.401 | 13.778 | 4.502 | 1.00 | 35.06 |
| ATOM | 399 | CG | LEU | 108 | 34.528 | 14.026 | 3.274 | 1.00 | 36.44 |
| ATOM | 400 | CD1 | LEU | 108 | 33.619 | 15.234 | 3.575 | 1.00 | 32.82 |
| ATOM | 401 | CD2 | LEU | 108 | 35.424 | 14.287 | 2.051 | 1.00 | 31.89 |
| ATOM | 402 | C | LEU | 108 | 37.189 | 12.363 | 5.498 | 1.00 | 35.31 |
| ATOM | 403 | O | LEU | 108 | 38.324 | 12.733 | 5.147 | 1.00 | 35.77 |
| ATOM | 404 | N | ILE | 109 | 36.902 | 11.932 | 6.719 | 1.00 | 35.87 |
| ATOM | 405 | CA | ILE | 109 | 37.967 | 11.681 | 7.697 | 1.00 | 36.24 |
| ATOM | 406 | CB | ILE | 109 | 37.423 | 11.276 | 9.099 | 1.00 | 36.35 |
| ATOM | 407 | CG1 | ILE | 109 | 36.700 | 12.451 | 9.785 | 1.00 | 34.30 |
| ATOM | 408 | CD1 | ILE | 109 | 35.538 | 12.010 | 10.760 | 1.00 | 34.62 |
| ATOM | 409 | CG2 | ILE | 109 | 38.606 | 10.707 | 10.022 | 1.00 | 34.86 |
| ATOM | 410 | C | ILE | 109 | 38.947 | 10.612 | 7.164 | 1.00 | 37.64 |
| ATOM | 411 | O | ILE | 109 | 40.149 | 10.863 | 7.137 | 1.00 | 37.15 |
| ATOM | 412 | N | LEU | 111 | 39.554 | 9.545 | 3.956 | 1.00 | 43.50 |
| ATOM | 413 | CA | LEU | 111 | 40.280 | 10.206 | 2.846 | 1.00 | 42.66 |
| ATOM | 414 | CB | LEU | 111 | 39.290 | 10.957 | 1.959 | 1.00 | 42.51 |
| ATOM | 415 | CG | LEU | 111 | 39.918 | 11.764 | 0.825 | 1.00 | 43.15 |
| ATOM | 416 | CD1 | LEU | 111 | 40.264 | 10.831 | −0.342 | 1.00 | 40.98 |
| ATOM | 417 | CD2 | LEU | 111 | 38.960 | 12.914 | 0.369 | 1.00 | 41.57 |
| ATOM | 418 | C | LEU | 111 | 41.349 | 11.201 | 3.254 | 1.00 | 42.41 |
| ATOM | 419 | O | LEU | 111 | 42.421 | 11.251 | 2.658 | 1.00 | 42.41 |
| ATOM | 420 | N | MET | 112 | 41.066 | 12.021 | 4.252 | 1.00 | 42.62 |
| ATOM | 421 | CA | MET | 112 | 41.880 | 13.247 | 4.443 | 1.00 | 43.13 |
| ATOM | 422 | CB | MET | 112 | 40.959 | 14.465 | 4.468 | 1.00 | 42.51 |
| ATOM | 423 | CG | MET | 112 | 40.316 | 14.825 | 3.152 | 1.00 | 44.00 |
| ATOM | 424 | SD | MET | 112 | 39.532 | 16.435 | 3.404 | 1.00 | 44.98 |
| ATOM | 425 | CE | MET | 112 | 41.061 | 17.283 | 3.656 | 1.00 | 47.38 |
| ATOM | 426 | C | MET | 112 | 42.723 | 13.327 | 5.699 | 1.00 | 42.32 |
| ATOM | 427 | O | MET | 112 | 43.693 | 14.104 | 5.770 | 1.00 | 41.25 |
| ATOM | 428 | N | ASP | 113 | 42.308 | 12.556 | 6.706 | 1.00 | 42.80 |
| ATOM | 429 | CA | ASP | 113 | 42.803 | 12.710 | 8.077 | 1.00 | 42.67 |
| ATOM | 430 | CB | ASP | 113 | 44.013 | 11.794 | 8.319 | 1.00 | 44.33 |
| ATOM | 431 | CG | ASP | 113 | 43.688 | 10.310 | 7.972 | 1.00 | 51.81 |
| ATOM | 432 | OD1 | ASP | 113 | 42.821 | 9.678 | 8.674 | 1.00 | 56.07 |
| ATOM | 433 | OD2 | ASP | 113 | 44.262 | 9.782 | 6.963 | 1.00 | 58.14 |
| ATOM | 434 | C | ASP | 113 | 43.046 | 14.189 | 8.406 | 1.00 | 40.37 |
| ATOM | 435 | O | ASP | 113 | 44.209 | 14.608 | 8.587 | 1.00 | 40.76 |
| ATOM | 436 | N | PRO | 114 | 41.934 | 14.982 | 8.520 | 1.00 | 38.64 |
| ATOM | 437 | CA | PRO | 114 | 41.934 | 16.449 | 8.721 | 1.00 | 37.02 |
| ATOM | 438 | CB | PRO | 114 | 40.504 | 16.827 | 8.300 | 1.00 | 36.78 |
| ATOM | 439 | CG | PRO | 114 | 39.690 | 15.693 | 8.712 | 1.00 | 36.74 |
| ATOM | 440 | CD | PRO | 114 | 40.547 | 14.456 | 8.514 | 1.00 | 37.94 |
| ATOM | 441 | C | PRO | 114 | 42.196 | 16.836 | 10.201 | 1.00 | 35.69 |
| ATOM | 442 | O | PRO | 114 | 41.920 | 16.015 | 11.060 | 1.00 | 36.68 |

TABLE 3-continued

| | | | | | | | | | |
|---|---|---|---|---|---|---|---|---|---|
| ATOM | 443 | N | ARG | 115 | 42.727 | 18.031 | 10.508 | 1.00 | 32.67 |
| ATOM | 444 | CA | ARG | 115 | 42.737 | 18.556 | 11.887 | 1.00 | 30.50 |
| ATOM | 445 | CB | ARG | 115 | 43.463 | 19.888 | 11.961 | 1.00 | 28.63 |
| ATOM | 446 | CG | ARG | 115 | 44.906 | 19.769 | 11.608 | 1.00 | 28.18 |
| ATOM | 447 | CD | ARG | 115 | 45.652 | 21.093 | 11.542 | 1.00 | 29.81 |
| ATOM | 448 | NE | ARG | 115 | 46.874 | 20.853 | 10.779 | 1.00 | 31.31 |
| ATOM | 449 | CZ | ARG | 115 | 47.599 | 21.756 | 10.133 | 1.00 | 33.47 |
| ATOM | 450 | NH1 | ARG | 115 | 47.318 | 23.056 | 10.158 | 1.00 | 31.18 |
| ATOM | 451 | NH2 | ARG | 115 | 48.640 | 21.329 | 9.439 | 1.00 | 37.87 |
| ATOM | 452 | C | ARG | 115 | 41.317 | 18.679 | 12.521 | 1.00 | 31.30 |
| ATOM | 453 | O | ARG | 115 | 41.059 | 18.176 | 13.614 | 1.00 | 30.15 |
| ATOM | 454 | N | TYR | 116 | 40.382 | 19.325 | 11.802 | 1.00 | 32.16 |
| ATOM | 455 | CA | TYR | 116 | 38.970 | 19.428 | 12.212 | 1.00 | 30.52 |
| ATOM | 456 | CB | TYR | 116 | 38.754 | 20.794 | 12.826 | 1.00 | 29.77 |
| ATOM | 457 | CG | TYR | 116 | 37.326 | 21.039 | 13.215 | 1.00 | 31.85 |
| ATOM | 458 | CD1 | TYR | 116 | 36.812 | 20.513 | 14.408 | 1.00 | 30.34 |
| ATOM | 459 | CE1 | TYR | 116 | 35.481 | 20.738 | 14.761 | 1.00 | 31.25 |
| ATOM | 460 | CZ | TYR | 116 | 34.645 | 21.495 | 13.916 | 1.00 | 30.45 |
| ATOM | 461 | OH | TYR | 116 | 33.333 | 21.695 | 14.289 | 1.00 | 33.06 |
| ATOM | 462 | CE2 | TYR | 116 | 35.134 | 22.033 | 12.740 | 1.00 | 31.10 |
| ATOM | 463 | CD2 | TYR | 116 | 36.460 | 21.807 | 12.383 | 1.00 | 28.87 |
| ATOM | 464 | C | TYR | 116 | 38.024 | 19.208 | 11.014 | 1.00 | 30.65 |
| ATOM | 465 | O | TYR | 116 | 38.345 | 19.614 | 9.892 | 1.00 | 30.59 |
| ATOM | 466 | N | ILE | 117 | 36.858 | 18.598 | 11.241 | 1.00 | 28.73 |
| ATOM | 467 | CA | ILE | 117 | 35.854 | 18.601 | 10.231 | 1.00 | 28.16 |
| ATOM | 468 | CB | ILE | 117 | 35.966 | 17.372 | 9.240 | 1.00 | 29.12 |
| ATOM | 469 | CG1 | ILE | 117 | 34.970 | 17.520 | 8.055 | 1.00 | 26.39 |
| ATOM | 470 | CD1 | ILE | 117 | 35.060 | 16.421 | 6.957 | 1.00 | 27.24 |
| ATOM | 471 | CG2 | ILE | 117 | 35.787 | 16.049 | 9.984 | 1.00 | 26.00 |
| ATOM | 472 | C | ILE | 117 | 34.465 | 18.682 | 10.879 | 1.00 | 28.42 |
| ATOM | 473 | O | ILE | 117 | 34.260 | 18.187 | 11.981 | 1.00 | 28.48 |
| ATOM | 474 | N | GLU | 118 | 33.529 | 19.334 | 10.195 | 1.00 | 27.95 |
| ATOM | 475 | CA | GLU | 118 | 32.112 | 19.252 | 10.530 | 1.00 | 28.61 |
| ATOM | 476 | CB | GLU | 118 | 31.668 | 20.450 | 11.359 | 1.00 | 28.35 |
| ATOM | 477 | CG | GLU | 118 | 32.180 | 21.743 | 10.808 | 1.00 | 33.29 |
| ATOM | 478 | CD | GLU | 118 | 31.593 | 22.927 | 11.498 | 1.00 | 36.95 |
| ATOM | 479 | OE1 | GLU | 118 | 31.715 | 23.099 | 12.730 | 1.00 | 37.45 |
| ATOM | 480 | OE2 | GLU | 118 | 30.996 | 23.727 | 10.782 | 1.00 | 42.14 |
| ATOM | 481 | C | GLU | 118 | 31.266 | 19.141 | 9.266 | 1.00 | 28.90 |
| ATOM | 482 | O | GLU | 118 | 31.639 | 19.581 | 8.163 | 1.00 | 29.81 |
| ATOM | 483 | N | VAL | 119 | 30.133 | 18.505 | 9.428 | 1.00 | 27.93 |
| ATOM | 484 | CA | VAL | 119 | 29.186 | 18.389 | 8.394 | 1.00 | 26.65 |
| ATOM | 485 | CB | VAL | 119 | 29.072 | 16.936 | 7.927 | 1.00 | 27.76 |
| ATOM | 486 | CG1 | VAL | 119 | 27.955 | 16.810 | 6.857 | 1.00 | 25.00 |
| ATOM | 487 | CG2 | VAL | 119 | 30.419 | 16.408 | 7.377 | 1.00 | 24.38 |
| ATOM | 488 | C | VAL | 119 | 27.852 | 18.812 | 9.041 | 1.00 | 27.53 |
| ATOM | 489 | O | VAL | 119 | 27.443 | 18.201 | 10.034 | 1.00 | 26.65 |
| ATOM | 490 | N | TRP | 120 | 27.207 | 19.855 | 8.480 | 1.00 | 26.32 |
| ATOM | 491 | CA | TRP | 120 | 25.868 | 20.268 | 8.865 | 1.00 | 25.22 |
| ATOM | 492 | CB | TRP | 120 | 25.916 | 21.710 | 9.300 | 1.00 | 24.66 |
| ATOM | 493 | CG | TRP | 120 | 24.772 | 22.213 | 10.090 | 1.00 | 23.83 |
| ATOM | 494 | CD1 | TRP | 120 | 23.579 | 21.635 | 10.258 | 1.00 | 24.59 |
| ATOM | 495 | NE1 | TRP | 120 | 22.795 | 22.427 | 11.084 | 1.00 | 29.40 |
| ATOM | 496 | CE2 | TRP | 120 | 23.501 | 23.551 | 11.434 | 1.00 | 24.59 |
| ATOM | 497 | CD2 | TRP | 120 | 24.753 | 23.450 | 10.825 | 1.00 | 22.94 |
| ATOM | 498 | CE3 | TRP | 120 | 25.730 | 24.447 | 11.087 | 1.00 | 25.61 |
| ATOM | 499 | CZ3 | TRP | 120 | 25.375 | 25.543 | 11.896 | 1.00 | 25.81 |
| ATOM | 500 | CH2 | TRP | 120 | 24.079 | 25.624 | 12.463 | 1.00 | 21.59 |
| ATOM | 501 | CZ2 | TRP | 120 | 23.149 | 24.625 | 12.276 | 1.00 | 22.78 |
| ATOM | 502 | C | TRP | 120 | 24.914 | 20.147 | 7.694 | 1.00 | 25.58 |
| ATOM | 503 | O | TRP | 120 | 25.110 | 20.784 | 6.644 | 1.00 | 24.48 |
| ATOM | 504 | N | GLY | 121 | 23.899 | 19.321 | 7.876 | 1.00 | 24.73 |
| ATOM | 505 | CA | GLY | 121 | 22.924 | 19.091 | 6.873 | 1.00 | 25.93 |
| ATOM | 506 | C | GLY | 121 | 21.616 | 19.716 | 7.277 | 1.00 | 27.00 |
| ATOM | 507 | O | GLY | 121 | 21.233 | 19.681 | 8.450 | 1.00 | 27.37 |
| ATOM | 508 | N | ASN | 136 | 30.653 | 16.831 | 14.148 | 1.00 | 27.30 |
| ATOM | 509 | CA | ASN | 136 | 32.002 | 17.319 | 13.914 | 1.00 | 29.52 |
| ATOM | 510 | CB | ASN | 136 | 32.146 | 18.721 | 14.480 | 1.00 | 30.32 |
| ATOM | 511 | CG | ASN | 136 | 32.092 | 18.720 | 15.989 | 1.00 | 33.09 |
| ATOM | 512 | OD1 | ASN | 136 | 31.961 | 17.636 | 16.598 | 1.00 | 33.19 |
| ATOM | 513 | ND2 | ASN | 136 | 32.190 | 19.908 | 16.606 | 1.00 | 29.70 |
| ATOM | 514 | C | ASN | 136 | 33.094 | 16.332 | 14.492 | 1.00 | 30.64 |
| ATOM | 515 | O | ASN | 136 | 32.777 | 15.211 | 14.918 | 1.00 | 30.23 |
| ATOM | 516 | N | TYR | 137 | 34.354 | 16.737 | 14.516 | 1.00 | 31.44 |
| ATOM | 517 | CA | TYR | 137 | 35.400 | 15.800 | 14.836 | 1.00 | 33.26 |
| ATOM | 518 | CB | TYR | 137 | 35.489 | 14.757 | 13.753 | 1.00 | 33.53 |
| ATOM | 519 | CG | TYR | 137 | 36.833 | 14.100 | 13.657 | 1.00 | 37.68 |
| ATOM | 520 | CD1 | TYR | 137 | 37.882 | 14.695 | 12.916 | 1.00 | 39.03 |
| ATOM | 521 | CE1 | TYR | 137 | 39.122 | 14.089 | 12.833 | 1.00 | 38.62 |
| ATOM | 522 | CZ | TYR | 137 | 39.312 | 12.858 | 13.475 | 1.00 | 37.04 |

TABLE 3-continued

| | | | | | | | | |
|---|---|---|---|---|---|---|---|---|
| ATOM | 523 | OH | TYR | 137 | 40.525 | 12.236 | 13.388 | 1.00 | 37.95 |
| ATOM | 524 | CE2 | TYR | 137 | 38.311 | 12.257 | 14.205 | 1.00 | 39.58 |
| ATOM | 525 | CD2 | TYR | 137 | 37.077 | 12.876 | 14.306 | 1.00 | 39.01 |
| ATOM | 526 | C | TYR | 137 | 36.684 | 16.558 | 14.878 | 1.00 | 34.30 |
| ATOM | 527 | O | TYR | 137 | 36.897 | 17.336 | 13.999 | 1.00 | 34.65 |
| ATOM | 528 | N | GLY | 138 | 37.514 | 16.329 | 15.904 | 1.00 | 34.97 |
| ATOM | 529 | CA | GLY | 138 | 38.871 | 16.847 | 16.012 | 1.00 | 36.70 |
| ATOM | 530 | C | GLY | 138 | 39.852 | 15.671 | 16.087 | 1.00 | 38.86 |
| ATOM | 531 | O | GLY | 138 | 39.526 | 14.615 | 16.616 | 1.00 | 39.30 |
| ATOM | 532 | N | ARG | 151 | 32.649 | 23.502 | 19.711 | 1.00 | 30.58 |
| ATOM | 533 | CA | ARG | 151 | 31.679 | 23.869 | 18.629 | 1.00 | 31.25 |
| ATOM | 534 | CB | ARG | 151 | 32.270 | 23.750 | 17.213 | 1.00 | 29.31 |
| ATOM | 535 | CG | ARG | 151 | 33.403 | 24.722 | 17.014 | 1.00 | 29.65 |
| ATOM | 536 | CD | ARG | 151 | 34.070 | 24.685 | 15.627 | 1.00 | 33.04 |
| ATOM | 537 | NE | ARG | 151 | 33.214 | 25.051 | 14.483 | 1.00 | 34.09 |
| ATOM | 538 | CZ | ARG | 151 | 33.217 | 26.222 | 13.823 | 1.00 | 29.45 |
| ATOM | 539 | NH1 | ARG | 151 | 34.015 | 27.264 | 14.154 | 1.00 | 18.79 |
| ATOM | 540 | NH2 | ARG | 151 | 32.400 | 26.339 | 12.797 | 1.00 | 26.66 |
| ATOM | 541 | C | ARG | 151 | 30.417 | 23.061 | 18.793 | 1.00 | 31.29 |
| ATOM | 542 | O | ARG | 151 | 29.337 | 23.531 | 18.460 | 1.00 | 31.42 |
| ATOM | 543 | N | ILE | 162 | 12.415 | 29.040 | 11.003 | 1.00 | 29.30 |
| ATOM | 544 | CA | ILE | 162 | 11.966 | 28.158 | 9.973 | 1.00 | 30.78 |
| ATOM | 545 | CB | ILE | 162 | 12.415 | 26.699 | 10.241 | 1.00 | 30.32 |
| ATOM | 546 | CG1 | ILE | 162 | 13.955 | 26.574 | 10.160 | 1.00 | 32.82 |
| ATOM | 547 | CD1 | ILE | 162 | 14.639 | 26.722 | 8.752 | 1.00 | 30.34 |
| ATOM | 548 | CG2 | ILE | 162 | 11.698 | 25.722 | 9.318 | 1.00 | 29.66 |
| ATOM | 549 | C | ILE | 162 | 10.438 | 28.188 | 9.964 | 1.00 | 31.75 |
| ATOM | 550 | O | ILE | 162 | 9.826 | 28.114 | 11.040 | 1.00 | 31.45 |
| ATOM | 551 | O6 | GDQ | 201 | 39.880 | 25.293 | −6.152 | 1.00 | 46.27 |
| ATOM | 552 | C6 | GDQ | 201 | 39.593 | 23.968 | −5.959 | 1.00 | 47.77 |
| ATOM | 553 | N1 | GDQ | 201 | 39.601 | 23.364 | −4.728 | 1.00 | 47.90 |
| ATOM | 554 | C5 | GDQ | 201 | 39.301 | 23.178 | −7.050 | 1.00 | 48.17 |
| ATOM | 555 | C7 | GDQ | 201 | 39.166 | 23.330 | −8.414 | 1.00 | 49.49 |
| ATOM | 556 | C77 | GDQ | 201 | 39.375 | 24.484 | −9.040 | 1.00 | 48.63 |
| ATOM | 557 | N77 | GDQ | 201 | 39.668 | 25.525 | −9.571 | 1.00 | 53.62 |
| ATOM | 558 | C8 | GDQ | 201 | 38.829 | 22.148 | −9.069 | 1.00 | 47.67 |
| ATOM | 559 | N9 | GDQ | 201 | 38.739 | 21.226 | −8.070 | 1.00 | 46.70 |
| ATOM | 560 | C4 | GDQ | 201 | 39.015 | 21.838 | −6.880 | 1.00 | 47.89 |
| ATOM | 561 | N3 | GDQ | 201 | 39.029 | 21.264 | −5.651 | 1.00 | 47.83 |
| ATOM | 562 | C2 | GDQ | 201 | 39.318 | 22.021 | −4.572 | 1.00 | 48.19 |
| ATOM | 563 | N2 | GDQ | 201 | 39.322 | 21.396 | −3.361 | 1.00 | 46.97 |
| ATOM | 564 | N | GLU | 25 | 49.175 | 37.893 | −15.307 | 1.00 | 54.82 |
| ATOM | 565 | CA | GLU | 25 | 49.977 | 36.804 | −14.720 | 1.00 | 53.68 |
| ATOM | 566 | CB | GLU | 25 | 51.192 | 36.541 | −15.595 | 1.00 | 54.71 |
| ATOM | 567 | CG | GLU | 25 | 50.885 | 36.602 | −17.100 | 1.00 | 59.15 |
| ATOM | 568 | CD | GLU | 25 | 49.943 | 35.470 | −17.540 | 1.00 | 64.93 |
| ATOM | 569 | OE1 | GLU | 25 | 50.055 | 34.345 | −16.969 | 1.00 | 65.43 |
| ATOM | 570 | OE2 | GLU | 25 | 49.102 | 35.709 | −18.455 | 1.00 | 67.14 |
| ATOM | 571 | C | GLU | 25 | 50.439 | 37.242 | −13.312 | 1.00 | 51.49 |
| ATOM | 572 | O | GLU | 25 | 50.717 | 38.444 | −13.088 | 1.00 | 51.01 |
| ATOM | 573 | N | TYR | 26 | 50.526 | 36.274 | −12.393 | 1.00 | 48.83 |
| ATOM | 574 | CA | TYR | 26 | 50.790 | 36.515 | −10.947 | 1.00 | 47.05 |
| ATOM | 575 | CB | TYR | 26 | 50.985 | 35.154 | −10.254 | 1.00 | 46.87 |
| ATOM | 576 | CG | TYR | 26 | 51.434 | 35.227 | −8.828 | 1.00 | 47.92 |
| ATOM | 577 | CD1 | TYR | 26 | 52.671 | 34.688 | −8.433 | 1.00 | 47.84 |
| ATOM | 578 | CE1 | TYR | 26 | 53.100 | 34.762 | −7.082 | 1.00 | 48.18 |
| ATOM | 579 | CZ | TYR | 26 | 52.269 | 35.386 | −6.131 | 1.00 | 48.18 |
| ATOM | 580 | OH | TYR | 26 | 52.662 | 35.492 | −4.804 | 1.00 | 47.03 |
| ATOM | 581 | CE2 | TYR | 26 | 51.035 | 35.918 | −6.520 | 1.00 | 46.39 |
| ATOM | 582 | CD2 | TYR | 26 | 50.628 | 35.840 | −7.852 | 1.00 | 47.18 |
| ATOM | 583 | C | TYR | 26 | 51.913 | 37.564 | −10.644 | 1.00 | 45.24 |
| ATOM | 584 | O | TYR | 26 | 53.043 | 37.429 | −11.089 | 1.00 | 44.91 |
| ATOM | 585 | N | TYR | 43 | 43.094 | 49.232 | 14.963 | 1.00 | 35.86 |
| ATOM | 586 | CA | TYR | 43 | 41.845 | 49.384 | 14.221 | 1.00 | 34.34 |
| ATOM | 587 | CB | TYR | 43 | 41.606 | 50.848 | 13.825 | 1.00 | 34.51 |
| ATOM | 588 | CG | TYR | 43 | 42.620 | 51.403 | 12.875 | 1.00 | 35.13 |
| ATOM | 589 | CD1 | TYR | 43 | 43.789 | 52.021 | 13.353 | 1.00 | 35.36 |
| ATOM | 590 | CE1 | TYR | 43 | 44.713 | 52.568 | 12.476 | 1.00 | 35.91 |
| ATOM | 591 | CZ | TYR | 43 | 44.482 | 52.488 | 11.092 | 1.00 | 36.72 |
| ATOM | 592 | OH | TYR | 43 | 45.423 | 53.020 | 10.229 | 1.00 | 39.91 |
| ATOM | 593 | CE2 | TYR | 43 | 43.341 | 51.894 | 10.591 | 1.00 | 35.17 |
| ATOM | 594 | CD2 | TYR | 43 | 42.406 | 51.355 | 11.490 | 1.00 | 33.94 |
| ATOM | 595 | C | TYR | 43 | 41.778 | 48.416 | 13.037 | 1.00 | 33.02 |
| ATOM | 596 | O | TYR | 43 | 42.773 | 47.896 | 12.622 | 1.00 | 33.74 |
| ATOM | 597 | N | PHE | 44 | 40.584 | 48.157 | 12.534 | 1.00 | 31.52 |
| ATOM | 598 | CA | PHE | 44 | 40.380 | 47.193 | 11.477 | 1.00 | 30.42 |
| ATOM | 599 | CB | PHE | 44 | 39.121 | 46.371 | 11.785 | 1.00 | 28.05 |
| ATOM | 600 | CG | PHE | 44 | 39.368 | 44.908 | 12.102 | 1.00 | 26.16 |
| ATOM | 601 | CD1 | PHE | 44 | 38.895 | 44.360 | 13.296 | 1.00 | 23.64 |
| ATOM | 602 | CE1 | PHE | 44 | 39.048 | 43.004 | 13.579 | 1.00 | 26.96 |

TABLE 3-continued

| | | | | | | | | | |
|---|---|---|---|---|---|---|---|---|---|
| ATOM | 603 | CZ | PHE | 44 | 39.695 | 42.170 | 12.652 | 1.00 | 27.27 |
| ATOM | 604 | CE2 | PHE | 44 | 40.193 | 42.728 | 11.450 | 1.00 | 24.84 |
| ATOM | 605 | CD2 | PHE | 44 | 40.022 | 44.075 | 11.193 | 1.00 | 23.20 |
| ATOM | 606 | C | PHE | 44 | 40.201 | 47.957 | 10.126 | 1.00 | 30.58 |
| ATOM | 607 | O | PHE | 44 | 39.488 | 48.958 | 10.052 | 1.00 | 30.26 |
| ATOM | 608 | N | VAL | 45 | 40.882 | 47.487 | 9.094 | 1.00 | 29.38 |
| ATOM | 609 | CA | VAL | 45 | 40.578 | 47.889 | 7.737 | 1.00 | 29.28 |
| ATOM | 610 | CB | VAL | 45 | 41.844 | 48.431 | 7.053 | 1.00 | 29.71 |
| ATOM | 611 | CG1 | VAL | 45 | 42.424 | 49.563 | 7.910 | 1.00 | 27.42 |
| ATOM | 612 | CG2 | VAL | 45 | 41.512 | 48.887 | 5.625 | 1.00 | 27.61 |
| ATOM | 613 | C | VAL | 45 | 40.073 | 46.699 | 6.946 | 1.00 | 28.37 |
| ATOM | 614 | O | VAL | 45 | 40.775 | 45.707 | 6.881 | 1.00 | 29.10 |
| ATOM | 615 | N | LYS | 46 | 38.862 | 46.788 | 6.372 | 1.00 | 27.37 |
| ATOM | 616 | CA | LYS | 46 | 38.313 | 45.744 | 5.461 | 1.00 | 26.68 |
| ATOM | 617 | CB | LYS | 46 | 36.862 | 45.397 | 5.804 | 1.00 | 26.88 |
| ATOM | 618 | CG | LYS | 46 | 36.313 | 44.223 | 4.931 | 1.00 | 25.08 |
| ATOM | 619 | CD | LYS | 46 | 34.964 | 43.720 | 5.314 | 1.00 | 25.24 |
| ATOM | 620 | CE | LYS | 46 | 34.072 | 44.791 | 5.955 | 1.00 | 28.89 |
| ATOM | 621 | NZ | LYS | 46 | 32.686 | 44.222 | 6.181 | 1.00 | 26.14 |
| ATOM | 622 | C | LYS | 46 | 38.344 | 46.164 | 3.973 | 1.00 | 27.02 |
| ATOM | 623 | O | LYS | 46 | 37.964 | 47.250 | 3.629 | 1.00 | 27.01 |
| ATOM | 624 | N | PHE | 47 | 38.863 | 45.314 | 3.111 | 1.00 | 28.84 |
| ATOM | 625 | CA | PHE | 47 | 38.615 | 45.418 | 1.644 | 1.00 | 29.05 |
| ATOM | 626 | CB | PHE | 47 | 39.885 | 45.190 | 0.860 | 1.00 | 28.82 |
| ATOM | 627 | CG | PHE | 47 | 40.967 | 46.166 | 1.206 | 1.00 | 33.70 |
| ATOM | 628 | CD1 | PHE | 47 | 41.906 | 45.865 | 2.202 | 1.00 | 33.29 |
| ATOM | 629 | CE1 | PHE | 47 | 42.870 | 46.771 | 2.548 | 1.00 | 37.36 |
| ATOM | 630 | CZ | PHE | 47 | 42.947 | 48.011 | 1.876 | 1.00 | 36.77 |
| ATOM | 631 | CE2 | PHE | 47 | 42.036 | 48.328 | 0.902 | 1.00 | 35.15 |
| ATOM | 632 | CD2 | PHE | 47 | 41.028 | 47.407 | 0.580 | 1.00 | 35.97 |
| ATOM | 633 | C | PHE | 47 | 37.557 | 44.433 | 1.154 | 1.00 | 29.27 |
| ATOM | 634 | O | PHE | 47 | 37.656 | 43.228 | 1.388 | 1.00 | 28.82 |
| ATOM | 635 | N | ASN | 48 | 36.544 | 44.969 | 0.481 | 1.00 | 29.67 |
| ATOM | 636 | CA | ASN | 48 | 35.565 | 44.180 | -0.238 | 1.00 | 29.45 |
| ATOM | 637 | CB | ASN | 48 | 34.187 | 44.785 | -0.092 | 1.00 | 29.55 |
| ATOM | 638 | CG | ASN | 48 | 33.812 | 45.036 | 1.358 | 1.00 | 31.72 |
| ATOM | 639 | OD1 | ASN | 48 | 33.656 | 44.091 | 2.151 | 1.00 | 31.64 |
| ATOM | 640 | ND2 | ASN | 48 | 33.639 | 46.309 | 1.710 | 1.00 | 28.68 |
| ATOM | 641 | C | ASN | 48 | 35.966 | 44.089 | -1.712 | 1.00 | 29.39 |
| ATOM | 642 | O | ASN | 48 | 36.181 | 45.074 | -2.366 | 1.00 | 30.66 |
| ATOM | 643 | N | CYS | 49 | 36.121 | 42.882 | -2.215 | 1.00 | 28.93 |
| ATOM | 644 | CA | CYS | 49 | 36.691 | 42.691 | -3.539 | 1.00 | 28.55 |
| ATOM | 645 | CB | CYS | 49 | 38.122 | 42.139 | -3.427 | 1.00 | 28.66 |
| ATOM | 646 | SG | CYS | 49 | 39.169 | 42.982 | -2.155 | 1.00 | 32.73 |
| ATOM | 647 | C | CYS | 49 | 35.822 | 41.722 | -4.303 | 1.00 | 27.45 |
| ATOM | 648 | O | CYS | 49 | 36.163 | 40.571 | -4.400 | 1.00 | 27.31 |
| ATOM | 649 | N | PRO | 50 | 34.677 | 42.187 | -4.815 | 1.00 | 26.98 |
| ATOM | 650 | CA | PRO | 50 | 33.704 | 41.358 | -5.540 | 1.00 | 28.14 |
| ATOM | 651 | CB | PRO | 50 | 32.460 | 42.229 | -5.577 | 1.00 | 27.05 |
| ATOM | 652 | CG | PRO | 50 | 32.834 | 43.500 | -4.917 | 1.00 | 27.46 |
| ATOM | 653 | CD | PRO | 50 | 34.269 | 43.589 | -4.773 | 1.00 | 26.73 |
| ATOM | 654 | C | PRO | 50 | 34.131 | 41.021 | -6.992 | 1.00 | 28.93 |
| ATOM | 655 | O | PRO | 50 | 33.454 | 40.277 | -7.662 | 1.00 | 29.56 |
| ATOM | 656 | N | GLU | 51 | 35.239 | 41.550 | -7.471 | 1.00 | 28.99 |
| ATOM | 657 | CA | GLU | 51 | 35.542 | 41.364 | -8.882 | 1.00 | 30.87 |
| ATOM | 658 | CB | GLU | 51 | 35.773 | 42.743 | -9.531 | 1.00 | 29.68 |
| ATOM | 659 | CG | GLU | 51 | 34.461 | 43.552 | -9.722 | 1.00 | 30.84 |
| ATOM | 660 | CD | GLU | 51 | 34.670 | 45.005 | -10.178 | 1.00 | 32.39 |
| ATOM | 661 | OE1 | GLU | 51 | 35.770 | 45.326 | -10.657 | 1.00 | 32.62 |
| ATOM | 662 | OE2 | GLU | 51 | 33.746 | 45.863 | -10.020 | 1.00 | 37.18 |
| ATOM | 663 | C | GLU | 51 | 36.729 | 40.420 | -9.058 | 1.00 | 30.84 |
| ATOM | 664 | O | GLU | 51 | 37.434 | 40.492 | -10.035 | 1.00 | 32.13 |
| ATOM | 665 | N | PHE | 52 | 36.952 | 39.517 | -8.104 | 1.00 | 31.69 |
| ATOM | 666 | CA | PHE | 52 | 38.030 | 38.514 | -8.232 | 1.00 | 31.23 |
| ATOM | 667 | CB | PHE | 52 | 38.386 | 37.828 | -6.871 | 1.00 | 31.35 |
| ATOM | 668 | CG | PHE | 52 | 39.611 | 36.960 | -6.961 | 1.00 | 28.85 |
| ATOM | 669 | CD1 | PHE | 52 | 40.889 | 37.530 | -6.947 | 1.00 | 25.99 |
| ATOM | 670 | CE1 | PHE | 52 | 42.029 | 36.739 | -7.043 | 1.00 | 23.31 |
| ATOM | 671 | CZ | PHE | 52 | 41.919 | 35.390 | -7.209 | 1.00 | 24.81 |
| ATOM | 672 | CE2 | PHE | 52 | 40.677 | 34.818 | -7.254 | 1.00 | 27.90 |
| ATOM | 673 | CD2 | PHE | 52 | 39.502 | 35.621 | -7.156 | 1.00 | 25.84 |
| ATOM | 674 | C | PHE | 52 | 37.720 | 37.432 | -9.243 | 1.00 | 30.68 |
| ATOM | 675 | O | PHE | 52 | 36.641 | 36.841 | -9.199 | 1.00 | 32.04 |
| ATOM | 676 | N | THR | 53 | 38.687 | 37.141 | -10.111 | 1.00 | 30.01 |
| ATOM | 677 | CA | THR | 53 | 38.664 | 35.956 | -10.997 | 1.00 | 29.44 |
| ATOM | 678 | CB | THR | 53 | 37.889 | 36.234 | -12.363 | 1.00 | 29.62 |
| ATOM | 679 | OG1 | THR | 53 | 37.847 | 35.032 | -13.160 | 1.00 | 29.40 |
| ATOM | 680 | CG2 | THR | 53 | 38.495 | 37.379 | -13.138 | 1.00 | 25.18 |
| ATOM | 681 | C | THR | 53 | 40.083 | 35.412 | -11.246 | 1.00 | 30.25 |
| ATOM | 682 | O | THR | 53 | 41.064 | 36.163 | -11.140 | 1.00 | 31.21 |

TABLE 3-continued

| | | | | | | | | | |
|---|---|---|---|---|---|---|---|---|---|
| ATOM | 683 | N | SER | 54 | 40.184 | 34.119 | −11.496 | 1.00 | 30.79 |
| ATOM | 684 | CA | SER | 54 | 41.424 | 33.459 | −11.879 | 1.00 | 32.95 |
| ATOM | 685 | CB | SER | 54 | 42.297 | 33.124 | −10.650 | 1.00 | 34.16 |
| ATOM | 686 | OG | SER | 54 | 41.611 | 32.236 | −9.771 | 1.00 | 35.15 |
| ATOM | 687 | C | SER | 54 | 41.066 | 32.175 | −12.573 | 1.00 | 34.08 |
| ATOM | 688 | O | SER | 54 | 39.919 | 32.011 | −12.987 | 1.00 | 33.43 |
| ATOM | 689 | N | LEU | 55 | 42.014 | 31.233 | −12.654 | 1.00 | 35.50 |
| ATOM | 690 | CA | LEU | 55 | 41.822 | 30.067 | −13.511 | 1.00 | 38.99 |
| ATOM | 691 | CB | LEU | 55 | 42.807 | 30.145 | −14.705 | 1.00 | 38.15 |
| ATOM | 692 | CG | LEU | 55 | 42.647 | 31.276 | −15.737 | 1.00 | 38.05 |
| ATOM | 693 | CD1 | LEU | 55 | 43.664 | 31.196 | −16.923 | 1.00 | 37.97 |
| ATOM | 694 | CD2 | LEU | 55 | 41.282 | 31.238 | −16.302 | 1.00 | 36.27 |
| ATOM | 695 | C | LEU | 55 | 41.913 | 28.720 | −12.764 | 1.00 | 41.28 |
| ATOM | 696 | O | LEU | 55 | 42.695 | 28.580 | −11.836 | 1.00 | 42.13 |
| ATOM | 697 | N | CYS | 56 | 41.111 | 27.735 | −13.140 | 1.00 | 45.15 |
| ATOM | 698 | CA | CYS | 56 | 41.284 | 26.387 | −12.587 | 1.00 | 48.21 |
| ATOM | 699 | CB | CYS | 56 | 40.075 | 25.528 | −12.936 | 1.00 | 48.98 |
| ATOM | 700 | SG | CYS | 56 | 40.243 | 23.736 | −12.722 | 1.00 | 48.04 |
| ATOM | 701 | C | CYS | 56 | 42.640 | 25.816 | −13.109 | 1.00 | 50.95 |
| ATOM | 702 | O | CYS | 56 | 42.955 | 25.956 | −14.300 | 1.00 | 51.40 |
| ATOM | 703 | N | PRO | 57 | 43.489 | 25.253 | −12.213 | 1.00 | 52.65 |
| ATOM | 704 | CA | PRO | 57 | 44.889 | 25.013 | −12.637 | 1.00 | 54.14 |
| ATOM | 705 | CB | PRO | 57 | 45.642 | 24.842 | −11.314 | 1.00 | 54.19 |
| ATOM | 706 | CG | PRO | 57 | 44.588 | 24.328 | −10.336 | 1.00 | 53.52 |
| ATOM | 707 | CD | PRO | 57 | 43.230 | 24.787 | −10.836 | 1.00 | 52.98 |
| ATOM | 708 | C | PRO | 57 | 45.063 | 23.781 | −13.555 | 1.00 | 55.54 |
| ATOM | 709 | O | PRO | 57 | 46.016 | 23.722 | −14.350 | 1.00 | 54.81 |
| ATOM | 710 | N | LYS | 58 | 44.128 | 22.829 | −13.446 | 1.00 | 57.50 |
| ATOM | 711 | CA | LYS | 58 | 44.049 | 21.682 | −14.364 | 1.00 | 59.13 |
| ATOM | 712 | CB | LYS | 58 | 43.390 | 20.459 | −13.703 | 1.00 | 59.05 |
| ATOM | 713 | CG | LYS | 58 | 42.852 | 19.399 | −14.694 | 1.00 | 60.63 |
| ATOM | 714 | CD | LYS | 58 | 41.954 | 18.339 | −13.989 | 1.00 | 60.64 |
| ATOM | 715 | CE | LYS | 58 | 41.087 | 17.521 | −14.973 | 1.00 | 62.65 |
| ATOM | 716 | NZ | LYS | 58 | 39.920 | 16.812 | −14.317 | 1.00 | 60.90 |
| ATOM | 717 | C | LYS | 58 | 43.283 | 22.126 | −15.614 | 1.00 | 59.19 |
| ATOM | 718 | O | LYS | 58 | 43.848 | 22.146 | −16.705 | 1.00 | 59.79 |
| ATOM | 719 | N | VAL | 59 | 42.023 | 22.530 | −15.427 | 1.00 | 58.64 |
| ATOM | 720 | CA | VAL | 59 | 41.091 | 22.837 | −16.536 | 1.00 | 57.13 |
| ATOM | 721 | CB | VAL | 59 | 39.619 | 22.857 | −16.016 | 1.00 | 57.65 |
| ATOM | 722 | CG1 | VAL | 59 | 38.693 | 23.422 | −17.024 | 1.00 | 58.60 |
| ATOM | 723 | CG2 | VAL | 59 | 39.162 | 21.438 | −15.633 | 1.00 | 58.09 |
| ATOM | 724 | C | VAL | 59 | 41.418 | 24.097 | −17.372 | 1.00 | 55.09 |
| ATOM | 725 | O | VAL | 59 | 41.268 | 24.080 | −18.580 | 1.00 | 56.14 |
| ATOM | 726 | N | GLY | 60 | 41.828 | 25.194 | −16.740 | 1.00 | 52.41 |
| ATOM | 727 | CA | GLY | 60 | 41.961 | 26.474 | −17.434 | 1.00 | 47.50 |
| ATOM | 728 | C | GLY | 60 | 40.683 | 27.301 | −17.479 | 1.00 | 45.30 |
| ATOM | 729 | O | GLY | 60 | 40.704 | 28.429 | −17.918 | 1.00 | 44.68 |
| ATOM | 730 | N | GLN | 61 | 39.569 | 26.730 | −17.037 | 1.00 | 43.47 |
| ATOM | 731 | CA | GLN | 61 | 38.283 | 27.409 | −16.913 | 1.00 | 43.06 |
| ATOM | 732 | CB | GLN | 61 | 37.186 | 26.386 | −16.571 | 1.00 | 42.84 |
| ATOM | 733 | CG | GLN | 61 | 35.792 | 26.965 | −16.271 | 1.00 | 46.97 |
| ATOM | 734 | CD | GLN | 61 | 34.702 | 25.892 | −16.088 | 1.00 | 48.50 |
| ATOM | 735 | OE1 | GLN | 61 | 33.523 | 26.106 | −16.446 | 1.00 | 53.52 |
| ATOM | 736 | NE2 | GLN | 61 | 35.096 | 24.725 | −15.528 | 1.00 | 52.86 |
| ATOM | 737 | C | GLN | 61 | 38.362 | 28.483 | −15.833 | 1.00 | 40.38 |
| ATOM | 738 | O | GLN | 61 | 38.938 | 28.269 | −14.787 | 1.00 | 39.46 |
| ATOM | 739 | N | PRO | 62 | 37.799 | 29.662 | −16.105 | 1.00 | 39.26 |
| ATOM | 740 | CA | PRO | 62 | 37.742 | 30.792 | −15.166 | 1.00 | 37.62 |
| ATOM | 741 | CB | PRO | 62 | 36.923 | 31.836 | −15.917 | 1.00 | 37.68 |
| ATOM | 742 | CG | PRO | 62 | 36.928 | 31.436 | −17.335 | 1.00 | 38.30 |
| ATOM | 743 | CD | PRO | 62 | 37.120 | 29.954 | −17.382 | 1.00 | 39.55 |
| ATOM | 744 | C | PRO | 62 | 36.966 | 30.446 | −13.889 | 1.00 | 36.24 |
| ATOM | 745 | O | PRO | 62 | 35.986 | 29.671 | −13.955 | 1.00 | 35.39 |
| ATOM | 746 | N | ASP | 63 | 37.390 | 31.043 | −12.761 | 1.00 | 34.81 |
| ATOM | 747 | CA | ASP | 63 | 36.666 | 30.992 | −11.482 | 1.00 | 33.85 |
| ATOM | 748 | CB | ASP | 63 | 37.523 | 30.460 | −10.304 | 1.00 | 35.11 |
| ATOM | 749 | CG | ASP | 63 | 38.321 | 29.171 | −10.609 | 1.00 | 42.47 |
| ATOM | 750 | OD1 | ASP | 63 | 37.687 | 28.192 | −11.128 | 1.00 | 45.14 |
| ATOM | 751 | OD2 | ASP | 63 | 39.573 | 29.151 | −10.243 | 1.00 | 44.13 |
| ATOM | 752 | C | ASP | 63 | 36.433 | 32.418 | −11.086 | 1.00 | 31.61 |
| ATOM | 753 | O | ASP | 63 | 37.265 | 33.293 | −11.427 | 1.00 | 30.61 |
| ATOM | 754 | N | PHE | 64 | 35.413 | 32.610 | −10.246 | 1.00 | 28.89 |
| ATOM | 755 | CA | PHE | 64 | 34.965 | 33.894 | −9.731 | 1.00 | 28.44 |
| ATOM | 756 | CB | PHE | 64 | 33.709 | 34.330 | −10.494 | 1.00 | 27.72 |
| ATOM | 757 | CG | PHE | 64 | 33.947 | 34.506 | −11.970 | 1.00 | 28.55 |
| ATOM | 758 | CD1 | PHE | 64 | 33.926 | 33.406 | −12.827 | 1.00 | 29.74 |
| ATOM | 759 | CE1 | PHE | 64 | 34.195 | 33.544 | −14.202 | 1.00 | 27.82 |
| ATOM | 760 | CZ | PHE | 64 | 34.509 | 34.793 | −14.702 | 1.00 | 28.20 |
| ATOM | 761 | CE2 | PHE | 64 | 34.533 | 35.923 | −13.860 | 1.00 | 29.67 |
| ATOM | 762 | CD2 | PHE | 64 | 34.253 | 35.775 | −12.491 | 1.00 | 28.64 |

TABLE 3-continued

| | | | | | | | | | |
|---|---|---|---|---|---|---|---|---|---|
| ATOM | 763 | C | PHE | 64 | 34.676 | 33.886 | −8.213 | 1.00 | 28.20 |
| ATOM | 764 | O | PHE | 64 | 34.058 | 32.959 | −7.698 | 1.00 | 28.02 |
| ATOM | 765 | N | ALA | 65 | 35.106 | 34.945 | −7.509 | 1.00 | 28.57 |
| ATOM | 766 | CA | ALA | 65 | 34.880 | 35.072 | −6.047 | 1.00 | 27.38 |
| ATOM | 767 | CB | ALA | 65 | 36.083 | 34.562 | −5.269 | 1.00 | 26.73 |
| ATOM | 768 | C | ALA | 65 | 34.647 | 36.476 | −5.658 | 1.00 | 27.14 |
| ATOM | 769 | O | ALA | 65 | 35.077 | 37.382 | −6.345 | 1.00 | 27.20 |
| ATOM | 770 | N | THR | 66 | 33.959 | 36.665 | −4.539 | 1.00 | 27.88 |
| ATOM | 771 | CA | THR | 66 | 34.161 | 37.880 | −3.739 | 1.00 | 29.11 |
| ATOM | 772 | CB | THR | 66 | 32.865 | 38.324 | −3.064 | 1.00 | 28.62 |
| ATOM | 773 | OG1 | THR | 66 | 31.893 | 38.546 | −4.055 | 1.00 | 32.67 |
| ATOM | 774 | CG2 | THR | 66 | 33.026 | 39.699 | −2.321 | 1.00 | 30.63 |
| ATOM | 775 | C | THR | 66 | 35.230 | 37.545 | −2.666 | 1.00 | 29.04 |
| ATOM | 776 | O | THR | 66 | 35.157 | 36.496 | −2.006 | 1.00 | 29.39 |
| ATOM | 777 | N | ILE | 67 | 36.187 | 38.435 | −2.463 | 1.00 | 29.87 |
| ATOM | 778 | CA | ILE | 67 | 37.164 | 38.251 | −1.396 | 1.00 | 29.83 |
| ATOM | 779 | CB | ILE | 67 | 38.587 | 38.232 | −1.944 | 1.00 | 30.58 |
| ATOM | 780 | CG1 | ILE | 67 | 38.746 | 37.168 | −3.049 | 1.00 | 28.17 |
| ATOM | 781 | CD1 | ILE | 67 | 40.222 | 37.168 | −3.597 | 1.00 | 30.71 |
| ATOM | 782 | CG2 | ILE | 67 | 39.613 | 37.990 | −0.826 | 1.00 | 32.44 |
| ATOM | 783 | C | ILE | 67 | 37.008 | 39.273 | −0.395 | 1.00 | 29.75 |
| ATOM | 784 | O | ILE | 67 | 36.863 | 40.562 | −0.776 | 1.00 | 30.09 |
| ATOM | 785 | N | TYR | 68 | 36.954 | 38.994 | 0.884 | 1.00 | 29.10 |
| ATOM | 786 | CA | TYR | 68 | 36.922 | 39.960 | 1.980 | 1.00 | 29.33 |
| ATOM | 787 | CB | TYR | 68 | 35.749 | 39.680 | 2.920 | 1.00 | 29.75 |
| ATOM | 788 | CG | TYR | 68 | 34.416 | 39.729 | 2.230 | 1.00 | 29.38 |
| ATOM | 789 | CD1 | TYR | 68 | 33.794 | 38.563 | 1.815 | 1.00 | 32.55 |
| ATOM | 790 | CE1 | TYR | 68 | 32.568 | 38.584 | 1.134 | 1.00 | 32.20 |
| ATOM | 791 | CZ | TYR | 68 | 31.963 | 39.819 | 0.883 | 1.00 | 33.29 |
| ATOM | 792 | OH | TYR | 68 | 30.740 | 39.851 | 0.231 | 1.00 | 32.89 |
| ATOM | 793 | CE2 | TYR | 68 | 32.572 | 41.015 | 1.294 | 1.00 | 29.83 |
| ATOM | 794 | CD2 | TYR | 68 | 33.783 | 40.965 | 1.962 | 1.00 | 31.54 |
| ATOM | 795 | C | TYR | 68 | 38.279 | 39.917 | 2.710 | 1.00 | 29.45 |
| ATOM | 796 | O | TYR | 68 | 38.779 | 38.853 | 3.103 | 1.00 | 29.05 |
| ATOM | 797 | N | ILE | 69 | 38.888 | 41.080 | 2.851 | 1.00 | 28.99 |
| ATOM | 798 | CA | ILE | 69 | 40.189 | 41.133 | 3.443 | 1.00 | 29.76 |
| ATOM | 799 | CB | ILE | 69 | 41.245 | 41.549 | 2.415 | 1.00 | 29.75 |
| ATOM | 800 | CG1 | ILE | 69 | 41.287 | 40.534 | 1.260 | 1.00 | 27.97 |
| ATOM | 801 | CD1 | ILE | 69 | 42.318 | 40.945 | 0.271 | 1.00 | 26.18 |
| ATOM | 802 | CG2 | ILE | 69 | 42.625 | 41.704 | 3.093 | 1.00 | 32.22 |
| ATOM | 803 | C | ILE | 69 | 40.152 | 42.132 | 4.557 | 1.00 | 29.86 |
| ATOM | 804 | O | ILE | 69 | 39.881 | 43.304 | 4.314 | 1.00 | 29.65 |
| ATOM | 805 | N | SER | 70 | 40.408 | 41.651 | 5.779 | 1.00 | 30.45 |
| ATOM | 806 | CA | SER | 70 | 40.364 | 42.506 | 6.981 | 1.00 | 30.03 |
| ATOM | 807 | CB | SER | 70 | 39.223 | 42.035 | 7.869 | 1.00 | 29.17 |
| ATOM | 808 | OG | SER | 70 | 38.002 | 42.191 | 7.194 | 1.00 | 30.13 |
| ATOM | 809 | C | SER | 70 | 41.687 | 42.374 | 7.736 | 1.00 | 30.78 |
| ATOM | 810 | O | SER | 70 | 42.155 | 41.252 | 7.957 | 1.00 | 30.80 |
| ATOM | 811 | N | TYR | 71 | 42.292 | 43.494 | 8.126 | 1.00 | 30.28 |
| ATOM | 812 | CA | TYR | 71 | 43.549 | 43.418 | 8.832 | 1.00 | 30.62 |
| ATOM | 813 | CB | TYR | 71 | 44.775 | 43.454 | 7.870 | 1.00 | 31.06 |
| ATOM | 814 | CG | TYR | 71 | 45.145 | 44.802 | 7.314 | 1.00 | 30.65 |
| ATOM | 815 | CD1 | TYR | 71 | 44.427 | 45.375 | 6.252 | 1.00 | 32.95 |
| ATOM | 816 | CE1 | TYR | 71 | 44.774 | 46.635 | 5.729 | 1.00 | 35.56 |
| ATOM | 817 | CZ | TYR | 71 | 45.853 | 47.307 | 6.284 | 1.00 | 35.18 |
| ATOM | 818 | OH | TYR | 71 | 46.233 | 48.540 | 5.823 | 1.00 | 33.86 |
| ATOM | 819 | CE2 | TYR | 71 | 46.553 | 46.731 | 7.335 | 1.00 | 32.70 |
| ATOM | 820 | CD2 | TYR | 71 | 46.208 | 45.482 | 7.808 | 1.00 | 30.48 |
| ATOM | 821 | C | TYR | 71 | 43.613 | 44.505 | 9.873 | 1.00 | 30.68 |
| ATOM | 822 | O | TYR | 71 | 42.887 | 45.490 | 9.763 | 1.00 | 30.21 |
| ATOM | 823 | N | ILE | 72 | 44.427 | 44.279 | 10.915 | 1.00 | 30.50 |
| ATOM | 824 | CA | ILE | 72 | 44.801 | 45.325 | 11.855 | 1.00 | 30.24 |
| ATOM | 825 | CB | ILE | 72 | 44.723 | 44.843 | 13.328 | 1.00 | 30.88 |
| ATOM | 826 | CG1 | ILE | 72 | 43.293 | 44.331 | 13.636 | 1.00 | 28.07 |
| ATOM | 827 | CD1 | ILE | 72 | 42.932 | 44.254 | 15.117 | 1.00 | 28.12 |
| ATOM | 828 | CG2 | ILE | 72 | 45.196 | 45.956 | 14.298 | 1.00 | 29.52 |
| ATOM | 829 | C | ILE | 72 | 46.233 | 45.708 | 11.494 | 1.00 | 30.72 |
| ATOM | 830 | O | ILE | 72 | 47.132 | 44.880 | 11.577 | 1.00 | 32.13 |
| ATOM | 831 | N | TYR | 86 | 47.188 | 43.969 | −7.901 | 1.00 | 33.33 |
| ATOM | 832 | CA | TYR | 86 | 47.644 | 42.673 | −7.427 | 1.00 | 32.84 |
| ATOM | 833 | CB | TYR | 86 | 48.059 | 42.760 | −5.941 | 1.00 | 32.11 |
| ATOM | 834 | CG | TYR | 86 | 48.309 | 41.413 | −5.307 | 1.00 | 31.82 |
| ATOM | 835 | CD1 | TYR | 86 | 49.426 | 40.641 | −5.667 | 1.00 | 28.59 |
| ATOM | 836 | CE1 | TYR | 86 | 49.653 | 39.402 | −5.081 | 1.00 | 32.86 |
| ATOM | 837 | CZ | TYR | 86 | 48.743 | 38.917 | −4.119 | 1.00 | 31.37 |
| ATOM | 838 | OH | TYR | 86 | 48.919 | 37.697 | −3.545 | 1.00 | 30.97 |
| ATOM | 839 | CE2 | TYR | 86 | 47.642 | 39.664 | −3.744 | 1.00 | 31.22 |
| ATOM | 840 | CD2 | TYR | 86 | 47.420 | 40.904 | −4.336 | 1.00 | 31.02 |
| ATOM | 841 | C | TYR | 86 | 46.587 | 41.608 | −7.700 | 1.00 | 31.81 |
| ATOM | 842 | O | TYR | 86 | 46.886 | 40.527 | −8.229 | 1.00 | 31.35 |

TABLE 3-continued

| | | | | | | | | | |
|---|---|---|---|---|---|---|---|---|---|
| ATOM | 843 | N | LEU | 87 | 45.344 | 41.910 | −7.359 | 1.00 | 31.78 |
| ATOM | 844 | CA | LEU | 87 | 44.248 | 40.955 | −7.633 | 1.00 | 31.82 |
| ATOM | 845 | CB | LEU | 87 | 42.984 | 41.397 | −6.890 | 1.00 | 32.18 |
| ATOM | 846 | CG | LEU | 87 | 43.082 | 41.369 | −5.328 | 1.00 | 31.56 |
| ATOM | 847 | CD1 | LEU | 87 | 41.740 | 41.655 | −4.733 | 1.00 | 32.47 |
| ATOM | 848 | CD2 | LEU | 87 | 43.559 | 40.055 | −4.866 | 1.00 | 26.18 |
| ATOM | 849 | C | LEU | 87 | 43.953 | 40.670 | −9.122 | 1.00 | 32.75 |
| ATOM | 850 | O | LEU | 87 | 43.561 | 39.559 | −9.485 | 1.00 | 32.73 |
| ATOM | 851 | N | PHE | 88 | 44.113 | 41.685 | −9.975 | 1.00 | 34.10 |
| ATOM | 852 | CA | PHE | 88 | 44.007 | 41.519 | −11.429 | 1.00 | 35.05 |
| ATOM | 853 | CB | PHE | 88 | 44.345 | 42.822 | −12.193 | 1.00 | 35.48 |
| ATOM | 854 | CG | PHE | 88 | 43.261 | 43.881 | −12.155 | 1.00 | 36.14 |
| ATOM | 855 | CD1 | PHE | 88 | 43.574 | 45.210 | −12.455 | 1.00 | 38.84 |
| ATOM | 856 | CE1 | PHE | 88 | 42.574 | 46.187 | −12.470 | 1.00 | 38.29 |
| ATOM | 857 | CZ | PHE | 88 | 41.255 | 45.846 | −12.145 | 1.00 | 38.18 |
| ATOM | 858 | CE2 | PHE | 88 | 40.933 | 44.522 | −11.828 | 1.00 | 36.77 |
| ATOM | 859 | CD2 | PHE | 88 | 41.938 | 43.554 | −11.836 | 1.00 | 38.00 |
| ATOM | 860 | C | PHE | 88 | 45.003 | 40.496 | −11.881 | 1.00 | 35.83 |
| ATOM | 861 | O | PHE | 88 | 44.743 | 39.762 | −12.839 | 1.00 | 35.38 |
| ATOM | 862 | N | SER | 89 | 46.172 | 40.477 | −11.234 | 1.00 | 35.76 |
| ATOM | 863 | CA | SER | 89 | 47.281 | 39.648 | −11.698 | 1.00 | 34.90 |
| ATOM | 864 | CB | SER | 89 | 48.554 | 39.994 | −10.908 | 1.00 | 35.63 |
| ATOM | 865 | OG | SER | 89 | 48.651 | 39.280 | −9.670 | 1.00 | 35.63 |
| ATOM | 866 | C | SER | 89 | 46.998 | 38.166 | −11.627 | 1.00 | 35.05 |
| ATOM | 867 | O | SER | 89 | 47.808 | 37.344 | −12.084 | 1.00 | 35.82 |
| ATOM | 868 | N | PHE | 90 | 45.883 | 37.781 | −11.009 | 1.00 | 34.87 |
| ATOM | 869 | CA | PHE | 90 | 45.508 | 36.352 | −10.968 | 1.00 | 34.62 |
| ATOM | 870 | CB | PHE | 90 | 44.711 | 35.996 | −9.706 | 1.00 | 34.78 |
| ATOM | 871 | CG | PHE | 90 | 45.531 | 35.947 | −8.462 | 1.00 | 36.36 |
| ATOM | 872 | CD1 | PHE | 90 | 45.881 | 37.114 | −7.796 | 1.00 | 34.82 |
| ATOM | 873 | CE1 | PHE | 90 | 46.655 | 37.075 | −6.648 | 1.00 | 37.21 |
| ATOM | 874 | CZ | PHE | 90 | 47.080 | 35.867 | −6.143 | 1.00 | 36.41 |
| ATOM | 875 | CE2 | PHE | 90 | 46.696 | 34.671 | −6.760 | 1.00 | 40.24 |
| ATOM | 876 | CD2 | PHE | 90 | 45.934 | 34.718 | −7.934 | 1.00 | 39.21 |
| ATOM | 877 | C | PHE | 90 | 44.642 | 36.004 | −12.149 | 1.00 | 34.30 |
| ATOM | 878 | O | PHE | 90 | 44.284 | 34.840 | −12.302 | 1.00 | 33.27 |
| ATOM | 879 | N | ARG | 91 | 44.275 | 37.005 | −12.960 | 1.00 | 34.65 |
| ATOM | 880 | CA | ARG | 91 | 43.222 | 36.815 | −13.969 | 1.00 | 36.62 |
| ATOM | 881 | CB | ARG | 91 | 42.956 | 38.099 | −14.757 | 1.00 | 36.64 |
| ATOM | 882 | CG | ARG | 91 | 41.894 | 38.018 | −15.831 | 1.00 | 35.88 |
| ATOM | 883 | CD | ARG | 91 | 41.751 | 39.410 | −16.406 | 1.00 | 33.61 |
| ATOM | 884 | NE | ARG | 91 | 40.653 | 39.549 | −17.340 | 1.00 | 30.74 |
| ATOM | 885 | CZ | ARG | 91 | 39.396 | 39.795 | −17.007 | 1.00 | 34.38 |
| ATOM | 886 | NH1 | ARG | 91 | 39.055 | 39.912 | −15.715 | 1.00 | 32.01 |
| ATOM | 887 | NH2 | ARG | 91 | 33.458 | 39.897 | −17.973 | 1.00 | 29.74 |
| ATOM | 888 | C | ARG | 91 | 43.542 | 35.667 | −14.895 | 1.00 | 37.03 |
| ATOM | 889 | O | ARG | 91 | 42.668 | 34.860 | −15.195 | 1.00 | 37.70 |
| ATOM | 890 | N | ASN | 92 | 44.799 | 35.573 | −15.305 | 1.00 | 38.94 |
| ATOM | 891 | CA | ASN | 92 | 45.219 | 34.494 | −16.159 | 1.00 | 42.43 |
| ATOM | 892 | CB | ASN | 92 | 45.690 | 35.038 | −17.547 | 1.00 | 43.10 |
| ATOM | 893 | CG | ASN | 92 | 44.538 | 35.851 | −18.298 | 1.00 | 46.75 |
| ATOM | 894 | OD1 | ASN | 92 | 43.371 | 35.388 | −18.437 | 1.00 | 49.26 |
| ATOM | 895 | ND2 | ASN | 92 | 44.872 | 37.062 | −18.738 | 1.00 | 50.32 |
| ATOM | 896 | C | ASN | 92 | 46.151 | 33.456 | −15.469 | 1.00 | 44.01 |
| ATOM | 897 | O | ASN | 92 | 46.872 | 32.696 | −16.129 | 1.00 | 44.78 |
| ATOM | 898 | N | HIS | 93 | 46.033 | 33.376 | −14.138 | 1.00 | 44.75 |
| ATOM | 899 | CA | HIS | 93 | 46.810 | 32.475 | −13.274 | 1.00 | 45.82 |
| ATOM | 900 | CB | HIS | 93 | 47.330 | 33.300 | −12.083 | 1.00 | 46.58 |
| ATOM | 901 | CG | HIS | 93 | 48.366 | 32.598 | −11.258 | 1.00 | 51.68 |
| ATOM | 902 | ND1 | HIS | 93 | 48.252 | 32.443 | −9.886 | 1.00 | 56.34 |
| ATOM | 903 | CE1 | HIS | 93 | 49.301 | 31.777 | −9.432 | 1.00 | 57.05 |
| ATOM | 904 | NE2 | HIS | 93 | 50.089 | 31.490 | −10.459 | 1.00 | 57.52 |
| ATOM | 905 | CD2 | HIS | 93 | 49.529 | 31.996 | −11.611 | 1.00 | 54.61 |
| ATOM | 906 | C | HIS | 93 | 45.970 | 31.296 | −12.775 | 1.00 | 44.81 |
| ATOM | 907 | O | HIS | 93 | 44.853 | 31.488 | −12.312 | 1.00 | 46.13 |
| ATOM | 908 | N | GLY | 94 | 46.485 | 30.078 | −12.897 | 1.00 | 44.84 |
| ATOM | 909 | CA | GLY | 94 | 45.818 | 28.850 | −12.399 | 1.00 | 44.49 |
| ATOM | 910 | C | GLY | 94 | 46.263 | 23.432 | −10.975 | 1.00 | 45.32 |
| ATOM | 911 | O | GLY | 94 | 47.457 | 28.196 | −10.729 | 1.00 | 45.94 |
| ATOM | 912 | N | ASP | 95 | 45.331 | 28.396 | −10.025 | 1.00 | 44.13 |
| ATOM | 913 | CA | ASP | 95 | 45.571 | 27.829 | −8.692 | 1.00 | 44.02 |
| ATOM | 914 | CB | ASP | 95 | 46.397 | 28.757 | −7.763 | 1.00 | 45.45 |
| ATOM | 915 | CG | ASP | 95 | 47.948 | 28.486 | −7.818 | 1.00 | 48.99 |
| ATOM | 916 | OD1 | ASP | 95 | 48.738 | 29.446 | −7.639 | 1.00 | 54.04 |
| ATOM | 917 | OD2 | ASP | 95 | 48.388 | 27.328 | −8.029 | 1.00 | 53.84 |
| ATOM | 918 | C | ASP | 95 | 44.223 | 27.468 | −8.056 | 1.00 | 42.25 |
| ATOM | 919 | O | ASP | 95 | 43.192 | 28.012 | −8.441 | 1.00 | 40.15 |
| ATOM | 920 | N | PHE | 96 | 44.261 | 26.531 | −7.109 | 1.00 | 41.12 |
| ATOM | 921 | CA | PHE | 96 | 43.096 | 26.125 | −6.335 | 1.00 | 40.60 |
| ATOM | 922 | CB | PHE | 96 | 43.393 | 24.853 | −5.554 | 1.00 | 41.69 |

TABLE 3-continued

| | | | | | | | | |
|---|---|---|---|---|---|---|---|---|
| ATOM | 923 | CG | PHE | 96 | 43.402 | 23.616 | −6.419 | 1.00 | 44.28 |
| ATOM | 924 | CD1 | PHE | 96 | 44.265 | 22.558 | −6.147 | 1.00 | 47.19 |
| ATOM | 925 | CE1 | PHE | 96 | 44.270 | 21.395 | −6.940 | 1.00 | 47.63 |
| ATOM | 926 | CZ | PHE | 96 | 43.401 | 21.294 | −8.029 | 1.00 | 46.71 |
| ATOM | 927 | CE2 | PHE | 96 | 42.538 | 22.368 | −8.332 | 1.00 | 48.63 |
| ATOM | 928 | CD2 | PHE | 96 | 42.551 | 23.522 | −7.529 | 1.00 | 46.24 |
| ATOM | 929 | C | PHE | 96 | 42.653 | 27.252 | −5.431 | 1.00 | 39.42 |
| ATOM | 930 | O | PHE | 96 | 43.469 | 28.115 | −5.117 | 1.00 | 38.89 |
| ATOM | 931 | N | HIS | 97 | 41.359 | 27.288 | −5.087 | 1.00 | 38.19 |
| ATOM | 932 | CA | HIS | 97 | 40.787 | 28.413 | −4.344 | 1.00 | 38.39 |
| ATOM | 933 | CB | HIS | 97 | 39.265 | 28.279 | −4.200 | 1.00 | 38.74 |
| ATOM | 934 | CG | HIS | 97 | 38.539 | 28.104 | −5.499 | 1.00 | 37.54 |
| ATOM | 935 | ND1 | HIS | 97 | 39.053 | 28.529 | −6.706 | 1.00 | 34.50 |
| ATOM | 936 | CE1 | HIS | 97 | 38.208 | 28.210 | −7.669 | 1.00 | 37.08 |
| ATOM | 937 | NE2 | HIS | 97 | 37.150 | 27.619 | −7.131 | 1.00 | 36.65 |
| ATOM | 938 | CD2 | HIS | 97 | 37.327 | 27.554 | −5.772 | 1.00 | 38.23 |
| ATOM | 939 | C | HIS | 97 | 41.434 | 28.549 | −2.966 | 1.00 | 38.73 |
| ATOM | 940 | O | HIS | 97 | 41.872 | 29.634 | −2.576 | 1.00 | 39.39 |
| ATOM | 941 | N | GLU | 98 | 41.567 | 27.433 | −2.261 | 1.00 | 38.84 |
| ATOM | 942 | CA | GLU | 98 | 42.179 | 27.405 | −0.914 | 1.00 | 39.63 |
| ATOM | 943 | CB | GLU | 98 | 42.217 | 25.978 | −0.374 | 1.00 | 38.95 |
| ATOM | 944 | CG | GLU | 98 | 40.884 | 25.273 | −0.442 | 1.00 | 38.77 |
| ATOM | 945 | CD | GLU | 98 | 40.647 | 24.477 | −1.726 | 1.00 | 41.29 |
| ATOM | 946 | OE1 | GLU | 98 | 41.030 | 24.942 | −2.838 | 1.00 | 39.69 |
| ATOM | 947 | OE2 | GLU | 98 | 40.033 | 23.375 | −1.619 | 1.00 | 40.24 |
| ATOM | 948 | C | GLU | 98 | 43.582 | 27.983 | −0.952 | 1.00 | 39.61 |
| ATOM | 949 | O | GLU | 98 | 43.972 | 28.784 | −0.108 | 1.00 | 40.07 |
| ATOM | 950 | N | ASP | 99 | 44.292 | 27.602 | −2.000 | 1.00 | 40.45 |
| ATOM | 951 | CA | ASP | 99 | 45.714 | 27.878 | −2.223 | 1.00 | 40.16 |
| ATOM | 952 | CB | ASP | 99 | 46.017 | 27.164 | −3.520 | 1.00 | 41.18 |
| ATOM | 953 | CG | ASP | 99 | 47.461 | 26.816 | −3.700 | 1.00 | 46.42 |
| ATOM | 954 | OD1 | ASP | 99 | 48.355 | 27.676 | −3.445 | 1.00 | 49.29 |
| ATOM | 955 | OD2 | ASP | 99 | 47.683 | 25.661 | −4.162 | 1.00 | 51.24 |
| ATOM | 956 | C | ASP | 99 | 45.851 | 29.361 | −2.427 | 1.00 | 39.47 |
| ATOM | 957 | O | ASP | 99 | 46.644 | 30.071 | −1.792 | 1.00 | 39.36 |
| ATOM | 958 | N | CYS | 100 | 45.024 | 29.822 | −3.343 | 1.00 | 38.90 |
| ATOM | 959 | CA | CYS | 100 | 44.857 | 31.212 | −3.680 | 1.00 | 38.74 |
| ATOM | 960 | CB | CYS | 100 | 43.628 | 31.311 | −4.585 | 1.00 | 39.56 |
| ATOM | 961 | SG | CYS | 100 | 43.707 | 32.668 | −5.646 | 1.00 | 48.85 |
| ATOM | 962 | C | CYS | 100 | 44.687 | 32.157 | −2.510 | 1.00 | 36.34 |
| ATOM | 963 | O | CYS | 100 | 45.348 | 33.190 | −2.486 | 1.00 | 38.03 |
| ATOM | 964 | N | MET | 101 | 43.784 | 31.852 | −1.568 | 1.00 | 33.49 |
| ATOM | 965 | CA | MET | 101 | 43.554 | 32.756 | −0.424 | 1.00 | 31.88 |
| ATOM | 966 | CB | MET | 101 | 42.275 | 32.415 | 0.366 | 1.00 | 31.59 |
| ATOM | 967 | CG | MET | 101 | 40.980 | 32.159 | −0.447 | 1.00 | 32.03 |
| ATOM | 968 | SD | MET | 101 | 40.572 | 33.525 | −1.537 | 1.00 | 36.28 |
| ATOM | 969 | CE | MET | 101 | 39.970 | 34.696 | −0.423 | 1.00 | 41.17 |
| ATOM | 970 | C | MET | 101 | 44.749 | 32.825 | 0.539 | 1.00 | 31.54 |
| ATOM | 971 | O | MET | 101 | 45.049 | 33.884 | 1.106 | 1.00 | 29.90 |
| ATOM | 972 | N | ASN | 102 | 45.417 | 31.689 | 0.716 | 1.00 | 31.49 |
| ATOM | 973 | CA | ASN | 102 | 46.666 | 31.638 | 1.461 | 1.00 | 32.81 |
| ATOM | 974 | CB | ASN | 102 | 47.048 | 30.193 | 1.678 | 1.00 | 32.88 |
| ATOM | 975 | CG | ASN | 102 | 46.275 | 29.576 | 2.840 | 1.00 | 32.88 |
| ATOM | 976 | OD1 | ASN | 102 | 46.439 | 30.008 | 3.985 | 1.00 | 33.79 |
| ATOM | 977 | ND2 | ASN | 102 | 45.428 | 28.582 | 2.554 | 1.00 | 30.76 |
| ATOM | 978 | C | ASN | 102 | 47.767 | 32.410 | 0.802 | 1.00 | 33.74 |
| ATOM | 979 | O | ASN | 102 | 48.495 | 33.164 | 1.471 | 1.00 | 35.24 |
| ATOM | 980 | N | ILE | 103 | 47.861 | 32.300 | −0.526 | 1.00 | 34.62 |
| ATOM | 981 | CA | ILE | 103 | 48.856 | 33.083 | −1.284 | 1.00 | 34.52 |
| ATOM | 982 | CB | ILE | 103 | 48.860 | 32.717 | −2.810 | 1.00 | 35.11 |
| ATOM | 983 | CG1 | ILE | 103 | 49.252 | 31.254 | −3.015 | 1.00 | 37.81 |
| ATOM | 984 | CD1 | ILE | 103 | 48.975 | 30.794 | −4.484 | 1.00 | 36.59 |
| ATOM | 985 | CG2 | ILE | 103 | 49.831 | 33.544 | −3.568 | 1.00 | 35.19 |
| ATOM | 986 | C | ILE | 103 | 48.622 | 34.557 | −1.089 | 1.00 | 32.34 |
| ATOM | 987 | O | ILE | 103 | 49.537 | 35.296 | −0.811 | 1.00 | 33.70 |
| ATOM | 988 | N | ILE | 104 | 47.386 | 35.005 | −1.203 | 1.00 | 31.68 |
| ATOM | 989 | CA | ILE | 104 | 47.087 | 36.444 | −1.032 | 1.00 | 30.78 |
| ATOM | 990 | CB | ILE | 104 | 45.562 | 36.725 | −1.347 | 1.00 | 31.36 |
| ATOM | 991 | CG1 | ILE | 104 | 45.289 | 36.459 | −2.851 | 1.00 | 30.04 |
| ATOM | 992 | CD1 | ILE | 104 | 43.800 | 36.432 | −3.259 | 1.00 | 30.68 |
| ATOM | 993 | CG2 | ILE | 104 | 45.085 | 38.140 | −0.830 | 1.00 | 29.89 |
| ATOM | 994 | C | ILE | 104 | 47.435 | 36.954 | 0.362 | 1.00 | 31.29 |
| ATOM | 995 | O | ILE | 104 | 47.875 | 38.121 | 0.569 | 1.00 | 30.30 |
| ATOM | 996 | N | MET | 105 | 47.110 | 36.109 | 1.339 | 1.00 | 32.11 |
| ATOM | 997 | CA | MET | 105 | 47.387 | 36.420 | 2.719 | 1.00 | 32.26 |
| ATOM | 998 | CB | MET | 105 | 46.688 | 35.423 | 3.689 | 1.00 | 31.48 |
| ATOM | 999 | CG | MET | 105 | 46.678 | 36.042 | 5.099 | 1.00 | 30.44 |
| ATOM | 1000 | SD | MET | 105 | 46.162 | 35.031 | 6.449 | 1.00 | 31.39 |
| ATOM | 1001 | CE | MET | 105 | 47.128 | 33.576 | 6.242 | 1.00 | 22.59 |
| ATOM | 1002 | C | MET | 105 | 48.895 | 36.459 | 2.942 | 1.00 | 32.40 |

TABLE 3-continued

| | | | | | | | | | |
|---|---|---|---|---|---|---|---|---|---|
| ATOM | 1003 | O | MET | 105 | 49.410 | 37.356 | 3.608 | 1.00 | 31.86 |
| ATOM | 1004 | N | ASN | 106 | 49.607 | 35.497 | 2.364 | 1.00 | 33.34 |
| ATOM | 1005 | CA | ASN | 106 | 51.060 | 35.505 | 2.509 | 1.00 | 34.87 |
| ATOM | 1006 | CB | ASN | 106 | 51.685 | 34.198 | 2.046 | 1.00 | 34.97 |
| ATOM | 1007 | CG | ASN | 106 | 51.274 | 33.053 | 2.937 | 1.00 | 36.61 |
| ATOM | 1008 | OD1 | ASN | 106 | 50.688 | 33.278 | 4.005 | 1.00 | 38.19 |
| ATOM | 1009 | ND2 | ASN | 106 | 51.499 | 31.831 | 2.495 | 1.00 | 38.28 |
| ATOM | 1010 | C | ASN | 106 | 51.721 | 36.717 | 1.919 | 1.00 | 35.70 |
| ATOM | 1011 | O | ASN | 106 | 52.550 | 37.358 | 2.573 | 1.00 | 35.96 |
| ATOM | 1012 | N | ASP | 107 | 51.306 | 37.116 | 0.728 | 1.00 | 35.91 |
| ATOM | 1013 | CA | ASP | 107 | 51.974 | 38.269 | 0.143 | 1.00 | 36.06 |
| ATOM | 1014 | CB | ASP | 107 | 51.603 | 38.415 | −1.333 | 1.00 | 37.13 |
| ATOM | 1015 | CG | ASP | 107 | 52.043 | 37.218 | −2.140 | 1.00 | 38.89 |
| ATOM | 1016 | OD1 | ASP | 107 | 53.021 | 36.546 | −1.703 | 1.00 | 42.31 |
| ATOM | 1017 | OD2 | ASP | 107 | 51.415 | 36.932 | −3.182 | 1.00 | 40.30 |
| ATOM | 1018 | C | ASP | 107 | 51.654 | 39.506 | 0.873 | 1.00 | 35.28 |
| ATOM | 1019 | O | ASP | 107 | 52.451 | 40.461 | 0.902 | 1.00 | 35.58 |
| ATOM | 1020 | N | LEU | 108 | 50.472 | 39.528 | 1.463 | 1.00 | 34.93 |
| ATOM | 1021 | CA | LEU | 108 | 50.060 | 40.734 | 2.234 | 1.00 | 34.30 |
| ATOM | 1022 | CB | LEU | 108 | 48.530 | 40.809 | 2.375 | 1.00 | 33.47 |
| ATOM | 1023 | CG | LEU | 108 | 47.672 | 41.268 | 1.174 | 1.00 | 34.12 |
| ATOM | 1024 | CD1 | LEU | 108 | 46.136 | 41.133 | 1.450 | 1.00 | 25.18 |
| ATOM | 1025 | CD2 | LEU | 108 | 47.995 | 42.692 | 0.679 | 1.00 | 30.20 |
| ATOM | 1026 | C | LEU | 108 | 50.741 | 40.803 | 3.612 | 1.00 | 34.33 |
| ATOM | 1027 | O | LEU | 108 | 51.045 | 41.908 | 4.108 | 1.00 | 32.72 |
| ATOM | 1028 | N | ILE | 109 | 50.945 | 39.639 | 4.235 | 1.00 | 35.34 |
| ATOM | 1029 | CA | ILE | 109 | 51.756 | 39.567 | 5.500 | 1.00 | 37.09 |
| ATOM | 1030 | CB | ILE | 109 | 51.735 | 38.148 | 6.106 | 1.00 | 35.97 |
| ATOM | 1031 | CG1 | ILE | 109 | 50.394 | 37.867 | 6.817 | 1.00 | 34.82 |
| ATOM | 1032 | CD1 | ILE | 109 | 50.162 | 36.292 | 6.920 | 1.00 | 31.58 |
| ATOM | 1033 | CG2 | ILE | 109 | 52.950 | 37.903 | 7.009 | 1.00 | 35.95 |
| ATOM | 1034 | C | ILE | 109 | 53.214 | 40.039 | 5.254 | 1.00 | 38.91 |
| ATOM | 1035 | O | ILE | 109 | 53.747 | 40.906 | 5.967 | 1.00 | 38.99 |
| ATOM | 1036 | N | GLU | 110 | 53.816 | 39.473 | 4.213 | 1.00 | 41.14 |
| ATOM | 1037 | CA | GLU | 110 | 55.142 | 39.837 | 3.739 | 1.00 | 44.63 |
| ATOM | 1038 | CB | GLU | 110 | 55.510 | 38.922 | 2.568 | 1.00 | 44.16 |
| ATOM | 1039 | CG | GLU | 110 | 56.876 | 39.075 | 1.955 | 1.00 | 48.43 |
| ATOM | 1040 | CD | GLU | 110 | 57.085 | 38.151 | 0.695 | 1.00 | 50.78 |
| ATOM | 1041 | OE1 | GLU | 110 | 56.130 | 37.977 | −0.148 | 1.00 | 58.62 |
| ATOM | 1042 | OE2 | GLU | 110 | 58.219 | 37.600 | 0.538 | 1.00 | 58.76 |
| ATOM | 1043 | C | GLU | 110 | 55.186 | 41.318 | 3.374 | 1.00 | 43.73 |
| ATOM | 1044 | O | GLU | 110 | 56.158 | 42.010 | 3.698 | 1.00 | 43.40 |
| ATOM | 1045 | N | ARG | 115 | 49.317 | 43.355 | 12.391 | 1.00 | 30.43 |
| ATOM | 1046 | CA | ARG | 115 | 49.122 | 42.666 | 13.688 | 1.00 | 28.80 |
| ATOM | 1047 | CB | ARG | 115 | 48.524 | 43.607 | 14.696 | 1.00 | 27.24 |
| ATOM | 1048 | CG | ARG | 115 | 49.480 | 44.797 | 14.854 | 1.00 | 28.13 |
| ATOM | 1049 | CD | ARG | 115 | 49.021 | 45.829 | 15.821 | 1.00 | 30.24 |
| ATOM | 1050 | NE | ARG | 115 | 49.994 | 46.913 | 15.837 | 1.00 | 31.62 |
| ATOM | 1051 | CZ | ARG | 115 | 49.711 | 48.175 | 16.086 | 1.00 | 33.29 |
| ATOM | 1052 | NH1 | ARG | 115 | 48.461 | 48.531 | 16.364 | 1.00 | 33.08 |
| ATOM | 1053 | NH2 | ARG | 115 | 50.682 | 49.072 | 16.033 | 1.00 | 32.97 |
| ATOM | 1054 | C | ARG | 115 | 48.286 | 41.422 | 13.479 | 1.00 | 29.25 |
| ATOM | 1055 | O | ARG | 115 | 48.535 | 40.356 | 14.063 | 1.00 | 28.81 |
| ATOM | 1056 | N | TYR | 116 | 47.261 | 41.579 | 12.632 | 1.00 | 28.80 |
| ATOM | 1057 | CA | TYR | 116 | 46.279 | 40.564 | 12.365 | 1.00 | 27.69 |
| ATOM | 1058 | CB | TYR | 116 | 45.077 | 40.781 | 13.272 | 1.00 | 27.92 |
| ATOM | 1059 | CG | TYR | 116 | 43.940 | 39.808 | 12.956 | 1.00 | 26.63 |
| ATOM | 1060 | CD1 | TYR | 116 | 44.018 | 38.483 | 13.349 | 1.00 | 26.72 |
| ATOM | 1061 | CE1 | TYR | 116 | 43.057 | 37.585 | 13.021 | 1.00 | 25.07 |
| ATOM | 1062 | CZ | TYR | 116 | 41.991 | 38.002 | 12.258 | 1.00 | 27.65 |
| ATOM | 1063 | OH | TYR | 116 | 41.005 | 37.103 | 11.955 | 1.00 | 30.89 |
| ATOM | 1064 | CE2 | TYR | 116 | 41.884 | 39.315 | 11.852 | 1.00 | 26.17 |
| ATOM | 1065 | CD2 | TYR | 116 | 42.860 | 40.195 | 12.171 | 1.00 | 26.32 |
| ATOM | 1066 | C | TYR | 116 | 45.836 | 40.759 | 10.910 | 1.00 | 28.81 |
| ATOM | 1067 | O | TYR | 116 | 45.688 | 41.914 | 10.448 | 1.00 | 28.65 |
| ATOM | 1068 | N | ILE | 117 | 45.556 | 39.657 | 10.218 | 1.00 | 28.31 |
| ATOM | 1069 | CA | ILE | 117 | 44.857 | 39.710 | 8.943 | 1.00 | 28.27 |
| ATOM | 1070 | CB | ILE | 117 | 45.844 | 40.005 | 7.796 | 1.00 | 29.22 |
| ATOM | 1071 | CG1 | ILE | 117 | 45.158 | 40.028 | 6.410 | 1.00 | 27.24 |
| ATOM | 1072 | CD1 | ILE | 117 | 46.196 | 40.353 | 5.327 | 1.00 | 27.68 |
| ATOM | 1073 | CG2 | ILE | 117 | 47.049 | 39.010 | 7.845 | 1.00 | 27.47 |
| ATOM | 1074 | C | ILE | 117 | 44.092 | 38.433 | 8.690 | 1.00 | 28.02 |
| ATOM | 1075 | O | ILE | 117 | 44.490 | 37.377 | 9.151 | 1.00 | 27.51 |
| ATOM | 1076 | N | GLU | 118 | 42.965 | 38.543 | 7.989 | 1.00 | 27.06 |
| ATOM | 1077 | CA | GLU | 118 | 42.201 | 37.395 | 7.553 | 1.00 | 27.80 |
| ATOM | 1078 | CB | GLU | 118 | 40.984 | 37.159 | 8.436 | 1.00 | 27.26 |
| ATOM | 1079 | CG | GLU | 118 | 39.996 | 38.325 | 8.524 | 1.00 | 25.50 |
| ATOM | 1080 | CD | GLU | 118 | 38.796 | 38.015 | 9.431 | 1.00 | 30.75 |
| ATOM | 1081 | OE1 | GLU | 118 | 38.938 | 37.361 | 10.503 | 1.00 | 35.47 |
| ATOM | 1082 | OE2 | GLU | 118 | 37.676 | 38.411 | 9.076 | 1.00 | 34.71 |

TABLE 3-continued

| | | | | | | | | | |
|---|---|---|---|---|---|---|---|---|---|
| ATOM | 1083 | C | GLU | 118 | 41.752 | 37.632 | 6.100 | 1.00 | 28.42 |
| ATOM | 1084 | O | GLU | 118 | 41.593 | 38.755 | 5.666 | 1.00 | 28.14 |
| ATOM | 1085 | N | VAL | 119 | 41.540 | 36.550 | 5.373 | 1.00 | 28.92 |
| ATOM | 1086 | CA | VAL | 119 | 41.110 | 36.581 | 3.987 | 1.00 | 28.21 |
| ATOM | 1087 | CB | VAL | 119 | 42.310 | 36.233 | 3.005 | 1.00 | 29.07 |
| ATOM | 1088 | CG1 | VAL | 119 | 41.841 | 36.310 | 1.510 | 1.00 | 28.56 |
| ATOM | 1089 | CG2 | VAL | 119 | 43.463 | 37.228 | 3.208 | 1.00 | 27.52 |
| ATOM | 1090 | C | VAL | 119 | 40.054 | 35.513 | 3.894 | 1.00 | 27.80 |
| ATOM | 1091 | O | VAL | 119 | 40.354 | 34.336 | 4.158 | 1.00 | 27.72 |
| ATOM | 1092 | N | TRP | 120 | 38.815 | 35.929 | 3.562 | 1.00 | 27.25 |
| ATOM | 1093 | CA | TRP | 120 | 37.676 | 35.000 | 3.333 | 1.00 | 27.20 |
| ATOM | 1094 | CB | TRP | 120 | 36.515 | 35.407 | 4.278 | 1.00 | 26.60 |
| ATOM | 1095 | CG | TRP | 120 | 35.491 | 34.402 | 4.514 | 1.00 | 26.10 |
| ATOM | 1096 | CD1 | TRP | 120 | 35.296 | 33.230 | 3.804 | 1.00 | 26.37 |
| ATOM | 1097 | NE1 | TRP | 120 | 34.229 | 32.552 | 4.313 | 1.00 | 27.03 |
| ATOM | 1098 | CE2 | TRP | 120 | 33.703 | 33.255 | 5.381 | 1.00 | 25.05 |
| ATOM | 1099 | CD2 | TRP | 120 | 34.492 | 34.421 | 5.550 | 1.00 | 22.86 |
| ATOM | 1100 | CE3 | TRP | 120 | 34.150 | 35.346 | 6.568 | 1.00 | 23.61 |
| ATOM | 1101 | CZ3 | TRP | 120 | 33.060 | 35.074 | 7.374 | 1.00 | 25.97 |
| ATOM | 1102 | CH2 | TRP | 120 | 32.275 | 33.873 | 7.175 | 1.00 | 27.78 |
| ATOM | 1103 | CZ2 | TRP | 120 | 32.599 | 32.958 | 6.201 | 1.00 | 21.16 |
| ATOM | 1104 | C | TRP | 120 | 37.245 | 35.090 | 1.814 | 1.00 | 27.84 |
| ATOM | 1105 | O | TRP | 120 | 36.764 | 36.130 | 1.369 | 1.00 | 27.40 |
| ATOM | 1106 | N | GLY | 121 | 37.442 | 34.030 | 1.032 | 1.00 | 27.57 |
| ATOM | 1107 | CA | GLY | 121 | 37.014 | 34.031 | −0.372 | 1.00 | 27.83 |
| ATOM | 1108 | C | GLY | 121 | 35.713 | 33.281 | −0.479 | 1.00 | 28.51 |
| ATOM | 1109 | O | GLY | 121 | 35.513 | 32.340 | 0.248 | 1.00 | 27.13 |
| ATOM | 1110 | N | LYS | 122 | 34.789 | 33.745 | −1.327 | 1.00 | 29.24 |
| ATOM | 1111 | CA | LYS | 122 | 33.531 | 33.060 | −1.498 | 1.00 | 28.64 |
| ATOM | 1112 | CB | LYS | 122 | 32.421 | 33.901 | −0.890 | 1.00 | 29.09 |
| ATOM | 1113 | CG | LYS | 122 | 32.548 | 33.989 | 0.667 | 1.00 | 29.14 |
| ATOM | 1114 | CD | LYS | 122 | 31.580 | 34.915 | 1.271 | 1.00 | 25.90 |
| ATOM | 1115 | CE | LYS | 122 | 31.743 | 34.916 | 2.771 | 1.00 | 30.47 |
| ATOM | 1116 | NZ | LYS | 122 | 30.588 | 35.634 | 3.387 | 1.00 | 33.80 |
| ATOM | 1117 | C | LYS | 122 | 33.356 | 32.839 | −3.012 | 1.00 | 29.89 |
| ATOM | 1118 | O | LYS | 122 | 33.009 | 33.767 | −3.738 | 1.00 | 29.56 |
| ATOM | 1119 | N | PHE | 123 | 33.638 | 31.608 | −3.468 | 1.00 | 29.77 |
| ATOM | 1120 | CA | PHE | 123 | 33.659 | 31.307 | −4.875 | 1.00 | 28.78 |
| ATOM | 1121 | CB | PHE | 123 | 34.710 | 30.257 | −5.217 | 1.00 | 27.79 |
| ATOM | 1122 | CG | PHE | 123 | 36.100 | 30.803 | −5.193 | 1.00 | 29.54 |
| ATOM | 1123 | CD1 | PHE | 123 | 36.777 | 30.991 | −3.970 | 1.00 | 26.50 |
| ATOM | 1124 | CE1 | PHE | 123 | 38.046 | 31.531 | −3.916 | 1.00 | 24.89 |
| ATOM | 1125 | CZ | PHE | 123 | 38.711 | 31.868 | −5.096 | 1.00 | 30.34 |
| ATOM | 1126 | CE2 | PHE | 123 | 38.062 | 31.658 | −6.358 | 1.00 | 31.05 |
| ATOM | 1127 | CD2 | PHE | 123 | 36.753 | 31.137 | −6.384 | 1.00 | 30.05 |
| ATOM | 1128 | C | PHE | 123 | 32.305 | 30.910 | −5.348 | 1.00 | 29.23 |
| ATOM | 1129 | O | PHE | 123 | 31.490 | 30.395 | −4.554 | 1.00 | 27.66 |
| ATOM | 1130 | N | THR | 124 | 32.049 | 31.188 | −6.648 | 1.00 | 28.92 |
| ATOM | 1131 | CA | THR | 124 | 30.783 | 30.757 | −7.277 | 1.00 | 28.20 |
| ATOM | 1132 | CB | THR | 124 | 30.450 | 31.598 | −8.576 | 1.00 | 29.27 |
| ATOM | 1133 | OG1 | THR | 124 | 31.467 | 31.352 | −9.534 | 1.00 | 27.12 |
| ATOM | 1134 | CG2 | THR | 124 | 30.392 | 33.125 | −8.296 | 1.00 | 23.99 |
| ATOM | 1135 | C | THR | 124 | 30.834 | 29.237 | −7.507 | 1.00 | 27.97 |
| ATOM | 1136 | O | THR | 124 | 31.904 | 28.662 | −7.567 | 1.00 | 28.78 |
| ATOM | 1137 | N | PRO | 125 | 29.673 | 28.570 | −7.534 | 1.00 | 28.21 |
| ATOM | 1138 | CA | PRO | 125 | 29.598 | 27.112 | −7.614 | 1.00 | 29.53 |
| ATOM | 1139 | CB | PRO | 125 | 28.123 | 26.823 | −7.416 | 1.00 | 28.34 |
| ATOM | 1140 | CG | PRO | 125 | 27.414 | 28.147 | −7.743 | 1.00 | 26.96 |
| ATOM | 1141 | CD | PRO | 125 | 28.345 | 29.195 | −7.362 | 1.00 | 27.65 |
| ATOM | 1142 | C | PRO | 125 | 30.134 | 26.505 | −8.911 | 1.00 | 32.62 |
| ATOM | 1143 | O | PRO | 125 | 30.247 | 27.205 | −9.893 | 1.00 | 34.11 |
| ATOM | 1144 | N | ARG | 126 | 30.546 | 25.236 | −8.878 | 1.00 | 33.81 |
| ATOM | 1145 | CA | ARG | 126 | 30.975 | 24.493 | −10.052 | 1.00 | 35.48 |
| ATOM | 1146 | CB | ARG | 126 | 32.490 | 24.472 | −10.203 | 1.00 | 35.66 |
| ATOM | 1147 | CG | ARG | 126 | 33.118 | 25.809 | −10.572 | 1.00 | 40.74 |
| ATOM | 1148 | CD | ARG | 126 | 32.817 | 26.143 | −12.054 | 1.00 | 46.49 |
| ATOM | 1149 | NE | ARG | 126 | 33.147 | 27.523 | −12.410 | 1.00 | 49.71 |
| ATOM | 1150 | CZ | ARG | 126 | 32.238 | 28.394 | −12.839 | 1.00 | 50.00 |
| ATOM | 1151 | NH1 | ARG | 126 | 30.971 | 28.029 | −12.960 | 1.00 | 50.10 |
| ATOM | 1152 | NH2 | ARG | 126 | 32.595 | 29.619 | −13.142 | 1.00 | 52.24 |
| ATOM | 1153 | C | ARG | 126 | 30.529 | 23.113 | −9.696 | 1.00 | 35.74 |
| ATOM | 1154 | O | ARG | 126 | 30.854 | 22.620 | −8.606 | 1.00 | 35.29 |
| ATOM | 1155 | N | GLY | 127 | 29.742 | 22.499 | −10.562 | 1.00 | 35.60 |
| ATOM | 1156 | CA | GLY | 127 | 29.184 | 21.200 | −10.246 | 1.00 | 36.66 |
| ATOM | 1157 | C | GLY | 127 | 28.218 | 21.292 | −9.065 | 1.00 | 37.25 |
| ATOM | 1158 | O | GLY | 127 | 27.900 | 20.288 | −8.435 | 1.00 | 38.77 |
| ATOM | 1159 | N | GLY | 128 | 27.738 | 22.496 | −8.783 | 1.00 | 36.25 |
| ATOM | 1160 | CA | GLY | 128 | 26.713 | 22.701 | −7.766 | 1.00 | 35.01 |
| ATOM | 1161 | C | GLY | 128 | 27.235 | 22.934 | −6.344 | 1.00 | 33.50 |
| ATOM | 1162 | O | GLY | 128 | 26.438 | 23.003 | −5.424 | 1.00 | 35.01 |

TABLE 3-continued

| | | | | | | | | |
|---|---|---|---|---|---|---|---|---|
| ATOM | 1163 | N | ILE | 129 | 28.545 | 23.072 | −6.196 | 1.00 | 31.65 |
| ATOM | 1164 | CA | ILE | 129 | 29.234 | 23.267 | −4.944 | 1.00 | 30.62 |
| ATOM | 1165 | CB | ILE | 129 | 30.129 | 22.051 | −4.606 | 1.00 | 31.63 |
| ATOM | 1166 | CG1 | ILE | 129 | 29.252 | 20.820 | −4.408 | 1.00 | 31.67 |
| ATOM | 1167 | CD1 | ILE | 129 | 29.988 | 19.620 | −4.510 | 1.00 | 35.41 |
| ATOM | 1168 | CG2 | ILE | 129 | 30.922 | 22.309 | −3.282 | 1.00 | 30.84 |
| ATOM | 1169 | C | ILE | 129 | 30.131 | 24.456 | −5.011 | 1.00 | 29.88 |
| ATOM | 1170 | O | ILE | 129 | 30.871 | 24.598 | −5.966 | 1.00 | 29.04 |
| ATOM | 1171 | N | SER | 130 | 30.086 | 25.315 | −3.980 | 1.00 | 29.92 |
| ATOM | 1172 | CA | SER | 130 | 30.966 | 26.468 | −3.909 | 1.00 | 29.06 |
| ATOM | 1173 | CB | SER | 130 | 30.155 | 27.751 | −3.734 | 1.00 | 27.81 |
| ATOM | 1174 | OG | SER | 130 | 29.155 | 27.530 | −2.788 | 1.00 | 25.44 |
| ATOM | 1175 | C | SER | 130 | 31.922 | 26.229 | −2.755 | 1.00 | 29.57 |
| ATOM | 1176 | O | SER | 130 | 31.550 | 25.527 | −1.810 | 1.00 | 31.56 |
| ATOM | 1177 | N | ILE | 131 | 33.126 | 26.798 | −2.850 | 1.00 | 29.08 |
| ATOM | 1178 | CA | ILE | 131 | 34.232 | 26.632 | −1.908 | 1.00 | 28.86 |
| ATOM | 1179 | CB | ILE | 131 | 35.472 | 26.113 | −2.633 | 1.00 | 28.88 |
| ATOM | 1180 | CG1 | ILE | 131 | 35.137 | 24.728 | −3.222 | 1.00 | 30.52 |
| ATOM | 1181 | CD1 | ILE | 131 | 36.134 | 24.187 | −4.126 | 1.00 | 32.39 |
| ATOM | 1182 | CG2 | ILE | 131 | 36.690 | 25.964 | −1.707 | 1.00 | 25.09 |
| ATOM | 1183 | C | ILE | 131 | 34.470 | 28.015 | −1.326 | 1.00 | 29.72 |
| ATOM | 1184 | O | ILE | 131 | 34.582 | 28.973 | −2.091 | 1.00 | 30.15 |
| ATOM | 1185 | N | ASP | 132 | 34.475 | 28.139 | 0.011 | 1.00 | 29.62 |
| ATOM | 1186 | CA | ASP | 132 | 34.743 | 29.415 | 0.681 | 1.00 | 29.94 |
| ATOM | 1187 | CB | ASP | 132 | 33.487 | 29.971 | 1.422 | 1.00 | 30.39 |
| ATOM | 1188 | CG | ASP | 132 | 32.189 | 30.041 | 0.514 | 1.00 | 31.97 |
| ATOM | 1189 | OD1 | ASP | 132 | 32.296 | 29.952 | −0.726 | 1.00 | 33.78 |
| ATOM | 1190 | OD2 | ASP | 132 | 31.054 | 30.178 | 1.032 | 1.00 | 31.91 |
| ATOM | 1191 | C | ASP | 132 | 35.923 | 29.211 | 1.636 | 1.00 | 30.44 |
| ATOM | 1192 | O | ASP | 132 | 35.741 | 28.788 | 2.783 | 1.00 | 31.92 |
| ATOM | 1193 | N | PRO | 133 | 37.153 | 29.485 | 1.183 | 1.00 | 30.13 |
| ATOM | 1194 | CA | PRO | 133 | 38.239 | 29.243 | 2.145 | 1.00 | 29.71 |
| ATOM | 1195 | CB | PRO | 133 | 39.488 | 29.130 | 1.258 | 1.00 | 29.80 |
| ATOM | 1196 | CG | PRO | 133 | 38.938 | 29.107 | −0.247 | 1.00 | 27.63 |
| ATOM | 1197 | CD | PRO | 133 | 37.680 | 29.934 | −0.124 | 1.00 | 30.08 |
| ATOM | 1198 | C | PRO | 133 | 38.416 | 30.458 | 3.009 | 1.00 | 29.71 |
| ATOM | 1199 | O | PRO | 133 | 38.358 | 31.585 | 2.468 | 1.00 | 31.12 |
| ATOM | 1200 | N | TYR | 134 | 38.712 | 30.237 | 4.304 | 1.00 | 28.33 |
| ATOM | 1201 | CA | TYR | 134 | 38.946 | 31.331 | 5.265 | 1.00 | 27.96 |
| ATOM | 1202 | CB | TYR | 134 | 37.788 | 31.438 | 6.250 | 1.00 | 27.23 |
| ATOM | 1203 | CG | TYR | 134 | 38.095 | 32.272 | 7.441 | 1.00 | 28.31 |
| ATOM | 1204 | CD1 | TYR | 134 | 38.591 | 31.679 | 8.625 | 1.00 | 28.38 |
| ATOM | 1205 | CE1 | TYR | 134 | 38.937 | 32.486 | 9.731 | 1.00 | 28.02 |
| ATOM | 1206 | CZ | TYR | 134 | 38.730 | 33.856 | 9.659 | 1.00 | 28.03 |
| ATOM | 1207 | OH | TYR | 134 | 38.980 | 34.661 | 10.747 | 1.00 | 30.83 |
| ATOM | 1208 | CE2 | TYR | 134 | 38.227 | 34.464 | 8.483 | 1.00 | 28.31 |
| ATOM | 1209 | CD2 | TYR | 134 | 37.937 | 33.678 | 7.396 | 1.00 | 29.27 |
| ATOM | 1210 | C | TYR | 134 | 40.252 | 31.102 | 5.987 | 1.00 | 28.16 |
| ATOM | 1211 | O | TYR | 134 | 40.530 | 30.030 | 6.515 | 1.00 | 28.45 |
| ATOM | 1212 | N | THR | 135 | 41.094 | 32.097 | 5.941 | 1.00 | 27.81 |
| ATOM | 1213 | CA | THR | 135 | 42.428 | 31.899 | 6.426 | 1.00 | 27.88 |
| ATOM | 1214 | CB | THR | 135 | 43.437 | 31.628 | 5.219 | 1.00 | 28.73 |
| ATOM | 1215 | OG1 | THR | 135 | 44.671 | 31.038 | 5.696 | 1.00 | 31.06 |
| ATOM | 1216 | CG2 | THR | 135 | 43.747 | 32.900 | 4.368 | 1.00 | 27.19 |
| ATOM | 1217 | C | THR | 135 | 42.713 | 33.144 | 7.270 | 1.00 | 27.23 |
| ATOM | 1218 | O | THR | 135 | 42.158 | 34.234 | 6.996 | 1.00 | 23.53 |
| ATOM | 1219 | N | ASN | 136 | 43.475 | 32.976 | 8.348 | 1.00 | 27.08 |
| ATOM | 1220 | CA | ASN | 136 | 43.851 | 34.163 | 9.167 | 1.00 | 29.24 |
| ATOM | 1221 | CB | ASN | 136 | 42.764 | 34.542 | 10.211 | 1.00 | 28.26 |
| ATOM | 1222 | CG | ASN | 136 | 42.710 | 33.564 | 11.377 | 1.00 | 30.88 |
| ATOM | 1223 | OD1 | ASN | 136 | 43.605 | 32.779 | 11.509 | 1.00 | 29.56 |
| ATOM | 1224 | ND2 | ASN | 136 | 41.632 | 33.580 | 12.182 | 1.00 | 25.17 |
| ATOM | 1225 | C | ASN | 136 | 45.285 | 34.078 | 9.761 | 1.00 | 30.07 |
| ATOM | 1226 | O | ASN | 136 | 45.968 | 33.088 | 9.549 | 1.00 | 30.23 |
| ATOM | 1227 | N | TYR | 137 | 45.740 | 35.121 | 10.455 | 1.00 | 30.31 |
| ATOM | 1228 | CA | TYR | 137 | 47.085 | 35.157 | 11.006 | 1.00 | 31.36 |
| ATOM | 1229 | CB | TYR | 137 | 48.097 | 35.441 | 9.903 | 1.00 | 31.97 |
| ATOM | 1230 | CG | TYR | 137 | 49.433 | 36.028 | 10.364 | 1.00 | 33.54 |
| ATOM | 1231 | CD1 | TYR | 137 | 49.583 | 37.430 | 10.570 | 1.00 | 31.94 |
| ATOM | 1232 | CE1 | TYR | 137 | 50.790 | 37.969 | 10.986 | 1.00 | 31.39 |
| ATOM | 1233 | CZ | TYR | 137 | 51.863 | 37.105 | 11.187 | 1.00 | 30.94 |
| ATOM | 1234 | OH | TYR | 137 | 53.051 | 37.631 | 11.554 | 1.00 | 37.36 |
| ATOM | 1235 | CE2 | TYR | 137 | 51.762 | 35.737 | 10.976 | 1.00 | 32.11 |
| ATOM | 1236 | CD2 | TYR | 137 | 50.552 | 35.199 | 10.572 | 1.00 | 30.78 |
| ATOM | 1237 | C | TYR | 137 | 47.128 | 36.277 | 12.034 | 1.00 | 31.66 |
| ATOM | 1238 | O | TYR | 137 | 46.534 | 37.308 | 11.829 | 1.00 | 31.62 |
| ATOM | 1239 | N | GLY | 138 | 47.783 | 36.037 | 13.166 | 1.00 | 31.67 |
| ATOM | 1240 | CA | GLY | 138 | 48.116 | 37.081 | 14.124 | 1.00 | 30.88 |
| ATOM | 1241 | C | GLY | 138 | 49.626 | 37.022 | 14.391 | 1.00 | 30.93 |
| ATOM | 1242 | O | GLY | 138 | 50.207 | 35.962 | 14.307 | 1.00 | 31.01 |

TABLE 3-continued

| | | | | | | | | |
|---|---|---|---|---|---|---|---|---|
| ATOM | 1243 | N | MET | 147 | 43.798 | 36.192 | 19.149 | 1.00 | 32.75 |
| ATOM | 1244 | CA | MET | 147 | 42.702 | 36.672 | 18.316 | 1.00 | 30.67 |
| ATOM | 1245 | CB | MET | 147 | 42.994 | 38.084 | 17.840 | 1.00 | 31.80 |
| ATOM | 1246 | CG | MET | 147 | 41.875 | 38.652 | 16.930 | 1.00 | 30.09 |
| ATOM | 1247 | SD | MET | 147 | 42.305 | 40.358 | 16.648 | 1.00 | 30.02 |
| ATOM | 1248 | CE | MET | 147 | 41.099 | 40.698 | 15.321 | 1.00 | 30.61 |
| ATOM | 1249 | C | MET | 147 | 42.448 | 35.773 | 17.117 | 1.00 | 29.50 |
| ATOM | 1250 | O | MET | 147 | 41.366 | 35.385 | 16.916 | 1.00 | 30.49 |
| ATOM | 1251 | N | ALA | 148 | 43.463 | 35.412 | 16.368 | 1.00 | 29.89 |
| ATOM | 1252 | CA | ALA | 148 | 43.339 | 34.549 | 15.205 | 1.00 | 29.83 |
| ATOM | 1253 | CB | ALA | 148 | 44.717 | 34.332 | 14.533 | 1.00 | 29.82 |
| ATOM | 1254 | C | ALA | 148 | 42.758 | 33.228 | 15.539 | 1.00 | 31.08 |
| ATOM | 1255 | O | ALA | 148 | 41.844 | 32.757 | 14.817 | 1.00 | 30.18 |
| ATOM | 1256 | N | GLU | 149 | 43.297 | 32.604 | 16.602 | 1.00 | 31.71 |
| ATOM | 1257 | CA | GLU | 149 | 42.851 | 31.281 | 17.096 | 1.00 | 33.63 |
| ATOM | 1258 | CB | GLU | 149 | 43.717 | 30.808 | 18.311 | 1.00 | 33.63 |
| ATOM | 1259 | CG | GLU | 149 | 45.126 | 30.241 | 17.911 | 1.00 | 38.61 |
| ATOM | 1260 | CD | GLU | 149 | 46.205 | 30.176 | 19.069 | 1.00 | 39.74 |
| ATOM | 1261 | OE1 | GLU | 149 | 45.849 | 30.330 | 20.282 | 1.00 | 43.99 |
| ATOM | 1262 | OE2 | GLU | 149 | 47.410 | 29.972 | 18.726 | 1.00 | 42.65 |
| ATOM | 1263 | C | GLU | 149 | 41.405 | 31.378 | 17.507 | 1.00 | 32.86 |
| ATOM | 1264 | O | GLU | 149 | 40.589 | 30.500 | 17.200 | 1.00 | 33.25 |
| ATOM | 1265 | N | TYR | 150 | 41.056 | 32.482 | 18.163 | 1.00 | 32.24 |
| ATOM | 1266 | CA | TYR | 150 | 39.649 | 32.716 | 18.553 | 1.00 | 31.77 |
| ATOM | 1267 | CB | TYR | 150 | 39.598 | 33.963 | 19.412 | 1.00 | 32.30 |
| ATOM | 1268 | CG | TYR | 150 | 38.236 | 34.486 | 19.680 | 1.00 | 32.47 |
| ATOM | 1269 | CD1 | TYR | 150 | 37.538 | 34.059 | 20.789 | 1.00 | 34.98 |
| ATOM | 1270 | CE1 | TYR | 150 | 36.301 | 34.506 | 21.067 | 1.00 | 34.89 |
| ATOM | 1271 | CZ | TYR | 150 | 35.719 | 35.413 | 20.217 | 1.00 | 36.73 |
| ATOM | 1272 | OH | TYR | 150 | 34.447 | 35.847 | 20.539 | 1.00 | 39.31 |
| ATOM | 1273 | CE2 | TYR | 150 | 36.379 | 35.863 | 19.086 | 1.00 | 33.73 |
| ATOM | 1274 | CD2 | TYR | 150 | 37.639 | 35.398 | 18.833 | 1.00 | 32.38 |
| ATOM | 1275 | C | TYR | 150 | 38.693 | 32.860 | 17.331 | 1.00 | 32.00 |
| ATOM | 1276 | O | TYR | 150 | 37.574 | 32.305 | 17.331 | 1.00 | 32.15 |
| ATOM | 1277 | N | ARG | 151 | 39.104 | 33.631 | 16.319 | 1.00 | 31.02 |
| ATOM | 1278 | CA | ARG | 151 | 38.239 | 33.874 | 15.138 | 1.00 | 30.65 |
| ATOM | 1279 | CB | ARG | 151 | 38.673 | 35.125 | 14.381 | 1.00 | 29.18 |
| ATOM | 1280 | CG | ARG | 151 | 38.528 | 36.349 | 15.209 | 1.00 | 28.55 |
| ATOM | 1281 | CD | ARG | 151 | 39.048 | 37.619 | 14.527 | 1.00 | 33.71 |
| ATOM | 1282 | NE | ARG | 151 | 38.349 | 37.985 | 13.283 | 1.00 | 30.74 |
| ATOM | 1283 | CZ | ARG | 151 | 37.469 | 38.984 | 13.166 | 1.00 | 31.02 |
| ATOM | 1284 | NH1 | ARG | 151 | 37.140 | 39.734 | 14.205 | 1.00 | 23.02 |
| ATOM | 1285 | NH2 | ARG | 151 | 36.916 | 39.242 | 11.984 | 1.00 | 30.86 |
| ATOM | 1286 | C | ARG | 151 | 38.191 | 32.628 | 14.228 | 1.00 | 31.10 |
| ATOM | 1287 | O | ARG | 151 | 37.192 | 32.394 | 13.489 | 1.00 | 31.98 |
| ATOM | 1288 | N | MET | 152 | 39.247 | 31.819 | 14.314 | 1.00 | 30.71 |
| ATOM | 1289 | CA | MET | 152 | 39.290 | 30.518 | 13.664 | 1.00 | 31.80 |
| ATOM | 1290 | CB | MET | 152 | 40.758 | 30.039 | 13.598 | 1.00 | 30.94 |
| ATOM | 1291 | CG | MET | 152 | 41.044 | 28.908 | 12.619 | 1.00 | 32.09 |
| ATOM | 1292 | SD | MET | 152 | 40.504 | 29.165 | 10.892 | 1.00 | 30.65 |
| ATOM | 1293 | CE | MET | 152 | 41.741 | 30.294 | 10.351 | 1.00 | 34.00 |
| ATOM | 1294 | C | MET | 152 | 38.336 | 29.540 | 14.383 | 1.00 | 32.90 |
| ATOM | 1295 | O | MET | 152 | 37.470 | 28.885 | 13.768 | 1.00 | 34.03 |
| ATOM | 1296 | N | MET | 153 | 38.446 | 29.481 | 15.705 | 1.00 | 34.78 |
| ATOM | 1297 | CA | MET | 153 | 37.679 | 28.520 | 16.514 | 1.00 | 36.74 |
| ATOM | 1298 | CB | MET | 153 | 38.173 | 28.550 | 17.984 | 1.00 | 35.77 |
| ATOM | 1299 | CG | MET | 153 | 37.296 | 27.780 | 18.995 | 1.00 | 40.50 |
| ATOM | 1300 | SD | MET | 153 | 38.145 | 27.270 | 20.576 | 1.00 | 45.95 |
| ATOM | 1301 | CE | MET | 153 | 39.344 | 26.101 | 19.938 | 1.00 | 42.27 |
| ATOM | 1302 | C | MET | 153 | 36.200 | 28.816 | 16.445 | 1.00 | 33.55 |
| ATOM | 1303 | O | MET | 153 | 35.352 | 27.903 | 16.495 | 1.00 | 34.35 |
| ATOM | 1304 | N | ASN | 154 | 35.888 | 30.104 | 16.376 | 1.00 | 31.98 |
| ATOM | 1305 | CA | ASN | 154 | 34.529 | 30.550 | 16.228 | 1.00 | 30.84 |
| ATOM | 1306 | CB | ASN | 154 | 34.303 | 31.793 | 17.078 | 1.00 | 31.28 |
| ATOM | 1307 | CG | ASN | 154 | 34.374 | 31.473 | 18.547 | 1.00 | 33.63 |
| ATOM | 1308 | OD1 | ASN | 154 | 33.378 | 31.052 | 19.153 | 1.00 | 32.40 |
| ATOM | 1309 | ND2 | ASN | 154 | 35.593 | 31.551 | 19.102 | 1.00 | 34.73 |
| ATOM | 1310 | C | ASN | 154 | 34.099 | 30.851 | 14.790 | 1.00 | 30.53 |
| ATOM | 1311 | O | ASN | 154 | 33.034 | 31.444 | 14.582 | 1.00 | 30.17 |
| ATOM | 1312 | N | HIS | 155 | 34.926 | 30.488 | 13.816 | 1.00 | 29.30 |
| ATOM | 1313 | CA | HIS | 155 | 34.622 | 30.807 | 12.411 | 1.00 | 29.01 |
| ATOM | 1314 | CB | HIS | 155 | 35.757 | 30.441 | 11.472 | 1.00 | 28.17 |
| ATOM | 1315 | CG | HIS | 155 | 35.449 | 30.740 | 10.038 | 1.00 | 30.06 |
| ATOM | 1316 | ND1 | HIS | 155 | 35.256 | 32.029 | 9.572 | 1.00 | 31.22 |
| ATOM | 1317 | CE1 | HIS | 155 | 34.997 | 31.982 | 8.276 | 1.00 | 29.19 |
| ATOM | 1318 | NE2 | HIS | 155 | 35.034 | 30.713 | 7.885 | 1.00 | 27.27 |
| ATOM | 1319 | CD2 | HIS | 155 | 35.292 | 29.916 | 8.969 | 1.00 | 25.44 |
| ATOM | 1320 | C | HIS | 155 | 33.392 | 30.102 | 11.974 | 1.00 | 27.94 |
| ATOM | 1321 | O | HIS | 155 | 33.296 | 28.873 | 12.032 | 1.00 | 28.54 |
| ATOM | 1322 | N | ASP | 156 | 32.412 | 30.886 | 11.585 | 1.00 | 28.59 |

TABLE 3-continued

| | | | | | | | | |
|---|---|---|---|---|---|---|---|---|
| ATOM | 1323 | CA | ASP | 156 | 31.303 | 30.386 | 10.803 | 1.00 | 30.00 |
| ATOM | 1324 | CB | ASP | 156 | 31.809 | 29.645 | 9.570 | 1.00 | 29.71 |
| ATOM | 1325 | CG | ASP | 156 | 30.947 | 29.879 | 8.329 | 1.00 | 31.63 |
| ATOM | 1326 | OD1 | ASP | 156 | 30.121 | 30.803 | 8.325 | 1.00 | 26.87 |
| ATOM | 1327 | OD2 | ASP | 156 | 31.134 | 29.109 | 7.336 | 1.00 | 32.52 |
| ATOM | 1328 | C | ASP | 156 | 30.467 | 29.456 | 11.603 | 1.00 | 31.07 |
| ATOM | 1329 | O | ASP | 156 | 30.092 | 28.419 | 11.093 | 1.00 | 30.99 |
| ATOM | 1330 | N | LEU | 157 | 30.158 | 29.811 | 12.847 | 1.00 | 31.23 |
| ATOM | 1331 | CA | LEU | 157 | 29.223 | 28.981 | 13.608 | 1.00 | 32.44 |
| ATOM | 1332 | CB | LEU | 157 | 29.208 | 29.367 | 15.101 | 1.00 | 32.22 |
| ATOM | 1333 | CG | LEU | 157 | 30.542 | 29.260 | 15.869 | 1.00 | 30.97 |
| ATOM | 1334 | CD1 | LEU | 157 | 30.911 | 27.809 | 16.005 | 1.00 | 31.32 |
| ATOM | 1335 | CD2 | LEU | 157 | 30.415 | 29.885 | 17.246 | 1.00 | 32.91 |
| ATOM | 1336 | C | LEU | 157 | 27.824 | 29.055 | 13.023 | 1.00 | 33.72 |
| ATOM | 1337 | O | LEU | 157 | 26.931 | 28.288 | 13.398 | 1.00 | 34.82 |
| ATOM | 1338 | N | TYR | 158 | 27.590 | 29.993 | 12.127 | 1.00 | 34.25 |
| ATOM | 1339 | CA | TYR | 158 | 26.289 | 30.038 | 11.494 | 1.00 | 35.32 |
| ATOM | 1340 | CB | TYR | 158 | 25.449 | 31.143 | 12.103 | 1.00 | 38.31 |
| ATOM | 1341 | CG | TYR | 158 | 25.008 | 30.850 | 13.523 | 1.00 | 40.98 |
| ATOM | 1342 | CD1 | TYR | 158 | 25.679 | 31.417 | 14.634 | 1.00 | 41.83 |
| ATOM | 1343 | CE1 | TYR | 158 | 25.259 | 31.146 | 15.946 | 1.00 | 42.46 |
| ATOM | 1344 | CZ | TYR | 158 | 24.155 | 30.300 | 16.131 | 1.00 | 44.17 |
| ATOM | 1345 | OH | TYR | 158 | 23.669 | 29.977 | 17.392 | 1.00 | 45.50 |
| ATOM | 1346 | CE2 | TYR | 158 | 23.496 | 29.724 | 15.039 | 1.00 | 45.65 |
| ATOM | 1347 | CD2 | TYR | 158 | 23.932 | 29.999 | 13.751 | 1.00 | 43.05 |
| ATOM | 1348 | C | TYR | 158 | 26.475 | 30.269 | 10.027 | 1.00 | 34.73 |
| ATOM | 1349 | O | TYR | 158 | 26.436 | 31.395 | 9.575 | 1.00 | 33.68 |
| ATOM | 1350 | N | PRO | 159 | 26.667 | 29.200 | 9.266 | 1.00 | 33.61 |
| ATOM | 1351 | CA | PRO | 159 | 26.979 | 29.445 | 7.861 | 1.00 | 33.70 |
| ATOM | 1352 | CB | PRO | 159 | 27.190 | 28.029 | 7.274 | 1.00 | 33.63 |
| ATOM | 1353 | CG | PRO | 159 | 27.209 | 27.046 | 8.425 | 1.00 | 33.25 |
| ATOM | 1354 | CD | PRO | 159 | 26.455 | 27.780 | 9.563 | 1.00 | 35.00 |
| ATOM | 1355 | C | PRO | 159 | 25.762 | 30.067 | 7.145 | 1.00 | 33.49 |
| ATOM | 1356 | O | PRO | 159 | 24.628 | 29.547 | 7.270 | 1.00 | 32.86 |
| ATOM | 1357 | N | GLU | 160 | 25.999 | 31.122 | 6.365 | 1.00 | 32.56 |
| ATOM | 1358 | CA | GLU | 160 | 24.949 | 31.707 | 5.521 | 1.00 | 31.97 |
| ATOM | 1359 | CB | GLU | 160 | 25.545 | 32.837 | 4.689 | 1.00 | 32.57 |
| ATOM | 1360 | CG | GLU | 160 | 26.075 | 32.287 | 3.405 | 1.00 | 37.82 |
| ATOM | 1361 | CD | GLU | 160 | 27.293 | 33.033 | 2.868 | 1.00 | 43.23 |
| ATOM | 1362 | OE1 | GLU | 160 | 27.156 | 34.148 | 2.291 | 1.00 | 37.19 |
| ATOM | 1363 | OE2 | GLU | 160 | 28.378 | 32.440 | 3.020 | 1.00 | 47.52 |
| ATOM | 1364 | C | GLU | 160 | 24.272 | 30.659 | 4.600 | 1.00 | 30.03 |
| ATOM | 1365 | O | GLU | 160 | 24.863 | 29.646 | 4.221 | 1.00 | 27.68 |
| ATOM | 1366 | N | THR | 161 | 22.990 | 30.872 | 4.319 | 1.00 | 29.69 |
| ATOM | 1367 | CA | THR | 161 | 22.218 | 29.964 | 3.480 | 1.00 | 30.14 |
| ATOM | 1368 | CB | THR | 161 | 20.774 | 30.376 | 3.569 | 1.00 | 30.65 |
| ATOM | 1369 | OG1 | THR | 161 | 20.387 | 30.230 | 4.913 | 1.00 | 32.28 |
| ATOM | 1370 | CG2 | THR | 161 | 19.827 | 29.504 | 2.662 | 1.00 | 27.14 |
| ATOM | 1371 | C | THR | 161 | 22.659 | 30.178 | 2.027 | 1.00 | 30.38 |
| ATOM | 1372 | O | THR | 161 | 22.796 | 31.324 | 1.600 | 1.00 | 30.40 |
| ATOM | 1373 | N | ILE | 162 | 22.935 | 29.099 | 1.313 | 1.00 | 30.78 |
| ATOM | 1374 | CA | ILE | 162 | 23.431 | 29.167 | −0.056 | 1.00 | 30.99 |
| ATOM | 1375 | CB | ILE | 162 | 24.884 | 28.742 | −0.140 | 1.00 | 32.08 |
| ATOM | 1376 | CG1 | ILE | 162 | 25.777 | 29.785 | 0.567 | 1.00 | 31.38 |
| ATOM | 1377 | CD1 | ILE | 162 | 26.002 | 31.067 | −0.248 | 1.00 | 32.15 |
| ATOM | 1378 | CG2 | ILE | 162 | 25.318 | 28.547 | −1.622 | 1.00 | 30.31 |
| ATOM | 1379 | C | ILE | 162 | 22.526 | 28.265 | −0.884 | 1.00 | 31.78 |
| ATOM | 1380 | O | ILE | 162 | 22.293 | 27.156 | −0.495 | 1.00 | 30.57 |
| ATOM | 1381 | N | ASP | 163 | 21.900 | 28.794 | −1.940 | 1.00 | 33.05 |
| ATOM | 1382 | CA | ASP | 163 | 21.007 | 27.980 | −2.768 | 1.00 | 34.39 |
| ATOM | 1383 | CB | ASP | 163 | 19.574 | 28.461 | −2.647 | 1.00 | 34.34 |
| ATOM | 1384 | CG | ASP | 163 | 19.391 | 29.877 | −3.148 | 1.00 | 35.74 |
| ATOM | 1385 | OD1 | ASP | 163 | 18.238 | 30.306 | −3.205 | 1.00 | 36.46 |
| ATOM | 1386 | OD2 | ASP | 163 | 20.389 | 30.588 | −3.455 | 1.00 | 37.00 |
| ATOM | 1387 | C | ASP | 163 | 21.440 | 27.997 | −4.235 | 1.00 | 35.45 |
| ATOM | 1388 | O | ASP | 163 | 20.769 | 27.435 | −5.106 | 1.00 | 36.25 |
| ATOM | 1389 | N | ASN | 164 | 22.549 | 28.669 | −4.503 | 1.00 | 35.87 |
| ATOM | 1390 | CA | ASN | 164 | 23.118 | 28.694 | −5.850 | 1.00 | 37.23 |
| ATOM | 1391 | CB | ASN | 164 | 23.262 | 27.279 | −6.439 | 1.00 | 36.18 |
| ATOM | 1392 | CG | ASN | 164 | 24.431 | 26.534 | −5.820 | 1.00 | 38.54 |
| ATOM | 1393 | OD1 | ASN | 164 | 25.175 | 27.109 | −4.993 | 1.00 | 35.02 |
| ATOM | 1394 | ND2 | ASN | 164 | 24.601 | 25.253 | −6.191 | 1.00 | 36.60 |
| ATOM | 1395 | C | ASN | 164 | 22.419 | 29.671 | −6.794 | 1.00 | 37.19 |
| ATOM | 1396 | O | ASN | 164 | 22.632 | 29.654 | −7.995 | 1.00 | 37.79 |
| ATOM | 1397 | O6 | GDQ | 201 | 41.711 | 55.587 | 1.265 | 1.00 | 47.86 |
| ATOM | 1398 | C6 | GDQ | 201 | 42.655 | 54.798 | 0.686 | 1.00 | 49.13 |
| ATOM | 1399 | N1 | GDQ | 201 | 43.162 | 53.755 | 1.386 | 1.00 | 48.48 |
| ATOM | 1400 | C5 | GDQ | 201 | 43.114 | 55.030 | −0.629 | 1.00 | 50.29 |
| ATOM | 1401 | C7 | GDQ | 201 | 42.895 | 55.934 | −1.676 | 1.00 | 49.19 |
| ATOM | 1402 | C77 | GDQ | 201 | 42.018 | 56.941 | −1.586 | 1.00 | 49.79 |

TABLE 3-continued

| | | | | | | | | |
|---|---|---|---|---|---|---|---|---|
| ATOM | 1403 | N77 | GDQ | 201 | 41.272 | 57.892 | −1.409 | 1.00 | 52.99 |
| ATOM | 1404 | C8 | GDQ | 201 | 43.665 | 55.676 | −2.796 | 1.00 | 48.54 |
| ATOM | 1405 | N9 | GDQ | 201 | 44.390 | 54.565 | −2.444 | 1.00 | 49.38 |
| ATOM | 1406 | C4 | GDQ | 201 | 44.083 | 54.188 | −1.156 | 1.00 | 49.87 |
| ATOM | 1407 | N3 | GDQ | 201 | 44.571 | 53.140 | −0.425 | 1.00 | 49.70 |
| ATOM | 1408 | C2 | GDQ | 201 | 44.090 | 52.944 | 0.845 | 1.00 | 48.62 |
| ATOM | 1409 | N2 | GDQ | 201 | 44.543 | 51.925 | 1.604 | 1.00 | 49.10 |
| ATOM | 1410 | O | HOH | 2 | 31.164 | 31.668 | 3.435 | 1.00 | 42.48 |
| ATOM | 1411 | O | HOH | 5 | 28.577 | 32.011 | 6.254 | 1.00 | 28.13 |
| ATOM | 1412 | O | HOH | 11 | 27.237 | 28.759 | 3.717 | 1.00 | 29.18 |
| ATOM | 1413 | O | HOH | 14 | 35.602 | 34.179 | 11.624 | 1.00 | 40.75 |
| ATOM | 1414 | O | HOH | 21 | 34.776 | 29.404 | 5.329 | 1.00 | 36.58 |
| ATOM | 1415 | O | HOH | 28 | 37.213 | 43.349 | −6.645 | 1.00 | 32.19 |
| ATOM | 1416 | O | HOH | 29 | 25.550 | 20.494 | −3.901 | 1.00 | 31.47 |
| ATOM | 1417 | O | HOH | 38 | 46.493 | 24.006 | −0.542 | 1.00 | 64.45 |
| ATOM | 1418 | O | HOH | 39 | 43.905 | 16.792 | 5.832 | 1.00 | 31.88 |
| ATOM | 1419 | O | HOH | 55 | 28.165 | 24.628 | 15.612 | 1.00 | 39.26 |
| ATOM | 1420 | O | HOH | 62 | 32.642 | 34.012 | 11.443 | 1.00 | 33.39 |
| ATOM | 1421 | O | HOH | 81 | 41.467 | 38.575 | −11.129 | 1.00 | 28.53 |
| ATOM | 1422 | O | HOH | 85 | 33.858 | 30.129 | −9.676 | 1.00 | 40.55 |
| ATOM | 1423 | O | HOH | 91 | 40.438 | 40.261 | −13.243 | 1.00 | 37.54 |
| ATOM | 1424 | O | HOH | 95 | 39.343 | 20.922 | −0.293 | 1.00 | 39.15 |
| ATOM | 1425 | O | HOH | 97 | 46.821 | 13.555 | −1.585 | 1.00 | 53.00 |
| ATOM | 1426 | O | HOH | 101 | 53.169 | 24.607 | 4.499 | 1.00 | 75.13 |
| ATOM | 1427 | O | HOH | 107 | 35.749 | 36.538 | 10.189 | 1.00 | 34.93 |
| ATOM | 1428 | O | HOH | 111 | 54.507 | 23.595 | 8.391 | 1.00 | 58.79 |
| ATOM | 1429 | O | HOH | 121 | 33.848 | 37.905 | −9.462 | 1.00 | 33.91 |
| ATOM | 1430 | O | HOH | 139 | 33.658 | 27.104 | −6.034 | 1.00 | 28.22 |
| ATOM | 1431 | O | HOH | 150 | 18.754 | 25.713 | −4.850 | 1.00 | 44.55 |
| ATOM | 1432 | O | HOH | 161 | 46.240 | 14.862 | 6.404 | 1.00 | 49.17 |
| ATOM | 1433 | O | HOH | 173 | 50.984 | 17.080 | 9.784 | 1.00 | 40.94 |
| ATOM | 1434 | O | HOH | 177 | 26.885 | 16.404 | −5.565 | 1.00 | 41.52 |
| ATOM | 1435 | O | HOH | 179 | 39.434 | 31.902 | −9.906 | 1.00 | 53.82 |
| ATOM | 1436 | O | HOH | 183 | 33.535 | 24.085 | −6.521 | 1.00 | 36.87 |
| ATOM | 1437 | O | HOH | 185 | 30.791 | 32.824 | 14.407 | 1.00 | 39.43 |
| ATOM | 1438 | O | HOH | 201 | 32.800 | 16.631 | −15.414 | 1.00 | 65.86 |
| ATOM | 1439 | O | HOH | 208 | 41.964 | 29.696 | −9.354 | 1.00 | 48.14 |
| ATOM | 1440 | O | HOH | 212 | 20.741 | 26.123 | 4.224 | 1.00 | 49.25 |
| ATOM | 1441 | O | HOH | 215 | 27.135 | 24.604 | −10.591 | 1.00 | 33.08 |
| ATOM | 1442 | O | HOH | 224 | 54.306 | 36.012 | 4.638 | 1.00 | 52.97 |
| ATOM | 1443 | O | HOH | 229 | 33.011 | 27.227 | 7.207 | 1.00 | 48.87 |
| ATOM | 1444 | O | HOH | 233 | 39.469 | 41.771 | −11.073 | 1.00 | 44.46 |
| ATOM | 1445 | O | HOH | 243 | 38.885 | 44.939 | −8.276 | 1.00 | 32.22 |
| ATOM | 1446 | O | HOH | 244 | 51.965 | 20.570 | −4.539 | 1.00 | 51.66 |
| ATOM | 1447 | O | HOH | 247 | 40.925 | 43.860 | −8.562 | 1.00 | 38.90 |
| ATOM | 1448 | O | HOH | 255 | 45.134 | 33.203 | −19.047 | 1.00 | 54.17 |
| TER | | | | | | | | | |

TABLE 4

REMARK  Accelrys ViewerPro PDB file
REMARK  Created:   Tue Dec 14 10:17:46 Pacific Standard Time 2010

| | | | | | | | | |
|---|---|---|---|---|---|---|---|---|
| ATOM | 1 | N | VAL | 30 | 53.715 | 44.304 | −7.467 | 1.00 | 45.50 |
| ATOM | 2 | CA | VAL | 30 | 52.899 | 45.528 | −7.615 | 1.00 | 44.60 |
| ATOM | 3 | CB | VAL | 30 | 51.745 | 45.426 | −8.661 | 1.00 | 44.72 |
| ATOM | 4 | CG1 | VAL | 30 | 50.776 | 44.265 | −8.361 | 1.00 | 44.74 |
| ATOM | 5 | CG2 | VAL | 30 | 52.308 | 45.344 | −10.047 | 1.00 | 46.76 |
| ATOM | 6 | C | VAL | 30 | 52.352 | 46.105 | −6.291 | 1.00 | 43.05 |
| ATOM | 7 | O | VAL | 30 | 52.036 | 47.289 | −6.214 | 1.00 | 42.14 |
| ATOM | 8 | N | LEU | 31 | 52.268 | 45.259 | −5.274 | 1.00 | 42.07 |
| ATOM | 9 | CA | LEU | 31 | 51.779 | 45.640 | −3.958 | 1.00 | 41.72 |
| ATOM | 10 | CB | LEU | 31 | 51.796 | 44.412 | −3.040 | 1.00 | 40.32 |
| ATOM | 11 | CG | LEU | 31 | 50.650 | 43.413 | −3.223 | 1.00 | 38.67 |
| ATOM | 12 | CD1 | LEU | 31 | 50.827 | 42.143 | −2.358 | 1.00 | 36.74 |
| ATOM | 13 | CD2 | LEU | 31 | 49.287 | 44.090 | −2.955 | 1.00 | 34.32 |
| ATOM | 14 | C | LEU | 31 | 52.548 | 46.829 | −3.362 | 1.00 | 42.69 |
| ATOM | 15 | O | LEU | 31 | 53.750 | 46.952 | −3.556 | 1.00 | 42.85 |
| ATOM | 16 | N | GLU | 32 | 51.852 | 47.717 | −2.658 | 1.00 | 43.58 |
| ATOM | 17 | CA | GLU | 32 | 52.489 | 48.893 | −2.090 | 1.00 | 45.28 |
| ATOM | 18 | CB | GLU | 32 | 52.443 | 50.086 | −3.049 | 1.00 | 45.66 |
| ATOM | 19 | CG | GLU | 32 | 53.519 | 50.136 | −4.068 | 1.00 | 51.00 |
| ATOM | 20 | CD | GLU | 32 | 53.184 | 51.101 | −5.180 | 1.00 | 58.30 |
| ATOM | 21 | OE1 | GLU | 32 | 52.900 | 50.612 | −6.300 | 1.00 | 62.65 |
| ATOM | 22 | OE2 | GLU | 32 | 53.172 | 52.338 | −4.946 | 1.00 | 61.68 |
| ATOM | 23 | C | GLU | 32 | 51.774 | 49.325 | −0.826 | 1.00 | 45.57 |
| ATOM | 24 | O | GLU | 32 | 50.571 | 49.069 | −0.658 | 1.00 | 43.65 |
| ATOM | 25 | N | SER | 33 | 52.519 | 50.067 | 0.005 | 1.00 | 46.01 |

TABLE 4-continued

| | | | | | | | | |
|---|---|---|---|---|---|---|---|---|
| ATOM | 26 | CA | SER | 33 | 52.084 | 50.499 | 1.324 | 1.00 | 46.38 |
| ATOM | 27 | CB | SER | 33 | 52.769 | 49.663 | 2.411 | 1.00 | 47.20 |
| ATOM | 28 | OG | SER | 33 | 54.189 | 49.706 | 2.281 | 1.00 | 46.32 |
| ATOM | 29 | C | SER | 33 | 52.439 | 51.939 | 1.556 | 1.00 | 46.76 |
| ATOM | 30 | O | SER | 33 | 53.371 | 52.484 | 0.954 | 1.00 | 46.67 |
| ATOM | 31 | N | PHE | 34 | 51.681 | 52.555 | 2.448 | 1.00 | 46.73 |
| ATOM | 32 | CA | PHE | 34 | 52.021 | 53.849 | 3.001 | 1.00 | 46.41 |
| ATOM | 33 | CB | PHE | 34 | 51.013 | 54.896 | 2.556 | 1.00 | 45.30 |
| ATOM | 34 | CG | PHE | 34 | 49.594 | 54.569 | 2.895 | 1.00 | 45.08 |
| ATOM | 35 | CD1 | PHE | 34 | 48.868 | 53.647 | 2.127 | 1.00 | 41.96 |
| ATOM | 36 | CE1 | PHE | 34 | 47.543 | 53.362 | 2.414 | 1.00 | 40.06 |
| ATOM | 37 | CZ | PHE | 34 | 46.901 | 53.994 | 3.468 | 1.00 | 41.83 |
| ATOM | 38 | CE2 | PHE | 34 | 47.603 | 54.915 | 4.258 | 1.00 | 43.64 |
| ATOM | 39 | CD2 | PHE | 34 | 48.947 | 55.219 | 3.957 | 1.00 | 43.81 |
| ATOM | 40 | C | PHE | 34 | 52.063 | 53.662 | 4.527 | 1.00 | 46.92 |
| ATOM | 41 | O | PHE | 34 | 51.603 | 52.622 | 5.031 | 1.00 | 47.04 |
| ATOM | 42 | N | PRO | 35 | 59.662 | 54.621 | 5.269 | 1.00 | 47.32 |
| ATOM | 43 | CA | PRO | 35 | 52.757 | 54.444 | 6.735 | 1.00 | 46.30 |
| ATOM | 44 | CB | PRO | 35 | 53.589 | 55.648 | 7.198 | 1.00 | 46.28 |
| ATOM | 45 | CG | PRO | 35 | 54.283 | 56.171 | 5.902 | 1.00 | 48.44 |
| ATOM | 46 | CD | PRO | 35 | 53.277 | 55.891 | 4.818 | 1.00 | 47.47 |
| ATOM | 47 | C | PRO | 35 | 51.388 | 54.535 | 7.394 | 1.00 | 45.82 |
| ATOM | 48 | O | PRO | 35 | 50.560 | 55.358 | 6.972 | 1.00 | 45.81 |
| ATOM | 49 | N | ASN | 36 | 51.170 | 53.704 | 8.420 | 1.00 | 44.03 |
| ATOM | 50 | CA | ASN | 36 | 50.077 | 53.867 | 9.350 | 1.00 | 43.55 |
| ATOM | 51 | CB | ASN | 36 | 50.062 | 52.647 | 10.269 | 1.00 | 42.05 |
| ATOM | 52 | CG | ASN | 36 | 48.878 | 52.584 | 11.215 | 1.00 | 39.57 |
| ATOM | 53 | OD1 | ASN | 36 | 48.758 | 51.605 | 11.987 | 1.00 | 36.94 |
| ATOM | 54 | ND2 | ASN | 36 | 48.007 | 53.588 | 11.188 | 1.00 | 36.21 |
| ATOM | 55 | C | ASN | 36 | 50.322 | 55.172 | 10.124 | 1.00 | 45.04 |
| ATOM | 56 | O | ASN | 36 | 51.369 | 55.382 | 10.742 | 1.00 | 46.02 |
| ATOM | 57 | N | LYS | 37 | 49.355 | 56.069 | 10.097 | 1.00 | 46.02 |
| ATOM | 58 | CA | LYS | 37 | 49.499 | 57.315 | 10.816 | 1.00 | 45.91 |
| ATOM | 59 | CB | LYS | 37 | 48.832 | 58.455 | 10.025 | 1.00 | 46.87 |
| ATOM | 60 | CG | LYS | 37 | 49.714 | 59.013 | 8.879 | 1.00 | 47.18 |
| ATOM | 61 | CD | LYS | 37 | 49.117 | 60.295 | 8.260 | 1.00 | 48.96 |
| ATOM | 62 | CE | LYS | 37 | 50.206 | 61.168 | 7.571 | 1.00 | 52.78 |
| ATOM | 63 | NZ | LYS | 37 | 49.706 | 61.921 | 6.351 | 1.00 | 56.07 |
| ATOM | 64 | C | LYS | 37 | 48.929 | 57.182 | 12.241 | 1.00 | 45.25 |
| ATOM | 65 | O | LYS | 37 | 48.996 | 58.124 | 13.016 | 1.00 | 45.71 |
| ATOM | 66 | N | HIS | 38 | 48.356 | 56.023 | 12.582 | 1.00 | 43.59 |
| ATOM | 67 | CA | HIS | 38 | 47.737 | 55.823 | 13.896 | 1.00 | 41.86 |
| ATOM | 68 | CB | HIS | 38 | 46.217 | 55.919 | 13.821 | 1.00 | 41.44 |
| ATOM | 69 | CG | HIS | 38 | 45.756 | 57.245 | 13.326 | 1.00 | 41.29 |
| ATOM | 70 | ND1 | HIS | 38 | 45.596 | 57.525 | 11.979 | 1.00 | 44.16 |
| ATOM | 71 | CE1 | HIS | 38 | 45.224 | 58.786 | 11.836 | 1.00 | 41.85 |
| ATOM | 72 | NE2 | HIS | 38 | 45.152 | 59.333 | 13.037 | 1.00 | 41.53 |
| ATOM | 73 | CD2 | HIS | 38 | 45.487 | 58.394 | 13.985 | 1.00 | 38.32 |
| ATOM | 74 | C | HIS | 38 | 48.205 | 54.506 | 14.445 | 1.00 | 41.25 |
| ATOM | 75 | O | HIS | 38 | 47.411 | 53.643 | 14.797 | 1.00 | 41.21 |
| ATOM | 76 | N | VAL | 39 | 49.526 | 54.384 | 14.497 | 1.00 | 41.34 |
| ATOM | 77 | CA | VAL | 39 | 50.254 | 53.203 | 14.934 | 1.00 | 42.22 |
| ATOM | 78 | CB | VAL | 39 | 51.779 | 53.421 | 14.851 | 1.00 | 41.92 |
| ATOM | 79 | CG1 | VAL | 39 | 52.501 | 52.116 | 15.067 | 1.00 | 43.48 |
| ATOM | 80 | CG2 | VAL | 39 | 52.159 | 53.951 | 13.502 | 1.00 | 43.32 |
| ATOM | 81 | C | VAL | 39 | 49.924 | 52.771 | 16.350 | 1.00 | 41.82 |
| ATOM | 82 | O | VAL | 39 | 49.855 | 51.599 | 16.626 | 1.00 | 42.98 |
| ATOM | 83 | N | ASP | 40 | 49.695 | 53.698 | 17.244 | 1.00 | 42.89 |
| ATOM | 84 | CA | ASP | 40 | 49.601 | 53.322 | 18.661 | 1.00 | 44.67 |
| ATOM | 85 | CB | ASP | 40 | 50.053 | 54.484 | 19.573 | 1.00 | 44.89 |
| ATOM | 86 | CG | ASP | 40 | 51.533 | 54.935 | 19.283 | 1.00 | 49.16 |
| ATOM | 87 | OD1 | ASP | 40 | 52.421 | 54.052 | 19.087 | 1.00 | 48.00 |
| ATOM | 88 | OD2 | ASP | 40 | 51.804 | 56.184 | 19.236 | 1.00 | 52.73 |
| ATOM | 89 | C | ASP | 40 | 48.215 | 52.847 | 18.988 | 1.00 | 44.01 |
| ATOM | 90 | O | ASP | 40 | 47.853 | 52.711 | 20.133 | 1.00 | 45.24 |
| ATOM | 91 | N | ARG | 41 | 47.438 | 52.569 | 17.957 | 1.00 | 43.43 |
| ATOM | 92 | CA | ARG | 41 | 46.019 | 52.229 | 18.130 | 1.00 | 42.17 |
| ATOM | 93 | CB | ARG | 41 | 45.179 | 53.439 | 17.715 | 1.00 | 41.97 |
| ATOM | 94 | CG | ARG | 41 | 43.710 | 53.179 | 17.767 | 1.00 | 43.99 |
| ATOM | 95 | CD | ARG | 41 | 42.984 | 54.369 | 17.283 | 1.00 | 47.23 |
| ATOM | 96 | NE | ARG | 41 | 42.978 | 55.410 | 18.307 | 1.00 | 48.29 |
| ATOM | 97 | CZ | ARG | 41 | 42.736 | 56.693 | 18.072 | 1.00 | 48.38 |
| ATOM | 98 | NH1 | ARG | 41 | 42.465 | 57.113 | 16.830 | 1.00 | 46.27 |
| ATOM | 99 | NH2 | ARG | 41 | 42.749 | 57.552 | 19.094 | 1.00 | 49.60 |
| ATOM | 100 | C | ARG | 41 | 45.664 | 50.992 | 17.292 | 1.00 | 40.27 |
| ATOM | 101 | O | ARG | 41 | 46.138 | 50.836 | 16.178 | 1.00 | 39.42 |
| ATOM | 102 | N | ASP | 42 | 44.867 | 50.090 | 17.841 | 1.00 | 39.05 |
| ATOM | 103 | CA | ASP | 42 | 44.358 | 48.965 | 17.044 | 1.00 | 37.67 |
| ATOM | 104 | CB | ASP | 42 | 44.076 | 47.801 | 17.941 | 1.00 | 37.69 |
| ATOM | 105 | CG | ASP | 42 | 45.299 | 47.103 | 18.344 | 1.00 | 37.73 |

TABLE 4-continued

| | | | | | | | | |
|---|---|---|---|---|---|---|---|---|
| ATOM | 106 | OD1 | ASP | 42 | 46.389 | 47.370 | 17.772 | 1.00 | 37.62 |
| ATOM | 107 | OD2 | ASP | 42 | 45.152 | 46.239 | 19.207 | 1.00 | 42.01 |
| ATOM | 108 | C | ASP | 42 | 43.081 | 49.300 | 16.290 | 1.00 | 36.81 |
| ATOM | 109 | O | ASP | 42 | 42.080 | 49.618 | 16.901 | 1.00 | 37.53 |
| ATOM | 110 | N | TYR | 43 | 43.094 | 49.232 | 14.963 | 1.00 | 35.86 |
| ATOM | 111 | CA | TYR | 43 | 41.845 | 49.384 | 14.221 | 1.00 | 34.34 |
| ATOM | 112 | CB | TYR | 43 | 41.606 | 50.848 | 13.825 | 1.00 | 34.51 |
| ATOM | 113 | CG | TYR | 43 | 42.620 | 51.403 | 12.875 | 1.00 | 35.13 |
| ATOM | 114 | CD1 | TYR | 43 | 43.789 | 52.021 | 13.353 | 1.00 | 35.36 |
| ATOM | 115 | CE1 | TYR | 43 | 44.713 | 52.568 | 12.476 | 1.00 | 35.91 |
| ATOM | 116 | CZ | TYR | 43 | 44.482 | 52.488 | 11.092 | 1.00 | 36.72 |
| ATOM | 117 | OH | TYR | 43 | 45.423 | 53.020 | 10.229 | 1.00 | 39.91 |
| ATOM | 118 | CE2 | TYR | 43 | 43.341 | 51.894 | 10.591 | 1.00 | 35.17 |
| ATOM | 119 | CD2 | TYR | 43 | 42.406 | 51.355 | 11.490 | 1.00 | 33.94 |
| ATOM | 120 | C | TYR | 43 | 41.778 | 48.416 | 13.037 | 1.00 | 33.02 |
| ATOM | 121 | O | TYR | 43 | 42.773 | 47.896 | 12.622 | 1.00 | 33.74 |
| ATOM | 122 | N | PHE | 44 | 40.584 | 48.157 | 12.534 | 1.00 | 31.52 |
| ATOM | 123 | CA | PHE | 44 | 40.380 | 47.193 | 11.477 | 1.00 | 30.42 |
| ATOM | 124 | CB | PHE | 44 | 39.121 | 46.371 | 11.785 | 1.00 | 28.05 |
| ATOM | 125 | CG | PHE | 44 | 39.368 | 44.908 | 12.102 | 1.00 | 26.16 |
| ATOM | 126 | CD1 | PHE | 44 | 38.895 | 44.360 | 13.296 | 1.00 | 23.64 |
| ATOM | 127 | CE1 | PHE | 44 | 39.048 | 43.004 | 13.579 | 1.00 | 26.96 |
| ATOM | 128 | CZ | PHE | 44 | 39.695 | 42.170 | 12.652 | 1.00 | 27.27 |
| ATOM | 129 | CE2 | PHE | 44 | 40.193 | 42.728 | 11.450 | 1.00 | 24.84 |
| ATOM | 130 | CD2 | PHE | 44 | 40.022 | 44.075 | 11.193 | 1.00 | 23.20 |
| ATOM | 131 | C | PHE | 44 | 40.201 | 47.957 | 10.126 | 1.00 | 30.58 |
| ATOM | 132 | O | PHE | 44 | 39.488 | 48.958 | 10.052 | 1.00 | 30.26 |
| ATOM | 133 | N | VAL | 45 | 40.882 | 47.487 | 9.094 | 1.00 | 29.38 |
| ATOM | 134 | CA | VAL | 45 | 40.578 | 47.889 | 7.737 | 1.00 | 29.28 |
| ATOM | 135 | CB | VAL | 45 | 41.844 | 48.431 | 7.053 | 1.00 | 29.71 |
| ATOM | 136 | CG1 | VAL | 45 | 42.424 | 49.563 | 7.910 | 1.00 | 27.42 |
| ATOM | 137 | CG2 | VAL | 45 | 41.512 | 48.887 | 5.625 | 1.00 | 27.61 |
| ATOM | 138 | C | VAL | 45 | 40.073 | 46.699 | 6.946 | 1.00 | 28.37 |
| ATOM | 139 | O | VAL | 43 | 40.775 | 45.707 | 6.881 | 1.00 | 29.10 |
| ATOM | 140 | N | LYS | 46 | 38.862 | 46.788 | 6.372 | 1.00 | 27.37 |
| ATOM | 141 | CA | LYS | 46 | 38.313 | 45.744 | 5.461 | 1.00 | 26.68 |
| ATOM | 142 | CB | LYS | 46 | 36.862 | 45.397 | 5.804 | 1.00 | 26.88 |
| ATOM | 143 | CG | LYS | 46 | 36.313 | 44.223 | 4.931 | 1.00 | 25.08 |
| ATOM | 144 | CD | LYS | 46 | 34.964 | 43.720 | 5.314 | 1.00 | 25.24 |
| ATOM | 145 | CE | LYS | 46 | 34.072 | 44.791 | 5.955 | 1.00 | 28.89 |
| ATOM | 146 | NZ | LYS | 46 | 32.686 | 44.222 | 6.181 | 1.00 | 26.14 |
| ATOM | 147 | C | LYS | 46 | 38.344 | 46.164 | 3.973 | 1.00 | 27.02 |
| ATOM | 148 | O | LYS | 46 | 37.964 | 47.250 | 3.629 | 1.00 | 27.01 |
| ATOM | 149 | N | PHE | 47 | 38.863 | 45.314 | 3.111 | 1.00 | 28.84 |
| ATOM | 150 | CA | PHE | 47 | 38.615 | 45.418 | 1.644 | 1.00 | 29.05 |
| ATOM | 151 | CB | PHE | 47 | 39.885 | 45.190 | 0.860 | 1.00 | 28.82 |
| ATOM | 152 | CG | PHE | 47 | 40.967 | 46.166 | 1.206 | 1.00 | 33.70 |
| ATOM | 153 | CD1 | PHE | 47 | 41.906 | 45.865 | 2.202 | 1.00 | 33.29 |
| ATOM | 154 | CE1 | PHE | 47 | 42.870 | 46.771 | 2.548 | 1.00 | 37.36 |
| ATOM | 155 | CZ | PHE | 47 | 42.947 | 48.011 | 1.876 | 1.00 | 36.77 |
| ATOM | 156 | CE2 | PHE | 47 | 42.036 | 48.328 | 0.902 | 1.00 | 35.15 |
| ATOM | 157 | CD2 | PHE | 47 | 41.028 | 47.407 | 0.580 | 1.00 | 35.97 |
| ATOM | 158 | C | PHE | 47 | 37.557 | 44.433 | 1.154 | 1.00 | 29.27 |
| ATOM | 159 | O | PHE | 47 | 37.656 | 43.228 | 1.388 | 1.00 | 28.82 |
| ATOM | 160 | N | ASN | 48 | 36.544 | 44.969 | 0.481 | 1.00 | 29.67 |
| ATOM | 161 | CA | ASN | 48 | 35.565 | 44.180 | −0.238 | 1.00 | 29.45 |
| ATOM | 162 | CB | ASN | 48 | 34.187 | 44.785 | −0.092 | 1.00 | 29.55 |
| ATOM | 163 | CG | ASN | 48 | 33.812 | 45.036 | 1.358 | 1.00 | 31.72 |
| ATOM | 164 | OD1 | ASN | 48 | 33.656 | 44.091 | 2.151 | 1.00 | 31.64 |
| ATOM | 165 | ND2 | ASN | 48 | 33.639 | 46.309 | 1.710 | 1.00 | 28.68 |
| ATOM | 166 | C | ASN | 48 | 35.966 | 44.089 | −1.712 | 1.00 | 29.39 |
| ATOM | 167 | O | ASN | 48 | 36.181 | 45.074 | −2.366 | 1.00 | 30.66 |
| ATOM | 168 | N | CYS | 49 | 36.121 | 42.882 | −2.215 | 1.00 | 28.93 |
| ATOM | 169 | CA | CYS | 49 | 36.691 | 42.691 | −3.539 | 1.00 | 28.55 |
| ATOM | 170 | CB | CYS | 49 | 38.122 | 42.139 | −3.427 | 1.00 | 28.66 |
| ATOM | 171 | SG | CYS | 49 | 39.169 | 42.982 | −2.155 | 1.00 | 32.73 |
| ATOM | 172 | C | CYS | 49 | 35.822 | 41.722 | −4.303 | 1.00 | 27.45 |
| ATOM | 173 | O | CYS | 49 | 36.163 | 40.571 | −4.400 | 1.00 | 27.31 |
| ATOM | 174 | N | PRO | 50 | 34.677 | 42.187 | −4.815 | 1.00 | 26.98 |
| ATOM | 175 | CA | PRO | 50 | 33.704 | 41.358 | −5.540 | 1.00 | 28.14 |
| ATOM | 176 | CB | PRO | 50 | 32.460 | 42.229 | −5.577 | 1.00 | 27.05 |
| ATOM | 177 | CG | PRO | 50 | 32.834 | 43.500 | −4.917 | 1.00 | 27.46 |
| ATOM | 178 | CD | PRO | 50 | 34.269 | 43.589 | −4.773 | 1.00 | 26.73 |
| ATOM | 179 | C | PRO | 50 | 34.131 | 41.021 | −6.992 | 1.00 | 28.93 |
| ATOM | 180 | O | PRO | 50 | 33.454 | 40.277 | −7.662 | 1.00 | 29.56 |
| ATOM | 181 | N | GLU | 51 | 35.239 | 41.550 | −7.471 | 1.00 | 28.99 |
| ATOM | 182 | CA | GLU | 51 | 35.542 | 41.364 | −8.882 | 1.00 | 30.87 |
| ATOM | 183 | CB | GLU | 51 | 35.773 | 42.743 | −9.531 | 1.00 | 29.68 |
| ATOM | 184 | CG | GLU | 51 | 34.461 | 43.552 | −9.722 | 1.00 | 30.84 |
| ATOM | 185 | CD | GLU | 51 | 34.670 | 45.005 | −10.178 | 1.00 | 32.39 |

TABLE 4-continued

| | | | | | | | | |
|---|---|---|---|---|---|---|---|---|
| ATOM | 186 | OE1 | GLU | 51 | 35.770 | 45.326 | −10.657 | 1.00 | 32.62 |
| ATOM | 187 | OE2 | GLU | 51 | 33.746 | 45.863 | −10.020 | 1.00 | 37.18 |
| ATOM | 188 | C | GLU | 51 | 36.729 | 40.420 | −9.058 | 1.00 | 30.84 |
| ATOM | 189 | O | GLU | 51 | 37.434 | 40.492 | −10.035 | 1.00 | 32.13 |
| ATOM | 190 | N | THR | 66 | 33.959 | 36.665 | −4.539 | 1.00 | 27.88 |
| ATOM | 191 | CA | THR | 66 | 34.161 | 37.880 | −3.739 | 1.00 | 29.11 |
| ATOM | 192 | CB | THR | 66 | 32.865 | 38.324 | −3.064 | 1.00 | 28.62 |
| ATOM | 193 | OG1 | THR | 66 | 31.893 | 38.546 | −4.055 | 1.00 | 32.67 |
| ATOM | 194 | CG2 | THR | 66 | 33.026 | 39.699 | −2.321 | 1.00 | 30.63 |
| ATOM | 195 | C | THR | 66 | 35.230 | 37.545 | −2.666 | 1.00 | 29.04 |
| ATOM | 196 | O | THR | 66 | 35.157 | 36.496 | −2.006 | 1.00 | 29.39 |
| ATOM | 197 | N | ILE | 67 | 36.187 | 38.435 | −2.463 | 1.00 | 29.87 |
| ATOM | 198 | CA | ILE | 67 | 37.164 | 38.251 | −1.396 | 1.00 | 29.83 |
| ATOM | 199 | CB | ILE | 67 | 38.587 | 38.232 | −1.944 | 1.00 | 30.58 |
| ATOM | 200 | CG1 | ILE | 67 | 38.746 | 37.168 | −3.049 | 1.00 | 28.17 |
| ATOM | 201 | CD1 | ILE | 67 | 40.222 | 37.168 | −3.597 | 1.00 | 30.71 |
| ATOM | 202 | CG2 | ILE | 67 | 39.613 | 37.990 | −0.826 | 1.00 | 32.44 |
| ATOM | 203 | C | ILE | 67 | 37.008 | 39.373 | −0.395 | 1.00 | 29.75 |
| ATOM | 204 | O | ILE | 67 | 36.863 | 40.562 | −0.776 | 1.00 | 30.09 |
| ATOM | 205 | N | TYR | 68 | 36.954 | 38.994 | 0.884 | 1.00 | 29.10 |
| ATOM | 206 | CA | TYR | 68 | 36.922 | 39.960 | 1.980 | 1.00 | 29.33 |
| ATOM | 207 | CB | TYR | 68 | 35.749 | 39.680 | 2.920 | 1.00 | 29.75 |
| ATOM | 208 | CG | TYR | 68 | 34.416 | 39.729 | 2.230 | 1.00 | 29.38 |
| ATOM | 209 | CD1 | TYR | 68 | 33.794 | 38.563 | 1.815 | 1.00 | 32.55 |
| ATOM | 210 | CE1 | TYR | 68 | 32.568 | 38.584 | 1.134 | 1.00 | 32.20 |
| ATOM | 211 | CZ | TYR | 68 | 31.963 | 39.819 | 0.883 | 1.00 | 33.29 |
| ATOM | 212 | OH | TYR | 68 | 30.740 | 39.851 | 0.231 | 1.00 | 32.89 |
| ATOM | 213 | CE2 | TYR | 68 | 32.572 | 41.015 | 1.294 | 1.00 | 29.83 |
| ATOM | 214 | CD2 | TYR | 68 | 33.783 | 40.965 | 1.962 | 1.00 | 31.54 |
| ATOM | 215 | C | TYR | 68 | 38.279 | 39.917 | 2.710 | 1.00 | 29.45 |
| ATOM | 216 | O | TYR | 68 | 38.779 | 38.853 | 3.103 | 1.00 | 29.05 |
| ATOM | 217 | N | ILE | 69 | 38.888 | 41.080 | 2.851 | 1.00 | 28.99 |
| ATOM | 218 | CA | ILE | 69 | 40.189 | 41.133 | 3.443 | 1.00 | 29.76 |
| ATOM | 219 | CB | ILE | 69 | 41.245 | 41.549 | 2.415 | 1.00 | 29.75 |
| ATOM | 220 | CG1 | ILE | 69 | 41.287 | 40.534 | 1.260 | 1.00 | 27.97 |
| ATOM | 221 | CD1 | ILE | 69 | 42.318 | 40.945 | 0.271 | 1.00 | 26.18 |
| ATOM | 222 | CG2 | ILE | 69 | 42.625 | 41.704 | 3.093 | 1.00 | 32.22 |
| ATOM | 223 | C | ILE | 69 | 40.152 | 42.132 | 4.557 | 1.00 | 29.86 |
| ATOM | 224 | O | ILE | 69 | 39.881 | 43.304 | 4.314 | 1.00 | 29.65 |
| ATOM | 225 | N | SER | 70 | 40.408 | 41.651 | 5.779 | 1.00 | 30.45 |
| ATOM | 226 | CA | SER | 70 | 40.364 | 42.506 | 6.981 | 1.00 | 30.03 |
| ATOM | 227 | CB | SER | 70 | 39.223 | 42.035 | 7.869 | 1.00 | 29.17 |
| ATOM | 228 | OG | SER | 70 | 33.002 | 42.191 | 7.194 | 1.00 | 30.13 |
| ATOM | 229 | C | SER | 70 | 41.687 | 42.374 | 7.736 | 1.00 | 30.78 |
| ATOM | 230 | O | SER | 70 | 42.155 | 41.252 | 7.957 | 1.00 | 30.80 |
| ATOM | 231 | N | TYR | 71 | 42.292 | 43.494 | 8.126 | 1.00 | 30.28 |
| ATOM | 232 | CA | TYR | 71 | 43.549 | 43.418 | 8.832 | 1.00 | 30.62 |
| ATOM | 233 | CB | TYR | 71 | 44.775 | 43.454 | 7.870 | 1.00 | 31.06 |
| ATOM | 234 | CG | TYR | 71 | 45.145 | 44.802 | 7.314 | 1.00 | 30.65 |
| ATOM | 235 | CD1 | TYR | 71 | 44.427 | 45.375 | 6.252 | 1.00 | 32.95 |
| ATOM | 236 | CE1 | TYR | 71 | 44.774 | 46.635 | 5.729 | 1.00 | 35.56 |
| ATOM | 237 | CZ | TYR | 71 | 45.853 | 47.307 | 6.284 | 1.00 | 35.18 |
| ATOM | 238 | OH | TYR | 71 | 46.233 | 48.540 | 5.823 | 1.00 | 33.86 |
| ATOM | 239 | CE2 | TYR | 71 | 46.553 | 46.731 | 7.335 | 1.00 | 32.70 |
| ATOM | 240 | CD2 | TYR | 71 | 46.208 | 45.482 | 7.808 | 1.00 | 30.48 |
| ATOM | 241 | C | TYR | 71 | 43.613 | 44.505 | 9.873 | 1.00 | 30.68 |
| ATOM | 242 | O | TYR | 71 | 42.887 | 45.490 | 9.763 | 1.00 | 30.21 |
| ATOM | 243 | N | ILE | 72 | 44.427 | 44.279 | 10.915 | 1.00 | 30.50 |
| ATOM | 244 | CA | ILE | 72 | 44.801 | 45.325 | 11.855 | 1.00 | 30.24 |
| ATOM | 245 | CB | ILE | 72 | 44.723 | 44.843 | 13.328 | 1.00 | 30.88 |
| ATOM | 246 | CG1 | ILE | 72 | 43.293 | 44.331 | 13.636 | 1.00 | 28.07 |
| ATOM | 247 | CD1 | ILE | 72 | 42.932 | 44.254 | 15.117 | 1.00 | 28.12 |
| ATOM | 248 | CG2 | ILE | 72 | 45.196 | 45.956 | 14.298 | 1.00 | 29.52 |
| ATOM | 249 | C | ILE | 72 | 46.233 | 45.708 | 11.494 | 1.00 | 30.72 |
| ATOM | 250 | O | ILE | 72 | 47.132 | 44.880 | 11.577 | 1.00 | 32.13 |
| ATOM | 251 | N | PRO | 73 | 46.464 | 46.964 | 11.090 | 1.00 | 30.34 |
| ATOM | 252 | CA | PRO | 73 | 47.842 | 47.268 | 10.709 | 1.00 | 31.27 |
| ATOM | 253 | CB | PRO | 73 | 47.707 | 48.597 | 9.924 | 1.00 | 29.95 |
| ATOM | 254 | CG | PRO | 73 | 46.473 | 49.180 | 10.372 | 1.00 | 27.98 |
| ATOM | 255 | CD | PRO | 73 | 45.602 | 48.157 | 11.030 | 1.00 | 29.81 |
| ATOM | 256 | C | PRO | 73 | 48.792 | 47.482 | 11.927 | 1.00 | 32.40 |
| ATOM | 257 | O | PRO | 73 | 48.349 | 47.835 | 13.032 | 1.00 | 31.23 |
| ATOM | 258 | N | ASP | 74 | 50.086 | 47.273 | 11.690 | 1.00 | 34.03 |
| ATOM | 259 | CA | ASP | 74 | 51.109 | 47.851 | 12.532 | 1.00 | 34.96 |
| ATOM | 260 | CB | ASP | 74 | 52.170 | 46.810 | 12.922 | 1.00 | 35.72 |
| ATOM | 261 | CG | ASP | 74 | 53.290 | 47.405 | 13.800 | 1.00 | 38.15 |
| ATOM | 262 | OD1 | ASP | 74 | 52.988 | 48.164 | 14.733 | 1.00 | 42.19 |
| ATOM | 263 | OD2 | ASP | 74 | 54.481 | 47.136 | 13.535 | 1.00 | 42.50 |
| ATOM | 264 | C | ASP | 74 | 51.669 | 49.122 | 11.858 | 1.00 | 35.88 |
| ATOM | 265 | O | ASP | 74 | 51.013 | 50.184 | 11.894 | 1.00 | 34.85 |

TABLE 4-continued

| | | | | | | | | |
|---|---|---|---|---|---|---|---|---|
| ATOM | 266 | N | GLU | 75 | 52.838 | 49.049 | 11.212 | 1.00 | 37.87 |
| ATOM | 267 | CA | GLU | 75 | 53.413 | 50.273 | 10.612 | 1.00 | 39.81 |
| ATOM | 268 | CB | GLU | 75 | 54.939 | 50.327 | 10.807 | 1.00 | 41.03 |
| ATOM | 269 | CG | GLU | 75 | 55.315 | 50.889 | 12.188 | 1.00 | 46.36 |
| ATOM | 270 | CD | GLU | 75 | 56.239 | 52.123 | 12.120 | 1.00 | 56.87 |
| ATOM | 271 | OE1 | GLU | 75 | 57.455 | 51.895 | 11.893 | 1.00 | 62.19 |
| ATOM | 272 | OE2 | GLU | 75 | 55.766 | 53.305 | 12.307 | 1.00 | 57.56 |
| ATOM | 273 | C | GLU | 75 | 52.994 | 50.577 | 9.159 | 1.00 | 39.88 |
| ATOM | 274 | O | GLU | 75 | 52.903 | 51.736 | 8.759 | 1.00 | 40.11 |
| ATOM | 275 | N | LYS | 76 | 52.699 | 49.531 | 8.402 | 1.00 | 39.86 |
| ATOM | 276 | CA | LYS | 76 | 52.432 | 49.634 | 6.976 | 1.00 | 40.44 |
| ATOM | 277 | CB | LYS | 76 | 53.398 | 48.679 | 6.234 | 1.00 | 40.71 |
| ATOM | 278 | CG | LYS | 76 | 54.876 | 49.164 | 6.254 | 1.00 | 41.97 |
| ATOM | 279 | CD | LYS | 76 | 55.838 | 48.116 | 5.709 | 1.00 | 42.76 |
| ATOM | 280 | CE | LYS | 76 | 57.257 | 48.735 | 5.566 | 1.00 | 46.94 |
| ATOM | 281 | NZ | LYS | 76 | 58.113 | 48.079 | 4.471 | 1.00 | 47.84 |
| ATOM | 282 | C | LYS | 76 | 50.951 | 49.336 | 6.618 | 1.00 | 39.57 |
| ATOM | 283 | O | LYS | 76 | 50.351 | 48.383 | 7.159 | 1.00 | 38.59 |
| ATOM | 284 | N | MET | 77 | 50.387 | 50.161 | 5.733 | 1.00 | 38.91 |
| ATOM | 285 | CA | MET | 77 | 49.063 | 49.946 | 5.129 | 1.00 | 39.54 |
| ATOM | 286 | CB | MET | 77 | 48.227 | 51.199 | 5.269 | 1.00 | 40.38 |
| ATOM | 287 | CG | MET | 77 | 48.552 | 51.943 | 6.526 | 1.00 | 42.11 |
| ATOM | 288 | SD | MET | 77 | 47.288 | 51.638 | 7.701 | 1.00 | 47.32 |
| ATOM | 289 | CE | MET | 77 | 46.598 | 53.275 | 7.750 | 1.00 | 44.61 |
| ATOM | 290 | C | MET | 77 | 49.190 | 49.618 | 3.639 | 1.00 | 39.84 |
| ATOM | 291 | O | MET | 77 | 49.984 | 50.241 | 2.943 | 1.00 | 40.60 |
| ATOM | 292 | N | VAL | 78 | 48.428 | 48.637 | 3.152 | 1.00 | 38.72 |
| ATOM | 293 | CA | VAL | 78 | 48.361 | 48.355 | 1.729 | 1.00 | 37.72 |
| ATOM | 294 | CB | VAL | 78 | 47.851 | 46.932 | 1.471 | 1.00 | 38.33 |
| ATOM | 295 | CG1 | VAL | 78 | 46.438 | 46.736 | 1.960 | 1.00 | 34.37 |
| ATOM | 296 | CG2 | VAL | 78 | 47.958 | 46.583 | −0.009 | 1.00 | 38.72 |
| ATOM | 297 | C | VAL | 78 | 47.530 | 49.462 | 0.992 | 1.00 | 37.83 |
| ATOM | 298 | O | VAL | 78 | 46.455 | 49.881 | 1.450 | 1.00 | 37.49 |
| ATOM | 299 | N | GLU | 79 | 48.094 | 49.992 | −0.086 | 1.00 | 37.59 |
| ATOM | 300 | CA | GLU | 79 | 47.451 | 51.030 | −0.918 | 1.00 | 38.47 |
| ATOM | 301 | CB | GLU | 79 | 48.563 | 51.788 | −1.681 | 1.00 | 39.42 |
| ATOM | 302 | CG | GLU | 79 | 48.125 | 53.075 | −2.306 | 1.00 | 42.55 |
| ATOM | 303 | CD | GLU | 79 | 47.283 | 52.824 | −3.569 | 1.00 | 45.29 |
| ATOM | 304 | OE1 | GLU | 79 | 47.644 | 51.874 | −4.300 | 1.00 | 48.69 |
| ATOM | 305 | OE2 | GLU | 79 | 46.284 | 53.558 | −3.816 | 1.00 | 40.76 |
| ATOM | 306 | C | GLU | 79 | 46.496 | 50.288 | −1.873 | 1.00 | 38.04 |
| ATOM | 307 | O | GLU | 79 | 46.860 | 49.225 | −2.414 | 1.00 | 37.98 |
| ATOM | 308 | N | SER | 80 | 45.261 | 50.777 | −2.012 | 1.00 | 37.39 |
| ATOM | 309 | CA | SER | 80 | 44.217 | 49.966 | −2.633 | 1.00 | 37.75 |
| ATOM | 310 | CB | SER | 80 | 42.824 | 50.412 | −2.252 | 1.00 | 37.68 |
| ATOM | 311 | OG | SER | 80 | 42.694 | 51.786 | −2.484 | 1.00 | 40.99 |
| ATOM | 312 | C | SER | 80 | 44.338 | 49.792 | −4.149 | 1.00 | 38.14 |
| ATOM | 313 | O | SER | 80 | 44.134 | 48.657 | −4.682 | 1.00 | 38.41 |
| ATOM | 314 | N | LYS | 81 | 44.713 | 50.859 | −4.844 | 1.00 | 38.05 |
| ATOM | 315 | CA | LYS | 81 | 45.170 | 50.677 | −6.249 | 1.00 | 38.29 |
| ATOM | 316 | CB | LYS | 81 | 45.701 | 51.970 | −6.862 | 1.00 | 38.47 |
| ATOM | 317 | CG | LYS | 81 | 45.713 | 51.882 | −8.388 | 1.00 | 43.77 |
| ATOM | 318 | CD | LYS | 81 | 45.607 | 53.265 | −9.061 | 1.00 | 49.29 |
| ATOM | 319 | CE | LYS | 81 | 46.989 | 53.855 | −9.329 | 1.00 | 54.55 |
| ATOM | 320 | NZ | LYS | 81 | 46.926 | 54.856 | −10.456 | 1.00 | 57.78 |
| ATOM | 321 | C | LYS | 81 | 46.148 | 49.510 | −6.468 | 1.00 | 36.81 |
| ATOM | 322 | O | LYS | 81 | 45.898 | 48.646 | −7.339 | 1.00 | 37.85 |
| ATOM | 323 | N | SER | 82 | 47.223 | 49.434 | −5.685 | 1.00 | 35.20 |
| ATOM | 324 | CA | SER | 82 | 48.189 | 48.306 | −5.802 | 1.00 | 33.64 |
| ATOM | 325 | CB | SER | 82 | 49.344 | 48.504 | −4.799 | 1.00 | 34.75 |
| ATOM | 326 | OG | SER | 82 | 48.945 | 48.222 | −3.463 | 1.00 | 33.65 |
| ATOM | 327 | C | SER | 82 | 47.545 | 46.954 | −5.577 | 1.00 | 32.78 |
| ATOM | 328 | O | SER | 82 | 47.929 | 45.933 | −6.160 | 1.00 | 33.37 |
| ATOM | 329 | N | LEU | 83 | 46.541 | 46.952 | −4.704 | 1.00 | 32.92 |
| ATOM | 330 | CA | LEU | 83 | 45.820 | 45.744 | −4.293 | 1.00 | 31.80 |
| ATOM | 331 | CB | LEU | 83 | 44.960 | 46.018 | −3.026 | 1.00 | 32.13 |
| ATOM | 332 | CG | LEU | 83 | 44.142 | 44.762 | −2.639 | 1.00 | 31.44 |
| ATOM | 333 | CD1 | LEU | 83 | 45.104 | 43.535 | −2.440 | 1.00 | 27.03 |
| ATOM | 334 | CD2 | LEU | 83 | 43.250 | 44.984 | −1.430 | 1.00 | 30.07 |
| ATOM | 335 | C | LEU | 83 | 44.938 | 45.258 | −5.447 | 1.00 | 31.38 |
| ATOM | 336 | O | LEU | 83 | 44.917 | 44.047 | −5.794 | 1.00 | 29.64 |
| ATOM | 337 | N | LYS | 84 | 44.184 | 46.208 | −5.987 | 1.00 | 32.24 |
| ATOM | 338 | CA | LYS | 84 | 43.429 | 46.045 | −7.269 | 1.00 | 34.04 |
| ATOM | 339 | CB | LYS | 84 | 42.876 | 47.412 | −7.724 | 1.00 | 33.44 |
| ATOM | 340 | CG | LYS | 84 | 42.205 | 47.366 | −9.097 | 1.00 | 35.85 |
| ATOM | 341 | CD | LYS | 84 | 41.943 | 48.771 | −9.662 | 1.00 | 35.52 |
| ATOM | 342 | CE | LYS | 84 | 43.184 | 49.337 | −10.340 | 1.00 | 38.91 |
| ATOM | 343 | NZ | LYS | 84 | 42.937 | 50.682 | −10.983 | 1.00 | 44.21 |
| ATOM | 344 | C | LYS | 84 | 44.297 | 45.400 | −8.362 | 1.00 | 33.50 |
| ATOM | 345 | O | LYS | 84 | 43.944 | 44.342 | −8.931 | 1.00 | 35.57 |

TABLE 4-continued

| | | | | | | | | |
|---|---|---|---|---|---|---|---|---|
| ATOM | 346 | N | LEU | 85 | 45.467 | 45.985 | −8.600 | 1.00 | 33.06 |
| ATOM | 347 | CA | LEU | 85 | 46.408 | 45.469 | −9.610 | 1.00 | 33.43 |
| ATOM | 348 | CB | LEU | 85 | 47.564 | 46.434 | −9.762 | 1.00 | 32.74 |
| ATOM | 349 | CG | LEU | 85 | 47.200 | 47.851 | −10.221 | 1.00 | 36.78 |
| ATOM | 350 | CD1 | LEU | 85 | 48.510 | 48.740 | −10.365 | 1.00 | 37.48 |
| ATOM | 351 | CD2 | LEU | 85 | 46.485 | 47.778 | −11.561 | 1.00 | 38.46 |
| ATOM | 352 | C | LEU | 85 | 46.909 | 44.105 | −9.187 | 1.00 | 33.59 |
| ATOM | 353 | O | LEU | 85 | 47.030 | 43.181 | −9.976 | 1.00 | 33.78 |
| ATOM | 354 | N | TYR | 86 | 47.188 | 43.969 | −7.901 | 1.00 | 33.33 |
| ATOM | 355 | CA | TYR | 86 | 47.644 | 42.673 | −7.427 | 1.00 | 32.84 |
| ATOM | 356 | CB | TYR | 86 | 48.059 | 42.760 | −5.941 | 1.00 | 32.11 |
| ATOM | 357 | CG | TYR | 86 | 48.309 | 41.413 | −5.307 | 1.00 | 31.82 |
| ATOM | 358 | CD1 | TYR | 86 | 49.426 | 40.641 | −5.667 | 1.00 | 28.59 |
| ATOM | 359 | CE1 | TYR | 86 | 49.653 | 39.402 | −5.081 | 1.00 | 32.86 |
| ATOM | 360 | CZ | TYR | 86 | 48.743 | 38.917 | −4.119 | 1.00 | 31.37 |
| ATOM | 361 | OH | TYR | 86 | 48.919 | 37.697 | −3.545 | 1.00 | 30.97 |
| ATOM | 362 | CE2 | TYR | 86 | 47.642 | 39.664 | −3.744 | 1.00 | 31.22 |
| ATOM | 363 | CD2 | TYR | 86 | 47.420 | 40.904 | −4.336 | 1.00 | 31.02 |
| ATOM | 364 | C | TYR | 86 | 46.587 | 41.608 | −7.700 | 1.00 | 31.81 |
| ATOM | 365 | O | TYR | 86 | 46.886 | 40.527 | −8.229 | 1.00 | 31.35 |
| ATOM | 366 | N | LEU | 111 | 54.113 | 41.836 | 2.769 | 1.00 | 43.58 |
| ATOM | 367 | CA | LEU | 111 | 54.071 | 43.276 | 2.434 | 1.00 | 43.00 |
| ATOM | 368 | CB | LEU | 111 | 52.858 | 43.625 | 1.544 | 1.00 | 43.28 |
| ATOM | 369 | CG | LEU | 111 | 52.691 | 45.130 | 1.294 | 1.00 | 42.64 |
| ATOM | 370 | CD1 | LEU | 111 | 53.761 | 45.690 | 0.369 | 1.00 | 42.17 |
| ATOM | 371 | CD2 | LEU | 111 | 51.317 | 45.494 | 0.772 | 1.00 | 42.29 |
| ATOM | 372 | C | LEU | 111 | 54.017 | 44.196 | 3.634 | 1.00 | 43.22 |
| ATOM | 373 | O | LEU | 111 | 54.622 | 45.256 | 3.629 | 1.00 | 42.68 |
| ATOM | 374 | N | MET | 112 | 53.223 | 43.821 | 4.637 | 1.00 | 43.26 |
| ATOM | 375 | CA | MET | 112 | 52.789 | 44.785 | 5.652 | 1.00 | 42.80 |
| ATOM | 376 | CB | MET | 112 | 51.264 | 44.808 | 5.725 | 1.00 | 42.78 |
| ATOM | 377 | CG | MET | 112 | 50.541 | 45.465 | 4.554 | 1.00 | 43.72 |
| ATOM | 378 | SD | MET | 112 | 48.784 | 45.254 | 4.869 | 1.00 | 44.73 |
| ATOM | 379 | CE | MET | 112 | 48.601 | 46.880 | 5.462 | 1.00 | 41.27 |
| ATOM | 380 | C | MET | 112 | 53.285 | 44.544 | 7.058 | 1.00 | 42.07 |
| ATOM | 381 | O | MET | 112 | 53.305 | 45.487 | 7.868 | 1.00 | 41.71 |
| ATOM | 382 | N | ASP | 113 | 53.594 | 43.285 | 7.370 | 1.00 | 41.30 |
| ATOM | 383 | CA | ASP | 113 | 53.843 | 42.864 | 8.771 | 1.00 | 40.65 |
| ATOM | 384 | CB | ASP | 113 | 55.168 | 43.478 | 9.282 | 1.00 | 41.44 |
| ATOM | 385 | CG | ASP | 113 | 55.944 | 42.558 | 10.253 | 1.00 | 46.21 |
| ATOM | 386 | OD1 | ASP | 113 | 57.182 | 42.801 | 10.359 | 1.00 | 50.69 |
| ATOM | 387 | OD2 | ASP | 113 | 55.358 | 41.618 | 10.891 | 1.00 | 46.74 |
| ATOM | 388 | C | ASP | 113 | 52.666 | 43.322 | 9.673 | 1.00 | 37.65 |
| ATOM | 389 | O | ASP | 113 | 52.869 | 44.128 | 10.616 | 1.00 | 36.01 |
| ATOM | 390 | N | PRO | 114 | 51.423 | 42.828 | 9.379 | 1.00 | 35.49 |
| ATOM | 391 | CA | PRO | 114 | 50.279 | 43.411 | 10.115 | 1.00 | 33.37 |
| ATOM | 392 | CB | PRO | 114 | 49.089 | 42.995 | 9.272 | 1.00 | 33.16 |
| ATOM | 393 | CG | PRO | 114 | 49.540 | 41.620 | 8.715 | 1.00 | 33.41 |
| ATOM | 394 | CD | PRO | 114 | 51.008 | 41.749 | 8.463 | 1.00 | 34.28 |
| ATOM | 395 | C | PRO | 114 | 50.167 | 42.805 | 11.510 | 1.00 | 31.89 |
| ATOM | 396 | O | PRO | 114 | 50.801 | 41.778 | 11.763 | 1.00 | 30.70 |
| ATOM | 397 | N | ARG | 115 | 49.317 | 43.355 | 12.391 | 1.00 | 30.43 |
| ATOM | 398 | CA | ARG | 115 | 49.122 | 42.666 | 13.688 | 1.00 | 28.80 |
| ATOM | 399 | CB | ARG | 115 | 48.524 | 43.607 | 14.696 | 1.00 | 27.24 |
| ATOM | 400 | CG | ARG | 115 | 49.480 | 44.797 | 14.854 | 1.00 | 28.13 |
| ATOM | 401 | CD | ARG | 115 | 49.021 | 45.829 | 15.821 | 1.00 | 30.24 |
| ATOM | 402 | NE | ARG | 115 | 49.994 | 46.913 | 15.837 | 1.00 | 31.62 |
| ATOM | 403 | CZ | ARG | 115 | 49.711 | 48.175 | 16.086 | 1.00 | 33.29 |
| ATOM | 404 | NH1 | ARG | 115 | 48.461 | 48.531 | 16.364 | 1.00 | 33.08 |
| ATOM | 405 | NH2 | ARG | 115 | 50.682 | 49.072 | 16.033 | 1.00 | 32.97 |
| ATOM | 406 | C | ARG | 115 | 48.286 | 41.422 | 13.479 | 1.00 | 29.25 |
| ATOM | 407 | O | ARG | 115 | 48.535 | 40.356 | 14.063 | 1.00 | 28.81 |
| ATOM | 408 | N | TYR | 116 | 47.261 | 41.579 | 12.632 | 1.00 | 28.80 |
| ATOM | 409 | CA | TYR | 116 | 46.279 | 40.564 | 12.365 | 1.00 | 27.69 |
| ATOM | 410 | CB | TYR | 116 | 45.077 | 40.781 | 13.272 | 1.00 | 27.92 |
| ATOM | 411 | CG | TYR | 116 | 43.940 | 39.808 | 12.956 | 1.00 | 26.63 |
| ATOM | 412 | CD1 | TYR | 116 | 44.018 | 38.483 | 13.349 | 1.00 | 26.72 |
| ATOM | 413 | CE1 | TYR | 116 | 43.057 | 37.585 | 13.021 | 1.00 | 25.07 |
| ATOM | 414 | CZ | TYR | 116 | 41.991 | 38.002 | 12.258 | 1.00 | 27.65 |
| ATOM | 415 | OH | TYR | 116 | 41.005 | 37.103 | 11.955 | 1.00 | 30.89 |
| ATOM | 416 | CE2 | TYR | 116 | 41.884 | 39.315 | 11.852 | 1.00 | 26.17 |
| ATOM | 417 | CD2 | TYR | 116 | 42.860 | 40.195 | 12.171 | 1.00 | 26.32 |
| ATOM | 418 | C | TYR | 116 | 45.836 | 40.759 | 10.910 | 1.00 | 28.81 |
| ATOM | 419 | O | TYR | 116 | 45.688 | 41.914 | 10.448 | 1.00 | 28.65 |
| ATOM | 420 | N | ILE | 117 | 45.556 | 39.657 | 10.218 | 1.00 | 28.31 |
| ATOM | 421 | CA | ILE | 117 | 44.857 | 39.710 | 8.943 | 1.00 | 28.27 |
| ATOM | 422 | CB | ILE | 117 | 45.844 | 40.005 | 7.796 | 1.00 | 29.22 |
| ATOM | 423 | CG1 | ILE | 117 | 45.158 | 40.028 | 6.410 | 1.00 | 27.24 |
| ATOM | 424 | CD1 | ILE | 117 | 46.196 | 40.353 | 5.327 | 1.00 | 27.68 |
| ATOM | 425 | CG2 | ILE | 117 | 47.049 | 39.010 | 7.845 | 1.00 | 27.47 |

TABLE 4-continued

| | | | | | | | | |
|---|---|---|---|---|---|---|---|---|
| ATOM | 426 | C | ILE | 117 | 44.092 | 38.433 | 8.690 | 1.00 | 28.02 |
| ATOM | 427 | O | ILE | 117 | 44.490 | 37.377 | 9.151 | 1.00 | 27.51 |
| ATOM | 428 | N | GLU | 118 | 42.965 | 38.543 | 7.989 | 1.00 | 27.06 |
| ATOM | 429 | CA | GLU | 118 | 42.201 | 37.395 | 7.553 | 1.00 | 27.80 |
| ATOM | 430 | CB | GLU | 118 | 40.984 | 37.159 | 8.436 | 1.00 | 27.26 |
| ATOM | 431 | CG | GLU | 118 | 39.996 | 38.325 | 8.524 | 1.00 | 25.50 |
| ATOM | 432 | CD | GLU | 118 | 38.796 | 38.015 | 9.431 | 1.00 | 30.75 |
| ATOM | 433 | OE1 | GLU | 118 | 38.938 | 37.361 | 10.503 | 1.00 | 35.47 |
| ATOM | 434 | OE2 | GLU | 118 | 37.676 | 38.411 | 9.076 | 1.00 | 34.71 |
| ATOM | 435 | C | GLU | 118 | 41.752 | 37.632 | 6.100 | 1.00 | 28.42 |
| ATOM | 436 | O | GLU | 118 | 41.593 | 38.755 | 5.666 | 1.00 | 28.14 |
| ATOM | 437 | N | VAL | 119 | 41.540 | 36.550 | 5.373 | 1.00 | 28.92 |
| ATOM | 438 | CA | VAL | 119 | 41.110 | 36.581 | 3.987 | 1.00 | 28.21 |
| ATOM | 439 | CB | VAL | 119 | 42.310 | 36.233 | 3.005 | 1.00 | 29.07 |
| ATOM | 440 | CG1 | VAL | 119 | 41.841 | 36.310 | 1.510 | 1.00 | 28.56 |
| ATOM | 441 | CG2 | VAL | 119 | 43.463 | 37.228 | 3.208 | 1.00 | 27.52 |
| ATOM | 442 | C | VAL | 119 | 40.054 | 35.513 | 3.894 | 1.00 | 27.80 |
| ATOM | 443 | O | VAL | 119 | 40.354 | 34.336 | 4.158 | 1.00 | 27.72 |
| ATOM | 444 | O6 | GDQ | 201 | 41.711 | 55.587 | 1.265 | 1.00 | 47.86 |
| ATOM | 445 | C6 | GDQ | 201 | 42.655 | 54.798 | 0.686 | 1.00 | 49.13 |
| ATOM | 446 | N1 | GDQ | 201 | 43.162 | 53.755 | 1.386 | 1.00 | 48.48 |
| ATOM | 447 | C5 | GDQ | 201 | 43.114 | 55.030 | −0.629 | 1.00 | 50.29 |
| ATOM | 448 | C7 | GDQ | 201 | 42.895 | 55.934 | −1.676 | 1.00 | 49.19 |
| ATOM | 449 | C77 | GDQ | 201 | 42.018 | 56.941 | −1.586 | 1.00 | 49.79 |
| ATOM | 450 | N77 | GDQ | 201 | 41.272 | 57.892 | −1.409 | 1.00 | 52.99 |
| ATOM | 451 | C8 | GDQ | 201 | 43.665 | 55.676 | −2.796 | 1.00 | 48.54 |
| ATOM | 452 | N9 | GDQ | 201 | 44.390 | 54.565 | −2.444 | 1.00 | 49.38 |
| ATOM | 453 | C4 | GDQ | 201 | 44.083 | 54.188 | −1.156 | 1.00 | 49.87 |
| ATOM | 454 | N3 | GDQ | 201 | 44.571 | 53.140 | −0.425 | 1.00 | 49.70 |
| ATOM | 455 | C2 | GDQ | 201 | 44.090 | 52.944 | 0.845 | 1.00 | 48.62 |
| ATOM | 456 | N2 | GDQ | 201 | 44.543 | 51.925 | 1.604 | 1.00 | 49.10 |
| ATOM | 457 | N | PHE | 47 | 24.748 | 57.709 | 15.494 | 1.00 | 42.64 |
| ATOM | 458 | CA | PHE | 47 | 24.653 | 58.672 | 14.418 | 1.00 | 44.82 |
| ATOM | 459 | CB | PHE | 47 | 25.629 | 59.823 | 14.648 | 1.00 | 46.09 |
| ATOM | 460 | CG | PHE | 47 | 25.432 | 60.987 | 13.713 | 1.00 | 49.93 |
| ATOM | 461 | CD1 | PHE | 47 | 26.233 | 61.127 | 12.566 | 1.00 | 53.12 |
| ATOM | 462 | CE1 | PHE | 47 | 26.050 | 62.220 | 11.663 | 1.00 | 52.76 |
| ATOM | 463 | CZ | PHE | 47 | 25.072 | 63.167 | 11.905 | 1.00 | 51.25 |
| ATOM | 464 | CE2 | PHE | 47 | 24.250 | 63.045 | 13.045 | 1.00 | 53.53 |
| ATOM | 465 | CD2 | PHE | 47 | 24.440 | 61.954 | 13.959 | 1.00 | 52.47 |
| ATOM | 466 | C | PHE | 47 | 24.971 | 57.931 | 13.129 | 1.00 | 45.33 |
| ATOM | 467 | O | PHE | 47 | 25.880 | 57.111 | 13.093 | 1.00 | 45.63 |
| ATOM | 468 | N | ASN | 48 | 24.171 | 58.162 | 12.092 | 1.00 | 46.34 |
| ATOM | 469 | CA | ASN | 48 | 24.371 | 57.567 | 10.762 | 1.00 | 47.16 |
| ATOM | 470 | CB | ASN | 48 | 23.110 | 56.730 | 10.478 | 1.00 | 48.74 |
| ATOM | 471 | CG | ASN | 48 | 23.006 | 56.191 | 9.044 | 1.00 | 55.54 |
| ATOM | 472 | OD1 | ASN | 48 | 23.561 | 56.742 | 8.070 | 1.00 | 62.83 |
| ATOM | 473 | ND2 | ASN | 48 | 22.236 | 55.102 | 8.904 | 1.00 | 60.32 |
| ATOM | 474 | C | ASN | 48 | 24.556 | 58.753 | 9.804 | 1.00 | 46.29 |
| ATOM | 475 | O | ASN | 48 | 23.686 | 59.619 | 9.735 | 1.00 | 45.40 |
| ATOM | 476 | N | CYS | 49 | 25.707 | 58.845 | 9.129 | 1.00 | 45.76 |
| ATOM | 477 | CA | CYS | 49 | 25.872 | 59.817 | 8.052 | 1.00 | 44.56 |
| ATOM | 478 | CB | CYS | 49 | 27.024 | 60.819 | 8.285 | 1.00 | 45.57 |
| ATOM | 479 | SG | CYS | 49 | 27.070 | 62.196 | 6.974 | 1.00 | 49.46 |
| ATOM | 480 | C | CYS | 49 | 26.048 | 59.202 | 6.668 | 1.00 | 43.45 |
| ATOM | 481 | O | CYS | 49 | 27.163 | 58.857 | 6.274 | 1.00 | 43.60 |
| ATOM | 482 | N | PRO | 50 | 24.963 | 59.146 | 5.882 | 1.00 | 42.35 |
| ATOM | 483 | CA | PRO | 50 | 25.097 | 58.598 | 4.533 | 1.00 | 41.90 |
| ATOM | 484 | CB | PRO | 50 | 23.664 | 58.171 | 4.210 | 1.00 | 41.25 |
| ATOM | 485 | CG | PRO | 50 | 22.830 | 59.231 | 4.910 | 1.00 | 41.28 |
| ATOM | 486 | CD | PRO | 50 | 23.586 | 59.594 | 6.169 | 1.00 | 41.52 |
| ATOM | 487 | C | PRO | 50 | 25.651 | 59.620 | 3.490 | 1.00 | 41.74 |
| ATOM | 488 | O | PRO | 50 | 25.928 | 59.256 | 2.361 | 1.00 | 42.38 |
| ATOM | 489 | N | GLU | 51 | 25.825 | 60.874 | 3.872 | 1.00 | 41.81 |
| ATOM | 490 | CA | GLU | 51 | 26.254 | 61.920 | 2.924 | 1.00 | 43.19 |
| ATOM | 491 | CB | GLU | 51 | 25.401 | 63.179 | 3.143 | 1.00 | 42.86 |
| ATOM | 492 | CG | GLU | 51 | 23.920 | 62.947 | 2.943 | 1.00 | 46.45 |
| ATOM | 493 | CD | GLU | 51 | 23.044 | 64.162 | 3.342 | 1.00 | 49.54 |
| ATOM | 494 | OE1 | GLU | 51 | 23.559 | 65.321 | 3.470 | 1.00 | 57.83 |
| ATOM | 495 | OE2 | GLU | 51 | 21.813 | 63.965 | 3.523 | 1.00 | 55.89 |
| ATOM | 496 | C | GLU | 51 | 27.736 | 62.298 | 3.017 | 1.00 | 40.52 |
| ATOM | 497 | O | GLU | 51 | 28.123 | 63.433 | 2.672 | 1.00 | 40.28 |
| ATOM | 498 | N | PHE | 52 | 28.587 | 61.364 | 3.463 | 1.00 | 37.78 |
| ATOM | 499 | CA | PHE | 52 | 29.963 | 61.756 | 3.731 | 1.00 | 34.29 |
| ATOM | 500 | CB | PHE | 52 | 30.692 | 60.800 | 4.699 | 1.00 | 32.48 |
| ATOM | 501 | CG | PHE | 52 | 32.101 | 61.217 | 4.973 | 1.00 | 31.39 |
| ATOM | 502 | CD1 | PHE | 52 | 32.382 | 62.243 | 5.899 | 1.00 | 27.24 |
| ATOM | 503 | CE1 | PHE | 52 | 33.713 | 62.616 | 6.147 | 1.00 | 28.62 |
| ATOM | 504 | CZ | PHE | 52 | 34.756 | 62.011 | 5.478 | 1.00 | 28.64 |
| ATOM | 505 | CE2 | PHE | 52 | 34.497 | 61.009 | 4.556 | 1.00 | 30.54 |

TABLE 4-continued

| | | | | | | | | |
|---|---|---|---|---|---|---|---|---|
| ATOM | 506 | CD2 | PHE | 52 | 33.163 | 60.621 | 4.291 | 1.00 | 29.35 |
| ATOM | 507 | C | PHE | 52 | 30.718 | 61.798 | 2.456 | 1.00 | 33.27 |
| ATOM | 508 | O | PHE | 52 | 30.651 | 60.834 | 1.701 | 1.00 | 33.06 |
| ATOM | 509 | N | THR | 53 | 31.504 | 62.855 | 2.236 | 1.00 | 32.76 |
| ATOM | 510 | CA | THR | 53 | 32.458 | 62.849 | 1.081 | 1.00 | 32.32 |
| ATOM | 511 | CB | THR | 53 | 31.821 | 63.443 | −0.290 | 1.00 | 31.64 |
| ATOM | 512 | OG1 | THR | 53 | 32.789 | 63.360 | −1.338 | 1.00 | 27.58 |
| ATOM | 513 | CG2 | THR | 53 | 31.444 | 64.894 | −0.121 | 1.00 | 28.54 |
| ATOM | 514 | C | THR | 53 | 33.731 | 63.608 | 1.368 | 1.00 | 32.59 |
| ATOM | 515 | O | THR | 53 | 33.683 | 64.620 | 2.017 | 1.00 | 33.75 |
| ATOM | 516 | N | SER | 54 | 34.843 | 63.144 | 0.838 | 1.00 | 33.72 |
| ATOM | 517 | CA | SER | 54 | 36.103 | 63.901 | 0.919 | 1.00 | 35.85 |
| ATOM | 518 | CB | SER | 54 | 36.819 | 63.538 | 2.216 | 1.00 | 35.22 |
| ATOM | 519 | OG | SER | 54 | 37.442 | 62.291 | 2.057 | 1.00 | 33.77 |
| ATOM | 520 | C | SER | 54 | 37.053 | 63.654 | −0.273 | 1.00 | 37.39 |
| ATOM | 521 | O | SER | 54 | 36.669 | 63.061 | −1.267 | 1.00 | 37.18 |
| ATOM | 522 | N | LEU | 55 | 38.306 | 64.067 | −0.153 | 1.00 | 40.28 |
| ATOM | 523 | CA | LEU | 55 | 39.246 | 63.973 | −1.271 | 1.00 | 43.35 |
| ATOM | 524 | CB | LEU | 55 | 39.790 | 65.389 | −1.639 | 1.00 | 42.47 |
| ATOM | 525 | CG | LEU | 55 | 38.779 | 66.527 | −1.992 | 1.00 | 40.35 |
| ATOM | 526 | CD1 | LEU | 55 | 39.432 | 67.854 | −2.503 | 1.00 | 33.89 |
| ATOM | 527 | CD2 | LEU | 55 | 37.749 | 66.059 | −3.012 | 1.00 | 37.65 |
| ATOM | 528 | C | LEU | 55 | 40.387 | 62.949 | −1.077 | 1.00 | 46.35 |
| ATOM | 529 | O | LEU | 55 | 41.053 | 62.952 | −0.047 | 1.00 | 47.81 |
| ATOM | 530 | N | CYS | 56 | 40.606 | 62.082 | −2.065 | 1.00 | 49.44 |
| ATOM | 531 | CA | CYS | 56 | 41.812 | 61.255 | −2.156 | 1.00 | 51.70 |
| ATOM | 532 | CB | CYS | 56 | 41.761 | 60.468 | −3.456 | 1.00 | 52.04 |
| ATOM | 533 | SG | CYS | 56 | 43.273 | 59.627 | −3.936 | 1.00 | 52.43 |
| ATOM | 534 | C | CYS | 56 | 43.076 | 62.138 | −2.109 | 1.00 | 53.76 |
| ATOM | 535 | O | CYS | 56 | 43.222 | 63.072 | −2.912 | 1.00 | 54.33 |
| ATOM | 536 | N | PRO | 57 | 44.007 | 61.871 | −1.168 | 1.00 | 55.15 |
| ATOM | 537 | CA | PRO | 57 | 44.991 | 62.955 | −0.924 | 1.00 | 56.01 |
| ATOM | 538 | CB | PRO | 57 | 45.697 | 62.527 | 0.380 | 1.00 | 55.67 |
| ATOM | 539 | CG | PRO | 57 | 45.586 | 61.045 | 0.398 | 1.00 | 55.68 |
| ATOM | 540 | CD | PRO | 57 | 44.282 | 60.674 | −0.351 | 1.00 | 55.25 |
| ATOM | 541 | C | PRO | 57 | 45.996 | 63.136 | −2.078 | 1.00 | 56.80 |
| ATOM | 542 | O | PRO | 57 | 46.605 | 64.202 | −2.208 | 1.00 | 56.61 |
| ATOM | 543 | N | LYS | 58 | 46.140 | 62.106 | −2.907 | 1.00 | 57.84 |
| ATOM | 544 | CA | LYS | 58 | 47.090 | 62.142 | −4.001 | 1.00 | 59.47 |
| ATOM | 545 | CB | LYS | 58 | 47.617 | 60.736 | −4.319 | 1.00 | 60.28 |
| ATOM | 546 | CG | LYS | 58 | 48.963 | 60.394 | −3.612 | 1.00 | 63.29 |
| ATOM | 547 | CD | LYS | 58 | 48.838 | 60.317 | −2.055 | 1.00 | 64.69 |
| ATOM | 548 | CE | LYS | 58 | 50.195 | 60.109 | −1.350 | 1.00 | 64.11 |
| ATOM | 549 | NZ | LYS | 58 | 51.077 | 59.195 | −2.131 | 1.00 | 64.02 |
| ATOM | 550 | C | LYS | 58 | 46.506 | 62.806 | −5.243 | 1.00 | 59.38 |
| ATOM | 551 | O | LYS | 58 | 47.079 | 63.771 | −5.788 | 1.00 | 59.15 |
| ATOM | 552 | N | VAL | 59 | 45.350 | 62.315 | −5.677 | 1.00 | 59.37 |
| ATOM | 553 | CA | VAL | 59 | 44.815 | 62.758 | −6.958 | 1.00 | 58.99 |
| ATOM | 554 | CB | VAL | 59 | 44.311 | 61.581 | −7.754 | 1.00 | 59.24 |
| ATOM | 555 | CG1 | VAL | 59 | 43.119 | 60.971 | −7.073 | 1.00 | 58.19 |
| ATOM | 556 | CG2 | VAL | 59 | 44.010 | 62.018 | −9.217 | 1.00 | 62.18 |
| ATOM | 557 | C | VAL | 59 | 43.745 | 63.844 | −6.834 | 1.00 | 57.82 |
| ATOM | 558 | O | VAL | 59 | 43.519 | 64.603 | −7.770 | 1.00 | 57.80 |
| ATOM | 559 | N | GLY | 60 | 43.106 | 63.927 | −5.675 | 1.00 | 56.74 |
| ATOM | 560 | CA | GLY | 60 | 42.031 | 64.898 | −5.462 | 1.00 | 55.41 |
| ATOM | 561 | C | GLY | 60 | 40.695 | 64.428 | −6.022 | 1.00 | 54.46 |
| ATOM | 562 | O | GLY | 60 | 39.750 | 65.213 | −6.072 | 1.00 | 54.71 |
| ATOM | 563 | N | GLN | 61 | 40.649 | 63.170 | −6.481 | 1.00 | 53.28 |
| ATOM | 564 | CA | GLN | 61 | 39.426 | 62.434 | −6.817 | 1.00 | 52.84 |
| ATOM | 565 | CB | GLN | 61 | 39.795 | 61.008 | −7.308 | 1.00 | 53.00 |
| ATOM | 566 | CG | GLN | 61 | 39.637 | 59.850 | −6.212 | 1.00 | 56.57 |
| ATOM | 567 | CD | GLN | 61 | 40.586 | 58.590 | −6.338 | 1.00 | 57.11 |
| ATOM | 568 | OE1 | GLN | 61 | 40.212 | 57.469 | −5.921 | 1.00 | 59.50 |
| ATOM | 569 | NE2 | GLN | 61 | 41.813 | 58.788 | −6.871 | 1.00 | 60.79 |
| ATOM | 570 | C | GLN | 61 | 38.591 | 62.342 | −5.533 | 1.00 | 49.52 |
| ATOM | 571 | O | GLN | 61 | 39.126 | 62.015 | −4.516 | 1.00 | 50.07 |
| ATOM | 572 | N | PRO | 62 | 37.300 | 62.689 | −5.567 | 1.00 | 47.30 |
| ATOM | 573 | CA | PRO | 62 | 36.410 | 62.522 | −4.419 | 1.00 | 44.65 |
| ATOM | 574 | CB | PRO | 62 | 35.121 | 63.205 | −4.868 | 1.00 | 44.86 |
| ATOM | 575 | CG | PRO | 62 | 35.494 | 64.078 | −6.008 | 1.00 | 46.60 |
| ATOM | 576 | CD | PRO | 62 | 36.602 | 63.328 | −6.703 | 1.00 | 47.39 |
| ATOM | 577 | C | PRO | 62 | 36.084 | 61.075 | −4.034 | 1.00 | 43.08 |
| ATOM | 578 | O | PRO | 62 | 36.215 | 60.142 | −4.836 | 1.00 | 42.60 |
| ATOM | 579 | N | ASP | 63 | 35.676 | 60.898 | −2.781 | 1.00 | 40.37 |
| ATOM | 580 | CA | ASP | 63 | 35.348 | 59.576 | −2.252 | 1.00 | 38.69 |
| ATOM | 581 | CB | ASP | 63 | 36.469 | 59.026 | −1.373 | 1.00 | 39.74 |
| ATOM | 582 | CG | ASP | 63 | 37.806 | 58.839 | −2.153 | 1.00 | 47.72 |
| ATOM | 583 | OD1 | ASP | 63 | 37.762 | 58.395 | −3.365 | 1.00 | 52.82 |
| ATOM | 584 | OD2 | ASP | 63 | 38.894 | 59.139 | −1.526 | 1.00 | 51.42 |
| ATOM | 585 | C | ASP | 63 | 34.080 | 59.752 | −1.452 | 1.00 | 34.25 |

TABLE 4-continued

| | | | | | | | | | |
|---|---|---|---|---|---|---|---|---|---|
| ATOM | 586 | O | ASP | 63 | 33.769 | 60.855 | −1.088 | 1.00 | 33.24 |
| ATOM | 587 | N | PHE | 64 | 33.334 | 58.678 | −1.243 | 1.00 | 31.02 |
| ATOM | 588 | CA | PHE | 64 | 32.000 | 58.795 | −0.653 | 1.00 | 29.15 |
| ATOM | 589 | CB | PHE | 64 | 30.906 | 58.806 | −1.736 | 1.00 | 27.83 |
| ATOM | 590 | CG | PHE | 64 | 31.077 | 59.940 | −2.741 | 1.00 | 28.44 |
| ATOM | 591 | CD1 | PHE | 64 | 32.039 | 59.845 | −3.745 | 1.00 | 26.72 |
| ATOM | 592 | CE1 | PHE | 64 | 32.245 | 60.891 | −4.639 | 1.00 | 30.21 |
| ATOM | 593 | CZ | PHE | 64 | 31.471 | 62.047 | −4.542 | 1.00 | 30.36 |
| ATOM | 594 | CE2 | PHE | 64 | 30.484 | 62.150 | −3.555 | 1.00 | 29.14 |
| ATOM | 595 | CD2 | PHE | 64 | 30.293 | 61.092 | −2.661 | 1.00 | 27.23 |
| ATOM | 596 | C | PHE | 64 | 31.819 | 57.655 | 0.320 | 1.00 | 28.21 |
| ATOM | 597 | O | PHE | 64 | 32.354 | 56.597 | 0.092 | 1.00 | 27.97 |
| ATOM | 598 | N | ALA | 65 | 31.033 | 57.865 | 1.368 | 1.00 | 28.63 |
| ATOM | 599 | CA | ALA | 65 | 30.889 | 56.873 | 2.444 | 1.00 | 28.95 |
| ATOM | 600 | CB | ALA | 65 | 32.079 | 56.937 | 3.410 | 1.00 | 28.11 |
| ATOM | 601 | C | ALA | 65 | 29.657 | 57.143 | 3.208 | 1.00 | 28.84 |
| ATOM | 602 | O | ALA | 65 | 29.168 | 58.269 | 3.237 | 1.00 | 26.69 |
| ATOM | 603 | N | THR | 66 | 29.151 | 56.085 | 3.827 | 1.00 | 30.26 |
| ATOM | 604 | CA | THR | 66 | 28.236 | 56.164 | 4.966 | 1.00 | 31.54 |
| ATOM | 605 | CB | THR | 66 | 27.240 | 54.998 | 4.911 | 1.00 | 31.74 |
| ATOM | 606 | OG1 | THR | 66 | 26.496 | 55.042 | 3.671 | 1.00 | 35.61 |
| ATOM | 607 | CG2 | THR | 66 | 26.210 | 55.073 | 6.044 | 1.00 | 34.49 |
| ATOM | 608 | C | THR | 66 | 29.154 | 56.036 | 6.235 | 1.00 | 32.82 |
| ATOM | 609 | O | THR | 66 | 30.132 | 55.231 | 6.263 | 1.00 | 33.44 |
| ATOM | 610 | N | ILE | 67 | 28.864 | 56.814 | 7.275 | 1.00 | 32.52 |
| ATOM | 611 | CA | ILE | 67 | 29.676 | 56.763 | 8.488 | 1.00 | 32.91 |
| ATOM | 612 | CB | ILE | 67 | 30.507 | 58.066 | 8.712 | 1.00 | 33.60 |
| ATOM | 613 | CG1 | ILE | 67 | 31.514 | 58.191 | 7.578 | 1.00 | 34.09 |
| ATOM | 614 | CD1 | ILE | 67 | 32.413 | 59.380 | 7.667 | 1.00 | 36.00 |
| ATOM | 615 | CG2 | ILE | 67 | 31.333 | 57.972 | 10.013 | 1.00 | 35.22 |
| ATOM | 616 | C | ILE | 67 | 28.806 | 56.441 | 9.655 | 1.00 | 33.06 |
| ATOM | 617 | O | ILE | 67 | 27.748 | 57.047 | 9.850 | 1.00 | 32.31 |
| ATOM | 618 | N | TYR | 68 | 29.204 | 55.432 | 10.412 | 1.00 | 33.27 |
| ATOM | 619 | CA | TYR | 68 | 28.418 | 55.086 | 11.589 | 1.00 | 34.99 |
| ATOM | 620 | CB | TYR | 68 | 28.043 | 53.606 | 11.604 | 1.00 | 36.66 |
| ATOM | 621 | CG | TYR | 68 | 27.316 | 53.169 | 10.342 | 1.00 | 41.76 |
| ATOM | 622 | CD1 | TYR | 68 | 28.029 | 52.743 | 9.194 | 1.00 | 46.27 |
| ATOM | 623 | CE1 | TYR | 68 | 27.353 | 52.355 | 8.032 | 1.00 | 46.31 |
| ATOM | 624 | CZ | TYR | 68 | 25.936 | 52.285 | 8.019 | 1.00 | 45.46 |
| ATOM | 625 | OH | TYR | 68 | 25.231 | 52.014 | 6.905 | 1.00 | 44.17 |
| ATOM | 626 | CE2 | TYR | 68 | 25.218 | 52.793 | 9.120 | 1.00 | 46.56 |
| ATOM | 627 | CD2 | TYR | 68 | 25.914 | 53.192 | 10.283 | 1.00 | 46.33 |
| ATOM | 628 | C | TYR | 68 | 29.280 | 55.404 | 12.765 | 1.00 | 33.70 |
| ATOM | 629 | O | TYR | 68 | 30.406 | 54.898 | 12.853 | 1.00 | 33.44 |
| ATOM | 630 | N | ILE | 69 | 28.738 | 56.238 | 13.643 | 1.00 | 33.19 |
| ATOM | 631 | CA | ILE | 69 | 29.353 | 56.678 | 14.901 | 1.00 | 33.81 |
| ATOM | 632 | CB | ILE | 69 | 29.583 | 58.209 | 14.941 | 1.00 | 34.25 |
| ATOM | 633 | CG1 | ILE | 69 | 30.455 | 58.642 | 13.761 | 1.00 | 32.07 |
| ATOM | 634 | CD1 | ILE | 69 | 30.439 | 60.107 | 13.474 | 1.00 | 31.28 |
| ATOM | 635 | CG2 | ILE | 69 | 30.238 | 58.642 | 16.268 | 1.00 | 33.83 |
| ATOM | 636 | C | ILE | 69 | 28.434 | 56.295 | 16.043 | 1.00 | 34.48 |
| ATOM | 637 | O | ILE | 69 | 27.244 | 56.641 | 16.026 | 1.00 | 34.60 |
| ATOM | 638 | N | SER | 70 | 28.954 | 55.519 | 17.000 | 1.00 | 33.79 |
| ATOM | 639 | CA | SER | 70 | 28.201 | 55.275 | 18.224 | 1.00 | 33.74 |
| ATOM | 640 | CB | SER | 70 | 27.489 | 53.924 | 18.176 | 1.00 | 34.66 |
| ATOM | 641 | OG | SER | 70 | 28.367 | 52.990 | 17.639 | 1.00 | 39.20 |
| ATOM | 642 | C | SER | 70 | 29.097 | 55.360 | 19.442 | 1.00 | 32.64 |
| ATOM | 643 | O | SER | 70 | 30.231 | 54.880 | 19.417 | 1.00 | 31.72 |
| ATOM | 644 | N | TYR | 71 | 28.592 | 55.971 | 20.511 | 1.00 | 31.90 |
| ATOM | 645 | CA | TYR | 71 | 29.448 | 56.246 | 21.637 | 1.00 | 31.51 |
| ATOM | 646 | CB | TYR | 71 | 30.206 | 57.583 | 21.446 | 1.00 | 31.88 |
| ATOM | 647 | CG | TYR | 71 | 29.319 | 58.800 | 21.586 | 1.00 | 33.11 |
| ATOM | 648 | CD1 | TYR | 71 | 28.614 | 59.295 | 20.480 | 1.00 | 31.23 |
| ATOM | 649 | CE1 | TYR | 71 | 27.783 | 60.403 | 20.588 | 1.00 | 33.23 |
| ATOM | 650 | CZ | TYR | 71 | 27.624 | 61.035 | 21.803 | 1.00 | 35.49 |
| ATOM | 651 | OH | TYR | 71 | 26.798 | 62.123 | 21.854 | 1.00 | 34.71 |
| ATOM | 652 | CE2 | TYR | 71 | 28.309 | 60.568 | 22.971 | 1.00 | 34.63 |
| ATOM | 653 | CD2 | TYR | 71 | 29.165 | 59.457 | 22.837 | 1.00 | 33.54 |
| ATOM | 654 | C | TYR | 71 | 28.626 | 56.197 | 22.900 | 1.00 | 31.26 |
| ATOM | 655 | O | TYR | 71 | 27.415 | 56.312 | 22.841 | 1.00 | 30.18 |
| ATOM | 656 | N | HIS | 93 | 38.637 | 68.301 | 2.050 | 1.00 | 48.66 |
| ATOM | 657 | CA | HIS | 93 | 39.824 | 67.843 | 2.777 | 1.00 | 49.97 |
| ATOM | 658 | CB | HIS | 93 | 39.485 | 67.640 | 4.276 | 1.00 | 50.51 |
| ATOM | 659 | CG | HIS | 93 | 40.639 | 67.158 | 5.110 | 1.00 | 55.87 |
| ATOM | 660 | ND1 | HIS | 93 | 41.614 | 68.004 | 5.607 | 1.00 | 59.84 |
| ATOM | 661 | CE1 | HIS | 93 | 42.499 | 67.299 | 6.297 | 1.00 | 60.29 |
| ATOM | 662 | NE2 | HIS | 93 | 42.134 | 66.028 | 6.271 | 1.00 | 59.44 |
| ATOM | 663 | CD2 | HIS | 93 | 40.977 | 65.911 | 5.535 | 1.00 | 58.67 |
| ATOM | 664 | C | HIS | 93 | 40.375 | 66.561 | 2.159 | 1.00 | 49.75 |
| ATOM | 665 | O | HIS | 93 | 39.633 | 65.590 | 2.013 | 1.00 | 50.39 |

TABLE 4-continued

| | | | | | | | | |
|---|---|---|---|---|---|---|---|---|
| ATOM | 666 | N | GLY | 94 | 41.671 | 66.559 | 1.827 | 1.00 | 49.84 |
| ATOM | 667 | CA | GLY | 94 | 42.372 | 65.389 | 1.288 | 1.00 | 50.07 |
| ATOM | 668 | C | GLY | 94 | 43.027 | 64.463 | 2.323 | 1.00 | 50.90 |
| ATOM | 669 | O | GLY | 94 | 43.812 | 64.926 | 3.152 | 1.00 | 51.40 |
| ATOM | 670 | N | ASP | 95 | 42.707 | 63.164 | 2.279 | 1.00 | 50.78 |
| ATOM | 671 | CA | ASP | 95 | 43.227 | 62.155 | 3.230 | 1.00 | 51.06 |
| ATOM | 672 | CB | ASP | 95 | 42.885 | 62.511 | 4.700 | 1.00 | 51.78 |
| ATOM | 673 | CG | ASP | 95 | 44.115 | 63.025 | 5.487 | 1.00 | 54.65 |
| ATOM | 674 | OD1 | ASP | 95 | 44.011 | 64.089 | 6.170 | 1.00 | 56.70 |
| ATOM | 675 | OD2 | ASP | 95 | 45.198 | 62.381 | 5.384 | 1.00 | 56.05 |
| ATOM | 676 | C | ASP | 95 | 42.732 | 60.736 | 2.927 | 1.00 | 50.22 |
| ATOM | 677 | O | ASP | 95 | 41.741 | 60.554 | 2.228 | 1.00 | 50.07 |
| ATOM | 678 | N | PHE | 96 | 43.423 | 59.729 | 3.460 | 1.00 | 49.00 |
| ATOM | 679 | CA | PHE | 96 | 42.999 | 58.364 | 3.251 | 1.00 | 47.90 |
| ATOM | 680 | CB | PHE | 96 | 44.164 | 57.392 | 3.404 | 1.00 | 49.17 |
| ATOM | 681 | CG | PHE | 96 | 45.178 | 57.489 | 2.300 | 1.00 | 50.56 |
| ATOM | 682 | CD1 | PHE | 96 | 46.518 | 57.697 | 2.586 | 1.00 | 54.11 |
| ATOM | 683 | CE1 | PHE | 96 | 47.480 | 57.799 | 1.557 | 1.00 | 55.36 |
| ATOM | 684 | CZ | PHE | 96 | 47.075 | 57.693 | 0.236 | 1.00 | 54.61 |
| ATOM | 685 | CE2 | PHE | 96 | 45.738 | 57.495 | −0.060 | 1.00 | 53.40 |
| ATOM | 686 | CD2 | PHE | 96 | 44.794 | 57.395 | 0.972 | 1.00 | 52.58 |
| ATOM | 687 | C | PHE | 96 | 41.826 | 58.027 | 4.157 | 1.00 | 46.75 |
| ATOM | 688 | O | PHE | 96 | 41.531 | 58.753 | 5.124 | 1.00 | 45.40 |
| ATOM | 689 | N | HIS | 97 | 41.124 | 56.951 | 3.795 | 1.00 | 46.15 |
| ATOM | 690 | CA | HIS | 97 | 39.905 | 56.533 | 4.496 | 1.00 | 45.85 |
| ATOM | 691 | CB | HIS | 97 | 39.187 | 55.396 | 3.755 | 1.00 | 45.95 |
| ATOM | 692 | CG | HIS | 97 | 38.861 | 55.704 | 2.327 | 1.00 | 45.17 |
| ATOM | 693 | ND1 | HIS | 97 | 38.854 | 56.989 | 1.819 | 1.00 | 46.08 |
| ATOM | 694 | CE1 | HIS | 97 | 38.528 | 56.955 | 0.541 | 1.00 | 43.94 |
| ATOM | 695 | NE2 | HIS | 97 | 38.306 | 55.698 | 0.201 | 1.00 | 46.28 |
| ATOM | 696 | CD2 | HIS | 97 | 38.497 | 54.896 | 1.304 | 1.00 | 45.40 |
| ATOM | 697 | C | HIS | 97 | 40.198 | 56.085 | 5.924 | 1.00 | 45.79 |
| ATOM | 698 | O | HIS | 97 | 39.432 | 56.374 | 6.812 | 1.00 | 46.05 |
| ATOM | 699 | N | GLU | 98 | 41.313 | 55.400 | 6.129 | 1.00 | 45.84 |
| ATOM | 700 | CA | GLU | 98 | 41.702 | 54.909 | 7.448 | 1.00 | 46.85 |
| ATOM | 701 | CB | GLU | 98 | 42.908 | 54.003 | 7.297 | 1.00 | 46.16 |
| ATOM | 702 | CG | GLU | 98 | 42.687 | 52.810 | 6.377 | 1.00 | 46.72 |
| ATOM | 703 | CD | GLU | 98 | 42.950 | 53.077 | 4.891 | 1.00 | 45.68 |
| ATOM | 704 | OE1 | GLU | 98 | 42.561 | 54.175 | 4.377 | 1.00 | 44.22 |
| ATOM | 705 | OE2 | GLU | 98 | 43.524 | 52.151 | 4.256 | 1.00 | 40.33 |
| ATOM | 706 | C | GLU | 98 | 42.069 | 56.101 | 8.323 | 1.00 | 47.68 |
| ATOM | 707 | O | GLU | 98 | 41.618 | 56.243 | 9.478 | 1.00 | 47.98 |
| ATOM | 708 | N | ASP | 99 | 42.891 | 56.964 | 7.748 | 1.00 | 48.09 |
| ATOM | 709 | CA | ASP | 99 | 43.208 | 58.224 | 8.363 | 1.00 | 48.47 |
| ATOM | 710 | CB | ASP | 99 | 44.178 | 59.046 | 7.488 | 1.00 | 49.11 |
| ATOM | 711 | CG | ASP | 99 | 44.874 | 60.185 | 8.273 | 1.00 | 55.52 |
| ATOM | 712 | OD1 | ASP | 99 | 44.566 | 60.404 | 9.485 | 1.00 | 60.51 |
| ATOM | 713 | OD2 | ASP | 99 | 45.748 | 60.885 | 7.685 | 1.00 | 60.85 |
| ATOM | 714 | C | ASP | 99 | 41.922 | 58.988 | 8.722 | 1.00 | 46.99 |
| ATOM | 715 | O | ASP | 99 | 41.797 | 59.405 | 9.860 | 1.00 | 47.32 |
| ATOM | 716 | N | CYS | 100 | 40.960 | 59.129 | 7.803 | 1.00 | 44.86 |
| ATOM | 717 | CA | CYS | 100 | 39.746 | 59.918 | 8.086 | 1.00 | 44.11 |
| ATOM | 718 | CB | CYS | 100 | 38.809 | 60.040 | 6.866 | 1.00 | 44.17 |
| ATOM | 719 | SG | CYS | 100 | 39.316 | 61.424 | 5.836 | 1.00 | 55.29 |
| ATOM | 720 | C | CYS | 100 | 38.946 | 59.420 | 9.247 | 1.00 | 41.17 |
| ATOM | 721 | O | CYS | 100 | 38.460 | 60.206 | 10.052 | 1.00 | 41.05 |
| ATOM | 722 | N | MET | 101 | 38.760 | 58.111 | 9.310 | 1.00 | 39.33 |
| ATOM | 723 | CA | MET | 101 | 38.001 | 57.544 | 10.411 | 1.00 | 37.87 |
| ATOM | 724 | CB | MET | 101 | 37.721 | 56.038 | 10.218 | 1.00 | 36.00 |
| ATOM | 725 | CG | MET | 101 | 36.908 | 55.706 | 8.921 | 1.00 | 36.42 |
| ATOM | 726 | SD | MET | 101 | 35.623 | 56.867 | 8.440 | 1.00 | 36.92 |
| ATOM | 727 | CE | MET | 101 | 34.366 | 56.319 | 9.474 | 1.00 | 39.82 |
| ATOM | 728 | C | MET | 101 | 38.736 | 57.867 | 11.730 | 1.00 | 36.66 |
| ATOM | 729 | O | MET | 101 | 38.108 | 58.305 | 12.673 | 1.00 | 36.54 |
| ATOM | 730 | N | ASN | 102 | 40.056 | 57.707 | 11.762 | 1.00 | 35.47 |
| ATOM | 731 | CA | ASN | 102 | 40.785 | 58.039 | 12.977 | 1.00 | 36.04 |
| ATOM | 732 | CB | ASN | 102 | 42.203 | 57.511 | 12.894 | 1.00 | 36.07 |
| ATOM | 733 | CG | ASN | 102 | 42.252 | 56.042 | 13.146 | 1.00 | 35.53 |
| ATOM | 734 | OD1 | ASN | 102 | 41.887 | 55.613 | 14.217 | 1.00 | 40.24 |
| ATOM | 735 | ND2 | ASN | 102 | 42.662 | 55.255 | 12.167 | 1.00 | 35.01 |
| ATOM | 736 | C | ASN | 102 | 40.698 | 59.504 | 13.418 | 1.00 | 35.78 |
| ATOM | 737 | O | ASN | 102 | 40.497 | 59.773 | 14.618 | 1.00 | 36.97 |
| ATOM | 738 | N | ILE | 103 | 40.749 | 60.425 | 12.452 | 1.00 | 34.63 |
| ATOM | 739 | CA | ILE | 103 | 40.619 | 61.866 | 12.672 | 1.00 | 34.33 |
| ATOM | 740 | CB | ILE | 103 | 40.897 | 62.641 | 11.349 | 1.00 | 35.07 |
| ATOM | 741 | CG1 | ILE | 103 | 42.374 | 62.453 | 10.944 | 1.00 | 32.25 |
| ATOM | 742 | CD1 | ILE | 103 | 42.710 | 63.027 | 9.533 | 1.00 | 35.97 |
| ATOM | 743 | CG2 | ILE | 103 | 40.499 | 64.098 | 11.472 | 1.00 | 32.92 |
| ATOM | 744 | C | ILE | 103 | 39.265 | 62.207 | 13.220 | 1.00 | 34.31 |
| ATOM | 745 | O | ILE | 103 | 39.128 | 63.012 | 14.139 | 1.00 | 34.95 |

TABLE 4-continued

| | | | | | | | | |
|---|---|---|---|---|---|---|---|---|
| ATOM | 746 | N | ILE | 104 | 38.243 | 61.555 | 12.695 | 1.00 | 34.09 |
| ATOM | 747 | CA | ILE | 104 | 36.907 | 61.829 | 13.170 | 1.00 | 33.06 |
| ATOM | 748 | CB | ILE | 104 | 35.831 | 61.150 | 12.292 | 1.00 | 33.30 |
| ATOM | 749 | CG1 | ILE | 104 | 35.743 | 61.847 | 10.915 | 1.00 | 34.67 |
| ATOM | 750 | CD1 | ILE | 104 | 34.897 | 61.097 | 9.885 | 1.00 | 33.61 |
| ATOM | 751 | CG2 | ILE | 104 | 34.493 | 61.226 | 12.955 | 1.00 | 31.83 |
| ATOM | 752 | C | ILE | 104 | 36.829 | 61.318 | 14.600 | 1.00 | 32.13 |
| ATOM | 753 | O | ILE | 104 | 36.400 | 62.006 | 15.482 | 1.00 | 31.46 |
| ATOM | 754 | N | MET | 105 | 37.253 | 60.095 | 14.828 | 1.00 | 31.52 |
| ATOM | 755 | CA | MET | 105 | 37.156 | 59.578 | 16.188 | 1.00 | 31.67 |
| ATOM | 756 | CB | MET | 105 | 37.586 | 58.123 | 16.268 | 1.00 | 31.16 |
| ATOM | 757 | CG | MET | 105 | 37.189 | 57.526 | 17.611 | 1.00 | 31.27 |
| ATOM | 758 | SD | MET | 105 | 37.682 | 55.837 | 17.799 | 1.00 | 30.70 |
| ATOM | 759 | CE | MET | 105 | 39.473 | 55.936 | 17.553 | 1.00 | 24.32 |
| ATOM | 760 | C | MET | 105 | 37.940 | 60.424 | 17.222 | 1.00 | 31.82 |
| ATOM | 761 | O | MET | 105 | 37.406 | 60.694 | 18.314 | 1.00 | 30.92 |
| ATOM | 762 | N | ASN | 106 | 39.196 | 60.790 | 16.872 | 1.00 | 32.84 |
| ATOM | 763 | CA | ASN | 106 | 40.025 | 61.689 | 17.697 | 1.00 | 33.67 |
| ATOM | 764 | CB | ASN | 106 | 41.412 | 61.949 | 17.084 | 1.00 | 33.24 |
| ATOM | 765 | CG | ASN | 106 | 42.306 | 60.712 | 17.136 | 1.00 | 36.96 |
| ATOM | 766 | OD1 | ASN | 106 | 41.906 | 59.687 | 17.710 | 1.00 | 38.40 |
| ATOM | 767 | ND2 | ASN | 106 | 43.526 | 60.787 | 16.532 | 1.00 | 40.29 |
| ATOM | 768 | C | ASN | 106 | 39.318 | 62.990 | 18.053 | 1.00 | 33.97 |
| ATOM | 769 | O | ASN | 106 | 39.201 | 63.296 | 19.238 | 1.00 | 34.30 |
| ATOM | 770 | N | ILE | 117 | 33.681 | 55.021 | 22.281 | 1.00 | 29.68 |
| ATOM | 771 | CA | ILE | 117 | 33.334 | 55.496 | 20.972 | 1.00 | 30.17 |
| ATOM | 772 | CB | ILE | 117 | 33.905 | 56.953 | 20.694 | 1.00 | 29.97 |
| ATOM | 773 | CG1 | ILE | 117 | 33.505 | 57.471 | 19.302 | 1.00 | 31.07 |
| ATOM | 774 | CD1 | ILE | 117 | 33.251 | 58.987 | 19.226 | 1.00 | 28.47 |
| ATOM | 775 | CG2 | ILE | 117 | 35.423 | 56.991 | 20.793 | 1.00 | 29.12 |
| ATOM | 776 | C | ILE | 117 | 33.802 | 54.459 | 19.916 | 1.00 | 30.95 |
| ATOM | 777 | O | ILE | 117 | 34.831 | 53.747 | 20.092 | 1.00 | 29.55 |
| ATOM | 778 | N | GLU | 118 | 33.043 | 54.397 | 18.824 | 1.00 | 29.51 |
| ATOM | 779 | CA | GLU | 118 | 33.464 | 53.697 | 17.613 | 1.00 | 30.75 |
| ATOM | 780 | CB | GLU | 118 | 32.990 | 52.247 | 17.601 | 1.00 | 29.98 |
| ATOM | 781 | CG | GLU | 118 | 31.517 | 52.084 | 17.770 | 1.00 | 30.81 |
| ATOM | 782 | CD | GLU | 118 | 31.047 | 50.631 | 17.574 | 1.00 | 33.92 |
| ATOM | 783 | OE1 | GLU | 118 | 31.625 | 49.667 | 18.153 | 1.00 | 34.31 |
| ATOM | 784 | OE2 | GLU | 118 | 30.053 | 50.444 | 16.827 | 1.00 | 39.00 |
| ATOM | 785 | C | GLU | 118 | 32.992 | 54.437 | 16.351 | 1.00 | 30.00 |
| ATOM | 786 | O | GLU | 118 | 31.936 | 55.054 | 16.328 | 1.00 | 28.90 |
| ATOM | 787 | N | VAL | 119 | 33.834 | 54.395 | 15.332 | 1.00 | 30.46 |
| ATOM | 788 | CA | VAL | 119 | 33.555 | 54.982 | 14.045 | 1.00 | 29.62 |
| ATOM | 189 | CB | VAL | 119 | 34.457 | 56.239 | 13.763 | 1.00 | 29.45 |
| ATOM | 790 | CG1 | VAL | 119 | 34.137 | 56.899 | 12.382 | 1.00 | 25.54 |
| ATOM | 791 | CG2 | VAL | 119 | 34.243 | 57.222 | 14.847 | 1.00 | 26.50 |
| ATOM | 792 | C | VAL | 119 | 33.768 | 53.875 | 13.032 | 1.00 | 30.31 |
| ATOM | 793 | O | VAL | 119 | 34.858 | 53.267 | 12.966 | 1.00 | 30.28 |
| ATOM | 794 | N | TRP | 120 | 32.695 | 53.599 | 12.277 | 1.00 | 30.34 |
| ATOM | 795 | CA | TRP | 120 | 32.689 | 52.632 | 11.202 | 1.00 | 29.58 |
| ATOM | 796 | CB | TRP | 120 | 31.670 | 51.573 | 11.497 | 1.00 | 29.57 |
| ATOM | 797 | CG | TRP | 120 | 31.910 | 50.327 | 10.693 | 1.00 | 29.15 |
| ATOM | 798 | CD1 | TRP | 120 | 32.764 | 50.186 | 9.645 | 1.00 | 30.14 |
| ATOM | 799 | NE1 | TRP | 120 | 32.748 | 48.894 | 9.194 | 1.00 | 30.95 |
| ATOM | 800 | CE2 | TRP | 120 | 31.845 | 48.178 | 9.947 | 1.00 | 29.45 |
| ATOM | 801 | CD2 | TRP | 120 | 31.282 | 49.059 | 10.880 | 1.00 | 28.43 |
| ATOM | 802 | CE3 | TRP | 120 | 30.342 | 48.563 | 11.803 | 1.00 | 32.37 |
| ATOM | 803 | CZ3 | TRP | 120 | 29.953 | 47.235 | 11.706 | 1.00 | 32.51 |
| ATOM | 804 | CH2 | TRP | 120 | 30.525 | 46.389 | 10.738 | 1.00 | 29.55 |
| ATOM | 805 | CZ2 | TRP | 120 | 31.460 | 46.849 | 9.854 | 1.00 | 27.43 |
| ATOM | 806 | C | TRP | 120 | 32.366 | 53.356 | 9.861 | 1.00 | 30.85 |
| ATOM | 807 | O | TRP | 120 | 31.266 | 53.854 | 9.653 | 1.00 | 30.27 |
| ATOM | 808 | N | GLY | 121 | 33.345 | 53.443 | 8.958 | 1.00 | 31.66 |
| ATOM | 809 | CA | GLY | 121 | 33.078 | 53.981 | 7.615 | 1.00 | 31.08 |
| ATOM | 810 | C | GLY | 121 | 32.910 | 52.950 | 6.508 | 1.00 | 31.49 |
| ATOM | 811 | O | GLY | 121 | 33.665 | 51.985 | 6.422 | 1.00 | 31.67 |
| ATOM | 812 | N | LYS | 122 | 31.927 | 53.171 | 5.629 | 1.00 | 31.48 |
| ATOM | 813 | CA | LYS | 122 | 31.718 | 52.265 | 4.533 | 1.00 | 31.09 |
| ATOM | 814 | CB | LYS | 122 | 30.389 | 51.571 | 4.680 | 1.00 | 32.01 |
| ATOM | 815 | CG | LYS | 122 | 30.440 | 50.581 | 5.788 | 1.00 | 33.22 |
| ATOM | 816 | CD | LYS | 122 | 29.157 | 49.842 | 5.988 | 1.00 | 35.54 |
| ATOM | 817 | CE | LYS | 122 | 29.238 | 49.243 | 7.395 | 1.00 | 40.37 |
| ATOM | 818 | NZ | LYS | 122 | 27.943 | 48.667 | 7.876 | 1.00 | 39.48 |
| ATOM | 819 | C | LYS | 122 | 31.799 | 53.038 | 3.243 | 1.00 | 31.01 |
| ATOM | 820 | O | LYS | 122 | 30.893 | 53.769 | 2.918 | 1.00 | 30.45 |
| ATOM | 821 | N | PHE | 123 | 32.916 | 52.898 | 2.539 | 1.00 | 30.51 |
| ATOM | 822 | CA | PHE | 123 | 33.188 | 53.707 | 1.365 | 1.00 | 30.87 |
| ATOM | 823 | CB | PHE | 123 | 34.660 | 54.082 | 1.271 | 1.00 | 29.37 |
| ATOM | 824 | CG | PHE | 123 | 35.048 | 55.181 | 2.217 | 1.00 | 31.57 |
| ATOM | 825 | CD1 | PHE | 123 | 35.280 | 54.900 | 3.596 | 1.00 | 34.46 |

TABLE 4-continued

| | | | | | | | | |
|---|---|---|---|---|---|---|---|---|
| ATOM | 826 | CE1 | PHE | 123 | 35.627 | 55.899 | 4.489 | 1.00 | 33.64 |
| ATOM | 827 | CZ | PHE | 123 | 35.731 | 57.220 | 4.027 | 1.00 | 34.14 |
| ATOM | 828 | CE2 | PHE | 123 | 35.490 | 57.505 | 2.668 | 1.00 | 34.45 |
| ATOM | 829 | CD2 | PHE | 123 | 35.157 | 56.475 | 1.779 | 1.00 | 28.20 |
| ATOM | 830 | C | PHE | 123 | 32.712 | 53.045 | 0.071 | 1.00 | 31.56 |
| ATOM | 831 | O | PHE | 123 | 32.672 | 51.811 | −0.034 | 1.00 | 31.78 |
| ATOM | 832 | N | THR | 124 | 32.385 | 53.873 | −0.927 | 1.00 | 31.67 |
| ATOM | 833 | CA | THR | 124 | 31.999 | 53.327 | −2.258 | 1.00 | 31.12 |
| ATOM | 834 | CB | THR | 124 | 31.218 | 54.263 | −3.113 | 1.00 | 29.90 |
| ATOM | 835 | OG1 | THR | 124 | 32.049 | 55.495 | −3.328 | 1.00 | 29.06 |
| ATOM | 836 | CG2 | THR | 124 | 29.993 | 54.830 | −2.358 | 1.00 | 29.97 |
| ATOM | 837 | C | THR | 124 | 33.244 | 52.808 | −2.969 | 1.00 | 30.92 |
| ATOM | 838 | O | THR | 124 | 34.358 | 53.283 | −2.679 | 1.00 | 31.62 |
| ATOM | 839 | N | PRO | 125 | 33.076 | 51.820 | −3.881 | 1.00 | 31.66 |
| ATOM | 840 | CA | PRO | 125 | 34.248 | 51.192 | −4.486 | 1.00 | 32.62 |
| ATOM | 841 | CB | PRO | 125 | 32.669 | 49.961 | −5.208 | 1.00 | 32.91 |
| ATOM | 842 | CG | PRO | 125 | 32.200 | 50.186 | −5.279 | 1.00 | 31.43 |
| ATOM | 843 | CD | PRO | 125 | 31.802 | 51.208 | −4.321 | 1.00 | 30.86 |
| ATOM | 844 | C | PRO | 125 | 35.044 | 52.084 | −5.417 | 1.00 | 34.34 |
| ATOM | 845 | O | PRO | 125 | 34.511 | 53.071 | −5.921 | 1.00 | 34.29 |
| ATOM | 846 | N | ARG | 126 | 36.339 | 51.775 | −5.578 | 1.00 | 35.55 |
| ATOM | 847 | CA | ARG | 126 | 37.204 | 52.454 | −6.556 | 1.00 | 36.86 |
| ATOM | 848 | CB | ARG | 126 | 38.114 | 53.489 | −5.896 | 1.00 | 36.86 |
| ATOM | 849 | CG | ARG | 126 | 37.427 | 54.727 | −5.380 | 1.00 | 42.43 |
| ATOM | 850 | CD | ARG | 126 | 36.746 | 55.554 | −6.501 | 1.00 | 50.65 |
| ATOM | 851 | NE | ARG | 126 | 36.056 | 56.770 | −6.022 | 1.00 | 55.97 |
| ATOM | 852 | CZ | ARG | 126 | 34.740 | 56.994 | −6.137 | 1.00 | 58.82 |
| ATOM | 853 | NH1 | ARG | 126 | 33.940 | 56.088 | −6.681 | 1.00 | 59.04 |
| ATOM | 854 | NH2 | ARG | 126 | 34.214 | 58.131 | −5.698 | 1.00 | 60.14 |
| ATOM | 855 | C | ARG | 126 | 38.060 | 51.358 | −7.124 | 1.00 | 36.57 |
| ATOM | 856 | O | ARG | 126 | 38.706 | 50.639 | −6.360 | 1.00 | 37.65 |
| ATOM | 857 | N | GLY | 127 | 38.043 | 51.163 | −8.440 | 1.00 | 35.58 |
| ATOM | 858 | CA | GLY | 127 | 38.743 | 50.011 | −8.999 | 1.00 | 33.48 |
| ATOM | 859 | C | GLY | 127 | 38.087 | 48.714 | −8.556 | 1.00 | 33.81 |
| ATOM | 860 | O | GLY | 127 | 38.748 | 47.662 | −8.490 | 1.00 | 34.75 |
| ATOM | 861 | N | GLY | 128 | 36.784 | 48.771 | −8.265 | 1.00 | 31.98 |
| ATOM | 862 | CA | GLY | 128 | 36.061 | 47.614 | −7.816 | 1.00 | 31.99 |
| ATOM | 863 | C | GLY | 128 | 36.284 | 47.151 | −6.381 | 1.00 | 31.84 |
| ATOM | 864 | O | GLY | 128 | 35.719 | 46.163 | −5.981 | 1.00 | 33.17 |
| ATOM | 865 | N | ILE | 129 | 37.104 | 47.850 | −5.610 | 1.00 | 31.05 |
| ATOM | 866 | CA | ILE | 129 | 37.377 | 47.472 | −4.215 | 1.00 | 31.68 |
| ATOM | 867 | CB | ILE | 129 | 38.904 | 47.354 | −3.973 | 1.00 | 31.43 |
| ATOM | 868 | CG1 | ILE | 129 | 39.468 | 46.197 | −4.781 | 1.00 | 30.96 |
| ATOM | 869 | CD1 | ILE | 129 | 40.997 | 45.993 | −4.596 | 1.00 | 33.21 |
| ATOM | 870 | CG2 | ILE | 129 | 39.232 | 47.166 | −2.495 | 1.00 | 31.24 |
| ATOM | 871 | C | ILE | 129 | 36.840 | 48.591 | −3.353 | 1.00 | 30.10 |
| ATOM | 872 | O | ILE | 129 | 37.174 | 49.722 | −3.610 | 1.00 | 31.71 |
| ATOM | 873 | N | SER | 130 | 35.990 | 48.295 | −2.379 | 1.00 | 29.38 |
| ATOM | 874 | CA | SER | 130 | 35.653 | 49.295 | −1.373 | 1.00 | 28.88 |
| ATOM | 875 | CB | SER | 130 | 34.126 | 49.233 | −1.182 | 1.00 | 28.32 |
| ATOM | 876 | OG | SER | 130 | 33.684 | 48.035 | −0.875 | 1.00 | 29.12 |
| ATOM | 877 | C | SER | 130 | 36.426 | 49.098 | −0.009 | 1.00 | 29.46 |
| ATOM | 878 | O | SER | 130 | 36.778 | 47.976 | 0.376 | 1.00 | 29.70 |
| ATOM | 879 | N | ILE | 131 | 36.638 | 50.179 | 0.739 | 1.00 | 30.63 |
| ATOM | 880 | CA | ILE | 131 | 37.364 | 50.105 | 2.027 | 1.00 | 31.23 |
| ATOM | 881 | CB | ILE | 131 | 38.559 | 51.077 | 2.052 | 1.00 | 31.38 |
| ATOM | 882 | CG1 | ILE | 131 | 39.366 | 50.937 | 0.755 | 1.00 | 33.26 |
| ATOM | 883 | CD1 | ILE | 131 | 40.614 | 51.829 | 0.650 | 1.00 | 32.05 |
| ATOM | 884 | CG2 | ILE | 131 | 39.483 | 50.790 | 3.251 | 1.00 | 30.53 |
| ATOM | 885 | C | ILE | 131 | 36.425 | 50.481 | 3.159 | 1.00 | 30.83 |
| ATOM | 886 | O | ILE | 131 | 35.742 | 51.452 | 3.053 | 1.00 | 30.60 |
| ATOM | 887 | N | ASP | 132 | 36.386 | 49.678 | 4.229 | 1.00 | 31.33 |
| ATOM | 888 | CA | ASP | 132 | 35.550 | 49.935 | 5.428 | 1.00 | 31.26 |
| ATOM | 889 | CB | ASP | 132 | 34.425 | 48.903 | 5.563 | 1.00 | 30.16 |
| ATOM | 890 | CG | ASP | 132 | 33.560 | 43.789 | 4.316 | 1.00 | 33.74 |
| ATOM | 891 | OD1 | ASP | 132 | 33.671 | 49.657 | 3.418 | 1.00 | 33.52 |
| ATOM | 892 | OD2 | ASP | 132 | 32.733 | 47.833 | 4.278 | 1.00 | 34.98 |
| ATOM | 893 | C | ASP | 132 | 36.428 | 49.862 | 6.703 | 1.00 | 30.74 |
| ATOM | 894 | O | ASP | 132 | 36.635 | 48.778 | 7.266 | 1.00 | 31.02 |
| ATOM | 895 | N | PRO | 133 | 36.920 | 51.013 | 7.164 | 1.00 | 30.59 |
| ATOM | 896 | CA | PRO | 133 | 37.764 | 51.077 | 8.340 | 1.00 | 29.65 |
| ATOM | 897 | CB | PRO | 133 | 33.584 | 52.360 | 8.109 | 1.00 | 29.09 |
| ATOM | 898 | CG | PRO | 133 | 38.134 | 52.884 | 6.709 | 1.00 | 30.29 |
| ATOM | 899 | CD | PRO | 133 | 36.745 | 52.363 | 6.588 | 1.00 | 29.91 |
| ATOM | 900 | C | PRO | 133 | 36.872 | 51.231 | 9.570 | 1.00 | 30.09 |
| ATOM | 901 | O | PRO | 133 | 35.913 | 52.013 | 9.578 | 1.00 | 30.80 |
| ATOM | 902 | N | TYR | 134 | 37.187 | 50.447 | 10.585 | 1.00 | 29.67 |
| ATOM | 903 | CA | TYR | 134 | 36.486 | 50.464 | 11.809 | 1.00 | 29.22 |
| ATOM | 904 | CB | TYR | 134 | 35.800 | 49.151 | 12.005 | 1.00 | 28.44 |
| ATOM | 905 | CG | TYR | 134 | 35.304 | 48.965 | 13.399 | 1.00 | 27.51 |

TABLE 4-continued

| ATOM | 906 | CD1 | TYR | 134 | 36.025 | 48.151 | 14.324 | 1.00 | 29.90 |
|---|---|---|---|---|---|---|---|---|---|
| ATOM | 907 | CE1 | TYR | 134 | 35.569 | 47.934 | 15.650 | 1.00 | 26.68 |
| ATOM | 908 | CZ | TYR | 134 | 34.441 | 48.586 | 16.047 | 1.00 | 29.03 |
| ATOM | 909 | OH | TYR | 134 | 33.972 | 48.412 | 17.294 | 1.00 | 27.72 |
| ATOM | 910 | CE2 | TYR | 134 | 33.707 | 49.405 | 15.143 | 1.00 | 30.71 |
| ATOM | 911 | CD2 | TYR | 134 | 34.155 | 49.572 | 13.816 | 1.00 | 26.32 |
| ATOM | 912 | C | TYR | 134 | 37.492 | 50.735 | 12.930 | 1.00 | 30.34 |
| ATOM | 913 | O | TYR | 134 | 38.524 | 50.076 | 13.091 | 1.00 | 28.89 |
| ATOM | 914 | N | THR | 135 | 37.158 | 51.736 | 13.707 | 1.00 | 30.26 |
| ATOM | 915 | CA | THR | 135 | 38.018 | 52.146 | 14.768 | 1.00 | 30.91 |
| ATOM | 916 | CB | THR | 135 | 38.747 | 53.385 | 14.302 | 1.00 | 30.38 |
| ATOM | 917 | OG1 | THR | 135 | 39.907 | 53.557 | 15.094 | 1.00 | 35.78 |
| ATOM | 918 | CG2 | THR | 135 | 37.821 | 54.638 | 14.395 | 1.00 | 30.34 |
| ATOM | 919 | C | THR | 135 | 37.172 | 52.323 | 16.088 | 1.00 | 30.40 |
| ATOM | 920 | O | THR | 135 | 35.991 | 52.657 | 16.053 | 1.00 | 30.54 |
| ATOM | 921 | N | ASN | 136 | 37.753 | 52.022 | 17.236 | 1.00 | 29.91 |
| ATOM | 922 | CA | ASN | 136 | 37.088 | 52.277 | 18.508 | 1.00 | 29.96 |
| ATOM | 923 | CB | ASN | 136 | 36.193 | 51.113 | 18.936 | 1.00 | 29.53 |
| ATOM | 924 | CG | ASN | 136 | 36.994 | 49.937 | 19.359 | 1.00 | 28.78 |
| ATOM | 925 | OD1 | ASN | 136 | 38.201 | 50.078 | 19.529 | 1.00 | 26.61 |
| ATOM | 926 | ND2 | ASN | 136 | 36.378 | 48.761 | 19.447 | 1.00 | 25.15 |
| ATOM | 927 | C | ASN | 136 | 38.110 | 52.621 | 19.630 | 1.00 | 30.78 |
| ATOM | 928 | O | ASN | 136 | 39.344 | 52.647 | 19.411 | 1.00 | 28.47 |
| ATOM | 929 | N | TYR | 137 | 37.562 | 52.905 | 20.814 | 1.00 | 31.12 |
| ATOM | 930 | CA | TYR | 137 | 38.313 | 53.514 | 21.906 | 1.00 | 31.64 |
| ATOM | 931 | CB | TYR | 137 | 38.571 | 54.984 | 21.602 | 1.00 | 33.33 |
| ATOM | 932 | CG | TYR | 137 | 38.879 | 55.837 | 22.836 | 1.00 | 37.62 |
| ATOM | 933 | CD1 | TYR | 137 | 37.822 | 56.361 | 23.626 | 1.00 | 37.34 |
| ATOM | 934 | CE1 | TYR | 137 | 38.080 | 57.119 | 24.722 | 1.00 | 36.16 |
| ATOM | 935 | CZ | TYR | 137 | 39.414 | 57.381 | 25.087 | 1.00 | 38.10 |
| ATOM | 936 | OH | TYR | 137 | 39.659 | 58.165 | 26.209 | 1.00 | 39.09 |
| ATOM | 937 | CE2 | TYR | 137 | 40.486 | 56.884 | 24.330 | 1.00 | 37.20 |
| ATOM | 938 | CD2 | TYR | 137 | 40.213 | 56.113 | 23.215 | 1.00 | 34.37 |
| ATOM | 939 | C | TYR | 137 | 37.467 | 53.400 | 23.140 | 1.00 | 30.38 |
| ATOM | 940 | O | TYR | 137 | 36.252 | 53.533 | 23.055 | 1.00 | 30.26 |
| ATOM | 941 | N | HIS | 155 | 35.262 | 42.027 | 15.880 | 1.00 | 29.86 |
| ATOM | 942 | CA | HIS | 155 | 34.640 | 42.920 | 14.879 | 1.00 | 29.59 |
| ATOM | 943 | CB | HIS | 155 | 35.513 | 44.133 | 14.577 | 1.00 | 28.65 |
| ATOM | 944 | CG | HIS | 155 | 35.000 | 44.961 | 13.452 | 1.00 | 27.72 |
| ATOM | 945 | ND1 | HIS | 155 | 33.759 | 45.563 | 13.489 | 1.00 | 25.74 |
| ATOM | 946 | CE1 | HIS | 155 | 33.566 | 46.222 | 12.359 | 1.00 | 25.85 |
| ATOM | 947 | NE2 | HIS | 155 | 34.650 | 46.103 | 11.614 | 1.00 | 25.48 |
| ATOM | 948 | CD2 | HIS | 155 | 35.556 | 45.304 | 12.266 | 1.00 | 25.46 |
| ATOM | 949 | C | HIS | 155 | 34.299 | 42.173 | 13.572 | 1.00 | 28.28 |
| ATOM | 950 | O | HIS | 155 | 35.153 | 41.438 | 13.015 | 1.00 | 27.64 |
| ATOM | 951 | O | HOH | 3 | 46.780 | 55.828 | 8.704 | 1.00 | 47.32 |
| ATOM | 952 | O | HOH | 4 | 50.902 | 46.456 | 9.307 | 1.00 | 33.52 |
| ATOM | 953 | O | HOH | 28 | 37.213 | 43.349 | −6.645 | 1.00 | 32.19 |
| ATOM | 954 | O | HOH | 47 | 36.570 | 52.332 | −1.279 | 1.00 | 24.90 |
| ATOM | 955 | O | HOH | 61 | 35.979 | 46.671 | 9.152 | 1.00 | 37.04 |
| ATOM | 956 | O | HOH | 82 | 41.234 | 50.892 | −5.807 | 1.00 | 38.48 |
| ATOM | 957 | O | HOH | 90 | 54.411 | 44.108 | 13.049 | 1.00 | 46.38 |
| ATOM | 958 | O | HOH | 92 | 37.581 | 60.398 | 0.659 | 1.00 | 67.71 |
| ATOM | 959 | O | HOH | 98 | 36.023 | 44.145 | 8.886 | 1.00 | 45.09 |
| ATOM | 960 | O | HOH | 109 | 46.737 | 49.479 | 13.659 | 1.00 | 35.03 |
| ATOM | 961 | O | HOH | 118 | 34.771 | 50.646 | −8.465 | 1.00 | 41.43 |
| ATOM | 962 | O | HOH | 132 | 45.935 | 60.032 | 4.495 | 1.00 | 33.56 |
| ATOM | 963 | O | HOH | 136 | 35.102 | 56.335 | −2.597 | 1.00 | 47.88 |
| ATOM | 964 | O | HOH | 143 | 44.970 | 50.059 | 3.968 | 1.00 | 31.95 |
| ATOM | 965 | O | HOH | 243 | 38.885 | 44.939 | −8.276 | 1.00 | 32.22 |
| ATOM | 966 | O | HOH | 247 | 40.925 | 43.860 | −8.562 | 1.00 | 38.90 |
| ATOM | 967 | O | HOH | 251 | 39.625 | 61.715 | 1.763 | 1.00 | 47.53 |
| TER | | | | | | | | | |

TABLE 5

| ATOM | 1 | N | ASN | 21 | −12.994 | 44.902 | 31.976 | 1.00 | 77.48 |
|---|---|---|---|---|---|---|---|---|---|
| ATOM | 2 | CA | ASN | 21 | −12.605 | 46.316 | 31.623 | 1.00 | 77.76 |
| ATOM | 3 | CB | ASN | 21 | −13.806 | 47.268 | 31.784 | 1.00 | 78.33 |
| ATOM | 4 | CG | ASN | 21 | −14.940 | 46.946 | 30.798 | 1.00 | 79.60 |
| ATOM | 5 | OD1 | ASN | 21 | −14.730 | 46.916 | 29.577 | 1.00 | 79.76 |
| ATOM | 6 | ND2 | ASN | 21 | −16.145 | 46.698 | 31.328 | 1.00 | 80.00 |
| ATOM | 7 | C | ASN | 21 | −11.320 | 46.836 | 32.324 | 1.00 | 77.04 |
| ATOM | 8 | O | ASN | 21 | −10.831 | 46.202 | 33.281 | 1.00 | 77.25 |
| ATOM | 9 | N | TYR | 22 | −10.817 | 47.998 | 31.863 | 1.00 | 75.75 |
| ATOM | 10 | CA | TYR | 22 | −9.368 | 48.336 | 31.878 | 1.00 | 74.20 |
| ATOM | 11 | CB | TYR | 22 | −8.879 | 48.520 | 30.428 | 1.00 | 74.59 |

TABLE 5-continued

| | | | | | | | | |
|---|---|---|---|---|---|---|---|---|
| ATOM | 12 | CG | TYR | 22 | −8.897 | 47.253 | 29.567 | 1.00 | 75.55 |
| ATOM | 13 | CD1 | TYR | 22 | −10.083 | 46.797 | 28.958 | 1.00 | 75.86 |
| ATOM | 14 | CE1 | TYR | 22 | −10.093 | 45.626 | 28.156 | 1.00 | 75.88 |
| ATOM | 15 | CZ | TYR | 22 | −8.911 | 44.912 | 27.950 | 1.00 | 75.44 |
| ATOM | 16 | OH | TYR | 22 | −8.911 | 43.766 | 27.157 | 1.00 | 74.92 |
| ATOM | 17 | CE2 | TYR | 22 | −7.722 | 45.356 | 28.531 | 1.00 | 75.09 |
| ATOM | 18 | CD2 | TYR | 22 | −7.721 | 46.520 | 29.337 | 1.00 | 76.17 |
| ATOM | 19 | C | TYR | 22 | −8.872 | 49.522 | 32.750 | 1.00 | 72.82 |
| ATOM | 20 | O | TYR | 22 | −9.312 | 50.674 | 32.593 | 1.00 | 72.91 |
| ATOM | 21 | N | LEU | 23 | −7.930 | 49.216 | 33.648 | 1.00 | 70.41 |
| ATOM | 22 | CA | LEU | 23 | −7.288 | 50.200 | 34.519 | 1.00 | 68.04 |
| ATOM | 23 | CB | LEU | 23 | −6.869 | 49.559 | 35.861 | 1.00 | 68.48 |
| ATOM | 24 | CG | LEU | 23 | −7.891 | 48.928 | 36.824 | 1.00 | 69.66 |
| ATOM | 25 | CD1 | LEU | 23 | −7.415 | 47.564 | 37.364 | 1.00 | 68.67 |
| ATOM | 26 | CD2 | LEU | 23 | −8.288 | 49.897 | 37.975 | 1.00 | 70.93 |
| ATOM | 27 | C | LEU | 23 | −6.038 | 50.687 | 33.805 | 1.00 | 65.77 |
| ATOM | 28 | O | LEU | 23 | −5.174 | 49.884 | 33.474 | 1.00 | 65.09 |
| ATOM | 29 | O3S | G6S | 202 | −11.169 | 39.440 | 21.298 | 1.00 | 0.80 |
| ATOM | 30 | S | G6S | 202 | −9.744 | 39.544 | 20.857 | 1.00 | 0.32 |
| ATOM | 31 | O1S | G6S | 202 | −9.054 | 40.576 | 21.672 | 1.00 | 0.47 |
| ATOM | 32 | O2S | G6S | 202 | −9.662 | 39.973 | 19.434 | 1.00 | 0.44 |
| ATOM | 33 | O6 | G6S | 202 | −8.995 | 38.075 | 21.034 | 1.00 | 0.52 |
| ATOM | 34 | C6 | G6S | 202 | −9.433 | 37.001 | 21.890 | 1.00 | 0.05 |
| ATOM | 35 | C5 | G6S | 202 | −8.372 | 36.587 | 22.941 | 1.00 | 0.81 |
| ATOM | 36 | O5 | G6S | 202 | −8.651 | 37.198 | 24.218 | 1.00 | 0.85 |
| ATOM | 37 | C4 | G6S | 202 | −6.864 | 36.723 | 22.559 | 1.00 | 0.89 |
| ATOM | 38 | O4 | G6S | 202 | −6.609 | 36.762 | 21.144 | 1.00 | 99.16 |
| ATOM | 39 | C3 | G6S | 202 | −6.076 | 37.873 | 23.216 | 1.00 | 99.15 |
| ATOM | 40 | O3 | G6S | 202 | −5.338 | 38.595 | 22.220 | 1.00 | 96.07 |
| ATOM | 41 | C2 | G6S | 202 | −6.832 | 38.822 | 24.181 | 1.00 | 99.78 |
| ATOM | 42 | O2 | G6S | 202 | −6.531 | 40.201 | 23.906 | 1.00 | 97.61 |
| ATOM | 43 | C1 | G6S | 202 | −8.347 | 38.597 | 24.275 | 1.00 | 0.22 |
| ATOM | 44 | O1 | G6S | 202 | −8.835 | 39.145 | 25.504 | 1.00 | 0.17 |
| ATOM | 45 | N | ASN | 21 | −6.347 | 6.610 | 11.027 | 1.00 | 76.18 |
| ATOM | 46 | CA | ASN | 21 | −6.828 | 7.604 | 12.046 | 1.00 | 76.06 |
| ATOM | 47 | CB | ASN | 21 | −7.767 | 6.922 | 13.061 | 1.00 | 76.90 |
| ATOM | 48 | CG | ASN | 21 | −9.264 | 7.033 | 12.670 | 1.00 | 78.87 |
| ATOM | 49 | OD1 | ASN | 21 | −9.751 | 8.115 | 12.286 | 1.00 | 79.27 |
| ATOM | 50 | ND2 | ASN | 21 | −9.994 | 5.910 | 12.787 | 1.00 | 78.83 |
| ATOM | 51 | C | ASN | 21 | −5.704 | 8.375 | 12.773 | 1.00 | 75.05 |
| ATOM | 52 | O | ASN | 21 | −4.633 | 7.811 | 13.037 | 1.00 | 75.14 |
| ATOM | 53 | N | TYR | 22 | −5.963 | 9.658 | 13.075 | 1.00 | 73.30 |
| ATOM | 54 | CA | TYR | 22 | −5.024 | 10.554 | 13.784 | 1.00 | 71.17 |
| ATOM | 55 | CB | TYR | 22 | −4.819 | 11.874 | 13.019 | 1.00 | 71.82 |
| ATOM | 56 | CG | TYR | 22 | −3.935 | 11.821 | 11.802 | 1.00 | 71.49 |
| ATOM | 57 | CD1 | TYR | 22 | −4.459 | 11.492 | 10.553 | 1.00 | 72.23 |
| ATOM | 58 | CE1 | TYR | 22 | −3.645 | 11.439 | 9.412 | 1.00 | 72.96 |
| ATOM | 59 | CZ | TYR | 22 | −2.297 | 11.740 | 9.521 | 1.00 | 72.71 |
| ATOM | 60 | OH | TYR | 22 | −1.493 | 11.699 | 8.405 | 1.00 | 72.62 |
| ATOM | 61 | CE2 | TYR | 22 | −1.757 | 12.086 | 10.758 | 1.00 | 73.45 |
| ATOM | 62 | CD2 | TYR | 22 | −2.584 | 12.127 | 11.891 | 1.00 | 72.44 |
| ATOM | 63 | C | TYR | 22 | −5.566 | 10.921 | 15.166 | 1.00 | 69.29 |
| ATOM | 64 | O | TYR | 22 | −6.686 | 11.426 | 15.313 | 1.00 | 69.25 |
| ATOM | 65 | N | LEU | 23 | −4.758 | 10.688 | 16.182 | 1.00 | 66.64 |
| ATOM | 66 | CA | LEU | 23 | −5.132 | 11.060 | 17.549 | 1.00 | 63.93 |
| ATOM | 67 | CB | LEU | 23 | −4.336 | 10.227 | 18.531 | 1.00 | 64.90 |
| ATOM | 68 | CG | LEU | 23 | −4.227 | 8.733 | 18.176 | 1.00 | 66.26 |
| ATOM | 69 | CD1 | LEU | 23 | −3.086 | 8.014 | 18.926 | 1.00 | 65.53 |
| ATOM | 70 | CD2 | LEU | 23 | −5.606 | 8.006 | 18.327 | 1.00 | 67.93 |
| ATOM | 71 | C | LEU | 23 | −4.810 | 12.531 | 17.660 | 1.00 | 61.09 |
| ATOM | 72 | O | LEU | 23 | −3.711 | 12.954 | 17.345 | 1.00 | 59.70 |
| ATOM | 73 | N | PHE | 24 | −5.792 | 13.306 | 18.096 | 1.00 | 58.58 |
| ATOM | 74 | CA | PHE | 24 | −5.551 | 14.687 | 18.474 | 1.00 | 56.64 |
| ATOM | 75 | CB | PHE | 24 | −6.471 | 15.653 | 17.722 | 1.00 | 56.03 |
| ATOM | 76 | CG | PHE | 24 | −6.259 | 15.642 | 16.222 | 1.00 | 56.10 |
| ATOM | 77 | CD1 | PHE | 24 | −7.352 | 15.698 | 15.344 | 1.00 | 55.47 |
| ATOM | 78 | CE1 | PHE | 24 | −7.163 | 15.673 | 13.959 | 1.00 | 54.37 |
| ATOM | 79 | CZ | PHE | 24 | −5.867 | 15.587 | 13.431 | 1.00 | 54.86 |
| ATOM | 80 | CE2 | PHE | 24 | −4.766 | 15.526 | 14.300 | 1.00 | 55.69 |
| ATOM | 81 | CD2 | PHE | 24 | −4.970 | 15.547 | 15.684 | 1.00 | 55.01 |
| ATOM | 82 | C | PHE | 24 | −5.591 | 14.888 | 19.992 | 1.00 | 55.70 |
| ATOM | 83 | O | PHE | 24 | −5.461 | 16.033 | 20.475 | 1.00 | 55.37 |
| ATOM | 84 | N | GLU | 25 | −5.744 | 13.774 | 20.730 | 1.00 | 53.85 |
| ATOM | 85 | CA | GLU | 25 | −5.568 | 13.755 | 22.198 | 1.00 | 51.90 |
| ATOM | 86 | CB | GLU | 25 | −6.628 | 12.890 | 22.896 | 1.00 | 53.16 |
| ATOM | 87 | CG | GLU | 25 | −7.993 | 12.810 | 22.235 | 1.00 | 56.60 |
| ATOM | 88 | CD | GLU | 25 | −8.687 | 14.150 | 22.185 | 1.00 | 60.77 |
| ATOM | 89 | OE1 | GLU | 25 | −8.629 | 14.873 | 23.215 | 1.00 | 60.96 |
| ATOM | 90 | OE2 | GLU | 25 | −9.285 | 14.479 | 21.112 | 1.00 | 63.56 |
| ATOM | 91 | C | GLU | 25 | −4.174 | 13.240 | 22.574 | 1.00 | 49.01 |

TABLE 5-continued

| | | | | | | | | |
|---|---|---|---|---|---|---|---|---|
| ATOM | 92 | O | GLU | 25 | −3.649 | 12.308 | 21.948 | 1.00 48.66 |
| ATOM | 93 | N | TYR | 26 | −3.606 | 13.817 | 23.622 | 1.00 45.71 |
| ATOM | 94 | CA | TYR | 26 | −2.213 | 13.575 | 24.001 | 1.00 43.62 |
| ATOM | 95 | CB | TYR | 26 | −1.939 | 14.257 | 25.337 | 1.00 43.09 |
| ATOM | 96 | CG | TYR | 26 | −0.599 | 13.938 | 25.997 | 1.00 41.77 |
| ATOM | 97 | CD1 | TYR | 26 | −0.565 | 13.233 | 27.214 | 1.00 38.81 |
| ATOM | 98 | CE1 | TYR | 26 | 0.630 | 12.962 | 27.857 | 1.00 39.58 |
| ATOM | 99 | CZ | TYR | 26 | 1.815 | 13.421 | 27.313 | 1.00 42.46 |
| ATOM | 100 | OH | TYR | 26 | 2.980 | 13.122 | 27.974 | 1.00 42.52 |
| ATOM | 101 | CE2 | TYR | 26 | 1.836 | 14.109 | 26.079 | 1.00 40.19 |
| ATOM | 102 | CD2 | TYR | 26 | 0.611 | 14.371 | 25.435 | 1.00 37.62 |
| ATOM | 103 | C | TYR | 26 | −1.778 | 12.107 | 24.042 | 1.00 42.34 |
| ATOM | 104 | O | TYR | 26 | −2.286 | 11.343 | 24.843 | 1.00 41.66 |
| ATOM | 105 | N | SER | 54 | −2.012 | 23.788 | 19.960 | 1.00 31.83 |
| ATOM | 106 | CA | SER | 54 | −2.610 | 23.179 | 21.146 | 1.00 33.32 |
| ATOM | 107 | CB | SER | 54 | −1.544 | 22.902 | 22.229 | 1.00 33.47 |
| ATOM | 108 | OG | SER | 54 | −0.994 | 24.120 | 22.715 | 1.00 33.23 |
| ATOM | 109 | C | SER | 54 | −3.661 | 24.144 | 21.696 | 1.00 34.99 |
| ATOM | 110 | O | SER | 54 | −3.961 | 25.141 | 21.075 | 1.00 34.15 |
| ATOM | 111 | N | LEU | 55 | −4.208 | 23.855 | 22.875 | 1.00 38.17 |
| ATOM | 112 | CA | LEU | 55 | −5.315 | 24.640 | 23.414 | 1.00 40.67 |
| ATOM | 113 | CB | LEU | 55 | −6.559 | 23.778 | 23.595 | 1.00 40.34 |
| ATOM | 114 | CG | LEU | 55 | −7.119 | 23.063 | 22.367 | 1.00 37.91 |
| ATOM | 115 | CD1 | LEU | 55 | −8.373 | 22.345 | 22.800 | 1.00 37.30 |
| ATOM | 116 | CD2 | LEU | 55 | −7.432 | 24.012 | 21.230 | 1.00 39.20 |
| ATOM | 117 | C | LEU | 55 | −4.935 | 25.321 | 24.692 | 1.00 43.65 |
| ATOM | 118 | O | LEU | 55 | −4.064 | 24.834 | 25.425 | 1.00 44.27 |
| ATOM | 119 | N | CYS | 56 | −5.529 | 26.494 | 24.896 | 1.00 46.46 |
| ATOM | 120 | CA | CYS | 56 | −5.442 | 27.214 | 26.148 | 1.00 48.90 |
| ATOM | 121 | CB | CYS | 56 | −5.937 | 28.650 | 25.952 | 1.00 49.06 |
| ATOM | 122 | SG | CYS | 56 | −5.837 | 29.698 | 27.414 | 1.00 50.31 |
| ATOM | 123 | C | CYS | 56 | −6.286 | 26.463 | 27.205 | 1.00 50.34 |
| ATOM | 124 | O | CYS | 56 | −7.471 | 26.153 | 26.961 | 1.00 50.82 |
| ATOM | 125 | N | PRO | 57 | −5.677 | 26.132 | 28.362 | 1.00 51.54 |
| ATOM | 126 | CA | PRO | 57 | −6.344 | 25.179 | 29.267 | 1.00 52.63 |
| ATOM | 127 | CB | PRO | 57 | −5.274 | 24.902 | 30.330 | 1.00 52.63 |
| ATOM | 128 | CG | PRO | 57 | −4.377 | 26.143 | 30.303 | 1.00 51.98 |
| ATOM | 129 | CD | PRO | 57 | −4.366 | 26.585 | 28.879 | 1.00 50.82 |
| ATOM | 130 | C | PRO | 57 | −7.618 | 25.738 | 29.917 | 1.00 53.90 |
| ATOM | 131 | O | PRO | 57 | −8.503 | 24.962 | 30.324 | 1.00 54.88 |
| ATOM | 132 | N | LYS | 58 | −7.707 | 27.065 | 29.975 | 1.00 54.79 |
| ATOM | 133 | CA | LYS | 58 | −8.760 | 27.785 | 30.656 | 1.00 55.67 |
| ATOM | 134 | CB | LYS | 58 | −8.185 | 28.994 | 31.424 | 1.00 56.91 |
| ATOM | 135 | CG | LYS | 58 | −7.868 | 28.699 | 32.904 | 1.00 59.21 |
| ATOM | 136 | CD | LYS | 58 | −6.400 | 28.263 | 33.166 | 1.00 62.63 |
| ATOM | 137 | CE | LYS | 58 | −6.232 | 27.349 | 34.438 | 1.00 62.29 |
| ATOM | 138 | NZ | LYS | 58 | −6.393 | 25.849 | 34.167 | 1.00 63.69 |
| ATOM | 139 | C | LYS | 58 | −9.873 | 28.225 | 29.715 | 1.00 55.58 |
| ATOM | 140 | O | LYS | 58 | −11.048 | 28.018 | 30.032 | 1.00 56.09 |
| ATOM | 141 | N | VAL | 59 | −9.516 | 28.835 | 28.576 | 1.00 54.74 |
| ATOM | 142 | CA | VAL | 59 | −10.495 | 29.254 | 27.545 | 1.00 52.88 |
| ATOM | 143 | CB | VAL | 59 | −10.062 | 30.547 | 26.843 | 1.00 52.91 |
| ATOM | 144 | CG1 | VAL | 59 | −10.096 | 31.737 | 27.800 | 1.00 53.31 |
| ATOM | 145 | CG2 | VAL | 59 | −8.689 | 30.412 | 26.261 | 1.00 52.44 |
| ATOM | 146 | C | VAL | 59 | −10.794 | 28.197 | 26.455 | 1.00 52.24 |
| ATOM | 147 | O | VAL | 59 | −11.843 | 28.249 | 25.814 | 1.00 52.31 |
| ATOM | 148 | N | GLY | 60 | −9.883 | 27.253 | 26.220 | 1.00 50.54 |
| ATOM | 149 | CA | GLY | 60 | −10.030 | 26.353 | 25.061 | 1.00 48.58 |
| ATOM | 150 | C | GLY | 60 | −9.691 | 27.000 | 23.704 | 1.00 47.45 |
| ATOM | 151 | O | GLY | 60 | −9.919 | 26.371 | 22.641 | 1.00 46.89 |
| ATOM | 152 | N | GLN | 61 | −9.165 | 28.241 | 23.728 | 1.00 45.26 |
| ATOM | 153 | CA | GLN | 61 | −8.682 | 28.935 | 22.505 | 1.00 44.42 |
| ATOM | 154 | CB | GLN | 61 | −8.461 | 30.445 | 22.743 | 1.00 43.87 |
| ATOM | 155 | CG | GLN | 61 | −8.509 | 31.305 | 21.438 | 1.00 49.56 |
| ATOM | 156 | CD | GLN | 61 | −7.584 | 32.609 | 21.424 | 1.00 49.55 |
| ATOM | 157 | OE1 | GLN | 61 | −6.818 | 32.872 | 22.372 | 1.00 58.03 |
| ATOM | 158 | NE2 | GLN | 61 | −7.703 | 33.421 | 20.351 | 1.00 50.79 |
| ATOM | 159 | C | GLN | 61 | −7.391 | 28.259 | 21.985 | 1.00 40.55 |
| ATOM | 160 | O | GLN | 61 | −6.489 | 27.907 | 22.768 | 1.00 39.97 |
| ATOM | 161 | N | PRO | 62 | −7.330 | 28.002 | 20.667 | 1.00 37.57 |
| ATOM | 162 | CA | PRO | 62 | −6.092 | 27.504 | 20.049 | 1.00 34.50 |
| ATOM | 163 | CB | PRO | 62 | −6.479 | 27.258 | 18.597 | 1.00 34.78 |
| ATOM | 164 | CG | PRO | 62 | −7.804 | 27.949 | 18.411 | 1.00 35.70 |
| ATOM | 165 | CD | PRO | 62 | −8.458 | 28.063 | 19.728 | 1.00 36.57 |
| ATOM | 166 | C | PRO | 62 | −4.880 | 28.447 | 20.155 | 1.00 32.05 |
| ATOM | 167 | O | PRO | 62 | −5.026 | 29.633 | 20.185 | 1.00 29.71 |
| ATOM | 168 | N | ASP | 63 | −3.694 | 27.846 | 20.236 | 1.00 31.14 |
| ATOM | 169 | CA | ASP | 63 | −2.413 | 28.498 | 20.359 | 1.00 30.90 |
| ATOM | 170 | CB | ASP | 63 | −1.861 | 28.261 | 21.785 | 1.00 32.30 |
| ATOM | 171 | CG | ASP | 63 | −2.528 | 29.168 | 22.831 | 1.00 41.48 |

TABLE 5-continued

| | | | | | | | | |
|---|---|---|---|---|---|---|---|---|
| ATOM | 172 | OD1 | ASP | 63 | −3.089 | 30.261 | 22.489 | 1.00 | 48.28 |
| ATOM | 173 | OD2 | ASP | 63 | −2.502 | 28.800 | 24.033 | 1.00 | 51.27 |
| ATOM | 174 | C | ASP | 63 | −1.523 | 27.848 | 19.287 | 1.00 | 28.42 |
| ATOM | 175 | O | ASP | 63 | −1.793 | 26.708 | 18.885 | 1.00 | 27.04 |
| ATOM | 176 | N | ARG | 91 | −3.099 | 18.671 | 19.435 | 1.00 | 32.06 |
| ATOM | 177 | CA | ARG | 91 | −4.020 | 19.543 | 18.691 | 1.00 | 33.93 |
| ATOM | 178 | CB | ARG | 91 | −4.329 | 18.975 | 17.314 | 1.00 | 32.54 |
| ATOM | 179 | CG | ARG | 91 | −5.098 | 19.936 | 16.401 | 1.00 | 33.90 |
| ATOM | 180 | CD | ARG | 91 | −5.554 | 19.192 | 15.143 | 1.00 | 31.62 |
| ATOM | 181 | NE | ARG | 91 | −6.181 | 20.057 | 14.146 | 1.00 | 35.99 |
| ATOM | 182 | CZ | ARG | 91 | −5.538 | 20.909 | 13.335 | 1.00 | 34.09 |
| ATOM | 183 | NH1 | ARG | 91 | −4.202 | 21.078 | 13.420 | 1.00 | 31.27 |
| ATOM | 184 | NH2 | ARG | 91 | −6.245 | 21.617 | 12.437 | 1.00 | 32.64 |
| ATOM | 185 | C | ARG | 91 | −5.277 | 19.874 | 19.482 | 1.00 | 35.44 |
| ATOM | 186 | O | ARG | 91 | −5.711 | 21.003 | 19.501 | 1.00 | 34.63 |
| ATOM | 187 | N | ASN | 92 | −5.818 | 18.918 | 20.225 | 1.00 | 38.69 |
| ATOM | 188 | CA | ASN | 92 | −6.984 | 19.236 | 21.031 | 1.00 | 41.67 |
| ATOM | 189 | CB | ASN | 92 | −8.126 | 18.364 | 20.554 | 1.00 | 43.01 |
| ATOM | 190 | CG | ASN | 92 | −9.469 | 18.778 | 21.140 | 1.00 | 48.25 |
| ATOM | 191 | OD1 | ASN | 92 | −10.054 | 18.021 | 21.932 | 1.00 | 54.32 |
| ATOM | 192 | ND2 | ASN | 92 | −9.979 | 19.969 | 20.760 | 1.00 | 50.71 |
| ATOM | 193 | C | ASN | 92 | −6.741 | 19.178 | 22.574 | 1.00 | 42.99 |
| ATOM | 194 | O | ASN | 92 | −7.672 | 19.080 | 23.377 | 1.00 | 44.64 |
| ATOM | 195 | N | HIS | 93 | −5.482 | 19.281 | 22.985 | 1.00 | 43.46 |
| ATOM | 196 | CA | HIS | 93 | −5.053 | 19.119 | 24.378 | 1.00 | 43.34 |
| ATOM | 197 | CB | HIS | 93 | −3.732 | 18.335 | 24.385 | 1.00 | 43.87 |
| ATOM | 198 | CG | HIS | 93 | −3.136 | 18.126 | 25.750 | 1.00 | 46.71 |
| ATOM | 199 | ND1 | HIS | 93 | −1.938 | 18.696 | 26.131 | 1.00 | 49.45 |
| ATOM | 200 | CE1 | HIS | 93 | −1.649 | 18.329 | 27.367 | 1.00 | 49.71 |
| ATOM | 201 | NE2 | HIS | 93 | −2.623 | 17.551 | 27.808 | 1.00 | 49.32 |
| ATOM | 202 | CD2 | HIS | 93 | −3.568 | 17.409 | 26.818 | 1.00 | 46.55 |
| ATOM | 203 | C | HIS | 93 | −4.805 | 20.478 | 25.011 | 1.00 | 42.85 |
| ATOM | 204 | O | HIS | 93 | −4.069 | 21.295 | 24.439 | 1.00 | 42.79 |
| ATOM | 205 | N | GLY | 94 | −5.374 | 20.711 | 26.191 | 1.00 | 42.52 |
| ATOM | 206 | CA | GLY | 94 | −5.185 | 21.974 | 26.911 | 1.00 | 43.43 |
| ATOM | 207 | C | GLY | 94 | −4.019 | 21.964 | 27.881 | 1.00 | 44.21 |
| ATOM | 208 | O | GLY | 94 | −3.951 | 21.072 | 28.692 | 1.00 | 45.14 |
| ATOM | 209 | O | HOH | 20 | −5.211 | 15.614 | 25.409 | 1.00 | 41.75 |
| ATOM | 210 | O | HOH | 112 | −5.998 | 32.041 | 25.975 | 1.00 | 53.31 |
| ATOM | 211 | O | HOH | 148 | −8.791 | 20.672 | 18.386 | 1.00 | 48.74 |
| ATOM | 212 | O | HOH | 149 | −1.901 | 19.846 | 14.793 | 1.00 | 40.80 |
| ATOM | 213 | O | HOH | 152 | −9.951 | 12.790 | 16.600 | 1.00 | 46.81 |
| ATOM | 214 | O | HOH | 162 | −8.767 | 40.966 | 29.438 | 1.00 | 53.57 |
| ATOM | 215 | O | HOH | 197 | −5.204 | 37.964 | 26.824 | 1.00 | 40.46 |
| ATOM | 216 | O | HOH | 209 | −4.931 | 10.265 | 21.846 | 1.00 | 58.34 |
| ATOM | 217 | O | HOH | 217 | −9.974 | 33.739 | 21.449 | 1.00 | 63.31 |
| ATOM | 218 | O | HOH | 223 | −7.059 | 18.630 | 27.537 | 1.00 | 44.78 |
| ATOM | 219 | N | ASN | 21 | −4.788 | 21.978 | 18.878 | 1.00 | 75.05 |
| ATOM | 220 | CA | ASN | 21 | −5.902 | 22.791 | 18.298 | 1.00 | 75.35 |
| ATOM | 221 | CB | ASN | 21 | −6.341 | 23.933 | 19.259 | 1.00 | 75.78 |
| ATOM | 222 | CG | ASN | 21 | −6.077 | 23.619 | 20.749 | 1.00 | 76.69 |
| ATOM | 223 | OD1 | ASN | 21 | −6.803 | 22.846 | 21.281 | 1.00 | 77.28 |
| ATOM | 224 | ND2 | ASN | 21 | −5.045 | 24.249 | 21.308 | 1.00 | 76.09 |
| ATOM | 225 | C | ASN | 21 | −5.486 | 23.389 | 16.939 | 1.00 | 74.71 |
| ATOM | 226 | O | ASN | 21 | −5.481 | 24.625 | 16.780 | 1.00 | 75.08 |
| ATOM | 227 | N | TYR | 22 | −5.126 | 22.512 | 15.983 | 1.00 | 73.57 |
| ATOM | 228 | CA | TYR | 22 | −4.629 | 22.885 | 14.620 | 1.00 | 71.80 |
| ATOM | 229 | CB | TYR | 22 | −3.093 | 23.003 | 14.582 | 1.00 | 72.49 |
| ATOM | 230 | CG | TYR | 22 | −2.519 | 24.259 | 15.203 | 1.00 | 73.51 |
| ATOM | 231 | CD1 | TYR | 22 | −2.054 | 24.260 | 16.524 | 1.00 | 74.27 |
| ATOM | 232 | CE1 | TYR | 22 | −1.523 | 25.414 | 17.105 | 1.00 | 75.09 |
| ATOM | 233 | CZ | TYR | 22 | −1.438 | 26.593 | 16.359 | 1.00 | 75.52 |
| ATOM | 234 | OH | TYR | 22 | −0.907 | 27.741 | 16.940 | 1.00 | 75.89 |
| ATOM | 235 | CE2 | TYR | 22 | −1.887 | 26.611 | 15.039 | 1.00 | 75.06 |
| ATOM | 236 | CD2 | TYR | 22 | −2.423 | 25.446 | 14.471 | 1.00 | 74.99 |
| ATOM | 237 | C | TYR | 22 | −5.044 | 21.833 | 13.590 | 1.00 | 69.73 |
| ATOM | 238 | O | TYR | 22 | −4.766 | 20.647 | 13.776 | 1.00 | 69.63 |
| ATOM | 239 | N | LEU | 23 | −5.697 | 22.267 | 12.510 | 1.00 | 67.13 |
| ATOM | 240 | CA | LEU | 23 | −6.064 | 21.365 | 11.407 | 1.00 | 64.76 |
| ATOM | 241 | CB | LEU | 23 | −7.290 | 21.897 | 10.640 | 1.00 | 65.44 |
| ATOM | 242 | CG | LEU | 23 | −8.647 | 22.056 | 11.367 | 1.00 | 67.86 |
| ATOM | 243 | CD1 | LEU | 23 | −9.681 | 22.852 | 10.511 | 1.00 | 68.53 |
| ATOM | 244 | CD2 | LEU | 23 | −9.237 | 20.701 | 11.853 | 1.00 | 68.46 |
| ATOM | 245 | C | LEU | 23 | −4.885 | 21.095 | 10.446 | 1.00 | 62.18 |
| ATOM | 246 | O | LEU | 23 | −4.323 | 22.016 | 9.849 | 1.00 | 61.84 |
| ATOM | 247 | N | PHE | 24 | −4.511 | 19.829 | 10.311 | 1.00 | 59.36 |
| ATOM | 248 | CA | PHE | 24 | −3.401 | 19.433 | 9.437 | 1.00 | 56.70 |
| ATOM | 249 | CB | PHE | 24 | −2.306 | 18.691 | 10.213 | 1.00 | 56.46 |
| ATOM | 250 | CG | PHE | 24 | −1.618 | 19.509 | 11.268 | 1.00 | 55.24 |
| ATOM | 251 | CD1 | PHE | 24 | −1.237 | 18.919 | 12.463 | 1.00 | 54.57 |

TABLE 5-continued

| | | | | | | | | |
|---|---|---|---|---|---|---|---|---|
| ATOM | 252 | CE1 | PHE | 24 | −0.581 | 19.670 | 13.448 | 1.00 | 54.68 |
| ATOM | 253 | CZ | PHE | 24 | −0.294 | 21.022 | 13.234 | 1.00 | 54.99 |
| ATOM | 254 | CE2 | PHE | 24 | −0.661 | 21.622 | 12.041 | 1.00 | 55.01 |
| ATOM | 255 | CD2 | PHE | 24 | −1.317 | 20.864 | 11.063 | 1.00 | 56.28 |
| ATOM | 256 | C | PHE | 24 | −3.885 | 18.581 | 8.256 | 1.00 | 55.67 |
| ATOM | 257 | O | PHE | 24 | −3.081 | 18.048 | 7.481 | 1.00 | 54.45 |
| ATOM | 258 | N | GLU | 25 | −5.214 | 18.449 | 8.166 | 1.00 | 54.82 |
| ATOM | 259 | CA | GLU | 25 | −5.931 | 17.984 | 6.965 | 1.00 | 53.68 |
| ATOM | 260 | CB | GLU | 25 | −7.083 | 17.082 | 7.381 | 1.00 | 54.71 |
| ATOM | 261 | CG | GLU | 25 | −6.728 | 16.130 | 8.534 | 1.00 | 59.15 |
| ATOM | 262 | CD | GLU | 25 | −5.667 | 15.096 | 8.119 | 1.00 | 64.93 |
| ATOM | 263 | OE1 | GLU | 25 | −5.693 | 14.659 | 6.932 | 1.00 | 65.43 |
| ATOM | 264 | OE2 | GLU | 25 | −4.819 | 14.726 | 8.982 | 1.00 | 67.14 |
| ATOM | 265 | C | GLU | 25 | −6.483 | 19.217 | 6.217 | 1.00 | 51.49 |
| ATOM | 266 | O | GLU | 25 | −6.881 | 20.216 | 6.861 | 1.00 | 51.01 |
| ATOM | 267 | N | LYS | 81 | −2.380 | 35.410 | 9.512 | 1.00 | 38.05 |
| ATOM | 268 | CA | LYS | 81 | −2.765 | 34.277 | 10.399 | 1.00 | 38.29 |
| ATOM | 269 | CB | LYS | 81 | −3.391 | 34.749 | 11.709 | 1.00 | 38.47 |
| ATOM | 270 | CG | LYS | 81 | −3.339 | 33.644 | 12.763 | 1.00 | 43.77 |
| ATOM | 271 | CD | LYS | 81 | −3.338 | 34.200 | 14.201 | 1.00 | 49.29 |
| ATOM | 272 | CE | LYS | 81 | −4.758 | 34.316 | 14.748 | 1.00 | 54.55 |
| ATOM | 273 | NZ | LYS | 81 | −4.748 | 34.281 | 16.256 | 1.00 | 57.78 |
| ATOM | 274 | C | LYS | 81 | −3.620 | 33.189 | 9.727 | 1.00 | 36.81 |
| ATOM | 275 | O | LYS | 81 | −3.257 | 31.991 | 9.784 | 1.00 | 37.85 |
| ATOM | 276 | N | SER | 82 | −4.711 | 33.566 | 9.064 | 1.00 | 35.20 |
| ATOM | 277 | CA | SER | 82 | −5.563 | 32.576 | 8.345 | 1.00 | 33.64 |
| ATOM | 278 | CB | SER | 82 | −6.768 | 33.295 | 7.704 | 1.00 | 34.75 |
| ATOM | 279 | OG | SER | 82 | −6.393 | 34.037 | 6.549 | 1.00 | 33.65 |
| ATOM | 280 | C | SER | 82 | −4.803 | 31.810 | 7.284 | 1.00 | 32.78 |
| ATOM | 281 | O | SER | 82 | −5.067 | 30.633 | 7.000 | 1.00 | 33.37 |
| ATOM | 282 | N | LEU | 85 | −2.532 | 29.241 | 8.910 | 1.00 | 33.06 |
| ATOM | 283 | CA | LEU | 85 | −3.383 | 28.091 | 9.263 | 1.00 | 33.43 |
| ATOM | 284 | CB | LEU | 85 | −4.618 | 28.578 | 9.988 | 1.00 | 32.74 |
| ATOM | 285 | CG | LEU | 85 | −4.371 | 29.330 | 11.303 | 1.00 | 36.78 |
| ATOM | 286 | CD1 | LEU | 85 | −5.753 | 29.754 | 11.965 | 1.00 | 37.48 |
| ATOM | 287 | CD2 | LEU | 85 | −3.604 | 28.431 | 12.259 | 1.00 | 38.46 |
| ATOM | 288 | C | LEU | 85 | −3.768 | 27.341 | 8.006 | 1.00 | 33.59 |
| ATOM | 289 | O | LEU | 85 | −3.773 | 26.121 | 7.949 | 1.00 | 33.78 |
| ATOM | 290 | N | TYR | 86 | −4.081 | 28.092 | 6.962 | 1.00 | 33.33 |
| ATOM | 291 | CA | TYR | 86 | −4.430 | 27.431 | 5.717 | 1.00 | 32.84 |
| ATOM | 292 | CB | TYR | 86 | −4.906 | 28.468 | 4.674 | 1.00 | 32.11 |
| ATOM | 293 | CG | TYR | 86 | −5.053 | 27.898 | 3.283 | 1.00 | 31.82 |
| ATOM | 294 | CD1 | TYR | 86 | −6.078 | 26.987 | 2.980 | 1.00 | 28.59 |
| ATOM | 295 | CE1 | TYR | 86 | −6.209 | 26.466 | 1.699 | 1.00 | 32.86 |
| ATOM | 296 | CZ | TYR | 86 | −5.294 | 26.854 | 0.698 | 1.00 | 31.37 |
| ATOM | 297 | OH | TYR | 86 | −5.376 | 26.342 | −0.559 | 1.00 | 30.97 |
| ATOM | 298 | CE2 | TYR | 86 | −4.283 | 27.755 | 0.974 | 1.00 | 31.22 |
| ATOM | 299 | CD2 | TYR | 86 | −4.157 | 28.273 | 2.259 | 1.00 | 31.02 |
| ATOM | 300 | C | TYR | 86 | −3.269 | 26.572 | 5.229 | 1.00 | 31.81 |
| ATOM | 301 | O | TYR | 86 | −3.446 | 25.398 | 4.869 | 1.00 | 31.35 |
| ATOM | 302 | N | PHE | 88 | −0.731 | 25.310 | 7.038 | 1.00 | 34.10 |
| ATOM | 303 | CA | PHE | 88 | −0.556 | 24.209 | 7.992 | 1.00 | 35.05 |
| ATOM | 304 | CB | PHE | 88 | −0.986 | 24.602 | 9.424 | 1.00 | 35.48 |
| ATOM | 305 | CG | PHE | 88 | −0.009 | 25.499 | 10.159 | 1.00 | 36.14 |
| ATOM | 306 | CD1 | PHE | 88 | −0.433 | 26.230 | 11.271 | 1.00 | 38.84 |
| ATOM | 307 | CE1 | PHE | 88 | 0.470 | 27.024 | 11.985 | 1.00 | 38.29 |
| ATOM | 308 | CZ | PHE | 88 | 1.803 | 27.121 | 11.564 | 1.00 | 38.18 |
| ATOM | 309 | CE2 | PHE | 88 | 2.236 | 26.406 | 10.443 | 1.00 | 36.77 |
| ATOM | 310 | CD2 | PHE | 88 | 1.327 | 25.603 | 9.752 | 1.00 | 38.00 |
| ATOM | 311 | C | PHE | 88 | −1.434 | 23.064 | 7.588 | 1.00 | 35.83 |
| ATOM | 312 | O | PHE | 88 | −1.070 | 21.904 | 7.798 | 1.00 | 35.38 |
| ATOM | 313 | N | SER | 89 | −2.619 | 23.382 | 7.059 | 1.00 | 35.76 |
| ATOM | 314 | CA | SER | 89 | −3.626 | 22.360 | 6.792 | 1.00 | 34.90 |
| ATOM | 315 | CB | SER | 89 | −4.956 | 23.030 | 6.403 | 1.00 | 35.63 |
| ATOM | 316 | OG | SER | 89 | −5.031 | 23.345 | 5.008 | 1.00 | 35.63 |
| ATOM | 317 | C | SER | 89 | −3.210 | 21.359 | 5.741 | 1.00 | 35.05 |
| ATOM | 318 | O | SER | 89 | −3.921 | 20.374 | 5.486 | 1.00 | 35.82 |
| ATOM | 319 | N | PRO | 57 | −2.847 | 45.975 | 14.351 | 1.00 | 55.15 |
| ATOM | 320 | CA | PRO | 57 | −3.937 | 46.836 | 14.874 | 1.00 | 56.01 |
| ATOM | 321 | CB | PRO | 57 | −4.647 | 47.348 | 13.604 | 1.00 | 55.67 |
| ATOM | 322 | CG | PRO | 57 | −4.398 | 46.294 | 12.585 | 1.00 | 55.68 |
| ATOM | 323 | CD | PRO | 57 | −3.039 | 45.637 | 12.929 | 1.00 | 55.25 |
| ATOM | 324 | C | PRO | 57 | −4.911 | 46.087 | 15.805 | 1.00 | 56.80 |
| ATOM | 325 | O | PRO | 57 | −5.612 | 46.715 | 16.603 | 1.00 | 56.61 |
| ATOM | 326 | N | LYS | 58 | −4.926 | 44.761 | 15.704 | 1.00 | 57.84 |
| ATOM | 327 | CA | LYS | 58 | −5.835 | 43.953 | 16.494 | 1.00 | 59.47 |
| ATOM | 328 | CB | LYS | 58 | −6.215 | 42.667 | 15.749 | 1.00 | 60.28 |
| ATOM | 329 | CG | LYS | 58 | −7.548 | 42.773 | 14.949 | 1.00 | 63.29 |
| ATOM | 330 | CD | LYS | 58 | −7.474 | 43.789 | 13.763 | 1.00 | 64.69 |
| ATOM | 331 | CE | LYS | 58 | −8.831 | 43.991 | 13.055 | 1.00 | 64.11 |

TABLE 5-continued

| | | | | | | | | | |
|---|---|---|---|---|---|---|---|---|---|
| ATOM | 332 | NZ | LYS | 58 | −9.593 | 42.713 | 12.971 | 1.00 | 64.02 |
| ATOM | 333 | C | LYS | 58 | −5.270 | 43.644 | 17.876 | 1.00 | 59.38 |
| ATOM | 334 | O | LYS | 58 | −5.910 | 43.920 | 18.910 | 1.00 | 59.15 |
| ATOM | 335 | N | VAL | 59 | −4.057 | 43.100 | 17.900 | 1.00 | 59.37 |
| ATOM | 336 | CA | VAL | 59 | −3.519 | 42.599 | 19.160 | 1.00 | 58.99 |
| ATOM | 337 | CB | VAL | 59 | −2.878 | 41.250 | 18.958 | 1.00 | 59.24 |
| ATOM | 338 | CG1 | VAL | 59 | −1.660 | 41.382 | 18.089 | 1.00 | 58.19 |
| ATOM | 339 | CG2 | VAL | 59 | −2.566 | 40.599 | 20.337 | 1.00 | 62.18 |
| ATOM | 340 | C | VAL | 59 | −2.561 | 43.573 | 19.848 | 1.00 | 57.82 |
| ATOM | 341 | O | VAL | 59 | −2.373 | 43.508 | 21.058 | 1.00 | 57.80 |
| TER | | | | | | | | | |

TABLE 6

| | | | | | | | | | |
|---|---|---|---|---|---|---|---|---|---|
| REMARK | Accelrys ViewerPro PDB file | | | | | | | | |
| REMARK | Created: Tue Dec 14 18:42:17 Pacific Standard Time 2010 | | | | | | | | |
| ATOM | 1 | N | VAL | 30 | −10.027 | 29.197 | 21.848 | 1.00 | 39.88 |
| ATOM | 2 | CA | VAL | 30 | −9.712 | 28.307 | 20.715 | 1.00 | 38.85 |
| ATOM | 3 | CB | VAL | 30 | −9.718 | 28.990 | 19.321 | 1.00 | 38.91 |
| ATOM | 4 | CG1 | VAL | 30 | −8.669 | 30.074 | 19.218 | 1.00 | 37.59 |
| ATOM | 5 | CG2 | VAL | 30 | −11.093 | 29.537 | 19.024 | 1.00 | 39.29 |
| ATOM | 6 | C | VAL | 30 | −8.454 | 27.495 | 20.885 | 1.00 | 38.01 |
| ATOM | 7 | O | VAL | 30 | −8.291 | 26.493 | 20.195 | 1.00 | 39.15 |
| ATOM | 8 | N | LEU | 31 | −7.586 | 27.895 | 21.813 | 1.00 | 36.59 |
| ATOM | 9 | CA | LEU | 31 | −6.320 | 27.193 | 22.025 | 1.00 | 36.17 |
| ATOM | 10 | CB | LEU | 31 | −5.411 | 27.946 | 22.979 | 1.00 | 36.01 |
| ATOM | 11 | CG | LEU | 31 | −4.853 | 29.272 | 22.527 | 1.00 | 33.94 |
| ATOM | 12 | CD1 | LEU | 31 | −4.256 | 29.966 | 23.707 | 1.00 | 31.75 |
| ATOM | 13 | CD2 | LEU | 31 | −3.780 | 29.007 | 21.480 | 1.00 | 31.12 |
| ATOM | 14 | C | LEU | 31 | −6.485 | 25.785 | 22.545 | 1.00 | 36.98 |
| ATOM | 15 | O | LEU | 31 | −7.317 | 25.523 | 23.433 | 1.00 | 36.75 |
| ATOM | 16 | N | LYS | 46 | 9.752 | 26.431 | 18.442 | 1.00 | 28.21 |
| ATOM | 17 | CA | LYS | 46 | 9.514 | 27.829 | 17.967 | 1.00 | 27.33 |
| ATOM | 18 | CB | LYS | 46 | 10.784 | 28.454 | 17.363 | 1.00 | 26.71 |
| ATOM | 19 | CG | LYS | 46 | 10.609 | 29.922 | 16.907 | 1.00 | 28.68 |
| ATOM | 20 | CD | LYS | 46 | 11.469 | 30.257 | 15.738 | 1.00 | 29.59 |
| ATOM | 21 | CE | LYS | 46 | 12.822 | 30.659 | 16.132 | 1.00 | 35.72 |
| ATOM | 22 | NZ | LYS | 46 | 13.871 | 30.248 | 15.017 | 1.00 | 33.53 |
| ATOM | 23 | C | LYS | 46 | 8.390 | 27.893 | 16.961 | 1.00 | 26.64 |
| ATOM | 24 | O | LYS | 46 | 8.386 | 27.140 | 16.036 | 1.00 | 26.42 |
| ATOM | 25 | N | PHE | 47 | 7.460 | 28.822 | 17.125 | 1.00 | 27.04 |
| ATOM | 26 | CA | PHE | 47 | 6.509 | 29.164 | 16.080 | 1.00 | 26.96 |
| ATOM | 27 | CB | PHE | 47 | 5.122 | 29.288 | 16.631 | 1.00 | 27.29 |
| ATOM | 28 | CG | PHE | 47 | 4.680 | 28.059 | 17.253 | 1.00 | 32.14 |
| ATOM | 29 | CD1 | PHE | 47 | 5.061 | 27.752 | 18.556 | 1.00 | 32.34 |
| ATOM | 30 | CE1 | PHE | 47 | 4.684 | 26.523 | 19.112 | 1.00 | 34.46 |
| ATOM | 31 | CZ | PHE | 47 | 3.922 | 25.627 | 18.386 | 1.00 | 33.35 |
| ATOM | 32 | CE2 | PHE | 47 | 3.532 | 25.925 | 17.103 | 1.00 | 35.35 |
| ATOM | 33 | CD2 | PHE | 47 | 3.926 | 27.138 | 16.530 | 1.00 | 35.90 |
| ATOM | 34 | C | PHE | 47 | 6.912 | 30.470 | 15.433 | 1.00 | 26.50 |
| ATOM | 35 | O | PHE | 47 | 7.119 | 31.479 | 16.125 | 1.00 | 25.24 |
| ATOM | 36 | N | ASN | 48 | 6.990 | 30.446 | 14.098 | 1.00 | 26.57 |
| ATOM | 37 | CA | ASN | 48 | 7.222 | 31.672 | 13.318 | 1.00 | 26.60 |
| ATOM | 38 | CB | ASN | 48 | 8.197 | 31.412 | 12.153 | 1.00 | 26.14 |
| ATOM | 39 | CG | ASN | 48 | 9.474 | 30.836 | 12.606 | 1.00 | 23.57 |
| ATOM | 40 | OD1 | ASN | 48 | 10.169 | 31.441 | 13.400 | 1.00 | 28.74 |
| ATOM | 41 | ND2 | ASN | 48 | 9.806 | 29.653 | 12.137 | 1.00 | 24.59 |
| ATOM | 42 | C | ASN | 48 | 5.894 | 32.145 | 12.824 | 1.00 | 26.71 |
| ATOM | 43 | O | ASN | 48 | 5.224 | 31.415 | 12.114 | 1.00 | 26.51 |
| ATOM | 44 | N | CYS | 49 | 5.506 | 33.376 | 13.174 | 1.00 | 27.64 |
| ATOM | 45 | CA | CYS | 49 | 4.144 | 33.833 | 12.886 | 1.00 | 28.17 |
| ATOM | 46 | CB | CYS | 49 | 3.345 | 33.977 | 14.190 | 1.00 | 28.79 |
| ATOM | 47 | SG | CYS | 49 | 3.437 | 32.546 | 15.288 | 1.00 | 32.41 |
| ATOM | 48 | C | CYS | 49 | 4.172 | 35.171 | 12.156 | 1.00 | 28.06 |
| ATOM | 49 | O | CYS | 49 | 4.010 | 36.181 | 12.783 | 1.00 | 26.43 |
| ATOM | 50 | N | PRO | 50 | 4.423 | 35.167 | 10.817 | 1.00 | 28.99 |
| ATOM | 51 | CA | PRO | 50 | 4.617 | 36.400 | 10.031 | 1.00 | 29.58 |
| ATOM | 52 | CB | PRO | 50 | 5.359 | 35.914 | 8.756 | 1.00 | 29.17 |
| ATOM | 53 | CG | PRO | 50 | 5.412 | 34.467 | 8.860 | 1.00 | 29.81 |
| ATOM | 54 | CD | PRO | 50 | 4.626 | 33.958 | 9.993 | 1.00 | 28.43 |
| ATOM | 55 | C | PRO | 50 | 3.346 | 37.097 | 9.626 | 1.00 | 29.99 |
| ATOM | 56 | O | PRO | 50 | 3.409 | 38.195 | 9.096 | 1.00 | 31.25 |
| ATOM | 57 | N | GLU | 51 | 2.213 | 36.484 | 9.888 | 1.00 | 30.28 |
| ATOM | 58 | CA | GLU | 51 | 0.947 | 36.995 | 9.431 | 1.00 | 31.01 |
| ATOM | 59 | CB | GLU | 51 | 0.195 | 35.883 | 8.744 | 1.00 | 31.20 |
| ATOM | 60 | CG | GLU | 51 | 0.898 | 35.423 | 7.474 | 1.00 | 31.72 |
| ATOM | 61 | CD | GLU | 51 | 0.223 | 34.224 | 6.826 | 1.00 | 39.70 |

TABLE 6-continued

| | | | | | | | | | |
|---|---|---|---|---|---|---|---|---|---|
| ATOM | 62 | OE1 | GLU | 51 | −0.864 | 33.794 | 7.339 | 1.00 | 41.03 |
| ATOM | 63 | OE2 | GLU | 51 | 0.791 | 33.703 | 5.815 | 1.00 | 39.79 |
| ATOM | 64 | C | GLU | 51 | 0.099 | 37.650 | 10.496 | 1.00 | 30.89 |
| ATOM | 65 | O | GLU | 51 | −1.107 | 37.724 | 10.383 | 1.00 | 32.20 |
| ATOM | 66 | N | PHE | 52 | 0.724 | 38.170 | 11.534 | 1.00 | 30.63 |
| ATOM | 67 | CA | PHE | 52 | −0.075 | 38.686 | 12.624 | 1.00 | 29.27 |
| ATOM | 68 | CB | PHE | 52 | 0.705 | 38.605 | 13.946 | 1.00 | 29.89 |
| ATOM | 69 | CG | PHE | 52 | −0.031 | 39.236 | 15.114 | 1.00 | 28.40 |
| ATOM | 70 | CD1 | PHE | 52 | −0.890 | 38.482 | 15.907 | 1.00 | 28.58 |
| ATOM | 71 | CE1 | PHE | 52 | −1.580 | 39.056 | 16.983 | 1.00 | 24.69 |
| ATOM | 72 | CZ | PHE | 52 | −1.404 | 40.368 | 17.259 | 1.00 | 27.97 |
| ATOM | 73 | CE2 | PHE | 52 | −0.557 | 41.156 | 16.447 | 1.00 | 29.23 |
| ATOM | 74 | CD2 | PHE | 52 | 0.125 | 40.578 | 15.399 | 1.00 | 26.27 |
| ATOM | 75 | C | PHE | 52 | −0.491 | 40.118 | 12.337 | 1.00 | 29.10 |
| ATOM | 76 | O | PHE | 52 | 0.323 | 40.920 | 11.880 | 1.00 | 28.69 |
| ATOM | 77 | N | ALA | 65 | 2.722 | 42.393 | 12.363 | 1.00 | 25.05 |
| ATOM | 78 | CA | ALA | 65 | 3.949 | 42.023 | 13.033 | 1.00 | 25.65 |
| ATOM | 79 | CB | ALA | 65 | 3.646 | 41.872 | 14.597 | 1.00 | 25.77 |
| ATOM | 80 | C | ALA | 65 | 4.391 | 40.689 | 12.554 | 1.00 | 24.74 |
| ATOM | 81 | O | ALA | 65 | 3.595 | 39.881 | 12.154 | 1.00 | 23.37 |
| ATOM | 82 | N | THR | 66 | 5.652 | 40.394 | 12.715 | 1.00 | 25.21 |
| ATOM | 83 | CA | THR | 66 | 5.993 | 38.982 | 12.790 | 1.00 | 26.25 |
| ATOM | 84 | CB | THR | 66 | 7.251 | 38.700 | 11.952 | 1.00 | 25.43 |
| ATOM | 85 | OG1 | THR | 66 | 6.923 | 38.942 | 10.577 | 1.00 | 27.57 |
| ATOM | 86 | CG2 | THR | 66 | 7.623 | 37.300 | 12.088 | 1.00 | 27.62 |
| ATOM | 87 | C | THR | 66 | 6.193 | 38.642 | 14.281 | 1.00 | 26.46 |
| ATOM | 88 | O | THR | 66 | 6.829 | 39.416 | 14.990 | 1.00 | 27.05 |
| ATOM | 89 | N | ILE | 67 | 5.654 | 37.521 | 14.746 | 1.00 | 26.09 |
| ATOM | 90 | CA | ILE | 67 | 5.819 | 37.110 | 16.151 | 1.00 | 25.88 |
| ATOM | 91 | CB | ILE | 67 | 4.439 | 36.948 | 16.853 | 1.00 | 27.19 |
| ATOM | 92 | CG1 | ILE | 67 | 3.680 | 38.280 | 16.894 | 1.00 | 26.17 |
| ATOM | 93 | CD1 | ILE | 67 | 2.275 | 37.999 | 17.230 | 1.00 | 28.34 |
| ATOM | 94 | CG2 | ILE | 67 | 4.609 | 36.554 | 18.301 | 1.00 | 27.68 |
| ATOM | 95 | C | ILE | 67 | 6.544 | 35.791 | 16.217 | 1.00 | 25.12 |
| ATOM | 96 | O | ILE | 67 | 6.210 | 34.852 | 15.485 | 1.00 | 23.17 |
| ATOM | 97 | N | TYR | 68 | 7.580 | 35.740 | 17.047 | 1.00 | 25.62 |
| ATOM | 98 | CA | TYR | 68 | 8.349 | 34.489 | 17.304 | 1.00 | 25.42 |
| ATOM | 99 | CB | TYR | 68 | 9.846 | 34.742 | 17.175 | 1.00 | 24.80 |
| ATOM | 100 | CG | TYR | 68 | 10.216 | 35.263 | 15.782 | 1.00 | 28.39 |
| ATOM | 101 | CD1 | TYR | 68 | 10.358 | 36.635 | 15.557 | 1.00 | 23.93 |
| ATOM | 102 | CE1 | TYR | 68 | 10.641 | 37.129 | 14.313 | 1.00 | 29.14 |
| ATOM | 103 | CZ | TYR | 68 | 10.815 | 36.239 | 13.225 | 1.00 | 31.13 |
| ATOM | 104 | OH | TYR | 68 | 11.139 | 36.764 | 11.975 | 1.00 | 29.59 |
| ATOM | 105 | CE2 | TYR | 68 | 10.669 | 34.875 | 13.412 | 1.00 | 30.72 |
| ATOM | 106 | CD2 | TYR | 68 | 10.386 | 34.384 | 14.695 | 1.00 | 25.51 |
| ATOM | 107 | C | TYR | 68 | 8.032 | 33.953 | 18.704 | 1.00 | 25.82 |
| ATOM | 108 | O | TYR | 68 | 8.297 | 34.631 | 19.684 | 1.00 | 26.19 |
| ATOM | 109 | N | VAL | 78 | 1.156 | 23.155 | 22.701 | 1.00 | 36.61 |
| ATOM | 110 | CA | VAL | 78 | 0.051 | 23.804 | 21.960 | 1.00 | 35.17 |
| ATOM | 111 | CB | VAL | 78 | 0.110 | 25.366 | 21.955 | 1.00 | 36.02 |
| ATOM | 112 | CG1 | VAL | 78 | 1.423 | 25.891 | 21.349 | 1.00 | 36.14 |
| ATOM | 113 | CG2 | VAL | 78 | −1.098 | 25.974 | 21.228 | 1.00 | 33.46 |
| ATOM | 114 | C | VAL | 78 | −0.056 | 23.246 | 20.537 | 1.00 | 35.32 |
| ATOM | 115 | O | VAL | 78 | 0.952 | 22.940 | 19.878 | 1.00 | 33.32 |
| ATOM | 116 | N | GLU | 79 | −1.299 | 23.132 | 20.084 | 1.00 | 35.31 |
| ATOM | 117 | CA | GLU | 79 | −1.584 | 22.611 | 18.788 | 1.00 | 35.07 |
| ATOM | 118 | CB | GLU | 79 | −2.944 | 21.906 | 18.834 | 1.00 | 35.69 |
| ATOM | 119 | CG | GLU | 79 | −3.207 | 21.034 | 17.587 | 1.00 | 40.72 |
| ATOM | 120 | CD | GLU | 79 | −3.716 | 21.830 | 16.403 | 1.00 | 45.36 |
| ATOM | 121 | OE1 | GLU | 79 | −4.736 | 22.551 | 16.573 | 1.00 | 47.59 |
| ATOM | 122 | OE2 | GLU | 79 | −3.103 | 21.725 | 15.301 | 1.00 | 47.64 |
| ATOM | 123 | C | GLU | 79 | −1.555 | 23.792 | 17.819 | 1.00 | 33.69 |
| ATOM | 124 | O | GLU | 79 | −2.202 | 24.797 | 18.054 | 1.00 | 31.63 |
| ATOM | 125 | N | SER | 80 | −0.773 | 23.659 | 16.743 | 1.00 | 33.31 |
| ATOM | 126 | CA | SER | 80 | −0.626 | 24.679 | 15.691 | 1.00 | 33.28 |
| ATOM | 127 | CB | SER | 80 | 0.021 | 24.059 | 14.496 | 1.00 | 33.95 |
| ATOM | 128 | OG | SER | 80 | 1.225 | 23.483 | 14.928 | 1.00 | 40.59 |
| ATOM | 129 | C | SER | 80 | −1.842 | 25.355 | 15.138 | 1.00 | 33.46 |
| ATOM | 130 | O | SER | 80 | −1.865 | 26.600 | 15.044 | 1.00 | 33.68 |
| ATOM | 131 | N | LYS | 81 | −2.821 | 24.553 | 14.689 | 1.00 | 33.65 |
| ATOM | 132 | CA | LYS | 81 | −3.991 | 25.115 | 14.082 | 1.00 | 34.76 |
| ATOM | 133 | CB | LYS | 81 | −4.921 | 24.047 | 13.541 | 1.00 | 35.65 |
| ATOM | 134 | CG | LYS | 81 | −6.297 | 24.607 | 12.985 | 1.00 | 39.18 |
| ATOM | 135 | CD | LYS | 81 | −7.212 | 23.473 | 12.479 | 1.00 | 39.66 |
| ATOM | 136 | CE | LYS | 81 | −6.411 | 22.451 | 11.558 | 1.00 | 48.39 |
| ATOM | 137 | NZ | LYS | 81 | −7.178 | 21.202 | 11.039 | 1.00 | 47.55 |
| ATOM | 138 | C | LYS | 81 | −4.705 | 25.957 | 15.108 | 1.00 | 33.64 |
| ATOM | 139 | O | LYS | 81 | −5.242 | 27.017 | 14.759 | 1.00 | 33.95 |
| ATOM | 140 | N | SER | 82 | −4.698 | 25.507 | 16.375 | 1.00 | 32.20 |
| ATOM | 141 | CA | SER | 82 | −5.380 | 26.282 | 17.407 | 1.00 | 30.55 |

TABLE 6-continued

| | | | | | | | | |
|---|---|---|---|---|---|---|---|---|
| ATOM | 142 | CB | SER | 82 | −5.617 | 25.478 | 18.701 | 1.00 | 30.70 |
| ATOM | 143 | OG | SER | 82 | −4.432 | 25.241 | 19.453 | 1.00 | 29.50 |
| ATOM | 144 | C | SER | 82 | −4.644 | 27.601 | 17.669 | 1.00 | 29.19 |
| ATOM | 145 | O | SER | 82 | −5.258 | 28.646 | 17.849 | 1.00 | 27.98 |
| ATOM | 146 | N | LEU | 83 | −3.329 | 27.543 | 17.676 | 1.00 | 28.73 |
| ATOM | 147 | CA | LEU | 83 | −2.548 | 28.761 | 17.749 | 1.00 | 29.29 |
| ATOM | 148 | CB | LEU | 83 | −1.055 | 28.384 | 17.815 | 1.00 | 30.66 |
| ATOM | 149 | CG | LEU | 83 | −0.296 | 29.708 | 17.889 | 1.00 | 28.90 |
| ATOM | 150 | CD1 | LEU | 83 | −0.611 | 30.422 | 19.214 | 1.00 | 26.97 |
| ATOM | 151 | CD2 | LEU | 83 | 1.149 | 29.445 | 17.690 | 1.00 | 25.69 |
| ATOM | 152 | C | LEU | 83 | −2.870 | 29.744 | 16.572 | 1.00 | 29.47 |
| ATOM | 153 | O | LEU | 83 | −3.168 | 30.941 | 16.797 | 1.00 | 28.25 |
| ATOM | 154 | N | LYS | 84 | −2.921 | 29.223 | 15.336 | 1.00 | 29.53 |
| ATOM | 155 | CA | LYS | 84 | −3.313 | 30.056 | 14.205 | 1.00 | 29.62 |
| ATOM | 156 | CB | LYS | 84 | −3.217 | 29.274 | 12.893 | 1.00 | 30.52 |
| ATOM | 157 | CG | LYS | 84 | −3.972 | 29.888 | 11.707 | 1.00 | 33.47 |
| ATOM | 158 | CD | LYS | 84 | −4.266 | 28.844 | 10.637 | 1.00 | 38.12 |
| ATOM | 159 | CE | LYS | 84 | −5.650 | 28.275 | 10.827 | 1.00 | 42.09 |
| ATOM | 160 | NZ | LYS | 84 | −6.014 | 27.397 | 9.687 | 1.00 | 45.75 |
| ATOM | 161 | C | LYS | 84 | −4.677 | 30.735 | 14.370 | 1.00 | 29.83 |
| ATOM | 162 | O | LYS | 84 | −4.838 | 31.939 | 14.130 | 1.00 | 28.57 |
| ATOM | 163 | N | LEU | 85 | −5.681 | 29.976 | 14.780 | 1.00 | 30.73 |
| ATOM | 164 | CA | LEU | 85 | −7.015 | 30.608 | 14.980 | 1.00 | 31.39 |
| ATOM | 165 | CB | LEU | 85 | −8.085 | 29.555 | 15.241 | 1.00 | 32.27 |
| ATOM | 166 | CG | LEU | 85 | −8.130 | 28.457 | 14.200 | 1.00 | 34.28 |
| ATOM | 167 | CD1 | LEU | 85 | −8.958 | 27.262 | 14.722 | 1.00 | 36.91 |
| ATOM | 168 | CD2 | LEU | 85 | −8.732 | 29.143 | 12.958 | 1.00 | 35.13 |
| ATOM | 169 | C | LEU | 85 | −6.991 | 31.603 | 16.132 | 1.00 | 30.61 |
| ATOM | 170 | O | LEU | 85 | −7.642 | 32.659 | 16.110 | 1.00 | 31.60 |
| ATOM | 171 | N | TYR | 86 | −6.230 | 31.266 | 17.143 | 1.00 | 30.00 |
| ATOM | 172 | CA | TYR | 86 | −6.030 | 32.184 | 18.243 | 1.00 | 30.34 |
| ATOM | 173 | CB | TYR | 86 | −5.151 | 31.534 | 19.311 | 1.00 | 29.45 |
| ATOM | 174 | CG | TYR | 86 | −4.787 | 32.481 | 20.378 | 1.00 | 28.30 |
| ATOM | 175 | CD1 | TYR | 86 | −5.769 | 33.034 | 21.231 | 1.00 | 25.94 |
| ATOM | 176 | CE1 | TYR | 86 | −5.381 | 33.976 | 22.295 | 1.00 | 26.67 |
| ATOM | 177 | CZ | TYR | 86 | −4.003 | 34.279 | 22.458 | 1.00 | 27.51 |
| ATOM | 178 | OH | TYR | 86 | −3.544 | 35.189 | 23.393 | 1.00 | 30.54 |
| ATOM | 179 | CE2 | TYR | 86 | −3.047 | 33.694 | 21.630 | 1.00 | 28.71 |
| ATOM | 180 | CD2 | TYR | 86 | −3.456 | 32.815 | 20.573 | 1.00 | 29.33 |
| ATOM | 181 | C | TYR | 86 | −5.454 | 33.528 | 17.785 | 1.00 | 29.86 |
| ATOM | 182 | O | TYR | 86 | −5.988 | 34.578 | 18.107 | 1.00 | 30.59 |
| ATOM | 183 | N | LEU | 87 | −4.345 | 33.491 | 17.056 | 1.00 | 30.90 |
| ATOM | 184 | CA | LEU | 87 | −3.739 | 34.716 | 16.504 | 1.00 | 29.69 |
| ATOM | 185 | CB | LEU | 87 | −2.406 | 34.397 | 15.844 | 1.00 | 29.57 |
| ATOM | 186 | CG | LEU | 87 | −1.341 | 33.881 | 16.831 | 1.00 | 29.35 |
| ATOM | 187 | CD1 | LEU | 87 | −0.060 | 33.751 | 16.088 | 1.00 | 26.50 |
| ATOM | 188 | CD2 | LEU | 87 | −1.138 | 34.780 | 18.072 | 1.00 | 22.21 |
| ATOM | 189 | C | LEU | 87 | −4.667 | 35.392 | 15.540 | 1.00 | 29.49 |
| ATOM | 190 | O | LEU | 87 | −4.741 | 36.615 | 15.518 | 1.00 | 29.08 |
| ATOM | 191 | N | PHE | 88 | −5.422 | 34.610 | 14.763 | 1.00 | 31.41 |
| ATOM | 192 | CA | PHE | 88 | −6.451 | 35.212 | 13.893 | 1.00 | 33.88 |
| ATOM | 193 | CB | PHE | 88 | −7.140 | 34.175 | 12.971 | 1.00 | 36.10 |
| ATOM | 194 | CG | PHE | 88 | −6.282 | 33.770 | 11.731 | 1.00 | 37.70 |
| ATOM | 195 | CD1 | PHE | 88 | −6.602 | 32.633 | 10.979 | 1.00 | 38.15 |
| ATOM | 196 | CE1 | PHE | 88 | −5.804 | 32.255 | 9.892 | 1.00 | 37.93 |
| ATOM | 197 | CZ | PHE | 88 | −4.657 | 33.023 | 9.525 | 1.00 | 39.92 |
| ATOM | 198 | CE2 | PHE | 88 | −4.312 | 34.157 | 10.250 | 1.00 | 38.80 |
| ATOM | 199 | CD2 | PHE | 88 | −5.131 | 34.517 | 11.371 | 1.00 | 40.71 |
| ATOM | 200 | C | PHE | 88 | −7.501 | 36.008 | 14.662 | 1.00 | 33.94 |
| ATOM | 201 | O | PHE | 88 | −8.033 | 36.970 | 14.107 | 1.00 | 34.36 |
| ATOM | 202 | N | SER | 89 | −7.768 | 35.638 | 15.938 | 1.00 | 32.64 |
| ATOM | 203 | CA | SER | 89 | −8.811 | 36.309 | 16.721 | 1.00 | 32.27 |
| ATOM | 204 | CB | SER | 89 | −9.280 | 35.421 | 17.889 | 1.00 | 31.84 |
| ATOM | 205 | OG | SER | 89 | −8.350 | 35.463 | 18.968 | 1.00 | 32.07 |
| ATOM | 206 | C | SER | 89 | −8.405 | 37.716 | 17.208 | 1.00 | 32.06 |
| ATOM | 207 | O | SER | 89 | −9.194 | 38.435 | 17.835 | 1.00 | 32.05 |
| ATOM | 208 | N | LYS | 122 | 7.565 | 41.780 | 16.334 | 1.00 | 24.36 |
| ATOM | 209 | CA | LYS | 122 | 8.356 | 42.708 | 15.507 | 1.00 | 23.32 |
| ATOM | 210 | CB | LYS | 122 | 9.464 | 41.954 | 14.742 | 1.00 | 23.06 |
| ATOM | 211 | CG | LYS | 122 | 10.642 | 41.528 | 15.686 | 1.00 | 24.84 |
| ATOM | 212 | CD | LYS | 122 | 11.690 | 40.740 | 14.927 | 1.00 | 25.66 |
| ATOM | 213 | CE | LYS | 122 | 12.973 | 40.581 | 15.714 | 1.00 | 30.58 |
| ATOM | 214 | NZ | LYS | 122 | 14.080 | 40.258 | 14.755 | 1.00 | 28.48 |
| ATOM | 215 | C | LYS | 122 | 7.436 | 43.404 | 14.573 | 1.00 | 23.02 |
| ATOM | 216 | O | LYS | 122 | 7.165 | 42.933 | 13.491 | 1.00 | 21.33 |
| ATOM | 217 | N | ILE | 162 | 17.614 | 48.303 | 11.131 | 1.00 | 34.11 |
| ATOM | 218 | CA | ILE | 162 | 16.251 | 48.557 | 10.697 | 1.00 | 35.37 |
| ATOM | 219 | CB | ILE | 162 | 15.251 | 48.647 | 11.867 | 1.00 | 33.88 |
| ATOM | 220 | CG1 | ILE | 162 | 15.099 | 47.211 | 12.546 | 1.00 | 34.92 |
| ATOM | 221 | CD1 | ILE | 162 | 14.500 | 46.216 | 11.657 | 1.00 | 33.57 |

TABLE 6-continued

| | | | | | | | | | |
|---|---|---|---|---|---|---|---|---|---|
| ATOM | 222 | CG2 | ILE | 162 | 13.875 | 49.124 | 11.377 | 1.00 | 35.20 |
| ATOM | 223 | C | ILE | 162 | 16.293 | 49.922 | 10.020 | 1.00 | 36.65 |
| ATOM | 224 | O | ILE | 162 | 16.908 | 50.846 | 10.540 | 1.00 | 36.63 |
| ATOM | 225 | O3S | G6S | 202 | −6.417 | 25.426 | 0.711 | 1.00 | 0.87 |
| ATOM | 226 | S | G6S | 202 | −5.861 | 24.491 | 1.721 | 1.00 | 0.84 |
| ATOM | 227 | O1S | G6S | 202 | −4.394 | 24.699 | 1.720 | 1.00 | 0.00 |
| ATOM | 228 | O2S | G6S | 202 | −6.128 | 23.096 | 1.294 | 1.00 | 0.46 |
| ATOM | 229 | O6 | G6S | 202 | −6.514 | 24.717 | 3.235 | 1.00 | 0.15 |
| ATOM | 230 | C6 | G6S | 202 | −6.407 | 23.744 | 4.298 | 1.00 | 0.76 |
| ATOM | 231 | C5 | G6S | 202 | −5.815 | 24.269 | 5.632 | 1.00 | 0.20 |
| ATOM | 232 | O5 | G6S | 202 | −5.455 | 25.669 | 5.607 | 1.00 | 0.47 |
| ATOM | 233 | C4 | G6S | 202 | −4.654 | 23.396 | 6.182 | 1.00 | 0.65 |
| ATOM | 234 | O4 | G6S | 202 | −4.830 | 22.013 | 5.790 | 1.00 | 0.12 |
| ATOM | 235 | C3 | G6S | 202 | −3.205 | 23.860 | 5.851 | 1.00 | 0.92 |
| ATOM | 236 | O3 | G6S | 202 | −2.631 | 23.077 | 4.786 | 1.00 | 0.71 |
| ATOM | 237 | C2 | G6S | 202 | −3.039 | 25.370 | 5.570 | 1.00 | 0.85 |
| ATOM | 238 | O2 | G6S | 202 | −1.849 | 25.641 | 4.806 | 1.00 | 0.58 |
| ATOM | 239 | C1 | G6S | 202 | −4.258 | 25.980 | 4.878 | 1.00 | 0.56 |
| ATOM | 240 | O1 | G6S | 202 | −4.113 | 27.396 | 4.800 | 1.00 | 0.12 |
| ATOM | 241 | N | THR | 124 | 8.162 | 23.859 | 6.927 | 1.00 | 28.52 |
| ATOM | 242 | CA | THR | 124 | 7.515 | 24.851 | 6.071 | 1.00 | 28.16 |
| ATOM | 243 | CB | THR | 124 | 7.359 | 24.295 | 4.602 | 1.00 | 28.66 |
| ATOM | 244 | OG1 | THR | 124 | 6.538 | 23.105 | 4.602 | 1.00 | 24.86 |
| ATOM | 245 | CG2 | THR | 124 | 8.781 | 23.937 | 3.994 | 1.00 | 25.85 |
| ATOM | 246 | C | THR | 124 | 6.141 | 25.208 | 6.709 | 1.00 | 29.59 |
| ATOM | 247 | O | THR | 124 | 5.563 | 24.383 | 7.435 | 1.00 | 29.24 |
| ATOM | 248 | N | PRO | 125 | 5.639 | 26.436 | 6.465 | 1.00 | 29.30 |
| ATOM | 249 | CA | PRO | 125 | 4.483 | 26.768 | 7.217 | 1.00 | 30.23 |
| ATOM | 250 | CB | PRO | 125 | 4.366 | 28.303 | 7.045 | 1.00 | 29.73 |
| ATOM | 251 | CG | PRO | 125 | 4.979 | 28.581 | 5.715 | 1.00 | 29.08 |
| ATOM | 252 | CD | PRO | 125 | 6.111 | 27.571 | 5.627 | 1.00 | 28.72 |
| ATOM | 253 | C | PRO | 125 | 3.218 | 26.060 | 6.795 | 1.00 | 31.25 |
| ATOM | 254 | O | PRO | 125 | 3.157 | 25.505 | 5.708 | 1.00 | 31.50 |
| ATOM | 255 | N | ARG | 126 | 2.239 | 26.059 | 7.705 | 1.00 | 32.08 |
| ATOM | 256 | CA | ARG | 126 | 0.853 | 25.532 | 7.490 | 1.00 | 33.66 |
| ATOM | 257 | CB | ARG | 126 | 0.642 | 24.193 | 8.230 | 1.00 | 33.84 |
| ATOM | 258 | CG | ARG | 126 | 0.745 | 22.919 | 7.428 | 1.00 | 40.80 |
| ATOM | 259 | CD | ARG | 126 | 1.893 | 23.006 | 6.433 | 1.00 | 49.19 |
| ATOM | 260 | NE | ARG | 126 | 1.976 | 21.898 | 5.465 | 1.00 | 53.43 |
| ATOM | 261 | CZ | ARG | 126 | 2.355 | 22.055 | 4.194 | 1.00 | 54.41 |
| ATOM | 262 | NH1 | ARG | 126 | 2.632 | 23.272 | 3.728 | 1.00 | 52.21 |
| ATOM | 263 | NH2 | ARG | 126 | 2.429 | 20.998 | 3.386 | 1.00 | 55.80 |
| ATOM | 264 | C | ARG | 126 | −0.021 | 26.560 | 8.163 | 1.00 | 32.80 |
| ATOM | 265 | O | ARG | 126 | 0.160 | 26.857 | 9.338 | 1.00 | 32.63 |
| ATOM | 266 | N | GLY | 127 | −0.945 | 27.141 | 7.445 | 1.00 | 32.28 |
| ATOM | 267 | CA | GLY | 127 | −1.814 | 28.067 | 8.064 | 1.00 | 33.33 |
| ATOM | 268 | C | GLY | 127 | −1.073 | 29.335 | 8.406 | 1.00 | 33.71 |
| ATOM | 269 | O | GLY | 127 | −1.587 | 30.135 | 9.168 | 1.00 | 36.24 |
| ATOM | 270 | N | GLY | 128 | 0.134 | 29.522 | 7.865 | 1.00 | 33.07 |
| ATOM | 271 | CA | GLY | 128 | 0.871 | 30.783 | 8.003 | 1.00 | 31.01 |
| ATOM | 272 | C | GLY | 128 | 1.919 | 30.731 | 9.089 | 1.00 | 30.37 |
| ATOM | 273 | O | GLY | 128 | 2.636 | 31.685 | 9.315 | 1.00 | 29.97 |
| ATOM | 274 | N | ILE | 129 | 2.040 | 29.580 | 9.720 | 1.00 | 30.13 |
| ATOM | 275 | CA | ILE | 129 | 2.834 | 29.438 | 10.920 | 1.00 | 30.80 |
| ATOM | 276 | CB | ILE | 129 | 1.846 | 29.137 | 12.140 | 1.00 | 31.06 |
| ATOM | 277 | CG1 | ILE | 129 | 1.178 | 30.432 | 12.588 | 1.00 | 31.42 |
| ATOM | 278 | CD1 | ILE | 129 | 0.149 | 30.230 | 13.677 | 1.00 | 31.28 |
| ATOM | 279 | CG2 | ILE | 129 | 2.537 | 28.447 | 13.309 | 1.00 | 30.12 |
| ATOM | 280 | C | ILE | 129 | 3.782 | 28.259 | 10.679 | 1.00 | 30.22 |
| ATOM | 281 | O | ILE | 129 | 3.322 | 27.210 | 10.335 | 1.00 | 29.71 |
| ATOM | 282 | N | SER | 130 | 5.088 | 28.440 | 10.887 | 1.00 | 29.49 |
| ATOM | 283 | CA | SER | 130 | 6.016 | 27.356 | 10.767 | 1.00 | 29.39 |
| ATOM | 284 | CB | SER | 130 | 7.180 | 27.700 | 9.824 | 1.00 | 29.82 |
| ATOM | 285 | OG | SER | 130 | 7.707 | 28.994 | 10.093 | 1.00 | 33.34 |
| ATOM | 286 | C | SER | 130 | 6.585 | 27.028 | 12.117 | 1.00 | 28.67 |
| ATOM | 287 | O | SER | 130 | 6.692 | 27.882 | 12.993 | 1.00 | 28.81 |
| ATOM | 288 | N | ILE | 131 | 7.011 | 25.792 | 12.255 | 1.00 | 28.29 |
| ATOM | 289 | CA | ILE | 131 | 7.371 | 25.258 | 13.543 | 1.00 | 28.60 |
| ATOM | 290 | CB | ILE | 131 | 6.533 | 24.026 | 13.875 | 1.00 | 28.00 |
| ATOM | 291 | CG1 | ILE | 131 | 5.053 | 24.371 | 13.948 | 1.00 | 29.12 |
| ATOM | 292 | CD1 | ILE | 131 | 4.241 | 23.189 | 14.520 | 1.00 | 31.67 |
| ATOM | 293 | CG2 | ILE | 131 | 6.933 | 23.476 | 15.240 | 1.00 | 30.30 |
| ATOM | 294 | C | ILE | 131 | 8.761 | 24.761 | 13.484 | 1.00 | 28.51 |
| ATOM | 295 | O | ILE | 131 | 9.032 | 23.907 | 12.665 | 1.00 | 30.21 |
| ATOM | 296 | N | ASP | 132 | 9.644 | 25.222 | 14.361 | 1.00 | 28.50 |
| ATOM | 297 | CA | ASP | 132 | 11.010 | 24.737 | 14.331 | 1.00 | 28.58 |
| ATOM | 298 | CB | ASP | 132 | 11.974 | 25.881 | 13.980 | 1.00 | 28.59 |
| ATOM | 299 | CG | ASP | 132 | 11.600 | 26.633 | 12.681 | 1.00 | 32.67 |
| ATOM | 300 | OD1 | ASP | 132 | 10.792 | 26.091 | 11.853 | 1.00 | 33.13 |
| ATOM | 301 | OD2 | ASP | 132 | 12.147 | 27.766 | 12.479 | 1.00 | 30.84 |

TABLE 6-continued

| | | | | | | | | |
|---|---|---|---|---|---|---|---|---|
| ATOM | 302 | C | ASP | 132 | 11.444 | 24.137 | 15.663 | 1.00 | 28.06 |
| ATOM | 303 | O | ASP | 132 | 12.013 | 24.854 | 16.495 | 1.00 | 29.94 |
| ATOM | 304 | N | PRO | 159 | 16.415 | 34.976 | 16.589 | 1.00 | 31.26 |
| ATOM | 305 | CA | PRO | 159 | 15.685 | 34.175 | 15.627 | 1.00 | 30.51 |
| ATOM | 306 | CB | PRO | 159 | 14.218 | 34.258 | 16.123 | 1.00 | 30.21 |
| ATOM | 307 | CG | PRO | 159 | 14.295 | 34.833 | 17.551 | 1.00 | 31.97 |
| ATOM | 308 | CD | PRO | 159 | 15.537 | 35.672 | 17.548 | 1.00 | 31.36 |
| ATOM | 309 | C | PRO | 159 | 15.732 | 34.728 | 14.195 | 1.00 | 30.10 |
| ATOM | 310 | O | PRO | 159 | 15.500 | 35.904 | 13.987 | 1.00 | 29.37 |
| ATOM | 311 | N | GLU | 160 | 15.986 | 33.868 | 13.216 | 1.00 | 30.16 |
| ATOM | 312 | CA | GLU | 160 | 16.056 | 34.287 | 11.808 | 1.00 | 32.04 |
| ATOM | 313 | CB | GLU | 160 | 16.394 | 33.069 | 10.935 | 1.00 | 30.18 |
| ATOM | 314 | CG | GLU | 160 | 15.200 | 32.081 | 10.771 | 1.00 | 34.46 |
| ATOM | 315 | CD | GLU | 160 | 15.572 | 30.767 | 10.043 | 1.00 | 35.57 |
| ATOM | 316 | OE1 | GLU | 160 | 16.665 | 30.687 | 9.481 | 1.00 | 41.25 |
| ATOM | 317 | OE2 | GLU | 160 | 14.777 | 29.801 | 10.036 | 1.00 | 41.34 |
| ATOM | 318 | C | GLU | 160 | 14.753 | 34.982 | 11.337 | 1.00 | 30.49 |
| ATOM | 319 | O | GLU | 160 | 13.656 | 34.622 | 11.783 | 1.00 | 31.95 |
| ATOM | 320 | N | THR | 161 | 14.864 | 35.989 | 10.481 | 1.00 | 29.64 |
| ATOM | 321 | CA | THR | 161 | 13.670 | 36.585 | 9.878 | 1.00 | 29.93 |
| ATOM | 322 | CB | THR | 161 | 14.010 | 37.825 | 9.073 | 1.00 | 29.91 |
| ATOM | 323 | OG1 | THR | 161 | 14.709 | 38.699 | 9.931 | 1.00 | 31.93 |
| ATOM | 324 | CG2 | THR | 161 | 12.784 | 38.579 | 8.601 | 1.00 | 30.92 |
| ATOM | 325 | C | THR | 161 | 12.960 | 35.585 | 8.987 | 1.00 | 29.45 |
| ATOM | 326 | O | THR | 161 | 13.597 | 34.923 | 8.182 | 1.00 | 26.77 |
| ATOM | 327 | N | ILE | 162 | 11.662 | 35.432 | 9.220 | 1.00 | 29.30 |
| ATOM | 328 | CA | ILE | 162 | 10.844 | 34.548 | 8.451 | 1.00 | 30.78 |
| ATOM | 329 | CB | ILE | 162 | 10.290 | 33.390 | 9.320 | 1.00 | 30.32 |
| ATOM | 330 | CG1 | ILE | 162 | 11.436 | 32.471 | 9.806 | 1.00 | 32.82 |
| ATOM | 331 | CD1 | ILE | 162 | 12.167 | 31.571 | 8.744 | 1.00 | 30.34 |
| ATOM | 332 | CG2 | ILE | 162 | 9.195 | 32.625 | 8.587 | 1.00 | 29.66 |
| ATOM | 333 | C | ILE | 162 | 9.657 | 35.351 | 7.921 | 1.00 | 31.75 |
| ATOM | 334 | O | ILE | 162 | 9.051 | 36.113 | 8.690 | 1.00 | 31.45 |
| ATOM | 335 | N | ASP | 163 | 9.345 | 35.185 | 6.626 | 1.00 | 32.01 |
| ATOM | 336 | CA | ASP | 163 | 8.215 | 35.871 | 5.970 | 1.00 | 33.79 |
| ATOM | 337 | CB | ASP | 163 | 8.697 | 37.063 | 5.098 | 1.00 | 34.23 |
| ATOM | 338 | CG | ASP | 163 | 9.591 | 36.629 | 3.921 | 1.00 | 36.10 |
| ATOM | 339 | OD1 | ASP | 163 | 9.955 | 35.407 | 3.834 | 1.00 | 36.53 |
| ATOM | 340 | OD2 | ASP | 163 | 9.956 | 37.510 | 3.082 | 1.00 | 34.45 |
| ATOM | 341 | C | ASP | 163 | 7.338 | 34.926 | 5.136 | 1.00 | 34.13 |
| ATOM | 342 | O | ASP | 163 | 6.446 | 35.373 | 4.435 | 1.00 | 34.59 |
| ATOM | 343 | N | ASN | 164 | 7.610 | 33.624 | 5.211 | 1.00 | 33.87 |
| ATOM | 344 | CA | ASN | 164 | 6.874 | 32.623 | 4.447 | 1.00 | 34.28 |
| ATOM | 345 | CB | ASN | 164 | 5.360 | 32.640 | 4.769 | 1.00 | 32.50 |
| ATOM | 346 | CG | ASN | 164 | 5.033 | 32.212 | 6.207 | 1.00 | 32.82 |
| ATOM | 347 | OD1 | ASN | 164 | 5.896 | 31.709 | 6.951 | 1.00 | 30.94 |
| ATOM | 348 | ND2 | ASN | 164 | 3.768 | 32.423 | 6.602 | 1.00 | 29.12 |
| ATOM | 349 | C | ASN | 164 | 7.084 | 32.642 | 2.912 | 1.00 | 34.97 |
| ATOM | 350 | O | ASN | 164 | 6.322 | 32.009 | 2.191 | 1.00 | 35.11 |
| ATOM | 351 | O6 | GDQ | 201 | 32.296 | 10.635 | 4.524 | 1.00 | 46.27 |
| ATOM | 352 | C6 | GDQ | 201 | 31.248 | 9.917 | 5.035 | 1.00 | 47.77 |
| ATOM | 353 | N1 | GDQ | 201 | 30.797 | 10.050 | 6.323 | 1.00 | 47.90 |
| ATOM | 354 | C5 | GDQ | 201 | 30.614 | 8.990 | 4.235 | 1.00 | 48.17 |
| ATOM | 355 | C7 | GDQ | 201 | 30.698 | 8.536 | 2.936 | 1.00 | 49.49 |
| ATOM | 356 | C77 | GDQ | 201 | 31.612 | 8.969 | 2.073 | 1.00 | 48.63 |
| ATOM | 357 | N77 | GDQ | 201 | 32.516 | 9.322 | 1.359 | 1.00 | 53.62 |
| ATOM | 358 | C8 | GDQ | 201 | 29.759 | 7.552 | 2.635 | 1.00 | 47.67 |
| ATOM | 359 | N9 | GDQ | 201 | 29.054 | 7.399 | 3.791 | 1.00 | 46.70 |
| ATOM | 360 | C4 | GDQ | 201 | 29.559 | 8.251 | 4.732 | 1.00 | 47.89 |
| ATOM | 361 | N3 | GDQ | 201 | 29.132 | 8.401 | 6.010 | 1.00 | 47.83 |
| ATOM | 362 | C2 | GDQ | 201 | 29.744 | 9.300 | 6.809 | 1.00 | 48.19 |
| ATOM | 363 | N2 | GDQ | 201 | 29.279 | 9.410 | 8.086 | 1.00 | 46.97 |
| ATOM | 364 | O | HOH | 15 | 12.739 | 32.238 | 13.145 | 1.00 | 22.43 |
| ATOM | 365 | O | HOH | 22 | 1.326 | 33.883 | 11.230 | 1.00 | 32.23 |
| ATOM | 366 | O | HOH | 26 | 16.791 | 31.461 | 14.101 | 1.00 | 27.14 |
| ATOM | 367 | O | HOH | 54 | 5.461 | 21.483 | 6.512 | 1.00 | 43.09 |
| ATOM | 368 | O | HOH | 56 | 14.379 | 28.163 | 13.181 | 1.00 | 40.09 |
| ATOM | 369 | O | HOH | 59 | 7.756 | 42.618 | 11.083 | 1.00 | 31.40 |
| ATOM | 370 | O | HOH | 64 | 5.460 | 23.872 | 10.260 | 1.00 | 28.09 |
| ATOM | 371 | O | HOH | 83 | −1.320 | 26.055 | 11.602 | 1.00 | 34.38 |
| ATOM | 372 | O | HOH | 87 | 11.302 | 39.575 | 11.622 | 1.00 | 32.69 |
| ATOM | 373 | O | HOH | 163 | 1.011 | 28.587 | 5.176 | 1.00 | 33.75 |
| ATOM | 374 | O | HOH | 172 | 2.688 | 24.876 | 11.423 | 1.00 | 32.80 |
| ATOM | 375 | O | HOH | 195 | −4.034 | 24.942 | 9.104 | 1.00 | 49.16 |
| ATOM | 376 | O | HOH | 222 | −1.338 | 32.478 | 10.369 | 1.00 | 44.82 |
| ATOM | 377 | O | HOH | 250 | 8.468 | 38.509 | 8.716 | 1.00 | 43.13 |
| ATOM | 378 | N | VAL | 45 | −0.428 | 34.615 | −13.880 | 1.00 | 29.60 |
| ATOM | 379 | CA | VAL | 45 | −0.613 | 34.033 | −12.573 | 1.00 | 28.86 |
| ATOM | 380 | CB | VAL | 45 | −1.922 | 33.297 | −12.471 | 1.00 | 31.08 |
| ATOM | 381 | CG1 | VAL | 45 | −3.110 | 34.214 | −12.950 | 1.00 | 28.95 |

TABLE 6-continued

| | | | | | | | | | |
|---|---|---|---|---|---|---|---|---|---|
| ATOM | 382 | CG2 | VAL | 45 | −2.161 | 32.868 | −10.989 | 1.00 | 31.47 |
| ATOM | 383 | C | VAL | 45 | 0.496 | 33.050 | −12.414 | 1.00 | 28.57 |
| ATOM | 384 | O | VAL | 45 | 0.614 | 32.125 | −13.233 | 1.00 | 28.70 |
| ATOM | 385 | N | LYS | 46 | 1.341 | 33.287 | −11.401 | 1.00 | 26.60 |
| ATOM | 386 | CA | LYS | 46 | 2.386 | 32.367 | −10.999 | 1.00 | 26.09 |
| ATOM | 387 | CB | LYS | 46 | 3.707 | 33.101 | −10.733 | 1.00 | 24.81 |
| ATOM | 388 | CG | LYS | 46 | 4.870 | 32.134 | −10.364 | 1.00 | 26.07 |
| ATOM | 389 | CD | LYS | 46 | 6.255 | 32.748 | −10.379 | 1.00 | 26.57 |
| ATOM | 390 | CE | LYS | 46 | 6.296 | 34.153 | −9.679 | 1.00 | 33.60 |
| ATOM | 391 | NZ | LYS | 46 | 7.742 | 34.567 | −9.412 | 1.00 | 35.91 |
| ATOM | 392 | C | LYS | 46 | 2.009 | 31.548 | −9.718 | 1.00 | 25.98 |
| ATOM | 393 | O | LYS | 46 | 1.562 | 32.117 | −8.720 | 1.00 | 25.25 |
| ATOM | 394 | N | PHE | 47 | 2.226 | 30.224 | −9.763 | 1.00 | 25.69 |
| ATOM | 395 | CA | PHE | 47 | 2.331 | 29.387 | −8.552 | 1.00 | 25.78 |
| ATOM | 396 | CB | PHE | 47 | 1.475 | 28.130 | −8.700 | 1.00 | 26.07 |
| ATOM | 397 | CG | PHE | 47 | 0.043 | 28.444 | −9.035 | 1.00 | 25.38 |
| ATOM | 398 | CD1 | PHE | 47 | −0.331 | 28.682 | −10.352 | 1.00 | 29.07 |
| ATOM | 399 | CE1 | PHE | 47 | −1.698 | 29.020 | −10.678 | 1.00 | 29.50 |
| ATOM | 400 | CZ | PHE | 47 | −2.640 | 29.125 | −9.652 | 1.00 | 26.40 |
| ATOM | 401 | CE2 | PHE | 47 | −2.262 | 28.907 | −8.358 | 1.00 | 24.93 |
| ATOM | 402 | CD2 | PHE | 47 | −0.922 | 28.563 | −8.042 | 1.00 | 27.19 |
| ATOM | 403 | C | PHE | 47 | 3.755 | 29.001 | −8.240 | 1.00 | 26.50 |
| ATOM | 404 | O | PHE | 47 | 4.449 | 28.416 | −9.088 | 1.00 | 26.93 |
| ATOM | 405 | N | ASN | 48 | 4.179 | 29.320 | −7.021 | 1.00 | 26.28 |
| ATOM | 406 | CA | ASN | 48 | 5.450 | 28.863 | −6.455 | 1.00 | 26.70 |
| ATOM | 407 | CB | ASN | 48 | 5.990 | 29.921 | −5.530 | 1.00 | 26.63 |
| ATOM | 408 | CG | ASN | 48 | 6.129 | 31.290 | −6.193 | 1.00 | 27.75 |
| ATOM | 409 | OD1 | ASN | 48 | 6.845 | 31.422 | −7.179 | 1.00 | 26.90 |
| ATOM | 410 | ND2 | ASN | 48 | 5.482 | 32.309 | −5.633 | 1.00 | 21.97 |
| ATOM | 411 | C | ASN | 48 | 5.180 | 27.619 | −5.641 | 1.00 | 27.42 |
| ATOM | 412 | O | ASN | 48 | 4.383 | 27.667 | −4.672 | 1.00 | 27.74 |
| ATOM | 413 | N | CYS | 49 | 5.801 | 26.502 | −6.022 | 1.00 | 27.81 |
| ATOM | 414 | CA | CYS | 49 | 5.512 | 25.182 | −5.444 | 1.00 | 27.79 |
| ATOM | 415 | CB | CYS | 49 | 4.824 | 24.261 | −6.442 | 1.00 | 27.88 |
| ATOM | 416 | SG | CYS | 49 | 3.489 | 25.101 | −7.349 | 1.00 | 33.42 |
| ATOM | 417 | C | CYS | 49 | 6.784 | 24.544 | −4.960 | 1.00 | 27.42 |
| ATOM | 418 | O | CYS | 49 | 7.248 | 23.644 | −5.563 | 1.00 | 27.36 |
| ATOM | 419 | N | PRO | 50 | 7.333 | 25.007 | −3.819 | 1.00 | 28.25 |
| ATOM | 420 | CA | PRO | 50 | 8.562 | 24.469 | −3.295 | 1.00 | 28.95 |
| ATOM | 421 | CB | PRO | 50 | 9.020 | 25.556 | −2.333 | 1.00 | 28.68 |
| ATOM | 422 | CG | PRO | 50 | 7.784 | 26.117 | −1.868 | 1.00 | 29.66 |
| ATOM | 423 | CD | PRO | 50 | 6.802 | 26.070 | −2.952 | 1.00 | 27.22 |
| ATOM | 424 | C | PRO | 50 | 8.388 | 23.118 | −2.571 | 1.00 | 30.16 |
| ATOM | 425 | O | PRO | 50 | 9.370 | 22.519 | −2.146 | 1.00 | 30.23 |
| ATOM | 426 | N | GLU | 51 | 7.180 | 22.566 | −2.506 | 1.00 | 30.75 |
| ATOM | 427 | CA | GLU | 51 | 7.084 | 21.267 | −1.832 | 1.00 | 30.88 |
| ATOM | 428 | CB | GLU | 51 | 5.969 | 21.317 | −0.770 | 1.00 | 30.96 |
| ATOM | 429 | CG | GLU | 51 | 6.448 | 22.205 | 0.398 | 1.00 | 30.27 |
| ATOM | 430 | CD | GLU | 51 | 5.343 | 22.646 | 1.336 | 1.00 | 34.08 |
| ATOM | 431 | OE1 | GLU | 51 | 4.195 | 22.157 | 1.229 | 1.00 | 37.55 |
| ATOM | 432 | OE2 | GLU | 51 | 5.618 | 23.523 | 2.163 | 1.00 | 33.25 |
| ATOM | 433 | C | GLU | 51 | 7.003 | 20.038 | −2.717 | 1.00 | 31.31 |
| ATOM | 434 | O | GLU | 51 | 6.656 | 18.955 | −2.253 | 1.00 | 32.45 |
| ATOM | 435 | N | PHE | 52 | 7.330 | 20.172 | −3.999 | 1.00 | 30.57 |
| ATOM | 436 | CA | PHE | 52 | 7.115 | 19.057 | −4.901 | 1.00 | 29.32 |
| ATOM | 437 | CB | PHE | 52 | 7.335 | 19.473 | −6.352 | 1.00 | 29.38 |
| ATOM | 438 | CG | PHE | 52 | 7.031 | 18.379 | −7.317 | 1.00 | 28.90 |
| ATOM | 439 | CD1 | PHE | 52 | 5.710 | 18.132 | −7.694 | 1.00 | 25.64 |
| ATOM | 440 | CE1 | PHE | 52 | 5.418 | 17.123 | −8.596 | 1.00 | 26.75 |
| ATOM | 441 | CZ | PHE | 52 | 6.428 | 16.306 | −9.069 | 1.00 | 25.36 |
| ATOM | 442 | CE2 | PHE | 52 | 7.761 | 16.528 | −8.677 | 1.00 | 28.36 |
| ATOM | 443 | CD2 | PHE | 52 | 8.053 | 17.550 | −7.797 | 1.00 | 26.05 |
| ATOM | 444 | C | PHE | 52 | 8.028 | 17.908 | −4.571 | 1.00 | 29.42 |
| ATOM | 445 | O | PHE | 52 | 9.190 | 18.137 | −4.241 | 1.00 | 29.42 |
| ATOM | 446 | N | ALA | 65 | 11.702 | 19.079 | −5.722 | 1.00 | 26.33 |
| ATOM | 447 | CA | ALA | 65 | 11.841 | 20.200 | −6.558 | 1.00 | 25.69 |
| ATOM | 448 | CB | ALA | 65 | 11.395 | 19.803 | −8.065 | 1.00 | 24.22 |
| ATOM | 449 | C | ALA | 65 | 11.015 | 21.374 | −6.057 | 1.00 | 25.67 |
| ATOM | 450 | O | ALA | 65 | 10.082 | 21.217 | −5.287 | 1.00 | 26.66 |
| ATOM | 451 | N | THR | 66 | 11.367 | 22.550 | −6.530 | 1.00 | 25.39 |
| ATOM | 452 | CA | THR | 66 | 10.494 | 23.699 | −6.552 | 1.00 | 27.61 |
| ATOM | 453 | CB | THR | 66 | 11.255 | 24.947 | −6.171 | 1.00 | 27.25 |
| ATOM | 454 | OG1 | THR | 66 | 11.651 | 24.821 | −4.818 | 1.00 | 30.69 |
| ATOM | 455 | CG2 | THR | 66 | 10.371 | 26.147 | −6.236 | 1.00 | 31.40 |
| ATOM | 456 | C | THR | 66 | 10.014 | 23.853 | −7.998 | 1.00 | 28.30 |
| ATOM | 457 | O | THR | 66 | 10.811 | 23.853 | −8.951 | 1.00 | 28.10 |
| ATOM | 458 | N | ILE | 67 | 8.713 | 23.994 | −8.164 | 1.00 | 28.94 |
| ATOM | 459 | CA | ILE | 67 | 8.150 | 24.189 | −9.492 | 1.00 | 28.94 |
| ATOM | 460 | CB | ILE | 67 | 7.093 | 23.079 | −9.743 | 1.00 | 29.43 |
| ATOM | 461 | CG1 | ILE | 67 | 7.799 | 21.726 | −9.628 | 1.00 | 28.57 |

TABLE 6-continued

| | | | | | | | | | |
|---|---|---|---|---|---|---|---|---|---|
| ATOM | 462 | CD1 | ILE | 67 | 6.888 | 20.606 | −9.787 | 1.00 | 29.91 |
| ATOM | 463 | CG2 | ILE | 67 | 6.385 | 23.253 | −11.087 | 1.00 | 29.92 |
| ATOM | 464 | C | ILE | 67 | 7.571 | 25.570 | −9.525 | 1.00 | 28.85 |
| ATOM | 465 | O | ILE | 67 | 6.967 | 25.978 | −8.528 | 1.00 | 29.21 |
| ATOM | 466 | N | TYR | 68 | 7.778 | 26.298 | −10.635 | 1.00 | 28.85 |
| ATOM | 467 | CA | TYR | 68 | 7.207 | 27.622 | −10.875 | 1.00 | 27.65 |
| ATOM | 468 | CB | TYR | 68 | 8.280 | 28.685 | −11.114 | 1.00 | 28.00 |
| ATOM | 469 | CG | TYR | 68 | 9.264 | 28.778 | −9.962 | 1.00 | 27.25 |
| ATOM | 470 | CD1 | TYR | 68 | 10.475 | 28.092 | −9.975 | 1.00 | 23.97 |
| ATOM | 471 | CE1 | TYR | 68 | 11.382 | 28.187 | −8.875 | 1.00 | 28.38 |
| ATOM | 472 | CZ | TYR | 68 | 10.998 | 28.939 | −7.745 | 1.00 | 28.49 |
| ATOM | 473 | OH | TYR | 68 | 11.777 | 29.080 | −6.599 | 1.00 | 26.21 |
| ATOM | 474 | CE2 | TYR | 68 | 9.759 | 29.598 | −7.732 | 1.00 | 29.17 |
| ATOM | 475 | CD2 | TYR | 68 | 8.923 | 29.525 | −8.807 | 1.00 | 27.85 |
| ATOM | 476 | C | TYR | 68 | 6.312 | 27.440 | −12.086 | 1.00 | 29.20 |
| ATOM | 477 | O | TYR | 68 | 6.779 | 26.982 | −13.159 | 1.00 | 29.47 |
| ATOM | 478 | N | ILE | 69 | 5.023 | 27.732 | −11.908 | 1.00 | 28.12 |
| ATOM | 479 | CA | ILE | 69 | 4.072 | 27.481 | −12.947 | 1.00 | 28.68 |
| ATOM | 480 | CB | ILE | 69 | 2.958 | 26.506 | −12.556 | 1.00 | 29.11 |
| ATOM | 481 | CG1 | ILE | 69 | 3.508 | 25.141 | −12.131 | 1.00 | 30.41 |
| ATOM | 482 | CD1 | ILE | 69 | 2.383 | 24.193 | −11.740 | 1.00 | 32.90 |
| ATOM | 483 | CG2 | ILE | 69 | 2.045 | 26.288 | −13.755 | 1.00 | 27.69 |
| ATOM | 484 | C | ILE | 69 | 3.415 | 28.817 | −13.191 | 1.00 | 28.58 |
| ATOM | 485 | O | ILE | 69 | 2.761 | 29.354 | −12.287 | 1.00 | 29.06 |
| ATOM | 486 | N | GLU | 79 | −7.804 | 26.045 | −9.570 | 1.00 | 38.71 |
| ATOM | 487 | CA | GLU | 79 | −8.009 | 26.274 | −8.147 | 1.00 | 39.26 |
| ATOM | 488 | CB | GLU | 79 | −9.313 | 25.615 | −7.675 | 1.00 | 39.82 |
| ATOM | 489 | CG | GLU | 79 | −9.912 | 26.214 | −6.377 | 1.00 | 41.73 |
| ATOM | 490 | CD | GLU | 79 | −9.108 | 25.821 | −5.134 | 1.00 | 44.42 |
| ATOM | 491 | OE1 | GLU | 79 | −8.850 | 24.602 | −4.995 | 1.00 | 45.96 |
| ATOM | 492 | OE2 | GLU | 79 | −8.696 | 26.716 | −4.330 | 1.00 | 43.13 |
| ATOM | 493 | C | GLU | 79 | −6.771 | 25.839 | −7.361 | 1.00 | 39.15 |
| ATOM | 494 | O | GLU | 79 | −6.247 | 24.734 | −7.544 | 1.00 | 39.58 |
| ATOM | 495 | N | SER | 80 | −6.279 | 26.731 | −6.506 | 1.00 | 39.14 |
| ATOM | 496 | CA | SER | 80 | −5.045 | 26.494 | −5.757 | 1.00 | 40.45 |
| ATOM | 497 | CB | SER | 80 | −4.765 | 27.669 | −4.813 | 1.00 | 40.98 |
| ATOM | 498 | OG | SER | 80 | −3.464 | 27.520 | −4.263 | 1.00 | 43.76 |
| ATOM | 499 | C | SER | 80 | −4.991 | 25.191 | −4.969 | 1.00 | 39.97 |
| ATOM | 500 | O | SER | 80 | −3.961 | 24.518 | −4.946 | 1.00 | 40.91 |
| ATOM | 501 | N | LYS | 81 | −6.084 | 24.856 | −4.285 | 1.00 | 40.44 |
| ATOM | 502 | CA | LYS | 81 | −6.127 | 23.672 | −3.434 | 1.00 | 39.60 |
| ATOM | 503 | CB | LYS | 81 | −7.283 | 23.776 | −2.421 | 1.00 | 40.23 |
| ATOM | 504 | CG | LYS | 81 | −7.534 | 22.468 | −1.552 | 1.00 | 41.71 |
| ATOM | 505 | CD | LYS | 81 | −8.738 | 22.613 | −0.562 | 1.00 | 43.35 |
| ATOM | 506 | CE | LYS | 81 | −10.088 | 22.088 | −1.110 | 1.00 | 51.29 |
| ATOM | 507 | NZ | LYS | 81 | −10.250 | 20.577 | −0.924 | 1.00 | 51.65 |
| ATOM | 508 | C | LYS | 81 | −6.185 | 22.404 | −4.278 | 1.00 | 37.68 |
| ATOM | 509 | O | LYS | 81 | −5.493 | 21.424 | −3.950 | 1.00 | 36.22 |
| ATOM | 510 | N | SER | 82 | −6.933 | 22.427 | −5.394 | 1.00 | 36.37 |
| ATOM | 511 | CA | SER | 82 | −6.869 | 21.290 | −6.342 | 1.00 | 36.60 |
| ATOM | 512 | CB | SER | 82 | −7.876 | 21.413 | −7.500 | 1.00 | 37.83 |
| ATOM | 513 | OG | SER | 82 | −7.629 | 22.506 | −8.389 | 1.00 | 38.89 |
| ATOM | 514 | C | SER | 82 | −5.447 | 21.041 | −6.860 | 1.00 | 36.09 |
| ATOM | 515 | O | SER | 82 | −4.966 | 19.871 | −6.863 | 1.00 | 35.12 |
| ATOM | 516 | N | LEU | 83 | −4.768 | 22.142 | −7.220 | 1.00 | 34.52 |
| ATOM | 517 | CA | LEU | 83 | −3.351 | 22.094 | −7.632 | 1.00 | 34.68 |
| ATOM | 518 | CB | LEU | 83 | −2.818 | 23.488 | −8.037 | 1.00 | 34.38 |
| ATOM | 519 | CG | LEU | 83 | −1.408 | 23.517 | −8.675 | 1.00 | 35.18 |
| ATOM | 520 | CD1 | LEU | 83 | −1.262 | 22.564 | −9.928 | 1.00 | 28.46 |
| ATOM | 521 | CD2 | LEU | 83 | −1.000 | 24.951 | −8.990 | 1.00 | 33.77 |
| ATOM | 522 | C | LEU | 83 | −2.441 | 21.449 | −6.596 | 1.00 | 34.51 |
| ATOM | 523 | O | LEU | 83 | −1.563 | 20.650 | −6.920 | 1.00 | 33.59 |
| ATOM | 524 | N | LYS | 84 | −2.663 | 21.805 | −5.340 | 1.00 | 35.31 |
| ATOM | 525 | CA | LYS | 84 | −1.933 | 21.244 | −4.241 | 1.00 | 35.99 |
| ATOM | 526 | CB | LYS | 84 | −2.400 | 21.935 | −2.946 | 1.00 | 35.66 |
| ATOM | 527 | CG | LYS | 84 | −1.943 | 21.284 | −1.673 | 1.00 | 37.97 |
| ATOM | 528 | CD | LYS | 84 | −2.708 | 21.894 | −0.461 | 1.00 | 37.55 |
| ATOM | 529 | CE | LYS | 84 | −3.851 | 21.001 | −0.020 | 1.00 | 39.56 |
| ATOM | 530 | NZ | LYS | 84 | −4.292 | 21.228 | 1.391 | 1.00 | 41.94 |
| ATOM | 531 | C | LYS | 84 | −2.167 | 19.743 | −4.207 | 1.00 | 36.20 |
| ATOM | 532 | O | LYS | 84 | −1.216 | 18.953 | −4.139 | 1.00 | 36.55 |
| ATOM | 533 | N | LEU | 85 | −3.433 | 19.345 | −4.278 | 1.00 | 36.49 |
| ATOM | 534 | CA | LEU | 85 | −3.789 | 17.941 | −4.349 | 1.00 | 36.64 |
| ATOM | 535 | CB | LEU | 85 | −5.319 | 17.806 | −4.349 | 1.00 | 36.98 |
| ATOM | 536 | CG | LEU | 85 | −6.191 | 17.803 | −3.067 | 1.00 | 39.95 |
| ATOM | 537 | CD1 | LEU | 85 | −5.499 | 18.399 | −1.833 | 1.00 | 41.97 |
| ATOM | 538 | CD2 | LEU | 85 | −7.568 | 18.489 | −3.275 | 1.00 | 37.78 |
| ATOM | 539 | C | LEU | 85 | −3.195 | 17.275 | −5.579 | 1.00 | 36.28 |
| ATOM | 540 | O | LEU | 85 | −2.618 | 16.202 | −5.500 | 1.00 | 35.95 |
| ATOM | 541 | N | TYR | 86 | −3.308 | 17.904 | −6.739 | 1.00 | 36.01 |

TABLE 6-continued

| | | | | | | | | |
|---|---|---|---|---|---|---|---|---|
| ATOM | 542 | CA | TYR | 86 | −2.652 | 17.330 | −7.917 | 1.00 | 35.20 |
| ATOM | 543 | CB | TYR | 86 | −2.896 | 18.243 | −9.096 | 1.00 | 36.62 |
| ATOM | 544 | CG | TYR | 86 | −2.234 | 17.811 | −10.358 | 1.00 | 38.86 |
| ATOM | 545 | CD1 | TYR | 86 | −2.556 | 16.584 | −10.977 | 1.00 | 37.52 |
| ATOM | 546 | CE1 | TYR | 86 | −1.914 | 16.212 | −12.173 | 1.00 | 39.96 |
| ATOM | 547 | CZ | TYR | 86 | −0.968 | 17.105 | −12.754 | 1.00 | 39.92 |
| ATOM | 548 | OH | TYR | 86 | −0.275 | 16.811 | −13.898 | 1.00 | 40.85 |
| ATOM | 549 | CE2 | TYR | 86 | −0.664 | 18.296 | −12.151 | 1.00 | 38.61 |
| ATOM | 550 | CD2 | TYR | 86 | −1.290 | 18.644 | −10.963 | 1.00 | 39.08 |
| ATOM | 551 | C | TYR | 86 | −1.160 | 17.092 | −7.697 | 1.00 | 34.75 |
| ATOM | 552 | O | TYR | 86 | −0.622 | 16.003 | −7.935 | 1.00 | 34.10 |
| ATOM | 553 | N | LEU | 87 | −0.455 | 18.089 | −7.188 | 1.00 | 35.13 |
| ATOM | 554 | CA | LEU | 87 | 0.984 | 17.876 | −6.955 | 1.00 | 35.00 |
| ATOM | 555 | CB | LEU | 87 | 1.728 | 19.185 | −6.780 | 1.00 | 35.12 |
| ATOM | 556 | CG | LEU | 87 | 1.595 | 20.223 | −7.900 | 1.00 | 36.20 |
| ATOM | 557 | CD1 | LEU | 87 | 2.167 | 21.559 | −7.466 | 1.00 | 32.77 |
| ATOM | 558 | CD2 | LEU | 87 | 2.267 | 19.733 | −9.204 | 1.00 | 34.84 |
| ATOM | 559 | C | LEU | 87 | 1.287 | 16.877 | −5.842 | 1.00 | 35.54 |
| ATOM | 560 | O | LEU | 87 | 2.283 | 16.120 | −5.926 | 1.00 | 33.45 |
| ATOM | 561 | N | PHE | 88 | 0.430 | 16.825 | −4.806 | 1.00 | 37.14 |
| ATOM | 562 | CA | PHE | 88 | 0.524 | 15.696 | −3.840 | 1.00 | 38.55 |
| ATOM | 563 | CB | PHE | 88 | −0.610 | 15.703 | −2.789 | 1.00 | 40.19 |
| ATOM | 564 | CG | PHE | 88 | −0.468 | 16.761 | −1.719 | 1.00 | 44.41 |
| ATOM | 565 | CD1 | PHE | 88 | −1.565 | 17.095 | −0.913 | 1.00 | 45.28 |
| ATOM | 566 | CE1 | PHE | 88 | −1.450 | 18.077 | 0.061 | 1.00 | 46.31 |
| ATOM | 567 | CZ | PHE | 88 | −0.228 | 18.744 | 0.247 | 1.00 | 45.62 |
| ATOM | 568 | CE2 | PHE | 88 | 0.867 | 18.424 | −0.548 | 1.00 | 46.65 |
| ATOM | 569 | CD2 | PHE | 88 | 0.747 | 17.436 | −1.520 | 1.00 | 46.40 |
| ATOM | 570 | C | PHE | 88 | 0.457 | 14.356 | −4.580 | 1.00 | 37.62 |
| ATOM | 571 | O | PHE | 88 | 1.143 | 13.419 | −4.218 | 1.00 | 37.12 |
| ATOM | 572 | N | SER | 89 | −0.385 | 14.282 | −5.611 | 1.00 | 37.50 |
| ATOM | 573 | CA | SER | 89 | −0.621 | 13.009 | −6.306 | 1.00 | 37.88 |
| ATOM | 574 | CB | SER | 89 | −1.796 | 13.077 | −7.284 | 1.00 | 38.18 |
| ATOM | 575 | OG | SER | 89 | −1.467 | 13.703 | −8.518 | 1.00 | 39.35 |
| ATOM | 576 | C | SER | 89 | 0.624 | 12.448 | −6.956 | 1.00 | 37.70 |
| ATOM | 577 | O | SER | 89 | 0.632 | 11.308 | −7.322 | 1.00 | 38.26 |
| ATOM | 578 | N | GLY | 121 | 10.730 | 23.550 | −13.517 | 1.00 | 24.73 |
| ATOM | 579 | CA | GLY | 121 | 11.036 | 22.759 | −12.381 | 1.00 | 25.93 |
| ATOM | 580 | C | GLY | 121 | 12.512 | 22.825 | −12.093 | 1.00 | 27.00 |
| ATOM | 581 | O | GLY | 121 | 13.337 | 22.830 | −13.011 | 1.00 | 27.37 |
| ATOM | 582 | N | LYS | 122 | 12.847 | 22.862 | −10.810 | 1.00 | 26.41 |
| ATOM | 583 | CA | LYS | 122 | 14.222 | 22.975 | −10.371 | 1.00 | 26.76 |
| ATOM | 584 | CB | LYS | 122 | 14.463 | 24.416 | −9.849 | 1.00 | 27.37 |
| ATOM | 585 | CG | LYS | 122 | 14.261 | 25.493 | −10.944 | 1.00 | 25.44 |
| ATOM | 586 | CD | LYS | 122 | 14.611 | 26.857 | −10.438 | 1.00 | 27.60 |
| ATOM | 587 | CE | LYS | 122 | 14.324 | 27.863 | −11.504 | 1.00 | 31.63 |
| ATOM | 588 | NZ | LYS | 122 | 15.191 | 29.054 | −11.424 | 1.00 | 40.28 |
| ATOM | 589 | C | LYS | 122 | 14.475 | 21.956 | −9.292 | 1.00 | 26.44 |
| ATOM | 590 | O | LYS | 122 | 14.057 | 22.145 | −8.143 | 1.00 | 27.76 |
| ATOM | 591 | N | PHE | 123 | 1.500 | 36.690 | −2.716 | 1.00 | 29.77 |
| ATOM | 592 | CA | PHE | 123 | 0.769 | 36.191 | −1.581 | 1.00 | 28.78 |
| ATOM | 593 | CB | PHE | 123 | −0.599 | 35.649 | −1.978 | 1.00 | 27.79 |
| ATOM | 594 | CG | PHE | 123 | −1.582 | 36.731 | −2.284 | 1.00 | 29.54 |
| ATOM | 595 | CD1 | PHE | 123 | −1.554 | 37.395 | −3.529 | 1.00 | 26.50 |
| ATOM | 596 | CE1 | PHE | 123 | −2.423 | 38.425 | −3.823 | 1.00 | 24.89 |
| ATOM | 597 | CZ | PHE | 123 | −3.392 | 38.807 | −2.894 | 1.00 | 30.34 |
| ATOM | 598 | CE2 | PHE | 123 | −3.467 | 38.130 | −1.632 | 1.00 | 31.05 |
| ATOM | 599 | CD2 | PHE | 123 | −2.546 | 37.104 | −1.342 | 1.00 | 30.05 |
| ATOM | 600 | C | PHE | 123 | 1.572 | 35.181 | −0.841 | 1.00 | 29.23 |
| ATOM | 601 | O | PHE | 123 | 2.441 | 34.511 | −1.438 | 1.00 | 27.66 |
| ATOM | 602 | N | THR | 124 | 1.306 | 35.097 | 0.484 | 1.00 | 28.92 |
| ATOM | 603 | CA | THR | 124 | 1.956 | 34.067 | 1.322 | 1.00 | 28.20 |
| ATOM | 604 | CB | THR | 124 | 1.935 | 34.451 | 2.857 | 1.00 | 29.27 |
| ATOM | 605 | OG1 | THR | 124 | 0.582 | 34.504 | 3.280 | 1.00 | 27.12 |
| ATOM | 606 | CG2 | THR | 124 | 2.594 | 35.831 | 3.133 | 1.00 | 23.99 |
| ATOM | 607 | C | THR | 124 | 1.327 | 32.699 | 1.006 | 1.00 | 27.97 |
| ATOM | 608 | O | THR | 124 | 0.218 | 32.635 | 0.510 | 1.00 | 28.78 |
| ATOM | 609 | N | PRO | 125 | 2.078 | 31.607 | 1.199 | 1.00 | 28.21 |
| ATOM | 610 | CA | PRO | 125 | 1.639 | 30.267 | 0.813 | 1.00 | 29.53 |
| ATOM | 611 | CB | PRO | 125 | 2.873 | 29.414 | 1.038 | 1.00 | 28.34 |
| ATOM | 612 | CG | PRO | 125 | 3.748 | 30.232 | 2.001 | 1.00 | 26.96 |
| ATOM | 613 | CD | PRO | 125 | 3.468 | 31.625 | 1.698 | 1.00 | 27.65 |
| ATOM | 614 | C | PRO | 125 | 0.427 | 29.735 | 1.578 | 1.00 | 32.62 |
| ATOM | 615 | O | PRO | 125 | 0.124 | 30.238 | 2.637 | 1.00 | 34.11 |
| ATOM | 616 | N | ARG | 126 | −0.311 | 28.790 | 0.992 | 1.00 | 33.81 |
| ATOM | 617 | CA | ARG | 126 | −1.423 | 28.113 | 1.639 | 1.00 | 35.48 |
| ATOM | 618 | CB | ARG | 126 | −2.768 | 28.715 | 1.257 | 1.00 | 35.66 |
| ATOM | 619 | CG | ARG | 126 | −3.031 | 30.108 | 1.814 | 1.00 | 40.74 |
| ATOM | 620 | CD | ARG | 126 | −3.321 | 30.024 | 3.333 | 1.00 | 46.49 |
| ATOM | 621 | NE | ARG | 126 | −3.314 | 31.330 | 3.992 | 1.00 | 49.71 |

TABLE 6-continued

| | | | | | | | | |
|---|---|---|---|---|---|---|---|---|
| ATOM | 622 | CZ | ARG | 126 | −2.460 | 31.642 | 4.962 | 1.00 50.00 |
| ATOM | 623 | NH1 | ARG | 126 | −1.566 | 30.758 | 5.373 | 1.00 50.10 |
| ATOM | 624 | NH2 | ARG | 126 | −2.502 | 32.832 | 5.514 | 1.00 52.24 |
| ATOM | 625 | C | ARG | 126 | −1.333 | 26.757 | 1.019 | 1.00 35.74 |
| ATOM | 626 | O | ARG | 126 | −1.285 | 26.644 | −0.215 | 1.00 35.29 |
| ATOM | 627 | N | GLY | 127 | −1.248 | 25.729 | 1.844 | 1.00 35.60 |
| ATOM | 628 | CA | GLY | 127 | −1.056 | 24.391 | 1.324 | 1.00 36.66 |
| ATOM | 629 | C | GLY | 127 | 0.303 | 24.262 | 0.636 | 1.00 37.25 |
| ATOM | 630 | O | GLY | 127 | 0.526 | 23.341 | −0.145 | 1.00 38.77 |
| ATOM | 631 | N | GLY | 128 | 1.215 | 25.174 | 0.945 | 1.00 36.25 |
| ATOM | 632 | CA | GLY | 128 | 2.587 | 25.092 | 0.459 | 1.00 35.01 |
| ATOM | 633 | C | GLY | 128 | 2.846 | 25.764 | −0.894 | 1.00 33.50 |
| ATOM | 634 | O | GLY | 128 | 3.942 | 25.641 | −1.416 | 1.00 35.01 |
| ATOM | 635 | N | ILE | 129 | 1.856 | 26.470 | −1.418 | 1.00 31.65 |
| ATOM | 636 | CA | ILE | 129 | 1.888 | 27.150 | −2.690 | 1.00 30.62 |
| ATOM | 637 | CB | ILE | 129 | 0.895 | 26.509 | −3.690 | 1.00 31.63 |
| ATOM | 638 | CG1 | ILE | 129 | 1.326 | 25.075 | −3.976 | 1.00 31.67 |
| ATOM | 639 | CD1 | ILE | 129 | 0.279 | 24.306 | −4.529 | 1.00 35.41 |
| ATOM | 640 | CG2 | ILE | 129 | 0.893 | 27.302 | −5.039 | 1.00 30.84 |
| ATOM | 641 | C | ILE | 129 | 1.485 | 28.578 | −2.539 | 1.00 29.88 |
| ATOM | 642 | O | ILE | 129 | 0.490 | 28.857 | −1.897 | 1.00 29.04 |
| ATOM | 643 | N | SER | 130 | 2.249 | 29.496 | −3.150 | 1.00 29.92 |
| ATOM | 644 | CA | SER | 130 | 1.909 | 30.909 | −3.127 | 1.00 29.06 |
| ATOM | 645 | CB | SER | 130 | 3.077 | 31.732 | −2.587 | 1.00 27.81 |
| ATOM | 646 | OG | SER | 130 | 4.261 | 31.270 | −3.159 | 1.00 25.44 |
| ATOM | 647 | C | SER | 130 | 1.536 | 31.301 | −4.545 | 1.00 29.57 |
| ATOM | 648 | O | SER | 130 | 2.039 | 30.679 | −5.486 | 1.00 31.56 |
| ATOM | 649 | N | ILE | 131 | 0.665 | 32.303 | −4.677 | 1.00 29.08 |
| ATOM | 650 | CA | ILE | 131 | 0.096 | 32.788 | −5.934 | 1.00 28.86 |
| ATOM | 651 | CB | ILE | 131 | −1.430 | 32.732 | −5.881 | 1.00 28.88 |
| ATOM | 652 | CG1 | ILE | 131 | −1.849 | 31.259 | −5.706 | 1.00 30.52 |
| ATOM | 653 | CD1 | ILE | 131 | −3.255 | 31.050 | −5.421 | 1.00 32.39 |
| ATOM | 654 | CG2 | ILE | 131 | −2.094 | 33.277 | −7.155 | 1.00 25.09 |
| ATOM | 655 | C | ILE | 131 | 0.593 | 34.217 | −6.071 | 1.00 29.72 |
| ATOM | 656 | O | ILE | 131 | 0.469 | 34.986 | −5.117 | 1.00 30.15 |
| ATOM | 657 | N | ASP | 132 | 1.214 | 34.557 | −7.212 | 1.00 29.62 |
| ATOM | 658 | CA | ASP | 132 | 1.691 | 35.919 | −7.471 | 1.00 29.94 |
| ATOM | 659 | CB | ASP | 132 | 3.249 | 36.003 | −7.521 | 1.00 30.39 |
| ATOM | 660 | CG | ASP | 132 | 3.963 | 35.356 | −6.261 | 1.00 31.97 |
| ATOM | 661 | OD1 | ASP | 132 | 3.301 | 35.113 | −5.232 | 1.00 33.78 |
| ATOM | 662 | OD2 | ASP | 132 | 5.188 | 35.082 | −6.293 | 1.00 31.91 |
| ATOM | 663 | C | ASP | 132 | 1.054 | 36.403 | −8.777 | 1.00 30.44 |
| ATOM | 664 | O | ASP | 132 | 1.574 | 36.146 | −9.868 | 1.00 31.92 |
| ATOM | 665 | O | HOH | 29 | 4.554 | 23.293 | −3.291 | 1.00 31.47 |
| ATOM | 666 | O | HOH | 114 | 7.725 | 30.166 | 6.977 | 1.00 52.76 |
| ATOM | 667 | O | HOH | 139 | −1.081 | 32.261 | −1.945 | 1.00 28.22 |
| ATOM | 668 | O | HOH | 177 | 1.396 | 19.946 | −3.619 | 1.00 41.52 |
| ATOM | 669 | O | HOH | 183 | −2.156 | 29.444 | −2.470 | 1.00 36.87 |
| ATOM | 670 | O | HOH | 201 | −7.819 | 20.995 | 3.164 | 1.00 65.86 |
| ATOM | 671 | O | HOH | 215 | 1.602 | 26.482 | 3.438 | 1.00 33.08 |
| TER | | | | | | | | |

TABLE 7

| | | | | | | | | |
|---|---|---|---|---|---|---|---|---|
| REMARK | | Accelrys ViewerPro PDB file | | | | | | |
| REMARK | | Created: | Tue Dec 14 18:55:58 Pacific Standard Time 2010 | | | | | |
| ATOM | 1 | N | ASN | 21 | 13.692 | −1.701 | −3.334 | 1.00 81.54 |
| ATOM | 2 | CA | ASN | 21 | 12.532 | −0.960 | −2.749 | 1.00 81.46 |
| ATOM | 3 | CB | ASN | 21 | 11.366 | −1.909 | −2.412 | 1.00 81.84 |
| ATOM | 4 | CG | ASN | 21 | 10.697 | −2.491 | −3.646 | 1.00 83.20 |
| ATOM | 5 | OD1 | ASN | 21 | 10.472 | −1.794 | −4.647 | 1.00 83.55 |
| ATOM | 6 | ND2 | ASN | 21 | 10.366 | −3.785 | −3.578 | 1.00 84.79 |
| ATOM | 7 | C | ASN | 21 | 12.928 | −0.209 | −1.485 | 1.00 80.69 |
| ATOM | 8 | O | ASN | 21 | 13.518 | −0.796 | −0.567 | 1.00 80.73 |
| ATOM | 9 | N | TYR | 22 | 12.586 | 1.078 | −1.435 | 1.00 79.35 |
| ATOM | 10 | CA | TYR | 22 | 12.879 | 1.901 | −0.262 | 1.00 77.81 |
| ATOM | 11 | CB | TYR | 22 | 13.315 | 3.320 | −0.669 | 1.00 79.28 |
| ATOM | 12 | CG | TYR | 22 | 14.638 | 3.304 | −1.409 | 1.00 81.40 |
| ATOM | 13 | CD1 | TYR | 22 | 14.676 | 3.185 | −2.804 | 1.00 82.49 |
| ATOM | 14 | CE1 | TYR | 22 | 15.897 | 3.123 | −3.491 | 1.00 83.45 |
| ATOM | 15 | CZ | TYR | 22 | 17.106 | 3.184 | −2.781 | 1.00 83.25 |
| ATOM | 16 | OH | TYR | 22 | 18.302 | 3.138 | −3.477 | 1.00 82.57 |
| ATOM | 17 | CE2 | TYR | 22 | 17.101 | 3.287 | −1.387 | 1.00 83.76 |
| ATOM | 18 | CD2 | TYR | 22 | 15.861 | 3.342 | −0.707 | 1.00 83.50 |
| ATOM | 19 | C | TYR | 22 | 11.715 | 1.908 | 0.726 | 1.00 75.40 |
| ATOM | 20 | O | TYR | 22 | 10.531 | 1.922 | 0.334 | 1.00 74.94 |
| ATOM | 21 | N | LEU | 23 | 12.080 | 1.865 | 2.006 | 1.00 72.28 |

TABLE 7-continued

| | | | | | | | | | |
|---|---|---|---|---|---|---|---|---|---|
| ATOM | 22 | CA | LEU | 23 | 11.134 | 1.804 | 3.117 | 1.00 | 69.17 |
| ATOM | 23 | CB | LEU | 23 | 11.861 | 1.311 | 4.374 | 1.00 | 69.64 |
| ATOM | 24 | CG | LEU | 23 | 12.622 | −0.017 | 4.233 | 1.00 | 69.82 |
| ATOM | 25 | CD1 | LEU | 23 | 14.072 | 0.114 | 4.703 | 1.00 | 70.20 |
| ATOM | 26 | CD2 | LEU | 23 | 11.899 | −1.160 | 4.940 | 1.00 | 69.88 |
| ATOM | 27 | C | LEU | 23 | 10.602 | 3.202 | 3.348 | 1.00 | 66.54 |
| ATOM | 28 | O | LEU | 23 | 11.383 | 4.120 | 3.535 | 1.00 | 65.88 |
| ATOM | 29 | N | PHE | 24 | 9.284 | 3.362 | 3.294 | 1.00 | 63.72 |
| ATOM | 30 | CA | PHE | 24 | 8.647 | 4.662 | 3.556 | 1.00 | 61.56 |
| ATOM | 31 | CB | PHE | 24 | 7.880 | 5.206 | 2.324 | 1.00 | 60.54 |
| ATOM | 32 | CG | PHE | 24 | 8.767 | 5.492 | 1.112 | 1.00 | 59.27 |
| ATOM | 33 | CD1 | PHE | 24 | 8.240 | 5.411 | −0.190 | 1.00 | 57.10 |
| ATOM | 34 | CE1 | PHE | 24 | 9.049 | 5.669 | −1.303 | 1.00 | 57.36 |
| ATOM | 35 | CZ | PHE | 24 | 10.430 | 6.009 | −1.125 | 1.00 | 57.15 |
| ATOM | 36 | CE2 | PHE | 24 | 10.965 | 6.081 | 0.161 | 1.00 | 54.36 |
| ATOM | 37 | CD2 | PHE | 24 | 10.134 | 5.829 | 1.268 | 1.00 | 57.17 |
| ATOM | 38 | C | PHE | 24 | 7.782 | 4.632 | 4.834 | 1.00 | 60.45 |
| ATOM | 39 | O | PHE | 24 | 7.090 | 5.605 | 5.163 | 1.00 | 59.97 |
| ATOM | 40 | N | TYR | 26 | 8.300 | 3.919 | 9.057 | 1.00 | 53.39 |
| ATOM | 41 | CA | TYR | 26 | 9.368 | 4.148 | 10.037 | 1.00 | 51.12 |
| ATOM | 42 | CB | TYR | 26 | 8.767 | 4.683 | 11.367 | 1.00 | 50.90 |
| ATOM | 43 | CG | TYR | 26 | 9.723 | 4.796 | 12.547 | 1.00 | 49.37 |
| ATOM | 44 | CD1 | TYR | 26 | 9.529 | 4.029 | 13.706 | 1.00 | 47.61 |
| ATOM | 45 | CE1 | TYR | 26 | 10.403 | 4.110 | 14.792 | 1.00 | 47.21 |
| ATOM | 46 | CZ | TYR | 26 | 11.486 | 4.987 | 14.723 | 1.00 | 50.33 |
| ATOM | 47 | OH | TYR | 26 | 12.370 | 5.102 | 15.782 | 1.00 | 48.17 |
| ATOM | 48 | CE2 | TYR | 26 | 11.692 | 5.768 | 13.572 | 1.00 | 48.10 |
| ATOM | 49 | CD2 | TYR | 26 | 10.813 | 5.669 | 12.504 | 1.00 | 47.36 |
| ATOM | 50 | C | TYR | 26 | 10.238 | 2.910 | 10.249 | 1.00 | 50.47 |
| ATOM | 51 | O | TYR | 26 | 9.737 | 1.829 | 10.532 | 1.00 | 49.58 |
| ATOM | 52 | N | ALA | 27 | 11.549 | 3.095 | 10.111 | 1.00 | 50.08 |
| ATOM | 53 | CA | ALA | 27 | 12.508 | 1.989 | 10.046 | 1.00 | 49.65 |
| ATOM | 54 | CB | ALA | 27 | 12.755 | 1.586 | 8.576 | 1.00 | 49.90 |
| ATOM | 55 | C | ALA | 27 | 13.841 | 2.331 | 10.698 | 1.00 | 49.17 |
| ATOM | 56 | O | ALA | 27 | 14.833 | 2.531 | 10.003 | 1.00 | 49.36 |
| ATOM | 57 | N | PHE | 47 | 25.062 | 17.040 | 9.763 | 1.00 | 25.69 |
| ATOM | 58 | CA | PHE | 47 | 24.285 | 16.712 | 8.552 | 1.00 | 25.78 |
| ATOM | 59 | CB | PHE | 47 | 23.624 | 15.343 | 8.700 | 1.00 | 26.07 |
| ATOM | 60 | CG | PHE | 47 | 24.612 | 14.259 | 9.035 | 1.00 | 25.38 |
| ATOM | 61 | CD1 | PHE | 47 | 25.005 | 14.054 | 10.352 | 1.00 | 29.07 |
| ATOM | 62 | CE1 | PHE | 47 | 25.981 | 13.040 | 10.678 | 1.00 | 29.50 |
| ATOM | 63 | CZ | PHE | 47 | 26.543 | 12.276 | 9.652 | 1.00 | 26.40 |
| ATOM | 64 | CE2 | PHE | 47 | 26.165 | 12.494 | 8.358 | 1.00 | 24.93 |
| ATOM | 65 | CD2 | PHE | 47 | 25.197 | 13.483 | 8.042 | 1.00 | 27.19 |
| ATOM | 66 | C | PHE | 47 | 23.238 | 17.752 | 8.240 | 1.00 | 26.50 |
| ATOM | 67 | O | PHE | 47 | 22.384 | 18.061 | 9.088 | 1.00 | 26.93 |
| ATOM | 68 | N | ASN | 48 | 23.303 | 18.279 | 7.021 | 1.00 | 26.28 |
| ATOM | 69 | CA | ASN | 48 | 22.271 | 19.151 | 6.455 | 1.00 | 26.70 |
| ATOM | 70 | CB | ASN | 48 | 22.917 | 20.148 | 5.530 | 1.00 | 26.63 |
| ATOM | 71 | CG | ASN | 48 | 24.033 | 20.953 | 6.193 | 1.00 | 27.75 |
| ATOM | 72 | OD1 | ASN | 48 | 23.790 | 21.639 | 7.179 | 1.00 | 26.90 |
| ATOM | 73 | ND2 | ASN | 48 | 25.239 | 20.902 | 5.633 | 1.00 | 21.97 |
| ATOM | 74 | C | ASN | 48 | 21.329 | 18.296 | 5.641 | 1.00 | 27.42 |
| ATOM | 75 | O | ASN | 48 | 21.769 | 17.629 | 4.672 | 1.00 | 27.74 |
| ATOM | 76 | N | CYS | 49 | 20.051 | 18.275 | 6.022 | 1.00 | 27.81 |
| ATOM | 77 | CA | CYS | 49 | 19.052 | 17.364 | 5.444 | 1.00 | 27.79 |
| ATOM | 78 | CB | CYS | 49 | 18.599 | 16.308 | 6.442 | 1.00 | 27.88 |
| ATOM | 79 | SG | CYS | 49 | 19.994 | 15.572 | 7.349 | 1.00 | 33.42 |
| ATOM | 80 | C | CYS | 49 | 17.864 | 18.147 | 4.960 | 1.00 | 27.42 |
| ATOM | 81 | O | CYS | 49 | 16.852 | 18.099 | 5.563 | 1.00 | 27.36 |
| ATOM | 82 | N | PRO | 50 | 17.990 | 18.854 | 3.819 | 1.00 | 28.25 |
| ATOM | 83 | CA | PRO | 50 | 16.910 | 19.650 | 3.295 | 1.00 | 28.95 |
| ATOM | 84 | CB | PRO | 50 | 17.622 | 20.590 | 2.333 | 1.00 | 28.68 |
| ATOM | 85 | CG | PRO | 50 | 18.726 | 19.800 | 1.868 | 1.00 | 29.66 |
| ATOM | 86 | CD | PRO | 50 | 19.176 | 18.926 | 2.952 | 1.00 | 27.22 |
| ATOM | 87 | C | PRO | 50 | 15.827 | 18.823 | 2.571 | 1.00 | 30.16 |
| ATOM | 88 | O | PRO | 50 | 14.817 | 19.374 | 2.146 | 1.00 | 30.23 |
| ATOM | 89 | N | GLU | 51 | 15.953 | 17.501 | 2.506 | 1.00 | 30.75 |
| ATOM | 90 | CA | GLU | 51 | 14.876 | 16.769 | 1.832 | 1.00 | 30.88 |
| ATOM | 91 | CB | GLU | 51 | 15.476 | 15.828 | 0.770 | 1.00 | 30.96 |
| ATOM | 92 | CG | GLU | 51 | 16.006 | 16.687 | −0.398 | 1.00 | 30.27 |
| ATOM | 93 | CD | GLU | 51 | 16.941 | 15.950 | −1.336 | 1.00 | 34.08 |
| ATOM | 94 | OE1 | GLU | 51 | 17.091 | 14.711 | −1.229 | 1.00 | 37.55 |
| ATOM | 95 | OE2 | GLU | 51 | 17.562 | 16.627 | −2.163 | 1.00 | 33.25 |
| ATOM | 96 | C | GLU | 51 | 13.852 | 16.084 | 2.717 | 1.00 | 31.31 |
| ATOM | 97 | O | GLU | 51 | 13.087 | 15.242 | 2.253 | 1.00 | 32.45 |
| ATOM | 98 | N | PHE | 52 | 13.804 | 16.434 | 3.999 | 1.00 | 30.57 |
| ATOM | 99 | CA | PHE | 52 | 12.946 | 15.690 | 4.901 | 1.00 | 29.32 |
| ATOM | 100 | CB | PHE | 52 | 13.197 | 16.089 | 6.352 | 1.00 | 29.38 |
| ATOM | 101 | CG | PHE | 52 | 12.401 | 15.278 | 7.317 | 1.00 | 28.90 |

TABLE 7-continued

| | | | | | | | | | |
|---|---|---|---|---|---|---|---|---|---|
| ATOM | 102 | CD1 | PHE | 52 | 12.848 | 14.011 | 7.694 | 1.00 | 25.64 |
| ATOM | 103 | CE1 | PHE | 52 | 12.120 | 13.254 | 8.596 | 1.00 | 26.75 |
| ATOM | 104 | CZ | PHE | 52 | 10.907 | 13.720 | 9.069 | 1.00 | 25.36 |
| ATOM | 105 | CE2 | PHE | 52 | 10.433 | 14.985 | 8.677 | 1.00 | 28.36 |
| ATOM | 106 | CD2 | PHE | 52 | 11.172 | 15.749 | 7.797 | 1.00 | 26.05 |
| ATOM | 107 | C | PHE | 52 | 11.495 | 15.907 | 4.571 | 1.00 | 29.42 |
| ATOM | 108 | O | PHE | 52 | 11.112 | 17.027 | 4.241 | 1.00 | 29.42 |
| ATOM | 109 | N | THR | 53 | 10.688 | 14.849 | 4.681 | 1.00 | 28.87 |
| ATOM | 110 | CA | THR | 53 | 9.246 | 14.931 | 4.491 | 1.00 | 29.86 |
| ATOM | 111 | CB | THR | 53 | 8.835 | 14.971 | 2.965 | 1.00 | 29.43 |
| ATOM | 112 | OG1 | THR | 53 | 7.463 | 15.266 | 2.864 | 1.00 | 29.24 |
| ATOM | 113 | CG2 | THR | 53 | 9.008 | 13.632 | 2.244 | 1.00 | 29.41 |
| ATOM | 114 | C | THR | 53 | 8.504 | 13.816 | 5.284 | 1.00 | 30.60 |
| ATOM | 115 | O | THR | 53 | 9.051 | 12.734 | 5.474 | 1.00 | 31.11 |
| ATOM | 116 | N | PHE | 64 | 7.144 | 19.152 | 5.330 | 1.00 | 30.47 |
| ATOM | 117 | CA | PHE | 64 | 8.494 | 19.197 | 4.755 | 1.00 | 28.47 |
| ATOM | 118 | CB | PHE | 64 | 8.437 | 19.872 | 3.371 | 1.00 | 28.12 |
| ATOM | 119 | CG | PHE | 64 | 7.610 | 19.102 | 2.353 | 1.00 | 28.68 |
| ATOM | 120 | CD1 | PHE | 64 | 6.222 | 19.187 | 2.352 | 1.00 | 30.31 |
| ATOM | 121 | CE1 | PHE | 64 | 5.465 | 18.482 | 1.430 | 1.00 | 31.76 |
| ATOM | 122 | CZ | PHE | 64 | 6.113 | 17.639 | 0.479 | 1.00 | 27.12 |
| ATOM | 123 | CE2 | PHE | 64 | 7.491 | 17.535 | 0.481 | 1.00 | 30.78 |
| ATOM | 124 | CD2 | PHE | 64 | 8.238 | 18.276 | 1.407 | 1.00 | 30.18 |
| ATOM | 125 | C | PHE | 64 | 9.375 | 19.990 | 5.682 | 1.00 | 27.63 |
| ATOM | 126 | O | PHE | 64 | 8.906 | 20.929 | 6.289 | 1.00 | 28.69 |
| ATOM | 127 | N | ALA | 65 | 10.672 | 19.674 | 5.722 | 1.00 | 26.33 |
| ATOM | 128 | CA | ALA | 65 | 11.573 | 20.355 | 6.558 | 1.00 | 25.69 |
| ATOM | 129 | CB | ALA | 65 | 11.452 | 19.770 | 8.065 | 1.00 | 24.22 |
| ATOM | 130 | C | ALA | 65 | 13.003 | 20.226 | 6.057 | 1.00 | 25.67 |
| ATOM | 131 | O | ALA | 65 | 13.333 | 19.340 | 5.287 | 1.00 | 26.66 |
| ATOM | 132 | N | THR | 66 | 13.846 | 21.119 | 6.530 | 1.00 | 25.39 |
| ATOM | 133 | CA | THR | 66 | 15.277 | 20.938 | 6.552 | 1.00 | 27.61 |
| ATOM | 134 | CB | THR | 66 | 15.977 | 22.221 | 6.171 | 1.00 | 27.25 |
| ATOM | 135 | OG1 | THR | 66 | 15.670 | 22.501 | 4.818 | 1.00 | 30.69 |
| ATOM | 136 | CG2 | THR | 66 | 17.458 | 22.055 | 6.236 | 1.00 | 31.40 |
| ATOM | 137 | C | THR | 66 | 15.650 | 20.599 | 7.998 | 1.00 | 28.30 |
| ATOM | 138 | O | THR | 66 | 15.252 | 21.289 | 8.951 | 1.00 | 28.10 |
| ATOM | 139 | N | ILE | 67 | 16.423 | 19.543 | 8.164 | 1.00 | 28.94 |
| ATOM | 140 | CA | ILE | 67 | 16.873 | 19.153 | 9.492 | 1.00 | 28.94 |
| ATOM | 141 | CB | ILE | 67 | 16.441 | 17.682 | 9.743 | 1.00 | 29.43 |
| ATOM | 142 | CG1 | ILE | 67 | 14.916 | 17.617 | 9.628 | 1.00 | 28.57 |
| ATOM | 143 | CD1 | ILE | 67 | 14.401 | 16.268 | 9.787 | 1.00 | 29.91 |
| ATOM | 144 | CG2 | ILE | 67 | 16.945 | 17.156 | 11.087 | 1.00 | 29.92 |
| ATOM | 145 | C | ILE | 67 | 18.359 | 19.342 | 9.525 | 1.00 | 28.85 |
| ATOM | 146 | O | ILE | 67 | 19.014 | 19.023 | 8.528 | 1.00 | 29.21 |
| ATOM | 147 | N | TYR | 68 | 18.886 | 19.885 | 10.635 | 1.00 | 28.85 |
| ATOM | 148 | CA | TYR | 68 | 20.318 | 20.053 | 10.875 | 1.00 | 27.65 |
| ATOM | 149 | CB | TYR | 68 | 20.702 | 21.513 | 11.114 | 1.00 | 28.00 |
| ATOM | 150 | CG | TYR | 68 | 20.290 | 22.412 | 9.962 | 1.00 | 27.25 |
| ATOM | 151 | CD1 | TYR | 68 | 19.091 | 23.118 | 9.975 | 1.00 | 23.97 |
| ATOM | 152 | CE1 | TYR | 68 | 18.720 | 23.951 | 8.875 | 1.00 | 28.38 |
| ATOM | 153 | CZ | TYR | 68 | 19.563 | 23.994 | 7.745 | 1.00 | 28.49 |
| ATOM | 154 | OH | TYR | 68 | 19.296 | 24.739 | 6.599 | 1.00 | 26.21 |
| ATOM | 155 | CE2 | TYR | 68 | 20.753 | 23.251 | 7.732 | 1.00 | 29.17 |
| ATOM | 156 | CD2 | TYR | 68 | 21.108 | 22.490 | 8.807 | 1.00 | 27.85 |
| ATOM | 157 | C | TYR | 68 | 20.608 | 19.186 | 12.086 | 1.00 | 29.20 |
| ATOM | 158 | O | TYR | 68 | 19.978 | 19.362 | 13.159 | 1.00 | 29.47 |
| ATOM | 159 | N | GLU | 79 | 26.458 | 6.264 | 9.570 | 1.00 | 38.71 |
| ATOM | 160 | CA | GLU | 79 | 26.759 | 6.201 | 8.147 | 1.00 | 39.26 |
| ATOM | 161 | CB | GLU | 79 | 26.840 | 4.742 | 7.675 | 1.00 | 39.82 |
| ATOM | 162 | CG | GLU | 79 | 27.658 | 4.523 | 6.377 | 1.00 | 41.73 |
| ATOM | 163 | CD | GLU | 79 | 26.916 | 5.023 | 5.134 | 1.00 | 44.42 |
| ATOM | 164 | OE1 | GLU | 79 | 25.731 | 4.637 | 4.995 | 1.00 | 45.96 |
| ATOM | 165 | OE2 | GLU | 79 | 27.485 | 5.827 | 4.330 | 1.00 | 43.13 |
| ATOM | 166 | C | GLU | 79 | 25.763 | 7.056 | 7.361 | 1.00 | 39.15 |
| ATOM | 167 | O | GLU | 79 | 24.544 | 6.957 | 7.544 | 1.00 | 39.58 |
| ATOM | 168 | N | SER | 80 | 26.289 | 7.928 | 6.506 | 1.00 | 39.14 |
| ATOM | 169 | CA | SER | 80 | 25.467 | 8.878 | 5.757 | 1.00 | 40.45 |
| ATOM | 170 | CB | SER | 80 | 26.344 | 9.708 | 4.813 | 1.00 | 40.98 |
| ATOM | 171 | OG | SER | 80 | 25.565 | 10.760 | 4.263 | 1.00 | 43.76 |
| ATOM | 172 | C | SER | 80 | 24.312 | 8.273 | 4.969 | 1.00 | 39.97 |
| ATOM | 173 | O | SER | 80 | 23.214 | 8.829 | 4.946 | 1.00 | 40.91 |
| ATOM | 174 | N | LYS | 81 | 24.568 | 7.159 | 4.285 | 1.00 | 40.44 |
| ATOM | 175 | CA | LYS | 81 | 23.564 | 6.530 | 3.434 | 1.00 | 39.60 |
| ATOM | 176 | CB | LYS | 81 | 24.232 | 5.581 | 2.421 | 1.00 | 40.23 |
| ATOM | 177 | CG | LYS | 81 | 23.225 | 4.710 | 1.552 | 1.00 | 41.71 |
| ATOM | 178 | CD | LYS | 81 | 23.952 | 3.739 | 0.562 | 1.00 | 43.35 |
| ATOM | 179 | CE | LYS | 81 | 24.173 | 2.308 | 1.110 | 1.00 | 51.29 |
| ATOM | 180 | NZ | LYS | 81 | 22.945 | 1.412 | 0.924 | 1.00 | 51.65 |
| ATOM | 181 | C | LYS | 81 | 22.495 | 5.846 | 4.278 | 1.00 | 37.68 |

TABLE 7-continued

| | | | | | | | | | |
|---|---|---|---|---|---|---|---|---|---|
| ATOM | 182 | O | LYS | 81 | 21.300 | 5.955 | 3.950 | 1.00 | 36.22 |
| ATOM | 183 | N | SER | 82 | 22.889 | 5.209 | 5.394 | 1.00 | 36.37 |
| ATOM | 184 | CA | SER | 82 | 21.872 | 4.696 | 6.342 | 1.00 | 36.60 |
| ATOM | 185 | CB | SER | 82 | 22.482 | 3.886 | 7.500 | 1.00 | 37.83 |
| ATOM | 186 | OG | SER | 82 | 23.305 | 4.646 | 8.389 | 1.00 | 38.89 |
| ATOM | 187 | C | SER | 82 | 20.946 | 5.803 | 6.860 | 1.00 | 36.09 |
| ATOM | 188 | O | SER | 82 | 19.692 | 5.635 | 6.863 | 1.00 | 35.12 |
| ATOM | 189 | N | LEU | 83 | 21.559 | 6.942 | 7.220 | 1.00 | 34.52 |
| ATOM | 190 | CA | LEU | 83 | 20.810 | 8.145 | 7.632 | 1.00 | 34.68 |
| ATOM | 191 | CB | LEU | 83 | 21.750 | 9.303 | 8.037 | 1.00 | 34.38 |
| ATOM | 192 | CG | LEU | 83 | 21.070 | 10.539 | 8.675 | 1.00 | 35.18 |
| ATOM | 193 | CD1 | LEU | 83 | 20.172 | 10.189 | 9.928 | 1.00 | 28.46 |
| ATOM | 194 | CD2 | LEU | 83 | 22.108 | 11.609 | 8.990 | 1.00 | 33.77 |
| ATOM | 195 | C | LEU | 83 | 19.796 | 8.611 | 6.596 | 1.00 | 34.51 |
| ATOM | 196 | O | LEU | 83 | 18.665 | 8.972 | 6.920 | 1.00 | 33.59 |
| ATOM | 197 | N | LYS | 84 | 20.215 | 8.596 | 5.340 | 1.00 | 35.31 |
| ATOM | 198 | CA | LYS | 84 | 19.364 | 8.948 | 4.241 | 1.00 | 35.99 |
| ATOM | 199 | CB | LYS | 84 | 20.196 | 8.889 | 2.946 | 1.00 | 35.66 |
| ATOM | 200 | CG | LYS | 84 | 19.404 | 8.959 | 1.673 | 1.00 | 37.97 |
| ATOM | 201 | CD | LYS | 84 | 20.315 | 8.602 | 0.461 | 1.00 | 37.55 |
| ATOM | 202 | CE | LYS | 84 | 20.113 | 7.166 | 0.020 | 1.00 | 39.56 |
| ATOM | 203 | NZ | LYS | 84 | 20.530 | 6.897 | −1.391 | 1.00 | 41.94 |
| ATOM | 204 | C | LYS | 84 | 18.181 | 7.995 | 4.207 | 1.00 | 36.20 |
| ATOM | 205 | O | LYS | 84 | 17.022 | 8.423 | 4.139 | 1.00 | 36.55 |
| ATOM | 206 | N | LEU | 85 | 18.470 | 6.699 | 4.278 | 1.00 | 36.49 |
| ATOM | 207 | CA | LEU | 85 | 17.432 | 5.689 | 4.349 | 1.00 | 36.64 |
| ATOM | 208 | CB | LEU | 85 | 18.080 | 4.297 | 4.349 | 1.00 | 36.98 |
| ATOM | 209 | CG | LEU | 85 | 18.513 | 3.540 | 3.067 | 1.00 | 39.95 |
| ATOM | 210 | CD1 | LEU | 85 | 18.684 | 4.437 | 1.833 | 1.00 | 41.97 |
| ATOM | 211 | CD2 | LEU | 85 | 19.796 | 2.690 | 3.275 | 1.00 | 37.78 |
| ATOM | 212 | C | LEU | 85 | 16.558 | 5.870 | 5.579 | 1.00 | 36.28 |
| ATOM | 213 | O | LEU | 85 | 15.340 | 5.834 | 5.500 | 1.00 | 35.95 |
| ATOM | 214 | N | TYR | 86 | 17.159 | 6.087 | 6.739 | 1.00 | 36.01 |
| ATOM | 215 | CA | TYR | 86 | 16.334 | 6.368 | 7.917 | 1.00 | 35.20 |
| ATOM | 216 | CB | TYR | 86 | 17.247 | 6.613 | 9.096 | 1.00 | 36.62 |
| ATOM | 217 | CG | TYR | 86 | 16.542 | 6.971 | 10.358 | 1.00 | 38.86 |
| ATOM | 218 | CD1 | TYR | 86 | 15.640 | 6.078 | 10.977 | 1.00 | 37.52 |
| ATOM | 219 | CE1 | TYR | 86 | 14.997 | 6.448 | 12.173 | 1.00 | 39.96 |
| ATOM | 220 | CZ | TYR | 86 | 15.297 | 7.714 | 12.754 | 1.00 | 39.92 |
| ATOM | 221 | OH | TYR | 86 | 14.696 | 8.167 | 13.898 | 1.00 | 40.85 |
| ATOM | 222 | CE2 | TYR | 86 | 16.177 | 8.573 | 12.151 | 1.00 | 38.61 |
| ATOM | 223 | CD2 | TYR | 86 | 16.791 | 8.205 | 10.963 | 1.00 | 39.08 |
| ATOM | 224 | C | TYR | 86 | 15.382 | 7.541 | 7.697 | 1.00 | 34.75 |
| ATOM | 225 | O | TYR | 86 | 14.170 | 7.463 | 7.935 | 1.00 | 34.10 |
| ATOM | 226 | N | LEU | 87 | 15.893 | 8.650 | 7.188 | 1.00 | 35.13 |
| ATOM | 227 | CA | LEU | 87 | 14.989 | 9.790 | 6.955 | 1.00 | 35.00 |
| ATOM | 228 | CB | LEU | 87 | 15.751 | 11.089 | 6.780 | 1.00 | 35.12 |
| ATOM | 229 | CG | LEU | 87 | 16.716 | 11.493 | 7.900 | 1.00 | 36.20 |
| ATOM | 230 | CD1 | LEU | 87 | 17.587 | 12.656 | 7.466 | 1.00 | 32.77 |
| ATOM | 231 | CD2 | LEU | 87 | 15.956 | 11.830 | 9.204 | 1.00 | 34.84 |
| ATOM | 232 | C | LEU | 87 | 13.972 | 9.553 | 5.842 | 1.00 | 35.54 |
| ATOM | 233 | O | LEU | 87 | 12.819 | 10.037 | 5.926 | 1.00 | 33.45 |
| ATOM | 234 | N | PHE | 88 | 14.356 | 8.785 | 4.806 | 1.00 | 37.14 |
| ATOM | 235 | CA | PHE | 88 | 13.331 | 8.302 | 3.840 | 1.00 | 38.55 |
| ATOM | 236 | CB | PHE | 88 | 13.904 | 7.323 | 2.789 | 1.00 | 40.19 |
| ATOM | 237 | CG | PHE | 88 | 14.749 | 7.975 | 1.719 | 1.00 | 44.41 |
| ATOM | 238 | CD1 | PHE | 88 | 15.587 | 7.192 | 0.913 | 1.00 | 45.28 |
| ATOM | 239 | CE1 | PHE | 88 | 16.380 | 7.783 | −0.061 | 1.00 | 46.31 |
| ATOM | 240 | CZ | PHE | 88 | 16.347 | 9.175 | −0.247 | 1.00 | 45.62 |
| ATOM | 241 | CE2 | PHE | 88 | 15.522 | 9.963 | 0.548 | 1.00 | 46.65 |
| ATOM | 242 | CD2 | PHE | 88 | 14.726 | 9.365 | 1.520 | 1.00 | 46.40 |
| ATOM | 243 | C | PHE | 88 | 12.204 | 7.574 | 4.580 | 1.00 | 37.62 |
| ATOM | 244 | O | PHE | 88 | 11.050 | 7.699 | 4.218 | 1.00 | 37.12 |
| ATOM | 245 | N | SER | 89 | 12.561 | 6.808 | 5.611 | 1.00 | 37.50 |
| ATOM | 246 | CA | SER | 89 | 11.577 | 5.967 | 6.306 | 1.00 | 37.88 |
| ATOM | 247 | CB | SER | 89 | 12.223 | 4.983 | 7.284 | 1.00 | 38.18 |
| ATOM | 248 | OG | SER | 89 | 12.601 | 5.581 | 8.518 | 1.00 | 39.35 |
| ATOM | 249 | C | SER | 89 | 10.468 | 6.764 | 6.956 | 1.00 | 37.70 |
| ATOM | 250 | O | SER | 89 | 9.477 | 6.201 | 7.332 | 1.00 | 38.26 |
| ATOM | 251 | N | PHE | 90 | 10.587 | 8.083 | 7.013 | 1.00 | 36.34 |
| ATOM | 252 | CA | PHE | 90 | 9.481 | 8.886 | 7.548 | 1.00 | 35.88 |
| ATOM | 253 | CB | PHE | 90 | 10.030 | 10.130 | 8.270 | 1.00 | 35.55 |
| ATOM | 254 | CG | PHE | 90 | 10.699 | 9.824 | 9.560 | 1.00 | 34.96 |
| ATOM | 255 | CD1 | PHE | 90 | 11.991 | 9.303 | 9.586 | 1.00 | 35.21 |
| ATOM | 256 | CE1 | PHE | 90 | 12.623 | 9.011 | 10.771 | 1.00 | 33.10 |
| ATOM | 257 | CZ | PHE | 90 | 11.986 | 9.238 | 11.945 | 1.00 | 36.55 |
| ATOM | 258 | CE2 | PHE | 90 | 10.684 | 9.766 | 11.947 | 1.00 | 38.06 |
| ATOM | 259 | CD2 | PHE | 90 | 10.057 | 10.063 | 10.755 | 1.00 | 35.73 |
| ATOM | 260 | C | PHE | 90 | 8.452 | 9.313 | 6.514 | 1.00 | 35.67 |
| ATOM | 261 | O | PHE | 90 | 7.433 | 9.915 | 6.867 | 1.00 | 35.03 |

TABLE 7-continued

| ATOM | 262 | N | ARG | 91 | 8.731 | 9.034 | 5.241 | 1.00 | 35.48 |
|---|---|---|---|---|---|---|---|---|---|
| ATOM | 263 | CA | ARG | 91 | 7.909 | 9.538 | 4.127 | 1.00 | 36.26 |
| ATOM | 264 | CB | ARG | 91 | 8.527 | 9.137 | 2.744 | 1.00 | 35.68 |
| ATOM | 265 | CG | ARG | 91 | 7.788 | 9.707 | 1.534 | 1.00 | 32.43 |
| ATOM | 266 | CD | ARG | 91 | 8.221 | 9.092 | 0.137 | 1.00 | 36.20 |
| ATOM | 267 | NE | ARG | 91 | 9.085 | 10.056 | −0.530 | 1.00 | 44.24 |
| ATOM | 268 | CZ | ARG | 91 | 8.723 | 10.921 | −1.467 | 1.00 | 42.01 |
| ATOM | 269 | NH1 | ARG | 91 | 7.535 | 10.933 | −1.989 | 1.00 | 41.45 |
| ATOM | 270 | NH2 | ARG | 91 | 9.601 | 11.770 | −1.908 | 1.00 | 50.38 |
| ATOM | 271 | C | ARG | 91 | 6.420 | 9.206 | 4.216 | 1.00 | 37.67 |
| ATOM | 272 | O | ARG | 91 | 5.579 | 10.046 | 3.931 | 1.00 | 36.52 |
| ATOM | 273 | N | ASN | 164 | 7.610 | 33.624 | 5.211 | 1.00 | 33.87 |
| ATOM | 274 | CA | ASN | 164 | 6.874 | 32.623 | 4.447 | 1.00 | 34.28 |
| ATOM | 275 | CB | ASN | 164 | 5.360 | 32.640 | 4.769 | 1.00 | 32.50 |
| ATOM | 276 | CG | ASN | 164 | 5.033 | 32.212 | 6.207 | 1.00 | 32.82 |
| ATOM | 277 | OD1 | ASN | 164 | 5.896 | 31.709 | 6.951 | 1.00 | 30.94 |
| ATOM | 278 | ND2 | ASN | 164 | 3.768 | 32.423 | 6.602 | 1.00 | 29.12 |
| ATOM | 279 | C | ASN | 164 | 7.084 | 32.642 | 2.912 | 1.00 | 34.97 |
| ATOM | 280 | O | ASN | 164 | 6.322 | 32.009 | 2.191 | 1.00 | 35.11 |
| ATOM | 281 | O6 | GDQ | 201 | 32.296 | 10.635 | 4.524 | 1.00 | 46.27 |
| ATOM | 282 | C6 | GDQ | 201 | 31.248 | 9.917 | 5.035 | 1.00 | 47.77 |
| ATOM | 283 | N1 | GDQ | 201 | 30.797 | 10.050 | 6.323 | 1.00 | 47.90 |
| ATOM | 284 | C5 | GDQ | 201 | 30.614 | 8.990 | 4.235 | 1.00 | 48.17 |
| ATOM | 285 | C7 | GDQ | 201 | 30.698 | 8.536 | 2.936 | 1.00 | 49.49 |
| ATOM | 286 | C77 | GDQ | 201 | 31.612 | 8.969 | 2.073 | 1.00 | 48.63 |
| ATOM | 287 | N77 | GDQ | 201 | 32.516 | 9.322 | 1.359 | 1.00 | 53.62 |
| ATOM | 288 | C8 | GDQ | 201 | 29.759 | 7.552 | 2.635 | 1.00 | 47.67 |
| ATOM | 289 | N9 | GDQ | 201 | 29.054 | 7.399 | 3.791 | 1.00 | 46.70 |
| ATOM | 290 | C4 | GDQ | 201 | 29.559 | 8.251 | 4.732 | 1.00 | 47.89 |
| ATOM | 291 | N3 | GDQ | 201 | 29.132 | 8.401 | 6.010 | 1.00 | 47.83 |
| ATOM | 292 | C2 | GDQ | 201 | 29.744 | 9.300 | 6.809 | 1.00 | 48.19 |
| ATOM | 293 | N2 | GDQ | 201 | 29.279 | 9.410 | 8.086 | 1.00 | 46.97 |
| ATOM | 294 | N | THR | 53 | 38.860 | 17.948 | −3.280 | 1.00 | 30.01 |
| ATOM | 295 | CA | THR | 53 | 38.183 | 16.694 | −3.678 | 1.00 | 29.44 |
| ATOM | 296 | CB | THR | 53 | 37.840 | 16.658 | −5.235 | 1.00 | 29.62 |
| ATOM | 297 | OG1 | THR | 53 | 37.131 | 15.442 | −5.556 | 1.00 | 29.40 |
| ATOM | 298 | CG2 | THR | 53 | 39.072 | 16.811 | −6.094 | 1.00 | 25.18 |
| ATOM | 299 | C | THR | 53 | 38.990 | 15.457 | −3.243 | 1.00 | 30.25 |
| ATOM | 300 | O | THR | 53 | 40.215 | 15.543 | −3.068 | 1.00 | 31.21 |
| ATOM | 301 | N | SER | 54 | 38.300 | 14.356 | −3.003 | 1.00 | 30.79 |
| ATOM | 302 | CA | SER | 54 | 38.904 | 13.065 | −2.708 | 1.00 | 32.95 |
| ATOM | 303 | CB | SER | 54 | 39.301 | 12.946 | −1.220 | 1.00 | 34.16 |
| ATOM | 304 | OG | SER | 54 | 38.154 | 13.067 | −0.381 | 1.00 | 35.15 |
| ATOM | 305 | C | SER | 54 | 37.889 | 12.001 | −3.016 | 1.00 | 34.08 |
| ATOM | 306 | O | SER | 54 | 36.913 | 12.280 | −3.712 | 1.00 | 33.43 |
| ATOM | 307 | N | LEU | 55 | 38.069 | 10.797 | −2.459 | 1.00 | 35.50 |
| ATOM | 308 | CA | LEU | 55 | 37.268 | 9.657 | −2.895 | 1.00 | 38.99 |
| ATOM | 309 | CB | LEU | 55 | 38.179 | 8.651 | −3.644 | 1.00 | 38.15 |
| ATOM | 310 | CG | LEU | 55 | 38.817 | 9.069 | −4.982 | 1.00 | 38.05 |
| ATOM | 311 | CD1 | LEU | 55 | 39.656 | 7.937 | −5.661 | 1.00 | 37.97 |
| ATOM | 312 | CD2 | LEU | 55 | 37.756 | 9.481 | −5.925 | 1.00 | 36.27 |
| ATOM | 313 | C | LEU | 55 | 36.465 | 8.986 | −1.761 | 1.00 | 41.28 |
| ATOM | 314 | O | LEU | 55 | 36.931 | 8.915 | −0.633 | 1.00 | 42.13 |
| ATOM | 315 | N | CYS | 56 | 35.259 | 8.514 | −2.036 | 1.00 | 45.15 |
| ATOM | 316 | CA | CYS | 56 | 34.534 | 7.710 | −1.045 | 1.00 | 48.21 |
| ATOM | 317 | CB | CYS | 56 | 33.081 | 7.551 | −1.475 | 1.00 | 48.98 |
| ATOM | 318 | SG | CYS | 56 | 32.106 | 6.272 | −0.638 | 1.00 | 48.04 |
| ATOM | 319 | C | CYS | 56 | 35.294 | 6.359 | −0.863 | 1.00 | 50.95 |
| ATOM | 320 | O | CYS | 56 | 35.713 | 5.744 | −1.855 | 1.00 | 51.40 |
| ATOM | 321 | N | PRO | 57 | 35.556 | 5.933 | 0.398 | 1.00 | 52.65 |
| ATOM | 322 | CA | PRO | 57 | 36.546 | 4.843 | 0.573 | 1.00 | 54.14 |
| ATOM | 323 | CB | PRO | 57 | 36.941 | 4.948 | 2.049 | 1.00 | 54.19 |
| ATOM | 324 | CG | PRO | 57 | 35.725 | 5.574 | 2.728 | 1.00 | 53.52 |
| ATOM | 325 | CD | PRO | 57 | 34.969 | 6.371 | 1.680 | 1.00 | 52.98 |
| ATOM | 326 | C | PRO | 57 | 35.998 | 3.439 | 0.227 | 1.00 | 55.54 |
| ATOM | 327 | O | PRO | 57 | 36.772 | 2.537 | −0.135 | 1.00 | 54.81 |
| ATOM | 328 | N | LYS | 58 | 34.672 | 3.284 | 0.324 | 1.00 | 57.50 |
| ATOM | 329 | CA | LYS | 58 | 33.977 | 2.071 | −0.134 | 1.00 | 59.13 |
| ATOM | 330 | CB | LYS | 58 | 32.663 | 1.836 | 0.632 | 1.00 | 59.05 |
| ATOM | 331 | CG | LYS | 58 | 31.664 | 0.888 | −0.073 | 1.00 | 60.63 |
| ATOM | 332 | CD | LYS | 58 | 30.258 | 0.913 | 0.598 | 1.00 | 60.64 |
| ATOM | 333 | CE | LYS | 58 | 29.146 | 0.312 | −0.291 | 1.00 | 62.65 |
| ATOM | 334 | NZ | LYS | 58 | 27.745 | 0.706 | 0.131 | 1.00 | 60.90 |
| ATOM | 335 | C | LYS | 58 | 33.732 | 2.204 | −1.640 | 1.00 | 59.19 |
| ATOM | 336 | O | LYS | 58 | 34.269 | 1.421 | −2.420 | 1.00 | 59.79 |
| ATOM | 337 | N | VAL | 59 | 32.970 | 3.230 | −2.031 | 1.00 | 58.64 |
| ATOM | 338 | CA | VAL | 59 | 32.501 | 3.415 | −3.423 | 1.00 | 57.13 |
| ATOM | 339 | CB | VAL | 59 | 31.314 | 4.428 | −3.464 | 1.00 | 57.65 |
| ATOM | 340 | CG1 | VAL | 59 | 31.000 | 4.843 | −4.851 | 1.00 | 58.60 |
| ATOM | 341 | CG2 | VAL | 59 | 30.061 | 3.818 | −2.811 | 1.00 | 58.09 |

TABLE 7-continued

| | | | | | | | | | |
|---|---|---|---|---|---|---|---|---|---|
| ATOM | 342 | C | VAL | 59 | 33.588 | 3.767 | −4.467 | 1.00 | 55.09 |
| ATOM | 343 | O | VAL | 59 | 33.546 | 3.270 | −5.578 | 1.00 | 56.14 |
| ATOM | 344 | N | GLY | 60 | 34.535 | 4.640 | −4.134 | 1.00 | 52.41 |
| ATOM | 345 | CA | GLY | 60 | 35.470 | 5.172 | −5.125 | 1.00 | 47.50 |
| ATOM | 346 | C | GLY | 60 | 34.968 | 6.404 | −5.865 | 1.00 | 45.30 |
| ATOM | 347 | O | GLY | 60 | 35.704 | 7.003 | −6.618 | 1.00 | 44.68 |
| ATOM | 348 | N | GLN | 61 | 33.709 | 6.771 | −5.661 | 1.00 | 43.47 |
| ATOM | 349 | CA | GLN | 61 | 33.098 | 7.979 | −6.206 | 1.00 | 43.06 |
| ATOM | 350 | CB | GLN | 61 | 31.585 | 7.965 | −5.934 | 1.00 | 42.84 |
| ATOM | 351 | CG | GLN | 61 | 30.815 | 9.238 | −6.328 | 1.00 | 46.97 |
| ATOM | 352 | CD | GLN | 61 | 29.288 | 9.110 | −6.178 | 1.00 | 48.50 |
| ATOM | 353 | OE1 | GLN | 61 | 28.513 | 9.704 | −6.959 | 1.00 | 53.52 |
| ATOM | 354 | NE2 | GLN | 61 | 28.847 | 8.327 | −5.167 | 1.00 | 52.86 |
| ATOM | 355 | C | GLN | 61 | 33.738 | 9.215 | −5.581 | 1.00 | 40.38 |
| ATOM | 356 | O | GLN | 61 | 33.987 | 9.250 | −4.394 | 1.00 | 39.46 |
| ATOM | 357 | N | PRO | 62 | 34.032 | 10.227 | −6.399 | 1.00 | 39.26 |
| ATOM | 358 | CA | PRO | 62 | 34.608 | 11.508 | −5.962 | 1.00 | 37.62 |
| ATOM | 359 | CB | PRO | 62 | 34.652 | 12.332 | −7.244 | 1.00 | 37.68 |
| ATOM | 360 | CG | PRO | 62 | 34.514 | 11.382 | −8.361 | 1.00 | 38.30 |
| ATOM | 361 | CD | PRO | 62 | 33.765 | 10.193 | −7.850 | 1.00 | 39.55 |
| ATOM | 362 | C | PRO | 62 | 33.692 | 12.251 | −4.981 | 1.00 | 36.24 |
| ATOM | 363 | O | PRO | 62 | 32.451 | 12.166 | −5.112 | 1.00 | 35.39 |
| ATOM | 364 | N | ASP | 63 | 34.310 | 12.988 | −4.041 | 1.00 | 34.81 |
| ATOM | 365 | CA | ASP | 63 | 33.615 | 13.918 | −3.138 | 1.00 | 33.85 |
| ATOM | 366 | CB | ASP | 63 | 33.883 | 13.641 | −1.635 | 1.00 | 35.11 |
| ATOM | 367 | CG | ASP | 63 | 33.749 | 12.160 | −1.212 | 1.00 | 42.47 |
| ATOM | 368 | OD1 | ASP | 63 | 32.689 | 11.539 | −1.559 | 1.00 | 45.14 |
| ATOM | 369 | OD2 | ASP | 63 | 34.699 | 11.672 | −0.463 | 1.00 | 44.13 |
| ATOM | 370 | C | ASP | 63 | 34.272 | 15.249 | −3.337 | 1.00 | 31.61 |
| ATOM | 371 | O | ASP | 63 | 35.487 | 15.294 | −3.648 | 1.00 | 30.61 |
| ATOM | 372 | N | PHE | 64 | 33.523 | 16.303 | −3.001 | 1.00 | 28.89 |
| ATOM | 373 | CA | PHE | 64 | 33.915 | 17.698 | −3.121 | 1.00 | 28.44 |
| ATOM | 374 | CB | PHE | 64 | 33.244 | 18.303 | −4.359 | 1.00 | 27.72 |
| ATOM | 375 | CG | PHE | 64 | 33.646 | 17.622 | −5.640 | 1.00 | 28.55 |
| ATOM | 376 | CD1 | PHE | 64 | 33.020 | 16.441 | −6.040 | 1.00 | 29.74 |
| ATOM | 377 | CE1 | PHE | 64 | 33.416 | 15.763 | −7.209 | 1.00 | 27.82 |
| ATOM | 378 | CZ | PHE | 64 | 34.461 | 16.270 | −7.957 | 1.00 | 28.20 |
| ATOM | 379 | CE2 | PHE | 64 | 35.108 | 17.463 | −7.578 | 1.00 | 29.67 |
| ATOM | 380 | CD2 | PHE | 64 | 34.698 | 18.137 | −6.416 | 1.00 | 28.64 |
| ATOM | 381 | C | PHE | 64 | 33.573 | 18.547 | −1.875 | 1.00 | 28.20 |
| ATOM | 382 | O | PHE | 64 | 32.483 | 18.436 | −1.322 | 1.00 | 28.02 |
| ATOM | 383 | N | PHE | 90 | 44.996 | 14.292 | −1.871 | 1.00 | 34.87 |
| ATOM | 384 | CA | PHE | 90 | 43.826 | 13.474 | −1.489 | 1.00 | 34.62 |
| ATOM | 385 | CB | PHE | 90 | 42.889 | 14.214 | −0.526 | 1.00 | 34.78 |
| ATOM | 386 | CG | PHE | 90 | 43.417 | 14.335 | 0.864 | 1.00 | 36.36 |
| ATOM | 387 | CD1 | PHE | 90 | 44.357 | 15.306 | 1.183 | 1.00 | 34.82 |
| ATOM | 388 | CE1 | PHE | 90 | 44.862 | 15.414 | 2.469 | 1.00 | 37.21 |
| ATOM | 389 | CZ | PHE | 90 | 44.425 | 14.559 | 3.455 | 1.00 | 36.41 |
| ATOM | 390 | CE2 | PHE | 90 | 43.437 | 13.608 | 3.177 | 1.00 | 40.24 |
| ATOM | 391 | CD2 | PHE | 90 | 42.948 | 13.488 | 1.870 | 1.00 | 39.21 |
| ATOM | 392 | C | PHE | 90 | 43.015 | 13.119 | −2.707 | 1.00 | 34.30 |
| ATOM | 393 | O | PHE | 90 | 42.034 | 12.393 | −2.578 | 1.00 | 33.27 |
| ATOM | 394 | N | ARG | 91 | 43.394 | 13.653 | −3.876 | 1.00 | 34.65 |
| ATOM | 395 | CA | ARG | 91 | 42.519 | 13.588 | −5.057 | 1.00 | 36.62 |
| ATOM | 396 | CB | ARG | 91 | 43.149 | 14.284 | −6.265 | 1.00 | 36.64 |
| ATOM | 397 | CG | ARG | 91 | 42.338 | 14.272 | −7.542 | 1.00 | 35.88 |
| ATOM | 398 | CD | ARG | 91 | 43.115 | 15.082 | −8.557 | 1.00 | 33.61 |
| ATOM | 399 | NE | ARG | 91 | 42.400 | 15.312 | −9.795 | 1.00 | 30.74 |
| ATOM | 400 | CZ | ARG | 91 | 41.534 | 16.291 | −10.004 | 1.00 | 34.38 |
| ATOM | 401 | NH1 | ARG | 91 | 41.243 | 17.151 | −9.016 | 1.00 | 32.01 |
| ATOM | 402 | NH2 | ARG | 91 | 40.925 | 16.397 | −11.204 | 1.00 | 29.74 |
| ATOM | 403 | C | ARG | 91 | 42.139 | 12.166 | −5.388 | 1.00 | 37.03 |
| ATOM | 404 | O | ARG | 91 | 40.979 | 11.894 | −5.679 | 1.00 | 37.70 |
| ATOM | 405 | N | ASN | 92 | 43.103 | 11.261 | −5.297 | 1.00 | 38.94 |
| ATOM | 406 | CA | ASN | 92 | 42.839 | 9.870 | −5.554 | 1.00 | 42.43 |
| ATOM | 407 | CB | ASN | 92 | 43.642 | 9.375 | −6.801 | 1.00 | 43.10 |
| ATOM | 408 | CG | ASN | 92 | 43.282 | 10.204 | −8.117 | 1.00 | 46.75 |
| ATOM | 409 | OD1 | ASN | 92 | 42.089 | 10.406 | −8.479 | 1.00 | 49.26 |
| ATOM | 410 | ND2 | ASN | 92 | 44.316 | 10.701 | −8.794 | 1.00 | 50.32 |
| ATOM | 411 | C | ASN | 92 | 42.892 | 8.964 | −4.290 | 1.00 | 44.01 |
| ATOM | 412 | O | ASN | 92 | 43.046 | 7.738 | −4.380 | 1.00 | 44.78 |
| ATOM | 413 | N | HIS | 93 | 42.655 | 9.585 | −3.129 | 1.00 | 44.75 |
| ATOM | 414 | CA | HIS | 93 | 42.657 | 8.938 | −1.808 | 1.00 | 45.82 |
| ATOM | 415 | CB | HIS | 93 | 43.484 | 9.819 | −0.855 | 1.00 | 46.58 |
| ATOM | 416 | CG | HIS | 93 | 43.815 | 9.164 | 0.451 | 1.00 | 51.68 |
| ATOM | 417 | ND1 | HIS | 93 | 43.532 | 9.748 | 1.675 | 1.00 | 56.34 |
| ATOM | 418 | CE1 | HIS | 93 | 43.921 | 8.940 | 2.647 | 1.00 | 57.05 |
| ATOM | 419 | NE2 | HIS | 93 | 44.443 | 7.851 | 2.100 | 1.00 | 57.52 |
| ATOM | 420 | CD2 | HIS | 93 | 44.392 | 7.968 | 0.728 | 1.00 | 54.61 |
| ATOM | 421 | C | HIS | 93 | 41.239 | 8.752 | −1.260 | 1.00 | 44.81 |

TABLE 7-continued

| | | | | | | | | | |
|---|---|---|---|---|---|---|---|---|---|
| ATOM | 422 | O | HIS | 93 | 40.441 | 9.680 | −1.290 | 1.00 | 46.13 |
| ATOM | 423 | N | GLY | 94 | 40.912 | 7.553 | −0.794 | 1.00 | 44.84 |
| ATOM | 424 | CA | GLY | 94 | 39.601 | 7.242 | −0.173 | 1.00 | 44.49 |
| ATOM | 425 | C | GLY | 94 | 39.595 | 7.374 | 1.371 | 1.00 | 45.32 |
| ATOM | 426 | O | GLY | 94 | 40.376 | 6.704 | 2.066 | 1.00 | 45.94 |
| ATOM | 427 | N | ASP | 95 | 38.769 | 8.268 | 1.909 | 1.00 | 44.13 |
| ATOM | 428 | CA | ASP | 95 | 38.517 | 8.356 | 3.353 | 1.00 | 44.02 |
| ATOM | 429 | CB | ASP | 95 | 39.668 | 9.032 | 4.144 | 1.00 | 45.45 |
| ATOM | 430 | CG | ASP | 95 | 40.731 | 8.014 | 4.704 | 1.00 | 48.99 |
| ATOM | 431 | OD1 | ASP | 95 | 41.927 | 8.383 | 4.810 | 1.00 | 54.04 |
| ATOM | 432 | OD2 | ASP | 95 | 40.388 | 6.855 | 5.047 | 1.00 | 53.84 |
| ATOM | 433 | C | ASP | 95 | 37.187 | 9.085 | 3.581 | 1.00 | 42.25 |
| ATOM | 434 | O | ASP | 95 | 36.732 | 9.828 | 2.717 | 1.00 | 40.15 |
| ATOM | 435 | N | PHE | 96 | 36.578 | 8.830 | 4.739 | 1.00 | 41.12 |
| ATOM | 436 | CA | PHE | 96 | 35.355 | 9.496 | 5.166 | 1.00 | 40.60 |
| ATOM | 437 | CB | PHE | 96 | 34.758 | 8.789 | 6.374 | 1.00 | 41.69 |
| ATOM | 438 | CG | PHE | 96 | 34.073 | 7.491 | 6.022 | 1.00 | 44.28 |
| ATOM | 439 | CD1 | PHE | 96 | 34.090 | 6.411 | 6.901 | 1.00 | 47.19 |
| ATOM | 440 | CE1 | PHE | 96 | 33.442 | 5.202 | 6.586 | 1.00 | 47.63 |
| ATOM | 441 | CZ | PHE | 96 | 32.773 | 5.070 | 5.367 | 1.00 | 46.71 |
| ATOM | 442 | CE2 | PHE | 96 | 32.768 | 6.147 | 4.456 | 1.00 | 48.63 |
| ATOM | 443 | CD2 | PHE | 96 | 33.424 | 7.345 | 4.788 | 1.00 | 46.24 |
| ATOM | 444 | C | PHE | 96 | 35.627 | 10.957 | 5.443 | 1.00 | 39.42 |
| ATOM | 445 | O | PHE | 96 | 36.775 | 11.305 | 5.709 | 1.00 | 38.89 |
| ATOM | 446 | N | HIS | 97 | 34.603 | 11.808 | 5.301 | 1.00 | 38.19 |
| ATOM | 447 | CA | HIS | 97 | 34.783 | 13.258 | 5.393 | 1.00 | 38.39 |
| ATOM | 448 | CB | HIS | 97 | 33.490 | 14.011 | 5.055 | 1.00 | 38.74 |
| ATOM | 449 | CG | HIS | 97 | 32.903 | 13.654 | 3.723 | 1.00 | 37.54 |
| ATOM | 450 | ND1 | HIS | 97 | 33.655 | 13.135 | 2.690 | 1.00 | 34.50 |
| ATOM | 451 | CE1 | HIS | 97 | 32.863 | 12.892 | 1.662 | 1.00 | 37.08 |
| ATOM | 452 | NE2 | HIS | 97 | 31.629 | 13.260 | 1.977 | 1.00 | 36.65 |
| ATOM | 453 | CD2 | HIS | 97 | 31.631 | 13.754 | 3.257 | 1.00 | 38.23 |
| ATOM | 454 | C | HIS | 97 | 35.278 | 13.664 | 6.782 | 1.00 | 38.73 |
| ATOM | 455 | O | HIS | 97 | 36.257 | 14.402 | 6.914 | 1.00 | 39.39 |
| ATOM | 456 | N | THR | 124 | 29.742 | 18.680 | −0.484 | 1.00 | 28.92 |
| ATOM | 457 | CA | THR | 124 | 28.525 | 18.728 | −1.322 | 1.00 | 28.20 |
| ATOM | 458 | CB | THR | 124 | 28.868 | 18.901 | −2.857 | 1.00 | 29.27 |
| ATOM | 459 | OG1 | THR | 124 | 29.590 | 17.756 | −3.280 | 1.00 | 27.12 |
| ATOM | 460 | CG2 | THR | 124 | 29.733 | 20.162 | −3.133 | 1.00 | 23.99 |
| ATOM | 461 | C | THR | 124 | 27.655 | 17.499 | −1.006 | 1.00 | 27.97 |
| ATOM | 462 | O | THR | 124 | 28.154 | 16.506 | −0.510 | 1.00 | 28.78 |
| ATOM | 463 | N | PRO | 125 | 26.334 | 17.603 | −1.199 | 1.00 | 28.21 |
| ATOM | 464 | CA | PRO | 125 | 25.392 | 16.553 | −0.813 | 1.00 | 29.53 |
| ATOM | 465 | CB | PRO | 125 | 24.037 | 17.195 | −1.038 | 1.00 | 28.34 |
| ATOM | 466 | CG | PRO | 125 | 24.308 | 18.362 | −2.001 | 1.00 | 26.96 |
| ATOM | 467 | CD | PRO | 125 | 25.654 | 18.816 | −1.698 | 1.00 | 27.65 |
| ATOM | 468 | C | PRO | 125 | 25.538 | 15.237 | −1.578 | 1.00 | 32.62 |
| ATOM | 469 | O | PRO | 125 | 26.125 | 15.227 | −2.637 | 1.00 | 34.11 |
| ATOM | 470 | N | ARG | 126 | 25.088 | 14.126 | −0.992 | 1.00 | 33.81 |
| ATOM | 471 | CA | ARG | 126 | 25.058 | 12.824 | −1.639 | 1.00 | 35.48 |
| ATOM | 472 | CB | ARG | 126 | 26.252 | 11.960 | −1.257 | 1.00 | 35.66 |
| ATOM | 473 | CG | ARG | 126 | 27.590 | 12.429 | −1.814 | 1.00 | 40.74 |
| ATOM | 474 | CD | ARG | 126 | 27.662 | 12.136 | −3.333 | 1.00 | 46.49 |
| ATOM | 475 | NE | ARG | 126 | 28.789 | 12.795 | −3.992 | 1.00 | 49.71 |
| ATOM | 476 | CZ | ARG | 126 | 28.633 | 13.691 | −4.962 | 1.00 | 50.00 |
| ATOM | 477 | NH1 | ARG | 126 | 27.420 | 14.023 | −5.373 | 1.00 | 50.10 |
| ATOM | 478 | NH2 | ARG | 126 | 29.684 | 14.249 | −5.514 | 1.00 | 52.24 |
| ATOM | 479 | C | ARG | 126 | 23.839 | 12.224 | −1.019 | 1.00 | 35.74 |
| ATOM | 480 | O | ARG | 126 | 23.717 | 12.209 | 0.215 | 1.00 | 35.29 |
| ATOM | 481 | N | GLY | 127 | 22.906 | 11.784 | −1.844 | 1.00 | 35.60 |
| ATOM | 482 | CA | GLY | 127 | 21.651 | 11.281 | −1.324 | 1.00 | 36.66 |
| ATOM | 483 | C | GLY | 127 | 20.860 | 12.393 | −0.636 | 1.00 | 37.25 |
| ATOM | 484 | O | GLY | 127 | 19.951 | 12.126 | 0.145 | 1.00 | 38.77 |
| ATOM | 485 | N | GLY | 128 | 21.194 | 13.639 | −0.945 | 1.00 | 36.25 |
| ATOM | 486 | CA | GLY | 128 | 20.437 | 14.786 | −0.459 | 1.00 | 35.01 |
| ATOM | 487 | C | GLY | 128 | 20.889 | 15.347 | 0.894 | 1.00 | 33.50 |
| ATOM | 488 | O | GLY | 128 | 20.235 | 16.234 | 1.416 | 1.00 | 35.01 |
| ATOM | 489 | N | ILE | 129 | 21.996 | 14.842 | 1.418 | 1.00 | 31.65 |
| ATOM | 490 | CA | ILE | 129 | 22.569 | 15.210 | 2.690 | 1.00 | 30.62 |
| ATOM | 491 | CB | ILE | 129 | 22.510 | 14.030 | 3.690 | 1.00 | 31.63 |
| ATOM | 492 | CG1 | ILE | 129 | 21.053 | 13.686 | 3.976 | 1.00 | 31.67 |
| ATOM | 493 | CD1 | ILE | 129 | 20.910 | 12.395 | 4.529 | 1.00 | 35.41 |
| ATOM | 494 | CG2 | ILE | 129 | 23.198 | 14.424 | 5.039 | 1.00 | 30.84 |
| ATOM | 495 | C | ILE | 129 | 24.007 | 15.575 | 2.539 | 1.00 | 29.88 |
| ATOM | 496 | O | ILE | 129 | 24.746 | 14.853 | 1.897 | 1.00 | 29.04 |
| ATOM | 497 | N | SER | 130 | 24.420 | 16.696 | 3.150 | 1.00 | 29.92 |
| ATOM | 498 | CA | SER | 130 | 25.813 | 17.108 | 3.127 | 1.00 | 29.06 |
| ATOM | 499 | CB | SER | 130 | 25.942 | 18.531 | 2.587 | 1.00 | 27.81 |
| ATOM | 500 | OG | SER | 130 | 24.950 | 19.325 | 3.159 | 1.00 | 25.44 |
| ATOM | 501 | C | SER | 130 | 26.339 | 16.981 | 4.545 | 1.00 | 29.57 |

TABLE 7-continued

| | | | | | | | | | |
|---|---|---|---|---|---|---|---|---|---|
| ATOM | 502 | O | SER | 130 | 25.549 | 17.105 | 5.486 | 1.00 | 31.56 |
| ATOM | 503 | N | ILE | 131 | 27.643 | 16.727 | 4.677 | 1.00 | 29.08 |
| ATOM | 504 | CA | ILE | 131 | 28.347 | 16.477 | 5.934 | 1.00 | 28.86 |
| ATOM | 505 | CB | ILE | 131 | 29.062 | 15.128 | 5.881 | 1.00 | 28.88 |
| ATOM | 506 | CG1 | ILE | 131 | 27.996 | 14.028 | 5.706 | 1.00 | 30.52 |
| ATOM | 507 | CD1 | ILE | 131 | 28.518 | 12.706 | 5.421 | 1.00 | 32.39 |
| ATOM | 508 | CG2 | ILE | 131 | 29.866 | 14.825 | 7.155 | 1.00 | 25.09 |
| ATOM | 509 | C | ILE | 131 | 29.336 | 17.622 | 6.071 | 1.00 | 29.72 |
| ATOM | 510 | O | ILE | 131 | 30.064 | 17.899 | 5.117 | 1.00 | 30.15 |
| ATOM | 511 | N | ASN | 164 | 20.552 | 22.746 | −0.945 | 1.00 | 35.87 |
| ATOM | 512 | CA | ASN | 164 | 21.113 | 21.845 | −1.951 | 1.00 | 37.23 |
| ATOM | 513 | CB | ASN | 164 | 20.407 | 20.477 | −1.955 | 1.00 | 36.18 |
| ATOM | 514 | CG | ASN | 164 | 20.831 | 19.627 | −0.771 | 1.00 | 38.54 |
| ATOM | 515 | OD1 | ASN | 164 | 21.710 | 20.043 | 0.018 | 1.00 | 35.02 |
| ATOM | 516 | ND2 | ASN | 164 | 20.212 | 18.444 | −0.619 | 1.00 | 36.60 |
| ATOM | 517 | C | ASN | 164 | 21.225 | 22.470 | −3.341 | 1.00 | 37.19 |
| ATOM | 518 | O | ASN | 164 | 21.469 | 21.790 | −4.323 | 1.00 | 37.79 |
| ATOM | 519 | O6 | GDQ | 201 | 51.673 | 34.977 | 1.685 | 1.00 | 47.86 |
| ATOM | 520 | C6 | GDQ | 201 | 51.979 | 33.654 | 1.751 | 1.00 | 49.13 |
| ATOM | 521 | N1 | GDQ | 201 | 51.693 | 32.967 | 2.883 | 1.00 | 48.48 |
| ATOM | 522 | C5 | GDQ | 201 | 52.577 | 32.974 | 0.668 | 1.00 | 50.29 |
| ATOM | 523 | C7 | GDQ | 201 | 53.031 | 33.252 | −0.628 | 1.00 | 49.19 |
| ATOM | 524 | C77 | GDQ | 201 | 52.946 | 34.470 | −1.174 | 1.00 | 49.79 |
| ATOM | 525 | N77 | GDQ | 201 | 52.924 | 35.622 | −1.582 | 1.00 | 52.99 |
| ATOM | 526 | C8 | GDQ | 201 | 53.562 | 32.149 | −1.273 | 1.00 | 48.54 |
| ATOM | 527 | N9 | GDQ | 201 | 53.432 | 31.139 | −0.353 | 1.00 | 49.38 |
| ATOM | 528 | C4 | GDQ | 201 | 52.867 | 31.624 | 0.805 | 1.00 | 49.87 |
| ATOM | 529 | N3 | GDQ | 201 | 52.561 | 30.957 | 1.960 | 1.00 | 49.70 |
| ATOM | 530 | C2 | GDQ | 201 | 51.970 | 31.654 | 2.984 | 1.00 | 48.62 |
| ATOM | 531 | N2 | GDQ | 201 | 51.652 | 31.039 | 4.142 | 1.00 | 49.10 |
| ATOM | 532 | O | HOH | 29 | 17.895 | 15.590 | 3.291 | 1.00 | 31.47 |
| ATOM | 533 | O | HOH | 50 | 11.133 | 11.719 | 4.314 | 1.00 | 34.62 |
| ATOM | 534 | O | HOH | 66 | 11.339 | 11.105 | 1.461 | 1.00 | 37.21 |
| ATOM | 535 | O | HOH | 81 | 42.003 | 17.079 | −3.720 | 1.00 | 28.53 |
| ATOM | 536 | O | HOH | 85 | 30.743 | 15.579 | −2.201 | 1.00 | 40.55 |
| ATOM | 537 | O | HOH | 108 | 11.807 | 19.103 | 2.222 | 1.00 | 36.21 |
| ATOM | 538 | O | HOH | 114 | 22.262 | 21.773 | −6.977 | 1.00 | 52.76 |
| ATOM | 539 | O | HOH | 139 | 28.479 | 15.194 | 1.945 | 1.00 | 28.22 |
| ATOM | 540 | O | HOH | 177 | 16.576 | 11.182 | 3.619 | 1.00 | 41.52 |
| ATOM | 541 | O | HOH | 179 | 36.242 | 13.883 | −1.120 | 1.00 | 53.82 |
| ATOM | 542 | O | HOH | 183 | 26.577 | 12.855 | 2.470 | 1.00 | 36.87 |
| ATOM | 543 | O | HOH | 201 | 22.092 | 3.726 | −3.164 | 1.00 | 65.86 |
| ATOM | 544 | O | HOH | 208 | 36.855 | 11.249 | 0.943 | 1.00 | 48.14 |
| ATOM | 545 | O | HOH | 215 | 22.133 | 14.628 | −3.438 | 1.00 | 33.08 |
| ATOM | 546 | O | HOH | 255 | 42.193 | 7.641 | −7.705 | 1.00 | 54.17 |
| ATOM | 547 | N | ASN | 21 | 33.459 | −0.108 | −10.354 | 1.00 | 76.18 |
| ATOM | 548 | CA | ASN | 21 | 34.628 | 0.742 | −10.764 | 1.00 | 76.06 |
| ATOM | 549 | CB | ASN | 21 | 35.644 | −0.091 | −11.570 | 1.00 | 76.90 |
| ATOM | 550 | CG | ASN | 21 | 36.765 | −0.698 | −10.687 | 1.00 | 78.87 |
| ATOM | 551 | OD1 | ASN | 21 | 37.351 | −0.010 | −9.827 | 1.00 | 79.27 |
| ATOM | 552 | ND2 | ASN | 21 | 37.071 | −1.987 | −10.916 | 1.00 | 78.83 |
| ATOM | 553 | C | ASN | 21 | 34.248 | 2.030 | −11.528 | 1.00 | 75.05 |
| ATOM | 554 | O | ASN | 21 | 33.285 | 2.031 | −12.306 | 1.00 | 75.14 |
| ATOM | 555 | N | TYR | 22 | 35.008 | 3.111 | −11.284 | 1.00 | 73.30 |
| ATOM | 556 | CA | TYR | 22 | 34.816 | 4.428 | −11.929 | 1.00 | 71.17 |
| ATOM | 557 | CB | TYR | 22 | 34.731 | 5.558 | −10.887 | 1.00 | 71.82 |
| ATOM | 558 | CG | TYR | 22 | 33.437 | 5.681 | −10.127 | 1.00 | 71.49 |
| ATOM | 559 | CD1 | TYR | 22 | 33.225 | 4.953 | −8.957 | 1.00 | 72.23 |
| ATOM | 560 | CE1 | TYR | 22 | 32.024 | 5.059 | −8.241 | 1.00 | 72.96 |
| ATOM | 561 | CZ | TYR | 22 | 31.035 | 5.920 | −8.690 | 1.00 | 72.71 |
| ATOM | 562 | OH | TYR | 22 | 29.857 | 6.036 | −7.988 | 1.00 | 72.62 |
| ATOM | 563 | CE2 | TYR | 22 | 31.235 | 6.668 | −9.848 | 1.00 | 73.45 |
| ATOM | 564 | CD2 | TYR | 22 | 32.439 | 6.544 | −10.557 | 1.00 | 72.44 |
| ATOM | 565 | C | TYR | 22 | 35.995 | 4.758 | −12.846 | 1.00 | 69.29 |
| ATOM | 566 | O | TYR | 22 | 37.162 | 4.754 | −12.433 | 1.00 | 69.25 |
| ATOM | 567 | N | LEU | 23 | 35.688 | 5.069 | −14.090 | 1.00 | 66.64 |
| ATOM | 568 | CA | LEU | 23 | 36.707 | 5.467 | −15.021 | 1.00 | 63.93 |
| ATOM | 569 | CB | LEU | 23 | 36.216 | 5.239 | −16.457 | 1.00 | 64.90 |
| ATOM | 570 | CG | LEU | 23 | 35.492 | 3.898 | −16.673 | 1.00 | 66.26 |
| ATOM | 571 | CD1 | LEU | 23 | 34.632 | 3.874 | −17.954 | 1.00 | 65.53 |
| ATOM | 572 | CD2 | LEU | 23 | 36.484 | 2.689 | −16.584 | 1.00 | 67.93 |
| ATOM | 573 | C | LEU | 23 | 36.968 | 6.935 | −14.768 | 1.00 | 61.09 |
| ATOM | 574 | O | LEU | 23 | 36.042 | 7.726 | −14.720 | 1.00 | 59.70 |
| ATOM | 575 | N | PHE | 24 | 38.232 | 7.279 | −14.568 | 1.00 | 58.58 |
| ATOM | 576 | CA | PHE | 24 | 38.636 | 8.672 | −14.527 | 1.00 | 56.64 |
| ATOM | 577 | CB | PHE | 24 | 39.388 | 9.010 | −13.236 | 1.00 | 56.03 |
| ATOM | 578 | CG | PHE | 24 | 38.548 | 8.836 | −11.987 | 1.00 | 56.10 |
| ATOM | 579 | CD1 | PHE | 24 | 39.100 | 8.270 | −10.828 | 1.00 | 55.47 |
| ATOM | 580 | CE1 | PHE | 24 | 38.326 | 8.092 | −9.677 | 1.00 | 54.37 |
| ATOM | 581 | CZ | PHE | 24 | 36.979 | 8.479 | −9.674 | 1.00 | 54.86 |

TABLE 7-continued

| | | | | | | | | |
|---|---|---|---|---|---|---|---|---|
| ATOM | 582 | CE2 | PHE | 24 | 36.414 | 9.043 | −10.830 | 1.00 | 55.69 |
| ATOM | 583 | CD2 | PHE | 24 | 37.200 | 9.210 | −11.976 | 1.00 | 55.01 |
| ATOM | 584 | C | PHE | 24 | 39.400 | 9.092 | −15.787 | 1.00 | 55.70 |
| ATOM | 585 | O | PHE | 24 | 39.868 | 10.247 | −15.879 | 1.00 | 55.37 |
| ATOM | 586 | N | GLU | 25 | 39.496 | 8.163 | −16.755 | 1.00 | 53.85 |
| ATOM | 587 | CA | GLU | 25 | 39.987 | 8.471 | −18.115 | 1.00 | 51.90 |
| ATOM | 588 | CB | GLU | 25 | 40.906 | 7.369 | −18.661 | 1.00 | 53.16 |
| ATOM | 589 | CG | GLU | 25 | 41.737 | 6.603 | −17.647 | 1.00 | 56.60 |
| ATOM | 590 | CD | GLU | 25 | 42.727 | 7.489 | −16.928 | 1.00 | 60.77 |
| ATOM | 591 | OE1 | GLU | 25 | 43.361 | 8.331 | −17.618 | 1.00 | 60.96 |
| ATOM | 592 | OE2 | GLU | 25 | 42.864 | 7.344 | −15.672 | 1.00 | 63.56 |
| ATOM | 593 | C | GLU | 25 | 38.816 | 8.672 | −19.084 | 1.00 | 49.01 |
| ATOM | 594 | O | GLU | 25 | 37.803 | 7.962 | −19.015 | 1.00 | 48.66 |
| ATOM | 595 | N | TYR | 26 | 38.982 | 9.605 | −20.009 | 1.00 | 45.71 |
| ATOM | 596 | CA | TYR | 26 | 37.901 | 10.049 | −20.890 | 1.00 | 43.62 |
| ATOM | 597 | CB | TYR | 26 | 38.475 | 10.999 | −21.936 | 1.00 | 43.09 |
| ATOM | 598 | CG | TYR | 26 | 37.537 | 11.400 | −23.073 | 1.00 | 41.77 |
| ATOM | 599 | CD1 | TYR | 26 | 37.817 | 10.995 | −24.391 | 1.00 | 38.81 |
| ATOM | 600 | CE1 | TYR | 26 | 37.008 | 11.374 | −25.448 | 1.00 | 39.58 |
| ATOM | 601 | CZ | TYR | 26 | 35.920 | 12.194 | −25.214 | 1.00 | 42.46 |
| ATOM | 602 | OH | TYR | 26 | 35.136 | 12.538 | −26.287 | 1.00 | 42.52 |
| ATOM | 603 | CE2 | TYR | 26 | 35.582 | 12.605 | −23.905 | 1.00 | 40.19 |
| ATOM | 604 | CD2 | TYR | 26 | 36.412 | 12.205 | −22.840 | 1.00 | 37.62 |
| ATOM | 605 | C | TYR | 26 | 37.085 | 8.938 | −21.557 | 1.00 | 42.34 |
| ATOM | 606 | O | TYR | 26 | 37.618 | 8.179 | −22.345 | 1.00 | 41.66 |
| ATOM | 607 | N | ALA | 27 | 35.790 | 8.899 | −21.253 | 1.00 | 41.10 |
| ATOM | 608 | CA | ALA | 27 | 34.889 | 7.795 | −21.583 | 1.00 | 40.13 |
| ATOM | 609 | CB | ALA | 27 | 34.607 | 6.945 | −20.351 | 1.00 | 39.28 |
| ATOM | 610 | C | ALA | 27 | 33.572 | 8.280 | −22.187 | 1.00 | 40.48 |
| ATOM | 611 | O | ALA | 27 | 32.531 | 8.246 | −21.528 | 1.00 | 39.77 |
| ATOM | 612 | N | LYS | 46 | 18.014 | 21.661 | −18.442 | 1.00 | 28.21 |
| ATOM | 613 | CA | LYS | 46 | 19.344 | 22.154 | −17.967 | 1.00 | 27.33 |
| ATOM | 614 | CB | LYS | 46 | 19.250 | 23.566 | −17.363 | 1.00 | 26.71 |
| ATOM | 615 | CG | LYS | 46 | 20.609 | 24.149 | −16.907 | 1.00 | 28.68 |
| ATOM | 616 | CD | LYS | 46 | 20.469 | 25.061 | −15.738 | 1.00 | 29.59 |
| ATOM | 617 | CE | LYS | 46 | 20.140 | 26.434 | −16.132 | 1.00 | 35.72 |
| ATOM | 618 | NZ | LYS | 46 | 19.260 | 27.137 | −15.017 | 1.00 | 33.53 |
| ATOM | 619 | C | LYS | 46 | 19.961 | 21.212 | −16.961 | 1.00 | 26.64 |
| ATOM | 620 | O | LYS | 46 | 19.311 | 20.832 | −16.036 | 1.00 | 26.42 |
| ATOM | 621 | N | PHE | 47 | 21.231 | 20.872 | −17.125 | 1.00 | 27.04 |
| ATOM | 622 | CA | PHE | 47 | 22.002 | 20.219 | −16.080 | 1.00 | 26.96 |
| ATOM | 623 | CB | PHE | 47 | 22.803 | 19.080 | −16.631 | 1.00 | 27.29 |
| ATOM | 624 | CG | PHE | 47 | 21.960 | 18.082 | −17.253 | 1.00 | 32.14 |
| ATOM | 625 | CD1 | PHE | 47 | 21.503 | 18.259 | −18.556 | 1.00 | 32.34 |
| ATOM | 626 | CE1 | PHE | 47 | 20.628 | 17.318 | −19.112 | 1.00 | 34.46 |
| ATOM | 627 | CZ | PHE | 47 | 20.233 | 16.210 | −18.386 | 1.00 | 33.35 |
| ATOM | 628 | CE2 | PHE | 47 | 20.686 | 16.021 | −17.103 | 1.00 | 35.35 |
| ATOM | 629 | CD2 | PHE | 47 | 21.539 | 16.969 | −16.530 | 1.00 | 35.90 |
| ATOM | 630 | C | PHE | 47 | 22.932 | 21.221 | −15.433 | 1.00 | 26.50 |
| ATOM | 631 | O | PHE | 47 | 23.702 | 21.905 | −16.125 | 1.00 | 25.24 |
| ATOM | 632 | N | ASN | 48 | 22.872 | 21.277 | −14.098 | 1.00 | 26.57 |
| ATOM | 633 | CA | ASN | 48 | 23.818 | 22.090 | −13.318 | 1.00 | 26.60 |
| ATOM | 634 | CB | ASN | 48 | 23.105 | 22.805 | −12.153 | 1.00 | 26.14 |
| ATOM | 635 | CG | ASN | 48 | 21.968 | 23.623 | −12.606 | 1.00 | 23.57 |
| ATOM | 636 | OD1 | ASN | 48 | 22.144 | 24.527 | −13.400 | 1.00 | 28.74 |
| ATOM | 637 | ND2 | ASN | 48 | 20.777 | 23.319 | −12.137 | 1.00 | 24.59 |
| ATOM | 638 | C | ASN | 48 | 24.891 | 21.177 | −12.824 | 1.00 | 26.71 |
| ATOM | 639 | O | ASN | 48 | 24.594 | 20.232 | −12.114 | 1.00 | 26.51 |
| ATOM | 640 | N | CYS | 49 | 26.151 | 21.456 | −13.174 | 1.00 | 27.64 |
| ATOM | 641 | CA | CYS | 49 | 27.228 | 20.505 | −12.886 | 1.00 | 28.17 |
| ATOM | 642 | CB | CYS | 49 | 27.752 | 19.885 | −14.190 | 1.00 | 28.79 |
| ATOM | 643 | SG | CYS | 49 | 26.467 | 19.250 | −15.288 | 1.00 | 32.41 |
| ATOM | 644 | C | CYS | 49 | 28.373 | 21.199 | −12.156 | 1.00 | 28.06 |
| ATOM | 645 | O | CYS | 49 | 29.329 | 21.563 | −12.783 | 1.00 | 26.43 |
| ATOM | 646 | N | PRO | 50 | 28.244 | 21.414 | −10.817 | 1.00 | 28.99 |
| ATOM | 647 | CA | PRO | 50 | 29.215 | 22.198 | −10.031 | 1.00 | 29.58 |
| ATOM | 648 | CB | PRO | 50 | 28.423 | 22.598 | −8.756 | 1.00 | 29.17 |
| ATOM | 649 | CG | PRO | 50 | 27.143 | 21.920 | −8.860 | 1.00 | 29.81 |
| ATOM | 650 | CD | PRO | 50 | 27.095 | 20.985 | −9.993 | 1.00 | 28.43 |
| ATOM | 651 | C | PRO | 50 | 30.454 | 21.446 | −9.626 | 1.00 | 29.99 |
| ATOM | 652 | O | PRO | 50 | 31.373 | 22.050 | −9.096 | 1.00 | 31.25 |
| ATOM | 653 | N | GLU | 51 | 30.490 | 20.159 | −9.888 | 1.00 | 30.28 |
| ATOM | 654 | CA | GLU | 51 | 31.565 | 19.318 | −9.431 | 1.00 | 31.01 |
| ATOM | 655 | CB | GLU | 51 | 30.978 | 18.110 | −8.744 | 1.00 | 31.20 |
| ATOM | 656 | CG | GLU | 51 | 30.228 | 18.489 | −7.474 | 1.00 | 31.72 |
| ATOM | 657 | CD | GLU | 51 | 29.527 | 17.305 | −6.826 | 1.00 | 39.70 |
| ATOM | 658 | OE1 | GLU | 51 | 29.698 | 16.149 | −7.339 | 1.00 | 41.03 |
| ATOM | 659 | OE2 | GLU | 51 | 28.792 | 17.537 | −5.815 | 1.00 | 39.79 |
| ATOM | 660 | C | GLU | 51 | 32.556 | 18.911 | −10.496 | 1.00 | 30.89 |
| ATOM | 661 | O | GLU | 51 | 33.223 | 17.903 | −10.383 | 1.00 | 32.20 |

TABLE 7-continued

| | | | | | | | | | |
|---|---|---|---|---|---|---|---|---|---|
| ATOM | 662 | N | PHE | 52 | 32.694 | 19.712 | −11.534 | 1.00 | 30.63 |
| ATOM | 663 | CA | PHE | 52 | 33.541 | 19.278 | −12.624 | 1.00 | 29.27 |
| ATOM | 664 | CB | PHE | 52 | 33.080 | 19.913 | −13.946 | 1.00 | 29.89 |
| ATOM | 665 | CG | PHE | 52 | 33.995 | 19.591 | −15.114 | 1.00 | 28.40 |
| ATOM | 666 | CD1 | PHE | 52 | 33.771 | 18.470 | −15.907 | 1.00 | 28.58 |
| ATOM | 667 | CE1 | PHE | 52 | 34.613 | 18.160 | −16.983 | 1.00 | 24.69 |
| ATOM | 668 | CZ | PHE | 52 | 35.662 | 18.968 | −17.259 | 1.00 | 27.97 |
| ATOM | 669 | CE2 | PHE | 52 | 35.921 | 20.096 | −16.447 | 1.00 | 29.23 |
| ATOM | 670 | CD2 | PHE | 52 | 35.079 | 20.397 | −15.399 | 1.00 | 26.27 |
| ATOM | 671 | C | PHE | 52 | 34.989 | 19.634 | −12.337 | 1.00 | 29.10 |
| ATOM | 672 | O | PHE | 52 | 35.276 | 20.740 | −11.880 | 1.00 | 28.69 |
| ATOM | 673 | N | THR | 53 | 35.879 | 18.664 | −12.600 | 1.00 | 29.45 |
| ATOM | 674 | CA | THR | 53 | 37.326 | 18.832 | −12.507 | 1.00 | 29.09 |
| ATOM | 675 | CB | THR | 53 | 37.843 | 18.455 | −11.101 | 1.00 | 28.45 |
| ATOM | 676 | OG1 | THR | 53 | 39.268 | 18.659 | −11.054 | 1.00 | 27.24 |
| ATOM | 677 | CG2 | THR | 53 | 37.484 | 17.025 | −10.776 | 1.00 | 25.51 |
| ATOM | 678 | C | THR | 53 | 38.062 | 18.013 | −13.596 | 1.00 | 30.39 |
| ATOM | 679 | O | THR | 53 | 37.605 | 16.954 | −13.998 | 1.00 | 29.67 |
| ATOM | 680 | N | SER | 54 | 39.223 | 18.520 | −14.021 | 1.00 | 31.83 |
| ATOM | 681 | CA | SER | 54 | 40.050 | 17.925 | −15.068 | 1.00 | 33.32 |
| ATOM | 682 | CB | SER | 54 | 39.542 | 18.318 | −16.473 | 1.00 | 33.47 |
| ATOM | 683 | OG | SER | 54 | 39.682 | 19.717 | −16.684 | 1.00 | 33.23 |
| ATOM | 684 | C | SER | 54 | 41.483 | 18.427 | −14.883 | 1.00 | 34.99 |
| ATOM | 685 | O | SER | 54 | 41.781 | 19.080 | −13.905 | 1.00 | 34.15 |
| ATOM | 686 | N | TYR | 68 | 27.162 | 24.434 | −17.047 | 1.00 | 25.62 |
| ATOM | 687 | CA | TYR | 68 | 25.694 | 24.475 | −17.304 | 1.00 | 25.42 |
| ATOM | 688 | CB | TYR | 68 | 25.164 | 25.898 | −17.175 | 1.00 | 24.80 |
| ATOM | 689 | CG | TYR | 68 | 25.431 | 26.479 | −15.782 | 1.00 | 28.39 |
| ATOM | 690 | CD1 | TYR | 68 | 26.548 | 27.288 | −15.557 | 1.00 | 23.93 |
| ATOM | 691 | CE1 | TYR | 68 | 26.834 | 27.780 | −14.313 | 1.00 | 29.14 |
| ATOM | 692 | CZ | TYR | 68 | 25.976 | 27.486 | −13.225 | 1.00 | 31.13 |
| ATOM | 693 | OH | TYR | 68 | 26.269 | 28.029 | −11.975 | 1.00 | 29.59 |
| ATOM | 694 | CE2 | TYR | 68 | 24.868 | 26.677 | −13.412 | 1.00 | 30.72 |
| ATOM | 695 | CD2 | TYR | 68 | 24.584 | 26.187 | −14.695 | 1.00 | 25.51 |
| ATOM | 696 | C | TYR | 68 | 25.388 | 23.932 | −18.704 | 1.00 | 25.82 |
| ATOM | 697 | O | TYR | 68 | 25.843 | 24.501 | −19.684 | 1.00 | 26.19 |
| ATOM | 698 | N | GLU | 79 | 20.682 | 10.441 | −20.084 | 1.00 | 35.31 |
| ATOM | 699 | CA | GLU | 79 | 20.374 | 9.934 | −18.788 | 1.00 | 35.07 |
| ATOM | 700 | CB | GLU | 79 | 20.443 | 8.403 | −18.834 | 1.00 | 35.69 |
| ATOM | 701 | CG | GLU | 79 | 19.819 | 7.740 | −17.587 | 1.00 | 40.72 |
| ATOM | 702 | CD | GLU | 79 | 20.763 | 7.697 | −16.403 | 1.00 | 45.36 |
| ATOM | 703 | OE1 | GLU | 79 | 21.898 | 7.174 | −16.573 | 1.00 | 47.59 |
| ATOM | 704 | OE2 | GLU | 79 | 20.366 | 8.175 | −15.301 | 1.00 | 47.64 |
| ATOM | 705 | C | GLU | 79 | 21.382 | 10.549 | −17.819 | 1.00 | 33.69 |
| ATOM | 706 | O | GLU | 79 | 22.576 | 10.492 | −18.054 | 1.00 | 31.63 |
| ATOM | 707 | N | SER | 80 | 20.876 | 11.160 | −16.743 | 1.00 | 33.31 |
| ATOM | 708 | CA | SER | 80 | 21.686 | 11.797 | −15.691 | 1.00 | 33.28 |
| ATOM | 709 | CB | SER | 80 | 20.825 | 12.048 | −14.496 | 1.00 | 33.95 |
| ATOM | 710 | OG | SER | 80 | 19.724 | 12.802 | −14.928 | 1.00 | 40.59 |
| ATOM | 711 | C | SER | 80 | 22.879 | 11.082 | −15.138 | 1.00 | 33.46 |
| ATOM | 712 | O | SER | 80 | 23.969 | 11.685 | −15.044 | 1.00 | 33.68 |
| ATOM | 713 | N | LYS | 81 | 22.674 | 9.833 | −14.689 | 1.00 | 33.65 |
| ATOM | 714 | CA | LYS | 81 | 23.746 | 9.101 | −14.082 | 1.00 | 34.76 |
| ATOM | 715 | CB | LYS | 81 | 23.286 | 7.762 | −13.541 | 1.00 | 35.65 |
| ATOM | 716 | CG | LYS | 81 | 24.459 | 6.850 | −12.985 | 1.00 | 39.18 |
| ATOM | 717 | CD | LYS | 81 | 23.934 | 5.491 | −12.479 | 1.00 | 39.66 |
| ATOM | 718 | CE | LYS | 81 | 22.649 | 5.673 | −11.558 | 1.00 | 48.39 |
| ATOM | 719 | NZ | LYS | 81 | 21.950 | 4.385 | −11.039 | 1.00 | 47.55 |
| ATOM | 720 | C | LYS | 81 | 24.832 | 8.904 | −15.108 | 1.00 | 33.64 |
| ATOM | 721 | O | LYS | 81 | 26.018 | 8.969 | −14.759 | 1.00 | 33.95 |
| ATOM | 722 | N | SER | 82 | 24.439 | 8.685 | −16.375 | 1.00 | 32.20 |
| ATOM | 723 | CA | SER | 82 | 25.451 | 8.482 | −17.407 | 1.00 | 30.55 |
| ATOM | 724 | CB | SER | 82 | 24.873 | 7.875 | −18.701 | 1.00 | 30.70 |
| ATOM | 725 | OG | SER | 82 | 24.075 | 8.782 | −19.453 | 1.00 | 29.50 |
| ATOM | 726 | C | SER | 82 | 26.225 | 9.779 | −17.669 | 1.00 | 29.19 |
| ATOM | 727 | O | SER | 82 | 27.437 | 9.769 | −17.849 | 1.00 | 27.98 |
| ATOM | 728 | N | LEU | 83 | 25.517 | 10.889 | −17.676 | 1.00 | 28.73 |
| ATOM | 729 | CA | LEU | 83 | 26.182 | 12.174 | −17.749 | 1.00 | 29.29 |
| ATOM | 730 | CB | LEU | 83 | 25.109 | 13.278 | −17.815 | 1.00 | 30.66 |
| ATOM | 731 | CG | LEU | 83 | 25.876 | 14.598 | −17.889 | 1.00 | 28.90 |
| ATOM | 732 | CD1 | LEU | 83 | 26.652 | 14.682 | −19.214 | 1.00 | 26.97 |
| ATOM | 733 | CD2 | LEU | 83 | 24.926 | 15.718 | −17.690 | 1.00 | 25.69 |
| ATOM | 734 | C | LEU | 83 | 27.194 | 12.387 | −16.572 | 1.00 | 29.47 |
| ATOM | 735 | O | LEU | 83 | 28.380 | 12.727 | −16.797 | 1.00 | 28.25 |
| ATOM | 736 | N | LYS | 84 | 26.768 | 12.082 | −15.336 | 1.00 | 29.53 |
| ATOM | 737 | CA | LYS | 84 | 27.686 | 12.159 | −14.205 | 1.00 | 29.62 |
| ATOM | 738 | CB | LYS | 84 | 26.961 | 11.851 | −12.893 | 1.00 | 30.52 |
| ATOM | 739 | CG | LYS | 84 | 27.870 | 11.504 | −11.707 | 1.00 | 33.47 |
| ATOM | 740 | CD | LYS | 84 | 27.113 | 10.728 | −10.637 | 1.00 | 38.12 |
| ATOM | 741 | CE | LYS | 84 | 27.312 | 9.244 | −10.827 | 1.00 | 42.09 |

TABLE 7-continued

| | | | | | | | | |
|---|---|---|---|---|---|---|---|---|
| ATOM | 742 | NZ | LYS | 84 | 26.733 | 8.490 | −9.687 | 1.00 | 45.75 |
| ATOM | 743 | C | LYS | 84 | 28.956 | 11.317 | −14.370 | 1.00 | 29.83 |
| ATOM | 744 | O | LYS | 84 | 30.079 | 11.780 | −14.130 | 1.00 | 28.57 |
| ATOM | 745 | N | LEU | 85 | 28.800 | 10.068 | −14.780 | 1.00 | 30.73 |
| ATOM | 746 | CA | LEU | 85 | 30.015 | 9.229 | −14.980 | 1.00 | 31.39 |
| ATOM | 747 | CB | LEU | 85 | 29.638 | 7.776 | −15.241 | 1.00 | 32.27 |
| ATOM | 748 | CG | LEU | 85 | 28.709 | 7.188 | −14.200 | 1.00 | 34.28 |
| ATOM | 749 | CD1 | LEU | 85 | 28.089 | 5.873 | −14.722 | 1.00 | 36.91 |
| ATOM | 750 | CD2 | LEU | 85 | 29.605 | 7.009 | −12.958 | 1.00 | 35.13 |
| ATOM | 751 | C | LEU | 85 | 30.865 | 9.747 | −16.132 | 1.00 | 30.61 |
| ATOM | 752 | O | LEU | 85 | 32.105 | 9.711 | −16.110 | 1.00 | 31.60 |
| ATOM | 753 | N | TYR | 86 | 30.192 | 10.238 | −17.143 | 1.00 | 30.00 |
| ATOM | 754 | CA | TYR | 86 | 30.887 | 10.870 | −18.243 | 1.00 | 30.34 |
| ATOM | 755 | CB | TYR | 86 | 29.885 | 11.306 | −19.311 | 1.00 | 29.45 |
| ATOM | 756 | CG | TYR | 86 | 30.523 | 12.095 | −20.378 | 1.00 | 28.30 |
| ATOM | 757 | CD1 | TYR | 86 | 31.493 | 11.521 | −21.231 | 1.00 | 25.94 |
| ATOM | 758 | CE1 | TYR | 86 | 32.115 | 12.328 | −22.295 | 1.00 | 26.67 |
| ATOM | 759 | CZ | TYR | 86 | 31.688 | 13.673 | −22.458 | 1.00 | 27.51 |
| ATOM | 760 | OH | TYR | 86 | 32.247 | 14.525 | −23.393 | 1.00 | 30.54 |
| ATOM | 761 | CE2 | TYR | 86 | 30.703 | 14.208 | −21.630 | 1.00 | 28.71 |
| ATOM | 762 | CD2 | TYR | 86 | 30.147 | 13.415 | −20.573 | 1.00 | 29.33 |
| ATOM | 763 | C | TYR | 86 | 31.763 | 12.041 | −17.785 | 1.00 | 29.86 |
| ATOM | 764 | O | TYR | 86 | 32.939 | 12.103 | −18.107 | 1.00 | 30.59 |
| ATOM | 765 | N | LEU | 87 | 31.177 | 12.983 | −17.056 | 1.00 | 30.90 |
| ATOM | 766 | CA | LEU | 87 | 31.934 | 14.120 | −16.504 | 1.00 | 29.69 |
| ATOM | 767 | CB | LEU | 87 | 30.992 | 15.115 | −15.844 | 1.00 | 29.57 |
| ATOM | 768 | CG | LEU | 87 | 30.012 | 15.779 | −16.831 | 1.00 | 29.35 |
| ATOM | 769 | CD1 | LEU | 87 | 29.259 | 16.824 | −16.088 | 1.00 | 26.50 |
| ATOM | 770 | CD2 | LEU | 87 | 30.689 | 16.404 | −18.072 | 1.00 | 22.21 |
| ATOM | 771 | C | LEU | 87 | 32.984 | 13.654 | −15.540 | 1.00 | 29.49 |
| ATOM | 772 | O | LEU | 87 | 34.080 | 14.202 | −15.518 | 1.00 | 29.08 |
| ATOM | 773 | N | PHE | 88 | 32.684 | 12.609 | −14.763 | 1.00 | 31.41 |
| ATOM | 774 | CA | PHE | 88 | 33.720 | 12.019 | −13.893 | 1.00 | 33.88 |
| ATOM | 775 | CB | PHE | 88 | 33.166 | 10.904 | −12.971 | 1.00 | 36.10 |
| ATOM | 776 | CG | PHE | 88 | 32.387 | 11.445 | −11.731 | 1.00 | 37.70 |
| ATOM | 777 | CD1 | PHE | 88 | 31.562 | 10.599 | −10.979 | 1.00 | 38.15 |
| ATOM | 778 | CE1 | PHE | 88 | 30.836 | 11.101 | −9.892 | 1.00 | 37.93 |
| ATOM | 779 | CZ | PHE | 88 | 30.927 | 12.478 | −9.525 | 1.00 | 39.92 |
| ATOM | 780 | CE2 | PHE | 88 | 31.737 | 13.344 | −10.250 | 1.00 | 38.80 |
| ATOM | 781 | CD2 | PHE | 88 | 32.458 | 12.815 | −11.371 | 1.00 | 40.71 |
| ATOM | 782 | C | PHE | 88 | 34.934 | 11.508 | −14.662 | 1.00 | 33.94 |
| ATOM | 783 | O | PHE | 88 | 36.023 | 11.528 | −14.107 | 1.00 | 34.36 |
| ATOM | 784 | N | SER | 89 | 34.747 | 11.092 | −15.938 | 1.00 | 32.64 |
| ATOM | 785 | CA | SER | 89 | 35.850 | 10.524 | −16.721 | 1.00 | 32.27 |
| ATOM | 786 | CB | SER | 89 | 35.315 | 9.674 | −17.889 | 1.00 | 31.84 |
| ATOM | 787 | OG | SER | 89 | 34.887 | 10.500 | −18.968 | 1.00 | 32.07 |
| ATOM | 788 | C | SER | 89 | 36.866 | 11.579 | −17.208 | 1.00 | 32.06 |
| ATOM | 789 | O | SER | 89 | 37.883 | 11.255 | −17.835 | 1.00 | 32.05 |
| ATOM | 790 | N | PHE | 90 | 36.598 | 12.841 | −16.920 | 1.00 | 31.68 |
| ATOM | 791 | CA | PHE | 90 | 37.586 | 13.893 | −17.143 | 1.00 | 31.27 |
| ATOM | 792 | CB | PHE | 90 | 36.868 | 15.205 | −17.417 | 1.00 | 31.63 |
| ATOM | 793 | CG | PHE | 90 | 36.293 | 15.296 | −18.812 | 1.00 | 33.46 |
| ATOM | 794 | CD1 | PHE | 90 | 35.051 | 14.751 | −19.103 | 1.00 | 29.46 |
| ATOM | 795 | CE1 | PEE | 90 | 34.507 | 14.828 | −20.413 | 1.00 | 33.96 |
| ATOM | 796 | CZ | PHE | 90 | 35.202 | 15.479 | −21.410 | 1.00 | 32.50 |
| ATOM | 797 | CE2 | PHE | 90 | 36.470 | 16.063 | −21.121 | 1.00 | 36.46 |
| ATOM | 798 | CD2 | PHE | 90 | 36.996 | 15.961 | −19.816 | 1.00 | 36.25 |
| ATOM | 799 | C | PHE | 90 | 38.547 | 14.096 | −15.996 | 1.00 | 30.99 |
| ATOM | 800 | O | PHE | 90 | 39.526 | 14.874 | −16.107 | 1.00 | 30.59 |
| ATOM | 801 | N | ARG | 91 | 38.271 | 13.421 | −14.882 | 1.00 | 32.06 |
| ATOM | 802 | CA | ARG | 91 | 38.997 | 13.676 | −13.629 | 1.00 | 33.93 |
| ATOM | 803 | CB | ARG | 91 | 38.472 | 12.805 | −12.498 | 1.00 | 32.54 |
| ATOM | 804 | CG | ARG | 91 | 39.024 | 13.175 | −11.117 | 1.00 | 33.90 |
| ATOM | 805 | CD | ARG | 91 | 38.617 | 12.107 | −10.100 | 1.00 | 31.62 |
| ATOM | 806 | NE | ARG | 91 | 38.983 | 12.438 | −8.724 | 1.00 | 35.99 |
| ATOM | 807 | CZ | ARG | 91 | 38.359 | 13.330 | −7.943 | 1.00 | 34.09 |
| ATOM | 808 | NH1 | ARG | 91 | 37.328 | 14.066 | −8.410 | 1.00 | 31.27 |
| ATOM | 809 | NH2 | ARG | 91 | 38.786 | 13.505 | −6.680 | 1.00 | 32.64 |
| ATOM | 810 | C | ARG | 91 | 40.505 | 13.569 | −13.797 | 1.00 | 35.44 |
| ATOM | 811 | O | ARG | 91 | 41.239 | 14.389 | −13.295 | 1.00 | 34.63 |
| ATOM | 812 | N | ASN | 164 | 37.282 | 36.882 | −7.815 | 1.00 | 38.98 |
| ATOM | 813 | CA | ASN | 164 | 37.987 | 35.694 | −7.304 | 1.00 | 38.32 |
| ATOM | 814 | CB | ASN | 164 | 39.470 | 35.729 | −7.673 | 1.00 | 37.51 |
| ATOM | 815 | CG | ASN | 164 | 39.710 | 35.902 | −9.190 | 1.00 | 38.10 |
| ATOM | 816 | OD1 | ASN | 164 | 38.812 | 35.677 | −10.019 | 1.00 | 33.68 |
| ATOM | 817 | ND2 | ASN | 164 | 40.917 | 36.338 | −9.540 | 1.00 | 34.99 |
| ATOM | 818 | C | ASN | 164 | 37.759 | 35.327 | −5.817 | 1.00 | 38.77 |
| ATOM | 819 | O | ASN | 164 | 38.607 | 34.631 | −5.192 | 1.00 | 39.55 |
| ATOM | 820 | O3S | G6S | 202 | 25.228 | 7.156 | −0.711 | 1.00 | 0.87 |
| ATOM | 821 | S | G6S | 202 | 24.140 | 7.170 | −1.721 | 1.00 | 0.84 |

TABLE 7-continued

| | | | | | | | | |
|---|---|---|---|---|---|---|---|---|
| ATOM | 822 | O1S | G6S | 202 | 23.587 | 8.544 | −1.720 | 1.00 | 0.00 |
| ATOM | 823 | O2S | G6S | 202 | 23.066 | 6.241 | −1.294 | 1.00 | 0.46 |
| ATOM | 824 | O6 | G6S | 202 | 24.663 | 6.717 | −3.235 | 1.00 | 0.15 |
| ATOM | 825 | C6 | G6S | 202 | 23.766 | 6.323 | −4.298 | 1.00 | 0.76 |
| ATOM | 826 | C5 | G6S | 202 | 23.925 | 7.099 | −5.632 | 1.00 | 0.20 |
| ATOM | 827 | O5 | G6S | 202 | 24.958 | 8.110 | −5.607 | 1.00 | 0.47 |
| ATOM | 828 | C4 | G6S | 202 | 22.589 | 7.668 | −6.182 | 1.00 | 0.65 |
| ATOM | 829 | O4 | G6S | 202 | 21.479 | 6.824 | −5.790 | 1.00 | 0.12 |
| ATOM | 830 | C3 | G6S | 202 | 22.266 | 9.154 | −5.851 | 1.00 | 0.92 |
| ATOM | 831 | O3 | G6S | 202 | 21.301 | 9.260 | −4.786 | 1.00 | 0.71 |
| ATOM | 832 | C2 | G6S | 202 | 23.491 | 10.053 | −5.570 | 1.00 | 0.85 |
| ATOM | 833 | O2 | G6S | 202 | 23.130 | 11.219 | −4.806 | 1.00 | 0.58 |
| ATOM | 834 | C1 | G6S | 202 | 24.628 | 9.302 | −4.878 | 1.00 | 0.56 |
| ATOM | 835 | O1 | G6S | 202 | 25.782 | 10.136 | −4.800 | 1.00 | 0.12 |
| ATOM | 836 | N | PHE | 52 | 7.330 | 20.172 | −3.999 | 1.00 | 30.57 |
| ATOM | 837 | CA | PHE | 52 | 7.115 | 19.057 | −4.901 | 1.00 | 29.32 |
| ATOM | 838 | CB | PHE | 52 | 7.335 | 19.473 | −6.352 | 1.00 | 29.38 |
| ATOM | 839 | CG | PHE | 52 | 7.031 | 18.379 | −7.317 | 1.00 | 28.90 |
| ATOM | 840 | CD1 | PHE | 52 | 5.710 | 18.132 | −7.694 | 1.00 | 25.64 |
| ATOM | 841 | CE1 | PHE | 52 | 5.418 | 17.123 | −8.596 | 1.00 | 26.75 |
| ATOM | 842 | CZ | PHE | 52 | 6.428 | 16.306 | −9.069 | 1.00 | 25.36 |
| ATOM | 843 | CE2 | PHE | 52 | 7.761 | 16.528 | −8.677 | 1.00 | 28.36 |
| ATOM | 844 | CD2 | PHE | 52 | 8.053 | 17.550 | −7.797 | 1.00 | 26.05 |
| ATOM | 845 | C | PHE | 52 | 8.028 | 17.908 | −4.571 | 1.00 | 29.42 |
| ATOM | 846 | O | PHE | 52 | 9.190 | 18.137 | −4.241 | 1.00 | 29.42 |
| ATOM | 847 | N | THR | 53 | 7.516 | 16.681 | −4.681 | 1.00 | 28.87 |
| ATOM | 848 | CA | THR | 53 | 8.308 | 15.473 | −4.491 | 1.00 | 29.86 |
| ATOM | 849 | CB | THR | 53 | 8.548 | 15.137 | −2.965 | 1.00 | 29.43 |
| ATOM | 850 | OG1 | THR | 53 | 9.489 | 14.096 | −2.864 | 1.00 | 29.24 |
| ATOM | 851 | CG2 | THR | 53 | 7.302 | 14.617 | −2.244 | 1.00 | 29.41 |
| ATOM | 852 | C | THR | 53 | 7.713 | 14.273 | −5.284 | 1.00 | 30.60 |
| ATOM | 853 | O | THR | 53 | 6.502 | 14.205 | −5.474 | 1.00 | 31.11 |
| ATOM | 854 | N | SER | 54 | 8.569 | 13.376 | −5.779 | 1.00 | 31.90 |
| ATOM | 855 | CA | SER | 54 | 8.156 | 12.168 | −6.505 | 1.00 | 34.24 |
| ATOM | 856 | CB | SER | 54 | 7.718 | 12.471 | −7.964 | 1.00 | 33.85 |
| ATOM | 857 | OG | SER | 54 | 8.699 | 13.156 | −8.732 | 1.00 | 34.45 |
| ATOM | 858 | C | SER | 54 | 9.275 | 11.150 | −6.504 | 1.00 | 36.26 |
| ATOM | 859 | O | SER | 54 | 10.237 | 11.282 | −5.766 | 1.00 | 36.99 |
| ATOM | 860 | N | LEU | 55 | 9.160 | 10.144 | −7.362 | 1.00 | 38.76 |
| ATOM | 861 | CA | LEU | 55 | 10.036 | 9.000 | −7.332 | 1.00 | 40.65 |
| ATOM | 862 | CB | LEU | 55 | 9.193 | 7.752 | −7.008 | 1.00 | 40.22 |
| ATOM | 863 | CG | LEU | 55 | 8.468 | 7.679 | −5.640 | 1.00 | 39.91 |
| ATOM | 864 | CD1 | LEU | 55 | 7.713 | 6.395 | −5.450 | 1.00 | 36.87 |
| ATOM | 865 | CD2 | LEU | 55 | 9.450 | 7.845 | −4.483 | 1.00 | 37.75 |
| ATOM | 866 | C | LEU | 55 | 10.791 | 8.809 | −8.640 | 1.00 | 42.66 |
| ATOM | 867 | O | LEU | 55 | 10.261 | 9.104 | −9.710 | 1.00 | 42.18 |
| ATOM | 868 | N | CYS | 56 | 12.031 | 8.319 | −8.535 | 1.00 | 45.64 |
| ATOM | 869 | CA | CYS | 56 | 12.835 | 7.864 | −9.676 | 1.00 | 47.46 |
| ATOM | 870 | CB | CYS | 56 | 14.227 | 7.483 | −9.179 | 1.00 | 47.73 |
| ATOM | 871 | SG | CYS | 56 | 15.444 | 7.053 | −10.461 | 1.00 | 49.73 |
| ATOM | 872 | C | CYS | 56 | 12.137 | 6.611 | −10.236 | 1.00 | 49.16 |
| ATOM | 873 | O | CYS | 56 | 11.838 | 5.695 | −9.460 | 1.00 | 48.69 |
| ATOM | 874 | N | PRO | 57 | 11.858 | 6.565 | −11.566 | 1.00 | 50.23 |
| ATOM | 875 | CA | PRO | 57 | 11.045 | 5.455 | −12.077 | 1.00 | 51.27 |
| ATOM | 876 | CB | PRO | 57 | 10.714 | 5.884 | −13.509 | 1.00 | 50.81 |
| ATOM | 877 | CG | PRO | 57 | 11.823 | 6.746 | −13.897 | 1.00 | 49.99 |
| ATOM | 878 | CD | PRO | 57 | 12.271 | 7.470 | −12.652 | 1.00 | 50.40 |
| ATOM | 879 | C | PRO | 57 | 11.765 | 4.087 | −12.045 | 1.00 | 52.30 |
| ATOM | 880 | O | PRO | 57 | 11.108 | 3.063 | −11.961 | 1.00 | 52.64 |
| ATOM | 881 | N | LYS | 58 | 13.091 | 4.078 | −12.075 | 1.00 | 54.16 |
| ATOM | 882 | CA | LYS | 58 | 13.835 | 2.818 | −12.039 | 1.00 | 56.16 |
| ATOM | 883 | CB | LYS | 58 | 15.118 | 2.867 | −12.894 | 1.00 | 57.06 |
| ATOM | 884 | CG | LYS | 58 | 15.178 | 1.704 | −13.922 | 1.00 | 60.28 |
| ATOM | 885 | CD | LYS | 58 | 16.562 | 1.028 | −14.025 | 1.00 | 64.21 |
| ATOM | 886 | CE | LYS | 58 | 16.570 | −0.023 | −15.154 | 1.00 | 64.13 |
| ATOM | 887 | NZ | LYS | 58 | 17.852 | 0.053 | −15.959 | 1.00 | 65.58 |
| ATOM | 888 | C | LYS | 58 | 14.119 | 2.371 | −10.592 | 1.00 | 56.38 |
| ATOM | 889 | O | LYS | 58 | 13.544 | 1.385 | −10.140 | 1.00 | 57.38 |
| ATOM | 890 | N | VAL | 59 | 14.980 | 3.090 | −9.862 | 1.00 | 56.15 |
| ATOM | 891 | CA | VAL | 59 | 15.125 | 2.881 | −8.403 | 1.00 | 55.14 |
| ATOM | 892 | CB | VAL | 59 | 16.354 | 3.613 | −7.855 | 1.00 | 55.05 |
| ATOM | 893 | CG1 | VAL | 59 | 17.567 | 3.313 | −8.722 | 1.00 | 55.49 |
| ATOM | 894 | CG2 | VAL | 59 | 16.113 | 5.093 | −7.809 | 1.00 | 54.75 |
| ATOM | 895 | C | VAL | 59 | 13.868 | 3.414 | −7.724 | 1.00 | 54.81 |
| ATOM | 896 | O | VAL | 59 | 13.095 | 4.161 | −8.326 | 1.00 | 55.98 |
| ATOM | 897 | N | GLY | 60 | 13.602 | 3.067 | −6.485 | 1.00 | 53.64 |
| ATOM | 898 | CA | GLY | 60 | 12.399 | 3.694 | −5.914 | 1.00 | 52.33 |
| ATOM | 899 | C | GLY | 60 | 12.601 | 5.085 | −5.306 | 1.00 | 50.31 |
| ATOM | 900 | O | GLY | 60 | 11.699 | 5.596 | −4.674 | 1.00 | 50.01 |
| ATOM | 901 | N | GLN | 61 | 13.776 | 5.681 | −5.486 | 1.00 | 48.88 |

TABLE 7-continued

| | | | | | | | | | |
|---|---|---|---|---|---|---|---|---|---|
| ATOM | 902 | CA | GLN | 61 | 14.218 | 6.826 | −4.661 | 1.00 | 49.29 |
| ATOM | 903 | CB | GLN | 61 | 15.717 | 7.067 | −4.820 | 1.00 | 49.10 |
| ATOM | 904 | CG | GLN | 61 | 16.574 | 5.907 | −4.353 | 1.00 | 53.70 |
| ATOM | 905 | CD | GLN | 61 | 18.071 | 6.264 | −4.164 | 1.00 | 55.70 |
| ATOM | 906 | OE1 | GLN | 61 | 18.971 | 5.517 | −4.639 | 1.00 | 62.01 |
| ATOM | 907 | NE2 | GLN | 61 | 18.347 | 7.412 | −3.477 | 1.00 | 60.03 |
| ATOM | 908 | C | GLN | 61 | 13.444 | 8.130 | −4.919 | 1.00 | 45.89 |
| ATOM | 909 | O | GLN | 61 | 13.137 | 8.434 | −6.070 | 1.00 | 45.98 |
| ATOM | 910 | N | PRO | 62 | 13.128 | 8.900 | −3.843 | 1.00 | 43.29 |
| ATOM | 911 | CA | PRO | 62 | 12.434 | 10.187 | −3.947 | 1.00 | 40.15 |
| ATOM | 912 | CB | PRO | 62 | 12.082 | 10.522 | −2.493 | 1.00 | 40.40 |
| ATOM | 913 | CG | PRO | 62 | 12.296 | 9.288 | −1.722 | 1.00 | 40.75 |
| ATOM | 914 | CD | PRO | 62 | 13.379 | 8.555 | −2.429 | 1.00 | 43.04 |
| ATOM | 915 | C | PRO | 62 | 13.298 | 11.299 | −4.515 | 1.00 | 37.93 |
| ATOM | 916 | O | PRO | 62 | 14.526 | 11.334 | −4.285 | 1.00 | 37.34 |
| ATOM | 917 | N | ASP | 63 | 12.649 | 12.187 | −5.259 | 1.00 | 34.80 |
| ATOM | 918 | CA | ASP | 63 | 13.273 | 13.405 | −5.768 | 1.00 | 34.59 |
| ATOM | 919 | CB | ASP | 63 | 13.275 | 13.490 | −7.300 | 1.00 | 35.69 |
| ATOM | 920 | CG | ASP | 63 | 13.948 | 12.307 | −7.986 | 1.00 | 43.45 |
| ATOM | 921 | OD1 | ASP | 63 | 15.016 | 11.811 | −7.513 | 1.00 | 49.93 |
| ATOM | 922 | OD2 | ASP | 63 | 13.374 | 11.864 | −9.032 | 1.00 | 50.25 |
| ATOM | 923 | C | ASP | 63 | 12.435 | 14.578 | −5.275 | 1.00 | 31.59 |
| ATOM | 924 | O | ASP | 63 | 11.294 | 14.416 | −4.865 | 1.00 | 29.24 |
| ATOM | 925 | N | PHE | 64 | 13.014 | 15.763 | −5.330 | 1.00 | 30.47 |
| ATOM | 926 | CA | PHE | 64 | 12.378 | 16.955 | −4.755 | 1.00 | 28.47 |
| ATOM | 927 | CB | PHE | 64 | 12.991 | 17.243 | −3.371 | 1.00 | 28.12 |
| ATOM | 928 | CG | PHE | 64 | 12.738 | 16.141 | −2.353 | 1.00 | 28.68 |
| ATOM | 929 | CD1 | PHE | 64 | 13.505 | 14.982 | −2.352 | 1.00 | 30.31 |
| ATOM | 930 | CE1 | PHE | 64 | 13.273 | 13.974 | −1.430 | 1.00 | 31.76 |
| ATOM | 931 | CZ | PHE | 64 | 12.219 | 14.114 | −0.479 | 1.00 | 27.12 |
| ATOM | 932 | CE2 | PHE | 64 | 11.440 | 15.255 | −0.481 | 1.00 | 30.78 |
| ATOM | 933 | CD2 | PHE | 64 | 11.708 | 16.272 | −1.407 | 1.00 | 30.18 |
| ATOM | 934 | C | PHE | 64 | 12.624 | 18.114 | −5.682 | 1.00 | 27.63 |
| ATOM | 935 | O | PHE | 64 | 13.672 | 18.177 | −6.289 | 1.00 | 28.69 |
| ATOM | 936 | N | ALA | 65 | 11.702 | 19.079 | −5.722 | 1.00 | 26.33 |
| ATOM | 937 | CA | ALA | 65 | 11.841 | 20.200 | −6.558 | 1.00 | 25.69 |
| ATOM | 938 | CB | ALA | 65 | 11.395 | 19.803 | −8.065 | 1.00 | 24.22 |
| ATOM | 939 | C | ALA | 65 | 11.015 | 21.374 | −6.057 | 1.00 | 25.67 |
| ATOM | 940 | O | ALA | 65 | 10.082 | 21.217 | −5.287 | 1.00 | 26.66 |
| ATOM | 941 | N | PHE | 90 | 1.707 | 13.210 | −7.013 | 1.00 | 36.34 |
| ATOM | 942 | CA | PHE | 90 | 2.955 | 12.654 | −7.548 | 1.00 | 35.88 |
| ATOM | 943 | CB | PHE | 90 | 3.758 | 13.751 | −8.270 | 1.00 | 35.55 |
| ATOM | 944 | CG | PHE | 90 | 3.158 | 14.178 | −9.560 | 1.00 | 34.96 |
| ATOM | 945 | CD1 | PHE | 90 | 2.061 | 15.036 | −9.586 | 1.00 | 35.21 |
| ATOM | 946 | CE1 | PHE | 90 | 1.492 | 15.437 | −10.771 | 1.00 | 33.10 |
| ATOM | 947 | CZ | PHE | 90 | 2.007 | 14.999 | −11.945 | 1.00 | 36.55 |
| ATOM | 948 | CE2 | PHE | 90 | 3.116 | 14.136 | −11.947 | 1.00 | 38.06 |
| ATOM | 949 | CD2 | PHE | 90 | 3.686 | 13.741 | −10.755 | 1.00 | 35.73 |
| ATOM | 950 | C | PHE | 90 | 3.839 | 11.976 | −6.514 | 1.00 | 35.67 |
| ATOM | 951 | O | PHE | 90 | 4.870 | 11.395 | −6.867 | 1.00 | 35.03 |
| ATOM | 952 | N | ARG | 91 | 3.458 | 12.078 | −5.241 | 1.00 | 35.48 |
| ATOM | 953 | CA | ARG | 91 | 4.306 | 11.618 | −4.127 | 1.00 | 36.26 |
| ATOM | 954 | CB | ARG | 91 | 3.649 | 11.953 | −2.744 | 1.00 | 35.68 |
| ATOM | 955 | CG | ARG | 91 | 4.513 | 11.598 | −1.534 | 1.00 | 32.43 |
| ATOM | 956 | CD | ARG | 91 | 3.763 | 11.666 | −0.137 | 1.00 | 36.20 |
| ATOM | 957 | NE | ARG | 91 | 4.166 | 12.896 | 0.530 | 1.00 | 44.24 |
| ATOM | 958 | CZ | ARG | 91 | 5.096 | 13.015 | 1.467 | 1.00 | 42.01 |
| ATOM | 959 | NH1 | ARG | 91 | 5.701 | 11.992 | 1.989 | 1.00 | 41.45 |
| ATOM | 960 | NH2 | ARG | 91 | 5.393 | 14.200 | 1.908 | 1.00 | 50.38 |
| ATOM | 961 | C | ARG | 91 | 4.763 | 10.163 | −4.216 | 1.00 | 37.67 |
| ATOM | 962 | O | ARG | 91 | 5.911 | 9.855 | −3.931 | 1.00 | 36.52 |
| ATOM | 963 | N | ASN | 92 | 3.889 | 9.236 | −4.598 | 1.00 | 41.48 |
| ATOM | 964 | CA | ASN | 92 | 4.404 | 7.866 | −4.788 | 1.00 | 45.39 |
| ATOM | 965 | CB | ASN | 92 | 3.967 | 6.913 | −3.650 | 1.00 | 46.29 |
| ATOM | 966 | CG | ASN | 92 | 4.498 | 7.413 | −2.219 | 1.00 | 52.03 |
| ATOM | 967 | OD1 | ASN | 92 | 5.727 | 7.314 | −1.880 | 1.00 | 52.31 |
| ATOM | 968 | ND2 | ASN | 92 | 3.567 | 7.994 | −1.410 | 1.00 | 53.50 |
| ATOM | 969 | C | ASN | 92 | 4.379 | 7.357 | −6.270 | 1.00 | 46.62 |
| ATOM | 970 | O | ASN | 92 | 4.216 | 6.171 | −6.580 | 1.00 | 47.65 |
| ATOM | 971 | N | HIS | 93 | 4.666 | 8.308 | −7.156 | 1.00 | 47.52 |
| ATOM | 972 | CA | HIS | 93 | 4.678 | 8.144 | −8.608 | 1.00 | 48.56 |
| ATOM | 973 | CB | HIS | 93 | 3.746 | 9.178 | −9.224 | 1.00 | 48.57 |
| ATOM | 974 | CG | HIS | 93 | 3.610 | 9.064 | −10.706 | 1.00 | 52.23 |
| ATOM | 975 | ND1 | HIS | 93 | 4.266 | 9.906 | −11.583 | 1.00 | 54.40 |
| ATOM | 976 | CE1 | HIS | 93 | 3.956 | 9.576 | −12.824 | 1.00 | 55.42 |
| ATOM | 977 | NE2 | HIS | 93 | 3.121 | 8.551 | −12.784 | 1.00 | 57.29 |
| ATOM | 978 | CD2 | HIS | 93 | 2.893 | 8.205 | −11.471 | 1.00 | 54.08 |
| ATOM | 979 | C | HIS | 93 | 6.075 | 8.214 | −9.213 | 1.00 | 48.30 |
| ATOM | 980 | O | HIS | 93 | 6.751 | 9.351 | −9.002 | 1.00 | 48.07 |
| ATOM | 981 | N | GLY | 94 | 6.479 | 7.303 | −9.983 | 1.00 | 47.98 |

TABLE 7-continued

| | | | | | | | | |
|---|---|---|---|---|---|---|---|---|
| ATOM | 982 | CA | GLY | 94 | 7.767 | 7.282 | −10.690 | 1.00 | 48.09 |
| ATOM | 983 | C | GLY | 94 | 7.704 | 7.850 | −12.120 | 1.00 | 48.30 |
| ATOM | 984 | O | GLY | 94 | 6.779 | 7.541 | −12.899 | 1.00 | 48.30 |
| ATOM | 985 | N | ASP | 95 | 8.687 | 8.696 | −12.443 | 1.00 | 47.87 |
| ATOM | 986 | CA | ASP | 95 | 8.848 | 9.387 | −13.742 | 1.00 | 47.26 |
| ATOM | 987 | CB | ASP | 95 | 7.628 | 10.225 | −14.157 | 1.00 | 47.30 |
| ATOM | 988 | CG | ASP | 95 | 6.784 | 9.558 | −15.288 | 1.00 | 53.37 |
| ATOM | 989 | OD1 | ASP | 95 | 7.273 | 8.604 | −15.981 | 1.00 | 57.20 |
| ATOM | 990 | OD2 | ASP | 95 | 5.609 | 9.987 | −15.488 | 1.00 | 56.37 |
| ATOM | 991 | C | ASP | 95 | 10.071 | 10.267 | −13.644 | 1.00 | 45.93 |
| ATOM | 992 | O | ASP | 95 | 10.387 | 10.788 | −12.566 | 1.00 | 44.85 |
| ATOM | 993 | N | PHE | 96 | 10.769 | 10.390 | −14.770 | 1.00 | 45.16 |
| ATOM | 994 | CA | PHE | 96 | 11.852 | 11.370 | −14.959 | 1.00 | 44.14 |
| ATOM | 995 | CB | PHE | 96 | 12.578 | 11.122 | −16.292 | 1.00 | 45.17 |
| ATOM | 996 | CG | PHE | 96 | 12.279 | 9.775 | −16.392 | 1.00 | 46.90 |
| ATOM | 997 | CD1 | PHE | 96 | 13.045 | 8.941 | −17.476 | 1.00 | 50.69 |
| ATOM | 998 | CE1 | PHE | 96 | 13.710 | 7.707 | −17.596 | 1.00 | 51.94 |
| ATOM | 999 | CZ | PHE | 96 | 14.608 | 7.310 | −16.604 | 1.00 | 50.11 |
| ATOM | 1000 | CE2 | PHE | 96 | 14.843 | 8.156 | −15.528 | 1.00 | 50.44 |
| ATOM | 1001 | CD2 | PHE | 96 | 14.193 | 9.365 | −15.435 | 1.00 | 48.33 |
| ATOM | 1002 | C | PHE | 96 | 11.331 | 12.827 | −14.886 | 1.00 | 42.30 |
| ATOM | 1003 | O | PHE | 96 | 10.144 | 13.099 | −15.145 | 1.00 | 41.46 |
| ATOM | 1004 | N | HIS | 97 | 12.215 | 13.760 | −14.524 | 1.00 | 40.24 |
| ATOM | 1005 | CA | HIS | 97 | 11.772 | 15.102 | −14.185 | 1.00 | 38.57 |
| ATOM | 1006 | CB | HIS | 97 | 12.905 | 15.960 | −13.601 | 1.00 | 38.59 |
| ATOM | 1007 | CG | HIS | 97 | 13.675 | 15.281 | −12.526 | 1.00 | 39.30 |
| ATOM | 1008 | ND1 | HIS | 97 | 13.116 | 14.332 | −11.698 | 1.00 | 39.03 |
| ATOM | 1009 | CE1 | HIS | 97 | 14.043 | 13.877 | −10.879 | 1.00 | 39.99 |
| ATOM | 1010 | NE2 | HIS | 97 | 15.181 | 14.490 | −11.146 | 1.00 | 39.16 |
| ATOM | 1011 | CD2 | HIS | 97 | 14.976 | 15.379 | −12.165 | 1.00 | 41.09 |
| ATOM | 1012 | C | HIS | 97 | 11.218 | 15.785 | −15.398 | 1.00 | 37.66 |
| ATOM | 1013 | O | HIS | 97 | 10.210 | 16.523 | −15.301 | 1.00 | 35.95 |
| ATOM | 1014 | N | TRP | 120 | 8.388 | 25.538 | −14.982 | 1.00 | 26.32 |
| ATOM | 1015 | CA | TRP | 120 | 9.813 | 25.399 | −14.737 | 1.00 | 25.22 |
| ATOM | 1016 | CB | TRP | 120 | 10.424 | 26.775 | −14.661 | 1.00 | 24.66 |
| ATOM | 1017 | CG | TRP | 120 | 11.892 | 26.868 | −14.809 | 1.00 | 23.83 |
| ATOM | 1018 | CD1 | TRP | 120 | 12.784 | 25.874 | −14.748 | 1.00 | 24.59 |
| ATOM | 1019 | NE1 | TRP | 120 | 14.058 | 26.384 | −14.953 | 1.00 | 29.40 |
| ATOM | 1020 | CE2 | TRP | 120 | 13.977 | 27.743 | −15.127 | 1.00 | 24.59 |
| ATOM | 1021 | CD2 | TRP | 120 | 12.625 | 28.084 | −15.043 | 1.00 | 22.94 |
| ATOM | 1022 | CE3 | TRP | 120 | 12.238 | 29.431 | −15.273 | 1.00 | 25.61 |
| ATOM | 1023 | CZ3 | TRP | 120 | 13.242 | 30.390 | −15.506 | 1.00 | 25.81 |
| ATOM | 1024 | CH2 | TRP | 120 | 14.604 | 30.006 | −15.545 | 1.00 | 21.59 |
| ATOM | 1025 | CZ2 | TRP | 120 | 14.985 | 28.690 | −15.398 | 1.00 | 22.78 |
| ATOM | 1026 | C | TRP | 120 | 10.062 | 24.686 | −13.424 | 1.00 | 25.58 |
| ATOM | 1027 | O | TRP | 120 | 9.641 | 25.157 | −12.353 | 1.00 | 24.48 |
| ATOM | 1028 | N | GLY | 121 | 10.730 | 23.550 | −13.517 | 1.00 | 24.73 |
| ATOM | 1029 | CA | GLY | 121 | 11.036 | 22.759 | −12.381 | 1.00 | 25.93 |
| ATOM | 1030 | C | GLY | 121 | 12.512 | 22.825 | −12.093 | 1.00 | 27.00 |
| ATOM | 1031 | O | GLY | 121 | 13.337 | 22.830 | −13.011 | 1.00 | 27.37 |
| ATOM | 1032 | N | LYS | 122 | 12.847 | 22.862 | −10.810 | 1.00 | 26.41 |
| ATOM | 1033 | CA | LYS | 122 | 14.222 | 22.975 | −10.371 | 1.00 | 26.76 |
| ATOM | 1034 | CB | LYS | 122 | 14.463 | 24.416 | −9.849 | 1.00 | 27.37 |
| ATOM | 1035 | CG | LYS | 122 | 14.261 | 25.493 | −10.944 | 1.00 | 25.44 |
| ATOM | 1036 | CD | LYS | 122 | 14.611 | 26.857 | −10.438 | 1.00 | 27.60 |
| ATOM | 1037 | CE | LYS | 122 | 14.324 | 27.863 | −11.504 | 1.00 | 31.63 |
| ATOM | 1038 | NZ | LYS | 122 | 15.191 | 29.054 | −11.424 | 1.00 | 40.28 |
| ATOM | 1039 | C | LYS | 122 | 14.475 | 21.956 | −9.292 | 1.00 | 26.44 |
| ATOM | 1040 | O | LYS | 122 | 14.057 | 22.145 | −8.143 | 1.00 | 27.76 |
| ATOM | 1041 | N | PHE | 123 | 15.133 | 20.872 | −9.658 | 1.00 | 26.32 |
| ATOM | 1042 | CA | PHE | 123 | 15.271 | 19.692 | −8.821 | 1.00 | 26.09 |
| ATOM | 1043 | CB | PHE | 123 | 15.259 | 18.400 | −9.661 | 1.00 | 25.12 |
| ATOM | 1044 | CG | PHE | 123 | 13.884 | 17.972 | −10.036 | 1.00 | 24.90 |
| ATOM | 1045 | CD1 | PHE | 123 | 13.183 | 18.660 | −11.034 | 1.00 | 22.78 |
| ATOM | 1046 | CE1 | PHE | 123 | 11.819 | 18.322 | −11.337 | 1.00 | 26.27 |
| ATOM | 1047 | CZ | PHE | 123 | 11.217 | 17.263 | −10.649 | 1.00 | 27.25 |
| ATOM | 1048 | CE2 | PHE | 123 | 11.945 | 16.549 | −9.655 | 1.00 | 25.30 |
| ATOM | 1049 | CD2 | PHE | 123 | 13.255 | 16.916 | −9.350 | 1.00 | 24.32 |
| ATOM | 1050 | C | PHE | 123 | 16.527 | 19.776 | −8.017 | 1.00 | 27.81 |
| ATOM | 1051 | O | PHE | 123 | 17.421 | 20.522 | −8.367 | 1.00 | 28.26 |
| ATOM | 1052 | N | THR | 124 | 16.582 | 18.998 | −6.927 | 1.00 | 28.52 |
| ATOM | 1053 | CA | THR | 124 | 17.764 | 18.934 | −6.071 | 1.00 | 28.16 |
| ATOM | 1054 | CB | THR | 124 | 17.361 | 18.521 | −4.602 | 1.00 | 28.66 |
| ATOM | 1055 | OG1 | THR | 124 | 16.741 | 17.215 | −4.602 | 1.00 | 24.86 |
| ATOM | 1056 | CG2 | THR | 124 | 16.340 | 19.573 | −3.994 | 1.00 | 25.85 |
| ATOM | 1057 | C | THR | 124 | 18.760 | 17.922 | −6.709 | 1.00 | 29.59 |
| ATOM | 1058 | O | THR | 124 | 18.335 | 17.009 | −7.435 | 1.00 | 29.24 |
| ATOM | 1059 | N | PRO | 125 | 20.075 | 18.102 | −6.465 | 1.00 | 29.30 |
| ATOM | 1060 | CA | PRO | 125 | 20.940 | 17.266 | −7.217 | 1.00 | 30.23 |
| ATOM | 1061 | CB | PRO | 125 | 22.328 | 17.933 | −7.045 | 1.00 | 29.73 |

TABLE 7-continued

| | | | | | | | | |
|---|---|---|---|---|---|---|---|---|
| ATOM | 1062 | CG | PRO | 125 | 22.262 | 18.602 | −5.715 | 1.00 | 29.08 |
| ATOM | 1063 | CD | PRO | 125 | 20.822 | 19.078 | −5.627 | 1.00 | 28.72 |
| ATOM | 1064 | C | PRO | 125 | 20.960 | 15.817 | −6.795 | 1.00 | 31.25 |
| ATOM | 1065 | O | PRO | 125 | 20.509 | 15.487 | −5.708 | 1.00 | 31.50 |
| ATOM | 1066 | N | ARG | 126 | 21.448 | 14.969 | −7.705 | 1.00 | 32.08 |
| ATOM | 1067 | CA | ARG | 126 | 21.685 | 13.505 | −7.490 | 1.00 | 33.66 |
| ATOM | 1068 | CB | ARG | 126 | 20.631 | 12.652 | −8.230 | 1.00 | 33.84 |
| ATOM | 1069 | CG | ARG | 126 | 19.476 | 12.105 | −7.428 | 1.00 | 40.80 |
| ATOM | 1070 | CD | ARG | 126 | 18.977 | 13.142 | −6.433 | 1.00 | 49.19 |
| ATOM | 1071 | NE | ARG | 126 | 17.976 | 12.660 | −5.465 | 1.00 | 53.43 |
| ATOM | 1072 | CZ | ARG | 126 | 17.923 | 13.067 | −4.194 | 1.00 | 54.41 |
| ATOM | 1073 | NH1 | ARG | 126 | 18.838 | 13.915 | −3.728 | 1.00 | 52.21 |
| ATOM | 1074 | NH2 | ARG | 126 | 16.970 | 12.603 | −3.386 | 1.00 | 55.80 |
| ATOM | 1075 | C | ARG | 126 | 23.012 | 13.262 | −8.163 | 1.00 | 32.80 |
| ATOM | 1076 | O | ARG | 126 | 23.179 | 13.567 | −9.338 | 1.00 | 32.63 |
| ATOM | 1077 | N | GLY | 127 | 23.977 | 12.752 | −7.445 | 1.00 | 32.28 |
| ATOM | 1078 | CA | GLY | 127 | 25.214 | 12.463 | −8.064 | 1.00 | 33.33 |
| ATOM | 1079 | C | GLY | 127 | 25.941 | 13.738 | −8.406 | 1.00 | 33.71 |
| ATOM | 1080 | O | GLY | 127 | 26.891 | 13.693 | −9.168 | 1.00 | 36.24 |
| ATOM | 1081 | N | GLY | 128 | 25.500 | 14.877 | −7.865 | 1.00 | 33.07 |
| ATOM | 1082 | CA | GLY | 128 | 26.223 | 16.146 | −8.003 | 1.00 | 31.01 |
| ATOM | 1083 | C | GLY | 128 | 25.654 | 17.027 | −9.089 | 1.00 | 30.37 |
| ATOM | 1084 | O | GLY | 128 | 26.122 | 18.125 | −9.315 | 1.00 | 29.97 |
| ATOM | 1085 | N | ILE | 129 | 24.597 | 16.557 | −9.720 | 1.00 | 30.13 |
| ATOM | 1086 | CA | ILE | 129 | 24.077 | 17.173 | −10.920 | 1.00 | 30.80 |
| ATOM | 1087 | CB | ILE | 129 | 24.310 | 16.167 | −12.140 | 1.00 | 31.06 |
| ATOM | 1088 | CG1 | ILE | 129 | 25.766 | 16.236 | −12.588 | 1.00 | 31.42 |
| ATOM | 1089 | CD1 | ILE | 129 | 26.105 | 15.244 | −13.677 | 1.00 | 31.28 |
| ATOM | 1090 | CG2 | ILE | 129 | 23.367 | 16.421 | −13.309 | 1.00 | 30.12 |
| ATOM | 1091 | C | ILE | 129 | 22.582 | 17.405 | −10.679 | 1.00 | 30.22 |
| ATOM | 1092 | O | ILE | 129 | 21.904 | 16.482 | −10.335 | 1.00 | 29.71 |
| ATOM | 1093 | N | SER | 130 | 22.086 | 18.626 | −10.887 | 1.00 | 29.49 |
| ATOM | 1094 | CA | SER | 130 | 20.683 | 18.888 | −10.767 | 1.00 | 29.39 |
| ATOM | 1095 | CB | SER | 130 | 20.399 | 20.068 | −9.824 | 1.00 | 29.82 |
| ATOM | 1096 | OG | SER | 130 | 21.256 | 21.171 | −10.093 | 1.00 | 33.34 |
| ATOM | 1097 | C | SER | 130 | 20.114 | 19.217 | −12.117 | 1.00 | 28.67 |
| ATOM | 1098 | O | SER | 130 | 20.801 | 19.736 | −12.993 | 1.00 | 28.81 |
| ATOM | 1099 | N | ILE | 131 | 18.831 | 18.968 | −12.255 | 1.00 | 28.29 |
| ATOM | 1100 | CA | ILE | 131 | 18.189 | 19.012 | −13.543 | 1.00 | 28.60 |
| ATOM | 1101 | CB | ILE | 131 | 17.541 | 17.671 | −13.875 | 1.00 | 28.00 |
| ATOM | 1102 | CG1 | ILE | 131 | 18.579 | 16.562 | −13.948 | 1.00 | 29.12 |
| ATOM | 1103 | CD1 | ILE | 131 | 17.962 | 15.267 | −14.520 | 1.00 | 31.67 |
| ATOM | 1104 | CG2 | ILE | 131 | 16.864 | 17.742 | −15.240 | 1.00 | 30.30 |
| ATOM | 1105 | C | ILE | 131 | 17.063 | 19.968 | −13.484 | 1.00 | 28.51 |
| ATOM | 1106 | O | ILE | 131 | 16.188 | 19.775 | −12.665 | 1.00 | 30.21 |
| ATOM | 1107 | N | ASP | 132 | 17.021 | 20.963 | −14.361 | 1.00 | 28.50 |
| ATOM | 1108 | CA | ASP | 132 | 15.918 | 21.903 | −14.331 | 1.00 | 28.58 |
| ATOM | 1109 | CB | ASP | 132 | 16.427 | 23.310 | −13.980 | 1.00 | 28.59 |
| ATOM | 1110 | CG | ASP | 132 | 17.265 | 23.362 | −12.681 | 1.00 | 32.67 |
| ATOM | 1111 | OD1 | ASP | 132 | 17.199 | 22.392 | −11.853 | 1.00 | 33.13 |
| ATOM | 1112 | OD2 | ASP | 132 | 17.973 | 24.403 | −12.479 | 1.00 | 30.84 |
| ATOM | 1113 | C | ASP | 132 | 15.181 | 21.979 | −15.663 | 1.00 | 28.06 |
| ATOM | 1114 | O | ASP | 132 | 15.518 | 22.831 | −16.495 | 1.00 | 29.94 |
| ATOM | 1115 | N | ASN | 164 | 25.314 | 23.402 | −5.211 | 1.00 | 33.87 |
| ATOM | 1116 | CA | ASN | 164 | 24.815 | 22.265 | −4.447 | 1.00 | 34.28 |
| ATOM | 1117 | CB | ASN | 164 | 25.587 | 20.962 | −4.769 | 1.00 | 32.50 |
| ATOM | 1118 | CG | ASN | 164 | 25.380 | 20.465 | −6.207 | 1.00 | 32.82 |
| ATOM | 1119 | OD1 | ASN | 164 | 24.513 | 20.961 | −6.951 | 1.00 | 30.94 |
| ATOM | 1120 | ND2 | ASN | 164 | 26.195 | 19.475 | −6.602 | 1.00 | 29.12 |
| ATOM | 1121 | C | ASN | 164 | 24.727 | 22.456 | −2.912 | 1.00 | 34.97 |
| ATOM | 1122 | O | ASN | 164 | 24.560 | 21.480 | −2.191 | 1.00 | 35.11 |
| ATOM | 1123 | O | HOH | 22 | 28.681 | 18.090 | −11.230 | 1.00 | 32.23 |
| ATOM | 1124 | O | HOH | 29 | 4.554 | 23.293 | −3.291 | 1.00 | 31.47 |
| ATOM | 1125 | O | HOH | 44 | 35.630 | 15.477 | −13.465 | 1.00 | 22.54 |
| ATOM | 1126 | O | HOH | 50 | 4.582 | 15.501 | −4.314 | 1.00 | 34.62 |
| ATOM | 1127 | O | HOH | 54 | 15.874 | 15.471 | −6.512 | 1.00 | 43.09 |
| ATOM | 1128 | O | HOH | 64 | 17.944 | 16.664 | −10.260 | 1.00 | 28.09 |
| ATOM | 1129 | O | HOH | 83 | 23.224 | 11.884 | −11.602 | 1.00 | 34.38 |
| ATOM | 1130 | O | HOH | 108 | 10.640 | 19.777 | −2.222 | 1.00 | 36.21 |
| ATOM | 1131 | O | HOH | 149 | 35.604 | 14.186 | −10.800 | 1.00 | 40.80 |
| ATOM | 1132 | O | HOH | 163 | 24.252 | 15.169 | −5.176 | 1.00 | 33.75 |
| ATOM | 1133 | O | HOH | 172 | 20.199 | 14.766 | −11.423 | 1.00 | 32.80 |
| ATOM | 1134 | O | HOH | 195 | 23.617 | 8.977 | −9.104 | 1.00 | 49.16 |
| ATOM | 1135 | O | HOH | 196 | 11.011 | 13.162 | −8.264 | 1.00 | 40.63 |
| ATOM | 1136 | O | HOH | 222 | 28.796 | 15.080 | −10.369 | 1.00 | 44.82 |
| ATOM | 1137 | O | HOH | 231 | 10.538 | 13.156 | −11.161 | 1.00 | 47.28 |
| TER | | | | | | | | | |

TABLE 8

| REMARK | Accelrys ViewerPro PDB file | | | | | | | |
|---|---|---|---|---|---|---|---|---|
| REMARK | Created: | Tue Dec 14 21:17:04 Pacific Standard Time 2010 | | | | | | |
| ATOM | 1 | N | ASN | 21 | 53.441 | 15.821 | −13.029 | 1.00 | 75.05 |
| ATOM | 2 | CA | ASN | 21 | 54.382 | 15.970 | −11.876 | 1.00 | 75.35 |
| ATOM | 3 | CB | ASN | 21 | 55.537 | 16.960 | −12.200 | 1.00 | 75.78 |
| ATOM | 4 | CG | ASN | 21 | 55.868 | 17.047 | −13.706 | 1.00 | 76.69 |
| ATOM | 5 | OD1 | ASN | 21 | 56.509 | 16.158 | −14.276 | 1.00 | 77.28 |
| ATOM | 6 | ND2 | ASN | 21 | 55.448 | 18.141 | −14.338 | 1.00 | 76.09 |
| ATOM | 7 | C | ASN | 21 | 53.627 | 16.447 | −10.618 | 1.00 | 74.75 |
| ATOM | 8 | O | ASN | 21 | 53.949 | 17.520 | −10.072 | 1.00 | 75.08 |
| ATOM | 9 | N | TYR | 22 | 52.625 | 15.658 | −10.185 | 1.00 | 73.57 |
| ATOM | 10 | CA | TYR | 22 | 51.729 | 15.970 | −9.026 | 1.00 | 71.80 |
| ATOM | 11 | CB | TYR | 22 | 50.460 | 16.724 | −9.468 | 1.00 | 72.49 |
| ATOM | 12 | CG | TYR | 22 | 50.652 | 18.190 | −9.794 | 1.00 | 73.51 |
| ATOM | 13 | CD1 | TYR | 22 | 50.840 | 18.614 | −11.115 | 1.00 | 74.27 |
| ATOM | 14 | CE1 | TYR | 22 | 51.018 | 19.965 | −11.425 | 1.00 | 75.09 |
| ATOM | 15 | CZ | TYR | 22 | 50.996 | 20.921 | −10.406 | 1.00 | 75.52 |
| ATOM | 16 | OH | TYR | 22 | 51.172 | 22.266 | −10.718 | 1.00 | 75.39 |
| ATOM | 17 | CE2 | TYR | 22 | 50.801 | 20.521 | −9.085 | 1.00 | 75.06 |
| ATOM | 18 | CD2 | TYR | 22 | 50.630 | 19.161 | −8.788 | 1.00 | 74.99 |
| ATOM | 19 | C | TYR | 22 | 51.291 | 14.684 | −8.325 | 1.00 | 69.73 |
| ATOM | 20 | O | TYR | 22 | 50.759 | 13.780 | −8.974 | 1.00 | 69.63 |
| ATOM | 21 | N | LEU | 23 | 51.504 | 14.607 | −7.010 | 1.00 | 67.13 |
| ATOM | 22 | CA | LEU | 23 | 51.041 | 13.461 | −6.211 | 1.00 | 64.76 |
| ATOM | 23 | CB | LEU | 23 | 51.904 | 13.280 | −4.947 | 1.00 | 65.44 |
| ATOM | 24 | CG | LEU | 23 | 53.413 | 12.965 | −5.082 | 1.00 | 67.86 |
| ATOM | 25 | CD1 | LEU | 23 | 54.161 | 13.087 | −3.717 | 1.00 | 68.53 |
| ATOM | 26 | CD2 | LEU | 23 | 53.689 | 11.593 | −5.760 | 1.00 | 68.46 |
| ATOM | 27 | C | LEU | 23 | 49.543 | 13.560 | −5.847 | 1.00 | 62.18 |
| ATOM | 28 | O | LEU | 23 | 49.103 | 14.518 | −5.205 | 1.00 | 61.84 |
| ATOM | 29 | N | VAL | 30 | 54.901 | 16.614 | 1.727 | 1.00 | 45.50 |
| ATOM | 30 | CA | VAL | 30 | 55.013 | 17.847 | 0.919 | 1.00 | 44.60 |
| ATOM | 31 | CB | VAL | 30 | 54.115 | 17.880 | −0.357 | 1.00 | 44.72 |
| ATOM | 32 | CG1 | VAL | 30 | 52.621 | 17.681 | −0.034 | 1.00 | 44.74 |
| ATOM | 33 | CG2 | VAL | 30 | 54.609 | 16.887 | −1.365 | 1.00 | 46.76 |
| ATOM | 34 | C | VAL | 30 | 54.838 | 19.159 | 1.713 | 1.00 | 43.05 |
| ATOM | 35 | O | VAL | 30 | 55.304 | 20.211 | 1.285 | 1.00 | 42.14 |
| ATOM | 36 | N | LEU | 31 | 54.183 | 19.065 | 2.862 | 1.00 | 42.07 |
| ATOM | 37 | CA | LEU | 31 | 53.934 | 20.203 | 3.733 | 1.00 | 41.72 |
| ATOM | 38 | CB | LEU | 31 | 53.133 | 19.736 | 4.955 | 1.00 | 40.32 |
| ATOM | 39 | CG | LEU | 31 | 51.632 | 19.520 | 4.739 | 1.00 | 38.67 |
| ATOM | 40 | CD1 | LEU | 31 | 50.936 | 18.916 | 5.980 | 1.00 | 36.74 |
| ATOM | 41 | CD2 | LEU | 31 | 50.950 | 20.833 | 4.295 | 1.00 | 34.32 |
| ATOM | 42 | C | LEU | 31 | 55.223 | 20.942 | 4.125 | 1.00 | 42.69 |
| ATOM | 43 | O | LEU | 31 | 56.261 | 20.323 | 4.316 | 1.00 | 42.85 |
| ATOM | 44 | N | PHE | 47 | 43.030 | 29.895 | 5.750 | 1.00 | 28.84 |
| ATOM | 45 | CA | PHE | 47 | 43.003 | 29.416 | 4.338 | 1.00 | 29.05 |
| ATOM | 46 | CB | PHE | 47 | 43.923 | 28.234 | 4.147 | 1.00 | 28.82 |
| ATOM | 47 | CG | PHE | 47 | 45.348 | 28.542 | 4.493 | 1.00 | 33.70 |
| ATOM | 48 | CD1 | PHE | 47 | 45.833 | 28.305 | 5.786 | 1.00 | 33.29 |
| ATOM | 49 | CE1 | PHE | 47 | 47.122 | 28.623 | 6.115 | 1.00 | 37.36 |
| ATOM | 50 | CZ | PHE | 47 | 47.987 | 29.165 | 5.139 | 1.00 | 36.77 |
| ATOM | 51 | CE2 | PHE | 47 | 47.531 | 29.409 | 3.869 | 1.00 | 35.15 |
| ATOM | 52 | CD2 | PHE | 47 | 46.197 | 29.114 | 3.551 | 1.00 | 35.97 |
| ATOM | 53 | C | PHE | 47 | 41.603 | 29.022 | 3.876 | 1.00 | 29.27 |
| ATOM | 54 | O | PHE | 47 | 40.930 | 28.211 | 4.513 | 1.00 | 28.82 |
| ATOM | 55 | N | ASN | 48 | 41.178 | 29.616 | 2.765 | 1.00 | 29.67 |
| ATOM | 56 | CA | ASN | 48 | 39.976 | 29.216 | 2.063 | 1.00 | 29.45 |
| ATOM | 57 | CB | ASN | 48 | 39.246 | 30.429 | 1.531 | 1.00 | 29.55 |
| ATOM | 58 | CG | ASN | 48 | 38.999 | 31.477 | 2.601 | 1.00 | 31.72 |
| ATOM | 59 | OD1 | ASN | 48 | 38.243 | 31.244 | 3.561 | 1.00 | 31.64 |
| ATOM | 60 | ND2 | ASN | 48 | 39.613 | 32.647 | 2.434 | 1.00 | 28.68 |
| ATOM | 61 | C | ASN | 48 | 40.343 | 28.260 | 0.927 | 1.00 | 29.39 |
| ATOM | 62 | O | ASN | 48 | 41.160 | 28.555 | 0.097 | 1.00 | 30.66 |
| ATOM | 63 | N | CYS | 49 | 39.766 | 27.076 | 0.923 | 1.00 | 28.93 |
| ATOM | 64 | CA | CYS | 49 | 40.195 | 26.030 | 0.019 | 1.00 | 28.55 |
| ATOM | 65 | CB | CYS | 49 | 40.980 | 24.948 | 0.780 | 1.00 | 28.66 |
| ATOM | 66 | SG | CYS | 49 | 42.229 | 25.609 | 1.975 | 1.00 | 32.73 |
| ATOM | 67 | C | CYS | 49 | 38.973 | 25.423 | −0.627 | 1.00 | 27.45 |
| ATOM | 68 | O | CYS | 49 | 38.547 | 24.373 | −0.218 | 1.00 | 27.31 |
| ATOM | 69 | N | PRO | 50 | 38.389 | 26.109 | −1.616 | 1.00 | 26.98 |
| ATOM | 70 | CA | PRO | 50 | 37.168 | 25.674 | −2.308 | 1.00 | 28.14 |
| ATOM | 71 | CB | PRO | 50 | 36.719 | 26.925 | −3.045 | 1.00 | 27.05 |
| ATOM | 72 | CG | PRO | 50 | 37.742 | 27.955 | −2.757 | 1.00 | 27.46 |
| ATOM | 73 | CD | PRO | 50 | 38.919 | 27.349 | −2.178 | 1.00 | 26.73 |
| ATOM | 74 | C | PRO | 50 | 37.404 | 24.537 | −3.335 | 1.00 | 28.93 |
| ATOM | 75 | O | PRO | 50 | 36.464 | 24.037 | −3.908 | 1.00 | 29.56 |
| ATOM | 76 | N | GLU | 51 | 38.636 | 24.126 | −3.561 | 1.00 | 28.99 |
| ATOM | 77 | CA | GLU | 51 | 38.863 | 23.181 | −4.643 | 1.00 | 30.87 |
| ATOM | 78 | CB | GLU | 51 | 39.933 | 23.754 | −5.594 | 1.00 | 29.68 |

TABLE 8-continued

| | | | | | | | | | |
|---|---|---|---|---|---|---|---|---|---|
| ATOM | 79 | CG | GLU | 51 | 39.404 | 24.923 | −6.469 | 1.00 | 30.84 |
| ATOM | 80 | CD | GLU | 51 | 40.487 | 25.651 | −7.281 | 1.00 | 32.39 |
| ATOM | 81 | OE1 | GLU | 51 | 41.586 | 25.094 | −7.441 | 1.00 | 32.62 |
| ATOM | 82 | OE2 | GLU | 51 | 40.269 | 26.818 | −7.734 | 1.00 | 37.18 |
| ATOM | 83 | C | GLU | 51 | 39.238 | 21.808 | −4.089 | 1.00 | 30.84 |
| ATOM | 84 | O | GLU | 51 | 39.908 | 21.043 | −4.739 | 1.00 | 32.13 |
| ATOM | 85 | N | PHE | 52 | 38.795 | 21.486 | −2.874 | 1.00 | 31.69 |
| ATOM | 86 | CA | PHE | 52 | 39.044 | 20.149 | −2.295 | 1.00 | 31.23 |
| ATOM | 87 | CB | PHE | 52 | 38.808 | 20.104 | −0.748 | 1.00 | 31.35 |
| ATOM | 88 | CG | PHE | 52 | 39.253 | 18.807 | −0.131 | 1.00 | 28.85 |
| ATOM | 89 | CD1 | PHE | 52 | 40.608 | 18.567 | 0.122 | 1.00 | 25.99 |
| ATOM | 90 | CE1 | PHE | 52 | 41.033 | 17.366 | 0.681 | 1.00 | 23.31 |
| ATOM | 91 | CZ | PHE | 52 | 40.136 | 16.373 | 0.942 | 1.00 | 24.81 |
| ATOM | 92 | CE2 | PHE | 52 | 38.810 | 16.579 | 0.675 | 1.00 | 27.90 |
| ATOM | 93 | CD2 | PHE | 52 | 38.365 | 17.807 | 0.103 | 1.00 | 25.84 |
| ATOM | 94 | C | PHE | 52 | 38.212 | 19.058 | −2.934 | 1.00 | 30.68 |
| ATOM | 95 | O | PHE | 52 | 36.997 | 19.208 | −3.062 | 1.00 | 32.04 |
| ATOM | 96 | N | THR | 53 | 38.860 | 17.948 | −3.280 | 1.00 | 30.01 |
| ATOM | 97 | CA | THR | 53 | 38.183 | 16.694 | −3.678 | 1.00 | 29.44 |
| ATOM | 98 | CB | THR | 53 | 37.840 | 16.658 | −5.235 | 1.00 | 29.62 |
| ATOM | 99 | OG1 | THR | 53 | 37.131 | 15.442 | −5.556 | 1.00 | 29.40 |
| ATOM | 100 | CG2 | THR | 53 | 39.072 | 16.811 | −6.094 | 1.00 | 25.18 |
| ATOM | 101 | C | THR | 53 | 38.990 | 15.457 | −3.243 | 1.00 | 30.25 |
| ATOM | 102 | O | THR | 53 | 40.215 | 15.543 | −3.068 | 1.00 | 31.21 |
| ATOM | 103 | N | SER | 54 | 38.300 | 14.356 | −3.003 | 1.00 | 30.79 |
| ATOM | 104 | CA | SER | 54 | 38.904 | 13.065 | −2.708 | 1.00 | 32.95 |
| ATOM | 105 | CB | SER | 54 | 39.301 | 12.946 | −1.220 | 1.00 | 34.16 |
| ATOM | 106 | OG | SER | 54 | 38.154 | 13.067 | −0.381 | 1.00 | 35.15 |
| ATOM | 107 | C | SER | 54 | 37.889 | 12.001 | −3.016 | 1.00 | 34.08 |
| ATOM | 108 | O | SER | 54 | 36.913 | 12.280 | −3.712 | 1.00 | 33.43 |
| ATOM | 109 | N | ASP | 63 | 34.310 | 12.988 | −4.041 | 1.00 | 34.81 |
| ATOM | 110 | CA | ASP | 63 | 33.615 | 13.918 | −3.138 | 1.00 | 33.85 |
| ATOM | 111 | CB | ASP | 63 | 33.883 | 13.641 | −1.635 | 1.00 | 35.11 |
| ATOM | 112 | CG | ASP | 63 | 33.749 | 12.160 | −1.212 | 1.00 | 42.47 |
| ATOM | 113 | OD1 | ASP | 63 | 32.689 | 11.539 | −1.559 | 1.00 | 45.14 |
| ATOM | 114 | OD2 | ASP | 63 | 34.699 | 11.672 | −0.463 | 1.00 | 44.13 |
| ATOM | 115 | C | ASP | 63 | 34.272 | 15.249 | −3.337 | 1.00 | 31.61 |
| ATOM | 116 | O | ASP | 63 | 35.487 | 15.294 | −3.648 | 1.00 | 30.61 |
| ATOM | 117 | N | PHE | 64 | 33.523 | 16.303 | −3.001 | 1.00 | 28.89 |
| ATOM | 118 | CA | PHE | 64 | 33.915 | 17.698 | −3.121 | 1.00 | 28.44 |
| ATOM | 119 | CB | PHE | 64 | 33.244 | 18.303 | −4.359 | 1.00 | 27.72 |
| ATOM | 120 | CG | PHE | 64 | 33.646 | 17.622 | −5.640 | 1.00 | 28.55 |
| ATOM | 121 | CD1 | PHE | 64 | 33.020 | 16.441 | −6.040 | 1.00 | 29.74 |
| ATOM | 122 | CE1 | PHE | 64 | 33.416 | 15.763 | −7.209 | 1.00 | 27.82 |
| ATOM | 123 | CZ | PHE | 64 | 34.461 | 16.270 | −7.957 | 1.00 | 28.20 |
| ATOM | 124 | CE2 | PHE | 64 | 35.108 | 17.463 | −7.578 | 1.00 | 29.67 |
| ATOM | 125 | CD2 | PHE | 64 | 34.698 | 18.137 | −6.416 | 1.00 | 28.64 |
| ATOM | 126 | C | PHE | 64 | 33.573 | 18.547 | −1.875 | 1.00 | 28.20 |
| ATOM | 127 | O | PHE | 64 | 32.483 | 18.436 | −1.322 | 1.00 | 28.02 |
| ATOM | 128 | N | ALA | 65 | 34.507 | 19.416 | −1.459 | 1.00 | 28.57 |
| ATOM | 129 | CA | ALA | 65 | 34.301 | 20.303 | −0.287 | 1.00 | 27.38 |
| ATOM | 130 | CB | ALA | 65 | 34.884 | 19.679 | 0.971 | 1.00 | 26.73 |
| ATOM | 131 | C | ALA | 65 | 34.945 | 21.616 | −0.485 | 1.00 | 27.14 |
| ATOM | 132 | O | ALA | 65 | 35.886 | 21.729 | −1.246 | 1.00 | 27.20 |
| ATOM | 133 | N | THR | 66 | 34.437 | 22.626 | 0.210 | 1.00 | 27.88 |
| ATOM | 134 | CA | THR | 66 | 35.279 | 23.770 | 0.582 | 1.00 | 29.11 |
| ATOM | 135 | CB | THR | 66 | 34.478 | 25.070 | 0.597 | 1.00 | 28.62 |
| ATOM | 136 | OG1 | THR | 66 | 33.918 | 25.269 | −0.677 | 1.00 | 32.67 |
| ATOM | 137 | CG2 | THR | 66 | 35.390 | 26.324 | 0.853 | 1.00 | 30.63 |
| ATOM | 138 | C | THR | 66 | 35.842 | 23.477 | 1.998 | 1.00 | 29.04 |
| ATOM | 139 | O | THR | 66 | 35.097 | 23.066 | 2.902 | 1.00 | 29.39 |
| ATOM | 140 | N | ILE | 67 | 37.125 | 23.721 | 2.204 | 1.00 | 29.87 |
| ATOM | 141 | CA | ILE | 67 | 37.708 | 23.582 | 3.534 | 1.00 | 29.83 |
| ATOM | 142 | CB | ILE | 67 | 38.859 | 22.582 | 3.534 | 1.00 | 30.58 |
| ATOM | 143 | CG1 | ILE | 67 | 38.416 | 21.220 | 2.963 | 1.00 | 28.17 |
| ATOM | 144 | CD1 | ILE | 67 | 39.620 | 20.207 | 2.974 | 1.00 | 30.71 |
| ATOM | 145 | CG2 | ILE | 67 | 39.441 | 22.400 | 4.944 | 1.00 | 32.44 |
| ATOM | 146 | C | ILE | 67 | 38.197 | 24.937 | 3.995 | 1.00 | 29.75 |
| ATOM | 147 | O | ILE | 67 | 38.834 | 25.691 | 3.218 | 1.00 | 30.09 |
| ATOM | 148 | N | TYR | 68 | 37.831 | 25.286 | 5.230 | 1.00 | 29.10 |
| ATOM | 149 | CA | TYR | 68 | 38.315 | 26.508 | 5.868 | 1.00 | 29.33 |
| ATOM | 150 | CB | TYR | 68 | 37.151 | 27.346 | 6.397 | 1.00 | 29.75 |
| ATOM | 151 | CG | TYR | 68 | 36.178 | 27.746 | 5.325 | 1.00 | 29.38 |
| ATOM | 152 | CD1 | TYR | 68 | 35.006 | 27.033 | 5.135 | 1.00 | 32.55 |
| ATOM | 153 | CE1 | TYR | 68 | 34.100 | 27.362 | 4.116 | 1.00 | 32.20 |
| ATOM | 154 | CZ | TYR | 68 | 34.394 | 28.446 | 3.284 | 1.00 | 33.29 |
| ATOM | 155 | OH | TYR | 68 | 33.494 | 28.795 | 2.288 | 1.00 | 32.89 |
| ATOM | 156 | CE2 | TYR | 68 | 35.574 | 29.186 | 3.456 | 1.00 | 29.83 |
| ATOM | 157 | CD2 | TYR | 68 | 36.451 | 28.838 | 4.468 | 1.00 | 31.54 |
| ATOM | 158 | C | TYR | 68 | 39.308 | 26.119 | 6.981 | 1.00 | 29.45 |

TABLE 8-continued

| | | | | | | | | | |
|---|---|---|---|---|---|---|---|---|---|
| ATOM | 159 | O | TYR | 68 | 39.026 | 25.278 | 7.847 | 1.00 | 29.05 |
| ATOM | 160 | N | GLU | 79 | 53.399 | 27.035 | 4.479 | 1.00 | 37.59 |
| ATOM | 161 | CA | GLU | 79 | 53.584 | 27.727 | 3.186 | 1.00 | 38.47 |
| ATOM | 162 | CB | GLU | 79 | 54.979 | 27.347 | 2.636 | 1.00 | 39.42 |
| ATOM | 163 | CG | GLU | 79 | 55.463 | 28.209 | 1.513 | 1.00 | 42.55 |
| ATOM | 164 | CD | GLU | 79 | 54.736 | 27.874 | 0.199 | 1.00 | 45.29 |
| ATOM | 165 | OE1 | GLU | 79 | 54.494 | 26.664 | −0.012 | 1.00 | 48.69 |
| ATOM | 166 | OE2 | GLU | 79 | 54.412 | 28.802 | −0.596 | 1.00 | 40.76 |
| ATOM | 167 | C | GLU | 79 | 52.447 | 27.239 | 2.269 | 1.00 | 38.04 |
| ATOM | 168 | O | GLU | 79 | 52.125 | 26.034 | 2.264 | 1.00 | 37.98 |
| ATOM | 169 | N | SER | 80 | 51.779 | 28.162 | 1.571 | 1.00 | 37.39 |
| ATOM | 170 | CA | SER | 80 | 50.506 | 27.825 | 0.940 | 1.00 | 37.75 |
| ATOM | 171 | CB | SER | 80 | 49.650 | 29.040 | 0.662 | 1.00 | 37.68 |
| ATOM | 172 | OG | SER | 80 | 50.402 | 29.990 | −0.039 | 1.00 | 40.99 |
| ATOM | 173 | C | SER | 80 | 50.604 | 26.933 | −0.300 | 1.00 | 38.14 |
| ATOM | 174 | O | SER | 80 | 49.790 | 25.972 | −0.464 | 1.00 | 38.41 |
| ATOM | 175 | N | LYS | 81 | 51.601 | 27.186 | −1.139 | 1.00 | 38.05 |
| ATOM | 176 | CA | LYS | 81 | 51.952 | 26.167 | −2.166 | 1.00 | 38.29 |
| ATOM | 177 | CB | LYS | 81 | 53.203 | 26.541 | −2.956 | 1.00 | 38.47 |
| ATOM | 178 | CG | LYS | 81 | 53.269 | 25.762 | −4.269 | 1.00 | 43.77 |
| ATOM | 179 | CD | LYS | 81 | 54.076 | 26.500 | −5.355 | 1.00 | 49.29 |
| ATOM | 180 | CE | LYS | 81 | 55.546 | 26.090 | −5.323 | 1.00 | 54.55 |
| ATOM | 181 | NZ | LYS | 81 | 56.188 | 26.320 | −6.669 | 1.00 | 57.78 |
| ATOM | 182 | C | LYS | 81 | 52.028 | 24.721 | −1.646 | 1.00 | 36.81 |
| ATOM | 183 | O | LYS | 81 | 51.366 | 23.822 | −2.213 | 1.00 | 37.85 |
| ATOM | 184 | N | SER | 82 | 52.774 | 24.477 | −0.570 | 1.00 | 35.20 |
| ATOM | 185 | CA | SER | 82 | 52.858 | 23.113 | 0.023 | 1.00 | 33.64 |
| ATOM | 186 | CB | SER | 82 | 53.818 | 23.128 | 1.230 | 1.00 | 34.75 |
| ATOM | 187 | OG | SER | 82 | 53.235 | 23.751 | 2.368 | 1.00 | 33.65 |
| ATOM | 188 | C | SER | 82 | 51.509 | 22.575 | 0.452 | 1.00 | 32.78 |
| ATOM | 189 | O | SER | 82 | 51.231 | 21.370 | 0.403 | 1.00 | 33.37 |
| ATOM | 190 | N | LEU | 83 | 50.652 | 23.495 | 0.887 | 1.00 | 32.92 |
| ATOM | 191 | CA | LEU | 83 | 49.317 | 23.186 | 1.406 | 1.00 | 31.80 |
| ATOM | 192 | CB | LEU | 83 | 48.714 | 24.415 | 2.145 | 1.00 | 32.13 |
| ATOM | 193 | CG | LEU | 83 | 47.275 | 24.110 | 2.627 | 1.00 | 31.44 |
| ATOM | 194 | CD1 | LEU | 83 | 47.272 | 22.824 | 3.530 | 1.00 | 27.03 |
| ATOM | 195 | CD2 | LEU | 83 | 46.619 | 25.291 | 3.322 | 1.00 | 30.07 |
| ATOM | 196 | C | LEU | 83 | 48.407 | 22.753 | 0.253 | 1.00 | 31.38 |
| ATOM | 197 | O | LEU | 83 | 47.678 | 21.729 | 0.339 | 1.00 | 29.64 |
| ATOM | 198 | N | LYS | 84 | 48.430 | 23.574 | −0.790 | 1.00 | 32.24 |
| ATOM | 199 | CA | LYS | 84 | 47.827 | 23.249 | −2.121 | 1.00 | 34.04 |
| ATOM | 200 | CB | LYS | 84 | 48.256 | 24.307 | −3.159 | 1.00 | 33.44 |
| ATOM | 201 | CG | LYS | 84 | 47.798 | 23.981 | −4.580 | 1.00 | 35.85 |
| ATOM | 202 | CD | LYS | 84 | 48.488 | 24.866 | −5.630 | 1.00 | 35.52 |
| ATOM | 203 | CE | LYS | 84 | 49.861 | 24.320 | −5.999 | 1.00 | 38.91 |
| ATOM | 204 | NZ | LYS | 84 | 50.532 | 25.118 | −7.094 | 1.00 | 44.21 |
| ATOM | 205 | C | LYS | 84 | 48.198 | 21.830 | −2.582 | 1.00 | 33.50 |
| ATOM | 206 | O | LYS | 84 | 47.315 | 20.984 | −2.853 | 1.00 | 35.57 |
| ATOM | 207 | N | LEU | 85 | 49.495 | 21.539 | −2.592 | 1.00 | 33.06 |
| ATOM | 208 | CA | LEU | 85 | 49.996 | 20.214 | −2.998 | 1.00 | 33.43 |
| ATOM | 209 | CB | LEU | 85 | 51.508 | 20.244 | −3.063 | 1.00 | 32.74 |
| ATOM | 210 | CG | LEU | 85 | 52.117 | 21.240 | −4.058 | 1.00 | 36.78 |
| ATOM | 211 | CD1 | LEU | 85 | 53.704 | 21.140 | −4.039 | 1.00 | 37.48 |
| ATOM | 212 | CD2 | LEU | 85 | 51.605 | 20.932 | −5.456 | 1.00 | 38.46 |
| ATOM | 213 | C | LEU | 85 | 49.530 | 19.170 | −2.007 | 1.00 | 33.59 |
| ATOM | 214 | O | LEU | 85 | 49.119 | 18.075 | −2.358 | 1.00 | 33.78 |
| ATOM | 215 | N | TYR | 86 | 49.575 | 19.526 | −0.733 | 1.00 | 33.33 |
| ATOM | 216 | CA | TYR | 86 | 49.111 | 18.578 | 0.265 | 1.00 | 32.84 |
| ATOM | 217 | CB | TYR | 86 | 49.384 | 19.118 | 1.687 | 1.00 | 32.11 |
| ATOM | 218 | CG | TYR | 86 | 48.715 | 18.313 | 2.775 | 1.00 | 31.82 |
| ATOM | 219 | CD1 | TYR | 86 | 49.153 | 17.015 | 3.086 | 1.00 | 28.59 |
| ATOM | 220 | CE1 | TYR | 86 | 48.534 | 16.278 | 4.088 | 1.00 | 32.86 |
| ATOM | 221 | CZ | TYR | 86 | 47.451 | 16.843 | 4.793 | 1.00 | 31.37 |
| ATOM | 222 | OH | TYR | 86 | 46.805 | 16.140 | 5.761 | 1.00 | 30.97 |
| ATOM | 223 | CE2 | TYR | 86 | 47.010 | 18.122 | 4.508 | 1.00 | 31.22 |
| ATOM | 224 | CD2 | TYR | 86 | 47.633 | 18.855 | 3.502 | 1.00 | 31.02 |
| ATOM | 225 | C | TYR | 86 | 47.647 | 18.227 | 0.022 | 1.00 | 31.81 |
| ATOM | 226 | O | TYR | 86 | 47.262 | 17.048 | 0.012 | 1.00 | 31.35 |
| ATOM | 227 | N | LEU | 87 | 46.825 | 19.242 | −0.194 | 1.00 | 31.78 |
| ATOM | 228 | CA | LEU | 87 | 45.397 | 18.990 | −0.488 | 1.00 | 31.82 |
| ATOM | 229 | CB | LEU | 87 | 44.615 | 20.304 | −0.402 | 1.00 | 32.18 |
| ATOM | 230 | CG | LEU | 87 | 44.563 | 20.959 | 1.019 | 1.00 | 31.56 |
| ATOM | 231 | CD1 | LEU | 87 | 43.635 | 22.132 | 1.000 | 1.00 | 32.47 |
| ATOM | 232 | CD2 | LEU | 87 | 44.106 | 19.982 | 2.020 | 1.00 | 26.18 |
| ATOM | 233 | C | LEU | 87 | 45.098 | 18.244 | −1.807 | 1.00 | 32.75 |
| ATOM | 234 | O | LEU | 87 | 44.137 | 17.476 | −1.892 | 1.00 | 32.73 |
| ATOM | 235 | N | PHE | 88 | 45.904 | 18.497 | −2.841 | 1.00 | 34.10 |
| ATOM | 236 | CA | PHE | 88 | 45.824 | 17.756 | −4.105 | 1.00 | 35.05 |
| ATOM | 237 | CB | PHE | 88 | 46.940 | 18.166 | −5.095 | 1.00 | 35.48 |
| ATOM | 238 | CG | PHE | 88 | 46.727 | 19.504 | −5.775 | 1.00 | 36.14 |

TABLE 8-continued

| | | | | | | | | | |
|---|---|---|---|---|---|---|---|---|---|
| ATOM | 239 | CD1 | PHE | 88 | 47.805 | 20.162 | −6.373 | 1.00 | 38.84 |
| ATOM | 240 | CE1 | PHE | 88 | 47.613 | 21.373 | −7.044 | 1.00 | 38.29 |
| ATOM | 241 | CZ | PHE | 88 | 46.340 | 21.957 | −7.087 | 1.00 | 38.18 |
| ATOM | 242 | CE2 | PHE | 88 | 45.256 | 21.316 | −6.478 | 1.00 | 36.77 |
| ATOM | 243 | CD2 | PHE | 88 | 45.460 | 20.097 | −5.829 | 1.00 | 38.00 |
| ATOM | 244 | C | PHE | 88 | 46.019 | 16.296 | −3.832 | 1.00 | 35.83 |
| ATOM | 245 | O | PHE | 88 | 45.435 | 15.456 | −4.522 | 1.00 | 35.38 |
| ATOM | 246 | N | SER | 89 | 46.884 | 15.982 | −2.863 | 1.00 | 35.76 |
| ATOM | 247 | CA | SER | 89 | 47.287 | 14.599 | −2.627 | 1.00 | 34.90 |
| ATOM | 248 | CB | SER | 89 | 48.447 | 14.561 | −1.617 | 1.00 | 35.63 |
| ATOM | 249 | OG | SER | 89 | 47.999 | 14.572 | −0.257 | 1.00 | 35.63 |
| ATOM | 250 | C | SER | 89 | 46.156 | 13.709 | −2.170 | 1.00 | 35.05 |
| ATOM | 251 | O | SER | 89 | 46.327 | 12.488 | −2.031 | 1.00 | 35.82 |
| ATOM | 252 | N | PHE | 90 | 44.996 | 14.292 | −1.871 | 1.00 | 34.87 |
| ATOM | 253 | CA | PHE | 90 | 43.826 | 13.474 | −1.489 | 1.00 | 34.62 |
| ATOM | 254 | CB | PHE | 90 | 42.889 | 14.214 | −0.526 | 1.00 | 34.78 |
| ATOM | 255 | CG | PHE | 90 | 43.417 | 14.335 | 0.864 | 1.00 | 36.36 |
| ATOM | 256 | CD1 | PHE | 90 | 44.357 | 15.306 | 1.183 | 1.00 | 34.82 |
| ATOM | 257 | CE1 | PHE | 90 | 44.862 | 15.414 | 2.469 | 1.00 | 37.21 |
| ATOM | 258 | CZ | PHE | 90 | 44.425 | 14.559 | 3.455 | 1.00 | 36.41 |
| ATOM | 259 | CE2 | PHE | 90 | 43.437 | 13.608 | 3.177 | 1.00 | 40.24 |
| ATOM | 260 | CD2 | PHE | 90 | 42.948 | 13.488 | 1.870 | 1.00 | 39.21 |
| ATOM | 261 | C | PHE | 90 | 43.015 | 13.119 | −2.707 | 1.00 | 34.30 |
| ATOM | 262 | O | PHE | 90 | 42.034 | 12.393 | −2.578 | 1.00 | 33.27 |
| ATOM | 263 | N | ARG | 91 | 43.394 | 13.653 | −3.876 | 1.00 | 34.65 |
| ATOM | 264 | CA | ARG | 91 | 42.519 | 13.588 | −5.057 | 1.00 | 36.62 |
| ATOM | 265 | CB | ARG | 91 | 43.149 | 14.284 | −6.265 | 1.00 | 36.64 |
| ATOM | 266 | CG | ARG | 91 | 42.338 | 14.272 | −7.542 | 1.00 | 35.88 |
| ATOM | 267 | CD | ARG | 91 | 43.115 | 15.082 | −8.557 | 1.00 | 33.61 |
| ATOM | 268 | NE | ARG | 91 | 42.400 | 15.312 | −9.795 | 1.00 | 30.74 |
| ATOM | 269 | CZ | ARG | 91 | 41.534 | 16.291 | −10.004 | 1.00 | 34.38 |
| ATOM | 270 | NH1 | ARG | 91 | 41.243 | 17.151 | −9.016 | 1.00 | 32.01 |
| ATOM | 271 | NH2 | ARG | 91 | 40.925 | 16.397 | −11.204 | 1.00 | 29.74 |
| ATOM | 272 | C | ARG | 91 | 42.139 | 12.166 | −5.388 | 1.00 | 37.03 |
| ATOM | 273 | O | ARG | 91 | 40.979 | 11.894 | −5.679 | 1.00 | 37.70 |
| ATOM | 274 | N | GLY | 121 | 35.180 | 21.526 | 7.163 | 1.00 | 27.57 |
| ATOM | 275 | CA | GLY | 121 | 34.943 | 21.094 | 5.780 | 1.00 | 27.83 |
| ATOM | 276 | C | GLY | 121 | 33.467 | 21.172 | 5.497 | 1.00 | 28.51 |
| ATOM | 277 | O | GLY | 121 | 32.683 | 20.935 | 6.382 | 1.00 | 27.13 |
| ATOM | 278 | N | LYS | 122 | 33.081 | 21.588 | 4.286 | 1.00 | 29.24 |
| ATOM | 279 | CA | LYS | 122 | 31.683 | 21.661 | 3.939 | 1.00 | 28.64 |
| ATOM | 280 | CB | LYS | 122 | 31.275 | 23.121 | 3.826 | 1.00 | 29.09 |
| ATOM | 281 | CG | LYS | 122 | 31.317 | 23.843 | 5.214 | 1.00 | 29.14 |
| ATOM | 282 | CD | LYS | 122 | 31.074 | 25.289 | 5.116 | 1.00 | 25.90 |
| ATOM | 283 | CE | LYS | 122 | 31.095 | 25.903 | 6.495 | 1.00 | 30.47 |
| ATOM | 284 | NZ | LYS | 122 | 30.577 | 27.300 | 6.414 | 1.00 | 33.80 |
| ATOM | 285 | C | LYS | 122 | 31.519 | 20.888 | 2.618 | 1.00 | 29.89 |
| ATOM | 286 | O | LYS | 122 | 31.863 | 21.398 | 1.554 | 1.00 | 29.56 |
| ATOM | 287 | N | PHE | 123 | 31.024 | 19.644 | 2.716 | 1.00 | 29.77 |
| ATOM | 288 | CA | PHE | 123 | 30.958 | 18.762 | 1.581 | 1.00 | 28.78 |
| ATOM | 289 | CB | PHE | 123 | 31.172 | 17.306 | 1.978 | 1.00 | 27.79 |
| ATOM | 290 | CG | PHE | 123 | 32.601 | 16.996 | 2.284 | 1.00 | 29.54 |
| ATOM | 291 | CD1 | PHE | 123 | 33.162 | 17.352 | 3.529 | 1.00 | 26.50 |
| ATOM | 292 | CE1 | PHE | 123 | 34.489 | 17.114 | 3.823 | 1.00 | 24.89 |
| ATOM | 293 | CZ | PHE | 123 | 35.304 | 16.466 | 2.894 | 1.00 | 30.34 |
| ATOM | 294 | CE2 | PHE | 123 | 34.755 | 16.062 | 1.632 | 1.00 | 31.05 |
| ATOM | 295 | CD2 | PHE | 123 | 33.406 | 16.347 | 1.342 | 1.00 | 30.05 |
| ATOM | 296 | C | PHE | 123 | 29.681 | 18.952 | 0.841 | 1.00 | 29.23 |
| ATOM | 297 | O | PHE | 123 | 28.667 | 19.369 | 1.438 | 1.00 | 27.66 |
| ATOM | 298 | N | ASN | 164 | 20.552 | 22.746 | −0.945 | 1.00 | 35.87 |
| ATOM | 299 | CA | ASN | 164 | 21.113 | 21.845 | −1.951 | 1.00 | 37.23 |
| ATOM | 300 | CB | ASN | 164 | 20.407 | 20.477 | −1.955 | 1.00 | 36.18 |
| ATOM | 301 | CG | ASN | 164 | 20.831 | 19.627 | −0.771 | 1.00 | 38.54 |
| ATOM | 302 | OD1 | ASN | 164 | 21.710 | 20.043 | 0.018 | 1.00 | 35.02 |
| ATOM | 303 | ND2 | ASN | 164 | 20.212 | 18.444 | −0.619 | 1.00 | 36.60 |
| ATOM | 304 | C | ASN | 164 | 21.225 | 22.470 | −3.341 | 1.00 | 37.19 |
| ATOM | 305 | O | ASN | 164 | 21.469 | 21.790 | −4.323 | 1.00 | 37.79 |
| ATOM | 306 | O6 | GDQ | 201 | 51.673 | 34.977 | 1.685 | 1.00 | 47.86 |
| ATOM | 307 | C6 | GDQ | 201 | 51.979 | 33.654 | 1.751 | 1.00 | 49.13 |
| ATOM | 308 | N1 | GDQ | 201 | 51.693 | 32.967 | 2.883 | 1.00 | 48.48 |
| ATOM | 309 | C5 | GDQ | 201 | 52.577 | 32.974 | 0.668 | 1.00 | 50.29 |
| ATOM | 310 | C7 | GDQ | 201 | 53.031 | 33.252 | −0.628 | 1.00 | 49.19 |
| ATOM | 311 | C77 | GDQ | 201 | 52.946 | 34.470 | −1.174 | 1.00 | 49.79 |
| ATOM | 312 | N77 | GDQ | 201 | 52.924 | 35.622 | −1.582 | 1.00 | 52.99 |
| ATOM | 313 | C8 | GDQ | 201 | 53.562 | 32.149 | −1.273 | 1.00 | 48.54 |
| ATOM | 314 | N9 | GDQ | 201 | 53.432 | 31.139 | −0.353 | 1.00 | 49.38 |
| ATOM | 315 | C4 | GDQ | 201 | 52.867 | 31.624 | 0.805 | 1.00 | 49.87 |
| ATOM | 316 | N3 | GDQ | 201 | 52.561 | 30.957 | 1.960 | 1.00 | 49.70 |
| ATOM | 317 | C2 | GDQ | 201 | 51.970 | 31.654 | 2.984 | 1.00 | 48.62 |
| ATOM | 318 | N2 | GDQ | 201 | 51.652 | 31.039 | 4.142 | 1.00 | 49.10 |

TABLE 8-continued

| | | | | | | | | |
|---|---|---|---|---|---|---|---|---|
| ATOM | 319 | N | SER | 54 | 50.888 | 43.757 | −3.487 | 1.00 | 33.72 |
| ATOM | 320 | CA | SER | 54 | 52.338 | 43.693 | −3.244 | 1.00 | 35.85 |
| ATOM | 321 | CB | SER | 54 | 52.589 | 43.666 | −1.739 | 1.00 | 35.22 |
| ATOM | 322 | OG | SER | 54 | 52.332 | 42.373 | −1.259 | 1.00 | 33.77 |
| ATOM | 323 | C | SER | 54 | 53.023 | 42.472 | −3.895 | 1.00 | 37.39 |
| ATOM | 324 | O | SER | 54 | 52.430 | 41.780 | −4.706 | 1.00 | 37.18 |
| ATOM | 325 | N | LEU | 55 | 54.256 | 42.181 | −3.506 | 1.00 | 40.28 |
| ATOM | 326 | CA | LEU | 55 | 55.021 | 41.110 | −4.146 | 1.00 | 43.35 |
| ATOM | 327 | CB | LEU | 55 | 56.340 | 41.680 | −4.756 | 1.00 | 42.47 |
| ATOM | 328 | CG | LEU | 55 | 56.261 | 42.856 | −5.782 | 1.00 | 40.35 |
| ATOM | 329 | CD1 | LEU | 55 | 57.622 | 43.240 | −6.452 | 1.00 | 33.89 |
| ATOM | 330 | CD2 | LEU | 55 | 55.236 | 42.575 | −6.873 | 1.00 | 37.65 |
| ATOM | 331 | C | LEU | 55 | 55.284 | 39.876 | −3.255 | 1.00 | 46.35 |
| ATOM | 332 | O | LEU | 55 | 55.737 | 40.014 | −2.124 | 1.00 | 47.81 |
| ATOM | 333 | N | CYS | 56 | 54.999 | 38.679 | −3.767 | 1.00 | 49.44 |
| ATOM | 334 | CA | CYS | 56 | 55.454 | 37.421 | −3.170 | 1.00 | 51.70 |
| ATOM | 335 | CB | CYS | 56 | 55.027 | 36.275 | −4.075 | 1.00 | 52.04 |
| ATOM | 336 | SG | CYS | 56 | 55.743 | 34.668 | −3.714 | 1.00 | 52.43 |
| ATOM | 337 | C | CYS | 56 | 56.987 | 37.429 | −2.997 | 1.00 | 53.76 |
| ATOM | 338 | O | CYS | 56 | 57.729 | 37.654 | −3.965 | 1.00 | 54.33 |
| ATOM | 339 | N | PRO | 57 | 57.491 | 37.195 | −1.766 | 1.00 | 55.15 |
| ATOM | 340 | CA | PRO | 57 | 58.911 | 37.584 | −1.578 | 1.00 | 56.01 |
| ATOM | 341 | CB | PRO | 57 | 59.114 | 37.519 | −0.050 | 1.00 | 55.67 |
| ATOM | 342 | CG | PRO | 57 | 58.121 | 36.516 | 0.418 | 1.00 | 55.68 |
| ATOM | 343 | CD | PRO | 57 | 56.920 | 36.571 | −0.558 | 1.00 | 55.25 |
| ATOM | 344 | C | PRO | 57 | 59.898 | 36.661 | −2.320 | 1.00 | 56.80 |
| ATOM | 345 | O | PRO | 57 | 61.038 | 37.056 | −2.582 | 1.00 | 56.61 |
| ATOM | 346 | N | LYS | 58 | 59.443 | 35.460 | −2.663 | 1.00 | 57.84 |
| ATOM | 347 | CA | LYS | 58 | 60.294 | 34.489 | −3.322 | 1.00 | 59.47 |
| ATOM | 348 | CB | LYS | 58 | 59.876 | 33.057 | −2.962 | 1.00 | 60.28 |
| ATOM | 349 | CG | LYS | 58 | 60.679 | 32.447 | −1.774 | 1.00 | 63.29 |
| ATOM | 350 | CD | LYS | 58 | 60.422 | 33.179 | −0.417 | 1.00 | 64.69 |
| ATOM | 351 | CE | LYS | 58 | 61.315 | 32.659 | 0.729 | 1.00 | 64.11 |
| ATOM | 352 | NZ | LYS | 58 | 61.511 | 31.184 | 0.637 | 1.00 | 64.02 |
| ATOM | 353 | C | LYS | 58 | 60.327 | 34.690 | −4.833 | 1.00 | 59.38 |
| ATOM | 354 | O | LYS | 58 | 61.407 | 34.838 | −5.440 | 1.00 | 59.15 |
| ATOM | 355 | N | VAL | 59 | 59.146 | 34.729 | −5.441 | 1.00 | 59.37 |
| ATOM | 356 | CA | VAL | 59 | 59.086 | 34.728 | −6.898 | 1.00 | 58.99 |
| ATOM | 357 | CB | VAL | 59 | 58.028 | 33.768 | −7.380 | 1.00 | 59.24 |
| ATOM | 358 | CG1 | VAL | 59 | 56.666 | 34.258 | −6.978 | 1.00 | 58.19 |
| ATOM | 359 | CG2 | VAL | 59 | 58.162 | 33.558 | −8.916 | 1.00 | 62.18 |
| ATOM | 360 | C | VAL | 59 | 58.894 | 36.118 | −7.505 | 1.00 | 57.82 |
| ATOM | 361 | O | VAL | 59 | 59.246 | 36.347 | −8.657 | 1.00 | 57.80 |
| ATOM | 362 | N | GLY | 60 | 58.357 | 37.046 | −6.724 | 1.00 | 56.74 |
| ATOM | 363 | CA | GLY | 60 | 58.085 | 38.397 | −7.216 | 1.00 | 55.41 |
| ATOM | 364 | C | GLY | 60 | 56.784 | 38.485 | −8.004 | 1.00 | 54.46 |
| ATOM | 365 | O | GLY | 60 | 56.520 | 39.513 | −8.623 | 1.00 | 54.71 |
| ATOM | 366 | N | GLN | 61 | 56.014 | 37.388 | −8.009 | 1.00 | 53.28 |
| ATOM | 367 | CA | GLN | 61 | 54.624 | 37.331 | −8.472 | 1.00 | 52.84 |
| ATOM | 368 | CB | GLN | 61 | 54.082 | 35.885 | −8.311 | 1.00 | 53.00 |
| ATOM | 369 | CG | GLN | 61 | 53.172 | 35.640 | −7.015 | 1.00 | 56.57 |
| ATOM | 370 | CD | GLN | 61 | 53.162 | 34.186 | −6.392 | 1.00 | 57.11 |
| ATOM | 371 | OE1 | GLN | 61 | 52.154 | 33.764 | −5.780 | 1.00 | 59.50 |
| ATOM | 372 | NE2 | GLN | 61 | 54.290 | 33.450 | −6.517 | 1.00 | 60.79 |
| ATOM | 373 | C | GLN | 61 | 53.816 | 38.290 | −7.589 | 1.00 | 49.52 |
| ATOM | 374 | O | GLN | 61 | 53.966 | 38.252 | −6.404 | 1.00 | 50.07 |
| ATOM | 375 | N | PRO | 62 | 53.011 | 39.189 | −8.166 | 1.00 | 47.30 |
| ATOM | 376 | CA | PRO | 62 | 52.124 | 40.059 | −7.396 | 1.00 | 44.65 |
| ATOM | 377 | CB | PRO | 62 | 51.555 | 41.006 | −8.450 | 1.00 | 44.86 |
| ATOM | 378 | CG | PRO | 62 | 52.464 | 40.913 | −9.619 | 1.00 | 46.60 |
| ATOM | 379 | CD | PRO | 62 | 52.931 | 39.480 | −9.613 | 1.00 | 47.39 |
| ATOM | 380 | C | PRO | 62 | 50.957 | 39.363 | −6.688 | 1.00 | 43.08 |
| ATOM | 381 | O | PRO | 62 | 50.549 | 38.250 | −7.044 | 1.00 | 42.60 |
| ATOM | 382 | N | ASP | 63 | 50.437 | 40.028 | −5.661 | 1.00 | 40.37 |
| ATOM | 383 | CA | ASP | 63 | 49.334 | 39.489 | −4.867 | 1.00 | 38.69 |
| ATOM | 384 | CB | ASP | 63 | 49.820 | 38.925 | −3.535 | 1.00 | 39.74 |
| ATOM | 385 | CG | ASP | 63 | 50.818 | 37.741 | −3.713 | 1.00 | 47.72 |
| ATOM | 386 | OD1 | ASP | 63 | 50.600 | 36.879 | −4.651 | 1.00 | 52.82 |
| ATOM | 387 | OD2 | ASP | 63 | 51.815 | 37.688 | −2.894 | 1.00 | 51.42 |
| ATOM | 388 | C | ASP | 63 | 48.383 | 40.640 | −4.645 | 1.00 | 34.25 |
| ATOM | 389 | O | ASP | 63 | 48.783 | 41.764 | −4.792 | 1.00 | 33.24 |
| ATOM | 390 | N | THR | 124 | 43.423 | 37.518 | −2.809 | 1.00 | 31.67 |
| ATOM | 391 | CA | THR | 124 | 42.881 | 36.704 | −3.933 | 1.00 | 31.12 |
| ATOM | 392 | CB | THR | 124 | 42.958 | 37.455 | −5.292 | 1.00 | 29.90 |
| ATOM | 393 | OG1 | THR | 124 | 44.319 | 37.744 | −5.576 | 1.00 | 29.06 |
| ATOM | 394 | CG2 | THR | 124 | 42.221 | 38.772 | −5.190 | 1.00 | 29.97 |
| ATOM | 395 | C | THR | 124 | 43.599 | 35.360 | −3.972 | 1.00 | 30.92 |
| ATOM | 396 | O | THR | 124 | 44.747 | 35.264 | −3.500 | 1.00 | 31.62 |
| ATOM | 397 | N | PRO | 125 | 42.930 | 34.310 | −4.507 | 1.00 | 31.66 |
| ATOM | 398 | CA | PRO | 125 | 43.516 | 32.973 | −4.441 | 1.00 | 32.62 |

TABLE 8-continued

| | | | | | | | | | |
|---|---|---|---|---|---|---|---|---|---|
| ATOM | 399 | CB | PRO | 125 | 42.360 | 32.048 | −4.866 | 1.00 | 32.91 |
| ATOM | 400 | CG | PRO | 125 | 41.343 | 32.932 | −5.495 | 1.00 | 31.43 |
| ATOM | 401 | CD | PRO | 125 | 41.583 | 34.319 | −5.121 | 1.00 | 30.86 |
| ATOM | 402 | C | PRO | 125 | 44.755 | 32.774 | −5.290 | 1.00 | 34.34 |
| ATOM | 403 | O | PRO | 125 | 44.972 | 33.525 | −6.239 | 1.00 | 34.29 |
| ATOM | 404 | N | ARG | 126 | 45.601 | 31.811 | −4.896 | 1.00 | 35.55 |
| ATOM | 405 | CA | ARG | 126 | 46.768 | 31.401 | −5.693 | 1.00 | 36.86 |
| ATOM | 406 | CB | ARG | 126 | 48.070 | 31.986 | −5.147 | 1.00 | 36.86 |
| ATOM | 407 | CG | ARG | 126 | 48.244 | 33.471 | −5.331 | 1.00 | 42.43 |
| ATOM | 408 | CD | ARG | 126 | 48.292 | 33.896 | −6.821 | 1.00 | 50.65 |
| ATOM | 409 | NE | ARG | 126 | 48.454 | 35.350 | −7.031 | 1.00 | 55.97 |
| ATOM | 410 | CZ | ARG | 126 | 47.560 | 36.135 | −7.648 | 1.00 | 58.82 |
| ATOM | 411 | NH1 | ARG | 126 | 46.415 | 35.640 | −8.097 | 1.00 | 59.04 |
| ATOM | 412 | NH2 | ARG | 126 | 47.806 | 37.429 | −7.812 | 1.00 | 60.14 |
| ATOM | 413 | C | ARG | 126 | 46.816 | 29.907 | −5.546 | 1.00 | 36.57 |
| ATOM | 414 | O | ARG | 126 | 46.833 | 29.411 | −4.418 | 1.00 | 37.65 |
| ATOM | 415 | N | GLY | 127 | 46.779 | 29.163 | −6.648 | 1.00 | 35.58 |
| ATOM | 416 | CA | GLY | 127 | 46.669 | 27.713 | −6.527 | 1.00 | 33.48 |
| ATOM | 417 | C | GLY | 127 | 45.329 | 27.321 | −5.928 | 1.00 | 33.81 |
| ATOM | 418 | O | GLY | 127 | 45.205 | 26.254 | −5.301 | 1.00 | 34.75 |
| ATOM | 419 | N | GLY | 128 | 44.314 | 28.167 | −6.127 | 1.00 | 31.98 |
| ATOM | 420 | CA | GLY | 128 | 43.006 | 27.914 | −5.591 | 1.00 | 31.99 |
| ATOM | 421 | C | GLY | 128 | 42.796 | 28.133 | −4.097 | 1.00 | 31.84 |
| ATOM | 422 | O | GLY | 128 | 41.719 | 27.897 | −3.607 | 1.00 | 33.17 |
| ATOM | 423 | N | ILE | 129 | 43.814 | 28.573 | −3.373 | 1.00 | 31.05 |
| ATOM | 424 | CA | ILE | 129 | 43.699 | 28.809 | −1.925 | 1.00 | 31.68 |
| ATOM | 425 | CB | ILE | 129 | 44.815 | 28.051 | −1.161 | 1.00 | 31.43 |
| ATOM | 426 | CG1 | ILE | 129 | 44.613 | 26.552 | −1.303 | 1.00 | 30.96 |
| ATOM | 427 | CD1 | ILE | 129 | 45.683 | 25.705 | −0.560 | 1.00 | 33.21 |
| ATOM | 428 | CG2 | ILE | 129 | 44.854 | 28.434 | 0.315 | 1.00 | 31.24 |
| ATOM | 429 | C | ILE | 129 | 43.895 | 30.292 | −1.714 | 1.00 | 30.10 |
| ATOM | 430 | O | ILE | 129 | 44.867 | 30.817 | −2.202 | 1.00 | 31.71 |
| ATOM | 431 | N | SER | 130 | 42.974 | 30.969 | −1.042 | 1.00 | 29.38 |
| ATOM | 432 | CA | SER | 130 | 43.245 | 32.330 | −0.597 | 1.00 | 28.88 |
| ATOM | 433 | CB | SER | 130 | 42.057 | 33.227 | −0.949 | 1.00 | 28.32 |
| ATOM | 434 | OG | SER | 130 | 40.886 | 32.666 | −0.402 | 1.00 | 29.12 |
| ATOM | 435 | C | SER | 130 | 43.637 | 32.425 | 0.931 | 1.00 | 29.46 |
| ATOM | 436 | O | SER | 130 | 43.203 | 31.614 | 1.759 | 1.00 | 29.70 |
| ATOM | 437 | N | ILE | 131 | 44.409 | 33.443 | 1.305 | 1.00 | 30.63 |
| ATOM | 438 | CA | ILE | 131 | 44.845 | 33.615 | 2.710 | 1.00 | 31.23 |
| ATOM | 439 | CB | ILE | 131 | 46.379 | 33.713 | 2.811 | 1.00 | 31.38 |
| ATOM | 440 | CG1 | ILE | 131 | 47.024 | 32.594 | 1.984 | 1.00 | 33.26 |
| ATOM | 441 | CD1 | ILE | 131 | 48.561 | 32.547 | 2.015 | 1.00 | 32.05 |
| ATOM | 442 | CG2 | ILE | 131 | 46.847 | 33.588 | 4.274 | 1.00 | 30.53 |
| ATOM | 443 | C | ILE | 131 | 44.251 | 34.895 | 3.270 | 1.00 | 30.83 |
| ATOM | 444 | O | ILE | 131 | 44.311 | 35.897 | 2.627 | 1.00 | 30.60 |
| ATOM | 445 | N | GLU | 160 | 33.027 | 33.216 | 5.921 | 1.00 | 32.84 |
| ATOM | 446 | CA | GLU | 160 | 32.172 | 33.506 | 4.777 | 1.00 | 34.81 |
| ATOM | 447 | CB | GLU | 160 | 32.443 | 34.906 | 4.193 | 1.00 | 34.98 |
| ATOM | 448 | CG | GLU | 160 | 33.930 | 35.134 | 3.781 | 1.00 | 39.80 |
| ATOM | 449 | CD | GLU | 160 | 34.171 | 36.469 | 3.109 | 1.00 | 39.43 |
| ATOM | 450 | OE1 | GLU | 160 | 33.182 | 37.043 | 2.604 | 1.00 | 47.34 |
| ATOM | 451 | OE2 | GLU | 160 | 35.341 | 36.943 | 3.082 | 1.00 | 44.14 |
| ATOM | 452 | C | GLU | 160 | 32.405 | 32.470 | 3.693 | 1.00 | 33.17 |
| ATOM | 453 | O | GLU | 160 | 33.494 | 31.936 | 3.580 | 1.00 | 32.43 |
| ATOM | 454 | N | ILE | 162 | 33.471 | 31.119 | 0.430 | 1.00 | 34.66 |
| ATOM | 455 | CA | ILE | 162 | 34.402 | 31.502 | −0.630 | 1.00 | 36.04 |
| ATOM | 456 | CB | ILE | 162 | 35.860 | 31.753 | −0.066 | 1.00 | 36.58 |
| ATOM | 457 | CG1 | ILE | 162 | 35.893 | 32.999 | 0.854 | 1.00 | 34.58 |
| ATOM | 458 | CD1 | ILE | 162 | 35.444 | 34.350 | 0.200 | 1.00 | 37.08 |
| ATOM | 459 | CG2 | ILE | 162 | 36.930 | 31.776 | −1.209 | 1.00 | 35.30 |
| ATOM | 460 | C | ILE | 162 | 34.380 | 30.440 | −1.739 | 1.00 | 37.19 |
| ATOM | 461 | O | ILE | 162 | 34.344 | 29.232 | −1.455 | 1.00 | 36.42 |
| ATOM | 462 | N | ASP | 163 | 34.374 | 30.882 | −2.999 | 1.00 | 38.13 |
| ATOM | 463 | CA | ASP | 163 | 34.262 | 29.911 | −4.116 | 1.00 | 39.80 |
| ATOM | 464 | CB | ASP | 163 | 32.770 | 29.714 | −4.571 | 1.00 | 39.55 |
| ATOM | 465 | CG | ASP | 163 | 32.173 | 30.945 | −5.277 | 1.00 | 41.28 |
| ATOM | 466 | OD1 | ASP | 163 | 31.081 | 30.861 | −5.915 | 1.00 | 44.69 |
| ATOM | 467 | OD2 | ASP | 163 | 32.775 | 32.031 | −5.205 | 1.00 | 45.38 |
| ATOM | 468 | C | ASP | 163 | 35.231 | 30.197 | −5.271 | 1.00 | 40.41 |
| ATOM | 469 | O | ASP | 163 | 35.280 | 29.459 | −6.248 | 1.00 | 41.17 |
| ATOM | 470 | N | ASN | 164 | 36.013 | 31.261 | −5.120 | 1.00 | 41.25 |
| ATOM | 471 | CA | ASN | 164 | 37.017 | 31.704 | −6.092 | 1.00 | 41.82 |
| ATOM | 472 | CB | ASN | 164 | 37.998 | 30.576 | −6.460 | 1.00 | 41.11 |
| ATOM | 473 | CG | ASN | 164 | 38.895 | 30.159 | −5.279 | 1.00 | 41.91 |
| ATOM | 474 | OD1 | ASN | 164 | 38.971 | 30.864 | −4.271 | 1.00 | 41.77 |
| ATOM | 475 | ND2 | ASN | 164 | 39.570 | 29.018 | −5.401 | 1.00 | 39.10 |
| ATOM | 476 | C | ASN | 164 | 36.391 | 32.410 | −7.317 | 1.00 | 43.13 |
| ATOM | 477 | O | ASN | 164 | 37.048 | 32.663 | −8.311 | 1.00 | 45.15 |
| ATOM | 478 | N | ARG | 165 | 35.128 | 32.779 | −7.215 | 1.00 | 43.18 |

TABLE 8-continued

| | | | | | | | | |
|---|---|---|---|---|---|---|---|---|
| ATOM | 479 | CA | ARG | 165 | 34.463 | 33.520 | −8.263 | 1.00 | 43.16 |
| ATOM | 480 | CB | ARG | 165 | 33.234 | 32.732 | −8.738 | 1.00 | 42.42 |
| ATOM | 481 | CG | ARG | 165 | 33.537 | 31.295 | −9.223 | 1.00 | 42.82 |
| ATOM | 482 | CD | ARG | 165 | 34.079 | 31.318 | −10.686 | 1.00 | 42.73 |
| ATOM | 483 | NE | ARG | 165 | 33.196 | 32.070 | −11.604 | 1.00 | 38.23 |
| ATOM | 484 | CZ | ARG | 165 | 33.421 | 32.177 | −12.912 | 1.00 | 37.84 |
| ATOM | 485 | NH1 | ARG | 165 | 34.511 | 31.600 | −13.439 | 1.00 | 31.52 |
| ATOM | 486 | NH2 | ARG | 165 | 32.561 | 32.852 | −13.690 | 1.00 | 36.57 |
| ATOM | 487 | C | ARG | 165 | 34.055 | 34.894 | −7.700 | 1.00 | 43.75 |
| ATOM | 488 | O | ARG | 165 | 34.540 | 35.956 | −8.077 | 1.00 | 44.03 |
| ATOM | 489 | OXT | ARG | 165 | 33.202 | 35.020 | −6.813 | 1.00 | 44.96 |
| ATOM | 490 | O | HOH | 28 | 41.231 | 24.792 | −2.764 | 1.00 | 32.19 |
| ATOM | 491 | O | HOH | 47 | 45.813 | 34.092 | −1.209 | 1.00 | 24.90 |
| ATOM | 492 | O | HOH | 81 | 42.003 | 17.079 | −3.720 | 1.00 | 28.53 |
| ATOM | 493 | O | HOH | 82 | 48.944 | 28.551 | −3.166 | 1.00 | 38.48 |
| ATOM | 494 | O | HOH | 91 | 42.370 | 17.841 | −6.487 | 1.00 | 37.54 |
| ATOM | 495 | O | HOH | 92 | 51.389 | 40.287 | −1.822 | 1.00 | 67.71 |
| ATOM | 496 | O | HOH | 118 | 43.882 | 30.461 | −7.597 | 1.00 | 41.43 |
| ATOM | 497 | O | HOH | 121 | 35.459 | 21.288 | −4.581 | 1.00 | 33.91 |
| ATOM | 498 | O | HOH | 136 | 47.189 | 37.120 | −4.185 | 1.00 | 47.88 |
| ATOM | 499 | O | HOH | 233 | 42.369 | 20.436 | −5.394 | 1.00 | 44.46 |
| ATOM | 500 | O | HOH | 243 | 43.638 | 24.320 | −4.167 | 1.00 | 32.22 |
| ATOM | 501 | O | HOH | 247 | 44.611 | 22.361 | −3.380 | 1.00 | 38.90 |
| ATOM | 502 | N | ASN | 21 | 60.463 | 34.633 | −13.976 | 1.00 | 77.48 |
| ATOM | 503 | CA | ASN | 21 | 60.433 | 35.996 | −13.328 | 1.00 | 77.76 |
| ATOM | 504 | CB | ASN | 21 | 61.816 | 36.356 | −12.753 | 1.00 | 78.33 |
| ATOM | 505 | CG | ASN | 21 | 62.233 | 35.419 | −11.609 | 1.00 | 79.60 |
| ATOM | 506 | OD1 | ASN | 21 | 61.512 | 35.274 | −10.612 | 1.00 | 79.76 |
| ATOM | 507 | ND2 | ASN | 21 | 63.399 | 34.774 | −11.755 | 1.00 | 80.00 |
| ATOM | 508 | C | ASN | 21 | 59.827 | 37.125 | −14.206 | 1.00 | 77.04 |
| ATOM | 509 | O | ASN | 21 | 59.633 | 36.933 | −15.423 | 1.00 | 77.25 |
| ATOM | 510 | N | TYR | 22 | 59.574 | 38.293 | −13.584 | 1.00 | 75.75 |
| ATOM | 511 | CA | TYR | 22 | 58.471 | 39.214 | −13.971 | 1.00 | 74.20 |
| ATOM | 512 | CB | TYR | 22 | 57.483 | 39.339 | −12.795 | 1.00 | 74.59 |
| ATOM | 513 | CG | TYR | 22 | 56.716 | 38.060 | −12.447 | 1.00 | 75.55 |
| ATOM | 514 | CD1 | TYR | 22 | 57.299 | 37.045 | −11.663 | 1.00 | 75.86 |
| ATOM | 515 | CE1 | TYR | 22 | 56.581 | 35.865 | −11.338 | 1.00 | 75.88 |
| ATOM | 516 | CZ | TYR | 22 | 55.270 | 35.700 | −11.788 | 1.00 | 75.44 |
| ATOM | 517 | OH | TYR | 22 | 54.556 | 34.546 | −11.467 | 1.00 | 74.92 |
| ATOM | 518 | CE2 | TYR | 22 | 54.668 | 36.700 | −12.553 | 1.00 | 75.09 |
| ATOM | 519 | CD2 | TYR | 22 | 55.393 | 37.871 | −12.880 | 1.00 | 76.17 |
| ATOM | 520 | C | TYR | 22 | 58.815 | 40.628 | −14.516 | 1.00 | 72.82 |
| ATOM | 521 | O | TYR | 22 | 59.484 | 41.436 | −13.850 | 1.00 | 72.91 |
| ATOM | 522 | N | LEU | 23 | 58.320 | 40.910 | −15.725 | 1.00 | 70.41 |
| ATOM | 523 | CA | LEU | 23 | 58.477 | 42.207 | −16.384 | 1.00 | 68.04 |
| ATOM | 524 | CB | LEU | 23 | 58.509 | 42.044 | −17.920 | 1.00 | 68.48 |
| ATOM | 525 | CG | LEU | 23 | 59.589 | 41.212 | −18.636 | 1.00 | 69.66 |
| ATOM | 526 | CD1 | LEU | 23 | 58.989 | 40.295 | −19.722 | 1.00 | 68.67 |
| ATOM | 527 | CD2 | LEU | 23 | 60.736 | 42.099 | −19.199 | 1.00 | 70.93 |
| ATOM | 528 | C | LEU | 23 | 57.269 | 43.051 | −16.012 | 1.00 | 65.77 |
| ATOM | 529 | O | LEU | 23 | 56.143 | 42.650 | −16.275 | 1.00 | 65.09 |
| ATOM | 530 | N | PHE | 24 | 57.490 | 44.214 | −15.404 | 1.00 | 63.20 |
| ATOM | 531 | CA | PHE | 24 | 56.376 | 45.108 | −15.078 | 1.00 | 60.69 |
| ATOM | 532 | CB | PHE | 24 | 56.399 | 45.505 | −13.586 | 1.00 | 60.55 |
| ATOM | 533 | CG | PHE | 24 | 56.242 | 44.326 | −12.623 | 1.00 | 60.16 |
| ATOM | 534 | CD1 | PHE | 24 | 57.092 | 44.193 | −11.513 | 1.00 | 59.27 |
| ATOM | 535 | CE1 | PHE | 24 | 56.958 | 43.105 | −10.621 | 1.00 | 59.30 |
| ATOM | 536 | CZ | PHE | 24 | 55.954 | 42.118 | −10.846 | 1.00 | 59.37 |
| ATOM | 537 | CE2 | PHE | 24 | 55.106 | 42.231 | −11.956 | 1.00 | 58.47 |
| ATOM | 538 | CD2 | PHE | 24 | 55.247 | 43.343 | −12.832 | 1.00 | 59.75 |
| ATOM | 539 | C | PHE | 24 | 56.337 | 46.321 | −16.013 | 1.00 | 59.28 |
| ATOM | 540 | O | PHE | 24 | 55.621 | 47.291 | −15.775 | 1.00 | 57.98 |
| ATOM | 541 | N | LYS | 46 | 35.504 | 33.716 | −22.547 | 1.00 | 27.94 |
| ATOM | 542 | CA | LYS | 46 | 35.594 | 34.813 | −21.609 | 1.00 | 28.72 |
| ATOM | 543 | CB | LYS | 46 | 34.280 | 35.047 | −20.885 | 1.00 | 28.72 |
| ATOM | 544 | CG | LYS | 46 | 34.103 | 36.549 | −20.715 | 1.00 | 31.74 |
| ATOM | 545 | CD | LYS | 46 | 33.725 | 37.082 | −19.357 | 1.00 | 29.01 |
| ATOM | 546 | CE | LYS | 46 | 32.261 | 36.921 | −19.061 | 1.00 | 34.07 |
| ATOM | 547 | NZ | LYS | 46 | 32.028 | 35.526 | −18.553 | 1.00 | 35.61 |
| ATOM | 548 | C | LYS | 46 | 36.742 | 34.689 | −20.587 | 1.00 | 29.00 |
| ATOM | 549 | O | LYS | 46 | 36.927 | 33.630 | −19.959 | 1.00 | 27.85 |
| ATOM | 550 | N | GLU | 79 | 46.675 | 31.937 | −24.957 | 1.00 | 31.85 |
| ATOM | 551 | CA | GLU | 79 | 47.010 | 31.100 | −23.819 | 1.00 | 32.97 |
| ATOM | 552 | CB | GLU | 79 | 48.402 | 30.489 | −24.060 | 1.00 | 33.09 |
| ATOM | 553 | CG | GLU | 79 | 48.782 | 29.305 | −23.179 | 1.00 | 36.28 |
| ATOM | 554 | CD | GLU | 79 | 49.298 | 29.747 | −21.783 | 1.00 | 42.29 |
| ATOM | 555 | OE1 | GLU | 79 | 50.240 | 30.593 | −21.719 | 1.00 | 43.14 |
| ATOM | 556 | OE2 | GLU | 79 | 48.757 | 29.243 | −20.750 | 1.00 | 42.65 |
| ATOM | 557 | C | GLU | 79 | 46.973 | 31.998 | −22.538 | 1.00 | 33.16 |
| ATOM | 558 | O | GLU | 79 | 47.579 | 33.059 | −22.486 | 1.00 | 33.58 |

TABLE 8-continued

| | | | | | | | | |
|---|---|---|---|---|---|---|---|---|
| ATOM | 559 | N | SER | 80 | 46.177 | 31.565 | −21.561 | 1.00 | 33.78 |
| ATOM | 560 | CA | SER | 80 | 45.918 | 32.180 | −20.255 | 1.00 | 34.02 |
| ATOM | 561 | CB | SER | 80 | 45.227 | 31.117 | −19.379 | 1.00 | 35.89 |
| ATOM | 562 | OG | SER | 80 | 44.418 | 31.682 | −18.363 | 1.00 | 38.47 |
| ATOM | 563 | C | SER | 80 | 47.125 | 32.721 | −19.504 | 1.00 | 34.03 |
| ATOM | 564 | O | SER | 80 | 47.119 | 33.887 | −19.073 | 1.00 | 34.32 |
| ATOM | 565 | N | LYS | 81 | 48.154 | 31.896 | −19.324 | 1.00 | 33.56 |
| ATOM | 566 | CA | LYS | 81 | 49.361 | 32.331 | −18.637 | 1.00 | 34.79 |
| ATOM | 567 | CB | LYS | 81 | 50.374 | 31.192 | −18.505 | 1.00 | 35.88 |
| ATOM | 568 | CG | LYS | 81 | 51.528 | 31.525 | −17.518 | 1.00 | 39.71 |
| ATOM | 569 | CD | LYS | 81 | 52.511 | 30.369 | −17.374 | 1.00 | 38.34 |
| ATOM | 570 | CE | LYS | 81 | 53.965 | 30.924 | −17.461 | 1.00 | 47.73 |
| ATOM | 571 | NZ | LYS | 81 | 55.069 | 29.852 | −17.650 | 1.00 | 47.03 |
| ATOM | 572 | C | LYS | 81 | 50.050 | 33.498 | −19.327 | 1.00 | 34.02 |
| ATOM | 573 | O | LYS | 81 | 50.539 | 34.410 | −18.624 | 1.00 | 33.61 |
| ATOM | 574 | N | SER | 82 | 50.129 | 33.472 | −20.682 | 1.00 | 31.13 |
| ATOM | 575 | CA | SER | 82 | 50.722 | 34.601 | −21.382 | 1.00 | 29.46 |
| ATOM | 576 | CB | SER | 82 | 50.940 | 34.274 | −22.897 | 1.00 | 30.51 |
| ATOM | 577 | OG | SER | 82 | 49.733 | 34.250 | −23.658 | 1.00 | 25.05 |
| ATOM | 578 | C | SER | 82 | 49.898 | 35.862 | −21.176 | 1.00 | 28.45 |
| ATOM | 579 | O | SER | 82 | 50.429 | 36.964 | −21.122 | 1.00 | 28.02 |
| ATOM | 580 | N | LEU | 83 | 48.585 | 35.704 | −21.062 | 1.00 | 28.58 |
| ATOM | 581 | CA | LEU | 83 | 47.709 | 36.847 | −20.889 | 1.00 | 28.75 |
| ATOM | 582 | CB | LEU | 83 | 46.246 | 36.400 | −21.072 | 1.00 | 28.91 |
| ATOM | 583 | CG | LEU | 83 | 45.223 | 37.495 | −20.745 | 1.00 | 28.13 |
| ATOM | 584 | CD1 | LEU | 83 | 45.474 | 38.773 | −21.618 | 1.00 | 22.93 |
| ATOM | 585 | CD2 | LEU | 83 | 43.846 | 37.002 | −20.907 | 1.00 | 25.01 |
| ATOM | 586 | C | LEU | 83 | 47.920 | 37.505 | −19.487 | 1.00 | 29.90 |
| ATOM | 587 | O | LEU | 83 | 47.920 | 38.759 | −19.345 | 1.00 | 29.32 |
| ATOM | 588 | N | LYS | 84 | 48.137 | 36.648 | −18.475 | 1.00 | 30.73 |
| ATOM | 589 | CA | LYS | 84 | 48.466 | 37.059 | −17.096 | 1.00 | 31.05 |
| ATOM | 590 | CB | LYS | 84 | 48.661 | 35.827 | −16.208 | 1.00 | 31.72 |
| ATOM | 591 | CG | LYS | 84 | 49.170 | 36.133 | −14.774 | 1.00 | 33.82 |
| ATOM | 592 | CD | LYS | 84 | 49.508 | 34.855 | −14.010 | 1.00 | 33.38 |
| ATOM | 593 | CE | LYS | 84 | 50.932 | 34.459 | −14.264 | 1.00 | 37.80 |
| ATOM | 594 | NZ | LYS | 84 | 51.170 | 33.043 | −13.784 | 1.00 | 41.84 |
| ATOM | 595 | C | LYS | 84 | 49.754 | 37.830 | −17.149 | 1.00 | 30.38 |
| ATOM | 596 | O | LYS | 84 | 49.800 | 38.960 | −16.737 | 1.00 | 29.79 |
| ATOM | 597 | N | LEU | 85 | 50.800 | 37.242 | −17.728 | 1.00 | 31.88 |
| ATOM | 598 | CA | LEU | 85 | 52.066 | 37.979 | −17.861 | 1.00 | 31.86 |
| ATOM | 599 | CB | LEU | 85 | 53.132 | 37.105 | −18.486 | 1.00 | 32.09 |
| ATOM | 600 | CG | LEU | 85 | 53.399 | 35.885 | −17.611 | 1.00 | 34.28 |
| ATOM | 601 | CD1 | LEU | 85 | 54.156 | 34.804 | −18.390 | 1.00 | 32.52 |
| ATOM | 602 | CD2 | LEU | 85 | 54.091 | 36.264 | −16.233 | 1.00 | 31.60 |
| ATOM | 603 | C | LEU | 85 | 51.921 | 39.288 | −18.630 | 1.00 | 32.05 |
| ATOM | 604 | O | LEU | 85 | 52.518 | 40.293 | −18.254 | 1.00 | 33.60 |
| ATOM | 605 | N | TYR | 86 | 51.135 | 39.288 | −19.714 | 1.00 | 31.49 |
| ATOM | 606 | CA | TYR | 86 | 50.995 | 40.498 | −20.538 | 1.00 | 30.33 |
| ATOM | 607 | CB | TYR | 86 | 50.178 | 40.215 | −21.833 | 1.00 | 29.59 |
| ATOM | 608 | CG | TYR | 86 | 49.630 | 41.414 | −22.567 | 1.00 | 26.68 |
| ATOM | 609 | CD1 | TYR | 86 | 50.455 | 42.200 | −23.345 | 1.00 | 24.51 |
| ATOM | 610 | CE1 | TYR | 86 | 49.966 | 43.249 | −24.057 | 1.00 | 24.37 |
| ATOM | 611 | CZ | TYR | 86 | 48.626 | 43.568 | −23.990 | 1.00 | 25.64 |
| ATOM | 612 | OH | TYR | 86 | 48.221 | 44.675 | −24.649 | 1.00 | 26.85 |
| ATOM | 613 | CE2 | TYR | 86 | 47.741 | 42.827 | −23.235 | 1.00 | 22.71 |
| ATOM | 614 | CD2 | TYR | 86 | 48.265 | 41.716 | −22.540 | 1.00 | 27.57 |
| ATOM | 615 | C | TYR | 86 | 50.355 | 41.555 | −19.723 | 1.00 | 30.64 |
| ATOM | 616 | O | TYR | 86 | 50.771 | 42.678 | −19.764 | 1.00 | 32.24 |
| ATOM | 617 | N | LEU | 87 | 49.315 | 41.205 | −18.982 | 1.00 | 31.89 |
| ATOM | 618 | CA | LEU | 87 | 48.617 | 42.195 | −18.183 | 1.00 | 31.70 |
| ATOM | 619 | CB | LEU | 87 | 47.269 | 41.676 | −17.749 | 1.00 | 30.92 |
| ATOM | 620 | CG | LEU | 87 | 46.183 | 41.524 | −18.815 | 1.00 | 30.71 |
| ATOM | 621 | CD1 | LEU | 87 | 44.992 | 40.947 | −18.153 | 1.00 | 30.43 |
| ATOM | 622 | CD2 | LEU | 87 | 45.796 | 42.808 | −19.511 | 1.00 | 27.38 |
| ATOM | 623 | C | LEU | 87 | 49.466 | 42.645 | −16.966 | 1.00 | 32.75 |
| ATOM | 624 | O | LEU | 87 | 49.368 | 43.792 | −16.543 | 1.00 | 33.05 |
| ATOM | 625 | N | PHE | 88 | 50.284 | 41.747 | −16.430 | 1.00 | 32.40 |
| ATOM | 626 | CA | PHE | 88 | 51.249 | 42.102 | −15.362 | 1.00 | 33.61 |
| ATOM | 627 | CB | PHE | 88 | 51.993 | 40.843 | −14.850 | 1.00 | 33.43 |
| ATOM | 628 | CG | PHE | 88 | 51.179 | 40.001 | −13.811 | 1.00 | 34.54 |
| ATOM | 629 | CD1 | PHE | 88 | 51.648 | 38.757 | −13.369 | 1.00 | 34.71 |
| ATOM | 630 | CE1 | PHE | 88 | 50.927 | 37.996 | −12.402 | 1.00 | 35.58 |
| ATOM | 631 | CZ | PHE | 88 | 49.675 | 38.509 | −11.868 | 1.00 | 38.71 |
| ATOM | 632 | CE2 | PHE | 88 | 49.200 | 39.741 | −12.294 | 1.00 | 36.46 |
| ATOM | 633 | CD2 | PHE | 88 | 49.963 | 40.478 | −13.266 | 1.00 | 37.35 |
| ATOM | 634 | C | PHE | 88 | 52.246 | 43.183 | −15.842 | 1.00 | 33.85 |
| ATOM | 635 | O | PHE | 88 | 52.735 | 44.015 | −15.050 | 1.00 | 33.57 |
| ATOM | 636 | N | SER | 89 | 52.504 | 43.209 | −17.156 | 1.00 | 33.74 |
| ATOM | 637 | CA | SER | 89 | 53.520 | 44.111 | −17.712 | 1.00 | 32.69 |
| ATOM | 638 | CB | SER | 89 | 54.008 | 43.635 | −19.115 | 1.00 | 33.24 |

TABLE 8-continued

| | | | | | | | | | |
|---|---|---|---|---|---|---|---|---|---|
| ATOM | 639 | OG | SER | 89 | 53.123 | 43.961 | −20.202 | 1.00 | 29.93 |
| ATOM | 640 | C | SER | 89 | 52.978 | 45.523 | −17.735 | 1.00 | 33.19 |
| ATOM | 641 | O | SER | 89 | 53.710 | 46.469 | −18.064 | 1.00 | 33.38 |
| ATOM | 642 | O3S | G6S | 202 | 52.852 | 28.533 | −7.410 | 1.00 | 0.80 |
| ATOM | 643 | S | G6S | 202 | 51.367 | 28.536 | −7.238 | 1.00 | 0.32 |
| ATOM | 644 | O1S | G6S | 202 | 50.895 | 29.937 | −7.089 | 1.00 | 0.47 |
| ATOM | 645 | O2S | G6S | 202 | 50.976 | 27.803 | −6.003 | 1.00 | 0.44 |
| ATOM | 646 | O6 | G6S | 202 | 50.649 | 27.825 | −8.553 | 1.00 | 0.52 |
| ATOM | 647 | C6 | G6S | 202 | 51.248 | 27.655 | −9.853 | 1.00 | 0.05 |
| ATOM | 648 | C5 | G6S | 202 | 50.442 | 28.334 | −10.989 | 1.00 | 0.81 |
| ATOM | 649 | O5 | G6S | 202 | 51.011 | 29.617 | −11.325 | 1.00 | 0.85 |
| ATOM | 650 | C4 | G6S | 202 | 48.890 | 28.417 | −10.843 | 1.00 | 0.89 |
| ATOM | 651 | O4 | G6S | 202 | 48.325 | 27.461 | −9.929 | 1.00 | 99.16 |
| ATOM | 652 | C3 | G6S | 202 | 48.290 | 29.798 | −10.517 | 1.00 | 99.15 |
| ATOM | 653 | O3 | G6S | 202 | 47.360 | 29.685 | −9.429 | 1.00 | 96.07 |
| ATOM | 654 | C2 | G6S | 202 | 49.259 | 30.993 | −10.332 | 1.00 | 99.78 |
| ATOM | 655 | O2 | G6S | 202 | 48.929 | 31.763 | −9.163 | 1.00 | 97.61 |
| ATOM | 656 | C1 | G6S | 202 | 50.752 | 30.641 | −10.356 | 1.00 | 0.22 |
| ATOM | 657 | O1 | G6S | 202 | 51.512 | 31.810 | −10.680 | 1.00 | 0.17 |
| ATOM | 658 | N | PRO | 50 | 28.244 | 21.414 | −10.817 | 1.00 | 28.99 |
| ATOM | 659 | CA | PRO | 50 | 29.215 | 22.198 | −10.031 | 1.00 | 29.58 |
| ATOM | 660 | CB | PRO | 50 | 28.423 | 22.598 | −8.756 | 1.00 | 29.17 |
| ATOM | 661 | CG | PRO | 50 | 27.143 | 21.920 | −8.860 | 1.00 | 29.81 |
| ATOM | 662 | CD | PRO | 50 | 27.095 | 20.985 | −9.993 | 1.00 | 28.43 |
| ATOM | 663 | C | PRO | 50 | 30.454 | 21.446 | −9.626 | 1.00 | 29.99 |
| ATOM | 664 | O | PRO | 50 | 31.373 | 22.050 | −9.096 | 1.00 | 31.25 |
| ATOM | 665 | N | GLU | 51 | 30.490 | 20.159 | −9.888 | 1.00 | 30.28 |
| ATOM | 666 | CA | GLU | 51 | 31.565 | 19.318 | −9.431 | 1.00 | 31.01 |
| ATOM | 667 | CB | GLU | 51 | 30.978 | 18.110 | −8.744 | 1.00 | 31.20 |
| ATOM | 668 | CG | GLU | 51 | 30.228 | 18.489 | −7.474 | 1.00 | 31.72 |
| ATOM | 669 | CD | GLU | 51 | 29.527 | 17.305 | −6.826 | 1.00 | 39.70 |
| ATOM | 670 | OE1 | GLU | 51 | 29.698 | 16.149 | −7.339 | 1.00 | 41.03 |
| ATOM | 671 | OE2 | GLU | 51 | 28.792 | 17.537 | −5.815 | 1.00 | 39.79 |
| ATOM | 672 | C | GLU | 51 | 32.556 | 18.911 | −10.496 | 1.00 | 30.89 |
| ATOM | 673 | O | GLU | 51 | 33.223 | 17.903 | −10.383 | 1.00 | 32.20 |
| ATOM | 674 | N | PHE | 52 | 32.694 | 19.712 | −11.534 | 1.00 | 30.63 |
| ATOM | 675 | CA | PHE | 52 | 33.541 | 19.278 | −12.624 | 1.00 | 29.27 |
| ATOM | 676 | CB | PHE | 52 | 33.080 | 19.913 | −13.946 | 1.00 | 29.89 |
| ATOM | 677 | CG | PHE | 52 | 33.995 | 19.591 | −15.114 | 1.00 | 28.40 |
| ATOM | 678 | CD1 | PHE | 52 | 33.771 | 18.470 | −15.907 | 1.00 | 28.58 |
| ATOM | 679 | CE1 | PHE | 52 | 34.613 | 18.160 | −16.983 | 1.00 | 24.69 |
| ATOM | 680 | CZ | PHE | 52 | 35.662 | 18.968 | −17.259 | 1.00 | 27.97 |
| ATOM | 681 | CE2 | PHE | 52 | 35.921 | 20.096 | −16.447 | 1.00 | 29.23 |
| ATOM | 682 | CD2 | PHE | 52 | 35.079 | 20.397 | −15.399 | 1.00 | 26.27 |
| ATOM | 683 | C | PHE | 52 | 34.989 | 19.634 | −12.337 | 1.00 | 29.10 |
| ATOM | 684 | O | PHE | 52 | 35.276 | 20.740 | −11.880 | 1.00 | 28.69 |
| ATOM | 685 | N | THR | 53 | 35.879 | 18.664 | −12.600 | 1.00 | 29.45 |
| ATOM | 686 | CA | THR | 53 | 37.326 | 18.832 | −12.507 | 1.00 | 29.09 |
| ATOM | 687 | CB | THR | 53 | 37.843 | 18.455 | −11.101 | 1.00 | 28.45 |
| ATOM | 688 | OG1 | THR | 53 | 39.268 | 18.659 | −11.054 | 1.00 | 27.24 |
| ATOM | 689 | CG2 | THR | 53 | 37.484 | 17.025 | −10.776 | 1.00 | 25.51 |
| ATOM | 690 | C | THR | 53 | 38.062 | 18.013 | −13.596 | 1.00 | 30.39 |
| ATOM | 691 | O | THR | 53 | 37.605 | 16.954 | −13.998 | 1.00 | 29.67 |
| ATOM | 692 | N | SER | 54 | 39.223 | 18.520 | −14.021 | 1.00 | 31.83 |
| ATOM | 693 | CA | SER | 54 | 40.050 | 17.925 | −15.068 | 1.00 | 33.32 |
| ATOM | 694 | CB | SER | 54 | 39.542 | 18.318 | −16.473 | 1.00 | 33.47 |
| ATOM | 695 | OG | SER | 54 | 39.682 | 19.717 | −16.684 | 1.00 | 33.23 |
| ATOM | 696 | C | SER | 54 | 41.483 | 18.427 | −14.883 | 1.00 | 34.99 |
| ATOM | 697 | O | SER | 54 | 41.781 | 19.080 | −13.905 | 1.00 | 34.15 |
| ATOM | 698 | N | LEU | 55 | 42.367 | 18.138 | −15.835 | 1.00 | 38.17 |
| ATOM | 699 | CA | LEU | 55 | 43.784 | 18.454 | −15.681 | 1.00 | 40.67 |
| ATOM | 700 | CB | LEU | 55 | 44.633 | 17.189 | −15.708 | 1.00 | 40.34 |
| ATOM | 701 | CG | LEU | 55 | 44.337 | 16.106 | −14.673 | 1.00 | 37.91 |
| ATOM | 702 | CD1 | LEU | 55 | 45.350 | 15.007 | −14.872 | 1.00 | 37.30 |
| ATOM | 703 | CD2 | LEU | 55 | 44.404 | 16.622 | −13.251 | 1.00 | 39.20 |
| ATOM | 704 | C | LEU | 55 | 44.243 | 19.439 | −16.711 | 1.00 | 43.65 |
| ATOM | 705 | O | LEU | 55 | 43.677 | 19.503 | −17.811 | 1.00 | 44.27 |
| ATOM | 706 | N | CYS | 56 | 45.206 | 20.263 | −16.305 | 1.00 | 46.46 |
| ATOM | 707 | CA | CYS | 56 | 45.912 | 21.152 | −17.201 | 1.00 | 48.90 |
| ATOM | 708 | CB | CYS | 56 | 46.701 | 22.184 | −16.389 | 1.00 | 49.06 |
| ATOM | 709 | SG | CYS | 56 | 47.593 | 23.405 | −17.367 | 1.00 | 50.31 |
| ATOM | 710 | C | CYS | 56 | 46.845 | 20.305 | −18.099 | 1.00 | 50.34 |
| ATOM | 711 | O | CYS | 56 | 47.635 | 19.482 | −17.589 | 1.00 | 50.82 |
| ATOM | 712 | N | PRO | 57 | 46.735 | 20.467 | −19.434 | 1.00 | 51.54 |
| ATOM | 713 | CA | PRO | 57 | 47.388 | 19.490 | −20.323 | 1.00 | 52.63 |
| ATOM | 714 | CB | PRO | 57 | 46.866 | 19.882 | −21.711 | 1.00 | 52.63 |
| ATOM | 715 | CG | PRO | 57 | 46.498 | 21.362 | −21.578 | 1.00 | 51.98 |
| ATOM | 716 | CD | PRO | 57 | 46.005 | 21.517 | −20.180 | 1.00 | 50.82 |
| ATOM | 717 | C | PRO | 57 | 48.922 | 19.553 | −20.285 | 1.00 | 53.90 |
| ATOM | 718 | O | PRO | 57 | 49.595 | 18.557 | −20.604 | 1.00 | 54.88 |

TABLE 8-continued

| | | | | | | | | | |
|---|---|---|---|---|---|---|---|---|---|
| ATOM | 719 | N | LYS | 58 | 49.445 | 20.704 | −19.869 | 1.00 | 54.79 |
| ATOM | 720 | CA | LYS | 58 | 50.859 | 21.010 | −19.879 | 1.00 | 55.67 |
| ATOM | 721 | CB | LYS | 58 | 51.099 | 22.460 | −20.350 | 1.00 | 56.91 |
| ATOM | 722 | CG | LYS | 58 | 51.388 | 22.586 | −21.860 | 1.00 | 59.21 |
| ATOM | 723 | CD | LYS | 58 | 50.130 | 22.869 | −22.727 | 1.00 | 62.63 |
| ATOM | 724 | CE | LYS | 58 | 50.254 | 22.345 | −24.208 | 1.00 | 62.29 |
| ATOM | 725 | NZ | LYS | 58 | 49.792 | 20.898 | −24.410 | 1.00 | 63.69 |
| ATOM | 726 | C | LYS | 58 | 51.521 | 20.767 | −18.530 | 1.00 | 55.58 |
| ATOM | 727 | O | LYS | 58 | 52.581 | 20.135 | −18.485 | 1.00 | 56.09 |
| ATOM | 728 | N | VAL | 59 | 50.917 | 21.267 | −17.444 | 1.00 | 54.74 |
| ATOM | 729 | CA | VAL | 59 | 51.421 | 21.046 | −16.067 | 1.00 | 52.88 |
| ATOM | 730 | CB | VAL | 59 | 51.163 | 22.260 | −15.166 | 1.00 | 52.91 |
| ATOM | 731 | CG1 | VAL | 59 | 51.991 | 23.465 | −15.607 | 1.00 | 53.31 |
| ATOM | 732 | CG2 | VAL | 59 | 49.711 | 22.627 | −15.158 | 1.00 | 52.44 |
| ATOM | 733 | C | VAL | 59 | 50.856 | 19.794 | −15.354 | 1.00 | 52.24 |
| ATOM | 734 | O | VAL | 59 | 51.473 | 19.284 | −14.420 | 1.00 | 52.31 |
| ATOM | 735 | N | GLY | 60 | 49.686 | 19.305 | −15.764 | 1.00 | 50.54 |
| ATOM | 736 | CA | GLY | 60 | 49.014 | 18.245 | −14.989 | 1.00 | 48.58 |
| ATOM | 737 | C | GLY | 60 | 48.341 | 18.733 | −13.691 | 1.00 | 47.45 |
| ATOM | 738 | O | GLY | 60 | 47.866 | 17.896 | −12.884 | 1.00 | 46.89 |
| ATOM | 739 | N | GLN | 61 | 48.307 | 20.064 | −13.479 | 1.00 | 45.26 |
| ATOM | 740 | CA | GLN | 61 | 47.586 | 20.678 | −12.333 | 1.00 | 44.42 |
| ATOM | 741 | CB | GLN | 61 | 47.987 | 22.155 | −12.119 | 1.00 | 43.87 |
| ATOM | 742 | CG | GLN | 61 | 47.731 | 22.676 | −10.667 | 1.00 | 49.56 |
| ATOM | 743 | CD | GLN | 61 | 47.363 | 24.226 | −10.534 | 1.00 | 49.55 |
| ATOM | 744 | OE1 | GLN | 61 | 47.220 | 24.948 | −11.541 | 1.00 | 58.03 |
| ATOM | 745 | NE2 | GLN | 61 | 47.252 | 24.715 | −9.280 | 1.00 | 50.79 |
| ATOM | 746 | C | GLN | 61 | 46.057 | 20.541 | −12.530 | 1.00 | 40.55 |
| ATOM | 747 | O | GLN | 61 | 45.530 | 20.745 | −13.639 | 1.00 | 39.97 |
| ATOM | 748 | N | PRO | 62 | 45.346 | 20.114 | −11.472 | 1.00 | 37.57 |
| ATOM | 749 | CA | PRO | 62 | 43.876 | 20.094 | −11.506 | 1.00 | 34.50 |
| ATOM | 750 | CB | PRO | 62 | 43.486 | 19.465 | −10.176 | 1.00 | 34.78 |
| ATOM | 751 | CG | PRO | 62 | 44.738 | 19.481 | −9.340 | 1.00 | 35.70 |
| ATOM | 752 | CD | PRO | 62 | 45.901 | 19.527 | −10.245 | 1.00 | 36.57 |
| ATOM | 753 | C | PRO | 62 | 43.205 | 21.468 | −11.694 | 1.00 | 32.05 |
| ATOM | 754 | O | PRO | 62 | 43.721 | 22.464 | −11.281 | 1.00 | 29.71 |
| ATOM | 755 | N | ASP | 63 | 42.053 | 21.454 | −12.362 | 1.00 | 31.14 |
| ATOM | 756 | CA | ASP | 63 | 41.239 | 22.599 | −12.684 | 1.00 | 30.90 |
| ATOM | 757 | CB | ASP | 63 | 41.325 | 22.867 | −14.206 | 1.00 | 32.30 |
| ATOM | 758 | CG | ASP | 63 | 42.634 | 23.566 | −14.606 | 1.00 | 41.48 |
| ATOM | 759 | OD1 | ASP | 63 | 43.305 | 24.240 | −13.756 | 1.00 | 48.28 |
| ATOM | 760 | OD2 | ASP | 63 | 43.022 | 23.456 | −15.797 | 1.00 | 51.27 |
| ATOM | 761 | C | ASP | 63 | 39.814 | 22.220 | −12.251 | 1.00 | 28.42 |
| ATOM | 762 | O | ASP | 63 | 39.500 | 21.024 | −12.182 | 1.00 | 27.04 |
| ATOM | 763 | N | PHE | 64 | 38.950 | 23.220 | −12.000 | 1.00 | 26.58 |
| ATOM | 764 | CA | PHE | 64 | 37.571 | 22.964 | −11.489 | 1.00 | 25.17 |
| ATOM | 765 | CB | PHE | 64 | 37.545 | 23.196 | −9.947 | 1.00 | 24.80 |
| ATOM | 766 | CG | PHE | 64 | 38.517 | 22.339 | −9.234 | 1.00 | 23.25 |
| ATOM | 767 | CD1 | PHE | 64 | 39.858 | 22.638 | −9.291 | 1.00 | 18.99 |
| ATOM | 768 | CE1 | PHE | 64 | 40.775 | 21.788 | −8.711 | 1.00 | 25.96 |
| ATOM | 769 | CZ | PHE | 64 | 40.353 | 20.660 | −8.050 | 1.00 | 22.65 |
| ATOM | 770 | CE2 | PHE | 64 | 39.013 | 20.349 | −8.038 | 1.00 | 25.11 |
| ATOM | 771 | CD2 | PHE | 64 | 38.104 | 21.180 | −8.619 | 1.00 | 17.63 |
| ATOM | 772 | C | PHE | 64 | 36.595 | 23.944 | −12.156 | 1.00 | 24.81 |
| ATOM | 773 | O | PHE | 64 | 36.962 | 25.054 | −12.424 | 1.00 | 24.53 |
| ATOM | 774 | N | ALA | 65 | 35.352 | 23.554 | −12.363 | 1.00 | 25.05 |
| ATOM | 775 | CA | ALA | 65 | 34.418 | 24.431 | −13.033 | 1.00 | 25.65 |
| ATOM | 776 | CB | ALA | 65 | 34.439 | 24.094 | −14.597 | 1.00 | 25.77 |
| ATOM | 777 | C | ALA | 65 | 33.042 | 24.147 | −12.554 | 1.00 | 24.74 |
| ATOM | 778 | O | ALA | 65 | 32.740 | 23.054 | −12.154 | 1.00 | 23.37 |
| ATOM | 779 | N | PHE | 123 | 35.115 | 28.338 | −14.979 | 1.00 | 24.66 |
| ATOM | 780 | CA | PHE | 123 | 36.231 | 27.708 | −14.313 | 1.00 | 25.71 |
| ATOM | 781 | CB | PHE | 123 | 37.352 | 27.432 | −15.308 | 1.00 | 25.39 |
| ATOM | 782 | CG | PHE | 123 | 37.146 | 26.154 | −16.080 | 1.00 | 25.58 |
| ATOM | 783 | CD1 | PHE | 123 | 36.303 | 26.130 | −17.208 | 1.00 | 23.88 |
| ATOM | 784 | CE1 | PHE | 123 | 36.066 | 24.956 | −17.902 | 1.00 | 27.12 |
| ATOM | 785 | CZ | PHE | 123 | 36.700 | 23.778 | −17.476 | 1.00 | 25.61 |
| ATOM | 786 | CE2 | PHE | 123 | 37.573 | 23.813 | −16.368 | 1.00 | 25.86 |
| ATOM | 787 | CD2 | PHE | 123 | 37.772 | 24.999 | −15.676 | 1.00 | 21.27 |
| ATOM | 788 | C | PHE | 123 | 36.733 | 28.584 | −13.202 | 1.00 | 27.78 |
| ATOM | 789 | O | PHE | 123 | 36.435 | 29.784 | −13.207 | 1.00 | 26.73 |
| ATOM | 790 | N | THR | 124 | 37.479 | 27.990 | −12.258 | 1.00 | 28.45 |
| ATOM | 791 | CA | THR | 124 | 33.052 | 28.780 | −11.172 | 1.00 | 29.21 |
| ATOM | 792 | CB | THR | 124 | 38.335 | 27.932 | −9.928 | 1.00 | 29.38 |
| ATOM | 793 | OG1 | THR | 124 | 39.204 | 26.840 | −10.266 | 1.00 | 29.10 |
| ATOM | 794 | CG2 | THR | 124 | 37.043 | 27.398 | −9.299 | 1.00 | 28.56 |
| ATOM | 795 | C | THR | 124 | 39.359 | 29.380 | −11.630 | 1.00 | 30.74 |
| ATOM | 796 | O | THR | 124 | 39.979 | 28.843 | −12.573 | 1.00 | 30.61 |
| ATOM | 797 | N | PRO | 125 | 39.805 | 30.487 | −10.978 | 1.00 | 31.11 |
| ATOM | 798 | CA | PRO | 125 | 40.960 | 31.157 | −11.553 | 1.00 | 31.41 |

TABLE 8-continued

| | | | | | | | | |
|---|---|---|---|---|---|---|---|---|
| ATOM | 799 | CB | PRO | 125 | 40.960 | 32.517 | −10.858 | 1.00 | 31.81 |
| ATOM | 800 | CG | PRO | 125 | 40.314 | 32.253 | −9.532 | 1.00 | 31.39 |
| ATOM | 801 | CD | PRO | 125 | 39.270 | 31.217 | −9.812 | 1.00 | 30.80 |
| ATOM | 802 | C | PRO | 125 | 42.286 | 30.468 | −11.375 | 1.00 | 31.85 |
| ATOM | 803 | O | PRO | 125 | 42.425 | 29.609 | −10.527 | 1.00 | 31.82 |
| ATOM | 804 | N | ARG | 126 | 43.253 | 30.872 | −12.196 | 1.00 | 33.65 |
| ATOM | 805 | CA | ARG | 126 | 44.643 | 30.386 | −12.170 | 1.00 | 35.35 |
| ATOM | 806 | CB | ARG | 126 | 44.867 | 29.366 | −13.279 | 1.00 | 35.69 |
| ATOM | 807 | CG | ARG | 126 | 43.946 | 28.160 | −13.183 | 1.00 | 43.61 |
| ATOM | 808 | CD | ARG | 126 | 44.705 | 26.987 | −12.545 | 1.00 | 50.39 |
| ATOM | 809 | NE | ARG | 126 | 43.886 | 26.236 | −11.591 | 1.00 | 55.49 |
| ATOM | 810 | CZ | ARG | 126 | 43.819 | 26.497 | −10.287 | 1.00 | 55.94 |
| ATOM | 811 | NH1 | ARG | 126 | 44.523 | 27.495 | −9.775 | 1.00 | 56.17 |
| ATOM | 812 | NH2 | ARG | 126 | 43.055 | 25.754 | −9.503 | 1.00 | 53.93 |
| ATOM | 813 | C | ARG | 126 | 45.463 | 31.566 | −12.570 | 1.00 | 33.98 |
| ATOM | 814 | O | ARG | 126 | 45.262 | 32.070 | −13.654 | 1.00 | 34.55 |
| ATOM | 815 | N | GLY | 127 | 46.412 | 31.985 | −11.749 | 1.00 | 33.08 |
| ATOM | 816 | CA | GLY | 127 | 47.164 | 33.232 | −11.992 | 1.00 | 31.37 |
| ATOM | 817 | C | GLY | 127 | 46.246 | 34.445 | −12.024 | 1.00 | 31.90 |
| ATOM | 818 | O | GLY | 127 | 46.531 | 35.450 | −12.738 | 1.00 | 32.33 |
| ATOM | 819 | N | GLY | 128 | 45.151 | 34.356 | −11.257 | 1.00 | 29.85 |
| ATOM | 820 | CA | GLY | 128 | 44.190 | 35.435 | −11.148 | 1.00 | 29.52 |
| ATOM | 821 | C | GLY | 128 | 43.144 | 35.555 | −12.249 | 1.00 | 29.89 |
| ATOM | 822 | O | GLY | 128 | 42.293 | 36.426 | −12.170 | 1.00 | 31.57 |
| ATOM | 823 | N | ILE | 129 | 43.223 | 34.718 | −13.281 | 1.00 | 28.05 |
| ATOM | 824 | CA | ILE | 129 | 42.332 | 34.811 | −14.472 | 1.00 | 28.03 |
| ATOM | 825 | CB | ILE | 129 | 43.203 | 34.838 | −15.798 | 1.00 | 27.24 |
| ATOM | 826 | CG1 | ILE | 129 | 44.113 | 36.071 | −15.781 | 1.00 | 25.80 |
| ATOM | 827 | CD1 | ILE | 129 | 44.676 | 36.415 | −17.145 | 1.00 | 30.11 |
| ATOM | 828 | CG2 | ILE | 129 | 42.314 | 34.715 | −17.101 | 1.00 | 26.81 |
| ATOM | 829 | C | ILE | 129 | 41.431 | 33.585 | −14.533 | 1.00 | 26.21 |
| ATOM | 830 | O | ILE | 129 | 41.934 | 32.482 | −14.440 | 1.00 | 27.19 |
| ATOM | 831 | N | SER | 130 | 40.136 | 33.755 | −14.694 | 1.00 | 24.89 |
| ATOM | 832 | CA | SER | 130 | 39.305 | 32.591 | −14.900 | 1.00 | 27.04 |
| ATOM | 833 | CB | SER | 130 | 38.185 | 32.561 | −13.881 | 1.00 | 26.36 |
| ATOM | 834 | OG | SER | 130 | 37.616 | 33.836 | −13.893 | 1.00 | 29.36 |
| ATOM | 835 | C | SER | 130 | 38.767 | 32.626 | −16.345 | 1.00 | 27.61 |
| ATOM | 836 | O | SER | 130 | 38.691 | 33.690 | −16.975 | 1.00 | 28.20 |
| ATOM | 837 | N | ILE | 131 | 38.460 | 31.457 | −16.876 | 1.00 | 29.41 |
| ATOM | 838 | CA | ILE | 131 | 38.052 | 31.297 | −18.298 | 1.00 | 28.69 |
| ATOM | 839 | CB | ILE | 131 | 39.036 | 30.360 | −19.019 | 1.00 | 29.39 |
| ATOM | 840 | CG1 | ILE | 131 | 40.461 | 30.861 | −18.796 | 1.00 | 26.63 |
| ATOM | 841 | CD1 | ILE | 131 | 41.533 | 29.889 | −19.302 | 1.00 | 32.14 |
| ATOM | 842 | CG2 | ILE | 131 | 38.722 | 30.262 | −20.528 | 1.00 | 29.11 |
| ATOM | 843 | C | ILE | 131 | 36.682 | 30.663 | −18.306 | 1.00 | 29.13 |
| ATOM | 844 | O | ILE | 131 | 36.524 | 29.577 | −17.741 | 1.00 | 30.99 |
| ATOM | 845 | N | ASN | 164 | 37.282 | 36.882 | −7.815 | 1.00 | 38.98 |
| ATOM | 846 | CA | ASN | 164 | 37.987 | 35.694 | −7.304 | 1.00 | 38.32 |
| ATOM | 847 | CB | ASN | 164 | 39.470 | 35.729 | −7.673 | 1.00 | 37.51 |
| ATOM | 848 | CG | ASN | 164 | 39.710 | 35.902 | −9.190 | 1.00 | 38.10 |
| ATOM | 849 | OD1 | ASN | 164 | 38.812 | 35.677 | −10.019 | 1.00 | 33.68 |
| ATOM | 850 | ND2 | ASN | 164 | 40.917 | 36.338 | −9.540 | 1.00 | 34.99 |
| ATOM | 851 | C | ASN | 164 | 37.759 | 35.327 | −5.817 | 1.00 | 38.77 |
| ATOM | 852 | O | ASN | 164 | 38.607 | 34.631 | −5.192 | 1.00 | 39.55 |
| ATOM | 853 | O | HOH | 13 | 43.750 | 39.334 | −13.145 | 1.00 | 28.96 |
| ATOM | 854 | O | HOH | 16 | 40.399 | 29.413 | −15.417 | 1.00 | 28.45 |
| ATOM | 855 | O | HOH | 43 | 40.476 | 25.942 | −12.392 | 1.00 | 25.27 |
| ATOM | 856 | O | HOH | 59 | 33.030 | 28.026 | −11.083 | 1.00 | 31.40 |
| ATOM | 857 | O | HOH | 67 | 39.649 | 21.814 | −18.865 | 1.00 | 47.03 |
| ATOM | 858 | O | HOH | 106 | 50.161 | 43.713 | −11.622 | 1.00 | 38.31 |
| ATOM | 859 | O | HOH | 112 | 47.845 | 25.173 | −15.269 | 1.00 | 53.31 |
| ATOM | 860 | O | HOH | 146 | 34.089 | 21.987 | −9.344 | 1.00 | 34.34 |
| ATOM | 861 | O | HOH | 162 | 54.541 | 32.509 | −14.452 | 1.00 | 53.57 |
| ATOM | 862 | O | HOH | 187 | 41.347 | 26.658 | −14.661 | 1.00 | 46.21 |
| ATOM | 863 | O | HOH | 188 | 46.213 | 38.062 | −13.128 | 1.00 | 32.16 |
| ATOM | 864 | O | HOH | 197 | 49.443 | 30.918 | −14.330 | 1.00 | 40.46 |
| ATOM | 865 | O | HOH | 198 | 47.210 | 39.209 | −14.726 | 1.00 | 36.63 |
| ATOM | 866 | O | HOH | 217 | 49.742 | 24.216 | −9.382 | 1.00 | 63.31 |
| ATOM | 867 | O | HOH | 250 | 29.116 | 26.588 | −8.716 | 1.00 | 43.13 |
| TER | | | | | | | | | |

The claimed invention is:

1. A crystal comprising *B. subtilis* nitrile oxidoreductase QueF:preQ$_0$ thiomide covalent complex, comprising the steps of:

placing a solution comprising QueF, in 100 mM Tris, pH 7.5 and 100 mM KCl, to preQo in 0.5% Dextran sulfate, in a protein:preQ molar ratio of approximately 1:5;

in the presence of a crystallization buffer comprising 16% PEG 550mme, 60mM Imidazole, 40 mM imidazole-Cl, pH 7.4 and 30 mM CaCl$_2$;

and placing under conditions to form a crystal of a *B. subtilis* nitrile oxidoreductase QueF:preQ$_0$ thiomide covalent complex wherein the QueF polypeptide comprises SEQ ID NO: 1.

* * * * *